US011702658B2

(12) United States Patent
Yuan et al.

(10) Patent No.: US 11,702,658 B2
(45) **Date of Patent: *Jul. 18, 2023**

(54) METHODS AND COMPOSITIONS FOR EDITING RNAS

(71) Applicants: EDIGENE THERAPEUTICS (BEIJING) INC., Beijing (CN); Peking University, Beijing (CN)

(72) Inventors: Pengfei Yuan, Beijing (CN); Yanxia Zhao, Beijing (CN); Nengyin Liu, Beijing (CN); Zexuan Yi, Beijing (CN); Gangbin Tang, Beijing (CN); Wensheng Wei, Beijing (CN); Liang Qu, Beijing (CN); Zongyi Yi, Beijing (CN); Shiyou Zhu, Beijing (CN); Chunhui Wang, Beijing (CN); Zhongzheng Cao, Beijing (CN); Zhuo Zhou, Beijing (CN)

(73) Assignees: EDIGENE THERAPEUTICS (BEIJING) INC., Beijing (CN); PEKING UNIVERSITY, Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/501,954

(22) Filed: Oct. 14, 2021

(65) Prior Publication Data

US 2022/0098587 A1 Mar. 31, 2022

Related U.S. Application Data

(63) Continuation of application No. PCT/CN2020/084922, filed on Apr. 15, 2020.

(30) Foreign Application Priority Data

Dec. 30, 2019 (WO) ................ PCT/CN2019/129952
Apr. 15, 2020 (WO) ................ PCT/CN2019/082713

(51) Int. Cl.

| | |
|---|---|
| ***C12N 15/113*** | (2010.01) |
| ***C12N 15/90*** | (2006.01) |
| ***C12N 15/10*** | (2006.01) |

(52) U.S. Cl.

CPC .......... *C12N 15/113* (2013.01); *C12N 15/102* (2013.01); *C12N 15/907* (2013.01); *C12N 2310/11* (2013.01); *C12N 2310/16* (2013.01); *C12N 2310/315* (2013.01); *C12N 2310/321* (2013.01); *C12N 2310/3519* (2013.01); *C12N 2310/531* (2013.01); *C12N 2310/533* (2013.01)

(58) Field of Classification Search

None

See application file for complete search history.

(56) References Cited

U.S. PATENT DOCUMENTS

| | | | | |
|---|---|---|---|---|
| 4,435,307 | A | 3/1984 | Barbesgaard et al. | |
| 5,773,244 | A | 6/1998 | Ares, Jr. et al. | |
| 9,650,627 | B1 | 5/2017 | Rosenthal et al. | |
| 10,941,402 | B2 | 3/2021 | Turunen et al. | |
| 2013/0253036 | A1 | 9/2013 | Collard et al. | |
| 2018/0208924 | A1 | 7/2018 | Fukuda et al. | |
| 2019/0040383 | A1 | 2/2019 | Klein et al. | |
| 2019/0093098 | A1* | 3/2019 | Stafforst | C12N 15/102 |
| 2019/0330622 | A1* | 10/2019 | Turunen | A61P 37/04 |
| 2019/0352641 | A1 | 11/2019 | Aalto et al. | |
| 2020/0308581 | A1 | 10/2020 | Clarke et al. | |
| 2021/0310026 | A1 | 10/2021 | Wei et al. | |
| 2021/0355494 | A1 | 11/2021 | Wei et al. | |
| 2022/0010333 | A1 | 1/2022 | Mali et al. | |
| 2022/0064633 | A1 | 3/2022 | Wei et al. | |
| 2022/0073915 | A1* | 3/2022 | Wettengel | C12N 15/111 |
| 2022/0110333 | A1 | 4/2022 | Gebhardt et al. | |
| 2022/0135963 | A1 | 5/2022 | Wei et al. | |
| 2022/0193142 | A1 | 6/2022 | Fang et al. | |
| 2022/0243194 | A1 | 8/2022 | Wei et al. | |
| 2022/0307020 | A1 | 9/2022 | Yuan et al. | |

FOREIGN PATENT DOCUMENTS

| | | | |
|---|---|---|---|
| CN | 107109413 | A | 8/2017 |
| CN | 109072239 | A | 12/2018 |
| CN | 109477103 | A | 3/2019 |
| CN | 109804069 | A | 5/2019 |
| CN | 109943586 | A | 6/2019 |
| CN | 110352244 | A | 10/2019 |
| JP | 2018506297 | A | 3/2016 |
| JP | 2017537618 | A | 12/2017 |
| TW | 202028466 | A | 8/2020 |
| TW | 202043249 | A | 12/2020 |
| WO | 2015134812 | A1 | 9/2015 |
| WO | 2016094845 | A2 | 6/2016 |

(Continued)

OTHER PUBLICATIONS

Abe, N. et al. (2018). "Preparation of Circular RNA In Vitro," Methods Mol. Biol. 1724:181-192.

Abudayyeh, O.O. et al. (Aug. 5, 2018). "C2c2 is a Single-Component Programmable RNA-Guided RNA-Targeting CRISPR Effector," Science 353:aaf5573-1-aff5573-9, 11 pages.

Abudayyeh, O.O. et al. (Jul. 26, 2019). "A Cytosine Deaminase for Programmable Single-Base RNA Editing," Science 365:382-386.

Aquino-Jarquin, G. (Mar. 31, 2020). "Novel Engineered Programmable Systems for ADAR-Mediated RNA Editing," Molecular Therapy Nucleic Acids 19:1065-1072.

(Continued)

*Primary Examiner* — Brian Whiteman

(74) *Attorney, Agent, or Firm* — Morrison & Foerster LLP

(57) ABSTRACT

The present application provides methods for editing RNA by introducing a deaminase-recruiting RNA in a host cell for deamination of an adenosine in a target RNA. The present application further provides deaminase-recruiting RNAs used in the RNA editing methods and compositions comprising the same.

16 Claims, 66 Drawing Sheets

Specification includes a Sequence Listing.

(56) References Cited

FOREIGN PATENT DOCUMENTS

| | | | | |
|---|---|---|---|---|
| WO | 2016097212 A1 | | 6/2016 | |
| WO | 2017010556 A1 | | 1/2017 | |
| WO | WO-2017050306 A1 | * | 3/2017 | C12N 15/102 |
| WO | 2017186739 A1 | | 11/2017 | |
| WO | 2017220751 A1 | | 12/2017 | |
| WO | 2018041873 A1 | | 3/2018 | |
| WO | 2018041973 A1 | | 3/2018 | |
| WO | 2018055134 A1 | | 3/2018 | |
| WO | 2018134301 A1 | | 7/2018 | |
| WO | 2018161032 A1 | | 9/2018 | |
| WO | 2018208998 A1 | | 11/2018 | |
| WO | 2019005886 A1 | | 1/2019 | |
| WO | 2019060746 A1 | | 3/2019 | |
| WO | 2019071048 A1 | | 4/2019 | |
| WO | 2019123429 A1 | | 6/2019 | |
| WO | 2019158475 A1 | | 8/2019 | |
| WO | 2019183641 A1 | | 9/2019 | |
| WO | 2020074001 A1 | | 4/2020 | |
| WO | 2020168051 A1 | | 8/2020 | |
| WO | 2020211780 A1 | | 10/2020 | |
| WO | 2021008447 A1 | | 1/2021 | |
| WO | 2021043278 A1 | | 3/2021 | |
| WO | 2021121266 A1 | | 6/2021 | |
| WO | 2021136404 A1 | | 7/2021 | |
| WO | 2021136408 A1 | | 7/2021 | |
| WO | 2021136520 A1 | | 7/2021 | |
| WO | 2022150974 A1 | | 7/2022 | |

OTHER PUBLICATIONS

Bass, B.L. et al. (Dec. 23, 1988). "An Unwinding Activity That Covalently Modifies Its Double-Stranded RNA Substrate," Cell 55:1089-1098.
Bazak, L. et al. (2014). "A-to-I RNA Editing Occurs at Over a Hundred Million Genomic Sites, Located in a Majority of Human Genes," Genome Res. 24:365-376.
Beaudry, D. et al. (1995). "An Efficient Strategy for the Synthesis of Circular RNA Molecules," Nucleic Acids Res. 23(15):3064-3066.
Bennett, C.F. (Jan. 27, 2019). "Therapeutic Antisense Oligonucleotides Are Coming of Age," Annu. Rev. Med. 70:307-321.
Boch, J. et al. (Dec. 11, 2009). "Breaking the Code of DNA Binding Specificity of TAL-Type III Effectors," Science 326(5959):1509-1512.
Burgess, D.J. (Oct. 2019). "Expanding Options for RNA Based Editors," Nature Reviews Genetics 20(10):563-563, 1 page.
Zuo, E. et al. (Feb. 28, 2019). "Cytosine Base Editor Generates Substantial Off-Target Single-Nucleotide Variants in Mouse Embryos," Science, 7 pages.
Charlesworth, C.T. et al. (2019, e-pub. Jan. 28, 2019). Identification of Preexisting Adaptive Immunity to Cas9 Proteins in Humans, Nat Med 25:249-254.
Chen, C.-X. et al. (2000). "A Third Member of the RNA-Specific Adenosine Deaminase Gene Family, ADAR3, Contains Both Single- and Double-Stranded RNA Binding Domains," RNA 6:755-767.
Chen, G.H. et al. (Apr. 3, 2019). "RNA-Guided Adenosine Deaminases: Advances and Challenges for Therapeutic RNA Editing," Biochemistry 58(15):1947-1957.
Chen, H. et al. (2020, e-pub. Mar. 30, 2020). "Preferential Production of RNA Rings by T4 RNA Ligase 2 Without Any Splint Through Rational Design of Precursor Strand," Nucleic Acids Research 48(9):e54, 12 pages.
Chen, L.L. (Apr. 2016). "The Biogenesis and Emerging Roles of Circular RNAs," Nat. Rev. Mol. Cell Biol. 17(4):205-211, 7 pages.
Chew, W.L. et al. (Oct. 2016). "A Multifunctional AAV-CRISPR-Cas9 and Its Host Response," Nat Methods 13(10):868-874.
Cong, L. et al. (Feb. 15, 2013, e-pub. Oct. 11, 2013). "Multiplex Genome Engineering Using CRISPR/Cas Systems," Science 339(6121):819-823, 9 pages.
Cox, D. B. T et al. (Nov. 24, 2017). "RNA Editing With CRISPR-Cas13," Science 358:1019-1027.
Crunkhorn, S. (Sep. 2019). "Expanding the RNA-Editing Toolbox," Nature Reviews Drug Discovery 18(9):667-667, 1 page.
Daniel, C. et al. (2017). "Editing Inducer Elements Increases A-to-I Editing Efficiency in the Mammalian Transcriptome," Genome Biol 18:195, 16 pages.
Dobin, A. et al. (2013, e-pub. Oct. 25, 2012). "STAR: Ultrafast Universal RNA-Seq Aligner," Bioinformatics 29:1-7.
Doubrovin, M. et al. (Jul. 31, 2001). "Imaging Transcriptional Regulation of p53-dependent Genes With Positron Emission Tomography In Vivo," Proc Natl Acad Sci USA 98(16):9300-9305, 14 pages.
Dykstra, P.B. et al. (Apr. 2022). "Engineering Synthetic RNA Devices for Cell Control," Nature Reviews Genetics 23:215-228.
Eggington, J.M. et al. (May 17, 2011). "Predicting Sites of ADAR Editing in Double-Stranded RNA," Nat. Commun. 2:319, 9 pages.
Enuka, Y. et al. (2016, e-pub. Dec. 10, 2015). "Circular RNAs Are Long-Lived and Display Only Minimal Early Alterations in Response to a Growth Factor," Nucleic Acids Res. 44(3):1370-1383.
Fire, A. et al. (Feb. 19, 1998). "Potent and Specific Genetic Interference by Double-Stranded RNA in Caenorhabditis elegans," Nature 391:806-811.
Floquet, C. (2011, e-pub. Dec. 10, 2010). "Rescue of Non-Sense Mutated p53 Tumor Suppressor Gene by Aminoglycosides," Nucleic Acids Res 39(8):3350-3362.
Fry, L.E. et al. (Jan. 25, 2020). "RNA Editing as a Therapeutic Approach for Retinal Gene Therapy Requiring Long Coding Sequences," International Journal of Molecular Sciences 21:77, 20 pages.
Fukuda, M. et al. (Feb. 2, 2017). "Construction of a Guide-RNA for Site-Directed RNA Mutagenesis Utilising Intracellular A-to-I RNA Editing," Scientific Reports 7:41478, 13 pages.
Fuster-García, C. et al. (Sep. 30, 2017). "USH2A Gene Editing Using the CRISPR System," Molecular Therapy Nucleic Acids 8:529-541.
Gallo, A. et al. (Sep. 2017, e-pub. Sep. 14, 2017). "ADAR RNA Editing in Human Disease; More to It Than Meets the I," Hum. Genet. 136(9):1265-1278.
Gaudelli, N. M. et al. (Nov. 23, 2017). "Programmable Base Editing of A*T to G*C in Genomic DNA Without DNA Cleavage," Nature 551:464-471.
Genomes Project Consortium (Nov. 1, 2012). "An Integrated Map of Genetic Variation From 1,092 Human Genomes," Nature 491:56-65.
Gibson, D.G. et al. (May 2009, e-pub. Apr. 12, 2009). "Enzymatic Assembly of DNA Molecules up to Several Hundred Kilobases," Nature Methods 6(5):343-347.
Grünewald, J. et al. (May 2019). "Transcriptome-Wide Off-Target RNA Editing Induced by CRISPR-Guided DNA Base Editors," Nature 569(7756):433-437, 34 pages.
Grünewald, J. et al. (Sep. 2019). "CRISPR DNA Base Editors With Reduced RNA Off-Target and Self-Editing Activities," Nat. Biotechnol. 37(9):1041-1048, 19 pages.
Haapaniemi, E. (2018, e-pub. Jun. 11, 2018). "CRISPR-Cas9 Genome Editing Induces a p53-Mediated DNA Damage Response," Nat Med 24:927-930.
Hanswillemenke, A. et al. (2015, e-pub. Nov. 23, 2015). "Site-Directed RNA Editing in Vivo Can Be Triggered by the Light-Driven Assembly of an Artificial Riboprotein," J Am Chem Soc 137:15875-15881.
Heep, M. et al. (Jan. 14, 2017). "Applying Human ADAR1p110 and ADAR1 p150 for Site-Directed RNA Editing-G/C Substitution Stabilizes GuideRNAs Against Editing," Genes (Basel) 8:34, 7 pages.
Ihry, R.J. et al. (Jul. 2018, e-pub. Jun. 11, 2018). "p53 Inhibits CRISPR-Cas9 Engineering in Human Pluripotent Stem Cells," Nat Med 24:939-946.
International Preliminary Report on Patentability Opinion, dated Apr. 8, 2021, for PCT Application No. PCT/CN2019/110782, filed Oct. 12, 2019, 7 pages.

(56) References Cited

OTHER PUBLICATIONS

International Preliminary Report on Patentability Opinion, dated Sep. 28, 2021, for PCT Application No. PCT/CN2020/084922, filed Apr. 15, 2020, 6 pages.
International Preliminary Report on Patentability, dated Jan. 18, 2022, for PCT Application No. PCT/CN2020/101246, filed Jul. 10, 2020, 7 pages.
International Search Report and Written Opinion, dated Jan. 9, 2020, for PCT Application No. PCT/CN2019/110782, filed Oct. 12, 2019, 13 pages.
International Search Report and Written Opinion, dated Jul. 24, 2020, for PCT Application No. PCT/CN2020/084922, filed Apr. 15, 2020, 13 pages.
International Search Report and Written Opinion, dated Oct. 12, 2020, for PCT Application No. PCT/CN2020/101246, filed Jul. 10, 2020, 13 pages.
International Search Report, dated Apr. 2, 2021, for PCT Application No. PCT/CN2020/142218, 12 pages. With English Translation.
International Search Report, dated Mar. 26, 2021, for PCT Application No. PCT/CN2020/141501, 14 pages. With English Translation.
International Search Report, dated Mar. 30, 2021, for PCT Application No. PCT/CN2020/141506, 14 pages. With English Translation.
Jin, S. et al. (2019, e-pub. Feb. 28, 2019). "Cytosine, But Not Adenine, Base Editors Induce Genome-Wide Off-Target Mutations in Rice," Science, 7 pages.
Jinek, M. et al. (Aug. 17, 2012). "A Programmable Dual-RNA-Guided DNA Endonuclease in Adaptive Bacterial Immunity," Science 337(6096):816-821.
Katrekar, D. et al. (Apr. 2019, e-pub. Feb. 8, 2019). "In Vivo RNA Editing of Point Mutations via RNA-Guided Adenosine Deaminases," Nat Methods 16:239-242.
Kern, S.E. et al. (Jun. 21, 1991). "Identification of p53 as a Sequence-Specific DNA-Binding Protein," Science 252:1708-1711.
Khosravi, H,M, et al. (2021, e-pub. Sep. 27, 2021). "Site-Directed RNA Editing Recent Advances and Open Challenges," RNA Biol. 18(S1):41-50.
Kim, D. et al. (2019, e-pub. Mar. 4, 2019). "Genome-Wide Target Specificity of CRISPR RNA-Guided Adenine Base Editors," Nat Biotechnol 37:430-435.
Komor, A. C. et al. (May 19, 2016). "Programmable Editing of a Target Base in Genomic DNA Without Double-Stranded DNA Cleavage," Nature 533:420-424.
Krawiiz, P.M. et al. (Sep. 30, 2014). "Screening for Single Nucleotide Variants, Small Indels and Exon Deletions With a Next-Generation Sequencing Based Gene Panel Approach for Usher Syndrome," Molecular Genetics & Genomic Medicine 2(5):393-401.
Kristensen, L.S. et al. (Nov. 2019, e-pub. Aug. 8, 2019). "The Biogenesis, Biology and Characterization of Circular RNAs," Nat. Rev. Genet. 20:675-691.
Kuttan, A. et al. (2012, e-pub. Nov. 5, 2012). "Mechanistic Insights Into Editing-Site Specificity of ADARs," Proc. Natl. Acad. Sci. USA 109:E3295-3304.
Landrum, M.J. et al. (2016, e-pub. Nov. 17, 2015). "ClinVar: Public Archive of Interpretations of Clinically Relevant Variants," Nucleic Acids Res 44:D862-D868.
Levanon, E.Y. et al. (Aug. 2004). "Systematic Identification of Abundant A-to-I Editing Sites in the Human Transcriptome," Nat Biotechnol 22(8):1001-1005.
Litke, J.L. et al. (Apr. 8, 2019). "Highly Efficient Expression of Circular RNA Aptamers in Cells Using Autocatalytic Transcripts," Nat Biotechnol. 37(6):667-675.
Ma, Y. et al. (Dec. 2016). "Targeted AID-Mediated Mutagenesis (TAM) Enables Efficient Genomic Diversification in Mammalian Cells," Nat Methods 13(12):1029-1035.
Mali, P. et al. (Feb. 15, 2013, e-pub. Jan. 3, 2013). "RNA Guided Human Genome Engineering via Cas9," Science 339(6121):823-826, 8 pages.
Mays, L.E. et al. (Jan. 2011). "The Complex and Evolving Story of T Cell Activation to AAV Vector-Encoded Transgene Products," Mol Ther 19(1):16-27.
Memczak, S. et al. (Mar. 21, 2013, e-pub. Feb. 27, 2013). "Circular RNAs Are a Large Class of Animal RNAs With Regulatory Potency," Nature 495(7441):333-338.
Merkle, T. et al. (2019, e-pub. Jan. 28, 2019). "Precise RNA Editing by Recruiting Endogenous ADARs With Antisense Oligonucleotides," Nat Biotechnol 37:133-138.
Miki, T. et al. (Apr. 1, 2019). "Induced Pluripotent Stem Cell Derivation and Ex Vivo Gene Correction Using Mucopolysaccharidosis Type 1 Disease Mouse Model," Stem Cells International 2019(6978303):1-10.
Miller, J.C. et al. (Feb. 2011, e-pub. Dec. 22, 2010). "A Tale Nuclease Architecture for Efficient Genome Editing," Nature Biotechnology 29(2):143-148.
Monteleone, L.R. et al. (Feb. 21, 2019). "A Bump-Hole Approach for Directed RNA Editing," Cell Chemical Biology 26(2):269-277.
Montiel-Gonzalez, M.F. (Nov. 5, 2013). "Correction of Mutations Within the Cystic Fibrosis Transmembrane Conductance Regulator by Site-Directed RNA Editing," Proc Natl Acad Sci USA 110:18285-18290.
Montiel-Gonzalez, M.F. et al. (2016). "An Efficient System for Selectively Altering Genetic Information Within mRNAs," Nucleic Acids Res 44:e157, 12 pages.
Moscou, M.J. et al. (Dec. 11, 2009, e-pub. Oct. 29, 2009). "A Simple Cipher Governs DNA Recognition by TAL Effectors," Science 326:1501, 1 page.
Nishikura, K. (2010). "Functions and Regulation of RNA Editing by ADAR Deaminases," Annu Rev Biochem 79:321-349.
Nishikura, K. (Feb. 2016). "A-to-I Editing of Coding and Non-Coding RNAs by ADARs," Nat Rev Mol Cell Biol 17:83-96.
Ou, L. et al. (Jan. 2019). "ZFN-Mediated In Vivo Genome Editing Corrects Murine Hurler Syndrome," Mol Ther 27(1):178-187.
Patterson, J. B. et al. (Oct. 1995). "Expression and Regulation by Interferon of a Double-Stranded-RNA-Specific Adenosine Deaminase From Human Cells: Evidence for Two Forms of the Deaminase," Mol Cell Biol 15(10):5376-5388.
Pertea, M. et al. (2016, e-pub. Aug. 11, 2016). "Transcript-Level Expression Analysis of RNA-Seq Experiments With HISAT, StringTie and Ballgown," Nat Protoc 11(9):1650-1667.
Platt, R.J. et al. (Oct. 9, 2014). "CRISPR-Cas9 Knockin Mice for Genome Editing and Cancer Modeling," Cell 159:440-455.
Porteus, M. H. et al. (Aug. 2005, e-pub. Aug. 8, 2005). "Gene Targeting Using Zinc Finger Nucleases," Nat Biotechnol 23(8):967-973.
Porto, E.M. et al. (2020). "Base Editing: Advances and Therapeutic Opportunities," Nature Reviews Drug Discovery 19(12):839-859.
Puttaraju, M. et al. (1992). "Group I Permuted Intron-Exon (PIE) Sequences Self-Splice to Produce Circular Exons," Nucleic Acids Res. 20(20):5357-5364.
Qu, L. et al. (Apr. 19, 2019). "Leveraging Endogenous ADAR for Programmable Editing on RNA," Biomedical Pioneering Innovation Center, 46 pages.
Qu, L. et al. (Sep. 30, 2019, e-pub. Jul. 15, 2019). "Programmable RNA Editing by Recruiting Endogenous ADAR Using Engineered RNAs," Nature Biotechnology 37:1059-1069.
Roberts, T.C. et al. (Oct. 2020). "Advances in Oligonucleotide Drug Delivery," Nat. Rev. Drug Discov. 19:673-694.
Samaridou, E. et al. (2020, e-pub. Jun. 8, 2020). "Lipid Nanoparticles for Nucleic Acid Delivery: Current Perspectives," Adv. Drug Deliv. Rev. 154-155:37-63.
Sawa, Y.A. et al. (2012). "The ADAR Protein Family," Genome Biol 13:252, 10 pages.
Schneider, M.F. et al. (2014, e-pub. Apr. 17, 2014). "Optimal GuideRNAs for Re-Directing Deaminase Activity of nADAR1 and hADAR2 in trans," Nucleic Acids Res 42(10):e87, 9 pages.
Schuh, R.S. et al. (2018, e-pub Dec. 31, 2017). "Gene Editing of MPS I Human Fibroblasts by Co-Delivery of a CRISPR/Cas9 Plasmid and a Donor Oligonucleotide Using Nanoemulsions as Nonviral Carriers," European Journal of Pharmaceutics and Biopharmaceutics, pp. 1-33.

(56) References Cited

OTHER PUBLICATIONS

Simhadri, V.L. et al. (Jun. 9, 2018). "Prevalence of Pre-Existing Antibodies to CRISPR-Associated Nuclease Cas9 in the USA Population," Mol Ther Methods Clin Dev 10:105-112.
Sinnamon, J.R. et al. (2017). "Site-Directed RNA Repair of Endogenous Mecp2 RNA In Neurons," Proc Natl Acad Sci USA 114: E9395-E9402.
Tan, M.H. et al. (Oct. 12, 2017). "Dynamic Landscape and Regulation of RNA Editing in Mammals," Nature 550:249-254.
Teoh, P.J. et al. (Sep. 20, 2018). "Aberrant Hyperediting of the Myeloma Transcriptome by ADAR1 Confers Oncogenicity and Is a Marker of Poor Prognosis," Blood 132(12):1304-1317.
Tian, N. et al. (2011, e-pub. Mar. 22, 2011). "A Structural Determinant Required for RNA Editing," Nucleic Acids Res. 39(13):5669-5681.
Tong, S. et al. (Nov. 2019). "Engineered Material for in vivo Delivery of Genome-Editing Machinery," Nature Reviews Material 4(11):726-737, 26 pages.
U.S. Appl. No. 17/607,796, Fang et al., filed Oct. 29, 2021 (Copy not submitted herewith pursuant to the waiver of 37 C.F.R. § 1.98(a)(2)(iii) issued by the Office on Sep. 21, 2004).
U.S. Appl. No. 17/573,525, Wei, et al, filed Jan. 11, 2022. (Copy not submitted herewith pursuant to the waiver of 37 C.F.R. § 1.98(a)(2)(iii) issued by the Office on Sep. 21, 2004.).
U.S. Appl. No. 17/593,811, Wei, et al, filed Sep. 24, 2021. (Copy not submitted herewith pursuant to the waiver of 37 C.F.R. § 1.98(a)(2)(iii) issued by the Office on Sep. 21, 2004.).
U.S. Appl. No. 17/603,918, Yuan, et al, filed Oct. 14, 2021. (Copy not submitted herewith pursuant to the waiver of 37 C.F.R. § 1.98(a)(2)(iii) issued by the Office on Sep. 21, 2004.).
U.S. Appl. No. 17/626,440, Wei, et al, filed Jan. 1, 2022. (Copy not submitted herewith pursuant to the waiver of 37 C.F.R. § 1.98(a)(2)(iii) issued by the Office on Sep. 21, 2004.).
Vallecillo-Viejo, I.C. (2017, e-pub. Nov. 3, 2017). "Abundant Off-Target Edits From Site-Directed RNA Editing Can Be Reduced by Nuclear Localization of the Editing Enzyme," RNA Biology 15:104-114.
Van Der Auwera, G.A. et al. (2013, e-pub. Oct. 2013). "From FastQ Data to High Confidence Variant Calls the Genome Analysis Toolkit Best Practices Pipeline," Curr Protoc Bioinformatics 43:11.10, 33 pages.
Vogel, P. et al. (2014). "Improving Site-Directed RNA Editing In Vitro and in Cell Culture by Chemical Modification of the GuideRNA," Angewandte Chemie 53:6267-6271.
Vogel, P. et al. (2017, e-pub. May 31, 2017). "Switching Protein Localization by Site-Directed RNA Editing under Control of Light," ACS Synthetic Biology 6:1642-1649.
Vogel, P. et al. (2018, e-pub. Jul. 2, 2018). "Efficient and Precise Editing of Endogenous Transcripts With SNAP-Tagged ADARs," Nat Methods 15:535-538, 20 pages.
Wagner, D. L. et al. (2018, e-pub. Oct. 29, 2018). "High Prevalence of *Streptococcus pyogenes* Cas9-Reactive T Cells Within the Adult Human Population," Nat Med 25:242-248.
Wagner, R.W. et al. (Oct. 1990). "Double-Stranded RNA Unwinding and Modifying Activity Is Detected Ubiquitously in Primary Tissues and Cell Lines," Mol Cell Biol 10(10):5586-5590.
Wahlstedt, H. et al. (Nov./Dec. 2011). "Site-Selective Versus Promiscuous A-to-I Editing," Wiley Interdisciplinary Reviews: RNA 2:761-771.
Wang, K. et al. (2010, e-pub. Jul. 3, 2010). "ANNOVAR: Functional Annotation of Genetic Variants From High-Throughput Sequencing Data," Nucleic Acids Res 38(16):e164, 7 pages.
Wang, Y. et al. (Sep. 22, 2015). "A Phenotypic Screen for Functional Mutants of Human Adenosine Deaminase Acting on RNA 1," ACS Chem Biol. 10(11):2512-2519.
Wesselhoeft, R.A. et al. (2018). "Engineering Circular RNA for Potent and Stable Translation in Eukaryotic Cells," Nat. Commun. 9:2629, 10 pages.
Wesselhoeft, R.A et al. (2019, e-pub. May 2, 2019). "RNA Circularization Diminishes Immunogenicity and Can Extend Translation Duration In Vivo," Mol. Cell 74: 508-520.
Wettengel, J. et al. (2016, e-pub. Oct. 7, 2016). "Harnessing Human ADAR2 for RNA Repair—Recoding a PINK1 Mutation Rescues Mitophagy," Nucleic Acids Res 45:2797-2808.
Wong, S.K. et al. (2001). "Substrate Recognition by ADAR1 and ADAR2," RNA 7:846-858.
Woolf, T.M. et al. (Aug. 31, 1995). "Toward the Therapeutic Editing of Mutated RNA Sequences," Proc Natl Acad Sci USA 92:8298-8302.
Yin, H. (Jun. 2017, e-pub. Mar. 24, 2017). "Delivery Technologies for Genome Editing," Nature Reviews Drug Discovery 16(6):387-399.
Yin, Q.-F. et al. (Oct. 26, 2012). "Long Noncoding RNAs With snoRNA Ends," Mol Cell. 48(2):219-230.
Zhang, A-X et al. (Jul. 15, 2018). "Progress in Base Editing Technology Based on CRISPR/Cas9 System and Its Application in Medical Research," Chin J Pharmacol Toxicol. 32(7):507-511. With English Abstract.
Zhang, X.O. et al. (Sep. 25, 2014). "Complementary Sequence-Mediated Exon Circularization," Cell 159:134-147.
Zheng, Y. et al. (2017, e-pub. Jan. 28, 2017). "DNA Editing in DNA/RNA Hybrids by Adenosine Deaminases That Act on RNA," Nucleic Acids Res 45(6):3369-3377.
Zhou, Y. et al. (2016, e-pub. Nov. 14, 2016). "Simultaneous Generation of Multi-Gene Knockouts in Human Cells," FEBS Letters 590:4343-4353.
Montiel-Gonzalez, M.F. et al. (Mar. 1, 2019, e-pub. Nov. 29, 2018). "Current Strategies for Site-Directed RNA Editing Using ADARs," Methods 156:16-24, 25 pages.
Eckstein, F. (Dec. 2014). "Phosphorothioates, Essential Components of Therapeutic Oligonucleotides," Nucleic Acid Therapeutics 24(6):374-387, 14 pages.
Genbank (May 31, 2018). NM_000203.4—"*Homo sapians* Iduronidase, Alpha-L_(IDUA), Transcript Varian 1, mRNA," 4 pages.
Pinzon, F.F. (2006). "Morality, Ethics and Bioethics as Social Limitations to the Protection of Inventions via Patents," Phronesis 13(3):1-2. English Abstract.
Pollard, K.M. et al. (Sep. 2013). "Interferon-γ and Systemic Autoimmunity," Discovery Medicine 16(87):123-131, 14 pages.
U.S. Appl. No. 17/786,433, Fang, et al, filed Jun. 16, 2022. (Copy not submitted herewith pursuant to the waiver of 37 C.F.R. § 1 98(a)(2)(iii) issued by the Office on Sep. 21, 2004.).
U.S. Appl. No. 17/790,484, Liu, et al, filed Jun. 30, 2022. (Copy not submitted herewith pursuant to the waiver of 37 C.F.R. § 1.98(a)(2)(iii) issued by the Office on Sep. 21, 2004.).
U.S. Appl. No. 17/790,487, Yuan, et al, filed Jun. 30, 2022. (Copy not submitted herewith pursuant to the waiver of 37 C.F.R. § 1.98(a)(2)(iii) issued by the Office on Sep. 21, 2004.).
U.S. Appl. No. 17/790,488, Yuan, et al, filed Jun. 30, 2022. (Copy not submitted herewith pursuant to the waiver of 37 C.F.R. § 1.98(a)(2)(iii) issued by the Office on Sep. 21, 2004.).
Vu, L.T. et al. (Apr. 2016, e-pub. Dec. 29, 2019). "Chemical RNA Editing for Genetic Restoration: The Relationship Between the Structure and Deamination Efficiency of Carboxyvinyldeoxyuridine Oligodeoxynucleotides," Chemical Biology & Drug Design 87(4):583-593.
Xiao, Q. (Mar. 22, 2019). "Application of CRISPR/Cas9-Based Gene Editing in HIV-1/AIDS Therapy," Frontiers in Cellular and Infection Microbiology 9(69):1-15.
Xu, L. et al. (Sep. 26, 2019). "CRISPR-Edited Stem Cells in a Patient With HIV and Acute Lymphocytic Leukemia," New England Journal of Medicine 381(13):1240-1247.
Zhang, X. et al. (Dec. 20, 2019). "Synthetic Biology in China: Review and Prospect," Science China Life Sciences 12:30-32, English Abstract, 30 pages.

* cited by examiner

A-G mismatch sites
dRNA-AG1: $A_{41}$, $A_{46}$, $A_{74}$
dRNA-AG2: $A_{41}$, $A_{43}$, $A_{45}$, $A_{46}$, $A_{74}$, $A_{79}$
dRNA-AG3: $A_{31}$, $A_{32}$, $A_{33}$, $A_{41}$, $A_{43}$, $A_{45}$, $A_{46}$, $A_{47}$, $A_{74}$, $A_{79}$
dRNA-AG4: $A_{7}$, $A_{31}$, $A_{32}$, $A_{33}$, $A_{40}$, $A_{41}$, $A_{43}$, $A_{45}$, $A_{46}$, $A_{47}$, $A_{74}$, $A_{79}$, $A_{95}$
FIG. 5E
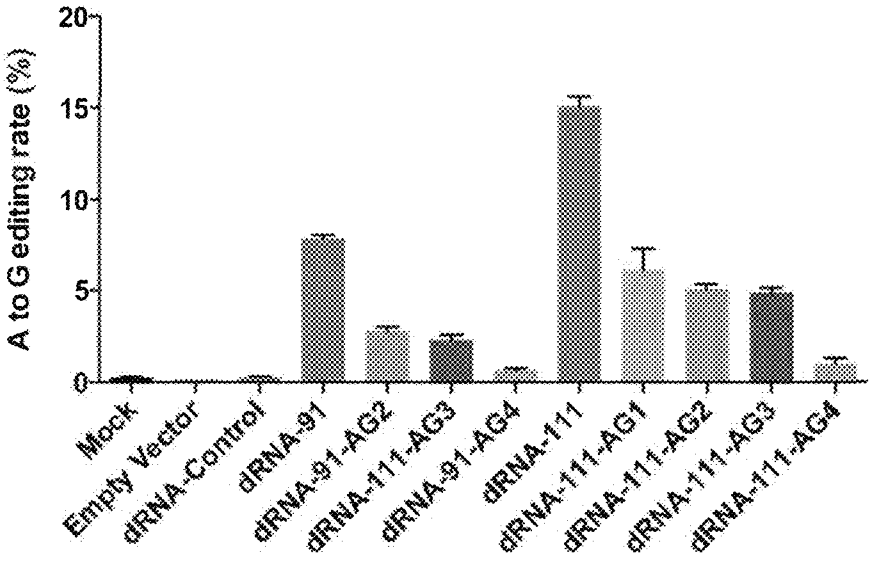
FIG. 5F
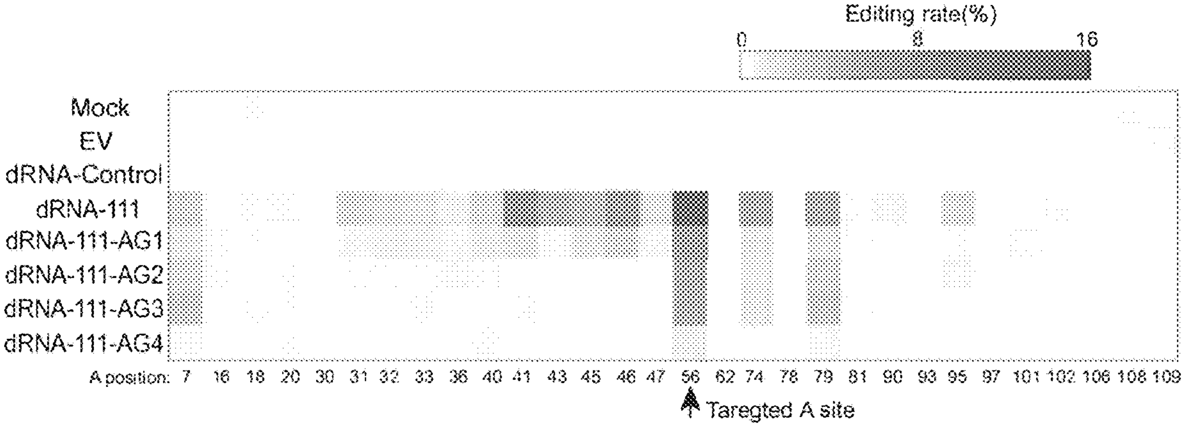
FIG. 5G

Allel-1: 17 bp deletion in exon 2

Mut CCACCTGTTCATTACAATGGCCCCTCAAAA-----------------TGAAAATGGCCAG SEQ ID NO: 439
    ||||||||||||||||||||||||||||||                 ||||||||||||
WT  CCACCTGTTCATTACAATGGCCCCTCAAAAGCAGGGTATGTTGACTTTGAAAATGGCCAG SEQ ID NO: 440

Allel-2: 1 bp insertion in exon 2

Mut CCACCTGTTCATTACAATGGCCCCTCAAAAAGCAGGGTATGTTGACTTTGAAAATGGCCAG SEQ ID NO: 441
    |||||||||||||||||||||||||||||| ||||||||||||||||||||||||||||
WT  CCACCTGTTCATTACAATGGCCCCTCAAAA GCAGGGTATGTTGACTTTGAAAATGGCCAG SEQ ID NO: 440

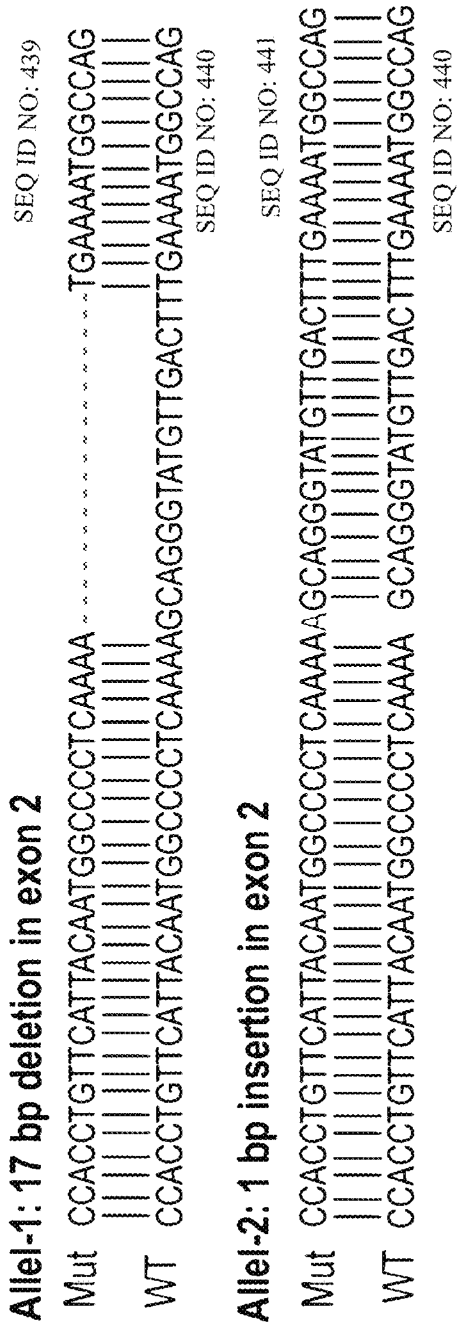

FIG.6E

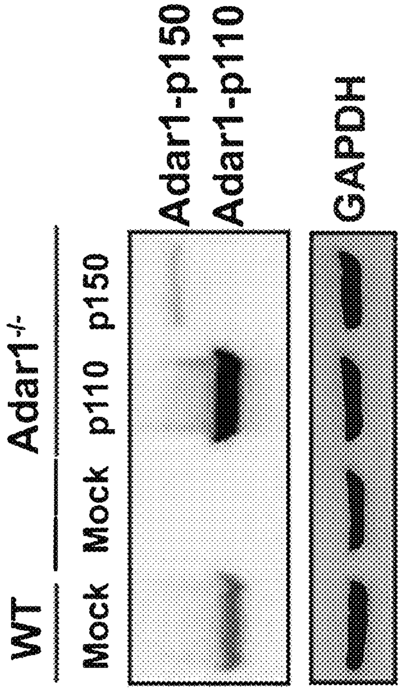

FIG.6F

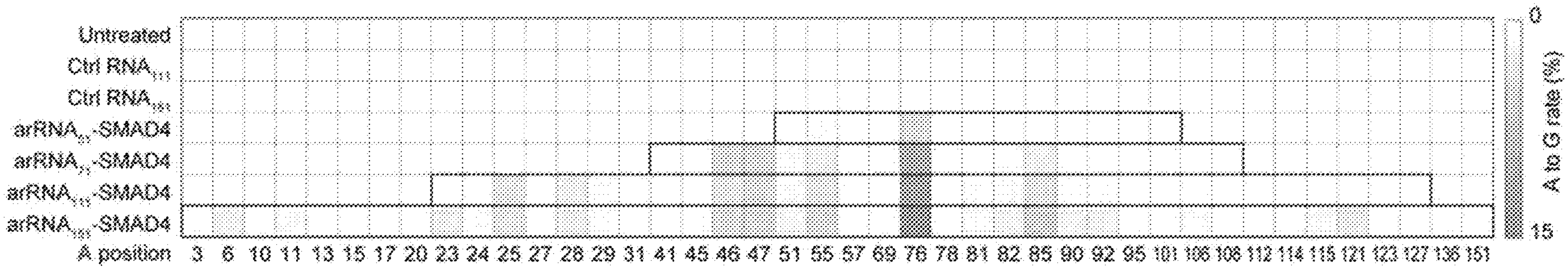
FIG.19D
*FANCC* transcript targeting
7 18 20 35 39 46 49 57 59 67 69 72/73 76 80 88 93/94 101
5'-CUGCGGAGGUCCCUUUGAGAGCUGGUUCCUGUUCAUUCACUUCGGAGGAUGGGCUGAGAUGGUGGCAGAGCAAUUACUGAUGUCGGCAGCCGAACCCCCCACGGCCCUG
129 132 144 149
CUGUGGCUCUUGGCCUUCUACUACGGCCCCCGUGAUGGGAGG-3'
SEQ ID NO: 454
FIG.19E
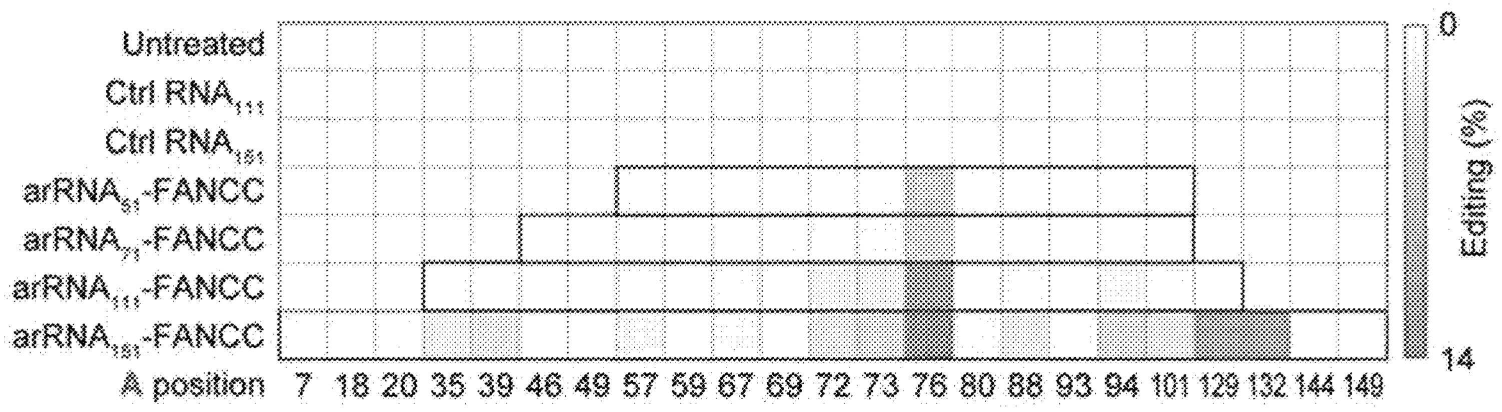
FIG.19F

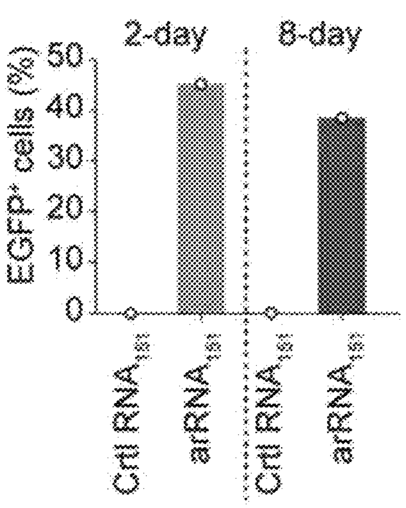
FIG.28A
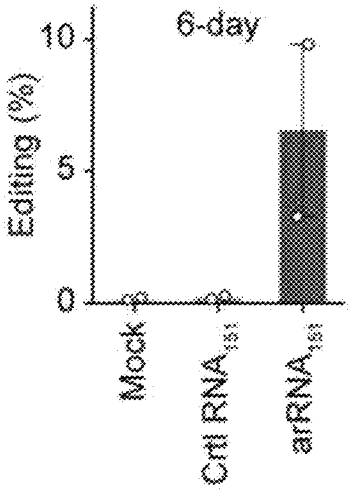
FIG.28B
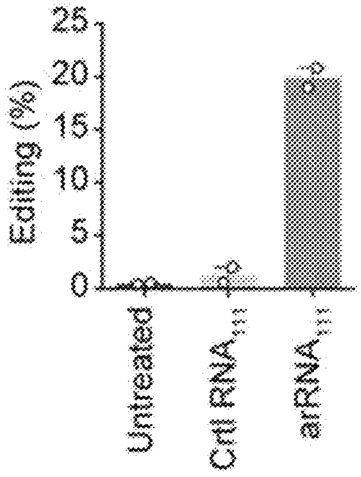
FIG.28D
***PPIB* transcript targeting**
SEQ ID NO: 477
5'-GAGCCCGCGAGCAACCCCAGUCCCCCCCACCCGCGCGUGGCGGCGCCGGCUCCCUAGCCACCGCGGCCCCACCCUCUUCCGGCCUCAGCUGUCCGGGCUGCUUUCGCCUCC-3'
3'-CUCGGGCGCUCGUUGGGGUCAGGGGGGGUGGGCGCGCACCGCCGCGGCCGAGGGA C GGUGGCGCCGGGGUGGGAGAAGGCCGGAGUCGACAGGCCCGACGAAAGCGGAGG-5'
arRNA$_{111}$-PPIB
SEQ ID NO: 478
FIG.28C

Reporter-1: (SEQ ID NO: 1, SEQ ID NO: 4, SEQ ID NO: 3)

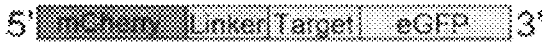

5'-
ATGGTGAGCAAGGGCGAGGAGGATAACATGGCCATCATCAAGGAGTTCATGCGCTTCAAGGTGCA
CATGGAGGGCTCCGTGAACGGCCACGAGTTCGAGATCGAGGGCGAGGGCGAGGGCCGCCCCTAC
GAGGGCACCCAGACCGCCAAGCTGAAGGTGACCAAGGGTGGCCCCCTGCCCTTCGCCTGGGACAT
CCTGTCCCCTCAGTTCATGTACGGCTCCAAGGCCTACGTGAAGCACCCCGCCGACATCCCCGACTA
CTTGAAGCTGTCCTTCCCCGAGGGCTTCAAGTGGGAGCGCGTGATGAACTTCGAGGACGGCGGCG
TGGTGACCGTGACCCAGGACTCCTCCCTGCAGGACGGCGAGTTCATCTACAAGGTGAAGCTGCGC
GGCACCAACTTCCCCTCCGACGGCCCCGTAATGCAGAAGAAGACCATGGGCTGGGAGGCCTCCTC
CGAGCGGATGTACCCCGAGGACGGCGCCCTGAAGGGCGAGATCAAGCAGAGGCTGAAGCTGAAG
GACGGCGGCCACTACGACGCTGAGGTCAAGACCACCTACAAGGCCAAGAAGCCCGTGCAGCTGCC
CGGCGCCTACAACGTCAACATCAAGTTGGACATCACCTCCCACAACGAGGACTACACCATCGTGGA
ACAGTACGAACGCGCCGAGGGCCGCCACTCCACCGGCGGCATGGACGAGCTGTACAAG *CTGCAG*
*GGCGGAGGAGGCAGC GGCGGAGGAGGCAGC GGCGGAGGAGGCAGC*
GCCTGCTCGCGATGCTAGAGGGCTCTGCCA
GTGAGCAAGGGCGAGGAGCTGTTCACCGGGGTGGTGCCCATCCTGGTCGAGCTGGACGGCGACGTAAAC
GGCCACAAGTTCAGCGTGTCCGGCGAGGGCGAGGGCGATGCCACCTACGGCAAGCTGACCCTGAAGTTC
ATCTGCACCACCGGCAAGCTGCCCGTGCCCTGGCCCACCCTCGTGACCACCCTGACCTACGGCGTGCAGT
GCTTCAGCCGCTACCCCGACCACATGAAGCAGCACGACTTCTTCAAGTCCGCCATGCCCGAAGGCTACGT
CCAGGAGCGCACCATCTTCTTCAAGGACGACGGCAACTACAAGACCCGCGCCGAGGTGAAGTTCGAGGG
CGACACCCTGGTGAACCGCATCGAGCTGAAGGGCATCGACTTCAAGGAGGACGGCAACATCCTGGGGCA
CAAGCTGGAGTACAACTACAACAGCCACAACGTCTATATCATGGCCGACAAGCAGAAGAACGGCATCAA
GGTGAACTTCAAGATCCGCCACAACATCGAGGACGGCAGCGTGCAGCTCGCCGACCACTACCAGCAGAA
CACCCCCATCGGCGACGGCCCCGTGCTGCTGCCCGACAACCACTACCTGAGCACCCAGTCCGCCCTGAGC
AAAGACCCCAACGAGAAGCGCGATCACATGGTCCTGCTGGAGTTCGTGACCGCCGCCGGGATCACTCTC
GGCATGGACGAGCTGTACAAGTAA-3'

FIG.30A

Reporter-2: (SEQ ID NO: 1, SEQ ID NO: 2, SEQ ID NO: 3)

5'-
ATGGTGAGCAAGGGCGAGGAGGATAACATGGCCATCATCAAGGAGTTCATGCGCTTCAAGGTGCA
CATGGAGGGCTCCGTGAACGGCCACGAGTTCGAGATCGAGGGCGAGGGCGAGGGCCGCCCCTAC
GAGGGCACCCAGACCGCCAAGCTGAAGGTGACCAAGGGTGGCCCCCTGCCCTTCGCCTGGGACAT
CCTGTCCCCTCAGTTCATGTACGGCTCCAAGGCCTACGTGAAGCACCCCGCCGACATCCCCGACTA
CTTGAAGCTGTCCTTCCCCGAGGGCTTCAAGTGGGAGCGCGTGATGAACTTCGAGGACGGCGGCG
TGGTGACCGTGACCCAGGACTCCTCCCTGCAGGACGGCGAGTTCATCTACAAGGTGAAGCTGCGC
GGCACCAACTTCCCCTCCGACGGCCCCGTAATGCAGAAGAAGACCATGGGCTGGGAGGCCTCCTC
CGAGCGGATGTACCCCGAGGACGGCGCCCTGAAGGGCGAGATCAAGCAGAGGCTGAAGCTGAAG
GACGGCGGCCACTACGACGCTGAGGTCAAGACCACCTACAAGGCCAAGAAGCCCGTGCAGCTGCC
CGGCGCCTACAACGTCAACATCAAGTTGGACATCACCTCCCACAACGAGGACTACACCATCGTGGA
ACAGTACGAACGCGCCGAGGGCCGCCACTCCACCGGCGGCATGGACGAGCTGTACAAG CTGCAG
*GGCGGAGGAGGCAGC GGCGGAGGAGGCAGC GGCGGAGGAGGCAGC*
AGAAGGTATACACGCCGGAAGAATCTGTAGAGATCCCCGGTCGCCACC
GTGAGCAAGGGCGAGGAGCTGTTCACCGGGGTGGTGCCCATCCTGGTCGAGCTGGACGGCGACGTAAAC
GGCCACAAGTTCAGCGTGTCCGGCGAGGGCGAGGGCGATGCCACCTACGGCAAGCTGACCCTGAAGTTC
ATCTGCACCACCGGCAAGCTGCCCGTGCCCTGGCCCACCCTCGTGACCACCCTGACCTACGGCGTGCAGT
GCTTCAGCCGCTACCCCGACCACATGAAGCAGCACGACTTCTTCAAGTCCGCCATGCCCGAAGGCTACGT
CCAGGAGCGCACCATCTTCTTCAAGGACGACGGCAACTACAAGACCCGCGCCGAGGTGAAGTTCGAGGG
CGACACCCTGGTGAACCGCATCGAGCTGAAGGGCATCGACTTCAAGGAGGACGGCAACATCCTGGGGCA
CAAGCTGGAGTACAACTACAACAGCCACAACGTCTATATCATGGCCGACAAGCAGAAGAACGGCATCAA
GGTGAACTTCAAGATCCGCCACAACATCGAGGACGGCAGCGTGCAGCTCGCCGACCACTACCAGCAGAA
CACCCCCATCGGCGACGGCCCCGTGCTGCTGCCCGACAACCACTACCTGAGCACCCAGTCCGCCCTGAGC
AAAGACCCCAACGAGAAGCGCGATCACATGGTCCTGCTGGAGTTCGTGACCGCCGCCGGGATCACTCTC
GGCATGGACGAGCTGTACAAGTAA-3'

FIG.30B

FIG.30C
mCherry
Linker
Target
eGFP

Reporter-3: (SEQ ID NO: 1, SEQ ID NO: 496, SEQ ID NO: 3)

5'-
ATGGTGAGCAAGGGCGAGGAGGATAACATGGCCATCATCAAGGAGTTCATGCGCTTCAAGGTGCACATG
GAGGGCTCCGTGAACGGCCACGAGTTCGAGATCGAGGGCGAGGGCGAGGGCCGCCCCTACGAGGGCAC
CCAGACCGCCAAGCTGAAGGTGACCAAGGGTGGCCCCCTGCCCTTCGCCTGGGACATCCTGTCCCCTCAG
TTCATGTACGGCTCCAAGGCCTACGTGAAGCACCCCGCCGACATCCCCGACTACTTGAAGCTGTCCTTCC
CCGAGGGCTTCAAGTGGGAGCGCGTGATGAACTTCGAGGACGGCGGCGTGGTGACCGTGACCCAGGACT
CCTCCCTGCAGGACGGCGAGTTCATCTACAAGGTGAAGCTGCGCGGCACCAACTTCCCCTCCGACGGCCC
CGTAATGCAGAAGAAGACCATGGGCTGGGAGGCCTCCTCCGAGCGGATGTACCCCGAGGACGGCGCCCT
GAAGGGCGAGATCAAGCAGAGGCTGAAGCTGAAGGACGGCGGCCACTACGACGCTGAGGTCAAGACCA
CCTACAAGGCCAAGAAGCCCGTGCAGCTGCCCGGCGCCTACAACGTCAACATCAAGTTGGACATCACCT
CCCACAACGAGGACTACACCATCGTGGAACAGTACGAACGCGCCGAGGGCCGCCACTCCACCGGCGGCA
TGGACGAGCTGTACAAG ctgcag *GGCGGAGGAGGCAGC*
GCCTGCTCGCGATGCTAGAGGGCTCTGCCA
GTGAGCAAGGGCGAGGAGCTGTTCACCGGGGTGGTGCCCATCCTGGTCGAGCTGGACGGCGACGTAAAC
GGCCACAAGTTCAGCGTGTCCGGCGAGGGCGAGGGCGATGCCACCTACGGCAAGCTGACCCTGAAGTTC
ATCTGCACCACCGGCAAGCTGCCCGTGCCCTGGCCCACCCTCGTGACCACCCTGACCTACGGCGTGCAGT
GCTTCAGCCGCTACCCCGACCACATGAAGCAGCACGACTTCTTCAAGTCCGCCATGCCCGAAGGCTACGT
CCAGGAGCGCACCATCTTCTTCAAGGACGACGGCAACTACAAGACCCGCGCCGAGGTGAAGTTCGAGGG
CGACACCCTGGTGAACCGCATCGAGCTGAAGGGCATCGACTTCAAGGAGGACGGCAACATCCTGGGGCA
CAAGCTGGAGTACAACTACAACAGCCACAACGTCTATATCATGGCCGACAAGCAGAAGAACGGCATCAA
GGTGAACTTCAAGATCCGCCACAACATCGAGGACGGCAGCGTGCAGCTCGCCGACCACTACCAGCAGAA
CACCCCCATCGGCGACGGCCCCGTGCTGCTGCCCGACAACCACTACCTGAGCACCCAGTCCGCCCTGAGC
AAAGACCCCAACGAGAAGCGCGATCACATGGTCCTGCTGGAGTTCGTGACCGCCGCCGGGATCACTCTC
GGCATGGACGAGCTGTACAAGTAA-3'

FIG.30C pLenti-dCas13-ADAR1DD SEQ ID NO: 483

5'-ATGGTG GATTACAAGGATGACGACGATAAG
ATGAAAGTGACGAAGGTAGGAGGCATTTCGCATAAGAAGTACACCGTCCGAAGGCCGCTTAGTGAAGTCA
GAATCGGAAGAAAAATCGCACAGACGAACGTCTGTCGGCGTTGCTTAATATGCGCCTTGACATGTATATCA
AGAATCCCAGCAGCACGGAAACCAAGGAAAATCAAAAACGCATTGGGAAATTAAAGAAATTCTTCTCAA
ACAAAATGGTCTATCTTAAAGACAATACCTTGAGTTTGAAGAATGGGAAAAAGGAGAACATTGATCGTG
AGTATTCTGAGACTGACATCCTTGAGAGCGATGTCCGTGACAAGAAAAACTTCGCCGTGTTGAAAAAGAT
CTATCTGAATGAAAACGTGAACTCGGAGGAATTGGAAGTTTTTCGTAACGACATTAAGAAGAAACTGAA
CAAAATCAACAGCCTGAAGTACTCATTTGAAAAGAATAAGGCGAATTATCAAAAGATTAATGAGAATAA
CATCGAGAAGGTTGAAGGTAAGTCAAAGCGTAACATTATTTACGATTATTATCGTGAGTCAGCGAAACGT
GACGCTTATGTAAGCAATGTGAAAGAAGCCTTTGATAAGCTTTACAAGGAAGAGGACATTGCAAAACTT
GTTCTTGAAATTGAGAACCTTACGAAGTTAGAGAAATACAAGATTCGCGAGTTCTACCACGAAATTATTG
GACGTAAGAATGACAAGGAAAACTTTGCAAAAATCATCTACGAAGAAATCCAGAATGTTAATAACATGA
AAGAGTTGATCGAGAAGGTACCGGACATGAGTGAGTTGAAAAAGAGCCAAGTATTTTACAAGTATTACT
TAGACAAAGAAGAGTTGAACGACAAGAACATCAAATACGCGTTTTGTCATTTCGTGGAAATCGAAATGA
GTCAGTTGCTGAAGAACTACGTATATAAGCGCTTAAGTAATATCTCGAATGACAAAATTAAGCGTATCTT
TGAATACCAGAACTTGAAAAAATTGATCGAAAATAAGCTGTTAAACAAACTTGACACGTACGTCCGTAAT
TGTGGAAAGTATAATTATTATTTGCAAGACGGCGAAATTGCCACTTCAGATTTTATCGCCCGCAACCGTC
AGAATGAAGCGTTTCTTCGCAACATCATTGGGGTGTCATCTGTGGCCTACTTTTCTCTTCGCAACATTCTT
GAAACGGAGAACGAGAATGATATTACTGGGCGTATGCGCGGCAAAACAGTTAAGAACAATAAAGGTGA
AGAGAAGTACGTGTCCGGAGAAGTTGATAAGATCTATAATGAAAATAAGAAGAACGAGGTTAAGGAGA
ACTTAAAAATGTTCTATTCGTACGATTTCAATATGGACAACAAGAATGAAATCGAAGATTTCTTCGCCAA
CATCGACGAGGCGATTTCTTCCATCGCTCACGGTATTGTCGCCTTCAACTTGGAATTAGAAGGTAAGGAT
ATCTTTGCGTTCAAGAACATTGCGCCATCCGAAATCTCAAAGAAGATGTTTCAGAATGAGATTAACGAGA
AAAAACTGAAATTGAAGATCTTTCGTCAACTGAACTCTGCCAACGTGTTCCGCTATCTCGAAAAGTATAA
AATTCTGAATTACCTTAAACGTACACGCTTCGAGTTTGTCAATAAAAATATCCCATTCGTCCCGTCTTTCA
CCAAATTATATTCGCGCATTGATGACCTGAAGAATAGTCTTGGGATTTACTGGAAAACTCCGAAAACAAA
CGACGACAATAAGACTAAGGAGATTATTGATGCCCAAATCTATTTGCTTAAAAACATCTATTACGGGGAG
TTCCTGAATTATTTCATGTCGAACAATGGTAATTTCTTTGAGATTTCTAAAGAAATCATCGAATTGAACAA
GAACGATAAACGCAACTTAAAGACTGGGTTTTACAAGCTGCAAAAGTTTGAAGACATCCAGGAGAAGAT
TCCAAAGGAATACTTGGCGAATATCCAGTCCCTGTACATGATTAATGCCGGTAATCAGGACGAAGAAGA
AAAGGACACTTATATTGATTTCATTCAAAAGATCTTCTTAAAGGGATTTATGACGTATCTTGCTAATAACG
GTCGTTTAAGTCTGATTTACATCGGCTCGGATGAAGAAACAAATACGTCATTAGCAGAAAAAGAAGCAAG
AGTTTGACAAGTTCTTGAAGAAGTACGAGCAGAACAATAATATCAAGATCCCCTATGAGATCAATGAATT
CCTGCGTGAGATCAAACTGGGAAACATCCTGAAGTATACTGAGCGTTTAAACATGTTCTACCTTATCTTA
AAGCTTTTGAATCACAAGGAGCTGACAAATCTGAAGGGTAGTCTTGAAAAATATCAGTCTGCCAATAAG
GAAGAAGCGTTCTCTGACCAATTGGAGTTAATTAACCTGCTTAACCTTGACAACAACCGCGTGACGGAAG
ACTTCGAATTAGAGGCCGACGAGATTGGAAAATTTCTTGATTTCAATGGCAACAAAGTTAAGGATAACAA
GGAACTGAAAAAGTTCGATACAAACAAGATCTACTTTGACGGCGAGAACATTATCAAACACCGTGCCTTC
TACAATATTAAGAAATATGGCATGTTAAACTTACTGGAGAAAATTGCCGACAAGGCTGGATACAAGATCT
CGATCGAAGAGCTGAAGAAATACTCCAATAAAAAGAATGAGATCGAGAAGAACCATAAGATGCAGGAA
AATCTGCACCGCAAATACGCTCGTCCCCGTAAAGACGAGAAGTTTACAGATGAGGACTATGAAAGTTAC
AAGCAAGCTATTGAGAATATTGAGGAGTACACCCACCTTAAGAACAAGGTAGAATTCAATGAGCTGAAT
TTACTGCAGGGCCTGTTGCTGCGCATTTTACATCGTTTAGTCGGATATACCTCAATTTGGGAACGCGATCT
GCGCTTCCGCCTTAAAGGTGAGTTCCCAGAAAACCAATACATCGAAGAGATCTTCAACTTTGAAAATAAG
AAGAACGTGAAGTACAAAGGGGGTCAGATTGTAGAGAAATACATTAAATTCTACAAGGAATTACATCAA
AATGATGAAGTTAAGATCAACAAGTACAGTTCCGCGAATATCAAGGTGTTGAAGCAAGAAAAAGAAGGAC
CTTTATATTGCTAATTACATCGCCCGCATTCAATTATATTCCTCACGCCGAGATCTCACTGCTGGAAGTCCT
TGAAAATTTGCGTAAATTGCTGTCCTACGATCGCAAACTGAAAAATGCCGTAATGAAATCAGTAGTTGAT
ATCCTTAAGGAGTATGGTTTTGTAGCCACATTCAAAATCGGGGCTGACAAGAAGATCGGTATTCAGACAC
TGGAGAGCGAAAAAATCGTGCATCTTAAGAATCTTAAGAAGAAGAAGTTAATGACTGACCGCAATTCCG
AGGAACTTTGCAAATTGGTGAAGATTATGTTTGAATACAAAATGGAAGAGAAAAAGTCTGAAAAC
*GGCGGCC A GGCGGAGGAGGCAGC GGCGGAGGAGGCAGC*
CTCCTCCTCTCAAGGTCCCCAGAAGCACAGCCAAAGACACTCCCTCTCACTGGCAGCACCTTCCATGACC
AGATAGCCATGCTGAGCCACCGGTGCTTCAACACTCTGACTAACAGCTTCCAGCCCTCCTTGCTCGGCCG
CAAGATTCTGGCCGCCATCATTATGAAAAAAGACTCTGAGGACATGGGTGTCGTCGTCAGCTTGGGAACA
GGGAATCGCTGTGTAAAAGGAGATTCTCTCAGCCTAAAAGGAGAAACTGTCAATGACTGCCATGCAGAA
ATAATCTCCCGGAGAGGCTTCATCAGGTTTCTCTACAGTGAGTTAATGAAATACAACTCCCAGACTGCGA
AGGATAGTATATTTGAACCTGCTAAGGGAGGAGAAAAGCTCCAAATAAAAAAGACTGTGTCATTCCATC
TGTATATCAGCACTGCTCCGTGTGGAGATGGCGCCCTCTTTGACAAGTCCTGCAGCGACCGTGCTATGGA
AAGCACAGAATCCCGCCACTACCCTGTCTTCGAGAATCCCAAACAAGGAAAGCTCCGCACCAAGGTGGA
GAACGGACAAGGCACAATCCCTGTGGAATCCAGTGACATTGTGCCTACGTGGGATGGCATTCGGCTCGG
GGAGAGACTCCGTACCATGTCCTGTAGTGACAAAATCCTACGCTGGAACGTGCTGGGCCTGCAAGGGGC
ACTGTTGACCCACTTCCTGCAGCCCATTTATCTCAAATCTGTCACATTGGGTTACCTTTTCAGCCAAGGGC
ATCTGACCCGTGCTATTTGCTGTCGTGTGACAAGAGATGGGAGTGCATTTGAGGATGGACTACGACATCC
CTTTATTGTCAACCACCCCAAGGTTGGCAGAGTCAGCATATATGATTCCAAAAGGCAATCCGGGAAGACT
AAGGAGACAAGCGTCAACTGGTGTCTGGCTGATGGCTATGACCTGGAGATCCTGGACGGTACCAGAGGC
ACTGTGGATGGGCCACGGAATGAATTGTCCCGGGTCTCCAAAAAGAACATTTTTCTTCTATTTAAGAAGC
TCTGCTCCTTCCGTTACCCGCAGGGATCTACTGAGACTCTCCTATGGTGAGGCCAAGAAAGCTGCCCGTGA
CTACGAGACGGCCAAGAACTACTTCAAAAAAGGCCTGAAGGATATGGGCTATGGGAACTGGATTAGCAA
ACCCCAGGAGGAAAAGAACTTTTATCTCTGCCCAGTATAG-3'

FIG.31 pLenti-MCS-mCherry backbone SEQ ID NO: 484

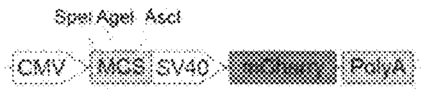

5'cgataagcttgggagttccgcgttacataacttacggtaaatggcccgcctggctgaccgcccaacgacccccgcccattgacgtcaataatgac
gtatgttcccatagtaacgccaatagggactttccattgacgtcaatgggtggagtatttacggtaaactgcccacttggcagtacatcaagtgtatcat
atgccaagtacgccccctattgacgtcaatgacggtaaatggcccgcctggcattatgcccagtacatgaccttatgggactttcctacttggcagtac
atctacgtattagtcatcgctattaccatggtgatgcggttttggcagtacatcaatgggcgtggatagcggtttgactcacggggatttccaagtctcc
accccattgacgtcaatgggagtttgttttggcaccaaaatcaacgggactttccaaaatgtcgtaacaactccgccccattgacgcaaatgggcggt
aggcgtgtacggtgggaggtctatataagcagagctcgtttagtgaaccgtcagatcgcctggagacgccatccacgctgttttgacctccatagaa
gacaccgactctagaggatccggactagtttaccggtgggggcccccggcgcgccggtgtacaccctgcaggggtttaaacccacgcgtcg
accagtggtcgaccctgtggaatgtgtgtcagttagggtgtggaaagtccccaggctccccagcaggcagaagtatgcaaagcatgcatctcaatt
agtcagcaaccaggtgtggaaagtccccaggctccccagcaggcagaagtatgcaaagcatgcatctcaattagtcagcaaccatagtcccgccc
ctaactccgcccatcccgcccctaactccgcccagttccgcccattctccgccccatggctgactaattttttttatttatgcagaggccgaggccgcct
cggcctctgagctattccagaagtagtgaggaggcttttttggaggcctaggcttttgcaaaaagctatcgctagctcgagatggtgagcaagggc
gaggaggataacatggccatcatcaaggagttcatgcgcttcaaggtgcacatggagggctccgtgaacggccacgagttcgagatcga
gggcgagggcgagggccgcccctacgagggcacccagaccgccaagctgaaggtgaccaagggtggccccctgcccttcgcctgggac
atcctgtcccctcagttcatgtacggctccaaggcctacgtgaagcaccccgccgacatccccgactacttgaagctgtccttccccgaggg
cttcaagtgggagcgcgtgatgaacttcgaggacggcggcgtggtgaccgtgacccaggactcctccctgcaggacggcgagttcatcta
caaggtgaagctgcgcggcaccaacttcccctccgacggccccgtaatgcagaagaagaccatgggctgggaggcctcctccgagcgga
tgtaccccgaggacggcgccctgaagggcgagatcaagcagaggctgaagctgaaggacggcggccactacgacgctgaggtcaaga
ccacctacaaggccaagaagcccgtgcagctgcccggcgcctacaacgtcaacatcaagttggacatcacctcccacaacgaggactac
accatcgtggaacagtacgaacgcgccgagggccgccactccaccggcggcatggacgagctgtacaagtaagctaagcacttcgtggcc
gaggagcaggactgagaattccagtcgacaatcaacctctggattacaaaatttgtgaaagattgactggtattcttaactatgttgctccttttacgctat
gtggatacgctgctttaatgcctttgtatcatgctattgcttcccgtatggctttcattttctcctccttgtataaatcctggttgctgtctctttatgaggagttg
tggcccgttgtcaggcaacgtggcgtggtgtgcactgtgtttgctgacgcaacccccactggttggggcattgccaccacctgtcagctcctttccgg
gactttcgctttccccctccctattgccacggcggaactcatcgccgcctgccttgcccgctgctggacaggggctcggctgttgggcactgacaatt
ccgtggtgttgtcggggaagctgacgtcctttccatggctgctcgcctgtgttgccacctggattctgcgcgggacgtccttctgctacgtcccttcgg
ccctcaatccagcggaccttccttcccgcggcctgctgccggctctgcggcctcttccgcgtcttcgccttcgccctcagacgagtcggatctccctt
gggccgcctccccgcctggaattcgagctcggtacctttaagaccaatgacttacaaggcagctgtagatcttagccactttttaaaagaaaagggg
ggactggaagggctaattcactcccaacgaagacaagatctgctttttgcttgtactgggtctctctggttagaccagatctgagcctgggagctctct
ggctaactagggaacccactgcttaagcctcaataaagcttgccttgagtgcttcaagtagtgtgtgcccgtctgttgtgtgactctggtaactagagat
ccctcagacccttttagtcagtgtggaaaatctctagcagtagtagttcatgtcatcttattattcagtatttataacttgcaaagaaatgaatatcagagag
tgagaggaacttgtttattgcagcttataatggttacaaataaagcaatagcatcacaaatttcacaaataaagcatttttttcactgcattct
agttgtggtttgtccaaactcatcaatgtatcttatcatgtctggctctagctatcccgccccta-3' (SEQ ID NO:342)

FIG.32 pLenti-arRNA-BFP backbone SEQ ID NO: 485

5'gagggcctatttcccatgattccttcatatttgcatatacgatacaaggctgttagagagataattagaattaatttgactgtaaaca
caaagatattagtacaaaatacgtgacgtagaaagtaataatttcttgggtagtttgcagttttaaaattatgttttaaaatggactatca
tatgcttaccgtaacttgaaagtatttcgatttcttggctttatatatcttgtggaaaggacgaaacaccgagagacgctggcttatcg
aaattaatacgactcactatagggagacccaagctggctagttaagctatcaacaagtttgtacaaaaaagctgaacgagaaacg
taaaatgatataaatatcaatatattaaattagattttgcataaaaaacagactacataatactgtaaaacacaacatatccagtcacta
tgaatcaactacttagatggtattagtgacctgtagtcgaccgacagccttccaaatgttcttcgggtgatgctgccaacttagtcga
ccgacagccttccaaatgttcttctcaaacggaatcgtcgtatccagcctactcgctattgtcctcaatgccgtattaaatcataaa
agaaataagaaaaagaggtgcgagcctcttttttgtgtgacaaaataaaaacatctacctattcatatacgctagtgtcatagtcctg
aaaatcatctgcatcaagaacaatttcacaactcttatacttttctcttacaagtcgttcggcttcatctggattttcagcctctatactta
ctaaacgtgataaagtttctgtaatttctactgtatcgacctgcagactggctgtgtataagggagcctgacatttatattccccaga
acatcaggttaatggcgtttttgatgtcattttcgcggtggctgagatcagccacttcttccccgataacggagaccggcac
actggccatatcggtggtcatcatgcgccagctttcatccccgatatgcaccaccgggtaaagttcacgggagactttatc
tgacagcagacgtgcactggccagggggatcaccatccgtcgcccgggcgtgtcaataatatcactctgtacatccaca
aacagacgataacggctctctcttttataggtgtaaaccttaaactgcattcaccagcccctgttctcgtcagcaaaagagc
cgttcatttcaataaaccgggcgacctcagccatcccttcctgattttccgcttccagcgttcggcacgcagacgacgggcttcat
tctgcatggttgtgcttaccagaccggagatattgacatcatatatgccttgagcaactgatagctgtcgctgtcaactgtcactgta
atacgctgcttcatagcatacctctttttgacatacttcgggtatacatatcagtatatattcttataccgcaaaaatcagcgcgcaaat
acgcatactgttatctggcttttagtaagccggatccacgcggcgtttacgccccgccctgccactcatcgcagtactgttgtaattca
ttaagcattctgccgacatggaagccatcacaaacggcatgatgaacctgaatcgccagcggcatcagcaccttgtcgccttgc
gtataatatttgcccatggtgaaaacgggggcgaagaagttgtccatattggccacgtttaaatcaaaactggtgaaactcaccca
gggattggctgagacgaaaaacatattctcaataaaccctttagggaaataggccaggttttcaccgtaacacgccacatcttgcg
aatatatgtgtagaaactgccggaaatcgtcgtggtattcactccagagcgatgaaaacgtttcagtttgctcatggaaaacggtgt
aacaagggtgaacactatcccatatcaccagctcaccgtctttcattgccatacggaattccggatgagcattcatcaggcgggc
aagaatgtgaataaaggccggataaaacttgtgcttatttttctttacggtctttaaaaaggccgtaatatccagctgaacggtctggt
tataggtacattgagcaactgactgaaatgcctcaaaatgttctttacgatgccattgggatatatcaacggtggtatatccagtgatt
tttttctccattttagcttccttagctcctgaaaatctcgataactcaaaaaatacgcccggtagtgatcttatttcattatggtgaaagtt
ggaacctcttacgtgccgatcaacgtctcattttcgccaaaagttggcccagggcttcccggtatcaacagggacaccaggattta
tttattctgcgaagtgatcttccgtcacaggtatttattcggcgcaaagtgcgtcgggtgatgctgccaacttagtcgactacaggtc
actaataccatctaagtagttgattcatagtgactggatatgttgtgttttacagtattatgtagtctgttttttatgcaaaatctaatttaat
atattgatatttatatcattttacgtttctcgttcagctttcttgtacaaagtggttgatctagagggcccgcggttcgaacgtctcttgat
catatggcgcgcccctcgaggtcgacggtatcgataagctcgcttcacgagattccagcaggtcgagggacctaataacttcgtat
agcatacattatacgaagttatattaagggttccaagcttaagcggccgcgtggataaccgtattaccgccatgcattagttattaat
agtaatcaattacggggtcattagttcatagcccatatatggagttccgcgttacataacttacggtaaatggcccgcctggctgac
cgcccaacgacccccgcccattgacgtcaataatgacgtatgttcccatagtaacgccaatagggactttccattgacgtcaatgg
gtggagtatttacggtaaactgcccacttggcagtacatcaagtgtatcatatgccaagtacgccccctattgacgtcaatgacggt
aaatggcccgcctggcattatgcccagtacatgaccttatgggactttcctacttggcagtacatctacgtattagtcatcgctattac
catggtgatgcggttttggcagtacatcaatgggcgtggatagcggtttgactcacggggatttccaagtctccaccccattgacg
tcaatgggagtttgttttggcaccaaaatcaacgggactttccaaaatgtcgtaacaactccgccccattgacgcaaatgggcggt
aggcgtgtacggtgggaggtctatataagcagagctggtttagtgaaccgtcagatccgctagcgccaccatgagcgagctga
ttaaggagaacatgcacatgaagctgtacatggagggcaccgtggacaaccatcacttcaagtgcacatccgagggcg
aaggcaagccctacgagggcacccagaccatgagaatcaaggtggtcgagggcggccctctccccttcgccttcgacat
cctggctactagcttcctctacggcagcaagaccttcatcaaccacacccagggcatccccgacttcttcaagcagtcctt
ccctgagggcttcacatgggagagagtcaccacatacgaagacgggggcgtgctgaccgctacccaggacaccagcct
ccaggacggctgcctcatctacaacgtcaagatcagaggggtgaacttcacatccaacggccctgtgatgcagaagaa
aacactcggctgggaggccttcaccgagactctgtaccccgctgacggcggcctggaaggcagaaacgacatggccct
gaagctcgtgggcgggagccatctgatcgcaaacatcaagaccacatatagatccaagaaacccgctaagaacctcaa
gatgcctggcgtctactatgtggactacagactggaaagaatcaaggaggccaacaacgagacctacgtcgagcagca
cgaggtggcagtggccagatactgcgacctccctagcaaactggggcacaaactcaattaa-3'

FIG.33

SEQ ID NO: 486

SEQ ID NO: 487

METHODS AND COMPOSITIONS FOR EDITING RNAS

CROSS REFERENCE TO RELATED APPLICATIONS

This application is a continuation application of International Application No. PCT/CN2020/084922, filed internationally on Apr. 15, 2020, which claims the priority benefits of International Application No. PCT/CN2019/082713 filed on Apr. 15, 2019, and International Application No. PCT/CN2019/129952 filed on Dec. 30, 2019, the contents of each of which are incorporated herein by reference in their entirety.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 792642001101SUB2SEQLIST.TXT, date recorded: Apr. 26, 2022, size: 166,170 bytes).

FIELD OF THE INVENTION

The present invention is related to methods and compositions for editing RNAs using an engineered RNA capable of recruiting an adenosine deaminase to deaminate one or more adenosines in target RNAs.

BACKGROUND OF THE INVENTION

Genome editing is a powerful tool for biomedical research and development of therapeutics for diseases. So far, the most popular genome editing technology is the Clustered Regularly Interspaced Short Palindromic Repeats (CRISPR)-Cas system, which was developed from the adaptive immune system of bacteria and archaea. CRISPR-Cas can precisely target and cleave genome DNA, generating Double-Strand DNA Break (DSB). DSB canbe repaired through non-homologous end joining (NHEJ) pathways, and often resulting in an insertion or deletion (Indel), which, in most cases, inactivates the gene. Alternatively, the homology-directed repair (HDR) pathway can repair the DSB using homologous templates dsDNA or ssDNA, and thus, achieve precise genome editing.

Recently, taking advantage of the deaminase proteins, such as Adenosine Deaminase Acting on RNA (ADAR), novel tools were developed for RNA editing. In mammalian cells, there are three types of ADAR proteins, ADAR1 (two isoforms, p110 and p150), ADAR2 and ADAR3 (catalytically inactive). The catalytic substrate of ADAR protein is double-stranded RNA.ADAR removes the —$NH_2$ group from an adenosine (A), converting A to inosine (I), which is recognized as guanosine (G) and paired with cytidine (C) during subsequent cellular transcription and translation processes. Researchers fused λN peptide to human ADAR1 or ADAR2 deaminase domain to construct the λN-ADARDD system, which could be guided to bind specific RNA targets by a fusion RNA consisting of BoxB stem loop and antisense RNA. This method converts target A to I by introducing an A-C mismatch at the target A base, resulting in an A to G RNA base editing. Other methods for RNA editing include fusing antisense RNA to R/G motif (ADAR-recruiting RNA scaffold) to edit target RNA by overexpressing ADAR1 or ADAR2 protein in mammalian cells, and using dCas13-ADAR to precisely target and edit RNA. In the application, PCT/EP2017/071912, a method of RNA editing was disclosed which does not require exogenous proteins or recruiting domain on nucleic acids. A synthesized RNA comprising a complementary sequence to the target RNA was used to induce an A to G base editing. The RNA used in the method is short (less than 54 nt) and must be specifically modified to increase the editing efficiency.

SUMMARY OF THE INVENTION

Nucleic acid editing carries enormous potential for biological research and the development of therapeutics. Most of the current tools for DNA or RNA editing rely on introducing exogenous proteins into living organisms, which is subject to potential risks or technical barriers due to possible aberrant effector activity, delivery limits and immunogenicity. Some other tools require complicated chemical modifications, however still resulting in a low editing efficiency. In some aspects, the present application provides a programmable approach that employs a short RNA to leverage a deaminase for targeted RNA editing, in some embodiments, the deaminase is an ADAR (Adenosine Deaminase Acting on RNA) protein, in some embodiments, the ADAR is an endogenous ADAR protein. In some aspects, the present application provides an engineered RNA that is partially complementary to the target transcript to recruit ADAR1 or ADAR2 to convert adenosine to inosine at a specific site in a target RNA. The methods described herein are collectively referred to as "LEAPER" (Leveraging Endogenous ADAR for Programmable Editing on RNA) and the ADAR-recruiting RNAs are referred to interchangeably as "dRNA" or "arRNA".

In one aspect, the present application provides a method for editing on a target RNA in a host cell, comprising introducing a deaminase-recruiting RNA (dRNA) or a construct encoding the deaminase-recruiting RNA into the host cell, wherein the dRNA comprises a complementary RNA sequence that hybridizes to the target RNA, and wherein the dRNA is capable of recruiting an deaminase to deaminate a target nucleotide, in some embodiments, an adenosine deaminase acting on RNA (ADAR) to deaminate a target adenosine (A) in the target RNA. In certain embodiments, the host cell is a eukaryotic cell. In some embodiments, the host cell is a mammalian cell. In some embodiments, the host cell is a human cell. In some embodiments, the host cell is a murine cell. In some embodiments, the host cell is a prokaryotic cell. In some embodiments, the host cell is a primary cell. In some embodiments, the host cell is a T cell.

In certain embodiments, the ADAR is naturally or endogenously present in the host cell, for example, naturally or endogenously present in the eukaryotic cell. In some embodiments, the ADAR is endogenously expressed by the host cell. In certain embodiments, the ADAR is exogenous to the host cell. In some embodiments, the ADAR is encoded by a nucleic acid (e.g., DNA or RNA). In some embodiments, the method comprises introducing the ADAR or a construct encoding the ADAR into the host cell. In some embodiments, the method does not comprise introducing any protein into the host cell. In certain embodiments, the ADAR is ADAR1 and/or ADAR 2. In some embodiments, the ADAR is one or more ADARs selected from the group consisting of hADAR1, hADAR2, murine ADAR1 and murine ADAR2.

In certain embodiments, the dRNA is not recognized by a Cas (CRISPR-associated protein). In some embodiments, the dRNA does not comprise crRNA, tracrRNA or gRNA used in a CRISPR/Cas system. In some embodiments, the method does not comprise introducing a Cas or Cas fusion protein into the host cell.

In certain embodiments, the deamination of the target A in the target RNA results in a missense mutation, an early stop codon, aberrant splicing, or alternative splicing in the target RNA. In some embodiments, the target RNA encodes a protein, and the deamination of the target A in the target RNA results in a point mutation, truncation, elongation and/or misfolding of the protein. In some embodiments, the deamination of the target A in the target RNA results in reversal of a missense mutation, an early stop codon, aberrant splicing, or alternative splicing in the target RNA. In some embodiments, wherein the target RNA encodes a truncated, elongated, mutated, or misfolded protein, the deamination of the target A in the target RNA results in a functional, full-length, correctly-folded and/or wild-type protein by reversal of a missense mutation, an early stop codon, aberrant splicing, or alternative splicing in the target RNA. In some embodiments, the target RNA is a regulatory RNA, and the deamination of the target A results in change in the expression of a downstream molecule regulated by the target RNA. In certain embodiments, the method is for leveraging an endogenous adenosine deaminase for editing on a target RNA to generate point mutation and/or misfolding of the protein encoded by the target RNA, and/or generating an early stop codon, an aberrant splice site, and/or an alternative splice site in the target RNA.

In certain embodiments, there is provided a method for editing a plurality of target RNAs in host cells, wherein the method comprises introducing a plurality of dRNAs or constructs encoding the a plurality of dRNAs into the host cells, wherein each of the plurality of deaminase-recruiting RNAs comprises a complementary RNA sequence that hybridizes to a corresponding target RNA in the plurality of target RNAs, and wherein each dRNA is capable of recruiting an adenosine deaminase acting on RNA (ADAR) to deaminate a target adenosine (A) in the corresponding target RNA.

In some embodiments, there is provided an edited RNA or a host cell having an edited RNA produced by any one of the methods of RNA editing as described above.

In one aspect, the present application provides a method for treating or preventing a disease or condition in an individual, comprising editing a target RNA associated with the disease or condition in a cell of the individual according to any one of the methods for RNA editing as described above. In some embodiments, the method comprises editing the target RNA in the cell ex vivo. In some embodiments, the method comprises administering the edited cell to the individual. In some embodiments, the method comprises administering to the individual an effective amount of the dRNA or construct encoding or comprising the dRNA. In some embodiments, the method further comprises introducing to the cell the ADAR or a construct (e.g., viral vector) encoding the ADAR. In some embodiments, the method further comprises administering to the individual the ADAR or a construct (e.g., viral vector) encoding the ADAR. In some embodiments, the disease or condition is a hereditary genetic disease. In some embodiments, the disease or condition is associated with one or more acquired genetic mutations, e.g., drug resistance.

One aspect of the present application provides a dRNA, comprising a complementary RNA sequence that hybridizes to the target RNA, for deamination of a target adenosine in a target RNA by recruiting a deaminase, in some embodiments, an Adenosine Deaminase Acting on RNA (ADAR), to deaminate a target adenosine in the target RNA.

In some embodiments according to any one of the methods or dRNAs described herein, the dRNA comprises an RNA sequence comprising a cytidine (C), adenosine (A) or uridine (U) directly opposite the target adenosine to be edited in the target RNA when binding with the target RNA. The cytidine (C), adenosine (A) and uridine (U) directly opposite the target adenosine are collectively referred to as "targeting nucleotide", or separately "targeting C", "targeting A", and "targeting U". In certain embodiments, the RNA sequence further comprises one or more guanosines each directly opposite a non-target adenosine(s) in the target RNA. In certain embodiments, the 5' nearest neighbor of the target A in the target RNA sequence is a nucleotide selected from U, C, A and G with the preference U>C≈A>G and the 3' nearest neighbor of the target A in the target RNA sequence is a nucleotide selected from G, C, A and U with the preference G>C>A≈U. In certain embodiments, the target A is in a three-base motif selected from the group consisting of UAG, UAC, UAA, UAU, CAG, CAC, CAA, CAU, AAG, AAC, AAA, AAU, GAG, GAC, GAA and GAU in the target RNA. In certain embodiments, wherein the three-base motif is UAG, the dRNA comprises an A directly opposite the U in the three-base motif, a C directly opposite the target A, and a C, G or U directly opposite the G in the three-base motif. In certain embodiments, wherein the three-base motif is UAG in the target RNA, the dRNA comprises ACC, ACG or ACU opposite the UAG of the target RNA.

In some embodiments according to any one of the methods or dRNAs described herein, the deaminase-recruiting RNA comprises more than 40, 45, 50, 55, 60, 65, 70, 75 or 80 nucleotides. In certain embodiments, the deaminase-recruiting RNA is 40-260, 45-250, 50-240, 60-230, 65-220, 70-210, 70-200, 70-190, 70-180, 70-170, 70-160, 70-150, 70-140, 70-130, 70-120, 70-110, 70-100, 70-90, 70-80, 75-200, 80-190, 85-180, 90-170, 95-160, 100-150 or 105-140 nucleotides in length. In some embodiments, the dRNA is about 60-200 (such as about any of 60-150, 65-140, 68-130, or 70-120) nucleotides long.

In some embodiments according to any one of the methods or dRNAs described herein, the dRNA described herein canbe characterized as comprising, from 5' end to 3' end: a 5' portion, a cytidine mismatch directly opposite to the target A in the target RNA, and a 3' portion. In some embodiments, the 3' portion is no shorter than about 7 nt (such as no shorter than 8 nt, no shorter than 9 nt, and no shorter than 10 nt) nucleotides. In some embodiments, the 3' portion is about 7 nt-25 nt nucleotide long (such as about 8 nt-25 nt, 9 nt-25 nt, 10 nt-25 nt, 11 nt-25 nt, 12 nt-25 nt, 13 nt-25 nt, 14 nt-25 nt, 15 nt-25 nt, 16 nt-25 nt, 17 nt-25 nt, 18 nt-25 nt, 19 nt-25 nt, 20 nt-25 nt, 21 nt-25 nt, 22 nt-25 nt, 23 nt-25 nt, 24 nt-25 nt, and for example, 10 nt-15 nt or 21 nt-25 nt nucleotides long). In some embodiments, the 5' portion is no shorter than about 25 (such as no shorter than about 30, no shorter than about 35 nt, no shorter than about 40 nt, and no shorter than about 45 nt) nucleotides. In some embodiments, the 5' portion is about 25 nt-85 nt nucleotides long (such as about 25 nt-80 nt, 25 nt-75 nt, 25 nt-70 nt, 25 nt-65 nt, 25 nt-60 nt, 30 nt-55 nt, 40 nt-55 nt, or 45 nt-55 nt nucleotides long). In some embodiments, the 5' portion is about 25 nt-85 nt nucleotides long (such as about 25 nt-80 nt, 25 nt-75 nt, 25 nt-70 nt, 25 nt-65 nt, 25 nt-60 nt, 30 nt-55 nt, 40 nt-55 nt, or 45 nt-55 nt nucleotides long), and the 3' portion is about 7 nt-25 nt nucleotide long (such as about 10 nt-15 nt or 21 nt-25 nt nucleotides long). In some embodiments, the 5' portion is longer than the 3' portion. In some embodiments, the 5' portion is about 55 nucleotides long, and the 3' portion is about 15 nucleotides long. In some embodiments, the position of the cytidine mismatch in the dRNA is according to any of the dRNAs described in the examples herein, and the dRNA can be, for example, in the format of Xnt-c-Ynt, wherein X represents the length of the 5' portion and Y represents the length of the 3' portion: 55 nt-c-35 nt, 55 nt-c-25 nt, 55 nt-c-24 nt, 55 nt-c-23 nt, 55 nt-c-22 nt, 55 nt-c-21 nt, 55 nt-c-20 nt, 55 nt-c-19 nt, 55 nt-c-18 nt, 55 nt-c-17 nt, 55 nt-c-16 nt, 55 nt-c-15 nt, 55 nt-c-14 nt, 55 nt-c-13 nt, 55 nt-c-12 nt, 55 nt-c-11 nt, 55 nt-c-10 nt, 55 nt-c-9 nt, 55 nt-c-8 nt, 55 nt-c-7 nt, 55 nt-n-20 nt, 50 nt-n-20 nt, 45 nt-n-20 nt, 55 nt-n-15 nt, 50 nt-n-15 nt, 45 nt-c-45 nt, 45 nt-c-55 nt, 54 nt-c-12 nt, 53 nt-c-13 nt, 52 nt-c-14 nt, 51 nt-c-15 nt, 50 nt-c-16 nt, 49 nt-c-17 nt, 48 nt-c-18 nt, 47 nt-c-19 nt, 46 nt-c-20 nt, 45 nt-c-21 nt, 44 nt-c-22 nt, 43 nt-c-23 nt, 54 nt- c-15 nt, 53 nt-c-16 nt, 52 nt-c-17 nt, 51 nt-c-18 nt, 50 nt-c-19 nt, 49 nt-c-20 nt, 48 nt-c-21 nt, 47 nt-c-22 nt, 46 nt-c-23 nt, 54 nt-c-17 nt, 53 nt-n-18 nt, 52 nt-n-19 nt, 51 nt-n-20 nt, 50 nt-n-21 nt, 49 nt-n-22 nt, and 48 nt-c-23.

In certain embodiments, the target RNA is an RNA selected from the group consisting of a pre-messenger RNA, a messenger RNA, a ribosomal RNA, a transfer RNA, a long non-coding RNA and a small RNA (e.g., miRNA).

In some embodiments according to any one of the methods or dRNAs described herein, the dRNA is a single-stranded RNA. In some embodiments, the complementary RNA sequence is single-stranded, and wherein the dRNA further comprises one or more double-stranded regions.

In some embodiments, the dRNA comprises one or more modifications, such as 2'-O-methylation and/or phosphorothioation. In some embodiments, the dRNA is of about 60-200 nucleotides long and comprises one or more modifications (such as 2'-O-methylation and/or phosphorothioation). In some embodiments, the dRNA comprises 2'-O-methylations in the first and last 3 nucleotides and/or phosphorothioations in the first and last 3 internucleotide linkages. In some embodiments, the dRNA comprises 2'-O-methylations in the first and last 3 nucleotides, phosphorothioations in the first and last 3 internucleotide linkages, and 2'-O-methylations in one or more uridines, for example on all uridines. In some embodiments, the dRNA comprises 2'-O-methylations in the first and last 3 nucleotides, phosphorothioations in the first and last 3 internucleotide linkages, 2'-O-methylations in a single or multiple or all uridines, and a modification in the nucleotide opposite to the target adenosine, and/or one or two nucleotides most adjacent to the nucleotide opposite to the target adenosine. In certain embodiments, the modification in the nucleotide opposite to the target adenosine, and/or one or two nucleotides most adjacent to the nucleotide opposite to the target adenosine is a 2'-O-methylation. In certain embodiments, the modification in the nucleotide opposite to the target adenosine, and/or one or two nucleotides most adjacent to the nucleotide opposite to the target adenosine is a phosphorothioate linkage, such as a 3'-phosphorothioation linkage. In certain embodiments, the dRNA comprises 2'-O-methylations in the first and last 3 nucleotides, phosphorothioations in the first and last 3 internucleotide linkages, 2'-O-methylations in all uridines, and a 2'-O-methylation in the nucleotide adjacent to the 3' terminus or 5' terminus of the nucleotide opposite to the target adenosine. In certain embodiments, the dRNA comprises 2'-O-methylations in the first and last 3 nucleotides, phosphorothioations in the first and last 3 internucleotide linkages, 2'-O-methylations in all uridines, and a 3'-phosphorothioation in the nucleotide opposite to the target adenosine and/or its 5' and/or 3' most adjacent nucleotides. In some embodiments, the dRNA comprises 2'-O-methylations in the first and last 5 nucleotides and phosphorothioations in the first and last 5 internucleotide linkages.

In certain embodiments according to any one of the methods described herein, the efficiency of editing on the target RNA is at least about 30%, such as at least about any one of 32%, 35%, 40%, 45%, 50%, 55%, 60%, 65%, 70%, 75%, 80%, 85%, 90% or higher.

In some embodiments, there is provided a construct (e.g., viral vector or plasmid) encoding any one of the dRNA described above. In some embodiments, the construct comprises a promoter operably linked to a sequence encoding the dRNA. In some embodiments, the construct is a DNA construct.

In some embodiments, there is provided a library comprising a plurality of the dRNAs according to any one of the dRNAs described above or a plurality of the constructs according to any one of the constructs described above.

Also provided are compositions, host cells, kits and articles of manufacture comprising any one of the dRNAs described herein, any one of the constructs described herein, or any one of the libraries described herein.

BRIEF DESCRIPTION OF THE DRAWINGS

FIGS. 1A and 1B show schematic representations of RNA editing with endogenous ADAR1 protein. FIG. 1C shows editing reporter mRNA with dRNA using endogenous ADAR1 protein. FIG. 1D shows statistical analysis of the results in FIG. 1B. FIG. 1E shows ADAR1 knockout and ADAR1(p110), ADAR1(p150) and ADAR2 rescue results. FIG. 1F shows statistical analysis of the results in FIG. 1D. FIG. 1G shows the effect of ADAR1(p110), ADAR1(p150) or ADAR2 overexpression on RNA editing mediated by dRNA in 293T-WT cells. FIG. 1H shows that deep sequencing (i.e., Next Generation Sequencing, NGS) results confirmed A to G editing in the targeting site.

FIG. 2A shows schematic representation of four kinds of base (A, U, C and G) identify opposite to the targeting adenosine. FIG. 2B shows effects of base identify opposite to the targeting adenosine on RNA editing efficiency by dRNA. FIG. 2C shows schematic representation of dRNA with one, two or three bases mismatched with UAG targeting site. FIG. 2D shows effects of one, two or three bases mismatched with UAG targeting site on Reporter RNA editing by dRNA. dRNA preferred A-C mismatch on the targeting adenosine. FIG. 2E shows schematic representation of dRNA with variant length. FIG. 2F shows the effect of dRNA length on RNA editing efficiency based on dual fluorescence reporter-2. FIG. 2G shows schematic representation of different A-C mismatch position. FIG. 2H shows effect of A-C mismatch position on RNA editing efficiency.

FIG. 3A shows percentage quantification of endogenous RNA editing efficiency at all 16 different 3-base motifs. FIG. 3B shows heatmap of 5' and 3' base preferences of endogenous RNA editing for 16 different 3 base motifs.

FIG. 4A shows schematic representation of KRAS mRNA target and dRNA with variant length. FIG. 4B shows editing the mRNA of endogenous KRAS gene with dRNA in 293T cells. Empty vector, dRNA-91 nt plasmids were transfected into 293T-WT cells, respectively. 60 hours later, the RNA was isolated for RT-PCR, and then cDNA was amplified and sequenced on Illumina NextSeq. FIG. 4C shows schematic representation of PPIB mRNA target (site1, site2 and site3) and the corresponding dRNA design. FIGS. 4D, 4E and 4F show editing the mRNA of endogenous PPIB gene with dRNA in 293T cells. FIG. 4G shows schematic representation of @-Actin mRNA target and dRNA (71-nt and 131-nt). FIG. 4H shows editing the mRNA of endogenous @-Actin gene with dRNA in 293T cells.

FIGS. 5A-5G show off-target analysis. FIG. 5A shows schematic representation of the sequence window in which A to I edits were analyzed for PPIB mRNA target (PPIB site 1). The black arrow indicates the targeted adenosine. FIG. 5B shows deep sequencing quantification of A to I RNA editing by 151-nt dRNA targeting PPIB mRNA target (PPIB site 1). FIG. 5C shows schematic representation of the sequence window in which A to I edits were analyzed for KRAS mRNA target. The black arrow indicates the targeted adenosine. FIG. 5D shows deep sequencing quantification of A to I RNA editing by 91-nt and 111-nt dRNA targeting KRAS mRNA target. FIG. 5E shows schematic representation of designed four kinds of 91-nt or 111-nt dRNA variants containing different A-G mismatch combinations. The A-G mismatch was designed based on the statistical results in FIG. 5D and existing knowledge on genic codes for different amino acids. FIG. 5F shows the results of targeted A56 editing by dRNA and different kinds of dRNA variants in FIG. 5E. FIG. 5G shows deep sequencing quantification of A to I RNA editing by 111-ntdRNA and four kinds of 111-nt dRNA variants targeting KRAS mRNA target.

FIGS. 6A-6H show RNA editing with single dRNA utilizing endogenous ADAR1 protein. FIG. 6A shows schematic representation of RNA editing by dLbuCas13-ADARDD fusion proteins. The catalytically inactive dLbuCas13 was fused to the RNA deaminase domains of ADAR1 or ADAR2. FIG. 6B shows schematic representation of dual fluorescence reporter mRNA target and guide RNA design. FIG. 6C shows statistical analysis of the results in FIGS. 6A and 6B. FIG. 6D shows the mRNA level of ADAR1 and ADAR2 in 293T-WT cells. FIG. 6E shows genotyping results of ADAR1 gene in 293T-ADAR1-KO cell lines by genome PCR. FIG. 6F shows the expression level of ADAR1(p110) and ADAR1(p150) in 293T-WT and 293T-ADAR1-KO cell lines via western blotting. FIG. 6G shows the effects of ADAR1(p110), ADAR1(p150) or ADAR2 overexpression on RNA editing mediated by dRNA in 293T-WT cells via FACS. FIG. 6H shows Sanger sequencing results showed A to G editing in the targeted adenosine site.

FIG. 7A shows schematic representation of dRNA with variant length and the targeted mRNA editing results by dRNA with variant length based on dual fluorescence reporter-1. FIG. 7B shows schematic representation of different A-C mismatch position and the effect of A-C mismatch position on RNA editing efficiency based on dual fluorescence reporter-1. FIG. 7C shows schematic representation of different A-C mismatch position and the effect of A-C mismatch position on RNA editing efficiency based on dual fluorescence reporter-3.

FIG. 8A shows editing the mRNA of endogenous β-Actin gene (site2) with dRNA in 293T cells. FIG. 8B shows editing the mRNA of endogenous GAPDH gene with dRNA in 293T cells.

FIG. 9A shows that reporter plasmids and dRNA plasmids were co-transfected into different cell lines, and the results showed that dRNA could function well in multiple cell lines, indicating the universality of dRNA application.

FIG. 10A, Schematic of dLbuCas13a-ADAR1$_{DD}$ (E1008Q) fusion protein and the corresponding crRNA. The catalytic inactive LbuCas13a was fused to the deaminase domain of ADAR1 (hyperactive E1008Q variant) using 3×GGGGS linker (SEQ ID NO: 488). The crRNA (crRNA$^{Cas13a}$) consisted of Lbu-crRNA scaffold and a spacer, which was complementary to the targeting RNA with an A-C mismatch as indicated. FIG. 10B, Schematic of dual fluorescent reporter system and the Lbu-crRNA with various lengths of spacers as indicated. FIG. 10C, Quantification of the EGFP positive (EGFP$^+$) cells. HEK293T cells stably expressing the Reporter-1 were transfected with indicated lengths of crRNA$^{Cas13a}$, with or without co-expression of the dLbuCas13a-ADAR1$_{DD}$ (E1008Q), followed by FACS analysis. Data are presented as the mean±s.e.m. (n=3). FIG. 10D, Representative FACS result from the experiment performed with the control (Ctrl crRNA$_{70}$) or the targeting spacer (crRNA$_{70}$).

FIG. 11A, Schematic of the Reporter-1 and the 70-nt arRNA. FIG. 11B, Representative FACS analysis of arRNA-induced EGFP expression in wild-type (HEK293T, upper) or ADAR1 knockout (HEK293T ADAR1$^{-/-}$, lower) cells stably expressing the Repoter-1. FIG. 11C, Western blot analysis showing expression levels of ADAR1 proteins in wild-type and HEK293T ADAR1$^{-/-}$ cells, as well as those in HEK293T ADAR1$^{-/-}$ cells transfected with ADAR1 isoforms (p110 and p150). FIG. 11D, Western blot analysis showing expression levels of ADAR2 proteins in wild-type and HEK293T ADAR1$^{-/-}$ cells, as well as those in HEK293T ADAR1$^{-/-}$ cells transfected with ADAR2. FIG. 11E, Quantification of the EGFP-positive (EGFP$^+$) cells. Reporter-1 and indicated ADAR-expressing constructs were co-transfected into HEK293T ADAR1$^{-/-}$ cells, along with the Ctrl RNA$_{70}$ or with the targeting arRNA$_{70}$, followed by FACS analysis. EGFP$^+$ percentages were normalized by transfection efficiency, which was determined by mCherry$^+$. Data are mean values±s.e.m. (n=4). FIG. 11F, The Electropherograms showing Sanger sequencing results in the Ctrl RNA$_{70}$ (upper) or the arRNA$_{70}$ (lower)-targeted region. FIG. 11G, Quantification of the A to I conversion rate at the targeted site by deep sequencing.

FIG. 12A, Quantitative PCR showing the mRNA levels of ADAR1 and ADAR2 in HEK293T cells. Data are presented as the mean±s.e.m. (n=3). FIG. 12B, Representative FACS results from FIG. 1*e*.

FIG. 14A, Western-blot results showing the expression levels of ADAR1, ADAR2 and ADAR3 in indicated human cell lines. 0-tubulin was used as a loading control. Data shown is the representative of three independent experiments. $ADAR1^{-/-}$/ADAR2 represents ADAR1-knockout HEK293T cells overexpressing ADAR2. FIG. 14B, Relative ADAR protein expression levels normalized by β-tubulin expression. FIG. 14C, Indicated human cells were transfected with Reporter-1, along with the 71-nt control arRNA (Ctrl $RNA_{71}$) or with the 71-nt targeting arRNA ($arRNA_{71}$) followed by FACS analysis. FIG. 14D, Indicated mouse cell lines were analyzed as described in FIG. 14C. $EGFP^+$ percentages were normalized by transfection efficiency, which was determined by $mCherry^+$. Error bars in FIGS. 14 *b*, 14C, and 14D all indicate the mean±s.e.m. (n=3); unpaired two-sided Student's t-test, *P<0.05; P<0.01; *P<0.001; ****P<0.0001; ns, not significant.

FIG. 16A, Top, schematic of the design of arRNAs with changed triplet (5'-CNA, N denotes A, U, C or G) opposite to the target UAG. Bottom, $EGFP^+$ percent showing the effects of variable bases opposite to the targeted adenosine on RNA editing efficiency. FIG. 16B, Top, the design of arRNAs with changed neighboring bases flanking the cytidine in the A-C mismatch (5'-$N^1CN^2$). Bottom, the effects of 16 different combinations of $N^1CN^2$ on RNA editing efficiency. FIG. 16C, Summary of the preference of 5' and 3' nearest neighboring sites of the cytidine in the A-C mismatch. FIG. 16D, Top, the design of arRNAs with variable length. Bottom, the effect of arRNA length on RNA editing efficiency based on Reporter-1 and Reporter-2.

FIG. 16E, Top, the design of arRNAs with variable A-C mismatch position. Bottom, the effect of A-C mismatch position on RNA editing efficiency based on Reporter 1 and Reporter-2. FIG. 16F, Top, the design of the triplet motifs in the reporter-3 with variable nearest neighboring bases surrounding the targeting adenosine (5'-$N^1AN^2$) and the opposite motif (5'-$N^2CN^1$) on the 111-nt arRNA ($arRNA_{111}$). Bottom, deep sequencing results showing the editing rate on targeted adenosine in the 5'-$N^1AN^2$ motif. FIG. 16G, Summary of the 5' and 3' base preferences of LEAPER-mediated editing at the Reporter-3. Error bars in FIGS. 16A, 16B, 16D, 16E and 16F all indicate mean values±s.e.m. (n=3).

FIG. 17A, Schematic of the targeting endogenous transcripts of four disease-related genes (PPIB, KRAS, SMAD4 and FANCC) and the corresponding arRNAs. FIG. 17B, Deep sequencing results showing the editing rate on targeted adenosine of the PPIB, KRAS, SM4D4 and FANCC transcripts by introducing indicated lengths of arRNAs. FIG. 17C, Deep sequencing results showing the editing rate on non-UAN sites of endogenous PPIB, FANCC and IDUA transcripts. FIG. 17D, Multiplex editing rate by two 111-nt arRNAs. Indicated arRNAs were transfected alone or were co-transfected into the HEK293T cells. The targeted editing at the two sites was measured from co-transfected cells. FIG. 17E, Schematic of the PPIB transcript sequence covered by the 151-nt arRNA. The black arrow indicates the targeted adenosine. All adenosines were marked in red. FIG. 17F, Heatmap of editing rate on adenosines covered by indicated lengths of arRNAs targeting the PPIB gene (marked in bold frame in blue). For the 111-nt arRNA or $arRNA_{151}$-PPIB covered region, the editing rates of A22, A30, A33, and A34 were determined by RNA-seq because of the lack of effective PCR primers for amplifying this region. Otherwise the editing rate was determined by targeted deep-sequencing analysis. FIG. 17G, Top, the design of the triplet motifs in the reporter-3 with variable nearest neighboring bases surrounding the targeting adenosine (5'-$N^1AN^2$) and the opposite motif (5'-$N^{2'}GN^{1'}$) in the 111-nt arRNA ($arRNA_{111}$). Bottom, deep sequencing results showing the editing rate. FIG. 17H, Top, the design of arRNAs with two consecutive mismatches in the 5'-$N^1GN^2$ motif opposite to the 5'-UAG or the 5'-AAG motifs. Deep sequencing results showing the editing rate by an $arRNA_{111}$ with two consecutive mismatches in the 5'-$N^1GN^2$ motif opposite to the 5'-UAG motif (bottom left) or the 5'-AAG motif (bottom right). FIG. 17I, Heatmap of the editing rate on adenosines covered by engineered $arRNA_{111}$ variants targeting the KRAS gene. Data in FIGS. 17B, 17C, 17D, 17G and 17H are presented as the mean±s.e.m. (n=3); unpaired two-sided Student's t-test, *P<0.05; P<0.01; *P<0.001; ****P<0.0001; NS, not significant. Data in (f and i) are presented as the mean (n=3).

FIG. 18A, Quantitative PCR showing the expression levels of targeted transcripts from PPIB, KRAS, SMAD4 and FANCC by the corresponding 151-nt arRNA or Control RNA in HEK293T cells. Data are presented as the mean±s.e.m. (n=3); unpaired two-sided Student's t-test, *P<0.05; P<0.01; *P<0.001; **P<0.0001; ns, not significant. FIG. 18**B, Western blot results showing the effects on protein products of targeted KRAS gene by 151-nt arRNA in HEK293T cells. β-tubulin was used as a loading control.

FIGS. 19A-19F show editing of endogenous transcripts with exemplary LEAPER methods. FIG. 19A, Schematic of the KARS transcript sequence covered by the 151-nt arRNA. The arrow indicates the targeting adenosine. All adenosines were marked in red. FIG. 19B, Heatmap of editing rate on adenosines covered by indicated arRNAs in the KARS transcript (marked in the bold frame in blue). FIG. 19C, Schematic of the SM4D4 transcript covered by the 151-nt arRNA. FIG. 19D, Heatmap of editing rate on adenosines covered by indicated arRNAs in the SM4D4 transcript. FIG. 19E, Schematic of the FANCC transcript covered by the 151-nt arRNA. FIG. 19F, Heatmap of editing rate on adenosines covered by indicated arRNAs in the FANCC transcript. For each arRNA, the region of duplex RNA is highlighted with bold frame in blue. Data (FIGS. 19B, 19D, and 19F) are presented as the mean (n=3).

FIGS. 20A and 20B, Transcriptome-wide off-targeting analysis of Ctrl $RNA_{151}$ and $arRNA_{151}$-PPIB. The on-targeting site (PPIB) is highlighted in red. The potential off-target sites identified in both Ctrl RNA and PPIB-targeting RNA groups are labeled in blue. FIG. 20C, The predicted annealing affinity between off-target sites and the corresponding Ctrl $RNA_{151}$ or $arRNA_{151}$-PPIB. The minimum free energy (ΔG) of double-stranded RNA formed by off-target sites (150-nt upstream and downstream of the editing sites) and the corresponding Ctrl $RNA_{151}$ or $arRNA_{151}$-PPIB was predicted with RNA hybrid, an online website tool. FIG. 20D, Top, schematic of the highly complementary region between $arRNA_{151}$-PPIB and the indicated potential off-target sites, which were predicted by searching homologous sequences through NCBI-BLAST. Bottom, Deep sequencing showing the editing rate on the on-target site and all predicted off-target sites of $arRNA_{151}$-PPIB. Data are presented as the mean±s.e.m. (n=3).

FIG. 21A, Schematic of the highly complementary region of $arRNA_{111}$-FANCC and the indicated potential off-target sequence, which were predicted by searching homologous sequences through NCBI-BLAST. FIG. 21B, Deep sequencing showing the editing rate on the on-target site and all predicted off-target sites of $arRNA_{111}$-FANCC. All data are presented as the mean±s.e.m. (n=3).

FIGS. 22A and 22B, Transcriptome-wide analysis of the effects of Ctrl $RNA_{151}$ (a) $arRNA_{151}$-PPIB (b) on native editing sites by transcriptome-wide RNA-sequencing. Pearson's correlation coefficient analysis was used to assess the differential RNA editing rate on native editing sites. FIGS. 22C and 22D, Differential gene expression analysis of the effects of Ctrl $RNA_{151}$ (c) $arRNA_{151}$-PPIB (d) with RNA-seq data at the transcriptome level. Pearson's correlation coefficient analysis was used to assess the differential gene expression. FIGS. 22E and 22F, Effect of arRNA transfection on innate immune response. The indicated arRNAs or the poly(I:C) were transfected into HEK293T cells. Total RNA was then analyzed using quantitative PCR to determine expression levels of IFN-β(e) and IL-6 (f). Data (e and f) are presented as the mean±s.e.m. (n=3).

FIG. 23A, Top, Schematic of the TP53 transcript sequence covered by the 111-nt arRNA containing c.158G>A clinical-relevant non-sense mutation (Trp53Ter). The black arrow indicates the targeted adenosine. All adenosines were marked in red. Bottom, the design of two optimized arRNAs targeting $TP53^{W53X}$ transcripts with A-G mismatch on $A^{46th}$ for $arRNA_{111}$-AG1, and on $A^{16th}$, $A^{46th}$, $A^{91th}$ and $A^{94th}$ together for $arRNA_{111}$-AG4 to minimize the potential off-targets on "editing-prone" motifs. FIG. 23B, Deep sequencing results showing the targeted editing on $TP53^{W53X}$ transcripts by $arRNA_{111}$, $arRNA_{111}$-AG1 and $arRNA_{111}$-AG4. FIG. 23C, Western blot showing the recovered production of full-length p53 protein from the $TP53^{W53X}$ transcripts in the HEK293T $TP53^{-/-}$ cells. FIG. 23D, Detection of the transcriptional regulatory activity of restored p53 protein using a p53-Firefly-luciferase reporter system, normalized by co-transfected *Renilla*-luciferase vector. Data (b, c and d) are presented as the mean±s.e.m. (n=3); unpaired two-sided Student's t-test, *P<0.05; P<0.01; *P<0.001; ****P<0.0001; ns, not significant.

FIG. 27A, Quantification of the EGFP-positive ($EGFP^+$) cells induced by LEAPER-mediated RNA editing. Human primary pulmonary fibroblasts and human primary bronchial epithelial cells were transfected with Reporter-1, along with the 151-nt control RNA (Ctrl $RNA_{151}$) or the 151-nt targeting arRNA ($arRNA_{151}$) followed by FACS analysis. FIGS. 27B and 27C, Deep sequencing results showing the editing rate on PPIB transcripts in human primary pulmonary fibroblasts, human primary bronchial epithelial cells (b), and human primary T cells (c). Data in a, b and Untreated group (c) are presented as the mean±s.e.m. (n=3); data of Ctrl $RNA_{151}$ and $arRNA_{151}$(c) are presented as the mean±s.e.m. (n=2).

FIGS. 28A-28D show targeted editing by lentiviral transduction of arRNA and electroporation of synthesized arRNA oligonucleotides. FIG. 28A, Quantification of the $EGFP^+$ cells. HEK293T cells stably expressing the Repoter-1 were infected with lentivirus expressing 151-nt of Ctrl RNA or the targeting arRNA. FACS analyses were performed 2 days and 8 days post infection. The ratios of $EGFP^+$ cells were normalized by lentiviral transduction efficiency ($BFP^+$ ratios). FIG. 28B, Deep sequencing results showing the editing rate on the PPIB transcripts upon lentiviral transduction of 151-nt arRNAs into HEK293T cells. FIG. 28C, Schematic of the PPIB sequence and the corresponding 111-nt targeting arRNA.*(in red) represents nucleotide with 2'-O-methylation and phosphorothioate linkage. FIG. 28D, Deep sequencing results showing the editing rate on the PPIB transcripts upon electroporation of 111-nt synthetic arRNA oligonucleotides into human primary T cells.

FIG. 29A, Top, genetic information of pathogenic mutation in patient-derived fibroblast GM06214; Medium, schematic of the IDUA mature mRNA sequence of GM06214 cells (Black) containing a homozygous TGG>TAG mutation in exon 9 of the IDUA gene (Trp402Ter), and the corresponding 111-nt targeting $arRNA_{111}$-IDUA-V1 (Blue); Bottom, schematic of the IDUA pre-mRNA sequence of GM06214 cells (Black) and the corresponding 111-nt targeting $arRNA_{111}$-IDUA-V2 (Blue).*(in red) represents nucleotides with 2'-O-methylation and phosphorothioate linkage. FIG. 29B, Measuring the catalytic activity of α-L-iduronidase with 4-methylumbelliferyl α-L-iduronidase substrate at different time points. Data are presented as the mean±s.e.m. (n=2). FIG. 29C, Deep sequencing results showing the targeted editing rate on IDUA transcripts in GM06214 cells, 48 hours post electroporation. FIG. 29D, Top, schematic of the IDUA transcript sequence covered by the 111-nt arRNAs. The arrow indicates the targeted adenosine. All adenosines were marked in red. Bottom, a heatmap of editing rate on adenosines covered by indicated arRNAs in the IDUA transcript (marked in the bold frame in blue). e, Quantitative PCR showing the expressions of type I interferon, interferon-stimulated genes, and pro-inflammatory genes upon arRNA or poly(I:C) electroporation. Data are presented as the mean (n=3).

FIGS. 30A-30C show three versions of dual fluorescence reporters (Reporter-1, -2 and -3), mCherry and EGFP. FIG. 30A, structure of Reporter-1, FIG. 30B, structure of Reporter-2, and FIG. 30C, structure of Reporter-3.

FIG. 31 shows the structure of the pLenti-dCas13-ADAR1DD.

FIG. 32 shows the structure of the pLenti-MCS-mCherry backbone.

FIG. 33 shows the structure of the pLenti-arRNA-BFP backbone.

FIG. 37A shows the construction of IDUA-reporter. FIG. 37B shows the editing efficiency of dRNAs of different lengths (symmetric truncations) in 293T-IDUA-Reporter cells using electroporation (293T cells with IDUA-reporter).

In FIG. 40A, bases on the 3' terminus of the dRNAs were reduced one by one from 55-c-25 to 55-c-10. In FIG. 40B, bases on the 3' terminus of the dRNA were reduced one by one from 55-c-16 to 55-c-5.

FIG. 43A shows the editing efficiency using enzyme activities. FIG. 43B show the editing efficiency using the A to G rate.

FIG. 45A shows the construction of USH2A construction. FIG. 45B shows the editing efficiency of dRNAs with 3' and 5' termini of equal length. FIG. 45C shows the editing efficiency of dRNAs with 3' and 5' termini of different lengths. FIG. 45D shows the relatively low editing efficiency of dRNAs of less than 60 nucleotides.

DETAILED DESCRIPTION OF THE INVENTION

Figure 1A:
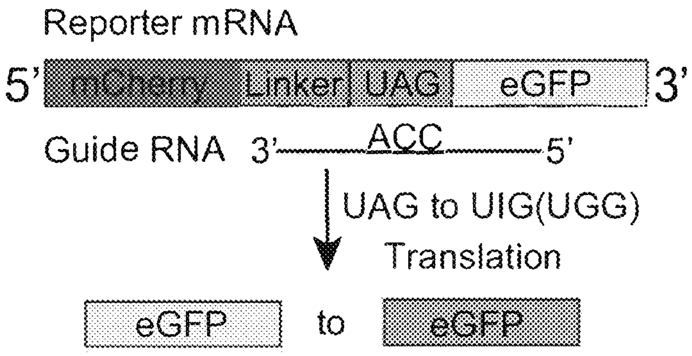
FIGS. 1A-1H show RNA editing with single dRNA utilizing endogenous ADAR1 protein.
Figure 1B:
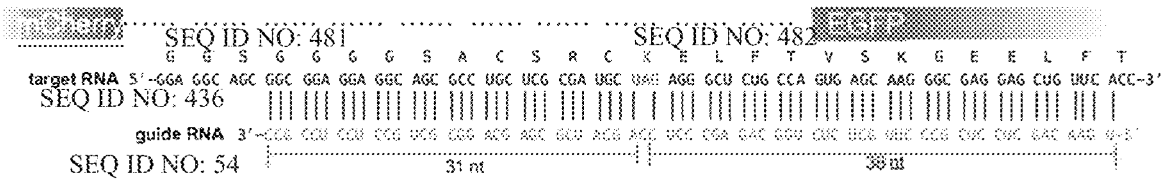
Figure 1C:
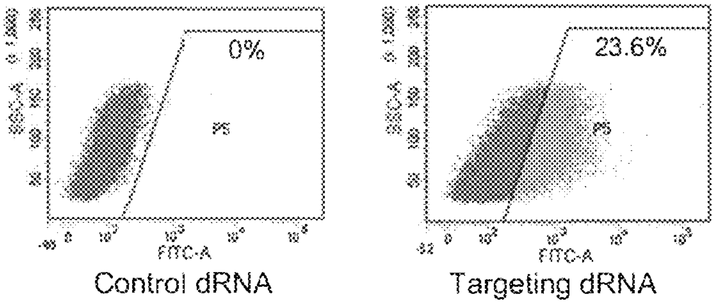
Figure 1D:
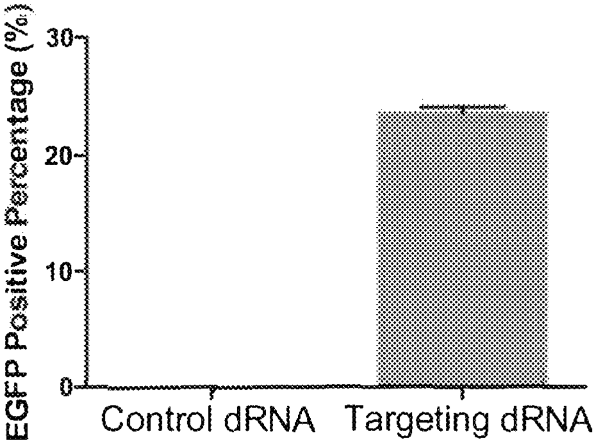

The present application provides RNA editing methods (referred herein as "LEAPER" methods) and specially designed RNAs, referred herein as deaminase-recruiting RNAs ("dRNAs") or ADAR-recruiting RNAs ("arRNAs"), to edit target RNAs in a host cell. Without being bound by any theory or hypothesis, the dRNA acts through hybridizing to its target RNA in a sequence-specific fashion to form a double-stranded RNA, which recruits an Adenosine Deaminase Acting on RNA (ADAR) to deaminate a target adenosine in the target RNA. As such, efficient RNA editing can be achieved in some embodiments without ectopic or overexpression of the ADAR proteins in the host cell. Also provided are methods and compositions for treating or preventing a disease or condition in an individual using the RNA editing methods.

The RNA editing methods described herein do not use fusion proteins comprising an ADAR and a protein that specifically binds to a guide nucleic acid, such as Cas. The deaminase-recruiting RNAs ("dRNA") described herein do not comprise crRNA, tracrRNA or gRNA used in the CRISPR/Cas system. In some embodiments, the dRNA does not comprise an ADAR-recruiting domain, or chemical modification(s). In some embodiments, the arRNA can be expressed from a plasmid or a viral vector, or synthesized as an oligonucleotide, which could achieve desirable editing efficiency. Without being bound by any theory or underlying mechanism, it was discovered that certain dRNA with specific length, location of the mismatch, and/or modification pattern demonstrate higher efficiency in RNA editing. The present application thus further provides improved RNA editing methods over those previously reported.

The LEAPER methods described herein have manageable off-target rates on the targeted transcripts and rare global off-targets. Inventors have used the LEAPER method to restore p53 function by repairing a specific cancer-relevant point mutation. The LEAPER methods described herein can also be applied to a broad spectrum of cell types including multiple human primary cells, and can be used to restore the α-L-iduronidase catalytic activity in Hurler syndrome patient-derived primary fibroblasts without evoking innate immune responses. In some embodiments, the LEAPER method involves a single molecule (i.e., dRNA) system. The LEAPER methods described herein enable precise and efficient RNA editing, which offers transformative potential for basic research and therapeutics.

Definitions

The present invention will be described with respect to particular embodiments and with reference to certain drawings but the invention is not limited thereto but only by the claims. Any reference signs in the claims shall not be construed as limiting the scope. Where the term "comprising" is used in the present description and claims, it does not exclude other elements or steps. Where an indefinite or definite article is used when referring to a singular noun e.g. "a" or "an", "the", this includes a plural of that noun unless something else is specifically stated. For the recitation of numeric ranges of nucleotides herein, each intervening number there between, is explicitly contemplated. For example, for the range of 40-260 nucleotides, any integer of nucleotides between 40 and 260 nucleotides is contemplated in addition to the numbers of 40 nucleotides and 260 nucleotides.

The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 2nd ed., Cold Spring Harbor Press, Plainsview, N.Y. (1989); and Ausubel et al., Current Protocols in Molecular Biology (Supplement 47), John Wiley & Sons, New York (1999), for definitions and terms of the art. The definitions provided herein should not be construed to have a scope less than understood by a person of ordinary skill in the art.

The terms "deaminase-recruiting RNA," "dRNA," "ADAR-recruiting RNA" and "arRNA" are used herein interchangeably to refer to an engineered RNA capable of recruiting an ADAR to deaminate a target adenosine in an RNA.

The terms "polynucleotide", "nucleotide sequence" and "nucleic acid" are used interchangeably. They refer to a polymeric form of nucleotides of any length, either deoxyribonucleotides or ribonucleotides, or analogs thereof. Two nucleotides are linked by a phosphodiester bond, and multiple nucleotides are linked by phosphodiester bonds to form polynucleotide or nucleic acid. The linkage between nucleotides can be phosphorothioated, called "phosphorothioate linkage" or "phosphorothioation linkage".

The terms "adenine", "guanine", "cytosine", "thymine", "uracil" and "hypoxanthine" as used herein refer to the nucleobases as such. The terms "adenosine", "guanosine", "cytidine", "thymidine", "uridine" and "inosine", refer to the nucleobases linked to the ribose or deoxyribose sugar moiety. The term "nucleoside" refers to the nucleobase linked to the ribose or deoxyribose. The term "nucleotide" refers to the respective nucleobase-ribosyl-phosphate or nucleobase-deoxyribosyl-phosphate. Sometimes the terms adenosine and adenine (with the abbreviation, "A"), guanosine and guanine (with the abbreviation, "G"), cytosine and cytidine (with the abbreviation, "C"), uracil and uridine (with the abbreviation, "U"), thymine and thymidine (with the abbreviation, "T"), inosine and hypo-xanthine (with the abbreviation, "I"), are used interchangeably to refer to the corresponding nucleobase, nucleoside or nucleotide. Sometimes the terms nucleobase, nucleoside and nucleotide are used interchangeably, unless the context clearly requires differently.

In the context of the present application, "target RNA" refers to an RNA sequence to which a deaminase-recruiting RNA sequence is designed to have perfect complementarity or substantial complementarity, and hybridization between the target sequence and the dRNA forms a double stranded RNA (dsRNA) region containing a target adenosine, which recruits an adenosine deaminase acting on RNA (ADAR) that deaminates the target adenosine. In some embodiments, the ADAR is naturally present in a host cell, such as a eukaryotic cell (preferably, a mammalian cell, more preferably, a human cell). In some embodiments, the ADAR is introduced into the host cell.

As used herein, "complementarity" refers to the ability of a nucleic acid to form hydrogen bond(s) with another nucleic acid by traditional Watson-Crick base-pairing. A percent complementarity indicates the percentage of residues in a nucleic acid molecule which can form hydrogen bonds (i.e., Watson-Crick base pairing) with a second nucleic acid (e.g., about 5, 6, 7, 8, 9, 10 out of 10, being about 50%, 60%, 70%, 80%, 90%, and 100% complementary respectively). "Perfectly complementary" means that all the contiguous residues of a nucleic acid sequence form hydrogen bonds with the same number of contiguous residues in a second nucleic acid sequence. "Substantially complementary" as used herein refers to a degree of complementarity that is at least about any one of 70%, 75%, 80%, 85%, 90%, 95%, 97%, 98%, 99%, or 100% over a region of about 40, 50, 60, 70, 80, 100, 150, 200, 250 or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. A sequence capable of hybridizing with a given sequence is referred to as the "complement" of the given sequence.

As used herein, the terms "cell", "cell line", and "cell culture" are used interchangeably and all such designations include progeny. It is understood that all progeny may not be precisely identical in DNA content, due to deliberate or inadvertent mutations. Variant progeny that have the same function or biological activity as the original cells are included.

Methods of RNA Editing

In this invention, the dRNA used herein comprises an RNA sequence comprising a cytidine (C), adenosine (A) or uridine (U) directly opposite the target adenosine to be edited in the target RNA when binding with the target RNA. The cytidine (C), adenosine (A) and uridine (U) directly opposite the target adenosine are collectively referred to as "targeting nucleotide", or separately "targeting C", "targeting A", and "targeting U". The targeting nucleotide and the two nucleotides directly adjacent to targeting nucleotide forms a triplet which is herein referred to as "targeting triplet".

In some embodiments, there is provided a method for editing a target RNA in a host cell (e.g., eukaryotic cell), comprising introducing a deaminase-recruiting RNA (dRNA) or a construct encoding the dRNA into the host cell, wherein the dRNA comprises a complementary RNA sequence that hybridizes to the target RNA, and wherein the dRNA is capable of recruiting an adenosine deaminase acting on RNA (ADAR) to deaminate a target adenosine (A) in the target RNA.

In some embodiments, there is provided a method for editing a target RNA in a host cell (e.g., eukaryotic cell), comprising introducing a dRNA or a construct encoding the dRNA into the host cell, wherein the dRNA comprises a complementary RNA sequence that hybridizes to the target RNA, and wherein the dRNA recruits an endogenously expressed ADAR of the host cell to deaminate a target A in the target RNA. In some embodiments, the method does not comprise introducing any protein or construct encoding a protein (e.g., Cas, ADAR or a fusion protein of ADAR and Cas) to the host cell.

In some embodiments, there is provided a method for editing a target RNA in a host cell (e.g., eukaryotic cell), comprising introducing: (a) a dRNA or a construct encoding the dRNA, and (b) an ADAR or a construct encoding the ADAR into the host cell, wherein the dRNA comprises a complementary RNA sequence that hybridizes to the target RNA, and wherein the dRNA recruits the ADAR to deaminate a target A in the target RNA. In some embodiments, the ADAR is an endogenously encoded ADAR of the host cell, wherein introduction of the ADAR comprises over-expressing the ADAR in the host cell. In some embodiments, the ADAR is exogenous to the host cell. In some embodiments, the construct encoding the ADAR is a vector, such as a plasmid, or a viral vector (e.g., a lentiviral vector).

In some embodiments, there is provided a method for editing a plurality (e.g., at least about 2, 3, 4, 5, 10, 20, 50, 100 or more) of target RNAs in host cells (e.g., eukaryotic cells), comprising introducing a plurality of dRNAs or constructs encoding the plurality of dRNAs into the host cell, wherein each dRNA comprises a complementary RNA sequence that hybridizes to a corresponding target RNA in the plurality of target RNAs, and wherein each dRNA is capable of recruiting an ADAR to deaminate a target A in the corresponding target RNA.

In some embodiments, there is provided a method for editing a plurality (e.g., at least about 2, 3, 4, 5, 10, 20, 50, 100 or more) of target RNAs in host cells (e.g., eukaryotic cells), comprising introducing a plurality of dRNAs or constructs encoding the plurality of dRNAs into the host cell, wherein each dRNA comprises a complementary RNA sequence that hybridizes to a corresponding target RNA in the plurality of target RNAs, and wherein each dRNA recruits an endogenously expressed ADAR to deaminate a target A in the corresponding target RNA.

In some embodiments, there is provided a method for editing a plurality (e.g., at least about 2, 3, 4, 5, 10, 20, 50, 100, 1000 or more) of target RNAs in host cells (e.g., eukaryotic cells), comprising introducing: (a) a plurality of dRNAs or constructs encoding the plurality of dRNAs, and (b) an ADAR or a construct encoding ADAR into the host cells, wherein each dRNA comprises a complementary RNA sequence that hybridizes to a corresponding target RNA in the plurality of target RNAs, and wherein each dRNA recruits the ADAR to deaminate a target A in the corresponding target RNA.

In one aspect, the present application provides a method for editing a plurality of RNAs in host cells by introducing a plurality of the deaminase-recruiting RNAs, one or more constructs encoding the deaminase-recruiting RNAs, or a library described herein, into the host cells.

In certain embodiments, the method for editing on a target RNA comprises introducing multiple deaminase-recruiting RNAs or one or more constructs comprising the multiple deaminase-recruiting RNAs into host cells to recruit adenosine deaminase acting on RNA (ADAR) to perform deamination reaction on one or more target adenosines in one or more target RNAs, wherein each deaminase-recruiting RNA comprises a RNA sequences complementary to a corresponding target RNA.

In one aspect, the present application provides a method for generating one or more modifications in a target RNA and/or the protein encoded by a target RNA in a host cell (e.g., eukaryotic cell), comprising introducing a dRNA or a construct encoding the dRNA into the host cell, wherein the dRNA comprises a complementary RNA sequence that hybridizes to the target RNA, and wherein the one or more modifications are selected from the group consisting of a point mutation of the protein encoded by the target RNA, misfolding of the protein encoded by the target RNA, an early stop codon in the target RNA, an aberrant splice site in the target RNA, and an alternative splice site in the target RNA.

In certain embodiments, the method for generating one or more modifications in a target RNA and/or the protein encoded by a target RNA in host cells (e.g., eukaryotic cells), comprises introducing a plurality of deaminase-recruiting RNAs or constructs encoding the plurality of deaminase-recruiting RNAs into the host cells, wherein each dRNA comprises a complementary RNA sequence that hybridizes to a corresponding target RNA in the plurality of target RNAs, and wherein each dRNA is capable of recruiting an ADAR to deaminate a target A in the corresponding target RNA.

In one aspect, the present application provides use of a deaminase-recruiting RNA according to any one of the dRNAs described herein for editing a target RNA in a host cell. In certain embodiments, the deaminase-recruiting RNA comprises a complementary RNA sequence that hybridizes to the target RNA to be edited.

In one aspect, the present application provides use of a deaminase-recruiting RNA according to any one of the dRNAs described herein for generating one or more modifications on a target RNA and/or the protein encoded by a target RNA, wherein the one or more modifications are selected from a group consisting of a point mutation of the protein encoded by the target RNA, misfolding of the protein encoded by the target RNA, an early stop codon in the target RNA, an aberrant splice site in the target RNA, and an alternative splice site in the target RNA. In certain embodiments, the deaminase-recruiting RNA comprises a complementary RNA sequence that hybridizes to the target RNA to be edited.

The invention also relates to a method for leveraging an endogenous adenosine deaminase for editing a target RNA in a eukaryotic cell, comprising introducing a dRNA or a construct encoding the dRNA, as described herein, into the eukaryotic cell to recruit naturally endogenous adenosine deaminase acting on RNA (ADAR) to perform deamination reaction on a target adenosine in the target RNA sequence.

In certain embodiments according to any one of the methods or use described herein, the dRNA comprises at least about any one of 40, 45, 50, 55, 60, 65, 70, 75, 80, 90, 100, 110, 120, 130, 140, 150, 160, 170, 180, 190, 200, 210, 220, 230, 240, or 250 nucleotides. In certain embodiments, the dRNA is about any one of 40-260, 45-250, 50-240, 60-230, 65-220, 70-220, 70-210, 70-200, 70-190, 70-180, 70-170, 70-160, 70-150, 70-140, 70-130, 70-120, 70-110, 70-100, 70-90, 70-80, 75-200, 80-190, 85-180, 90-170, 95-160, 100-200, 100-150, 100-175, 110-200, 110-175, 110-150, or 105-140 nucleotides in length. In some embodiments the dRNA is about 60-200, such as about any of 60-150, 65-140, 68-130, or 70-120) nucleotides long. In some embodiments, the dRNA is about 71 nucleotides long. In some embodiments, the dRNA is about 111 nucleotides long.

In certain embodiments according to any one of the methods or use described herein, the dRNA does not comprise an ADAR-recruiting domain. "ADAR-recruiting domain" can be a nucleotide sequence or structure that binds at high affinity to ADAR, or a nucleotide sequence that binds to a binding partner fused to ADAR in an engineered ADAR construct. Exemplary ADAR-recruiting domains include, but are not limited to, GluR-2, GluR-B (R/G), GluR-B (Q/R), GluR-6 (R/G), 5HT2C, and FlnA (Q/R) domain; see, for example, Wahlstedt, Helene, and Marie, "Site-selective versus promiscuous A-to-I editing." Wiley Interdisciplinary Reviews: RNA 2.6 (2011): 761-771, which is incorporated hereinby reference in its entirety. In some embodiments, the dRNA does not comprise a double-stranded portion. In some embodiments, the dRNA does not comprise a hairpin, such as MS2 stem loop. In some embodiments, the dRNA is single stranded. In some embodiments, the dRNA does not comprise a DSB-binding domain. In some embodiments, the dRNA consists of (or consists essentially of) the complementary RNA sequence.

In certain embodiments according to any one of the methods or use described herein, the dRNA does not comprise chemical modifications. In some embodiments, the dRNA does not comprise a chemically modified nucleotide, such as 2'-O-methyl nucleotide or a nucleotide having a phosphorothioate linkage. In some embodiments, the dRNA comprises 2'-O-methylation and phosphorothioate linkage only at the first three and last three residues. In some embodiments, the dRNA is not an antisense oligonucleotide (ASO).

In certain embodiments according to any one of the methods or use described herein, the host cell is a prokaryotic cell. In some embodiments, the host cell is a eukaryotic cell. Preferably, the host cell is a mammalian cell. Most preferably, the host cell is a human cell. In some embodiments, the host cell is a murine cell. In some embodiments, the host cell is a plant cell or a fungal cell.

In some embodiments according to any one of the methods or use described herein, the host cell is a cell line, such as HEK293T, HT29, A549, HepG2, RD, SF268, SW13 and HeLa cell. In some embodiments, the host cell is a primary cell, such as fibroblast, epithelial, or immune cell. In some embodiments, the host cell is a T cell. In some embodiments, the host cell is a post-mitosis cell. In some embodiments, the host cell is a cell of the central nervous system (CNS), such as a brain cell, e.g., a cerebellum cell.

In some embodiments, there is provided a method of editing a target RNA in a primary host cell (e.g., T cell or a CNS cell) comprising introducing a dRNA or a construct encoding the dRNA into the host cell, wherein the dRNA comprises a complementary RNA sequence that hybridizes to the target RNA, and wherein the dRNA recruits an endogenously expressed ADAR of the host cell to deaminate a target A in the target RNA.

In certain embodiments according to any one of the methods or use described herein, the ADAR is endogenous to the host cell. In some embodiments, the adenosine deaminase acting on RNA (ADAR) is naturally or endogenously present in the host cell, for example, naturally or endogenously present in the eukaryotic cell. In some embodiments, the ADAR is endogenously expressed by the host cell. In certain embodiments, the ADAR is exogenously introduced into the host cell. In some embodiments, the ADAR is ADAR1 and/or ADAR2. In certain embodiments, the ADAR is one or more ADARs selected from the group consisting of hADAR1, hADAR2, mouse ADAR1 and ADAR2. In some embodiments, the ADAR is ADAR1, such as p110 isoform of ADAR1 ("$ADAR1^{p110}$") and/or p150 isoform of ADAR1 ("$ADAR1^{p150}$"). In some embodiments, the ADAR is ADAR2. In some embodiments, the ADAR is an ADAR2 expressed by the host cell, e.g., ADAR2 expressed by cerebellum cells.

In some embodiments, the ADAR is an ADAR exogenous to the host cell. In some embodiments, the ADAR is a hyperactive mutant of a naturally occurring ADAR. In some embodiments, the ADAR is ADAR1 comprising an E1008Q mutation. In some embodiments, the ADAR is not a fusion protein comprising a binding domain. In some embodiments, the ADAR does not comprise an engineered double-strand nucleic acid-binding domain. In some embodiments, the ADAR does not comprise a MCP domain that binds to MS2 hairpin that is fused to the complementary RNA sequence in the dRNA. In some embodiments, the ADAR does not comprise a DSB.

In some embodiments according to any one of the methods or use described herein, the host cell has high expression level of ADAR1 (such as $ADAR1^{p110}$ and/or $ADAR1^{p150}$), e.g., at least about any one of 10%, 20%, 50%, 100%, 2×, 3×, 5×, or more relative to the protein expression level of β-tubulin. In some embodiments, the host cell has high expression level of ADAR2, e.g., at least about any one of 10%, 20%, 50%, 100%, 2×, 3×, 5×, or more relative to the protein expression level of β-tubulin. In some embodiments, the host cell has low expression level of ADAR3, e.g., no more than about any one of 5×, 3×, 2×, 100%, 50%, 20% or less relative to the protein expression level of β-tubulin.

In certain embodiments according to any one of the methods or use described herein, the complementary RNA sequence comprises a cytidine, adenosine or uridine directly opposite the target A in the target RNA. In some embodiments, complementary RNA sequence comprises a cytidine mismatch directly opposite the target A in the target RNA. In some embodiments, the cytidine mismatch is located at least 5 nucleotides, e.g., at least 10, 15, 20, 25, 30, or more nucleotides, away from the 5' end of the complementary RNA sequence. In some embodiments, the cytidine mismatch is located at least 20 nucleotides, e.g., at least 25, 30, 35, or more nucleotides, away from the 3' end of the complementary RNA sequence. In some embodiments, the cytidine mismatch is not located within 20 (e.g., 15, 10, 5 or fewer) nucleotides away from the 3' end of the complementary RNA sequence. In some embodiments, the cytidine mismatch is located at least 20 nucleotides (e.g., at least 25, 30, 35, or more nucleotides) away from the 3' end and at least 5 nucleotides (e.g., at least 10, 15, 20, 25, 30, or more nucleotides) away from the 5' end of the complementary RNA sequence. In some embodiments, the cytidine mismatch is located in the center of the complementary RNA sequence. In some embodiments, the cytidine mismatch is located within 20 nucleotides (e.g., 15, 10, 9, 8, 7, 6, 5, 4, 3, 2, or 1 nucleotide) of the center of the complementary sequence in the dRNA.

The dRNA described herein can also be characterized as comprising, from 5' end to 3' end: a 5' portion, a cytidine mismatch directly opposite to the target A in the target RNA, and a 3' portion. In some embodiments, the 3' portion is no shorter than about 7 nt (such as no shorter than 8 nt, no shorter than 9 nt, and no shorter than 10 nt) nucleotides. In some embodiments, the 3' portion is about 7 nt-25 nt nucleotide long (such as about 10 nt-15 nt or 21 nt-25 nt nucleotides long). In some embodiments, the 5' portion is no shorter than about 25 (such as no shorter than about 30, no shorter than about 35 nt, no shorter than about 40 nt, and no shorter than about 45 nt) nucleotides. In some embodiments, the 5' portion is about 25 nt-85 nt nucleotides long (such as about 25 nt-80 nt, 25 nt-75 nt, 25 nt-70 nt, 25 nt-65 nt, 25 nt-60 nt, 30 nt-55 nt, 40 nt-55 nt, or 45 nt-55 nt nucleotides long). In some embodiments, the 5' portion is about 25 nt-85 nt nucleotides long (such as about 25 nt-80 nt, 25 nt-75 nt, 25 nt-70 nt, 25 nt-65 nt, 25 nt-60 nt, 30 nt-55 nt, 40 nt-55 nt, or 45 nt-55 nt nucleotides long), and the 3' portion is about 7 nt-25 nt nucleotide long (such as about 10 nt-15 nt or 21 nt-25 nt nucleotides long). In some embodiments, the 5' portion is longer than the 3' portion. In some embodiments, the 5' portion is about 55 nucleotides long, and the 3' portion is about 15 nucleotides long.

In some embodiments, the position of the cytidine mismatch in the dRNA is according to any of the dRNAs described in the examples herein, and the dRNA can be, for example, in the format of Xnt-c-Ynt, wherein X represents the length of the 5' portion and Y represents the length of the 3' portion: 55 nt-c-35 nt, 55 nt-c-25 nt, 55 nt-c-24 nt, 55 nt-c-23 nt, 55 nt-c-22 nt, 55 nt-c-21 nt, 55 nt-c-20 nt, 55 nt-c-19 nt, 55 nt-c-18 nt, 55 nt-c-17 nt, 55 nt-c-16 nt, 55 nt-c-15 nt, 55 nt-c-14 nt, 55 nt-c-13 nt, 55 nt-c-12 nt, 55 nt-c-11 nt, 55 nt-c-10 nt, 55 nt-c-9 nt, 55 nt-c-8 nt, 55 nt-c-7 nt, 55 nt-n-20 nt, 50 nt-n-20 nt, 45 nt-n-20 nt, 55 nt-n-15 nt, 50 nt-n-15 nt, 45 nt-c-45 nt, 45 nt-c-55 nt, 54 nt-c-12 nt, 53 nt-c-13 nt, 52 nt-c-14 nt, 51 nt-c-15 nt, 50 nt-c-16 nt, 49 nt-c-17 nt, 48 nt-c-18 nt, 47 nt-c-19 nt, 46 nt-c-20 nt, 45 nt-c-21 nt, 44 nt-c-22 nt, 43 nt-c-23 nt, 54 nt-c-15 nt, 53 nt-c-16 nt, 52 nt-c-17 nt, 51 nt-c-18 nt, 50 nt-c-19 nt, 49 nt-c-20 nt, 48 nt-c-21 nt, 47 nt-c-22 nt, 46 nt-c-23 nt, 54 nt-c-17 nt, 53 nt-n-18 nt, 52 nt-n-19 nt, 51 nt-n-20 nt, 50 nt-n-21 nt, 49 nt-n-22 nt, 48 nt-c-23.

In certain embodiments according to any one of the methods or use described herein, the complementary RNA sequence further comprises one or more guanosine(s), such as 1, 2, 3, 4, 5, 6, or more Gs, that is each directly opposite a non-target adenosine in the target RNA. In some embodiments, the complementary RNA sequence comprises two or more consecutive mismatch nucleotides (e.g., 2, 3, 4, 5, or more mismatch nucleotides) opposite a non-target adenosine in the target RNA. In some embodiments, the target RNA comprises no more than about 20 non-target As, such as no more than about any one of 15, 10, 9, 8, 7, 6, 5, 4, 3, 2, or 1 non-target A. The Gs and consecutive mismatch nucleotides opposite non-target As may reduce off-target editing effects by ADAR.

In certain embodiments according to any one of the methods or use described herein, the 5' nearest neighbor of the target A is a nucleotide selected from U, C, A and G with the preference U>C≈A>G and the 3' nearest neighbor of the target A is a nucleotide selected from G, C, A and U with the preference G>C>A≈U. In certain embodiments, the target A is in a three-base motif selected from the group consisting of UAG, UAC, UAA, UAU, CAG, CAC, CAA, CAU, AAG, AAC, AAA, AAU, GAG, GAC, GAA and GAU in the target RNA. In certain embodiments, the three-base motif is UAG, and the dRNA comprises an A directly opposite the U in the three-base motif, a C directly opposite the target A, and a C, G or U directly opposite the G in the three-base motif. In certain embodiments, the three-base motif is UAG in the target RNA, and the dRNA comprises ACC, ACG or ACU that is opposite the UAG of the target RNA. In certain embodiments, the three-base motif is UAG in the target RNA, and the dRNA comprises ACC that is opposite the UAG of the target RNA.

In some embodiments, the dRNA comprises one or more modifications. Exemplary modifications to the dRNA include, but are not limited to, phosphorothioate backbone modification, 2'-substitutions in the ribose (such as 2'-O-methylation and 2'-fluoro substitutions), LNA, and L-RNA. In some embodiments, the dRNA comprises one or more modifications, such as 2'-O-methylation and/or phosphorothioation. In some embodiments, the dRNA is of about 60-200 (This range covers any consecutive positive integers between the numbers 60 and 200, for example, 60, 65, 70, 75, 80, 85, 90, 95, 100, 105, 110, 115, 120, 130, 140, 150, 160, 170, 180, 190, 200) nucleotides long and comprises one or more modifications (such as 2'-O-methylation and/or 3'-phosphorothioation). In some embodiments, the dRNA is of about 60-200 nucleotides long and comprises one or more modifications. In some embodiments, the dRNA is of about 60-200 nucleotides long and comprises 2'-O-methylation and/or phosphorothioation modifications. In some embodiments, the dRNA comprises 2'-O-methylations in the first and last 3 nucleotides and/or phosphorothioations in the first and last 3 internucleotide linkages. In some embodiments, the dRNA comprises 2'-O-methylations in the first and last 3 nucleotides, phosphorothioations in the first and last 3 internucleotide linkages, and 2'-O-methylations in one or more uridines, for example on all uridines. In some embodiments, the dRNA comprises 2'-O-methylations in the first and last 3 nucleotides, phosphorothioations in the first and last 3 internucleotide linkages, 2'-O-methylations in a single or multiple or all uridines, and a modification in the nucleotide opposite to the target adenosine, and/or one or two nucleotides most adjacent to the nucleotide opposite to the target adenosine. In certain embodiments, the modification in the nucleotide opposite to the target adenosine, and/or one or two nucleotides most adjacent to the nucleotide opposite to the target adenosine is a 2'-O-methylation. In certain embodiments, the modification in the nucleotide opposite to the target adenosine, and/or one or two nucleotides most adjacent to the nucleotide opposite to the target adenosine is a phosphorothioate linkage, such as a 3'-phosphorothiation linkage. In certain embodiments, the dRNA comprises 2'-O-methylations in the first and last 3 nucleotides, phosphorothioations in the first and last 3 internucleotide linkages, 2'-O-methylations in all uridines, and a 2'-O-methylation in the nucleotide adjacent to the 3' terminus and/or 5' terminus of the nucleotide opposite to the target adenosine. In certain embodiments, the dRNA comprises 2'-O-methylations in the first and last 3 nucleotides, phosphorothioations in the first and last 3 internucleotide linkages, 2'-O-methylations in a single or multiple or all uridines, and a phosphorothioate linkage such as 3'-phosphorothioate linkage in the nucleotide opposite to the target adenosine and/or its 5' and/or 3' most adjacent nucleotides. In some embodiments, the dRNA comprises 2'-O-methylations in the first and last 5 nucleotides and phosphorothioations in the first and last 5 internucleotide linkages.

In certain embodiments according to any one of the methods or use described herein, the target RNA is any one selected from the group consisting of a pre-messenger RNA, a messenger RNA, a ribosomal RNA, a transfer RNA, a long non-coding RNA and a small RNA (e.g., miRNA). In some embodiments, the target RNA is a pre-messenger RNA. In some embodiments, the target RNA is a messenger RNA.

In certain embodiments according to any one of the methods or use described herein, the method further comprises introducing an inhibitor of ADAR3 to the host cell. In some embodiments, the inhibitor of ADAR3 is an RNAi against ADAR3, such as a shRNA against ADAR3 or a siRNA against ADAR3. In some embodiments, the method further comprises introducing a stimulator of interferon to the host cell. In some embodiments, the ADAR is inducible by interferon, for example, the ADAR is $ADAR^{p150}$. In some embodiments, the stimulator of interferon is IFNα. In some embodiments, the inhibitor of ADAR3 and/or the stimulator of interferon are encoded by the same construct (e.g., vector) that encodes the dRNA.

In certain embodiments according to any one of the methods or use described herein, the efficiency of editing of the target RNA is at least about 20%, such as at least about any one of 25%, 30%, 35%, 40%, 45%, 50%, 55%, 60%, 65%, 70%, 75%, 80%, 85%, 90% or higher. In some embodiments, the efficiency of editing is determined by Sanger sequencing. In some embodiments, the efficiency of editing is determined by next-generation sequencing.

In certain embodiments according to any one of the methods or use described herein, the method has low off-target editing rate. In some embodiments, the method has lower than about 1% (e.g., no more than about any one of 0.5%, 0.1%, 0.05%, 0.01%, 0.001% or lower) editing efficiency on non-target As in the target RNA. In some embodiments, the method does not edit non-target As in the target RNA. In some embodiments, the method has lower than about 0.1% (e.g., no more than about any one of 0.05%, 0.01%, 0.005%, 0.001%, 0.0001% or lower) editing efficiency on As in non-target RNA.

In certain embodiments according to any one of the methods or use described herein, the method does not induce immune response, such as innate immune response. In some embodiments, the method does not induce interferon and/or interleukin expression in the host cell. In some embodiments, the method does not induce IFN-β and/or IL-6 expression in the host cell.

Also provided are edited RNA or host cells having an edited RNA produced by any one of the methods described herein. In some embodiments, the edited RNA comprises an inosine. In some embodiments, the host cell comprises an RNA having a missense mutation, an early stop codon, an alternative splice site, or an aberrant splice site. In some embodiments, the host cell comprises a mutant, truncated, or misfolded protein.

"Host cell" as described herein refers to any cell type that can be used as a host cell provided it can be modified as described herein. For example, the host cell may be a host cell with endogenously expressed adenosine deaminase acting on RNA (ADAR), or may be a host cell into which an adenosine deaminase acting on RNA (ADAR) is introduced by a known method in the art. For example, the host cell may be a prokaryotic cell, a eukaryotic cell or a plant cell. In some embodiments, the host cell is derived from a pre-established cell line, such as mammalian cell lines including human cell lines or non-human cell lines. In some embodiments, the host cell is derived from an individual, such as a human individual.

"Introducing" or "introduction" used herein means delivering one or more polynucleotides, such as dRNAs or one or more constructs including vectors as described herein, one or more transcripts thereof, to a host cell. The invention serves as a basic platform for enabling targeted editing of RNA, for example, pre-messenger RNA, a messenger RNA, a ribosomal RNA, a transfer RNA, a long non-coding RNA and a small RNA (such as miRNA). The methods of the present application can employ many delivery systems, including but not limited to, viral, liposome, electroporation, microinjection and conjugation, to achieve the introduction of the dRNA or construct as described herein into a host cell. Conventional viral and non-viral based gene transfer methods can be used to introduce nucleic acids into mammalian cells or target tissues. Such methods can be used to administer nucleic acids encoding dRNA of the present application to cells in culture, or in a host organism. Non-viral vector delivery systems include DNA plasmids, RNA (e.g. a transcript of a construct described herein), naked nucleic acid, and nucleic acid complexed with a delivery vehicle, such as a liposome. Viral vector delivery systems include DNA and RNA viruses, which have either episomal or integrated genomes for delivery to the host cell.

Methods of non-viral delivery of nucleic acids include lipofection, nucleofection, microinjection, biolistics, virosomes, liposomes, immunoliposomes, polycation or lipid: nucleic acid conjugates, electroporation, nanoparticles, exosomes, microvesicles, or gene-gun, naked DNA and artificial virions.

The use of RNA or DNA viral based systems for the delivery of nucleic acids has high efficiency in targeting a virus to specific cells and trafficking the viral payload to the cellular nuclei.

In certain embodiments according to any one of the methods or use described herein, the method comprises introducing a viral vector (such as lentiviral vector) encoding the dRNA to the host cell. In some embodiments, the method comprises introducing a plasmid encoding the dRNA to the host cell. In some embodiments, the method comprises introducing (e.g., by electroporation) the dRNA (e.g., synthetic dRNA) into the host cell. In some embodiments, the method comprises transfection of the dRNA into the host cell.

After deamination, modification of the target RNA and/or the protein encoded by the target RNA, can be determined using different methods depending on the positions of the targeted adenosines in the target RNA. For example, in order to determine whether "A" has been edited to "I" in the target RNA, RNA sequencing methods known in the art can be used to detect the modification of the RNA sequence. When the target adenosine is located in the coding region of an mRNA, the RNA editing may cause changes to the amino acid sequence encoded by the mRNA. For example, point mutations may be introduced to the mRNA of an innate or acquired point mutation in the mRNA may be reversed to yield wild-type gene product(s) because of the conversion of "A" to "I". Amino acid sequencing by methods known in the art can be used to find any changes of amino acid residues in the encoded protein. Modifications of a stop codon may be determined by assessing the presence of a functional, elongated, truncated, full-length and/or wild-type protein. For example, when the target adenosine is located in a UGA, UAG, or UAA stop codon, modification of the target A (UGA or UAG) or As (UAA) may create a read-through mutation and/or an elongated protein, or a truncated protein encoded by the target RNA may be reversed to create a functional, full-length and/or wild-type protein. Editing of a target RNA may also generate an aberrant splice site, and/or alternative splice site in the target RNA, thus leading to an elongated, truncated, or misfolded protein, or an aberrant splicing or alternative splicing site encoded in the target RNA may be reversed to create a functional, correctly-folding, full-length and/or wild-type protein. In some embodiments, the present application contemplates editing of both innate and acquired genetic changes, for example, missense mutation, early stop codon, aberrant splicing or alternative splicing site encoded by a target RNA. Using known methods to assess the function of the protein encoded by the target RNA can find out whether the RNA editing achieves the desired effects. Because deamination of the adenosine (A) to an inosine (I) may correct a mutated A at the target position in a mutant RNA encoding a protein, identification of the deamination into inosine may provide assessment on whether a functional protein is present, or whether a disease or drug resistance-associated RNA caused by the presence of a mutated adenosine is reversed or partly reversed. Similarly, because deamination of the adenosine (A) to an inosine (I) may introduce a point mutation in the resulting protein, identification of the deamination into inosine may provide a functional indication for identifying a cause of disease or a relevant factor of a disease.

When the presence of a target adenosine causes aberrant splicing, the read-out may be the assessment of occurrence and frequency of aberrant splicing. On the other hand, when the deamination of a target adenosine is desirable to introduce a splice site, then similar approaches can be used to check whether the required type of splicing occurs. An exemplary suitable method to identify the presence of an inosine after deamination of the target adenosine is RT-PCR and sequencing, using methods that are well-known to the person skilled in the art.

The effects of deamination of target adenosine(s) include, for example, point mutation, early stop codon, aberrant splice site, alternative splice site and misfolding of the resulting protein. These effects may induce structural and functional changes of RNAs and/or proteins associated with diseases, whether they are genetically inherited or caused by acquired genetic mutations, or may induce structural and functional changes of RNAs and/or proteins associated with occurrence of drug resistance. Hence, the dRNAs, the constructs encoding the dRNAs, and the RNA editing methods of present application can be used in prevention or treatment of hereditary genetic diseases or conditions, or diseases or conditions associated with acquired genetic mutations by changing the structure and/or function of the disease-associated RNAs and/or proteins.

In some embodiments, the target RNA is a regulatory RNA. In some embodiments, the target RNA to be edited is a ribosomal RNA, a transfer RNA, a long non-coding RNA or a small RNA (e.g., miRNA, pri-miRNA, pre-miRNA, piRNA, siRNA, snoRNA, snRNA, exRNA or scaRNA). The effects of deamination of the target adenosines include, for example, structural and functional changes of the ribosomal RNA, transfer RNA, long non-coding RNA or small RNA (e.g., miRNA), including changes of three-dimensional structure and/or loss of function or gain of function of the target RNA. In some embodiments, deamination of the target As in the target RNA changes the expression level of one or more downstream molecules (e.g., protein, RNA and/or metabolites) of the target RNA. Changes of the expression level of the downstream molecules can be increase or decrease in the expression level.

Some embodiments of the present application involve multiplex editing of target RNAs in host cells, which are useful for screening different variants of a target gene or different genes in the host cells. In some embodiments, wherein the method comprises introducing a plurality of dRNAs to the host cells, at least two of the dRNAs of the plurality of dRNAs have different sequences and/or have different target RNAs. In some embodiments, each dRNA has a different sequence and/or different target RNA. In some embodiments, the method generates a plurality (e.g., at least 2, 3, 5, 10, 50, 100, 1000 or more) of modifications in a single target RNA in the host cells. In some embodiments, the method generates a modification in a plurality (e.g., at least 2, 3, 5, 10, 50, 100, 1000 or more) of target RNAs in the host cells. In some embodiments, the method comprises editing a plurality of target RNAs in a plurality of populations of host cells. In some embodiments, each population of host cells receive a different dRNA or a dRNAs having a different target RNA from the other populations of host cells.

Deaminase-Recruiting RNA, Construct, and Library

In one aspect, the present application provides a deaminase-recruiting RNA useful for any one of the methods described herein. Any one of the dRNAs described in this section may be used in the methods of RNA editing and treatment described herein. It is intended that any of the features and parameters described herein for dRNAs can be combined with each other, as if each and every combination is individually described. The dRNAs described herein do not comprise a tracrRNA, crRNA or gRNA used in a CRISPR/Cas system.

In some embodiments, there is provided a deaminase-recruiting RNA (dRNA) for deamination of a target adenosine in a target RNA by recruiting an ADAR, comprising a complementary RNA sequence that hybridizes to the target RNA.

In one aspect, the present provides a construct comprising any one of the deaminase-recruiting RNAs described herein. In certain embodiments, the construct is a viral vector (preferably a lentivirus vector) or a plasmid. In some embodiments, the construct encodes a single dRNA. In some embodiments, the construct encodes a plurality (e.g., about any one of 1, 2, 3, 4, 5, 10, 20 or more) dRNAs.

In one aspect, the present application provides a library comprising a plurality of the deaminase-recruiting RNAs or a plurality of the constructs described herein.

In one aspect, the present application provides a composition or a host cell comprising the deaminase-recruiting RNA or the construct described herein. In certain embodiments, the host cell is a prokaryotic cell or a eukaryotic cell. Preferably, the host cell is a mammalian cell. Most preferably, the host cell is a human cell.

In certain embodiments according to any one of the dRNAs, constructs, libraries or compositions described herein, the complementary RNA sequence comprises a cytidine, adenosine or uridine directly opposite the target adenosine to be edited in the target RNA. In certain embodiments, the complementary RNA sequence further comprises one or more guanosine(s) that is each directly opposite a non-target adenosine in the target RNA. In certain embodiments, the 5' nearest neighbor of the target A is a nucleotide selected from U, C, A and G with the preference U>C≈A>G and the 3' nearest neighbor of the target A is a nucleotide selected from G, C, A and U with the preference G>C>A≈U. In some embodiments, the 5' nearest neighbor of the target A is U. In some embodiments, the 5' nearest neighbor of the target A is C or A. In some embodiments, the 3' nearest neighbor of the target A is G. In some embodiments, the 3' nearest neighbor of the target A is C.

In certain embodiments according to any one of the dRNAs, constructs, libraries or compositions described herein, the target A is in a three-base motif selected from the group consisting of UAG, UAC, UAA, UAU, CAG, CAC, CAA, CAU, AAG, AAC, AAA, AAU, GAG, GAC, GAA and GAU in the target RNA. In certain embodiments, the three-base motif is UAG, and the dRNA comprises an A directly opposite the U in the three-base motif, a C directly opposite the target A, and a C, G or U directly opposite the G in the three-base motif. In certain embodiments, the three-base motif is UAG in the target RNA, and the dRNA comprises ACC, ACG or ACU that is opposite the UAG of the target RNA.

In some embodiments, the dRNA comprises a cytidine mismatch directly opposite the target A in the target RNA. In some embodiments, the cytidine mismatch is close to the center of the complementary RNA sequence, such as within 20, 15, 10, 5, 4, 3, 2, or 1 nucleotide away from the center of the complementary RNA sequence. In some embodiments, the cytidine mismatch is at least 5 nucleotides away from the 5' end of the complementary RNA sequence. In some embodiments, the cytidine mismatch is at least 20 nucleotides away from the 3' end of the complementary RNA sequence.

In certain embodiments according to any one of the dRNAs, constructs, libraries or compositions described herein, the dRNA comprises at least about any one of 40, 45, 50, 55, 60, 65, 70, 75, 80, 90, 100, 110, 120, 130, 140, 150, 160, 170, 180, 190, 200, 210, 220, 230, 240, or 250 nucleotides. In certain embodiments, the dRNA is about any one of 40-260, 45-250, 50-240, 60-230, 65-220, 70-210, 70-200, 70-190, 70-180, 70-170, 70-160, 70-150, 70-140, 70-130, 70-120, 70-110, 70-100, 70-90, 70-80, 75-200, 80-190, 85-180, 90-170, 95-160, 100-150 or 105-140 nucleotides in length. In some embodiments the dRNA is about 60-200 (such as about any of 60-150, 65-140, 68-130, or 70-120) nucleotides long.

The dRNA of the present application comprises a complementary RNA sequence that hybridizes to the target RNA. The complementary RNA sequence is perfectly complementary or substantially complementarity to the target RNA to allow hybridization of the complementary RNA sequence to the target RNA. In some embodiments, the complementary RNA sequence has 100% sequence complementarity as the target RNA. In some embodiments, the complementary RNA sequence is at least about any one of 70%, 80%, 85%, 90%, 95%, 96%, 97%, 98%, or 99% or more complementary to over a continuous stretch of at least about any one of 20, 40, 60, 80, 100, 150, 200, or more nucleotides in the target RNA. In some embodiments, the dsRNA formed by hybridization between the complementary RNA sequence and the target RNA has one or more (e.g., 1, 2, 3, 4, 5, 6, 7, 8, 9, 10 or more) non-Watson-Crick base pairs (i.e., mismatches).

ADAR, for example, human ADAR enzymes edit double stranded RNA (dsRNA) structures with varying specificity, depending on a number of factors. One important factor is the degree of complementarity of the two strands making up the dsRNA sequence. Perfect complementarity of between the dRNA and the target RNA usually causes the catalytic domain of ADAR to deaminate adenosines in a non-discriminative manner. The specificity and efficiency of ADAR can be modified by introducing mismatches in the dsRNA region. For example, A-C mismatch is preferably recommended to increase the specificity and efficiency of deamination of the adenosine to be edited. Conversely, at the other A (adenosine) positions than the target A (i.e., "non-target A"), the G-A mismatch can reduce off-target editing. Perfect complementarity is not necessarily required for a dsRNA formation between the dRNA and its target RNA, provided there is substantial complementarity for hybridization and formation of the dsRNA between the dRNA and the target RNA. In some embodiments, the dRNA sequence or single-stranded RNA region thereof has at least about any one of 70%, 80%, 85%, 90%, 95%, 96%, 97%, 98%, or 99% of sequence complementarity to the target RNA, when optimally aligned. Optimal alignment may be determined with the use of any suitable algorithm for aligning sequences, non-limiting examples of which include the Smith-Waterman algorithm, the Needleman-Wimsch algorithm, algorithms based on the Burrows-Wheeler Transform (e.g. the Burrows Wheeler Aligner).

The nucleotides neighboring the target adenosine also affect the specificity and efficiency of deamination. For example, the 5' nearest neighbor of the target adenosine to be edited in the target RNA sequence has the preference U>C≈A>G and the 3' nearest neighbor of the target adenosine to be edited in the target RNA sequence has the preference G>C>A≈U in terms of specificity and efficiency of deamination of adenosine. In some embodiments, when the target adenosine may be in a three-base motif selected from the group consisting of UAG, UAC, UAA, UAU, CAG, CAC, CAA, CAU, AAG, AAC, AAA, AAU, GAG, GAC, GAA and GAU in the target RNA, the specificity and efficiency of deamination of adenosine are higher than adenosines in other three-base motifs. In some embodiments, where the target adenosine to be edited is in the three-base motif UAG, UAC, UAA, UAU, CAG, CAC, AAG, AAC or AAA, the efficiency of deamination of adenosine is much higher than adenosines in other motifs. With respect to the same three-base motif, different designs of dRNA may also lead to different deamination efficiency. Taking the three-base motif UAG as an example, in some embodiments, when the dRNA comprises cytidine (C) directly opposite the target adenosine to be edited, adenosine (A) directly opposite the uridine, and cytidine (C), guanosine (G) or uridine (U) directly opposite the guanosine, the efficiency of deamination of the target adenosine is higher than that using other dRNA sequences. In some embodiments, when the dRNA comprises ACC, ACG or ACU opposite UAG of the target RNA, the editing efficiency of the A in the UAG of the target RNA may reach about 25%-30%.

Besides the target adenosines, there may be one or more adenosines in the target RNA which are not desirable to be edited. With respect to these adenosines, it is preferable to reduce their editing efficiency as much as possible. It is found by this invention that where guanosine is directly opposite an adenosine in the target RNA, the deamination efficiency is significantly decreased. Therefore, in order to decrease off-target deamination, dRNAs can be designed to comprise one or more guanosines directly opposite one or more adenosine(s) other than the target adenosine to be edited in the target RNA.

The desired level of specificity and efficiency of editing the target RNA sequence may depend on different applications. Following the instructions in the present patent application, those of skill in the art will be capable of designing a dRNA having complementary or substantially complementary sequence to the target RNA sequence according to their needs, and, with some trial and error, obtain their desired results. As used herein, the term "mismatch" refers to opposing nucleotides in a double stranded RNA (dsRNA) which do not form perfect base pairs according to the Watson-Crick base pairing rules. Mismatch base pairs include, for example, G-A, C-A, U-C, A-A, G-G, C-C, U-U base pairs. Taking A-C match as an example, where a target A is to be edited in the target RNA, a dRNA is designed to comprise a C opposite the A to be edited, generating a A-C mismatch in the dsRNA formed by hybridization between the target RNA and dRNA.

In some embodiments, the dsRNA formed by hybridization between the dRNA and the target RNA does not comprise a mismatch. In some embodiments, the dsRNA formed by hybridization between the dRNA and the target RNA comprises one or more, such as any one of 1, 2, 3, 4, 5, 6, 7 or more mismatches (e.g., the same type of different types of mismatches). In some embodiments, the dsRNA formed by hybridization between the dRNA and the target RNA comprises one or more kinds of mismatches, for example, 1, 2, 3, 4, 5, 6, 7 kinds of mismatches selected from the group consisting of G-A, C-A, U-C, A-A, G-G, C-C and U-U.

The mismatch nucleotides in the dsRNA formed by hybridization between the dRNA and the target RNA can form bulges which can promote the efficiency of editing of the target RNA. There may be one (which is only formed at the target adenosine) or more bulges formed by the mismatches. The additional bulge-inducing mismatches may be upstream and/or downstream of the target adenosine. The bulges may be single-mismatch bulges (caused by one mismatching base pair) or multi-mismatch bulges (caused by more than one consecutive mismatching base pairs, preferably two or three consecutive mismatching base pairs).

The complementary RNA sequence in the dRNA is single-stranded. The dRNA may be entirely single-stranded or have one or more (e.g., 1, 2, 3, or more) double-stranded regions and/or one or more stem loop regions. In some embodiments, the complementary RNA sequence is at least about any one of 40, 45, 50, 55, 60, 65, 70, 75, 80, 90, 100, 110, 120, 130, 140, 150, 160, 170, 180, 190, 200 or more nucleotides. In certain embodiments, the complementary RNA sequence is about any one of 40-260, 45-250, 50-240, 60-230, 65-220, 70-220, 70-210, 70-200, 70-190, 70-180, 70-170, 70-160, 70-150, 70-140, 70-130, 70-120, 70-110, 70-100, 70-90, 70-80, 75-200, 80-190, 85-180, 90-170, 95-160, 100-200, 100-150, 100-175, 110-200, 110-175, 110-150, or 105-140 nucleotides in length. In some embodiments, the dRNA is about 60-200 (such as about any of 60-150, 65-140, 68-130, or 70-120) nucleotides long. In some embodiments, the complementary RNA sequence is about 71 nucleotides long. In some embodiments, the complementary RNA sequence is about 111 nucleotides long.

In some embodiments, the dRNA, apart from the complementary RNA sequence, further comprises regions for stabilizing the dRNA, for example, one or more double-stranded regions and/or stem loop regions. In some embodiments, the double-stranded region or stem loop region of the dRNA comprises no more than about any one of 200, 150, 100, 50, 40, 30, 20, 10 or fewer base-pairs. In some embodiments, the dRNA does not comprise a stem loop or double-stranded region. In some embodiments, the dRNA comprises an ADAR-recruiting domain. In some embodiments, the dRNA does not comprise an ADAR-recruiting domain.

The dRNA may comprise one or more modifications. In some embodiments, the dRNA has one or more modified nucleotides, including nucleobase modification and/or backbone modification. In some embodiments, the dRNA is of about 60-200 nucleotides long and comprises one or more modifications (such as 2'-O-methylation and/or phosphorothioation). In some embodiments, the modified dRNA comprises, from 5' end to 3' end: a 5' portion, a cytidine mismatch directly opposite the target A in the target RNA, and a 3' portion, wherein the 3' portion is no shorter than about 7 nt (such as no shorter than 8 nt, no shorter than 9 nt, and no shorter than 10 nt) nucleotides. In some embodiments, the 5' portion is no shorter than about 25 (such as no shorter than about 30, no shorter than about 35 nt, no shorter than about 40 nt, and no shorter than about 45 nt) nucleotides. In some embodiments, the 5' portion is about 25 nt-85 nt nucleotides long (such as about 25 nt-80 nt, 25 nt-75 nt, 25 nt-70 nt, 25 nt-65 nt, 25 nt-60 nt, 30 nt-55 nt, 40 nt-55 nt, or 45 nt-55 nt nucleotides long). In some embodiments, the 3' portion is about 7 nt-25 nt nucleotide long (such as about 10 nt-15 nt or 21 nt-25 nt nucleotides long). In some embodiments, the 5' portion is about 25 nt-85 nt nucleotides long (such as about 25 nt-80 nt, 25 nt-75 nt, 25 nt-70 nt, 25 nt-65 nt, 25 nt-60 nt, 30 nt-55 nt, 40 nt-55 nt, or 45 nt-55 nt nucleotides long), and the 3' portion is about 7 nt-25 nt nucleotide long (such as about 10 nt-15 nt or 21 nt-25 nt nucleotides long). In some embodiments, the 5' portion is longer than the 3' portion. In some embodiments, the 5' portion is about 55 nucleotides long, and the 3' portion is about 15 nucleotides long. In some embodiments, the position of the cytidine mismatch in the dRNA is according to any of the dRNAs described in the examples herein, and the dRNA can be, in the format of Xnt-c-Ynt, wherein X represents the length of the 5' portion and Y represents the length of the 3' portion: 55 nt-c-35 nt, 55 nt-c-25 nt, 55 nt-c-24 nt, 55 nt-c-23 nt, 55 nt-c-22 nt, 55 nt-c-21 nt, 55 nt-c-20 nt, 55 nt-c-19 nt, 55 nt-c-18 nt, 55 nt-c-17 nt, 55 nt-c-16 nt, 55 nt-c-15 nt, 55 nt-c-14 nt, 55 nt-c-13 nt, 55 nt-c-12 nt, 55 nt-c-11 nt, 55 nt-c-10 nt, 55 nt-c-9 nt, 55 nt-c-8 nt, 55 nt-c-7 nt, 55 nt-n-20 nt, 50 nt-n-20 nt, 45 nt-n-20 nt, 55 nt-n-15 nt, 50 nt-n-15 nt, 45 nt-c-45 nt, 45 nt-c-55 nt, 54 nt-c-12 nt, 53 nt-c-13 nt, 52 nt-c-14 nt, 51 nt-c-15 nt, 50 nt-c-16 nt, 49 nt-c-17 nt, 48 nt-c-18 nt, 47 nt-c-19 nt, 46 nt-c-20 nt, 45 nt-c-21 nt, 44 nt-c-22 nt, 43 nt-c-23 nt, 54 nt-c-15 nt, 53 nt-c-16 nt, 52 nt-c-17 nt, 51 nt-c-18 nt, 50 nt-c-19 nt, 49 nt-c-20 nt, 48 nt-c-21 nt, 47 nt-c-22 nt, 46 nt-c-23 nt, 54 nt-c-17 nt, 53 nt-n-18 nt, 52 nt-n-19 nt, 51 nt-n-20 nt, 50 nt-n-21 nt, 49 nt-n-22 nt, 48 nt-c-23.

In some embodiments, the dRNA is of about 60-200 nucleotides long and comprises one or more modifications (such as 2'-O-methylation and/or phosphorothioation). In some embodiments, the dRNA comprises 2'-O-methylations in the first and last 3 nucleotides and/or phosphorothioations in the first and last 3 internucleotide linkages. In some embodiments, the dRNA comprises 2'-O-methylations in the first and last 3 nucleotides, phosphorothioations in the first and last 3 internucleotide linkages, and 2'-O-methylations in one or more uridines, for example on all uridines. In some embodiments, the dRNA comprises 2'-O-methylations in the first and last 3 nucleotides, phosphorothioations in the first and last 3 internucleotide linkages, 2'-O-methylations in a single or multiple or all uridines, and a modification in the nucleotide opposite to the target adenosine, and/or one or two nucleotides most adjacent to the nucleotide opposite to the target adenosine. In certain embodiments, the modification in the nucleotide opposite to the target adenosine, and/or one or two nucleotides most adjacent to the nucleotide opposite to the target adenosine is a 2'-O-methylation. In certain embodiments, the modification in the nucleotide opposite to the target adenosine, and/or one or two nucleotides most adjacent to the nucleotide opposite to the target adenosine is a phosphorothioate linkage, such as a 3'-phosphorothiation linkage. In certain embodiments, the dRNA comprises 2'-O-methylations in the first and last 3 nucleotides, phosphorothioations in the first and last 3 internucleotide linkages, 2'-O-methylations in all uridines, and a 2'-O-methylation in the nucleotide adjacent to the 3' terminus or 5' terminus of the nucleotide opposite to the target adenosine. In certain embodiments, the dRNA comprises 2'-O-methylations in the first and last 3 nucleotides, phosphorothioations in the first and last 3 internucleotide linkages, 2'-O-methylations in all uridines, and a 3'-phosphorothioation in the nucleotide opposite to the target adenosine and/or its 5' and/or 3' most adjacent nucleotides. In some embodiments, the dRNA comprises 2'-O-methylations in the first and last 5 nucleotides and phosphorothioations in the first and last 5 internucleotide linkages. The present application also contemplates a construct comprising the dRNA described herein. The term "construct" as used herein refers to DNA or RNA molecules that comprise a coding nucleotide sequence that can be transcribed into RNAs or expressed into proteins. In some embodiments, the construct contains one or more regulatory elements operably linked to the nucleotide sequence encoding the RNA or protein. When the construct is introduced into a host cell, under suitable conditions, the coding nucleotide sequence in the construct can be transcribed or expressed.

In some embodiments, the construct comprises a promoter that is operably linked, or spatially connected to the coding nucleotide sequence, such that the promoter controls the transcription or expression of the coding nucleotide sequence. A promoter may be positioned 5' (upstream) of a coding nucleotide sequence under its control. The distance between the promoter and the coding sequence may be approximately the same as the distance between that promoter and the gene it controls in the gene from which the promoter is derived. As is known in the art, variation in this distance may be accommodated without loss of promoter function. In some embodiments, the construct comprises a 5' UTR and/or a 3'UTR that regulates the transcription or expression of the coding nucleotide sequence.

In some embodiments, the construct is a vector encoding any one of the dRNAs disclosed in the present application. The term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the transcription or expression of coding nucleotide sequences to which they are operatively linked. Such vectors are referred to herein as "expression vectors".

Recombinant expression vectors can comprise a nucleic acid of the invention in a form suitable for transcription or expression of the nucleic acid in a host cell. In some embodiments, the recombinant expression vector includes one or more regulatory elements, which may be selected on the basis of the host cells to be used for transcription or expression, which is operatively linked to the nucleic acid sequence to be transcribed or expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

In some embodiments, there is provided a construct (e.g., vector, such as viral vector) comprising a nucleotide sequence encoding the dRNA. In some embodiments, there is provided a construct (e.g., vector, such as viral vector) comprising a nucleotide sequence encoding the ADAR. In some embodiments, there is provided a construct comprising a first nucleotide sequence encoding the dRNA and a second nucleotide sequence encoding the ADAR. In some embodiments, the first nucleotide sequence and the second nucleotide sequence are operably linked to the same promoter. In some embodiments, the first nucleotide sequence and the second nucleotide sequence are operably linked to different promoters. In some embodiments, the promoter is inducible. In some embodiments, the construct does not encode for the ADAR. In some embodiments, the vector further comprises nucleic acid sequence(s) encoding an inhibitor of ADAR3 (e.g., ADAR3 shRNA or siRNA) and/or a stimulator of interferon (e.g., IFN-α).

Methods of Treatment

The RNA editing methods and compositions described herein may be used to treat or prevent a disease or condition in an individual, including, but not limited to hereditary genetic diseases and drug resistance.

In some embodiments, there is provided a method of editing a target RNA in a cell of an individual (e.g., human individual) ex vivo, comprising editing the target RNA using any one of the methods of RNA editing described herein.

In some embodiments, there is provided a method of editing a target RNA in a cell of an individual (e.g., human individual) ex vivo, comprising introducing a dRNA or a construct encoding the dRNA into the cell of the individual, wherein the dRNA comprises a complementary RNA sequence that hybridizes to the target RNA, and wherein the dRNA is capable of recruiting an ADAR to deaminate a target A in the target RNA. In some embodiments, the target RNA is associated with a disease or condition of the individual. In some embodiments, the disease or condition is a hereditary genetic disease or a disease or condition associated with one or more acquired genetic mutations (e.g., drug resistance). In some embodiments, the method further comprises obtaining the cell from the individual.

In some embodiments, there is provided a method of treating or preventing a disease or condition in an individual (e.g., human individual), comprising editing a target RNA associated with the disease or condition in a cell of the individual using any one of the methods of RNA editing described herein.

In some embodiments, there is provided a method of treating or preventing a disease or condition in an individual (e.g., human individual), comprising introducing a dRNA or a construct encoding the dRNA into an isolated cell of the individual ex vivo, wherein the dRNA comprises a complementary RNA sequence that hybridizes to a target RNA associated with the disease or condition, and wherein the dRNA is capable of recruiting an ADAR to deaminate a target A in the target RNA. In some embodiments, the ADAR is an endogenously expressed ADAR in the isolated cell. In some embodiments, the method comprises introducing the ADAR or a construct encoding the ADAR to the isolated cell. In some embodiments, the method further comprises culturing the cell having the edited RNA. In some embodiments, the method further comprises administering the cell having the edited RNA to the individual. In some embodiments, the disease or condition is a hereditary genetic disease or a disease or condition associated with one or more acquired genetic mutations (e.g., drug resistance).

In some embodiments, there is provided a method of treating or preventing a disease or condition in an individual (e.g., human individual), comprising introducing a dRNA or a construct encoding the dRNA into an isolated cell of the individual ex vivo, wherein the dRNA comprises a complementary RNA sequence that hybridizes to a target RNA associated with the disease or condition, and wherein the dRNA is capable of recruiting an endogenously expressed ADAR of the host cell to deaminate a target A in the target RNA. In some embodiments, the method further comprises culturing the cell having the edited RNA. In some embodiments, the method further comprises administering the cell having the edited RNA to the individual. In some embodiments, the disease or condition is a hereditary genetic disease or a disease or condition associated with one or more acquired genetic mutations (e.g., drug resistance).

In some embodiments, there is provided a method of treating or preventing a disease or condition in an individual (e.g., human individual), comprising administering an effective amount of a dRNA or a construct encoding the dRNA to the individual, wherein the dRNA comprises a complementary RNA sequence that hybridizes to a target RNA associated with the disease or condition, and wherein the dRNA is capable of recruiting an ADAR to deaminate a target A in the target RNA. In some embodiments, the ADAR is an endogenously expressed ADAR in the cells of the individual. In some embodiments, the method comprises administering the ADAR or a construct encoding the ADAR to the individual. In some embodiments, the disease or condition is a hereditary genetic disease or a disease or condition associated with one or more acquired genetic mutations (e.g., drug resistance).

Diseases and conditions suitable for treatment using the methods of the present application include diseases associated with a mutation, such as a G to A mutation, e.g., a G to A mutation that results in missense mutation, early stop codon, aberrant splicing, or alternative splicing in an RNA transcript. Examples of disease-associated mutations that may be restored by the methods of the present application include, but are not limited to, $TP53^{W53X}$ (e.g., 158G>A) associated with cancer, $IDUA^{W402X}$ (e.g., TGG>TAG mutation in exon 9) associated with Mucopolysaccharidosis type I (MPS I), $COL3A1^{W1278X}$ (e.g., 3833G>A mutation) associated with Ehlers-Danlos syndrome, $BMPR2^{W298X}$ (e.g., 893G>A) associated with primary pulmonary hypertension, $AHI1^{W725X}$ (e.g., 2174G>A) associated with Joubert syndrome, $FANCC^{W506X}$ (e.g., 1517G>A) associated with Fanconi anemia, $MYBPC3^{W1098X}$ (e.g., 3293G>A) associated with primary familial hypertrophic cardiomyopathy, and $IL2RG^{W237X}$ (e.g., 710G>A) associated with X-linked severe combined immunodeficiency. In some embodiments, the disease or condition is a cancer. In some embodiments, the disease or condition is a monogenetic disease. In some embodiments, the disease or condition is a polygenetic disease.

In some embodiments, there is provided a method of treating a cancer associated with a target RNA having a mutation (e.g., G>A mutation) in an individual, comprising introducing a dRNA or a construct encoding the dRNA into an isolated cell of the individual ex vivo, wherein the dRNA comprises a complementary RNA sequence that hybridizes to the target RNA, and wherein the dRNA is capable of recruiting an ADAR to deaminate a target A in the target RNA, thereby rescuing the mutation in the target RNA. In some embodiments, the ADAR is an endogenously expressed ADAR in the isolated cell. In some embodiments, the method comprises introducing the ADAR or a construct encoding the ADAR to the isolated cell. In some embodiments, the target RNA is $TP53^{W53X}$ (e.g., 158G>A). In some embodiments, the dRNA comprises the nucleic acid sequence of SEQ ID NO: 195, 196 or 197.

In some embodiments, there is provided a method of treating or preventing a cancer with a target RNA having a mutation (e.g., G>A mutation) in an individual, comprising administering an effective amount of a dRNA or a construct encoding the dRNA to the individual, wherein the dRNA comprises a complementary RNA sequence that hybridizes to the target RNA associated with the disease or condition, and wherein the dRNA is capable of recruiting an ADAR to deaminate a target A in the target RNA, thereby rescuing the mutation in the target RNA. In some embodiments, the ADAR is an endogenously expressed ADAR in the cells of the individual. In some embodiments, the method comprises administering the ADAR or a construct encoding the ADAR to the individual. In some embodiments, the target RNA is $TP53^{W53X}$ (e.g., 158G>A). In some embodiments, the dRNA comprises the nucleic acid sequence of SEQ ID NO: 195, 196 or 197.

In some embodiments, there is provided a method of treating MPS I (e.g., Hurler syndrome or Scheie syndrome) associated with a target RNA having a mutation (e.g., G>A mutation) in an individual, comprising introducing a dRNA or a construct encoding the dRNA into an isolated cell of the individual ex vivo, wherein the dRNA comprises a complementary RNA sequence that hybridizes to the target RNA, and wherein the dRNA is capable of recruiting an ADAR to deaminate a target A in the target RNA, thereby rescuing the mutation in the target RNA. In some embodiments, the ADAR is an endogenously expressed ADAR in the isolated cell. In some embodiments, the method comprises introducing the ADAR or a construct encoding the ADAR to the isolated cell. In some embodiments, the target RNA is $IDUA^{W402X}$ (e.g., TGG>TAG mutation in exon 9). In some embodiments, the dRNA comprises the nucleic acid sequence of SEQ ID NO: 204 or 205.

In some embodiments, there is provided a method of treating or preventing MPS I (e.g., Hurler syndrome or Scheie syndrome) with a target RNA having a mutation (e.g., G>A mutation) in an individual, comprising administering an effective amount of a dRNA or a construct encoding the dRNA to the individual, wherein the dRNA comprises a complementary RNA sequence that hybridizes to the target RNA associated with the disease or condition, and wherein the dRNA is capable of recruiting an ADAR to deaminate a target A in the target RNA, thereby rescuing the mutation in the target RNA. In some embodiments, the ADAR is an endogenously expressed ADAR in the cells of the individual. In some embodiments, the method comprises administering the ADAR or a construct encoding the ADAR to the individual. In some embodiments, the target RNA is $IDUA^{W402X}$ (e g TGG>TAG mutation in exon 9). In some embodiments, the dRNA comprises the nucleic acid sequence of SEQ ID NO: 204 or 205.

In some embodiments, there is provided a method of treating a disease or condition Ehlers-Danlos syndrome associated with a target RNA having a mutation (e.g., G>A mutation) in an individual, comprising introducing a dRNA or a construct encoding the dRNA into an isolated cell of the individual ex vivo, wherein the dRNA comprises a complementary RNA sequence that hybridizes to the target RNA, and wherein the dRNA is capable of recruiting an ADAR to deaminate a target A in the target RNA, thereby rescuing the mutation in the target RNA. In some embodiments, the ADAR is an endogenously expressed ADAR in the isolated cell. In some embodiments, the method comprises introducing the ADAR or a construct encoding the ADAR to the isolated cell. In some embodiments, the target RNA is COL3A1$^{W1278X}$ (e.g., 3833G>A mutation). In some embodiments, the dRNA comprises the nucleic acid sequence of SEQ ID NO: 198.

In some embodiments, there is provided a method of treating or preventing Ehlers-Danlos syndrome with a target RNA having a mutation (e.g., G>A mutation) in an individual, comprising administering an effective amount of a dRNA or a construct encoding the dRNA to the individual, wherein the dRNA comprises a complementary RNA sequence that hybridizes to the target RNA associated with the disease or condition, and wherein the dRNA is capable of recruiting an ADAR to deaminate a target A in the target RNA, thereby rescuing the mutation in the target RNA. In some embodiments, the ADAR is an endogenously expressed ADAR in the cells of the individual. In some embodiments, the method comprises administering the ADAR or a construct encoding the ADAR to the individual. In some embodiments, the target RNA is COL3A1$^{W1278X}$ (e.g., 3833G>A mutation). In some embodiments, the dRNA comprises the nucleic acid sequence of SEQ ID NO: 198.

In some embodiments, there is provided a method of treating primary pulmonary hypertension associated with a target RNA having a mutation (e.g., G>A mutation) in an individual, comprising introducing a dRNA or a construct encoding the dRNA into an isolated cell of the individual ex vivo, wherein the dRNA comprises a complementary RNA sequence that hybridizes to the target RNA, and wherein the dRNA is capable of recruiting an ADAR to deaminate a target A in the target RNA, thereby rescuing the mutation in the target RNA. In some embodiments, the ADAR is an endogenously expressed ADAR in the isolated cell. In some embodiments, the method comprises introducing the ADAR or a construct encoding the ADAR to the isolated cell. In some embodiments, the target RNA is BMPR2$^{W298X}$ (e.g., 893G>A). In some embodiments, the dRNA comprises the nucleic acid sequence of SEQ ID NO: 199.

In some embodiments, there is provided a method of treating or preventing primary pulmonary hypertension with a target RNA having a mutation (e.g., G>A mutation) in an individual, comprising administering an effective amount of a dRNA or a construct encoding the dRNA to the individual, wherein the dRNA comprises a complementary RNA sequence that hybridizes to the target RNA associated with the disease or condition, and wherein the dRNA is capable of recruiting an ADAR to deaminate a target A in the target RNA, thereby rescuing the mutation in the target RNA. In some embodiments, the ADAR is an endogenously expressed ADAR in the cells of the individual. In some embodiments, the method comprises administering the ADAR or a construct encoding the ADAR to the individual. In some embodiments, the target RNA is BMPR2$^{W298X}$ (e.g., 893G>A). In some embodiments, the dRNA comprises the nucleic acid sequence of SEQ ID NO: 199.

In some embodiments, there is provided a method of treating Joubert syndrome associated with a target RNA having a mutation (e.g., G>A mutation) in an individual, comprising introducing a dRNA or a construct encoding the dRNA into an isolated cell of the individual ex vivo, wherein the dRNA comprises a complementary RNA sequence that hybridizes to the target RNA, and wherein the dRNA is capable of recruiting an ADAR to deaminate a target A in the target RNA, thereby rescuing the mutation in the target RNA. In some embodiments, the ADAR is an endogenously expressed ADAR in the isolated cell. In some embodiments, the method comprises introducing the ADAR or a construct encoding the ADAR to the isolated cell. In some embodiments, the target RNA is AHI1$^{W725X}$ (e.g., 2174G>A). In some embodiments, the dRNA comprises the nucleic acid sequence of SEQ ID NO: 200.

In some embodiments, there is provided a method of treating or preventing Joubert syndrome with a target RNA having a mutation (e.g., G>A mutation) in an individual, comprising administering an effective amount of a dRNA or a construct encoding the dRNA to the individual, wherein the dRNA comprises a complementary RNA sequence that hybridizes to the target RNA associated with the disease or condition, and wherein the dRNA is capable of recruiting an ADAR to deaminate a target A in the target RNA, thereby rescuing the mutation in the target RNA. In some embodiments, the ADAR is an endogenously expressed ADAR in the cells of the individual. In some embodiments, the method comprises administering the ADAR or a construct encoding the ADAR to the individual. In some embodiments, the target RNA is AHI1$^{W725X}$ (e.g., 2174G>A). In some embodiments, the dRNA comprises the nucleic acid sequence of SEQ ID NO: 200.

In some embodiments, there is provided a method of treating Fanconi anemia associated with a target RNA having a mutation (e.g., G>A mutation) in an individual, comprising introducing a dRNA or a construct encoding the dRNA into an isolated cell of the individual ex vivo, wherein the dRNA comprises a complementary RNA sequence that hybridizes to the target RNA, and wherein the dRNA is capable of recruiting an ADAR to deaminate a target A in the target RNA, thereby rescuing the mutation in the target RNA. In some embodiments, the ADAR is an endogenously expressed ADAR in the isolated cell. In some embodiments, the method comprises introducing the ADAR or a construct encoding the ADAR to the isolated cell. In some embodiments, the target RNA is FANCC$^{W506X}$ (e.g., 1517G>A). In some embodiments, the dRNA comprises the nucleic acid sequence of SEQ ID NO: 201.

In some embodiments, there is provided a method of treating or preventing Fanconi anemia with a target RNA having a mutation (e.g., G>A mutation) in an individual, comprising administering an effective amount of a dRNA or a construct encoding the dRNA to the individual, wherein the dRNA comprises a complementary RNA sequence that hybridizes to the target RNA associated with the disease or condition, and wherein the dRNA is capable of recruiting an ADAR to deaminate a target A in the target RNA, thereby rescuing the mutation in the target RNA. In some embodiments, the ADAR is an endogenously expressed ADAR in the cells of the individual. In some embodiments, the method comprises administering the ADAR or a construct encoding the ADAR to the individual. In some embodiments, the target RNA is FANCC$^{W506X}$ (e.g., 1517G>A). In some embodiments, the dRNA comprises the nucleic acid sequence of SEQ ID NO: 201.

In some embodiments, there is provided a method of treating primary familial hypertrophic cardiomyopathy associated with a target RNA having a mutation (e.g., G>A mutation) in an individual, comprising introducing a dRNA or a construct encoding the dRNA into an isolated cell of the individual ex vivo, wherein the dRNA comprises a complementary RNA sequence that hybridizes to the target RNA, and wherein the dRNA is capable of recruiting an ADAR to deaminate a target A in the target RNA, thereby rescuing the mutation in the target RNA. In some embodiments, the ADAR is an endogenously expressed ADAR in the isolated cell. In some embodiments, the method comprises introducing the ADAR or a construct encoding the ADAR to the isolated cell. In some embodiments, the target RNA is MYBPC3$^{W1098X}$ (e.g., 3293G>A). In some embodiments, the dRNA comprises the nucleic acid sequence of SEQ ID NO: 202.

In some embodiments, there is provided a method of treating or preventing primary familial hypertrophic cardiomyopathy with a target RNA having a mutation (e.g., G>A mutation) in an individual, comprising administering an effective amount of a dRNA or a construct encoding the dRNA to the individual, wherein the dRNA comprises a complementary RNA sequence that hybridizes to the target RNA associated with the disease or condition, and wherein the dRNA is capable of recruiting an ADAR to deaminate a target A in the target RNA, thereby rescuing the mutation in the target RNA. In some embodiments, the ADAR is an endogenously expressed ADAR in the cells of the individual. In some embodiments, the method comprises administering the ADAR or a construct encoding the ADAR to the individual. In some embodiments, the target RNA is MYBPC3$^{W1098X}$ (e.g., 3293G>A). In some embodiments, the dRNA comprises the nucleic acid sequence of SEQ ID NO: 202.

In some embodiments, there is provided a method of treating X-linked severe combined immunodeficiency associated with a target RNA having a mutation (e.g., G>A mutation) in an individual, comprising introducing a dRNA or a construct encoding the dRNA into an isolated cell of the individual ex vivo, wherein the dRNA comprises a complementary RNA sequence that hybridizes to the target RNA, and wherein the dRNA is capable of recruiting an ADAR to deaminate a target A in the target RNA, thereby rescuing the mutation in the target RNA. In some embodiments, the ADAR is an endogenously expressed ADAR in the isolated cell. In some embodiments, the method comprises introducing the ADAR or a construct encoding the ADAR to the isolated cell. In some embodiments, the target RNA is IL2RG$^{W237X}$ (e.g., 710G>A). In some embodiments, the dRNA comprises the nucleic acid sequence of SEQ ID NO: 203.

In some embodiments, there is provided a method of treating or preventing X-linked severe combined immunodeficiency with a target RNA having a mutation (e.g., G>A mutation) in an individual, comprising administering an effective amount of a dRNA or a construct encoding the dRNA to the individual, wherein the dRNA comprises a complementary RNA sequence that hybridizes to the target RNA associated with the disease or condition, and wherein the dRNA is capable of recruiting an ADAR to deaminate a target A in the target RNA, thereby rescuing the mutation in the target RNA. In some embodiments, the ADAR is an endogenously expressed ADAR in the cells of the individual. In some embodiments, the method comprises administering the ADAR or a construct encoding the ADAR to the individual. In some embodiments, the target RNA is IL2RG$^{W237X}$ (e.g., 710G>A). In some embodiments, the dRNA comprises the nucleic acid sequence of SEQ ID NO: 203.

As used herein, "treatment" or "treating" is an approach for obtaining beneficial or desired results including clinical results. For purposes of this invention, beneficial or desired clinical results include, but are not limited to, one or more of the following: decreasing one more symptoms resulting from the disease, diminishing the extent of the disease, stabilizing the disease (e.g., preventing or delaying the worsening of the disease), preventing or delaying the spread (e.g., metastasis) of the disease, preventing or delaying the occurrence or recurrence of the disease, delay or slowing the progression of the disease, ameliorating the disease state, providing a remission (whether partial or total) of the disease, decreasing the dose of one or more other medications required to treat the disease, delaying the progression of the disease, increasing the quality of life, and/or prolonging survival. Also encompassed by "treatment" is a reduction of pathological consequence of the disease or condition. The methods of the invention contemplate any one or more of these aspects of treatment.

The terms "individual," "subject" and "patient" are used interchangeably herein to describe a mammal, including humans. An individual includes, but is not limited to, human, bovine, horse, feline, canine, rodent, or primate. In some embodiments, the individual is human. In some embodiments, an individual suffers from a disease or condition, such as drug resistance. In some embodiments, the individual is in need of treatment.

As is understood in the art, an "effective amount" refers to an amount of a composition (e.g., dRNA or constructs encoding the dRNA) sufficient to produce a desired therapeutic outcome (e.g., reducing the severity or duration of, stabilizing the severity of, or eliminating one or more symptoms of a disease or condition). For therapeutic use, beneficial or desired results include, e.g., decreasing one or more symptoms resulting from the disease (biochemical, histologic and/or behavioral), including its complications and intermediate pathological phenotypes presented during development of the disease, increasing the quality of life of those suffering from the disease or condition, decreasing the dose of other medications required to treat the disease, enhancing effect of another medication, delaying the progression of the disease, and/or prolonging survival of patients.

Generally, dosages, schedules, and routes of administration of the compositions (e.g., dRNA or construct encoding dRNA) may be determined according to the size and condition of the individual, and according to standard pharmaceutical practice. Exemplary routes of administration include intravenous, intra-arterial, intraperitoneal, intrapulmonary, intravesicular, intramuscular, intra-tracheal, subcutaneous, intraocular, intrathecal, or transdermal.

The RNA editing methods of the present application can not only be used in animal cells, for example mammalian cells, but also may be used in modification of RNAs of plant or fungi, for example, in plants or fungi that have endogenously expressed ADARs. The methods described herein can be used to generate genetically engineered plant and fungi with improved properties.

Compositions, Kits and Articles of Manufacture

Also provided herein are compositions (such as pharmaceutical compositions) comprising any one of the dRNAs, constructs, libraries, or host cells having edited RNA as described herein.

In some embodiments, there is provided a pharmaceutical composition comprising any one of the dRNAs or constructs encoding the dRNA described herein, and a pharmaceutically acceptable carriers, excipients or stabilizers (Remington's Pharmaceutical Sciences 16th edition, Osol, A. Ed. (1980)). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). In some embodiments, lyophilized formulations are provided. Pharmaceutical compositions to be used for in vivo administration must be sterile. This is readily accomplished by, e.g., filtration through sterile filtration membranes.

Further provided are kits useful for any one of the methods of RNA editing or methods of treatment described herein, comprising any one of the dRNAs, constructs, compositions, libraries, or edited host cells as described herein.

In some embodiments, there is provided a kit for editing a target RNA in a host cell, comprising a dRNA, wherein the dRNA comprises a complementary RNA sequence that hybridizes to the target RNA, wherein the dRNA is capable of recruiting an ADAR to deaminate an A in the target RNA. In some embodiments, the kit further comprises an ADAR or a construct encoding an ADAR. In some embodiments, the kit further comprises an inhibitor of ADAR3 or a construct thereof. In some embodiments, the kit further comprises a stimulator of interferon or a construct thereof. In some embodiments, the kit further comprises an instruction for carrying out any one of the RNA editing methods described herein.

The kits of the present application are in suitable packaging. Suitable packaging includes, but is not limited to, vials, bottles, jars, flexible packaging (e.g., sealed Mylar or plastic bags), and the like. Kits may optionally provide additional components such as transfection or transduction reagents, cell culturing medium, buffers, and interpretative information.

The present application thus also provides articles of manufacture. The article of manufacture can comprise a container and a label or package insert on or associated with the container. Suitable containers include vials (such as sealed vials), bottles, jars, flexible packaging, and the like. In some embodiments, the container holds a pharmaceutical composition, and may have a sterile access port (for example the container may be an intravenous solution bag or a vial having a stopper pierceable by a hypodermic injection needle). The container holding the pharmaceutical composition may be a multi-use vial, which allows for repeat administrations (e.g. from 2-6 administrations) of the reconstituted formulation. Package insert refers to instructions customarily included in commercial packages of therapeutic products that contain information about the indications, usage, dosage, administration, contraindications and/or warnings concerning the use of such products. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kits or article of manufacture may include multiple unit doses of the pharmaceutical compositions and instructions for use, packaged in quantities sufficient for storage and use in pharmacies, for example, hospital pharmacies and compounding pharmacies.

EXEMPLARY EMBODIMENTS

Among the embodiments provided herein are:

1. A method for editing a target RNA in a host cell, comprising introducing a deaminase-recruiting RNA (dRNA) or a construct encoding the dRNA into the host cell, wherein the dRNA comprises a complementary RNA sequence that hybridizes to the target RNA, and wherein the deaminase-recruiting RNA is capable of recruiting an adenosine deaminase acting on RNA (ADAR) to deaminate a target adenosine in the target RNA.
2. The method of embodiment 1, wherein the RNA sequence comprises a cytidine, adenosine or uridine directly opposite the target adenosine in the target RNA.
3. The method of embodiment 2, wherein the RNA sequence comprises a cytidine mismatch directly opposite the target adenosine in the target RNA.
4. The method of embodiment 3, wherein the cytidine mismatch is located at least 20 nucleotides away from the 3' end of the complementary sequence, and at least 5 nucleotides away from the 5' end of the complementary sequence in the dRNA.
5. The method of embodiment 4, wherein the cytidine mismatch is located within 10 nucleotides from the center (e.g., at the center) of the complementary sequence in the dRNA.
6. The method of any one of embodiments 1-5, wherein the RNA sequence further comprises one or more guanosines each opposite a non-target adenosine in the target RNA.
7. The method of any one of embodiments 1-6, wherein the complementary sequence comprises two or more consecutive mismatch nucleotides opposite a non-target adenosine in the target RNA.
8. The method of any one of embodiments 1-7, wherein the 5' nearest neighbor of the target adenosine in the target RNA is a nucleotide selected from U, C, A and G with the preference U>C≈A>G and the 3' nearest neighbor of the target adenosine in the target RNA is a nucleotide selected from G, C, A and U with the preference G>C>A≈U.
9. The method of any one of embodiments 1-8, wherein the target adenosine is in a three-base motif selected from the group consisting of UAG, UAC, UAA, UAU, CAG, CAC, CAA, CAU, AAG, AAC, AAA, AAU, GAG, GAC, GAA and GAU in the target RNA.
10. The method of embodiment 9, wherein the three-base motif is UAG, and wherein the deaminase-recruiting RNA comprises an A directly opposite the uridine in the three-base motif, a cytidine directly opposite the target adenosine, and a cytidine, guanosine or uridine directly opposite the guanosine in the three-base motif.
11. The method of any one of embodiments 1-10, wherein the deaminase-recruiting RNA is about 40-260 nucleotides in length.
12. The method of embodiment 11, wherein the deaminase-recruiting RNA is about 60-230 nucleotides in length.
13. The method of embodiment 11 or 12, wherein the dRNA is more than about 60 nucleotides in length.
14. The method of any one of embodiments 11-13, wherein the dRNA is about 100 to about 150 (e.g., about 110-150) nucleotides in length.
15. The method of any one of embodiments 1-14, wherein the target RNA is an RNA selected from the group consisting of a pre-messenger RNA, a messenger RNA, a ribosomal RNA, a transfer RNA, a long non-coding RNA and a small RNA.

16. The method of embodiment 15, wherein the target RNA is a pre-messenger RNA.

17. The method of any one of embodiments 1-16, wherein the ADAR is endogenously expressed by the host cell.

18. The method of any one of embodiments 1-16, wherein the ADAR is exogenous to the host cell.

19. The method of embodiment 18, further comprising introducing the ADAR to the host cell.

20. The method of embodiment 18 or 19, wherein the ADAR comprises an E1008 mutation.

21. The method of any one of embodiments 1-20, wherein the deaminase-recruiting RNA is a single-stranded RNA.

22. The method of any one of embodiments 1-20, wherein the complementary RNA sequence is single-stranded, and wherein the deaminase-recruiting RNA further comprises one or more double-stranded regions.

23. The method of any one of embodiments 1-22, wherein the dRNA does not comprise an ADAR-recruiting domain (e.g., a DSB-binding domain, a GluR2 domain, or a MS2 domain).

24. The method of any one of embodiments 1-23, wherein the dRNA does not comprise a chemically modified nucleotide (e.g., 2'-O-methylation or phosphorothioation).

25. The method of embodiment 26, wherein the deamination of the target adenosine in the target RNA results in point mutation, truncation, elongation and/or misfolding of the protein encoded by the target RNA, or a functional, full-length, correctly-folded and/or wild-type protein by reversal of a missense mutation, an early stop codon, aberrant splicing, or alternative splicing in the target RNA.

26. The method of any one of embodiments 1-27, wherein the host cell is a eukaryotic cell.

27. The method of embodiment 28, wherein the host cell is a mammalian cell.

28. The method of embodiment 29, wherein the host cell is a human or mouse cell.

29. The method of embodiment 29 or 30, wherein the ADAR is ADAR1 and/or ADAR2.

30. The method of any one of embodiments 1-31, wherein the host cell is a primary cell.

31. The method of embodiment 32, wherein the host cell is a T cell.

32. The method of embodiment 32, wherein the host cell is a post-mitotic cell.

33. The method of any one of embodiments 1-34, further comprising introducing an inhibitor of ADAR3 to the host cell.

34. The method of any one of embodiments 1-35, further comprising introducing a stimulator of interferon to the host cell.

35. The method of any one of embodiments 1-36, comprising introducing a plurality of dRNAs each targeting a different target RNA.

36. The method of any one of embodiments 1-37, wherein the efficiency of editing the target RNA is at least about 30% (e.g., at least about 30%, 35%, 40%, 45%, 50%, 55%, 60%, 65%, 70%, 75%, 80%, 85%, 90% or higher).

37. The method of any one of embodiments 1-38, wherein the dRNA does not induce immune response.

38. An edited RNA or a host cell having an edited RNA produced by the method of any one of embodiments 1-39.

39. A method for treating or preventing a disease or condition in an individual, comprising editing a target RNA associated with the disease or condition in a cell of the individual according to any one of the embodiments 1-39.

40. The method of embodiment 41, wherein the disease or condition is a hereditary genetic disease or a disease or condition associated with one or more acquired genetic mutations.

41. The method of embodiment 41 or 42, wherein the target RNA has a G to A mutation.

42. The method of any one of embodiments 41-43, wherein disease or condition is a monogenetic disease or condition.

43. The method of any one of embodiments 41-44, wherein the disease or condition is a polygenetic disease or condition.

44. The method of any one of embodiments 41-45, wherein:

(i) the target RNA is TP53, and the disease or condition is cancer;

(ii) the target RNA is IDUA, and the disease or condition is Mucopolysaccharidosis type I (MPS I);

(iii) the target RNA is COL3A1, and the disease or condition is Ehlers-Danlos syndrome;

(iv) the target RNA is BMPR2, and the disease or condition is Joubert syndrome;

(v) the target RNA is FANCC, and the disease or condition is Fanconi anemia;

(vi) the target RNA is MYBPC3, and the disease or condition is primary familial hypertrophic cardiomyopathy; or (vii) the target RNA is IL2RG, and the disease or condition is X-linked severe combined immunodeficiency.

45. A deaminase-recruiting RNA (dRNA) for deamination of a target adenosine in a target RNA by recruiting an Adenosine Deaminase Acting on RNA (ADAR), comprising a complementary RNA sequence that hybridizes to the target RNA.

46. The deaminase-recruiting RNA of embodiment 47, wherein the RNA sequence comprises a cytosine, adenosine or U directly opposite the target adenosine in the target RNA.

47. The dRNA of embodiment 48, wherein the RNA sequence comprises a cytidine mismatch directly opposite the target adenosine in the target RNA.

48. The dRNA of embodiment 49, wherein the cytidine mismatch is located at least 20 nucleotides away from the 3' end of the complementary sequence, and at least 5 nucleotides away from the 5' end of the complementary sequence in the dRNA.

49. The dRNA of embodiment 50, wherein the cytidine mismatch is located within 10 nucleotides from the center (e.g., at the center) of the complementary sequence in the dRNA.

50. The deaminase-recruiting RNA of any one of embodiments 47-51, wherein the RNA sequence further comprises one or more guanosines each directly opposite a non-target adenosine in the target RNA.

51. The dRNA of any one of embodiments 47-51, wherein the complementary sequence comprises two or more consecutive mismatch nucleotides opposite a non-target adenosine in the target RNA.

52. The deaminase-recruiting RNA of any one of embodiments 47-53, wherein the target adenosine is in a three-base motif selected from the group consisting of UAG, UAC, UAA, UAU, CAG, CAC, CAA, CAU, AAG, AAC, AAA, AAU, GAG, GAC, GAA and GAU in the target RNA.

53. The deaminase-recruiting RNA of embodiment 54, wherein the three-base motif is UAG, and wherein the dRNA comprises an adenosine directly opposite the uridine in the three-base motif, a cytosine directly opposite the target adenosine, and a cytidine, guanosine or uridine directly opposite the guanosine in the three-base motif.

54. The deaminase-recruiting RNA of embodiment 55, wherein the three-base motif is UAG in the target RNA, and wherein the deaminase-recruiting RNA comprises ACC, ACG or ACU opposite the UAG of the target RNA.

55. The deaminase-recruiting RNA of any one of embodiments 47-56, wherein the deaminase-recruiting RNA is about 40-260 nucleotides in length.

56. The dRNA of embodiment 57, wherein the dRNA is more than about 70 nucleotides in length.

57. The dRNA of embodiment 57 or 58, wherein the dRNA is about 100 to about 150 nucleotides (e.g., about 110-150) in length.

58. The dRNA of any one of embodiments 47-59, wherein the dRNA does not comprise an ADAR-recruiting domain (e.g., a DSB-binding domain, a GluR2 domain, or a MS2 domain).

59. The dRNA of any one of embodiments 47-60, wherein the dRNA does not comprise a chemically modified nucleotide (e.g., 2'-O-methylation or phosphorothioation).

60. A construct encoding the deaminase-recruiting RNA of any one of embodiments 47-61.

61. The construct of embodiment 62, wherein the construct is a viral vector (e.g., lentiviral vector) or a plasmid.

62. A library comprising a plurality of the deaminase-recruiting RNAs of any one of embodiments 47-61 or the construct of embodiment 62 or 63.

63. A composition comprising the deaminase-recruiting RNA of any one of embodiments 47-61, the construct of embodiment 62 or 63, or the library of embodiment 64.

64. A host cell comprising the deaminase-recruiting RNA of any one of embodiments 47-61 or the construct of embodiment 62 or 63.

65. The host cell of embodiment 66, wherein the host cell is a eukaryotic cell.

66. The host cell of embodiment 66 or 67, wherein the host cell is a primary cell.

67. A kit for editing a target RNA in a host cell, comprising a deaminase-recruiting RNA, wherein the deaminase-recruiting RNA comprises a complementary RNA sequence that hybridizes to the target RNA, wherein the deaminase-recruiting RNA is capable of recruiting an ADAR to deaminate a target adenosine in the target RNA.

68. A deaminase-recruiting RNA (dRNA) of 60-200 nucleotides, wherein:

1) the dRNA comprises a complementary RNA sequence capable of hybridizing to a target RNA;

2) the dRNA is capable of recruiting a deaminase or a construct comprising a deaminase or a construct comprising a catalytic domain of a deaminase to deaminate a target adenosine in the target RNA; 3) the dRNA comprises one or more chemical modifications.

69. The dRNA of embodiment 68, wherein the dRNA is longer than about any of 60 nt, 65 nt, 70 nt, 80 nt, 90 nt, 100 nt, or 110 nt.

70. The dRNA of embodiment 1 or embodiment 69, comprising one or more mismatches, wobbles and/or bulges with the complementary target RNA region.

71. The dRNA of any one of embodiments 68-70, wherein the complementary RNA sequence comprises a cytidine, adenosine or uridine directly opposite to a target adenosine in the target RNA.

72. The dRNA of embodiment 71, wherein the cytidine, adenosine or uridine directly opposite to the target adenosine locates at least about 7 nucleotides away from the 3' end, for example at least about 8, 9, 10 or more nucleotides from the 3' end, or about 7-25 nt from the 3' end.

73. The dRNA of any one of embodiments 71-72, wherein the cytidine, adenosine or uridine directly opposite to the target adenosine locates at least about 25 nucleotides away from the 5' end, for example at least about 30, 35, 40, 45, 50 or 55 nucleotides from the 5' end, or about 45-55 nt from the 5' end.

74. The dRNA of any of embodiments 71-73, wherein the lengths of the 5' and 3' sequences flanking the cytidine, adenosine or uridine directly opposite to the target adenosine are unequal.

75. The dRNA of any of embodiments 71-74, wherein the length of the 5' sequence flanking the cytidine, adenosine or uridine directly opposite to the target adenosine is longer than the 3' sequence.

76. The dRNA of any one of embodiments 68-75, comprising a cytidine directly opposite to the target adenosine in the target RNA.

77. The dRNA of any one of embodiments 68-76, wherein the complementary RNA sequence comprises one or more guanosines each opposite to a non-target adenosine in the target RNA.

78. The dRNA of any one of embodiments 68-77, wherein the complementary sequence comprises two or more consecutive mismatch nucleotides opposite to a non-target adenosine in the target RNA.

79. The dRNA of any one of embodiments 68-78, wherein the 5' nearest neighbor of the target adenosine in the target RNA is a nucleotide selected from U, C, A and G with the preference U>C≈A>G and the 3' nearest neighbor of the target adenosine in the target RNA is a nucleotide selected from G, C, A and U with the preference G>C>A≈U.

80. The dRNA of any one of embodiments 68-79, wherein the target adenosine is in a three-base motif selected from the group consisting of UAG, UAC, UAA, UAU, CAG, CAC, CAA, CAU, AAG, AAC, AAA, AAU, GAG, GAC, GAA and GAU in the target RNA.

81. The dRNA of embodiment 80, wherein the three-base motif is UAG, and wherein the dRNA comprises an A directly opposite to the uridine in the three-base motif, a cytidine directly opposite to the target adenosine, and a cytidine, guanosine or uridine directly opposite the guanosine in the three-base motif.

82. The dRNA of embodiment 81, comprising a 5'-CCA-3' directly opposite to the three-base motif of UAG.

83. The dRNA of any one of embodiments 68-82, wherein the chemical modification is methylation and/or phosphorothioation, for example 2'-O-methylation and/or internucleotide phosphorothioate linkage.

84. The dRNA of embodiment 83, wherein the chemical modification comprises a 2'-O-methylation in the first and last 1-5, 2-5, 3-5, 4-5 nucleotides and/or phosphorothioations in the first and last 1-5, 2-5, 3-5, 4-5 internucleotide linkages.

85. The dRNA of embodiment 83 or embodiment 84, wherein the chemical modification comprises a 2'-O-methylation and/or a 3'-phosphorothioation in the nucleotide opposite to the target adenosine and/or its 5' and/or 3' most adjacent nucleotides.

86. The dRNA of any one of embodiments 1-85, the chemical modification is selected from a group consisting of:

1) 2'-O-methylations in the first and last 3 nucleotides and/or phosphorothioations in the first and last 3 internucleotide linkages;

2) 2'-O-methylations in the first and last 3 nucleotides, phosphorothioations in the first and last 3 internucleotide linkages, and 2'-O-methylations in one or more uridines, for example on all uridines;

3) 2'-O-methylations in the first and last 3 nucleotides, phosphorothioations in the first and last 3 internucleotide linkages, 2'-O-methylations in a single or multiple or all uridines, and a modification in the nucleotide opposite to the target adenosine, and/or its 5' and/or 3' most adjacent nucleotides;

4) 2'-O-methylations in the first and last 3 nucleotides, phosphorothioations in the first and last 3 internucleotide linkages, 2'-O-methylations in all uridines, and a 2'-O-methylation in the nucleotide most adjacent to the 3' terminus and/or 5' terminus of the nucleotide opposite to the target adenosine;

5) 2'-O-methylations in the first and last 3 nucleotides, phosphorothioations in the first and last 3 internucleotide linkages, 2'-O-methylations in all uridines, and a 3'phosphorothiation in the nucleotide opposite to the target adenosine and/or its 5' and/or 3' most adjacent nucleotides; and 6) 2'-O-methylations in the first and last 5 nucleotides and phosphorothioations in the first and last 5 internucleotide linkages.

87. The dRNA of embodiment 86, wherein the modification in the nucleotide opposite to the target adenosine, and/or one or two nucleotides most adjacent to the nucleotide opposite to the target adenosine is 2'-O-methylation or phosphorothioate linkage, such as a 3'-phosphorothiation linkage.

88. The dRNA of any one of embodiments 68-87, which does not comprise an ADAR-recruiting domain capable of forming an intramolecular stem loop structure for binding an ADAR enzyme.

89. A construct comprising or encoding a dRNA of any one of embodiments 68-88.

90. A method for editing a target RNA in a host cell, comprising introducing a dRNA of any one of embodiments 68-89 into host cells, including, but not limited to eukaryotic cell, primary cell, T cell, mammalian cell, human cell, murine cell, etc., by infection, electrotransfection, lipofection, endocytosis, liposome or lipid nanoparticle delivery, etc.

91. The method of embodiment 90, further comprises introducing an inhibitor of ADAR3 to the host cell.

92. The method of embodiment 90 or embodiment 91, further comprises introducing a stimulator of interferon to the host cell.

93. The method of any one of embodiments 90-92, comprising introducing a plurality of the dRNAs each targeting a different target RNA.

94. The method of any one of embodiments 90-93, wherein the dRNA does not induce immune response.

95. The method of any one of embodiments 90-94, further comprises introducing an exogenous ADAR to the host cell.

96. The method of embodiment 95, wherein the ADAR is an ADAR1 comprising an E1008 mutation.

97. A composition, cell, library or kit comprising the dRNAs of any one of embodiments 68-89

EXAMPLE

The examples below are intended to be purely exemplary of the present application and should therefore not be considered to limit the invention in any way. The following examples and detailed description are offered by way of illustration and not by way of limitation.

Materials and Methods

Plasmids Construction

The dual fluorescence reporter was cloned by PCR amplifying mCherry and EGFP (the EGFP first codon ATG was deleted) coding DNA, the 3×GS linker and targeting DNA sequence were added via primers during PCR. Then the PCR products were cleaved and linked by Type IIs restriction enzyme BsmB1 (Thermo) and T4 DNA ligase (NEB), which then were inserted into pLenti backbone (pLenti-CMV-MCS-SV-Bsd, Stanley Cohen Lab, Stanford University).

The dLbuCas13 DNA was PCR amplified from the Lbu plasmids (Addgene #83485). The ADAR1DD and ADAR2DD were amplified from ADAR1(p150) cDNA and ADAR2 cDNA, both of which were gifts from Han's lab at Xiamen University. The ADAR1DD or ADAR2DD were fused to dLbuCas13 DNA by overlap-PCR, and the fused PCR products were inserted into pLenti backbone.

For expression of dRNA in mammalian cells, the dRNA sequences were directly synthesized (for short dRNAs) and annealed or PCR amplified by synthesizing overlapping ssDNA, and the products were cloned into the corresponding vectors under U6 expression by Golden-gate cloning.

The full lengthADAR1(p110) and ADAR1(p150) were PCR amplified from ADAR1(p150) cDNA, and the full length ADAR2 were PCR amplified from ADAR2 cDNA, which were then cloned into pLenti backbone, respectively.

For the three versions of dual fluorescence reporters (Reporter-1, -2 and -3), mCherry and EGFP (the start codon ATG of EGFP was deleted) coding sequences were PCR amplified, digested using BsmBI (Thermo Fisher Scientific, ER0452), followed by T4 DNA ligase (NEB, M0202L)-mediated ligation with GGGGS (SEQ ID NO: 488) linkers. The ligation product was subsequently inserted into the pLenti-CMV-MCS-PURO backbone.

For the dLbuCas13-ADARDD (E1008Q) expressing construct, the ADAR1DD gene was amplified from the ADAR1$^{p150}$ construct (a gift from Jiahuai Han's lab, Xiamen University). The dLbuCas13 gene was amplified by PCR from the Lbu_C2c2_R472A_H477A_R1048A_H1053A plasmid (Addgene #83485). The ADAR1DD (hyperactive E1008Q variant) was generated by overlap-PCR and then fused to dLbuCas13. The ligation products were inserted into the pLenti-CMV-MCS-BSD backbone.

For arRNA-expressing construct, the sequences of arRNAs were synthesized and golden-gate cloned into the pLenti-sgRNA-lib 2.0 (Addgene #89638) backbone, and the transcription of arRNA was driven by hU6 promoter. For the ADAR expressing constructs, the full length ADAR1$^{p110}$ and ADAR1$^{p150}$ were PCR amplified from the ADAR$^{p150}$ construct, and the full length ADAR2 were PCR amplified from the ADAR2 construct (a gift from Jiahuai Han's lab, Xiamen University). The amplified products were then cloned into the pLenti-CMV-MCS-BSD backbone.

For the constructs expressing genes with pathogenic mutations, full length coding sequences of TP53 (ordered from Vigenebio) and other 6 disease-relevant genes (COL3A1, BMPR2, AHI1, FANCC, MYBPC3 and IL2RG, gifts from Jianwei Wang's lab, Institute of pathogen biology, Chinese Academy of Medical Sciences) were amplified from the constructs encoding the corresponding genes with introduction of G>A mutations through mutagenesis PCR. The amplified products were cloned into the pLenti-CMV-MCS-mCherry backbone through Gibson cloning method[59].

Mammalian Cell Lines and Cell Culture

Mammalian cell lines were cultured Dulbecco's Modified Eagle Medium (10-013-CV, Corning, Tewksbury, Mass., USA), adding 10% fetal bovine serum (Lanzhou Bailing Biotechnology Co., Ltd., Lanzhou, China), supplemented with 1% penicillin-streptomycin under 5% $CO_2$ at 37° C. The ADAR1-KO cell line was purchased from EdiGene China, and the genotyping results were also provided by EdiGene China.

The HeLa and B16 cell lines were from Z. Jiang's laboratory (Peking University). And the HEK293T cell line was from C. Zhang's laboratory (Peking University). RD cell line was from J Wang's laboratory (Institute of Pathogen Biology, Peking Union Medical College & Chinese Academy of Medical Sciences). SF268 cell lines were from Cell Center, Institute of Basic Medical Sciences, Chinese Academy of Medical Sciences. A549 and SW13 cell lines were from EdiGene Inc. HepG2, HT29, NIH3T3, and MEF cell lines were maintained in our laboratory at Peking University. These mammalian cell lines were cultured in Dulbecco's Modified Eagle Medium (Corning, 10-013-CV) with 10% fetal bovine serum (CellMax, SA201.02), additionally supplemented with 1% penicillin-streptomycin under 5% $CO_2$ at 37° C. Unless otherwise described, cells were transfected with the X-tremeGENE HP DNA transfection reagent (Roche, 06366546001) according to the manufacturer's instruction.

The human primary pulmonary fibroblasts (#3300) and human primary bronchial epithelial cells (#3210) were purchased from ScienCell Research Laboratories, Inc. and were cultured in Fibroblast Medium (ScienCell, #2301) and Bronchial Epithelial Cell Medium (ScienCell, #3211), respectively. Both media were supplemented with 15% fetal bovine serum (BI) and 1% penicillin-streptomycin. The primary GM06214 (Hurler syndrome patient derived fibroblast; homozygous of a TGG>TAG mutation at nucleotide 1293 in exon 9 of the IDUA gene [Trp402Ter (W402X)]) and GM01323 (Scheie syndrome patient derived fibroblast, having 0.3% IDUA activity compared to WT cells. Much milder symptoms than Hurler syndrome. Compound heterozygote: a G>A transition in intron 5, in position −7 from exon 6 (IVS5AS-7G>A) and TGG>TAG at nucleotide 1293 in exon 9 of the IDUA gene [Trp402Ter (W402X)]. Serving as a positive control in examples in this invention) cells were ordered from Coriell Institute for Medical Research and cultured in Dulbecco's Modified Eagle Medium (Corning, 10-013-CV) with 15% fetal bovine serum (BI) and 1% penicillin-streptomycin. All cells were cultured under 5% $CO_2$ at 37° C.

Reporter System Transfection, FACS Analysis and Sanger Sequencing

For dual fluorescence reporter editing experiments, 293T-WT cells or 293T-ADAR1-KO cells were seeded in 6 wells plates ($6\times10^5$ cells/well), 24 hours later, 1.5 μg reporter plasmids and 1.5 μg dRNA plasmids were co-transfected using the X-tremeGENE HP DNA transfection reagent (06366546001; Roche, Mannheim, German), according to the supplier's protocols. 48 to 72 hours later, collected cells and performed FACS analysis. For further confirming the reporter mRNA editing, we sorted the EGFP-positive cells from 293T-WT cells transfected with reporter and dRNA plasmids using a FACS Aria flow cytometer (BD Biosciences), followed by total RNA isolation (TIANGEN, DP430). Then the RNA was reverse-transcribed into cDNA via RT-PCR (TIANGEN, KR103-04), and the targeted locus were PCR amplified with the corresponding primer pairs (23 PCR cycles) and the PCR products were purified for Sanger sequencing.

For ADAR1(p110), ADAR1(p150) or ADAR2 rescue and overexpression experiments, 293T-WT cells or 293T-ADAR1-KO cells were seeded in 12 wells plates ($2.5\times10^5$ cells/well), 24 hours later, 0.5 μg reporter plasmids, 0.5 μg dRNA plasmids and 0.5 μg ADAR1/2 plasmids (pLenti backbone as control) were co-transfected using the X-tremeGENE HP DNA transfection reagent (06366546001, Roche, Mannheim, German). 48 to 72 hours later, collected cells and performed FACS analysis.

For endogenous mRNA experiments, 293T-WT cells were seeded in 6 wells plates ($6\times10^5$ cells/well), When approximately 70% confluent, 3 μg dRNA plasmids were transfected using the X-tremeGENE HP DNA transfection reagent (06366546001, Roche, Mannheim, German). 72 hours later, collected cells and sorted GFP-positive or BFP-positive cells (according to the corresponding fluorescence maker) via FACS for the following RNA isolation.

Isolation and Culture of Human Primary T Cells

Primary human T cells were isolated from leukapheresis products from healthy human donor. Briefly, Peripheral blood mononuclear cells (PBMCs) were isolated by Ficoll centrifugation (Dakewei, AS 1114546), and T cells were isolated by magnetic negative selection using an EasySep Human T Cell Isolation Kit (STEMCELL, 17951) from PBMCs. After isolation, T cells were cultured in X-vivo15 medium, 10% FBS and IL2 (1000 U/ml) and stimulated with CD3/CD28 DynaBeads (ThermoFisher, 11131D) for 2 days. Leukapheresis products from healthy donors were acquired from AllCells LLC China. All healthy donors provided informed consent.

Lenti-Virus Package and Reporter Cells Line Construction

The expression plasmid was co-transfected into HEK293T-WT cells, together with two viral packaging plasmids, pR8.74 and pVSVG (Addgene) via the X-tremeGENE HP DNA transfection reagent. 72 hours later, the supernatant virus was collected and stored at -80° C. The HEK293T-WT cells were infected with lenti-virus, 72 hours later, mCherry-positive cells were sorted via FACS and cultured to select a single clone cell lines stably expressing dual fluorescence reporter system with much low EGFP background by limiting dilution method.

For the stable reporter cell lines, the reporter constructs (pLenti-CMV-MCS-PURO backbone) were co-transfected into HEK293T cells, together with two viral packaging plasmids, pR8.74 and pVSVG. 72 hours later, the supernatant virus was collected and stored at −80° C. The HEK293T cells were infected with lentivirus, then mCherry-positive cells were sorted via FACS and cultured to select a single clone cell lines stably expressing dual fluorescence reporter system without detectable EGFP background. The HEK293T $ADAR1^{-/-}$ and TP53 cell lines were generated according to a previously reported method[60]. ADAR1-targeting sgRNA and PCR amplified donor DNA containing CMV-driven puromycin resistant gene were co-transfected into HEK293T cells. Then cells were treated with puromycin 7 days after transfection. Single clones were isolated from puromycin resistant cells followed by verification through sequencing and Western blot.

RNA Editing of Endogenous or Exogenous-Expressed Transcripts

For assessing RNA editing on the dual fluorescence reporter, HEK293T cells or HEK293T $ADAR1^{-/-}$ cells were seeded in 6-well plates ($6\times10^5$ cells/well). 24 hours later, cells were co-transfected with 1.5 μg reporter plasmids and 1.5 μg arRNA plasmids. To examine the effect of $ADAR1^{p110}$, $ADAR1^{p150}$ or ADAR2 protein expression, the editing efficiency was assayed by EGFP positive ratio and deep sequencing.

HEK293T ADAR1$^{-/-}$ cells were seeded in 12-well plates ($2.5\times10^5$ cells/well). 24 hours later, cells were co-transfected with 0.5 μg of reporter plasmids, 0.5 μg arRNA plasmids and 0.5 μg ADAR1/2 plasmids (pLenti backbone as control). The editing efficiency was assayed by EGFP positive ratio and deep sequencing.

To assess RNA editing on endogenous mRNA transcripts, HEK293T cells were seeded in 6-well plates ($6\times10^5$ cells/well). Twenty-four hours later, cells were transfected with 3 μg of arRNA plasmids. The editing efficiency was assayed by deep sequencing.

To assess RNA editing efficiency in multiple cell lines, 8-9×104 (RD, SF268, HeLa) or $1.5\times10^5$ (HEK293T) cells were seeded in 12-well plates. For cells difficult to transfect, such as HT29, A549, HepG2, SW13, NIH3T3, MEF and B16, $2\text{-}2.5\times10^5$ cells were seeded in 6-well plate. Twenty-four hours later, reporters and arRNAs plasmid were co-transfected into these cells. The editing efficiency was assayed by EGFP positive ratio.

To evaluate EGFP positive ratio, at 48 to 72 hrs post transfection, cells were sorted and collected by Fluorescence-activated cell sorting (FACS) analysis. The mCherry signal was served as a fluorescent selection marker for the reporter/arRNA-expressing cells, and the percentages of EGFP$^+$/mCherry$^+$ cells were calculated as the readout for editing efficiency.

For NGS quantification of the A to I editing rate, at 48 to 72 hr post transfection, cells were sorted and collected by FACS assay and were then subjected to RNA isolation (TIANGEN, DP420). Then, the total RNAs were reverse-transcribed into cDNA via RT-PCR (TIANGEN, KR103-04), and the targeted locus was PCR amplified with the corresponding primers listed in Table 1.

TABLE 1

| Name of Primer | Sequence (5'--->3') |
|---|---|
| mCherry-SpeI-F | tataactagtatggtgagcaagggcgaggag (SEQ ID NO: 206) |
| mCherry-BsmBI-R1 | tatacgtctcatctacagattcttccggcgtgtataccttc (SEQ ID NO: 207) |
| EGFP-BsmBI-F1 (Reporter-1) | tatacgtctcatagagatccccggtcgccaccgtgagcaagggcgaggagctg (SEQ ID NO: 208) |
| EGFP-AscI-R | tataggcgcgccttacttgtacagctcgtccatgcc (SEQ ID NO: 209) |
| mCherry-BsmBI-R2 | tatacgtctcaaggcgctgcctcctccgccgctgcctcctccgccgctgcctcctccgccctgcagcttgtacagctcgtccatgccgccggtg (SEQ ID NO: 210) |
| EGFP-BsmBI-F2 (Reporter-2) | tatacgtctcagcctgctcgcgatgctagagggctctgccagtgagcaagggcgaggagctg (SEQ ID NO: 211) |

TABLE 1-continued

| Name of Primer | Sequence (5'--->3') |
|---|---|
| LbuCas13-SpeI-F | tataactagtatggtggattacaaggatgacgacgataagatgaaagtgacgaaggtaggaggcatttcg (SEQ ID NO: 212) |
| LbuCas13-AscI-R | atatggcgcgccgttttcagactttttctcttccatttgtattcaaacataatcttcac (SEQ ID NO: 213) |
| hADAR1$_{DD}$-AscI-F | TATAGGCGCGCCAGGCGGAGGAGGCAGCGGCGGAGGAGGCAGCCTCCTCCTCTCAAGGTCCCCAGAAGC (SEQ ID NO: 214) |
| hADAR1$_{DD}$-SbfI-R | tatacctgcaggctacaccttgcgtttttcttgggtactgggcagagataaaagttcttttcc (SEQ ID NO: 215) |
| Deep-seq-F (Reporter-1) | cactccaccggcggcatggacgag (SEQ ID NO: 216) |
| Deep-seq-R (Reporter-1) | cacgctgaacttgtggccgtttacgtcg (SEQ ID NO: 217) |
| ADAR1-p150-SpeI-F | tataactagtatgaatccgcggcaggggtattccctcagc (SEQ ID NO: 218) |
| ADAR1-p150-AscI-R | tataggcgcgccctacttatcgtcgtcatccttgtaatctactgggcagagataaaagttcttttcctcctgg (SEQ ID NO: 219) |
| ADAR2-SpeI-F | tataactagtatggatatagaagatgaagaaaacatgagttc (SEQ ID NO: 220) |
| ADAR2-AscI-R | tataggcgcgccctacttatcgtcgtcatccttgtaatcgggcgtgagtgagaactggtcctgctcg (SEQ ID NO: 221) |
| ADAR1-p110-SpeI-F | tataactagtatggccgagatcaaggagaaaatctgc (SEQ ID NO: 222) |
| ADAR1-p110-AscI-R | tataggcgcgccctacttatcgtcgtcatccttgtaatctactgggcagagataaaagttcttttcctcctgg (SEQ ID NO: 223) |
| KRAS-deep-seq-F | cgccatttcggactgggag (SEQ ID NO: 224) |
| KRAS-deep-seq-R | agagacaggtttctccatcaattac (SEQ ID NO: 225) |

TABLE 1-continued

| Name of Primer | Sequence (5'--->3') |
|---|---|
| PPIB-deep-seq-F | gagcccgcgagcaacc (SEQ ID NO: 226) |
| PPIB-deep-seq-R | gcagcaggaagaagacg gac (SEQ ID NO: 227) |
| FANCC-deep-seq-F1 (TAG site) | agaagcagttgaagacc agactc (SEQ ID NO: 228) |
| FANCC-deep-seq-R (TAC site) | ggccttcacctggacca tag (SEQ ID NO: 229) |
| FANCC-deep-seq-F2 (TAC site) | agagaagcagttgaaga ccaga (SEQ ID NO: 230) |
| FANCC-deep-seq-R2 (TAC site) | cggccttcacctggacc ata (SEQ ID NO: 231) |
| FANCC-deep-seq-F3 (TAC site) | cagagaagcagttgaag accaga (SEQ ID NO: 232) |
| FANCC-decp-seq-R3 (TAC site) | cggccttcacctggacc ata (SEQ ID NO: 233) |
| SMAD4-deep-seq-F1 | tttgtgaaaggctgggg acc (SEQ ID NO: 234) |
| SMAD4-deep-seq-R1 | acaggattgtattttgt agtccacc (SEQ ID NO: 235) |
| SMAD4-deep-seq-F2 | aggatgagttttgtgaa aggctg (SEQ ID NO: 236) |
| SMAD4-deep-seq-R2 | attttgtagtccaccat cctgata (SEQ ID NO: 237) |
| SMAD4-deep-seq-F3 | gatgagttttgtgaaag gctgg (SEQ ID NO: 238) |
| SMAD4-deep-seq-R3 | attttgtagtccaccat cctgataa (SEQ ID NO: 239) |
| TRAPPC12-deep-seq-F | cgaagagaacgagaccg cat (SEQ ID NO: 240) |
| TRAPPC12-deep-seq-R | gaagatggtgcacaecg gg (SEQ ID NO: 241) |
| TARDBP-deep-seq-F | gacagatgcttcatcag cagtg (SEQ ID NO: 242) |
| TARDBP-deep-seq-R | cgaacaaagccaaaccc cttt (SEQ ID NO: 243) |
| COL3A1-deep-seq-F | tctgttaatggacaaat agaaagcc (SEQ ID NO: 244) |
| COL3A1-deep-seq-R | ggaacattcaaaggatt ggcact (SEQ ID NO: 245) |

TABLE 1-continued

| Name of Primer | Sequence (5'--->3') |
|---|---|
| BMPR2-deep-seq-F | agtcactgcagatggac gca (SEQ ID NO: 246) |
| BMPR2-deep-seq-R | atctcgatgggaaattg caggt (SEQ ID NO: 247) |
| AHI1-deep-seq-F | icagagttttacctcat ccttcttt (SEQ ID NO: 248) |
| AHI1-deep-seq-R | cctgaatacatatgatg accttcag (SEQ ID NO: 249) |
| FANCC-deep-seq-F (Site2) | agggcacagacacagae ctc (SEQ ID NO: 250) |
| FANCC-deep-seq-R (Site2) | agggctttcaatgccaa gacg (SEQ ID NO: 251) |
| MYBPC3-deep-seq-F | tgacaagccaagtcctc cc (SEQ ID NO: 252) |
| MYBPC3-deep-seq-R | attgccaatgatgagct ctgg (SEQ ID NO: 253) |
| IL2RG-deep-seq-F | ttatagacataagttct ccttgcct (SEQ ID NO: 254) |
| IL2RG-deep-seq-R | tcaatcccatggagcca aca (SEQ ID NO: 255) |
| 1-deep-seq-F (Reporter-3) | tacacgacgctcttccg atcttaagtagaggccg ccactccaccggcggc (SEQ ID NO: 256) |
| 2-deep-seq-F (Reporter-3) | tacacgacgctcttccg atctatcatgcttagcc gccactccaccggcggc (SEQ ID NO: 257) |
| 3-deep-seq-F (Reporter-3) | tacacgacgctcttccg atctgatgcacatctgc cgccactccaccggcgg c (SEQ ID NO: 258) |
| 4-deep-seq-F (Reportcr-3) | tacacgacgctcttccg atctcgattgctcgacg ccgccactccaccggcg gc (SEQ ID NO: 259) |
| 5-deep-seq-F (Reporter-3) | tacacgacgctcttccg atcttcgatagcaattc gccgccactccaccggc ggc (SEQ ID NO: 260) |
| 6-deep-seq-F (Reporter-3) | tacacgacgctcttccg atctatcgatagttgct tgccgccactccaccgg cggc (SEQ ID NO: 261) |

TABLE 1-continued

| Name of Primer | Sequence (5'--->3') |
|---|---|
| 7-deep-seq-F (Reporter-3) | tacacgacgctcttccgatctgatcgatccagttaggccgccactccaccggcggc (SEQ ID NO: 262) |
| 8-deep-seq-F (Reporter-3) | tacacgacgctcttccgatctcgatcgatttgagcctgccgccactccaccggcggc (SEQ ID NO: 263) |
| 9-deep-seq-F (Reporter-3) | tacacgacgctcttccgatctacgatcgatacacgatcgccgccactccaccggcggc (SEQ ID NO: 264) |
| 10-deep-seq-F (Reporter-3) | tacacgacgctcttccgatcttacgatcgatggtccagagccgccactccaccggcggc (SEQ ID NO: 265) |
| 1-deep-seq-R (Reporter-3) | agacgtgtgctcttccgatcttaagtagagtcgccgtccagctcgaccag (SEQ ID NO: 266) |
| 2-deep-seq-R (Reporter-3) | agacgtgtgctcttccgatctatcatgcttatcgccgtccagctcgaccag (SEQ ID NO: 267) |
| 3-deep-seq-R (Reporter-3) | agacgtgtgctcttccgatctgatgcacatcttcgccgtccagctcgaccag (SEQ ID NO: 268) |
| 4-deep-seq-R (Reporter-3) | agacgtgtgctcttccgatctcgattgctcgactcgccgtccagctcgaccag (SEQ ID NO: 269) |
| 5-deep-seq-R (Reporter-3) | agacgtgtgctcttccgatcttcgatagcaattctcgccgtccagctcgaccag (SEQ ID NO: 270) |
| 6-deep-seq-R (Reporter-3) | agacgtgtgctcttccgatctatcgatagttgctttcgccgtccagctcgaccag (SEQ ID NO: 271) |
| 7-deep-seq-R (Reporter-3) | agacgtgtgctcttccgatctgatcgatccagttagtcgccgtccagctcgaccag (SEQ ID NO: 272) |
| 8-deep-seq-R (Reporter-3) | agacgtgtgctcttccgatctcgatcgatttgagccttcgccgtccagctcgaccag (SEQ ID NO: 273) |
| 9-deep-seq-R (Reporter-3) | agacgtgtgctcttccgatctacgatcgatacacgatctcgccgtccagctcgaccag (SEQ ID NO: 274) |

TABLE 1-continued

| Name of Primer | Sequence (5'--->3') |
|---|---|
| 10-deep-seq-R (Rcporter-3) | agacgtgtgctcttccgatcttacgatcgatggtccagatcgccgtccagctcgaccag (SEQ ID NO: 275) |
| ST3GAL1-deep-seq-F | ggggaactcgggcaacct (SEQ ID NO: 276) |
| ST3GAL1-deep-seq-R | gaatcggatctgccccgtg (SEQ ID NO: 277) |
| EHD2-deep-seq-F | catcgaggccaagctggaa (SEQ ID NO: 278) |
| EHD2-deep-seq-R | gtagtgaggagggagacccc (SEQ ID NO: 279) |
| OSTM1-AS1-deep-seq-F | aagcctccttccttccccaa (SEQ ID NO: 280) |
| OSTM1-AS1-deep-seq-R | atcgatacactccctagccca (SEQ ID NO: 281) |
| IL6-qPCR-F1 | acaaattcggtacatcctcgac (SEQ ID NO: 282) |
| IL6-qPCR-R1 | ttcagccatctttggaaggtt (SEQ ID NO: 283) |
| INF-β-qPCR-F1 | acgccgcattgaccatctat (SEQ ID NO: 284) |
| INF-β-qPCR-R1 | tagccaggaggttctcaaca (SEQ ID NO: 285) |
| GAPDH-F1 | ggcatggactgtggtcatgag (SEQ ID NO: 286) |
| GAPDH-R1 | tgcaccaccaactgcttagc (SEQ ID NO: 287) |
| Reporter-1-qPCR-F | ccccgtaatgcagaagaagacc (SEQ ID NO: 288) |
| Reporter-1-qPCR-R | gtccttcagcttcagcctctg (SEQ ID NO: 289) |
| PPIB-qPCR-F | aacgcaacatgaaggtgctc (SEQ ID NO: 290) |
| PPIB-qPCR-R | accttgacggtgactttggg (SEQ ID NO: 291) |
| KRAS-qPCR-F | cagtgcaatgagggaccagt (SEQ ID NO: 292) |
| KRAS-qPCR-R | aggaccataggtacatcttcagag (SEQ ID NO: 293) |

TABLE 1-continued

| Name of Primer | Sequence (5'--->3') |
|---|---|
| SMAD4-qPCR-F | cgaacgagttgtatcac ctgga (SEQ ID NO: 294) |
| SMAD4-qPCR-R | cgatggctgtccctcaa agt (SEQ ID NO: 295) |
| FANCC-qPCR-F | agttgctcttttcactc aaggtc (SEQ ID NO: 296) |
| FANCC-qPCR-R | ttctctctgagttcaga cgct (SEQ ID NO: 297) |
| PPIB-deep-seq-F (AAG site) | tacacgacgctcttccg atcttaagtagagtggc acaggaggaaagagcat c (SEQ ID NO: 298) |
| PPIB-deep-scq-R (AAG site) | agacgtgtgctcttccg atcttaagtagaggcac cacctccatgccctc (SEQ ID NO: 299) |
| PPIB-deep-scq-F (CAG site) | tacacgacgctcttccg atcttaagtagagcatc gcagactgcggcaag (SEQ ID NO: 300) |
| PPIB-deep-seq-R (CAG site) | agacgtgtgctcttccg atcttaagtagagagtc catgggcctgtggaatg t (SEQ ID NO: 301) |
| FANCC-deep-seq-F2 (AAG/CAG site) | gaaaaactggcccgaga gc (SEQ ID NO: 302) |
| FANCC-deep-seq-R2 (AAG/CAG site) | ctgagtctgggctgagg gac (SEQ ID NO: 303) |
| IDUA-deep-seq-F | cgcttccaggtcaacaa cac (SEQ ID NO: 304) |
| EDUA-deep-scq-R | ctcgcgtagatcagcac cg (SEQ ID NO: 305) |
| p53-deep-scq-F | cccctctgagtcaggaa acat (SEQ ID NO: 306) |
| p53-deep-scq-R | gaagatgacaggggcca gg (SEQ ID NO: 307) |
| IFN-β-qPCR-F | tagcactggctggaatg ag (SEQ ID NO: 308) |
| IFN-β-qPCR-R | gtttcggaggtaacctg taag (SEQ ID NO: 309) |
| ISG56-qPCR-F | tacagcaaccatgagta caa (SEQ ID NO: 310) |
| ISG56-qPCR-R | tcaggtgtttcacatag gc (SEQ ID NO: 311) |

TABLE 1-continued

| Name of Primer | Sequence (5'--->3') |
|---|---|
| ISG54-qPCR-F | ctgcaaccatgagtgag aa (SEQ ID NO: 312) |
| ISG54-qPCR-R | Cctttgaggtgcttta gatag (SEQ ID NO: 313) |
| IL-6-qPCR-F | gccctgagaaaggagac at (SEQ ID NO: 314) |
| IL-6-qPCR-R | ctgttctggaggtactc taggtat (SEQ ID NO: 315) |
| IL-8-qPCR-F | tttgaagagggctgaga a (SEQ ID NO: 316) |
| IL-8-qPCR-R | tgttctggatatttcat gg (SEQ ID NO: 317) |
| RANTES-qPCR-F | catctgcctccccatat tcc (SEQ ID NO: 318) |
| RANTES-qPCR-R | tccatcctagctcatct ccaaa (SEQ ID NO: 319) |
| IL-12-qPCR-F | tgctccagaaggccaga c (SEQ ID NO: 320) |
| IL-12-qPCR-R | ttcataaatactactaa ggcacagg (SEQ ID NO: 321) |
| IL-iβ-qPCR-F | acagatgaagtgctcct tcca (SEQ ID NO: 322) |
| IL-iβ-qPCR-R | gtcggagattcgtagct ggat (SEQ ID NO: 323) |
| MCP1-qPCR-F | cattgtggccaaggaga tctg (SEQ ID NO: 324) |
| MCP1-qPCR-R | cttcggagtttgggttt gctt (SEQ ID NO: 325) |
| MIP1A-qPCR-F | catcacttgctgctgac acg (SEQ ID NO: 326) |
| MIP1A-qPCR-R | tgtggaatctgccggga g (SEQ ID NO: 327) |
| IP10-qPCR-F | ctgactctaagtggcat t (SEQ ID NO: 328) |
| IP10-qPCR-R | tgatggccttcgattct g (SEQ ID NO: 329) |
| GAPDH-qPCR-F2 | cggagtcaacggatttg gtcgta (SEQ ID NO: 330) |

TABLE 1-continued

| Name of Primer | Sequence (5'--->3') |
|---|---|
| GAPDH-qPCR-R2 | agccttctccatggtgg tgaagac (SEQ ID NO: 331) |

The PCR products were purified for Sanger sequencing or NGS (Illumina HiSeq X Ten).

Deep Sequencing

For endogenous mRNA editing experiments, 293T-WT cells were seeded on 6 wells plates ($6\times10^5$ cells/well), When approximately 70% confluent, HEK293 cells were transfected with 3 μg dRNA using the X-tremeGENE HP DNA transfection reagent (Roche). 72 hours later, sorted GFP-positive or BFP-positive cells (according to the corresponding fluorescence marker) via FACS, followed by RNA isolation. Then the isolated RNA was reverse-transcribed into cDNA via RT-PCR, and specific targeted gene locus were amplified with the corresponding primer pairs (23 PCR cycles) and sequenced on an Illumina NextSeq.

Testing in Multiple Cell Lines

Besides HEK293T (positive control) and HEK293T ADAR1$^{-/-}$ (negative control) cells, one mouse cell line (NIH3T3) as well as seven human cell lines (RD, HeLa, SF268, A549, HepG2, HT-29, SW13) originating from different tissues and organs were selected to perform the experiment. For the cell lines with higher transfection efficiency, about 8-$9\times10^4$ cells (RD, HeLa, SF268) or $1.5\times10^5$ (HEK293T) were plated onto each well of 12-well plate, as for the ones (A549, HepG2, HT-29, SW13, NIH3T3) which are difficult to transfect, 2-$2.5\times10^5$ cells were plated in 6-well plate. And all these cells were maintained in Dulbecco's modified Eagle's medium (DMEM, Corning) supplemented with 10% fetal bovine serum (FBS, CellMax) with 5% $CO_2$ in 37° C. 24 hrs later, CG2 reporter and 71 nt dRNA (35-C-35) plasmid were co-transfected into different type of cells with X-tremeGENE HP DNA transfection reagent (Roche). 48 hrs after transfection, cells were trypsinized and analyzed through FACS (BD). Because the cells with low transfection efficiency had quite fewer mCherry and BFP positive cells, we increased the total cell number for FACS analysis to $1\times10^5$ for those cells plated onto 6-well plate.

RNA Editing Analysis for Targeted Sites

For deep sequencing analysis, an index was generated using the targeted site sequence (upstream and downstream 20-nt) of arRNA covering sequences. Reads were aligned and quantified using BWA version 0.7.10-r789. Alignment BAMs were then sorted by Samtools, and RNA editing sites were analyzed using REDitools version 1.0.4. The parameters are as follows: -U [AG or TC]-t 8 -n 0.0 -T 6-6 -e -d -u. All the significant A>G conversion within arRNA targeting region calculated by Fisher's exact test (p-value<0.05) were considered as edits by arRNA. The conversions except for targeted adenosine were off-target edits. The mutations that appeared in control and experimental groups simultaneously were considered as SNP.

Transcriptome-Wide RNA-Sequencing Analysis

The Ctrl $RNA_{151}$ or $arRNA_{151}$-PPIB-expressing plasmids with BFP expression cassette were transfected into HEK293T cells. The BFP$^+$ cells were enriched by FACS 48 hours after transfection, and RNAs were purified with RNAprep Pure Micro kit (TIANGEN, DP420). The mRNA was then purified using NEBNext Poly(A) mRNA Magnetic Isolation Module (New England Biolabs, E7490), processed with the NEBNext Ultra II RNA Library Prep Kit for Illumina (New England Biolabs, E7770), followed by deep sequencing analysis using Illumina HiSeq X Ten platform (2×150-bp paired end; 30G for each sample). To exclude nonspecific effect caused by transfection, we included the mock group in which we only treated cells with transfection reagent. Each group contained four replications.

The bioinformatics analysis pipeline was referred to the work by Vogel et al[22]. The quality control of analysis was conducted by using FastQC, and quality trim was based on Cutadapt (the first 6-bp for each reads were trimmed and up to 20-bp were quality trimmed). AWK scripts were used to filtered out the introduced arRNAs. After trimming, reads with lengths less than 90-nt were filtered out. Subsequently, the filtered reads were mapped to the reference genome (GRCh38-hg38) by STAR software[61]. We used the GATK Haplotypcaller[62] to call the variants. The raw VCF files generated by GATK were filtered and annotated by GATK VariantFiltration, bcftools and ANNOVAR[63]. The variants in dbSNP, 1000 Genome[64], EVS were filtered out. The shared variants in four replicates of each group were then selected as the RNA editing sites. The RNA editing level of Mock group was viewed as the background, and the global targets of Ctrl $RNA_{151}$ and $arRNA_{151}$-PPIB were obtained by subtracting the variants in the Mock group.

To assess if LEAPER perturbs natural editing homeostasis, we analyzed the global editing sites shared by Mock group and $arRNA_{151}$-PPIB group (or Ctrl $RNA_{151}$ group). The differential RNA editing rates at native A-to-I editing sites were assessed with Pearson's correlation coefficient analysis. Pearson correlations of editing rate between Mock group and $arRNA_{151}$-PPIB group (or Ctrl $RNA_{151}$ group) were calculated and annotated in FIG. 6.

$$\rho(X, Y) = \frac{E[(X-\mu_X)(Y-\mu_Y)]}{\sigma_X\sigma_Y}$$

Figure 6A:
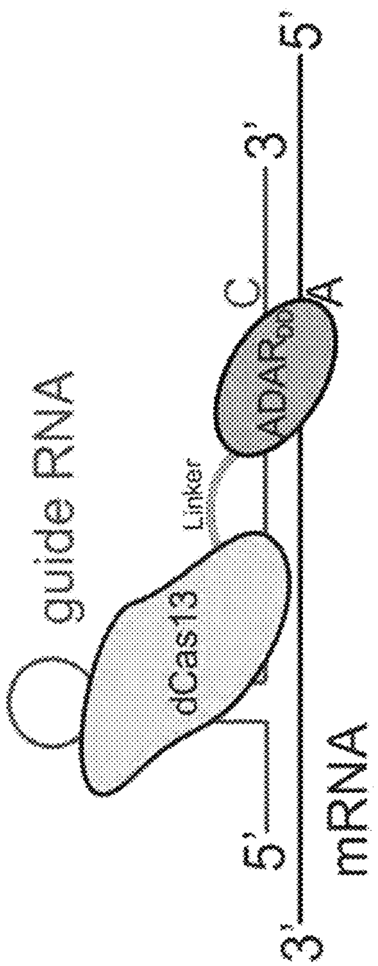
Figure 6B:
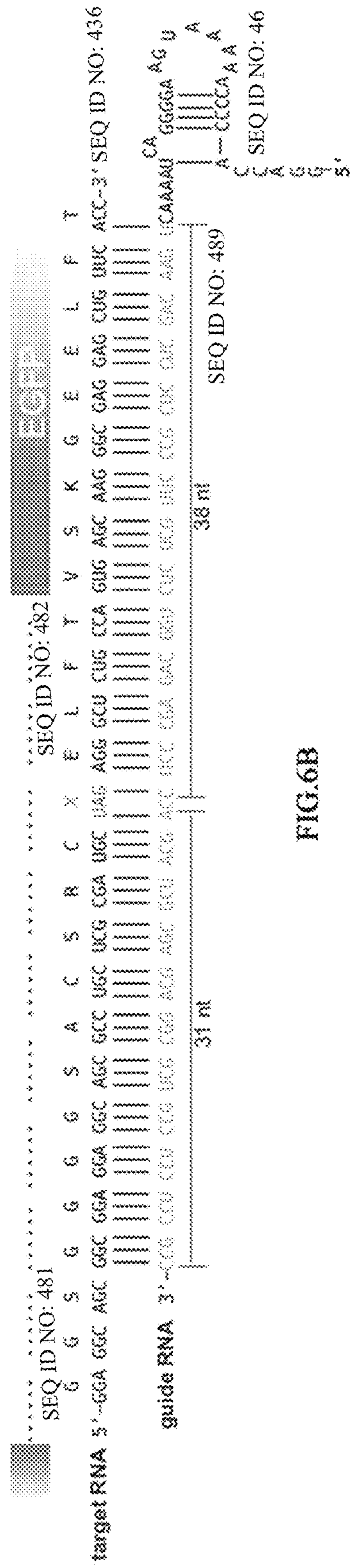
Figure 6D:
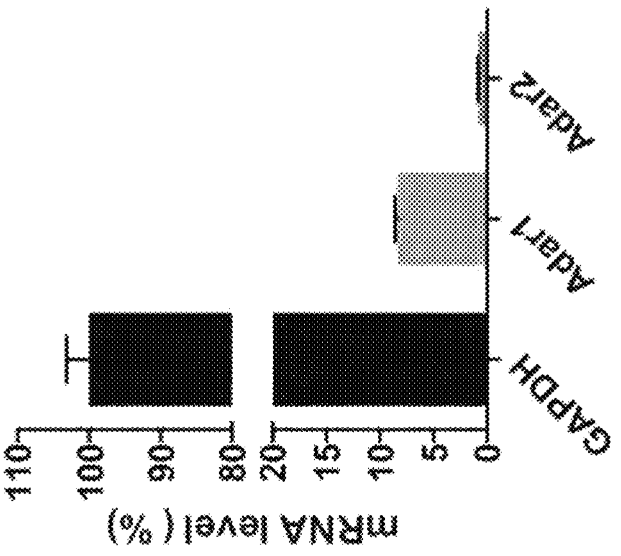

X means the editing rate of each site in the Mock group; Y means the editing rate of each site in the Ctrl $RNA_{151}$ group (FIG. 6*a*) or $arRNA_{151}$-PPIB group (FIG. 6*b*); $\sigma_x$ is the standard deviation of X; $\sigma_Y$ is the standard deviation of Y; $\mu_X$ is the mean of X; $\mu_Y$ is the mean of Y; E is the expectation.

The RNA-Seq data were analysed for the interrogation of possible transcriptional changes induced by RNA editing events. The analysis of transcriptome-wide gene expression was performed using HISAT2 and STRINGTIE software[65]. We used Cutadapt and FastQC for the quality control of the sequencing data. The sequencing reads were then mapped to reference genome (GRCh38-hg38) using HISAT2, followed by Pearson's correlation coefficient analysis as mentioned above.

Western Blot

We used the mouse monoclonal primary antibodies respectively against ADAR1 (Santa Cruz, sc-271854), ADAR2 (Santa Cruz, sc-390995), ADAR3 (Santa Cruz, sc-73410), p53 (Santa Cruz, sc-99), KRAS (Sigma, SAB1404011); GAPDH (Santa Cruz, sc-47724) and β-tubulin (CWBiotech, CW0098). The HRP-conjugated goat anti-mouse IgG (H+L, 115-035-003) secondary antibody was purchased from Jackson ImmunoResearch. $2\times10^6$ cells were sorted to be lysed and an equal amount of each lysate was loaded for SDS-PAGE. Then, sample proteins were transferred onto PVDF membrane (Bio-Rad Laboratories) and immunoblotted with primary antibodies against one of the ADAR enzymes (anti-ADAR1, 1:500; anti-ADAR2, 1:100; anti-ADAR3, 1:800), followed by secondary antibody incubation (1:10,000) and exposure. The β-Tubulin was re-probed on the same PVDF membrane after stripping of the ADAR proteins with the stripping buffer (CWBiotech, CW0056). The experiments were repeated three times. The semi-quantitative analysis was done with Image Lab software.

Cytokine Expression Assay

HEK293T cells were seeded on 12 wells plates ($2\times10^5$ cells/well). When approximately 70% confluent, cells were transfected with 1.5 μg of arRNA. As a positive control, 1 μg of poly(I:C) (Invitrogen, tlrl-picw) was transfected. Forty-eight hours later, cells were collected and subjected to RNA isolation (TIANGEN, DP430). Then, the total RNAs were reverse-transcribed into cDNA via RT-PCR (TIANGEN, KR103-04), and the expression of IFN-0 and IL-6 were measured by quantitative PCR (TAKARA, RR820A). The sequences of the primers were listed in Table1.

Transcriptional Regulatory Activity Assay of p53

The $TP53^{W53X}$ cDNA-expressing plasmids and arRNA-expressing plasmids were co-transfected into HEK293T $TP53^{-/-}$ cells, together with p53-Firefly-luciferase cis-reporting plasmids (YRGene, VXS0446) and *Renilla*-luciferase plasmids (a gift from Z. Jiang's laboratory, Peking University) for detecting the transcriptional regulatory activity of p53. 48 hrs later, the cells were harvested and assayed with the Promega Dual-Glo Luciferase Assay System (Promega, E4030) according to the manufacturer protocol. Briefly, 150 μL Dual-Glo Luciferase Reagent was added to the harvested cell pellet, and 30 minutes later, the Firefly luminescence was measured by adding 100 μL Dual-Glo Luciferase Reagent (cell lysis) to 96-well white plate by Infinite M200 reader (TECAN). 30 min later, 100 μL Dual-Glo stop and Glo Reagent were sequentially added to each well to measure the *Renilla* luminescence and calculate the ratio of Firefly luminescence to *Renilla* luminescence.

Electroporation in Primary Cells

For arRNA-expressing plasmids electroporation in the human primary pulmonary fibroblasts or human primary bronchial epithelial cells, 20 μg plasmids were electroporated with Nucleofector™ 2b Device (Lonza) and Basic Nucleofector™ Kit (Lonza, VPI-1002), and the electroporation program was U-023. For arRNA-expressing plasmids electroporation in human primary T cells, 20 μg plasmids were electroporated into human primary T with Nucleofector™ 2b Device (Lonza) and Human T cell Nucleofector™ Kit (Lonza, VPA-1002), and the electroporation program was T-024. Forty-eight hours post-electroporation, cells were sorted and collected by FACS assay and were then subjected to the following deep-sequencing for targeted RNA editing assay. The electroporation efficiency was normalized according to the fluorescence marker.

For the chemosynthetic arRNA or control RNA electroporation in human primary T cells or primary GM06214 cells, RNA oligo was dissolved in 100 μL opti-MEM medium (Gbico, 31985070) with the final concentration 2 μM. Then 1x10E6 GM06214 cells or 3x10E6 T cells were resuspended with the above electroporation mixture and electroporated with Agile Pulse In Vivo device (BTX) at 450 V for 1 ms. Then the cells were transferred to warm culture medium for the following assays.

α-L-Iduronidase (IDUA) Catalytic Activity Assay

The harvested cell pellet was resuspended and lysed with 28 μL 0.5% Triton X-100 in 1×PBS buffer on ice for 30 minutes. And then 25 μL of the cell lysis was added to 25 μL 190 μM 4-methylumbelliferyl-α-L-iduronidase substrate (Cayman, 2A-19543-500), which was dissolved in 0.4 M sodium formate buffer containing 0.2% Triton X-100, pH 3.5, and incubated for 90 minutes at 37° C. in the dark. The catalytic reaction was quenched by adding 200 μL 0.5M NaOH/Glycine buffer, pH 10.3, and then centrifuged for 2 minutes at 4° C. The supernatant was transferred to a 96-well plate, and fluorescence was measured at 365 nm excitation wavelength and 450 nm emission wavelength with Infinite M200 reader (TECAN).

Example 1. Testing the RNA Editing Method of the Invention on a Reporter

It has been reported that Cas13 family proteins (C2c2) can edit RNA in mammalian cells. We further tested this system under various conditions. First, we constructed a dual fluorescence reporter system based on mCherry and EGFP fluorescence by introducing 3×GS linker targeting sequence containing stop codon between mCherry and EGFP gene. In addition, we deleted the start codon ATG of EGFP in order to reduce the leakage of EGFP translation.

Dual fluorescence reporter-1 comprises sequence of mCherry (SEQ ID NO:1), sequence comprising 3×GS linker and the targeted A (SEQ ID NO:2), and sequence of eGFP (SEQ ID NO:3).

(SEQ ID NO: 1)

```
atggtgagcaagggcgaggaggataacatggccat
catcaaggagttcatgcgcttcaaggtgcacatgg
agggctccgtgaacggccacgagttcgagatcga
gggcgagggcgagggccgcccctacgagggcaccc
agaccgccaagctgaaggtgaccaagggtggccc
cctgcccttcgcctgggacatcctgtcccctcagt
tcatgtacggctccaaggcctacgtgaagcacccc
gccgacatccccgactacttgaagctgtccttcc
ccgagggcttcaagtgggagcgcgtgatgaacttc
gaggacggcggcgtggtgaccgtgacccaggact
cctccctgcaggacggcgagttcatctacaaggtg
aagctgcgcggcaccaacttcccctccgacggccc
cgtaatgcagaagaagaccatgggctgggaggcc
tcctccgagcggatgtaccccgaggacggcgccct
gaagggcgagatcaagcagaggctgaagctgaag
gacggcggccactacgacgctgaggtcaagaccac
ctacaaggccaagaagcccgtgcagctgcccggcg
cctacaacgtcaacatcaagttggacatcacctc
```

-continued ccacaacgaggactacaccatcgtggaacagtacg aacgcgccgagggccgccactccaccggcggcat ggacgagctgtacaag
(sequence of mCherry)

(SEQ ID NO: 2)
ctgcagggcggaggaggcagcggcggaggaggcag cggcggaggaggcagcagaaggtatacacgccgga agaatctgtagagatccccggtcgccacc
(sequence comprising 3 × GS linker
(shown as italic and bold
characters) and the targeted A
(shown as larger and bold A))

(SEQ ID NO: 3)
gtgagcaagggcgaggagctgttcaccggggtggt gcccatcctggtcgagctggacggcgacgtaaacg gccacaagttcagcgtgtccggcgagggcgaggg cgatgccacctacggcaagctgaccctgaagttca tctgcaccaccggcaagctgcccgtgccctggcc caccctcgtgaccaccctgacctacggcgtgcagt gcttcagccgctaccccgaccacatgaagcagcac gacttcttcaagtccgccatgcccgaaggctacg tccaggagcgcaccatcttcttcaaggacgacggc aactacaagacccgcgccgaggtgaagttcgagg gcgacaccctggtgaaccgcatcgagctgaagggc atcgacttcaaggaggacggcaacatcctggggca caagctggagtacaactacaacagccacaacgtc tatatcatggccgacaagcagaagaacggcatcaa ggtgaacttcaagatccgccacaacatcgaggac ggcagcgtgcagctcgccgaccactaccagcagaa cacccccatcggcgacggccccgtgctgctgcccg acaaccactacctgagcacccagtccgccctgag caaagaccccaacgagaagcgcgatcacatggtcc tgctggagttcgtgaccgccgccgggatcactct cggcatggacgagctgtacaagtaa
(sequence of eGFP)

Dual fluorescence reporter-2 comprises sequence of mCherry (SEQ ID NO:1), sequence comprising 3×GS linker (shown as italic and bold characters) and the targeted A (shown as larger and bold A) (SEQ ID NO:4), and sequence of eGFP (SEQ ID NO:3).

(SEQ ID NO: 4))
ctgcag*ggcggaggaggcagcggcggaggaggcagcggcggaggaggcagc* cctgctcgcgatgctagagggctctgcca
(sequence comprising 3 × GS linker
(shown as italic and bold characters) and the
targeted A (shown as larger and bold characters))

Dual fluorescence reporter-3 comprises sequence of mCherry (SEQ ID NO:1), sequence comprising 1×GS linker (shown as italic and bold characters) and the targeted A (SEQ ID NO:5), and sequence of eGFP (SEQ ID NO:3).

(SEQ ID NO: 5)
ctgcag*ggcggaggaggcagc*gcctgctcgcgatgctagagggctct gcca
(sequence comprising 1 × GS linker (shown as
italic and bold characters) and the targeted A
(shown as larger and bold A))

Figure 6C:
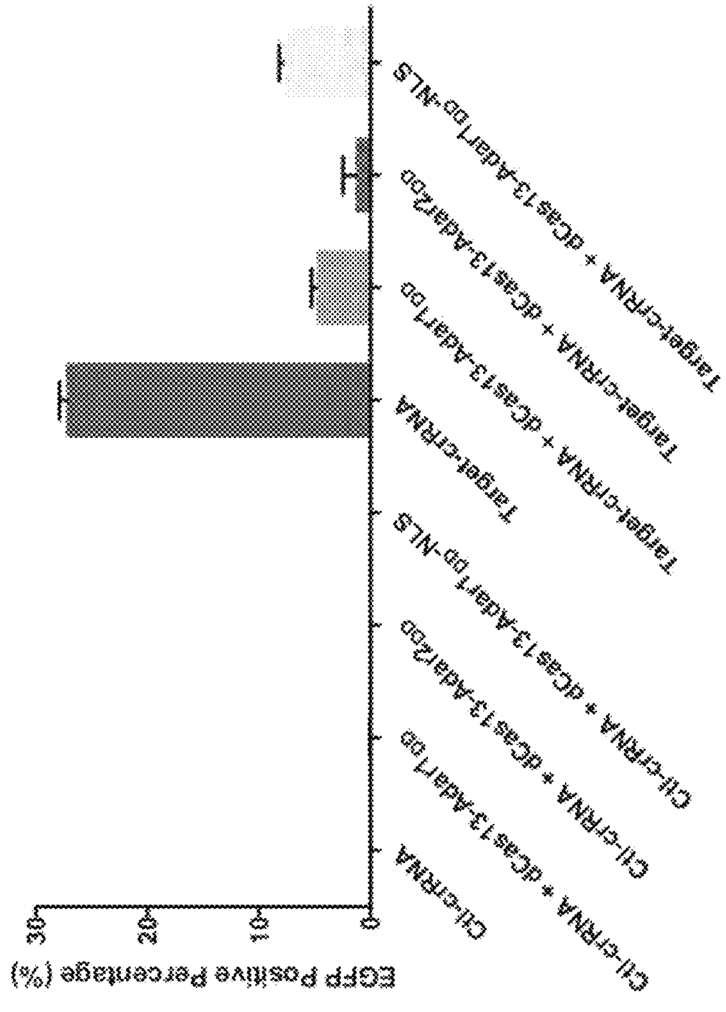
Figure 6G:
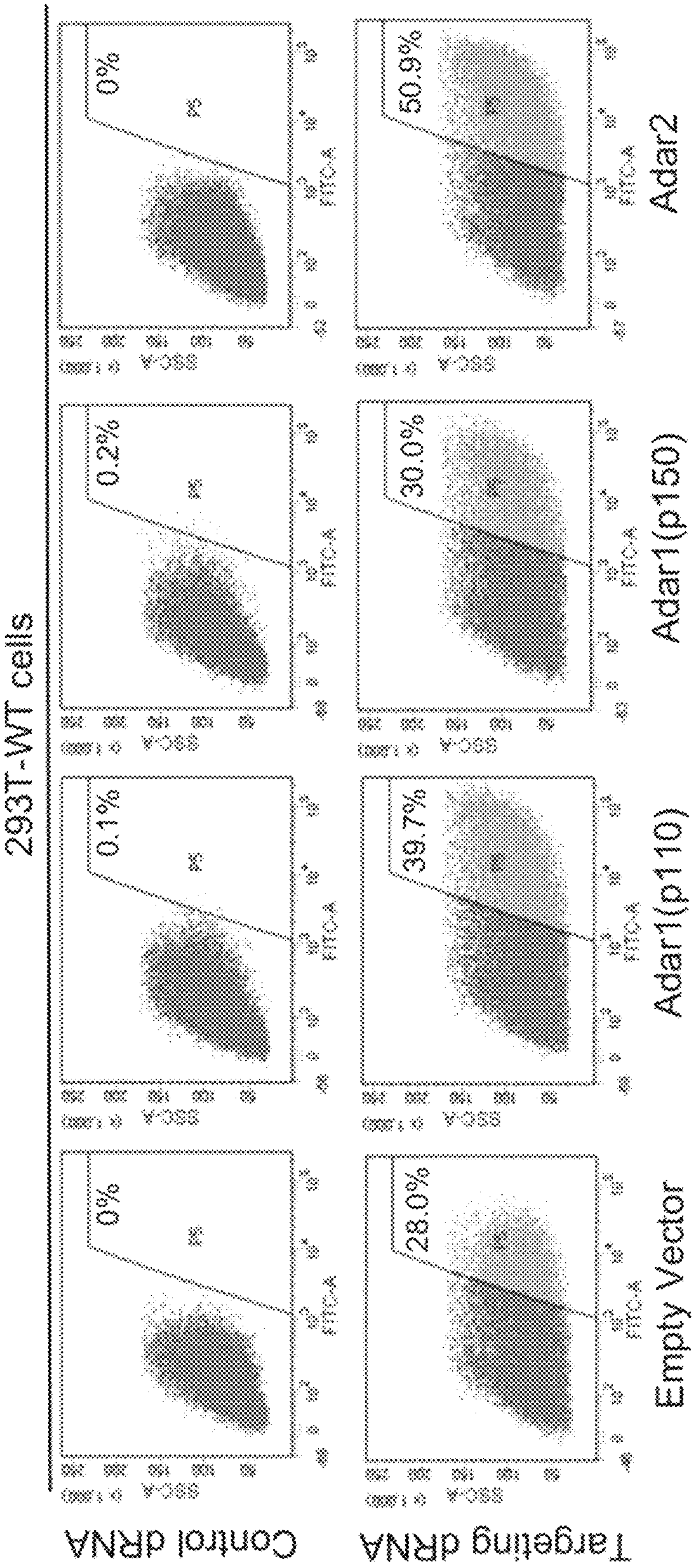

We cloned mCherry-3×GS linker-TAG-EGFP into pLenti-backbone, and the reporter plasmid was packed into lentivirus, which infected 293T cells constructing stable cell line expressing the dual fluorescence reporter. Then, we selected a single clone with low EGFP fluorescence background as the reporter system. We tiled LbucC2c2 crRNA guides with spacers from 28 to 78 nucleotides long across the targeting adenosine to test the optimal crRNA design. We found that longer crRNA guides conferred higher EGFP positive efficiency. Strikingly, when we transfected targeting crRNA plasmids without co-transfection of any dC2c2-ADARDD-expressing plasmids, the EGFP protein is substantially expressed. For example, the crRNA guide with the sequence: ggaccaccccaaaaaugaauauaaccaaaacugaacagcuc-cucgcccuugcucacuggcagagcc cuccagcaucgcgagcaggcgcugc-cuccuccgcc (SEQ ID NO: 6) conferred over 25% EGFP positive efficiency. This indicates that adenine in the stop codon UAG is largely edited. In contrast, the random crRNA could not render the EGFP negative cells into positive (FIGS. 6A, 6B and 6C). Based on these results, we inferred that overexpression of a RNA transcript alone could leverage endogenous ADAR enzyme to edit RNA.

Figure 1E:
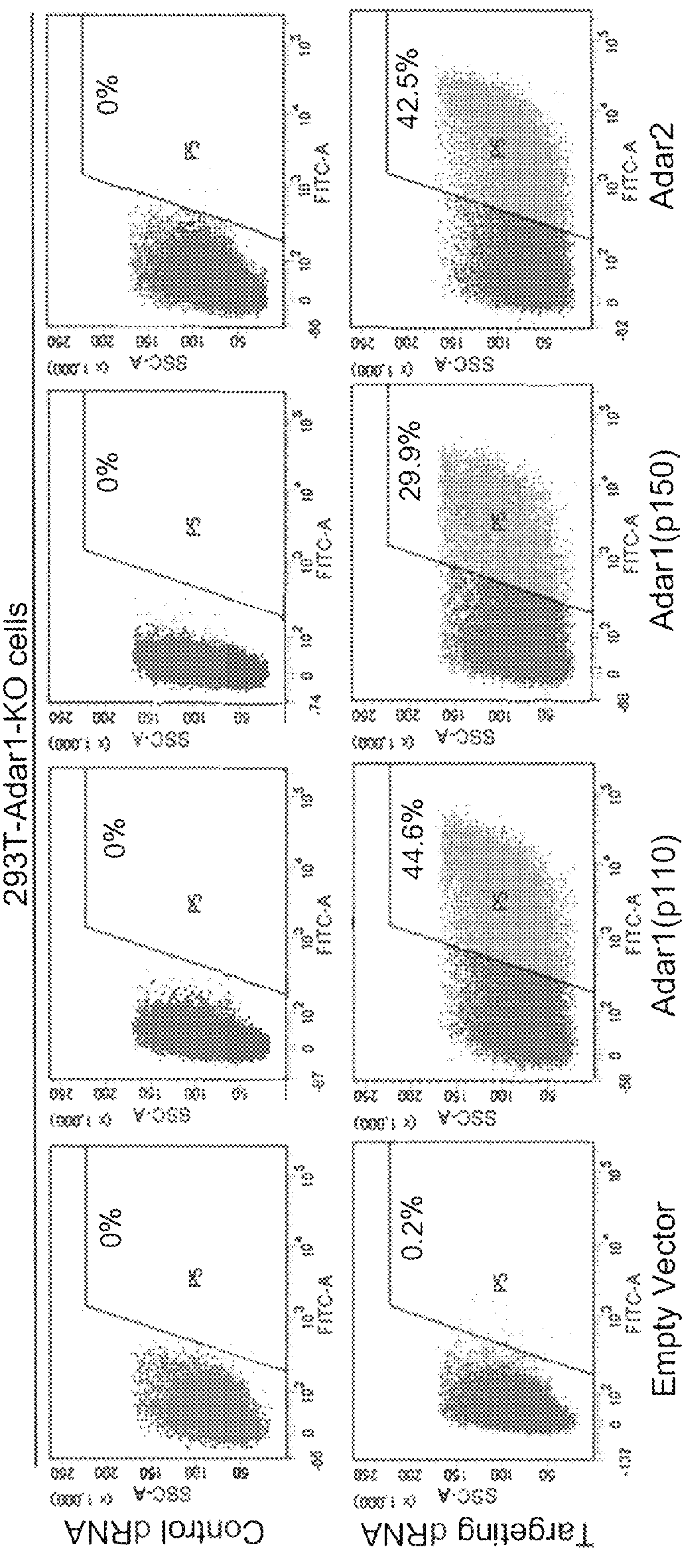
Figure 1F:
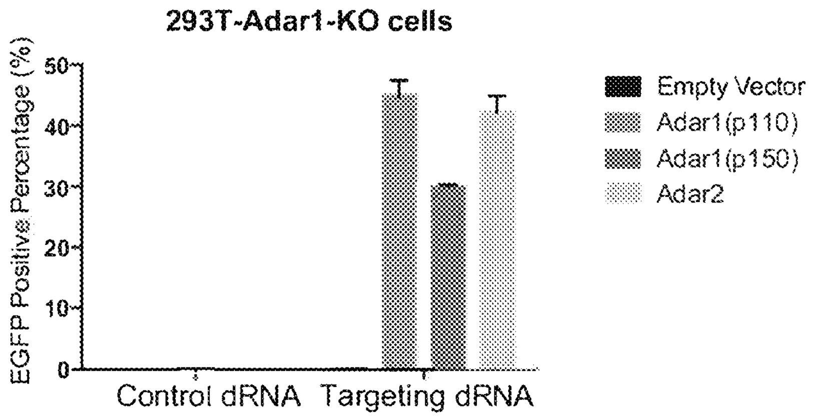
Figure 1G:
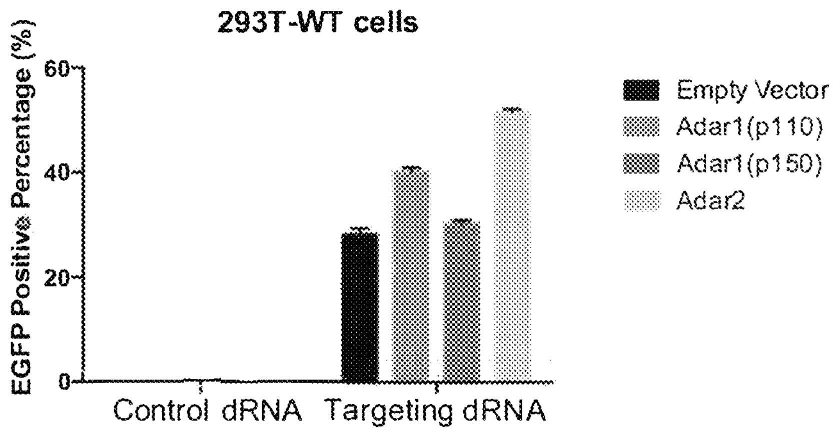

Further, we deleted the scaffold RNA sequence on the RNA guides, creating a linear guide RNA. We found 70-nucleotides long RNA (aaaccgagggau-cauaggggacugaauccaccauucuucucccaaucccugcaacuccuuc-uuccccugc (SEQ ID NO: 7)) complementary to the targeting RNA with an A-C mismatch could efficiently convert the EGFP negative cells into EGFP positive cells, while the 70-nt random RNA (ugaacagcuccucgcccuugcuca-cuggcagagcccuccagcaucgcgagcaggcgcugccuccuccgcc (SEQ ID NO: 8)) could not (FIGS. 1A, 1B, 1C, and 1D). We thus designate this RNA as dRNA (Deaminase-recruiting RNA). To verify that the cellular endogenous ADAR could be recruited to conduct adenine deamination by dRNA, we performed experiments in the ADAR1 p110 and ADAR1 p150 double knockout 293T cell lines (FIGS. 6E and 6F). Because ADAR1 is ubiquitously expressed while ADAR2 is mainly expressed in brain at high level. So we proposed the targeting Adenine deamination by dRNA was mainly mediated by ADAR1 but not ADAR2. As expected, the targeting dRNA could not trigger EGFP expression in 293T-ADAR1−/− cells, but overexpressing either exogenous ADAR1 p110, p150 or ADAR2 could rescue the EGFP expression in 293T-ADAR1−/− cells (FIGS. 1E and 1F), suggesting that in 293 Tcells, the dRNA could recruit ADAR1 or ADAR2 to mediate adenine deamination on a target RNA. Moreover, we found ADAR1-p110 and ADAR2 have higher editing activity than ADAR1-p150 (FIG. 1G and FIG. 6G), possible due to the different cell localization of ADAR1-p110 and ADAR1-p150.

Figure 1H:
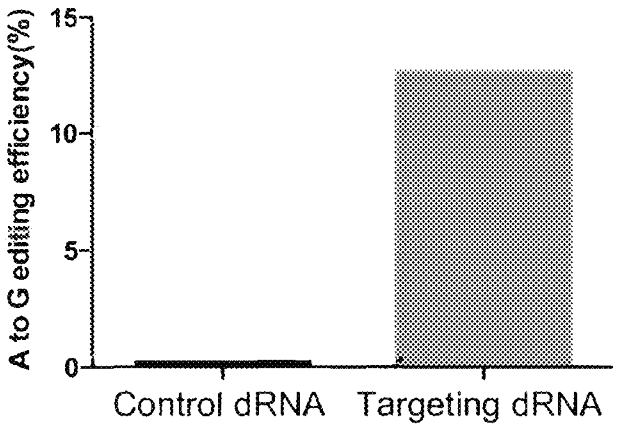
Figure 6H:
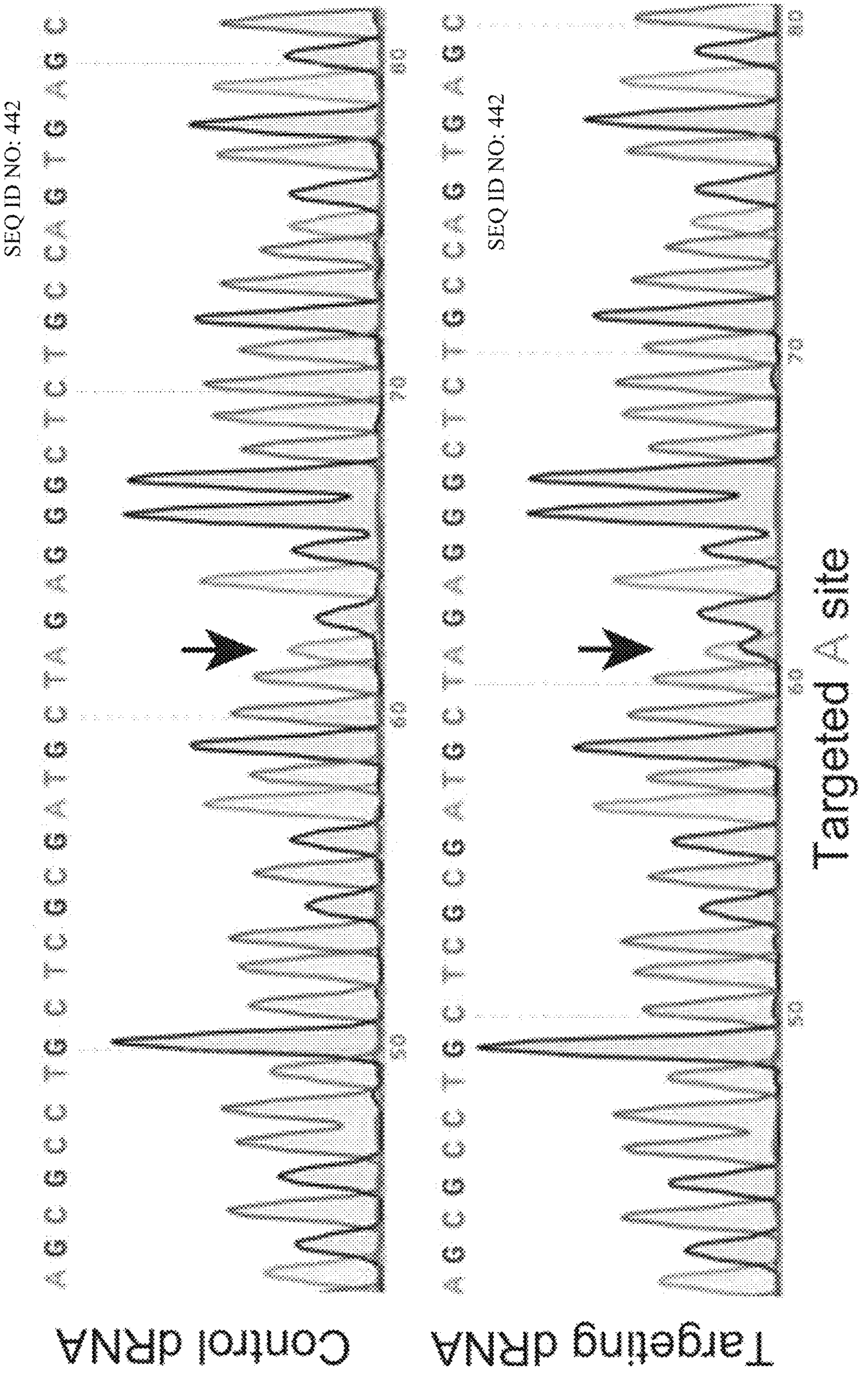

In order to determine the restoration of EGFP fluorescence was due to the targeting RNA editing events, we directly measured the dRNA-mediated editing of Reporter-2 transcripts via RT-PCR followed by targeted Sanger sequencing and Next-generation sequencing. The sequencing results showed the A to G base conversion in the targeted Adenine (A-C mismatch site) and the editing rate could reach to 13% (FIG. 6H and FIG. 1H). Besides, we also observed slightly A to G editing during the sequence windows near the targeted Adenine, most possibly due to the increased duplex RNA regions, later, we would try to get rid of the unexpected editing with several strategies.

Example 2. Optimizing the Factors for Designing dRNAs

Figure 2A:
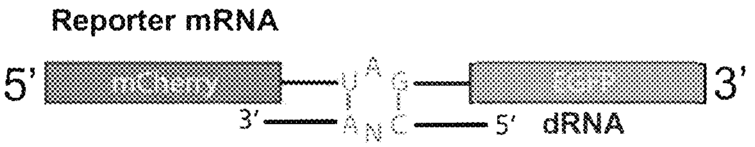
FIGS. 2A-2H show optimization of dRNAs.
Figure 2B:
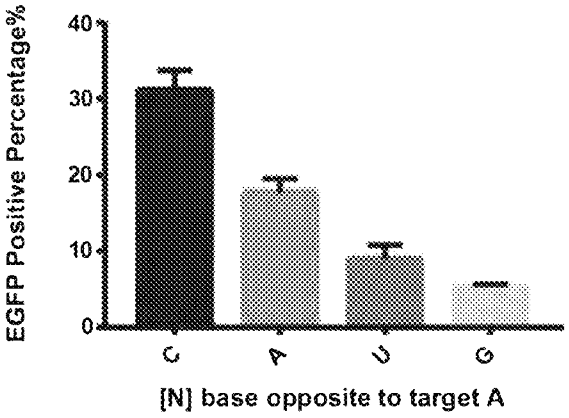
Figure 2C:
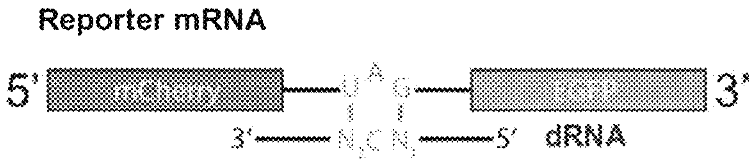
Figure 2D:
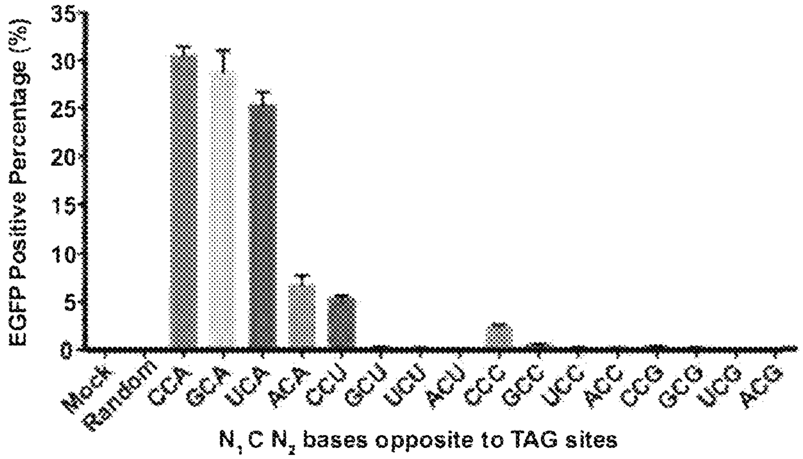
Figure 2E:
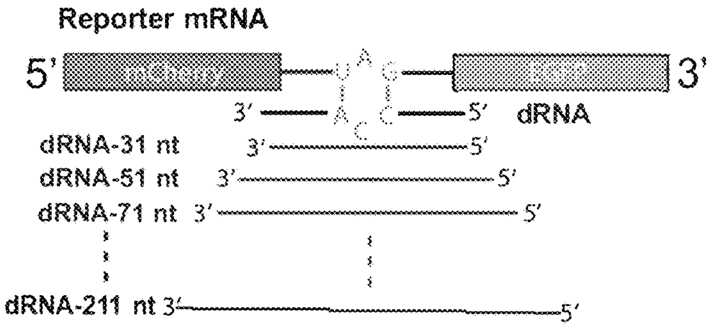
Figure 2F:
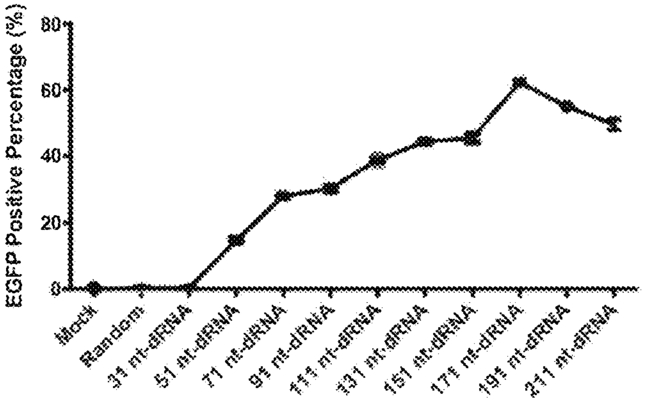
Figure 2G:
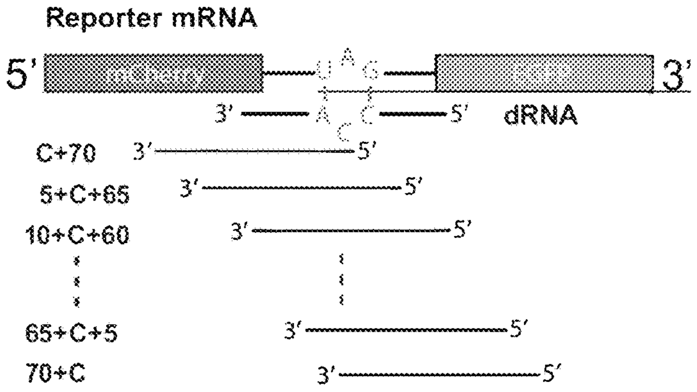
Figure 2H:
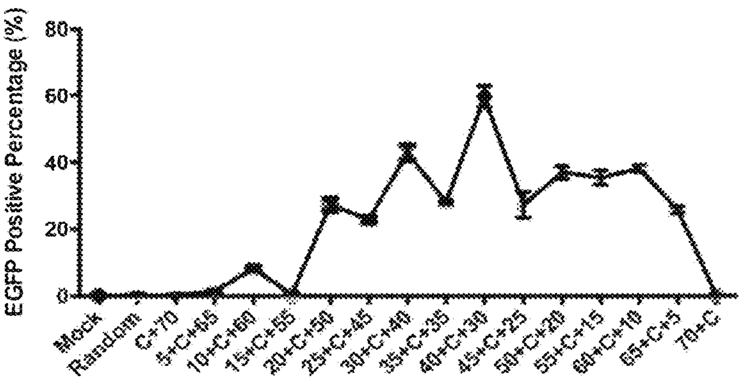

Next, we set out to optimize the dRNA to achieve higher editing efficiency. First, we aimed to determine which base in the opposite site of the targeted adenine favors editing. Previous studies showed the opposite base of targeted adenosine would affect the editing efficiently. We thus designed 71 nt dRNAs with a mismatch N (A, U, C and G) in the middle position opposite to targeted A. Based on the FACS results, we found that the four different dRNAs editing efficiently as follow: C>A>U>G (FIGS. 2A and 2B). Recently, it has been reported that little bubble in the target UAG site may be of benefit to the editing efficiency. Therefore, we designed dRNAs containing two or three mismatch bases with target UAG site to test our hypothesis. 16 different 71 nt dRNAs were designed and constructed on the dRNA vector with BFP marker using Golden Gate cloning method. We found that the dRNAs with CCA and GCA sequence are of the highest efficiency, which means the little bubble contribute little to A-I editing, at least in the case of UAG target site. Besides, four dRNAs of NCA sequence have higher percentage of GFP positive cells, leading to the conclusion that complementary U-A base pair may be important for ADAR editing (FIGS. 2C and 2D). Subsequently, we test the efficiency of different length of dRNA based on Reporter. dRNAs were designed a mismatch C in the middle position with different length ranging from 31 nt to 221 nt. We found that editing efficiency increases with longer dRNA. The peak of editing of reporter system is located at 171 nt dRNA. 51 ntdRNA could light up reporter system with a good efficiency (18%) (FIGS. 2E and 2F). Finally, we examined whether the position of mismatch C of dRNA affect the editing efficiency. dRNAs were kept the same 71 nt length, a mismatch C in different position from transcription beginning was designed. Based on the FACS results, we found that the location of the opposite mismatch C could affect the editing efficiency, and the mismatch C located in the 5' or 3' of dRNA has a lower efficiency (FIGS. 2G and 2H).

16 different reporter comprising target sequences containing all possible 3 base motifs were constructed through Gibson cloning, and then cloned into pLenti backbone (pLenti-CMV-MCS-SV-Bsd, Stanley Cohen Lab, Stanford University). The target sequences are shown as follows.

```
Target sequences containing all
possible 3 base motifs:
TAT:
                                (SEQ ID NO: 9)
atggacgagctgtacaagctgcagggcggaggagg

cagcgcctgctcgcgatgctatagggctctgccag

tgagcaagggcgaggagctgttcaccggggtggtg

cccatc
```

```
-continued
TAA:
                                (SEQ ID NO: 10)
atggacgagctgtacaagctgcagggcggaggagg

cagcgcctgctcgcgatgctaaagggctctgccag

tgagcaagggcgaggagctgttcaccggggtggtg

cccatc

TAC:
                                (SEQ ID NO: 11)
atggacgagctgtacaagctgcagggcggaggagg

cagcgcctgctcgcgatgctacagggctctgccag

tgagcaagggcgaggagctgttcaccggggtggtg

cccatc

TAG:
                                (SEQ ID NO: 12)
atggacgagctgtacaagctgcagggcggaggagg

cagcgcctgctcgcgatgctagagggctctgccag

tgagcaagggcgaggagctgttcaccggggtggtg

cccatc

AAT:
                                (SEQ ID NO: 13)
atggacgagctgtacaagctgcagggcggaggagg

cagcgcctgctcgcgatgcaatagggctctgccag

tgagcaagggcgaggagctgttcaccggggtggtg

cccatc

AAA:
                                (SEQ ID NO: 14)
atggacgagctgtacaagctgcagggcggaggagg

cagcgcctgctcgcgatgcaaaagggctctgccag

tgagcaagggcgaggagctgttcaccggggtggtg

cccatc

AAC:
                                (SEQ ID NO: 15)
atggacgagctgtacaagctgcagggcggaggagg

cagcgcctgctcgcgatgcaacagggctctgccag

tgagcaagggcgaggagctgttcaccggggtggtg

cccatc

AAG:
                                (SEQ ID NO: 16)
atggacgagctgtacaagctgcagggcggaggagg

cagcgcctgctcgcgatgcaagagggctctgccag

tgagcaagggcgaggagctgttcaccggggtggtg

cccatc

CAT:
                                (SEQ ID NO: 17)
atggacgagctgtacaagctgcagggcggaggagg

cagcgcctgctcgcgatgccatagggctctgccag

tgagcaagggcgaggagctgttcaccggggtggtg

cccatc
```

-continued

CAA:

(SEQ ID NO: 18)

```
atggacgagctgtacaagctgcagggcggaggagg
cagcgcctgctcgcgatgccaaagggctctgccag
tgagcaagggcgaggagctgttcaccggggtggtg
cccatc
```

CAC:

(SEQ ID NO: 19)

```
atggacgagctgtacaagctgcagggcggaggagg
cagcgcctgctcgcgatgccacagggctctgccag
tgagcaagggcgaggagctgttcaccggggtggtg
cccatc
```

CAG:

(SEQ ID NO: 20)

```
atggacgagctgtacaagctgcagggcggaggagg
cagcgcctgctcgcgatgccagagggctctgccag
tgagcaagggcgaggagctgttcaccggggtggtg
cccatc
```

GAT:

(SEQ ID NO: 21)

```
atggacgagctgtacaagctgcagggcggaggagg
cagcgcctgctcgcgatgcgatagggctctgccag
tgagcaagggcgaggagctgttcaccggggtggtg
cccatc
```

GAA:

(SEQ ID NO: 22)

```
atggacgagctgtacaagctgcagggcggaggagg
cagcgcctgctcgcgatgcgaaagggctctgccag
tgagcaagggcgaggagctgttcaccggggtggtg
cccatc
```

GAC:

(SEQ ID NO: 23)

```
atggacgagctgtacaagctgcagggcggaggagg
cagcgcctgctcgcgatgcgacagggctctgccag
tgagcaagggcgaggagctgttcaccggggtggtg
cccatc
```

GAG:

(SEQ ID NO: 24)

```
atggacgagctgtacaagctgcagggcggaggagg
cagcgcctgctcgcgatgcgagagggctctgccag
tgagcaagggcgaggagctgttcaccggggtggtg
cccatc
```

dRNAs were kept same 111 bp length and designed a mismatch C at the center towards the target A.

In 12-well cell culture cluster, $2\times10^5$ cells HEK293T were plated to the each well and each experiment was performed for three replicates. 24 hrs later, 0.5 μg dRNA plasmid and 0.5 μg reporter target plasmid were co-transfected to the cells using the X-tremeGENE HP DNA transfection reagent (Roche). 48 hrs later, cells were trypsinized and selected for mCherry positive cells through FACS (BD). A total of $4\times10^5$ cells were harvested and total RNA was extracted using RNAprep pure Cell/Bacteria Kit (TIANGEN DP430). The cDNAs were synthesized from 2 μg of total RNA using Quantscript RT Kit (TIANGEN KR103-04). And the 111 target regions were amplified through PCR and sent for deep sequencing.

Figure 3A:
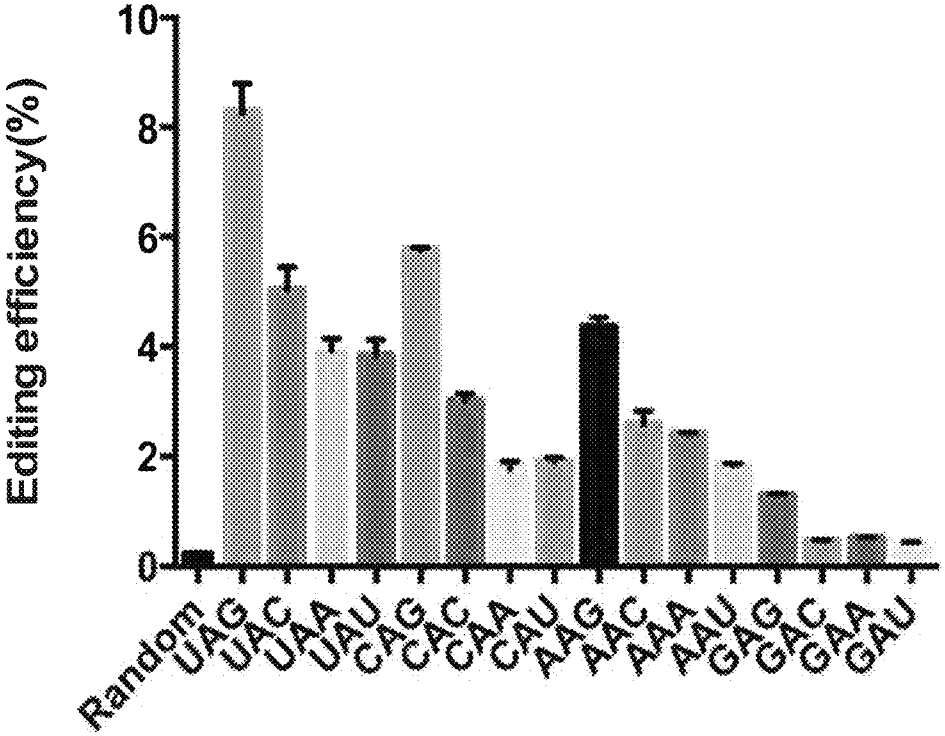
FIGS. 3A-3B show editing flexibility for endogenous RNA editing through exemplary RNA editing method of the present application.
Figure 3B:
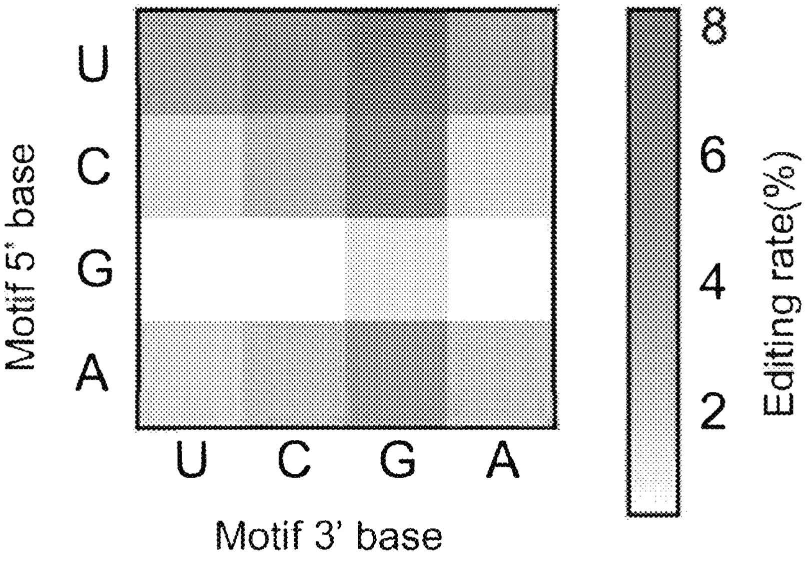

We found that all 16 different 3 base motifs can be edited through an exemplary RNA editing method of the present application, albeit with a variable efficiency. In sum, the results indicate the 5' nearest neighbor of A to be edited has the preference U>C≈A>G and 3' nearest neighbor of A to be edited has the preference G>C>A≈U. Data were presented as bar chart in FIG. 3A or heatmap of FIG. 3B.

Example 3. Editing RNA Transcribed from Endogenous Genes

Figure 4A:
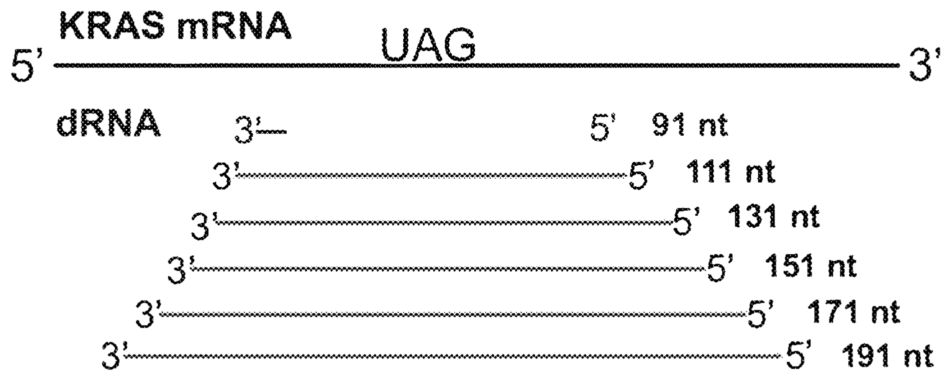
FIGS. 4A-4H show editing the mRNA of endogenous genes with dRNA in 293T cells.

Next, we tested whether dRNA could mediate mRNA transcribed from endogenous genes. We designed dRNA targeting four genes KRAS, PPIB, R-Actin and GAPDH. For KRAS mRNA, we designed 91, 111, 131, 151, 171 and 191 nucleotides long dRNAs (FIG. 4A) with sequences as shown below.

91-nt KRAS-dRNA (SEQ ID NO: 25)

```
uagcuguaucgucaaggcacucuugccuacgccacc
agcuccaaccaccacaaguuuauauucagucauuuu
cagcaggccucucucccgc
```

111-nt KRAS-dRNA (SEQ ID NO: 26)

```
gauucugaauuagcuguaucgucaaggcacucuugc
cuacgccaccagcuccaacuaccacaaguuuauauu
cagucauuuucagcaggccucucucccgcaccuggg
agc
```

131-nt KRAS-dRNA (SEQ ID NO: 27)

```
uccacaaaaugauucugaauuagcuguaucgucaagg
cacucuugccuacgccaccagcuccaacuaccacaag
uuuauauucagucauuuucagcaggccucucucccgc
accugggagccgcugagccu
```

151-nt KRAS-dRNA (SEQ ID NO: 28)

```
aucauauucguccacaaaaugauucugaauuagcugua
ucgucaaggcacucuugccuacgccaccagcuccaacc
accacaaguuuauauucagucauuuucagcaggccucu
cucccgcaccugggagccgcugagccucuggccccgc
```

171-nt KRAS-dRNA (SEQ ID NO: 29)

```
cuauuguuggaucauauucguccacaaaaugauucuga
auuagcuguaucgucaaggcacucuugccuacgccacc
agcuccaaccaccacaaguuuauauucagucauuuuca
gcaggccucucucccgcaccugggagccgcugagccuc
uggccccgccgccgccuuc
```

Figure 4B:
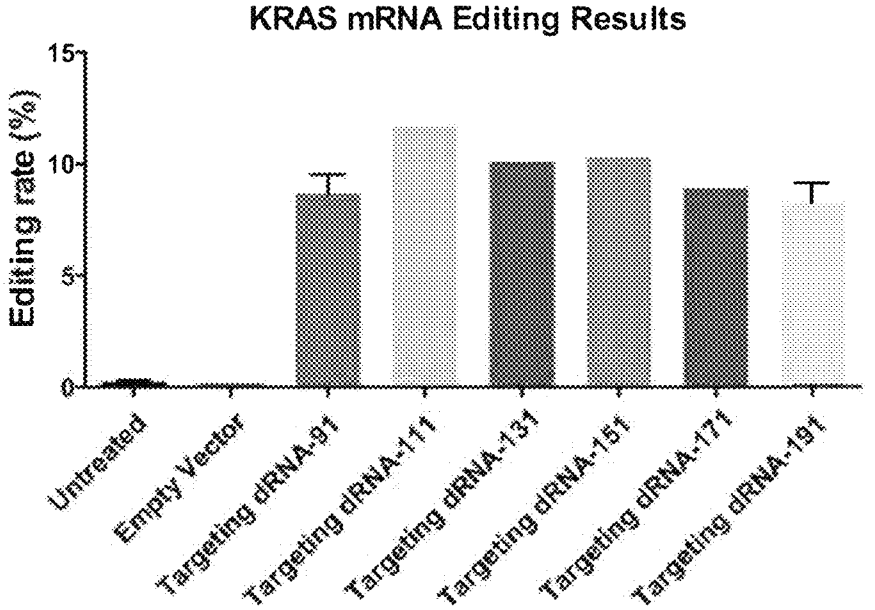
Figure 4C:
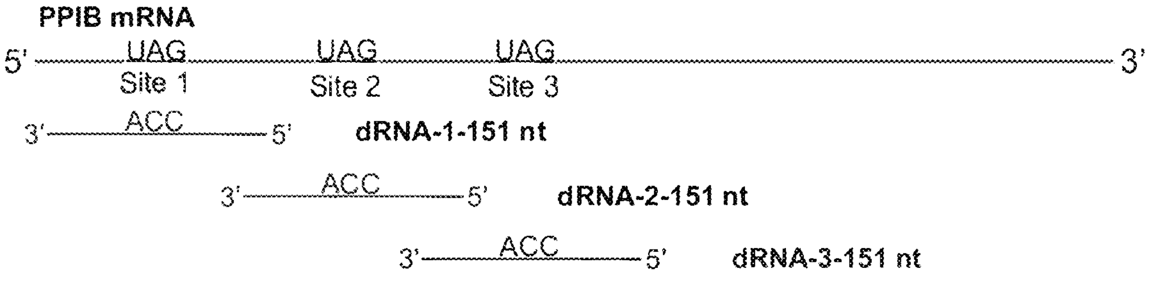

-continued 191-nt KRAS-dRNA
(SEQ ID NO: 30)
uaggaauccucuauuguuggaucauauucguccacaaa augauucugaauuagcuguaucgucaaggcacucuugc cuacgccaccagcuccaaccaccacaaguuuauauuca gucauuuucagcaggccucucuccccgcaccugggagcc gcugagccucuggccccgccgccgccuucagugccugc g The Next-generation sequencing results showed that the dRNAs could edit the targeted KRAS mRNA with up to 11.7% editing efficiency (FIG. 4B). For endogenous PPIB mRNA, the targeted three sites: site1, site2 and site3. We designed 151 nucleotides long dRNA for each site (FIG. 4C) with sequences as shown below. 151-nt PPIB-dRNA (site 1)

Figure 4D:
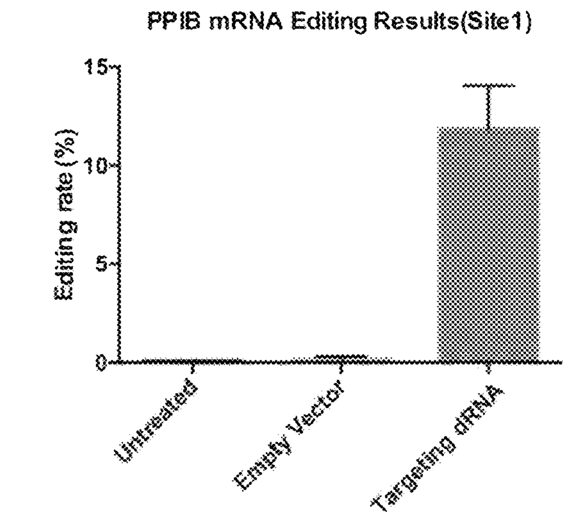
Figure 4E:
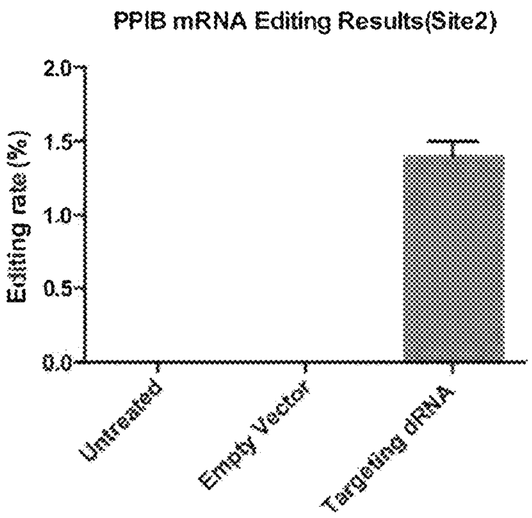
Figure 4F:
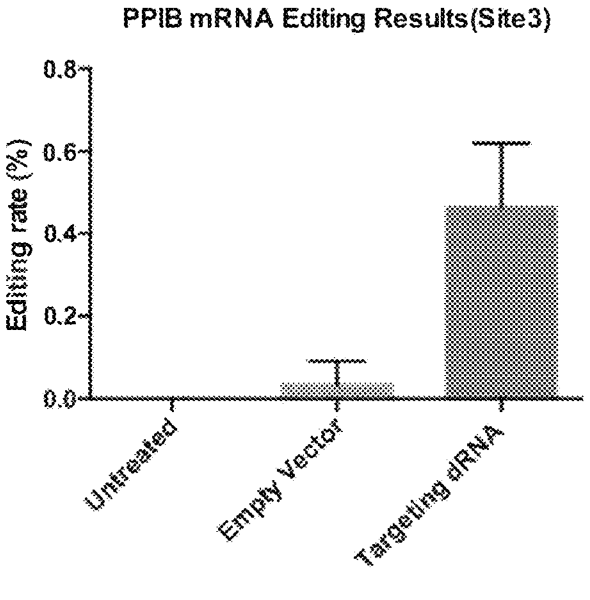

(SEQ ID NO: 31)
gaggcgcagcauccacaggcggaggcgaaagcagcccgga cagcugaggccggaagagggugggggccgcgguggccaggg agccggcgccgccacgcgcgggugggggggacugggguug cucgcgggcuccgggcgggcggcgggcgccg 151-nt PPIB-dRNA (site 2)
(SEQ ID NO: 32)
uccuguagcuaaggccacaaaauuauccacuguuuuugga acagucuuuccgaagagaccaaagaucacccggcccacau cuucaucuccaauucguaggucaaaanacaccuugacggu gacuuugggccccuucuucuucucaucggcc 151-nt PPIB-dRNA (site 3)
(SEQ ID NO: 33)
gcccuggaucaugaaguccuugauuacacgauggaauuug cuguuuuuguagccaaauccuuucucuccuguagccaagg ccacaaaauuauccacuguuuuuggaacagucuuuccgaa gagaccaaagaucacccggccuacaucuuca The Next-generation sequencing results showed that the dRNA could edit PPIB mRNA site1 efficiently with up to 14% editing rate (FIG. 4D). For PPIB mRNA site2 and site3, the editing efficiency was 1.5% and 0.6% (FIGS. 4E and 4F). For endogenous $-Actin mRNA, we selected two targeted site and designed dRNA for each site (FIG. 4G) with sequences as shown below.

Figure 4H:
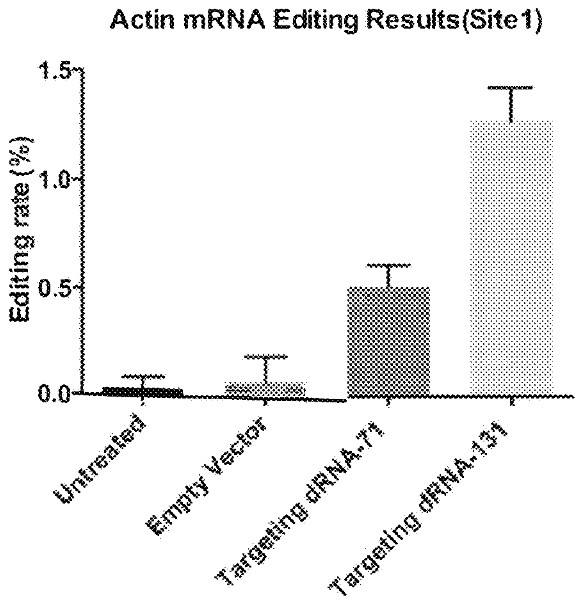
Figure 8A:
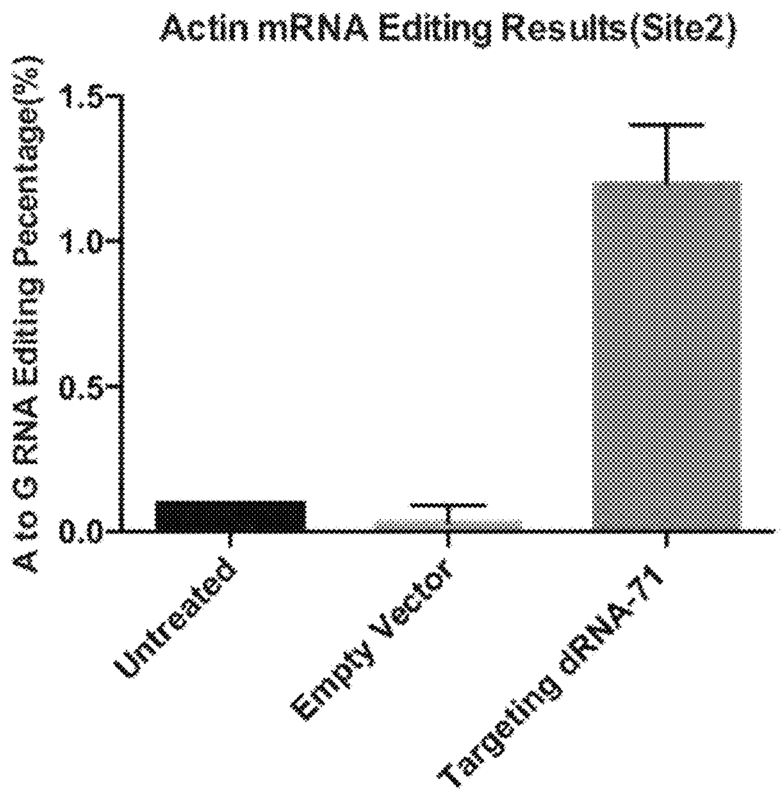
FIGS. 8A-8B shows editing the mRNA of endogenous genes with dRNA in 293T cells.
Figure 8B:
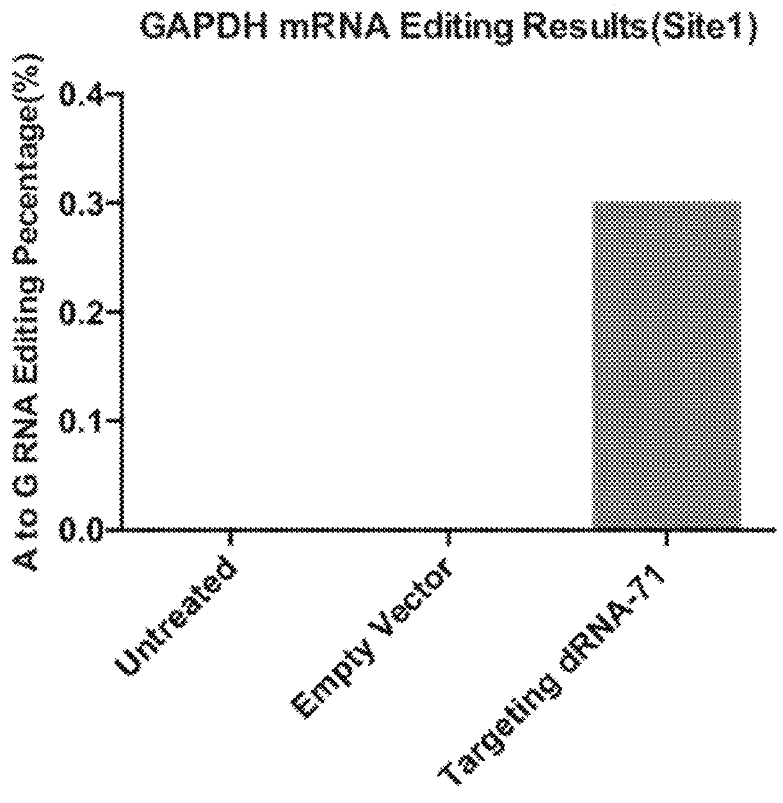

72-nt β-Actin-dRNA (site 1)
(SEQ ID NO: 34)
gcgcaagunagguuuugucaagaaagggguguaacgcaacc aagucauaguccgccuagaagcauuugggug 131-nt β-Actin-dRNA (site 1)
(SEQ ID NO: 35)
gccaugccaaucucaucuuguuuucugcgcaaguuagguu uugucaagaaaggguguaacgcaaccaagucauaguccgc cuagaagcauuugcgguggacgauggaggggccggacucg ucauacuccug -continued 70-nt β-Actin-dRNA (site 2)
(SEQ ID NO: 36)
ggacuuccuguaacaacgcaucucauauuuggaaugacca uuaaaaaaacaacaaugugcaaucaaaguc We found that dRNA could edit @-Actin mRNA both site1 and site2, with up to 1.4% editing efficiency for each site (FIG. 4H and FIG. 8A). We also observed longer dRNA conferred higher editing efficiency, with 0.6% for dRNA-71 nt and 1.4% for dRNA-131 nt (FIG. 3H). For another housekeeping gene GAPDH, we used 71 nt dRNA (caaggugcggcuccggccccucccucuucaaggggguccacauggcaacugugaggaggggagauucagug (SEQ ID NO: 37)), and the editing efficiency is 0.3%, may be due to the short dRNA length (FIG. 8B).

Example 4. Off-Targeting Analysis on an Exemplary LEAPER Method

Figure 5A:
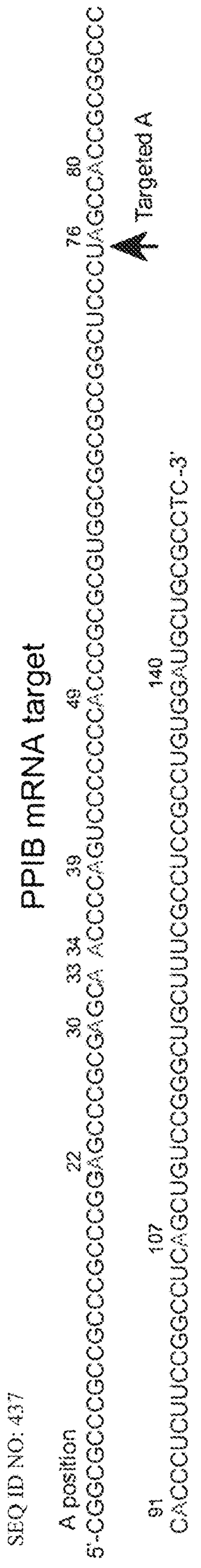
Figure 5B:
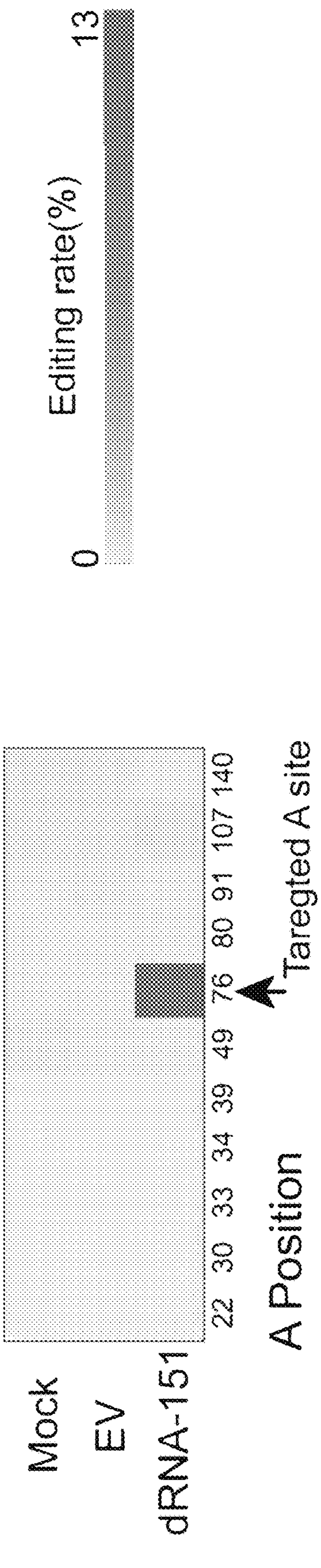

For therapeutic application, the precision of editing is pivotal. Next, we tried to characterize the specificity of an exemplary RNA editing system of the present application. We selected endogenous PPIB site1 and KRAS site for analysis. For PPIB site1, we could see during the dRNA covered regions, there were several A bases flanking the targeted A76, such as A22, A30, A33, A34, A39, A49, A80, A91, A107 and A140. It revealed that those flanking A bases were barely edited, while the targeted A76 base (A-C mismatch) showed up to 14% editing efficiency (FIGS. 5A and 5B).

Figure 5C:
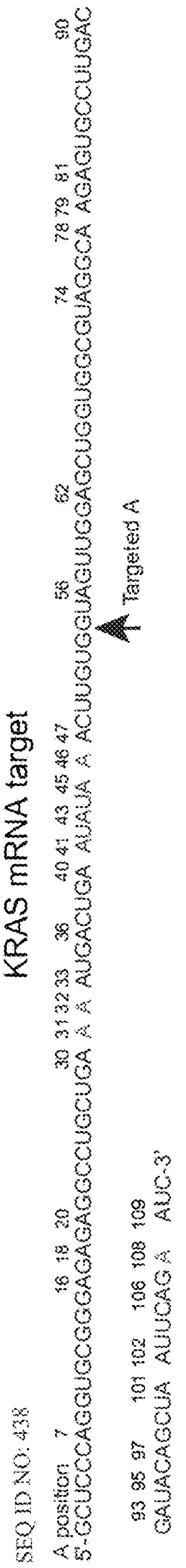
Figure 5D:
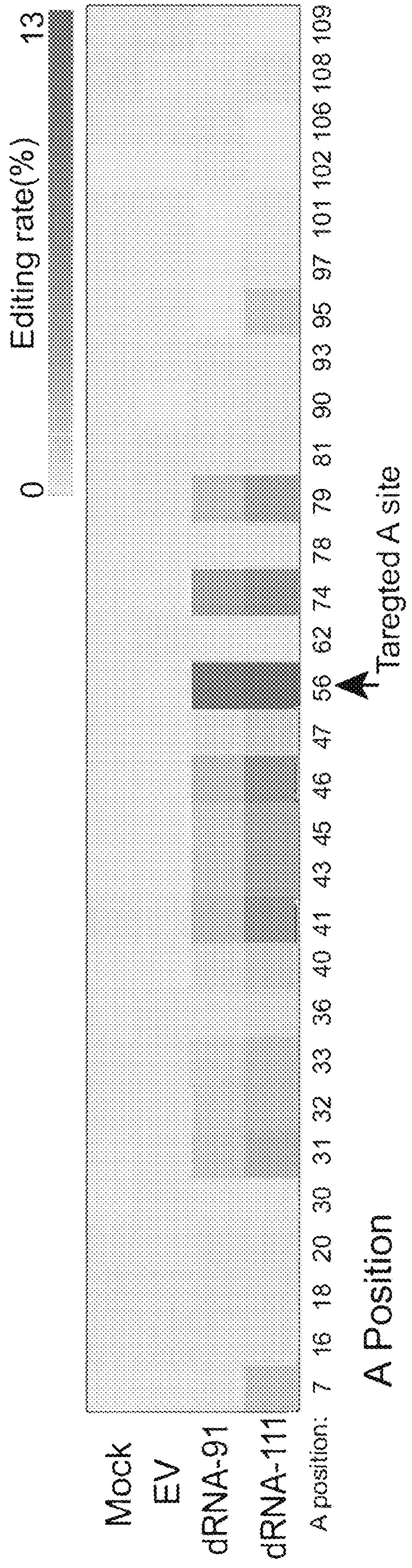

As for KRAS site, we could see in the dRNA covered region, there are many adenines flanking the targeted A56 base, up to 29 flanking A bases. From the KRAS mRNA editing results, we found that while the targeted A56 base (A-C mismatch) showed up to 11.7% editing efficiency, the flanking adenine could be edited (FIGS. 5C and 5D). A variety of the off-targeted adenines were edited, while adenines such as A41, A43, A45, A46, A74, A79 showed more editing. We found the 5' nearest neighbor of those unedited A bases were G or C, whereas the 5' nearest neighbor of those efficiently edited adenines was T or A. Based on this observation, we set out to design dRNA to minimize the off-target editing of those adenines that are prone to be edited. In our study, we have found ADAR preferred A-C mismatch to A-A, A-U, and, the A-G mismatch was the least preferred. So, we proposed that for the off-targeting A bases to which the 5' nearest neighbor was U or A, A-G mismatch might reduce or diminish the off-targeting effects. Previous study has reported A-G mismatch could block the deamination editing by ADAR.

So next we designed three kinds of 91-nt dRNA variants and four kinds of 111-nt dRNA variants (with sequences as shown below) containing different A-G mismatch combinations based on the statistical results in FIG. 5D and existing knowledge: dRNA-AG1 (A41, A46, A74); dRNA-AG2 (A41, A43, A45, A46, A74, A79); dRNA-AG3 (A31, A32, A33, A41, A43, A45, A46, A47, A74, A79); dRNA-AG4 (A7, A31, A32, A33, A40, A41, A43, A45, A46, A47, A74, A79, A95) (FIG. 4E).

KRAS-dRNA-91-AG2

(SEQ ID NO: 38)
UAGCUGUAUCGUCAAGGCACUCgUGCCgACGCCACCAGCUCC

AACcACCACAAGgggAgAgUCAGUCAgggUCAGCAGGCCUCU

CUCCCGC

KRAS-dRNA-91-AG3
(SEQ ID NO: 39)
UAGCUGUAUCGUCAAGGCACUCUUGCCgACGCCACCAGCUCC

AACcACCACAAGUgUAUAgUCAGUCAUUUUCAGCAGGCCUCU

CUCCCGC

KRAS-dRNA-91-AG4
(SEQ ID NO: 40)
UAGCUGGAUCGUCAAGGCACUCGUGCCGACGCCACCAGCUCC

AACCACCACAAGGGGAGAGGCAGUCAGGGUCAGCAGGCCUCU

CUCCCGC

KRAS-dRNA-111-AG1
(SEQ ID NO: 41)
GAUUCUGAAUUAGCUGUAUCGUCAAGGCACUCUUGCCgACGC

CACCAGCUCCAACcACCACAAGUgUAUAgUCAGUCAUUUUCA

GCAGGCCUCUCUCCCGCACCUGGGAGC

KRAS-dRNA-111-AG2
(SEQ ID NO: 42)
GAUUCUGAAUUAGCUGUAUCGUCAAGGCACUCgUGCCgACGC

CACCAGCUCCAACcACCACAAGUggAgAgUCAGUCAUUUUCA

GCAGGCCUCUCUCCCGCACCUGGGAGC

KRAS-dRNA-111-AG3
(SEQ ID NO: 43)
GAUUCUGAAUUAGCUGUAUCGUCAAGGCACUCgUGCCgACGC

CACCAGCUCCAACcACCACAAGgggAgAgUCAGUCAgggUCA

GCAGGCCUCUCUCCCGCACCUGGGAGC

KRAS-dRNA-111-AG4
(SEQ ID NO: 44)
GCUCCCCGGUGCGGGAGAGAGGCCUGCUGACCCUGACUGCCU

CUCCCCUUGUGGUGGUUGGAGCUGGUGGCGUCGGCACGAGUG

CCUUGACGAUCCAGCUAAUUCAGAAUC

Figure 4G:
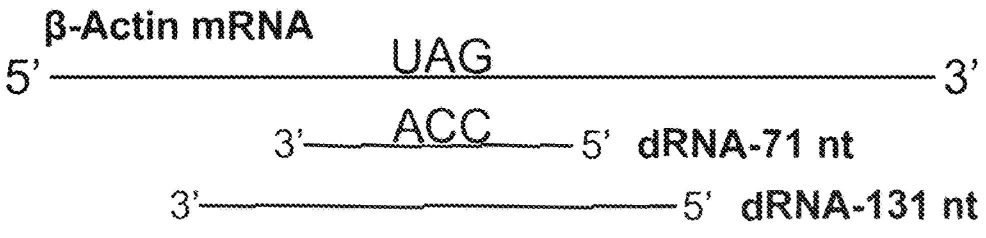

Then these dRNAs were transfected into HEK293T cells, and empty vector and 71-nt non-targeting dRNA control: (tctcagtccaatgtatggtccgagcacaagctctaatcaaagtccgcgggtgta-gaccggttgccatagga (SEQ ID NO: 45)) were used as negative controls. For 91-nt dRNAs, the deep sequencing results showed that the on-target editing (A56) was reduced to 2.8% for dRNA-91-AG2, 2.3% for dRNA-91-AG3 and 0.7% for dRNA-91-AG4, compared to the on-target editing (A56) efficiency 7.9% for dRNA-91 without A-G mismatch (FIG. 4F). For 91-nt dRNAs, the on-target editing (A56) was reduced to 5.1% for dRNA-111-AG2 and 4.9% for dRNA-111-AG3 compared to the on-target editing (A56) efficiency 15.1% for dRNA-111 without A-G mismatch (FIG. 4F), which indicating longer dRNA could bear more A-G mismatch. So next we selected 111-nt dRNA for detailed off-target analysis. The flanking A bases editing were wiped out dramatically except for A7 and A79 (FIG. 4G). For A7 base, the off-target effect could be prevented by a further A-G mismatch design at this site, which is absent in the current dRNA design. For A79 base, introducing adjacent two A-G mismatch A78/A79 might help to wipe out the off-target effects. Based on such results, applying the RNA editing systems of the present application to cure genetic diseases is very promising and encouraging.

Example 5. Testing an Exemplary LEAPER Method in Multiple Cell Lines

Figure 9:
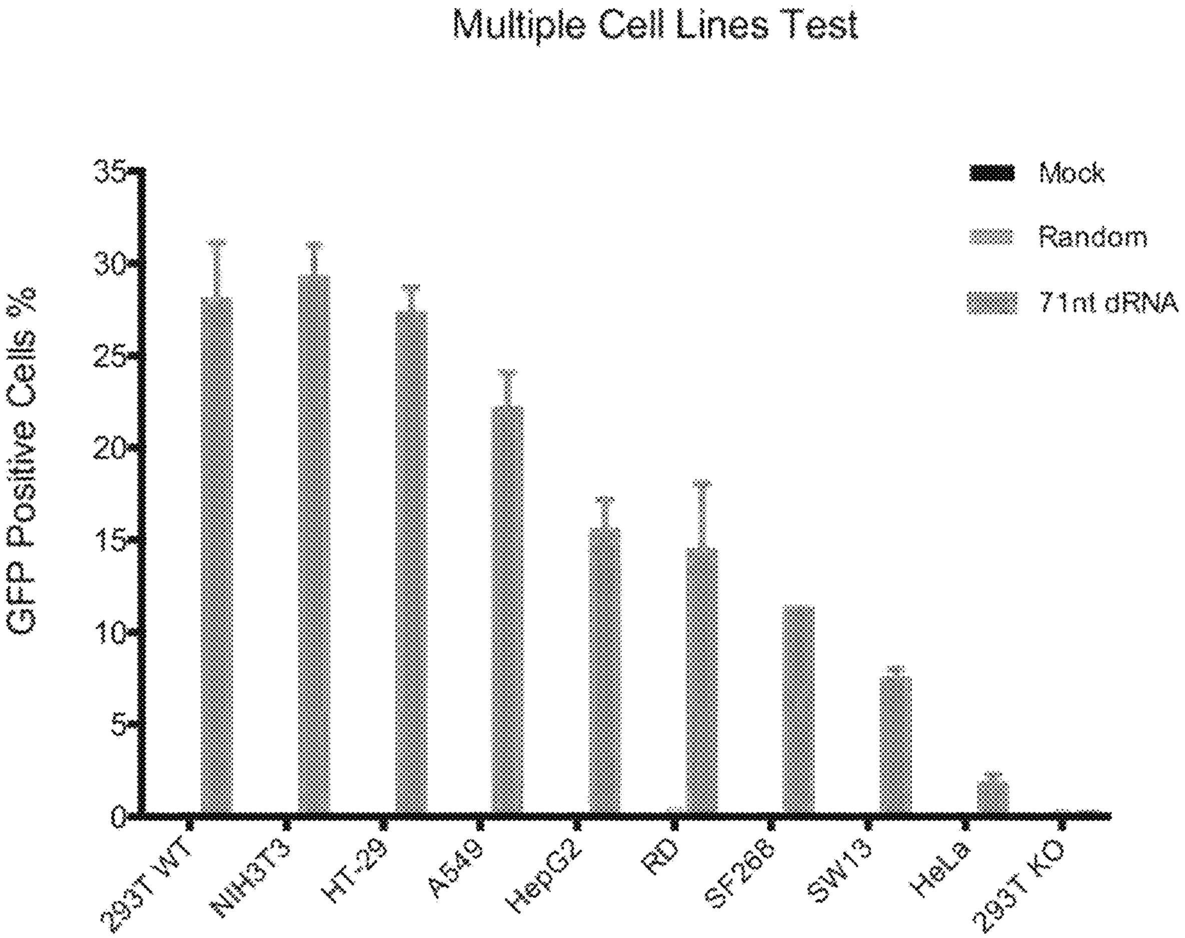
FIG. 9 shows RNA editing by dRNA in different cell lines.

Through the results in HEK293T cells, we supposed that the double strand RNA formed by linear dRNA and its target RNA could recruit endogenous ADAR protein for A-I editing. To confirm the hypothesis, we chose more cell lines to test our RNA editing method. The results are shown in FIG. 9. Those results in multiple cell lines proved the universality of our RNA editing method. Firstly, despite of the various editing efficiency, using dRNA to recruit endogenous ADAR was suitable for multiple human cell lines, which was originated from 7 different tissues and organs. Furthermore, this method could not only work in human cells, but also in mouse cells, providing the possibility to conduct experiments on a mouse.

Example 6. Leveraging Endogenous ADAR for RNA Editing

Figure 10A:
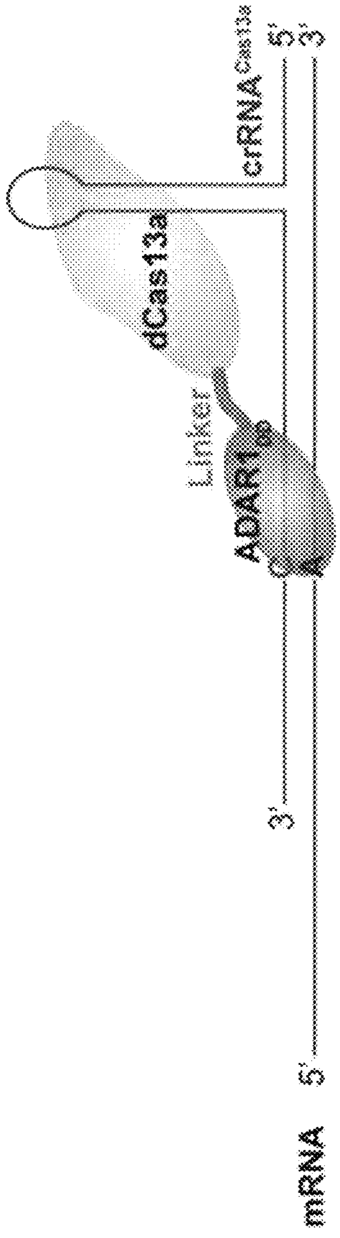
FIGS. 10A-10D show exploration of an efficient exemplary RNA editing platform.
Figure 10B:
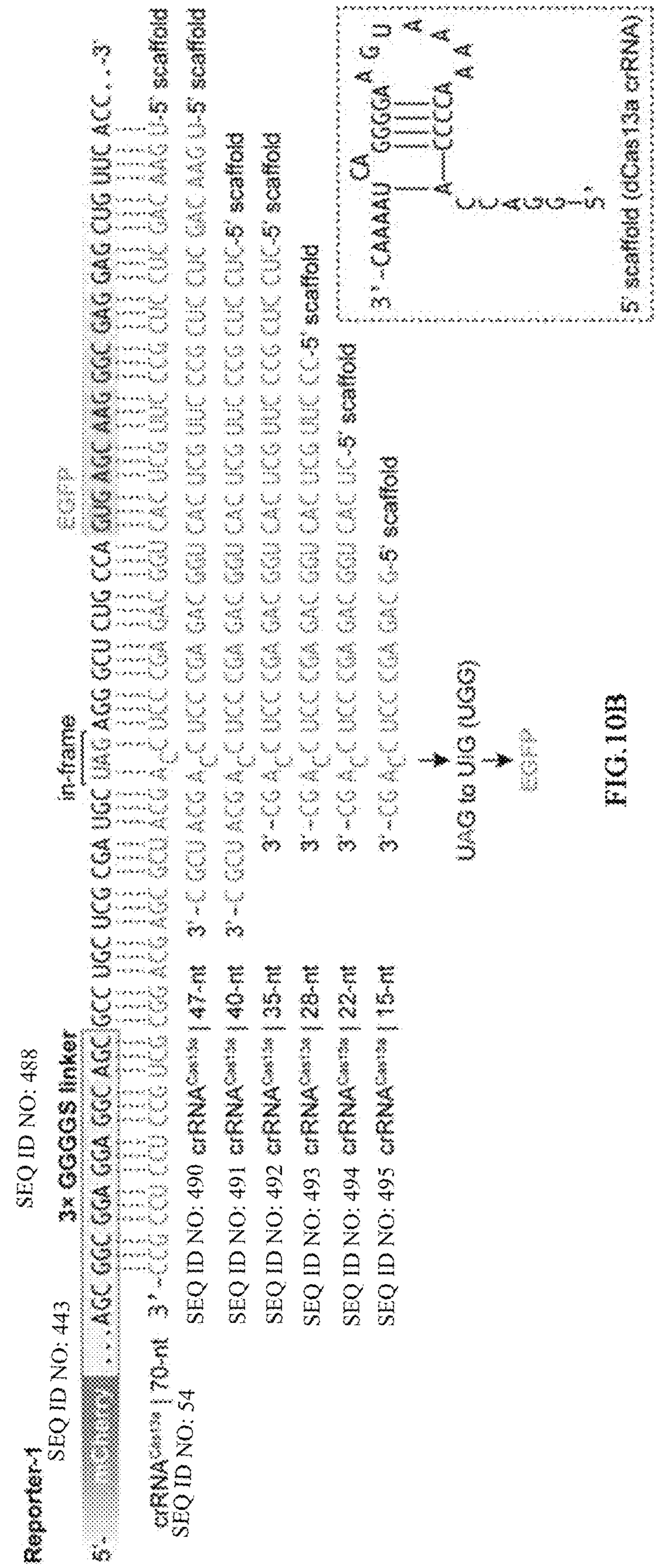

In an attempt to explore an efficient RNA editing platform, we fused the deaminase domain of the hyperactive E1008Q mutant ADAR1 (ADAR1DD)40 to the catalytic inactive LbuCas13 (dCas13a), an RNA-guided RNA-targeting CRISPR effector[41] (FIG. 10A). To assess RNA editing efficiency, we constructed a surrogate reporter harbouring mCherry and EGFP genes linked by a sequence comprising a 3×GGGGS (SEQ ID NO: 488)-coding region and an in-frame UAG stop codon (Reporter-1, FIG. 10B). The reporter-transfected cells only expressed mCherry protein, while targeted editing on the UAG of the reporter transcript could convert the stop codon to UIG and consequently permit the downstream EGFP expression. Such a reporter allows us to measure the A-to-I editing efficiency through monitoring EGFP level. We then designed hU6 promoter-driven crRNAs (CRISPR RNAs) containing 5' scaffolds subjected for Cas13a recognition and variable lengths of spacer sequences for targeting (crRNA$^{Cas13a}$, following LbuCas13 crRNA sequences).

TABLE 2

LbuCas13 crRNA sequences

| Name | Sequence | Source |
|---|---|---|
| LbuCas13/Cas13a crRNA scaffold | ggaccaccccaaaaa ugaaggggacuaaaac (SEQ ID NO: 46) | FIG. 10 |
| Ctrl crRNA$_{70}$ | aaaccgagggaucaua ggggacugaauccacc auucuucucccaaucc cugcaacuccuucuuc cccugc (SEQ ID NO: 47) | FIG. 10 |
| Spacer of crRNA$_{15}$ | gcagagccucCagc (SEQ ID NO: 48) | FIG. 10 |
| Spacer of crRNA$_{22}$ | cucacuggcagagccu cCagc (SEQ ID NO: 49) | FIG. 10 |

TABLE 2-continued

| LbuCas13 crRNA sequences | | |
|---|---|---|
| Name | Sequence | Source |
| Spacer of $crRNA_{28}$ | cccuugcucacuggca<br>gagccucCagc<br>(SEQ ID NO: 50) | FIG. 10 |
| Spacer of $crRNA_{35}$ | cucucgcccuugcuca<br>cuggcagagccucCagc<br>(SEQ ID NO: 51) | FIG. 10 |
| Spacer of $crRNA_{40}$ | cucucgcccuugcuca<br>cuggcagagccucCagc<br>aucgc<br>(SEQ ID NO: 52) | FIG. 10 |
| Spacer of $crRNA_{47}$ | ugaacagcucucgcccu<br>ugcucacuggcagagcc<br>ucCagcaucgc<br>(SEQ ID NO: 53) | FIG. 10 |
| Spacer of $crRNA_{70}$ | ugaacagcuccucgccc<br>uugcucacuggcagagc<br>ccucCagcaucgcgagc<br>aggcgcugccuccuccg<br>cc<br>(SEQ ID NO: 54) | FIG. 10 |

Figure 10C:
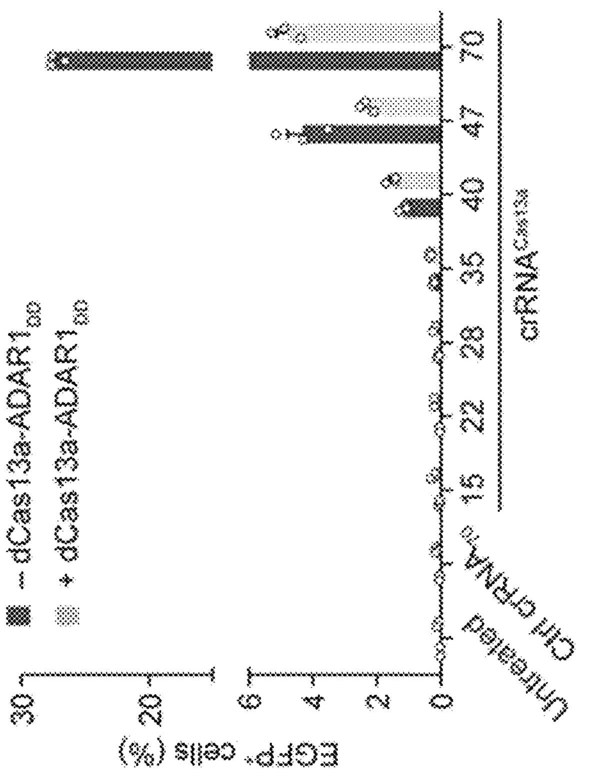
Figure 10D:
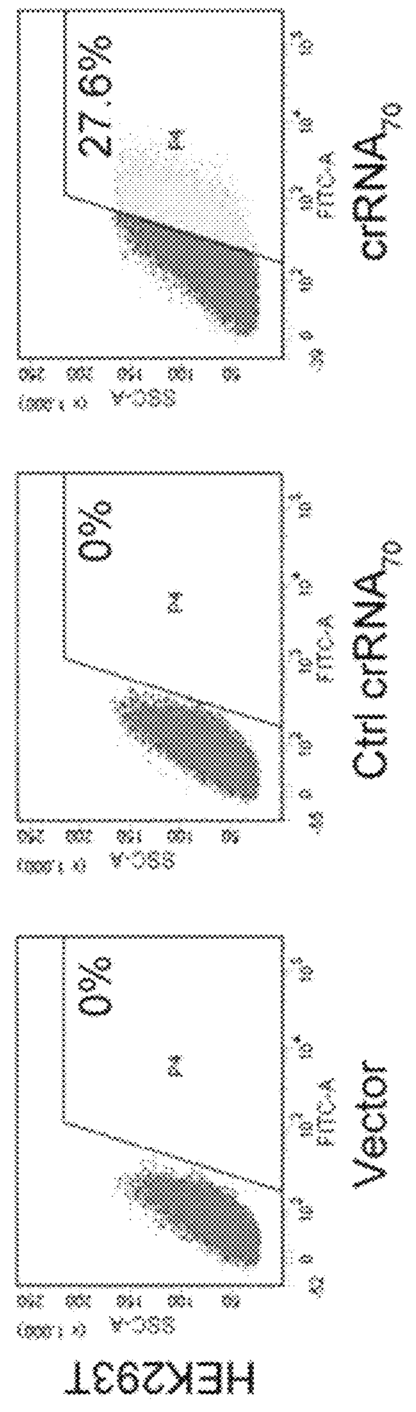

The sequences complementary to the target transcripts all contain CCA opposite to the UAG codon so as to introduce a cytidine (C) mis-pairing with the adenosine (A) (FIG. 10B) because adenosine deamination preferentially occurs in the A-C mismatch site[13,14]. To test the optimal length of the crRNA, non-targeting or targeting crRNAs of different lengths were co-expressed with dCas13a-ADAR1DD proteins in HEK293T cells stably expressing the Reporter-1. Evident RNA editing effects indicated by the appearance of EGFP expression were observed with crRNAs containing matching sequences at least 40-nt long, and the longer the crRNAs the higher the EGFP positive percentage (FIG. 10C). Surprisingly, expression of long $crRNA^{Cas13a}$ alone appeared sufficient to activate EGFP expression, and the co-expression of dCas13a-ADAR1DD rather decreased crRNA activity (FIGS. 10C, 10D). The EGFP expression was clearly sequence-dependent because the 70-nt (exclusive of the 5' scaffold for the length calculation) control RNA could not activate EGFP expression (FIGS. 10C, 10D).

Figure 11A:
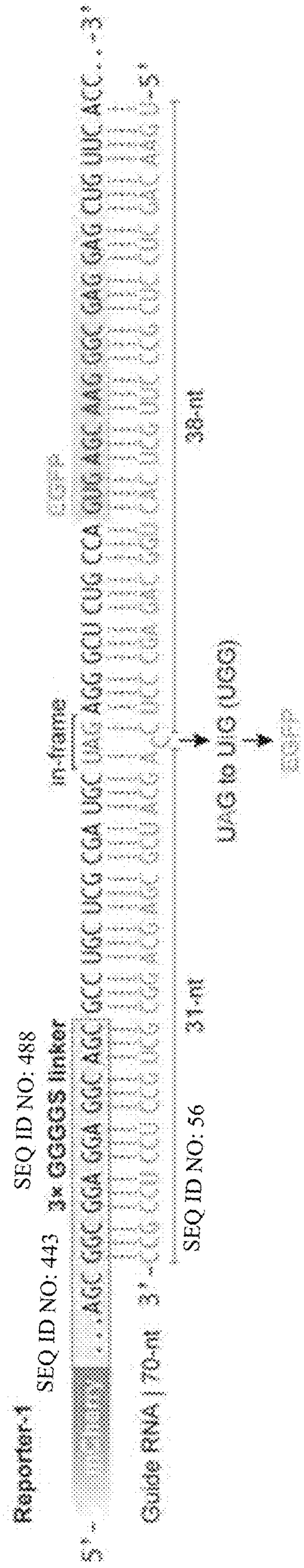
FIGS. 11A-11G show exemplary methods of leveraging endogenous ADAR1 protein for targeted RNA editing.

With the surprising finding that certain long engineered $crRNA^{Cas13a}$ enabled RNA editing independent of dCas13a-$ADAR1_{DD}$, we decided to remove the Cas13a-recruiting scaffold sequence from the crRNA. Because the $crRNA_{70}$ had the highest activity to trigger EGFP expression (FIG. 10C, 10D), we chose the same 70-nt long guide RNA without the Cas13a-recruiting scaffold for further test (FIG. 11A and the Sequences of arRNAs in Table 3 and control RNAs used in the examples).

TABLE 3

Figures 16A, 16B, 16C:
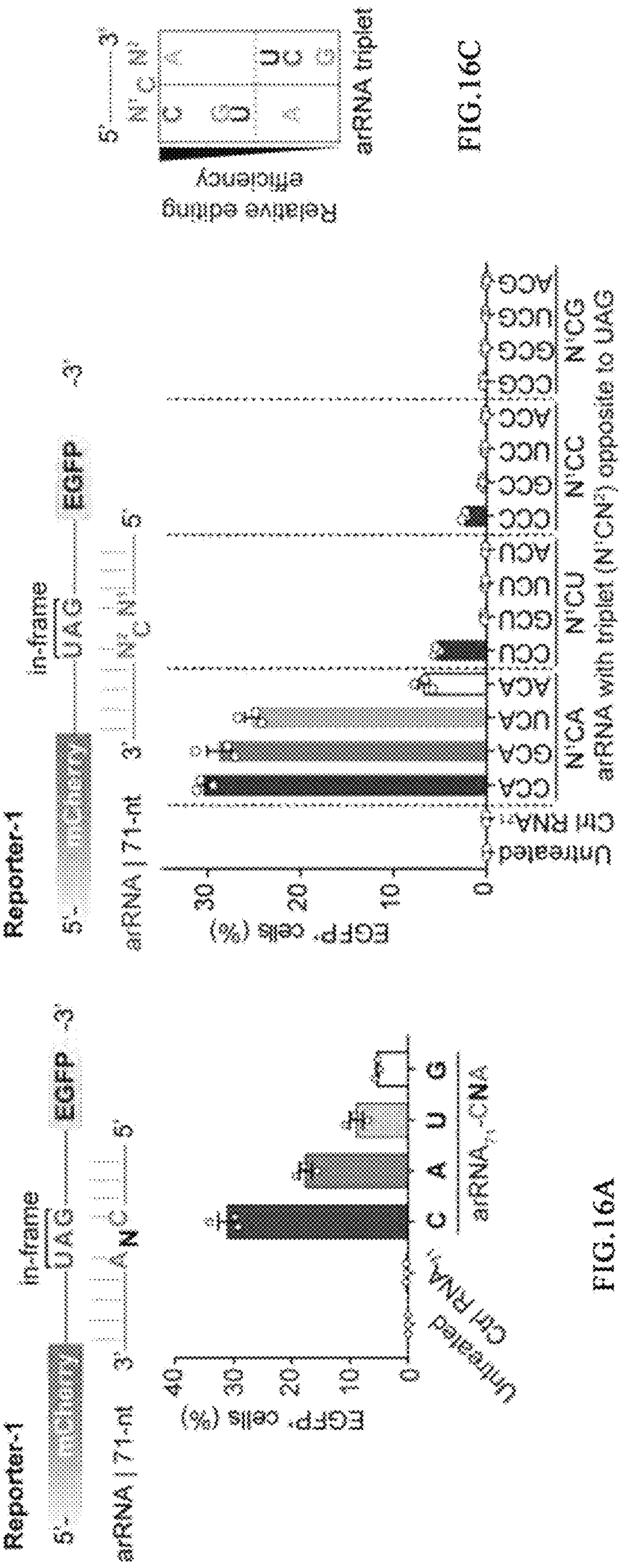
FIGS. 16A-16G show characterization and optimization of exemplary LEAPER methods.

| Name | Sequence (5' -> 3') | Source |
|---|---|---|
| Ctrl $RNA_{70}$ | Aaaccgagggaucauaggggacugaauccaccauucuucucccaaucccugcaacuccuucu<br>uccccugc<br>(SEQ ID NO: 55) | FIG. 11 |
| $arRNA_{70}$ | ugaacagcuccucgcccuugcucacuggcagagcccucCagcaucgcgagcaggcgcugccu<br>ccuccgcc<br>(SEQ ID NO: 56) | |
| Ctrl $RNA_{71}$ | Ucucaguccaauguaugguccgagcacaagcucuaaucaaaguccgcggguguagaccgguu<br>gccauagga<br>(SEQ ID NO: 57) | FIG. 14<br>and<br>FIG. 16 |
| $arRNA_{71}$ | acagcuccucgcccuugcucacuggcagagcccucCagcaucgcgagcaggcgcugccuccu<br>ccgccgcug<br>(SEQ ID NO: 58) | |
| $arRNA_{71}$-CAA | acagcuccucgcccuugcucacuggcagagcccucAagcaucgcgagcaggcgcugccuccu<br>ccgccgcug<br>(SEQ ID NO: 59) | FIG. 16A |
| $arRNA_{71}$-CUA | acagcuccucgcccuugcucacuggcagagcccucUagcaucgcgagcaggcgcugccuccu<br>ccgccgcug<br>(SEQ ID NO: 60) | |
| $arRNA_{71}$-CGA | acagcuccucgcccuugcucacuggcagagcccucGagcaucgcgagcaggcgcugccuccu<br>ccgccgcug<br>(SEQ ID NO: 61) | |
| $arRNA_{71}$-GCA | acagcuccucgcccuugcucacuggcagagcccuGCAgcaucgcgagcaggcgcugccuccu<br>ccgccgcug<br>(SEQ ID NO: 62) | FIG. 16B,<br>c |
| $arRNA_{71}$-UCA | acagcuccucgcccuugcucacuggcagagcccuUCAgcaucgcgagcaggcgcugccuccu<br>ccgccgcug<br>(SEQ ID NO: 63) | |
| $arRNA_{71}$-ACA | acagcuccucgcccuugcucacuggcagagcccuACAgcaucgcgagcaggcgcugccuccu<br>ccgccgcug<br>(SEQ ID NO: 64) | |
| $arRNA_{71}$-CCU | acagcuccucgcccuugcucacuggcagagcccuCCUgcaucgcgagcaggcgcugccuccu<br>ccgccgcug<br>(SEQ ID NO: 65) | |
| $arRNA_{71}$-GCU | acagcuccucgcccuugcucacuggcagagcccuGCUgcaucgcgagcaggcgcugccuccu<br>ccgccgcug<br>(SEQ ID NO: 66) | |
| $arRNA_{71}$-UCU | acagcuccucgcccuugcucacuggcagagcccuUCUgcaucgcgagcaggcgcugccuccu<br>ccgccgcug<br>(SEQ ID NO: 67) | |

TABLE 3-continued

Figure 16D:
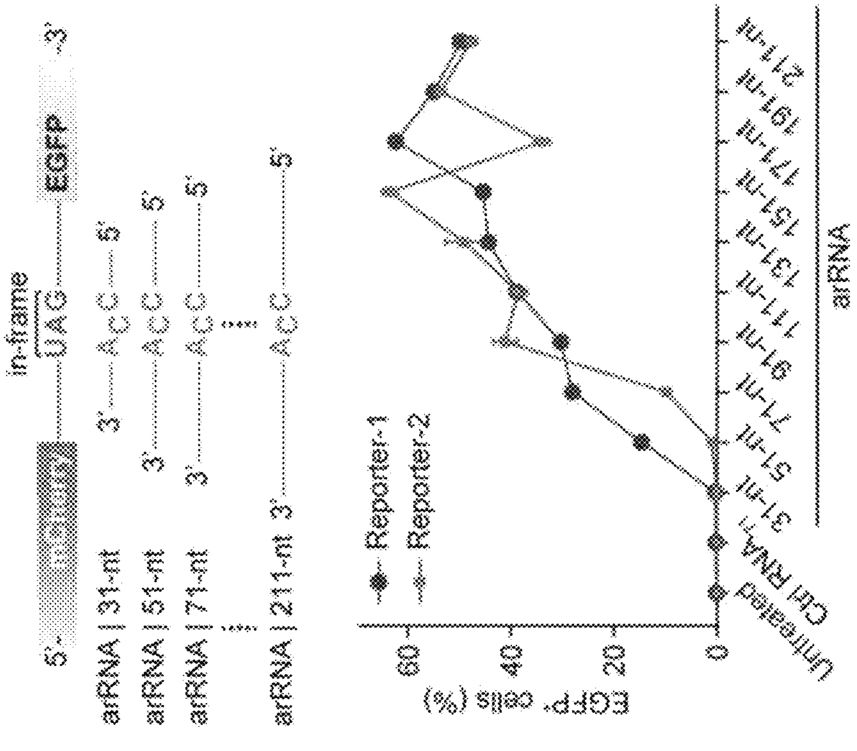

| Name | Sequence (5' -> 3') | Source |
|---|---|---|
| arRNA$_{71}$-ACU | acagcuccucgcccuugcucacuggcagagcccuACUgcaucgcgagcaggcgcugccuccuccgccgcug (SEQ ID NO: 68) | |
| arRNA$_{71}$-CCC | acagcuccucgcccuugcucacuggcagagcccuCCCgcaucgcgagcaggcgcugccuccuccgccgcug (SEQ ID NO: 69) | |
| arRNA$_{71}$-GCC | acagcuccucgcccuugcucacuggcagagcccuGCCgcaucgcgagcaggcgcugccuccuccgccgcug (SEQ ID NO: 70) | |
| arRNA$_{71}$-UCC | acagcuccucgcccuugcucacuggcagagcccuUCCgcaucgcgagcaggcgcugccuccuccgccgcug (SEQ ID NO: 71) | |
| arRNA$_{71}$-ACC | acagcuccucgcccuugcucacuggcagagcccuACCgcaucgcgagcaggcgcugccuccuccgccgcug (SEQ ID NO: 72) | |
| arRNA$_{71}$-CCG | acagcuccucgcccuugcucacuggcagagcccuCCGgcaucgcgagcaggcgcugccuccuccgccgcug (SEQ ID NO: 73) | |
| arRNA$_{71}$-GCG | acagcuccucgcccuugcucacuggcagagcccuGCUgcaucgcgagcaggcgcugccuccuccgccgcug (SEQ ID NO: 74) | |
| arRNA$_{71}$-UCG | acagcuccucgcccuugcucacuggcagagcccuUCGgcaucgcgagcaggcgcugccuccuccgccgcug Q ID NO: 75) | |
| arRNA$_{71}$-ACG | acagcuccucgcccuugcucacuggcagagcccuACGgcaucgcgagcaggcgcugccuccuccgccgcug (SEQ ID NO: 76) | |
| arRNA$_{31}$-Reporter-1 | acuggcagagcccucCagcaucgcgagcagg (SEQ ID NO: 77) | FIG. 16D and FIG. 27 |
| arRNA$_{51}$-Reporter-1 | acccuugcucacuggcagagcccucCagcaucgcgagcaggcgcugccucc (SEQ ID NO: 78) | |
| arRNA$_{91}$-Reporter-1 | acagcuccucgcccuugcucacuggcagagcccucCagcaucgcgagcaggcgcugccuccuccgccgcug (SEQ ID NO: 79) | |
| arRNA$_{111}$-Reporter-1 | accccggugaacagcuccucgcccuugcucacuggcagagcccucCagcaucgcgagcaggcgcugccuccuccgccgcugccuccuccgc (SEQ ID NO: 80) | |
| arRNA$_{131}$-Reporter-1 | gcucgaccaggaugggcaccaccccggugaacagcuccucgcccuugcucacuggcagagcccucCagcaucgcgagcaggcgcugccuccuccgccgcugccuccuccgccgcugccuccuccgcccugc (SEQ ID NO: 81) | |
| arRNA$_{151}$-Reporter-1 | ucgccguccagcucgaccaggaugggcaccaccccggugaacagcuccucgcccuugcucacuggcagagcccucCagcaucgcgagcaggcgcugccuccuccgccgcugccuccuccgccgcugccuccuccgcccugcagcuuguaca (SEQ ID NO: 82) | |
| arRNA$_{171}$-Reporter-1 | gccguuuacgucgccguccagcucgaccaggaugggcaccaccccggugaacagcuccucgcccuugcucacuggcagagcccucCagcaucgcgagcaggcgcugccuccuccgccgcugccuccuccgccgcugccuccuccgcccugcagcuuguacagcucguccau (SEQ ID NO: 83) | |
| arRNA$_{191}$-Reporter-1 | ugaacuuguggccguuuacgucgccguccagcucgaccaggaugggcaccaccccggugaacagcuccucgcccuugcucacuggcagagcccucCagcaucgcgagcaggcgcugccuccuccgccgcugccuccuccgccgcugccuccuccgcccugcagcuuguacagcucguccaugccgccggug (SEQ ID NO: 84) | |
| arRNA$_{211}$-Reporter-1 | ccggacacgcugaacuuguggccguuuacgucgccguccagcucgaccaggaugggcaccaccccggugaacagcuccucgcccuugcucacuggcagagcccucCagcaucgcgagcaggcgcugccuccuccgccgcugccuccuccgccgcugccuccuccgcccugcagcuuguacagcucguccaugccgccgguggaguggcggc (SEQ ID NO: 85) | |
| arRNA$_{31}$-Reporter-2 | gcgaccggggaucucCacagauucuuccggc (SEQ ID NO: 86) | |
| arRNA$_{51}$-Reporter-2 | acucacgguggcgaccggggaucucCacagauucuuccggcguguauaccu (SEQ ID NO: 87) | |
| arRNA$_{71}$-Reporter-2 | ccucgcccuugcucacgguggcgaccggggaucucCacagauucuuccggcguguauaccuucugcugccu (SEQ ID NO: 88) | |
| arRNA$_{91}$-Reporter-2 | gugaacagcuccucgcccuugcucacgguggcgaccggggaucucCacagauucuuccggcguguauaccuucugcugccuccuccgccgc (SEQ ID NO: 89) | |
| arRNA$_{111}$-Reporter-2 | caccaccccggugaacagcuccucgcccuugcucacgguggcgaccggggaucucCacagauucuuccggcguguauaccuucugcugccuccuccgccgcugccuccucc (SEQ ID NO: 90) | |
| arRNA$_{131}$-Reporter-2 | ccaggaugggcaccaccccggugaacagcuccucgcccuugcucacgguggcgaccggggaucucCacagauucuuccggcguguauaccuucugcugccuccuccgccgcugccuccuccgccgcugccu (SEQ ID NO: 91) | |

TABLE 3-continued

Figure 16E:
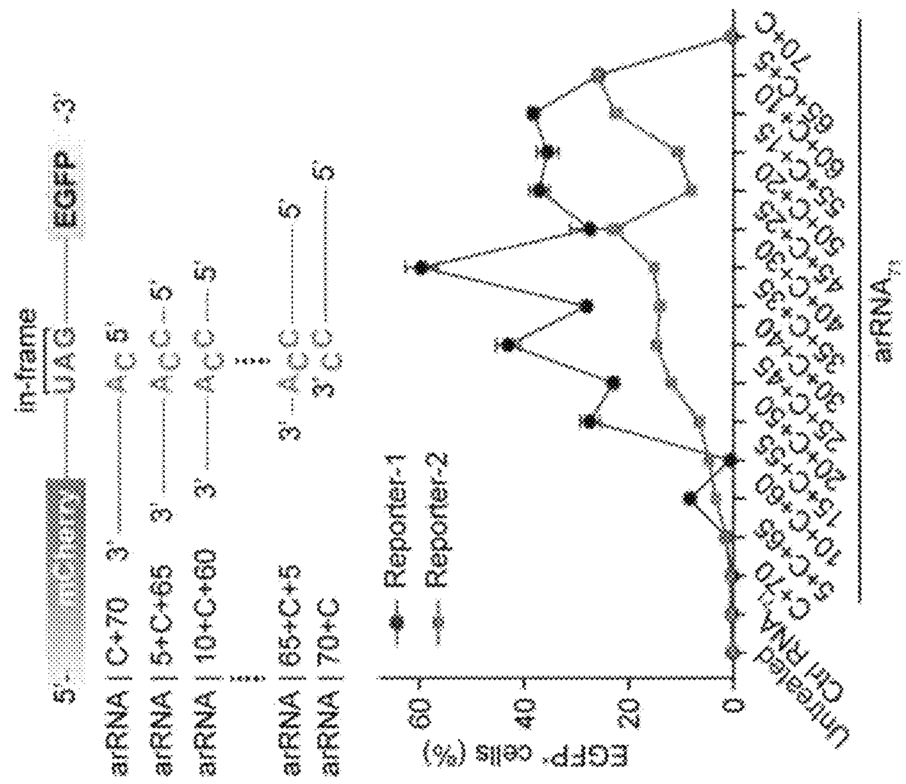

| Name | Sequence (5' -> 3') | Source |
|---|---|---|
| arRNA$_{151}$-Reporter-2 | uccagcucgaccaggaugggcaccaccccggugaacagcuccucgcccuugcucacgguggcgaccggggaucucCacagauucuuccggcguguauaccuucugcugccuccuccgccgcugccuccuccgccgcugccuccuccgcccu (SEQ ID NO: 92) | |
| arRNA$_{171}$-Reporter-2 | cggcgacguauccagcucgaccaggaugggcaccaccccggugaacagcuccucgcccuugcucacgguggcgaccggggaucucCacagauucuuccggcguguauaccuucugcugccuccuccgccgcugccuccuccgccgcugccuccuccgcccugcagcuugua (SEQ ID NO: 93) | |
| arRNA$_{191}$-Reporter-2 | uguggccguuuacgucgccguccagcucgaccaggaugggcaccaccccggugaacagcuccucgcccuugcucacgguggcgaccggggaucucCacagauucuuccggcguguauaccuucugcugccuccuccgccgcugccuccuccgccgcugccuccuccgcccugcagcuuguacagcucgucc (SEQ ID NO: 94) | |
| arRNA$_{211}$-Reporter-2 | acgcugaacuuguggccguuuacgucgccguccagcucgaccaggaugggcaccaccccggugaacagcuccucgcccuugcucacgguggcgaccggggaucucCacagauucuuccggcguguauaccuucugcugccuccuccgccgcugccuccuccgccgcugccuccuccgcccugcagcuuguacagcucguccaugccgccgg (SEQ ID NO: 95) | |
| arRNA$_{71}$(C + 70)-Reporter-1 | Cagcaucgcgagcaggcgcugccuccuccgccgcugccuccuccgccgcugccuccuccgcccugcagcuu (SEQ ID NO: 96) | FIG. 16E |
| arRNA$_{71}$(5 + C + 65)-Reporter-1 | cccucCagcaucgcgagcaggcgcugccuccuccgccgcugccuccuccgccgcugccuccuccgcccugc (SEQ ID NO: 97) | |
| arRNA$_{71}$(10 + C + 60)-Reporter-1 | cagagcccucCagcaucgcgagcaggcgcugccuccuccgccgcugccuccuccgccgcugccuccuccgc (SEQ ID NO: 98) | |
| arRNA$_{71}$(15 + C + 55)-Reporter 1 | acuggcagagcccucCagcaucgcgagcaggcgcugccuccuccgccgcugccuccuccgccgcugccucc (SEQ ID NO: 99) | |
| arRNA$_{71}$(20 + C + 50)-Reporter-1 | ugcucacuggcagagcccucCagcaucgcgagcaggcgcugccuccuccgccgcugccuccuccgccgcug (SEQ ID NO: 100) | |
| arRNA$_{71}$(25 + C + 45)-Reporter-1 | gcccuugcucacuggcagagcccucCagcaucgcgagcaggcgcugccuccuccgccgcugccuccuccgc (SEQ ID NO: 101) | |
| arRNA$_{71}$(30 + C + 40)-Reporter-1 | uccucgcccuugcucacuggcagagcccucCagcaucgcgagcaggcgcugccuccuccgccgcugccucc (SEQ ID NO: 102) | |
| arRNA$_{71}$(40 + C + 30)-Reporter-1 | ggugaacagcuccucgcccuugcucacuggcagagcccucCagcaucgcgagcaggcgcugccuccuccgc (SEQ ID NO: 103) | |
| arRNA$_{71}$(45 + C + 25)-Reporter-1 | accccggugaacagcuccucgcccuugcucacuggcagagcccucCagcaucgcgagcaggcgcugccucc (SEQ ID NO: 104) | |
| arRNA$_{71}$(50 + C + 20)-Reporter-1 | gcaccaccccggugaacagcuccucgcccuugcucacuggcagagcccucCagcaucgcgagcaggcgcug (SEQ ID NO: 105) | |
| arRNA$_{71}$(55 + C + 15)-Reporter-1 | gaugggcaccaccccggugaacagcuccucgcccuugcucacuggcagagcccucCagcaucgcgagcagg (SEQ ID NO: 106) | |
| arRNA$_{71}$(60 + C + 10)-Reporter-1 | accaggaugggcaccaccccggugaacagcuccucgcccuugcucacuggcagagcccucCagcaucgcga (SEQ ID NO: 107) | |
| arRNA$_{71}$(65 + C + 5)-Reporter-1 | gcucgaccaggaugggcaccaccccggugaacagcuccucgcccuugcucacuggcagagcccucCagcau (SEQ ID NO: 108) | |
| arRNA$_{71}$(70 + C)-Reporter-1 | guccagcucgaccaggaugggcaccaccccggugaacagcuccucgcccuugcucacuggcagagcccucC (SEQ ID NO: 109) | |
| arRNA$_{71}$(C + 70)-Reporter-2 | Cacagauucuuccggcguguauaccuucugcugccuccuccgccgcugccuccuccgccgcugccuccucc (SEQ ID NO: 110) | |
| arRNA$_{71}$(5 + C + 65)-Reporter-2 | aucucCacagauucuuccggcgruguauaccuucugcugccuccuccgccgcugccuccuccgccgcugccu (SEQ ID NO: 111) | |
| arRNA$_{71}$(10 + C + 60)-Reporter-2 | cggggaucucCacagauucuuccggcguguauaccuucugcugccuccuccgccgcugccuccuccgccgc (SEQ ID NO: 112) | |
| arRNA$_{71}$(15 + C + 55)-Reporter-2 | gcgaccggggaucucCacagauucuuccggcgruguauaccuucugcugccuccuccgccgcugccuccucc (SEQ ID NO: 113) | |
| arRNA$_{71}$(20 + C + 50)-Reporter-2 | cgguggcgaccggggaucucCacagauucuuccggcgruguauaccuucugcugccuccuccgccgcugccu (SEQ ID NO: 114) | |

TABLE 3-continued

Figure 16G:
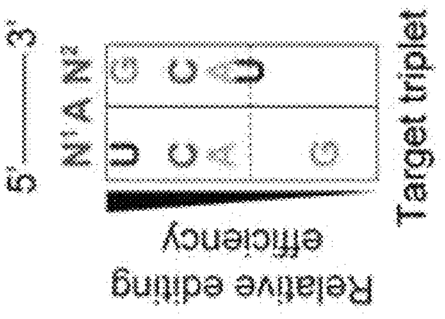
Figure 16F:
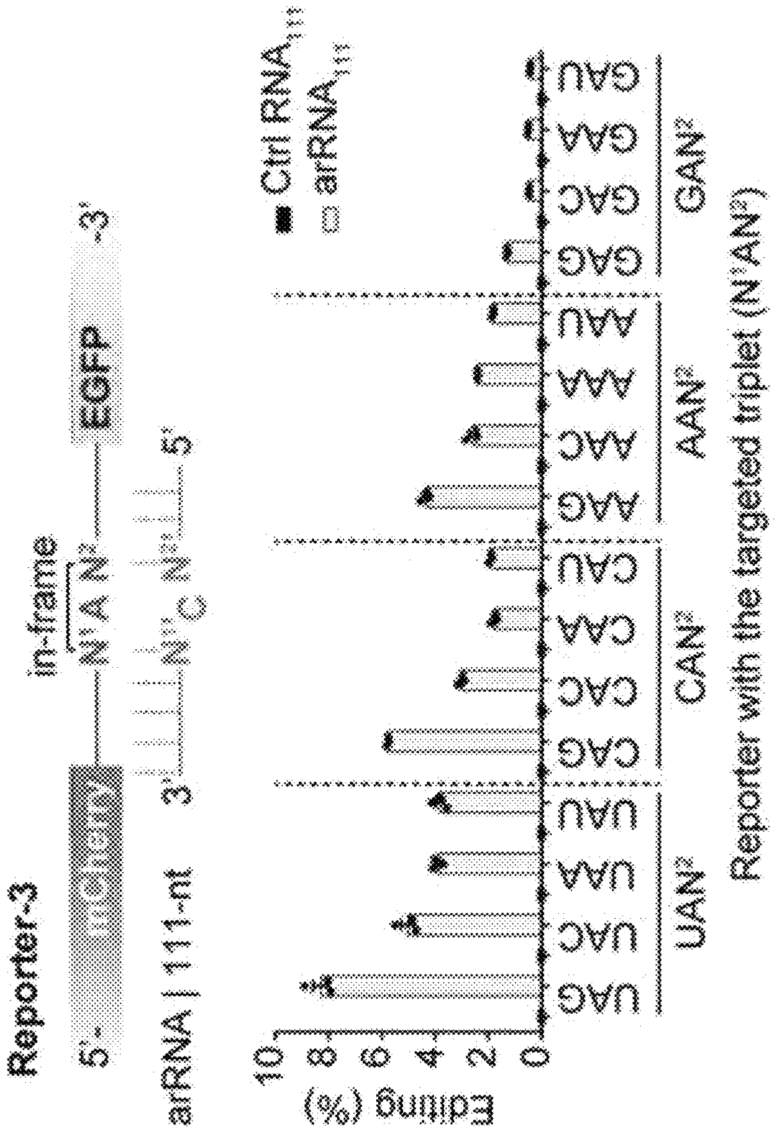

| Name | Sequence (5' -> 3') | Source |
|---|---|---|
| arRNA$_{71}$(25 + C + 45)-<br>Reporter-2 | gcucacgguggcgaccggggaucucCacagauucuuccggcgruguauaccuucugcugccu<br>ccuccgccgc<br>(SEQ ID NO: 115) | |
| arRNA$_{71}$(30 + C + 40)-<br>Reporter-2 | cccuugcucacgguggcgaccggggaucucCacagauucuuccggcguguauaccuucugcu<br>gccuccucc<br>(SEQ ID NO: 116) | |
| arRNA$_{71}$(40 + C + 30)-<br>Reporter-2 | cagcuccucgcccuugcucacgguggcgaccggggaucucCacagauucuuccggcguguau<br>accuucugc<br>(SEQ ID NO: 117) | |
| arRNA$_{71}$(45 + C + 25)-<br>Reporter-2 | gugaacagcuccucgcccuugcucacgguggcgaccggggaucucCacagauucuuccggcg<br>uguauaccu<br>(SEQ ID NO: 118) | |
| arRNA$_{71}$(50 + C + 20)-<br>Reporter-2 | ccccggugaacagcuccucgcccuugcucacgguggcgaccggggaucucCacagauucuuc<br>cggcgugua<br>(SEQ ID NO: 119) | |
| arRNA$_{71}$(55 + C + 15)-<br>Reporter-2 | caccaccccggugaacagcuccucgcccuugcucacgguggcgaccggggaucucCacagau<br>ucuuccggc<br>(SEQ ID NO: 120) | |
| arRNA$_{71}$(60 + C + 10)-<br>Reporter-2 | augggcaccaccccggugaacagcuccucgcccuugcucacgguggcgaccggggaucucCa<br>cagauucuu<br>(SECI ID NO: 121) | |
| arRNA$_{71}$(65 + C + 5)-<br>Reporter-2 | ccaggaugggcaccaccccggugaacagcuccucgcccuugcucacgguggcgaccggggau<br>cucCacaga<br>(SEQ ID NO: 122) | |
| arRNA$_{71}$(70 + C)-<br>Reporter-2 | cucgaccaggaugggcaccaccccggugaacagcuccucgcccuugcucacgguggcgaccg<br>gggaucucC<br>(SEQ ID NO: 123) | |
| arRNA$_{111}$-CCA-<br>Reporter-3 (UAG) | gaugggcaccaccccggugaacagcuccucgcccuugcucacuggcagagcccucCagcauc<br>ccuccuccgcccugcagcuuguacagcucguccau<br>(SEQ ID NO: 124) | FIG. 16F,<br>g |
| arRNA$_{111}$-GCA-<br>Reporter-3 (UAC) | gaugggcaccaccccggugaacagcuccucgcccuugcucacuggcagagcccugCagcauc<br>gcgagcaggcgcu<br>gccuccuccgcccugcagcuuguacagcucguccau<br>(SEQ ID NO: 125) | |
| arRNA$_{111}$-UCA-<br>Reporter-3 (UAA) | gaugggcaccaccccggugaacagcuccucgcccuugcucacuggcagagcccuuCagcauc<br>gcgagcaggcgcugccuccuccgcccugcagcuuguacagcucguccau<br>(SEQ ID NO: 126) | |
| arRNA$_{111}$-ACA-<br>Reporter-3 (UAU) | gaugggcaccaccccggugaacagcuccucgcccuugcucacuggcagagcccuaCagcauc<br>gcgagcaggcgcugccuccuccgcccugcagcuuguacagcucguccau<br>(SEQ ID NO: 127) | |
| arRNA$_{111}$-CCG-<br>Reporter-3 (CAG) | gaugggcaccaccccggugaacagcuccucgcccuugcucacuggcagagcccucCggcauc<br>gcgagcaggcgcugccuccuccgcccugcagcuuguacagcucguccau<br>(SEQ ID NO: 128) | |
| arRNA$_{111}$-GCG-<br>Reporter-3 (CAC) | gaugggcaccaccccggugaacagcuccucgcccuugcucacuggcagagcccugCggcauc<br>gcgagcaggcgcugccuccuccgcccugcagcuuguacagcucguccau<br>(SEQ ID NO: 129) | |
| arRNA$_{111}$-UCG-<br>Reporter-3 (CAA) | gaugggcaccaccccggugaacagcuccucgcccuugcucacuggcagagcccuuCggcauc<br>gcgagcaggcgcugccuccuccgcccugcagcuuguacagcucguccau<br>(SEQ ID NO: 130) | |
| arRNA$_{111}$-ACG-<br>Reporter-3 (CAU) | gaugggcaccaccccggugaacagcuccucgcccuugcucacuggcagagcccuaCggcauc<br>gcgagcaggcgcugccuccuccgcccugcagcuuguacagcucguccau<br>(SEQ ID NO: 131) | |
| arRNA$_{111}$-CCU-<br>Reporter-3 (AAG) | gaugggcaccaccccggugaacagcuccucgcccuugcucacuggcagagcccucCugcauc<br>gcgagcaggcgcugccuccuccgcccugcagcuuguacagcucguccau<br>(SEQ ID NO: 132) | |
| arRNA$_{111}$-GCU-<br>Reporter-3 (AAC) | gaugggcaccaccccggugaacagcuccucgcccuugcucacuggcagagcccugCugcauc<br>gcgagcaggcgcugccuccuccgcccugcagcuuguacagcucguccau<br>(SEQ ID NO: 133) | |
| arRNA$_{111}$-ACU-<br>Reporter-3 (AAA) | gaugggcaccaccccggugaacagcuccucgcccuugcucacuggcagagcccuaCugcauc<br>gcgagcaggcgcugccuccuccgcccugcagcuuguacagcucguccau<br>(SEQ ID NO: 134) | |
| arRNA$_{111}$-UCU-<br>Reporter-3 (AAU) | gaugggcaccaccccggugaacagcuccucgcccuugcucacuggcagagcccuuCugcauc<br>gcgagcaggcgcugccuccuccgcccugcagcuuguacagcucguccau<br>(SEQ ID NO: 135) | |
| arRNA$_{111}$-CCC-<br>Reporter-3 (GAG) | gaugggcaccaccccggugaacagcuccucgcccuugcucacuggcagagcccucCcgcauc<br>gcgagcaggcgcugccuccuccgcccugcagcuuguacagcucguccau<br>(SEQ ID NO: 136) | |
| arRNA$_{111}$-GCC-<br>Reporter-3 (GAC) | gaugggcaccaccccggugaacagcuccucgcccuugcucacuggcagagcccugCcgcauc<br>gcgagcaggcgcugccuccuccgcccugcagcuuguacagcucguccau<br>(SEQ ID NO: 137) | |
| arRNA$_{111}$-UCC-<br>Reporter-3 (GAA) | gaugggcaccaccccggugaacagcuccucgcccuugcucacuggcagagcccuuCcgcauc<br>gcgagcaggcgcugccuccuccgcccugcagcuuguacagcucguccau<br>(SEQ ID NO: 138) | |
| arRNA$_{111}$-ACC-<br>Reporter-3 (GAU) | gaugggcaccaccccggugaacagcuccucgcccuugcucacuggcagagcccuaCcgcauc<br>gcgagcaggcgcugccuccuccgcccugcagcuuguacagcucguccau<br>(SEQ ID NO: 139) | |

TABLE 3-continued

Figure 17B:
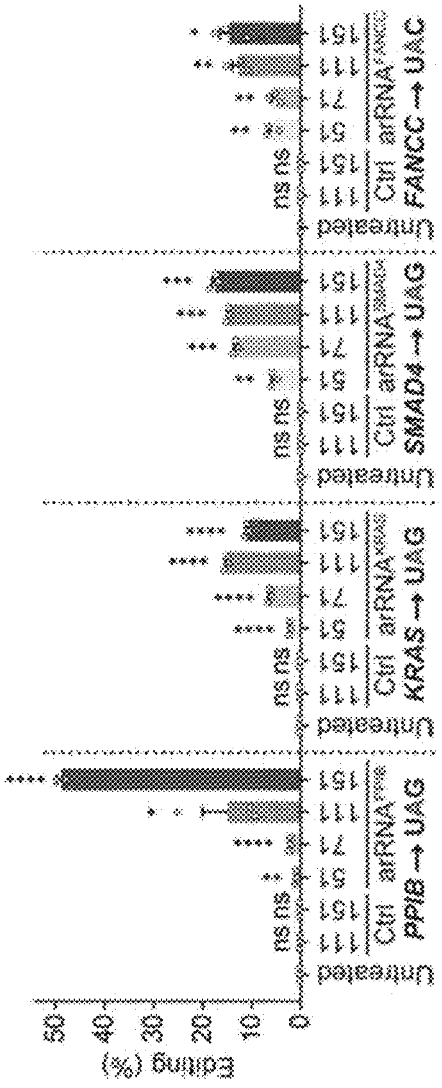
FIGS. 17A-17I show editing of endogenous transcripts with exemplary LEAPER methods.
Figure 17F:
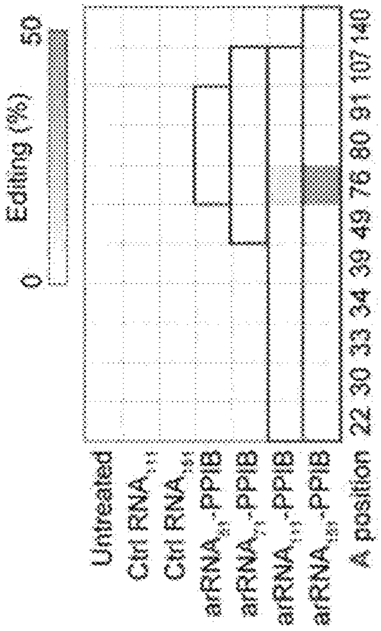
Figure 17D:
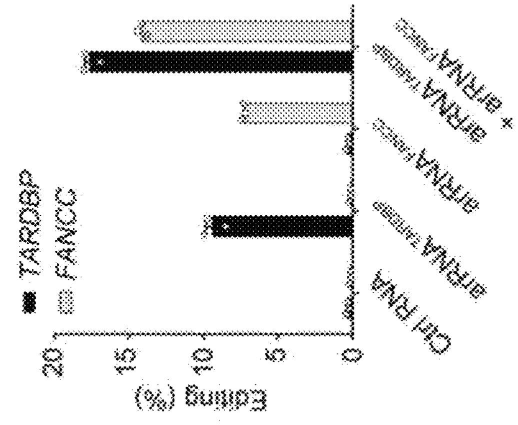
Figure 17A:
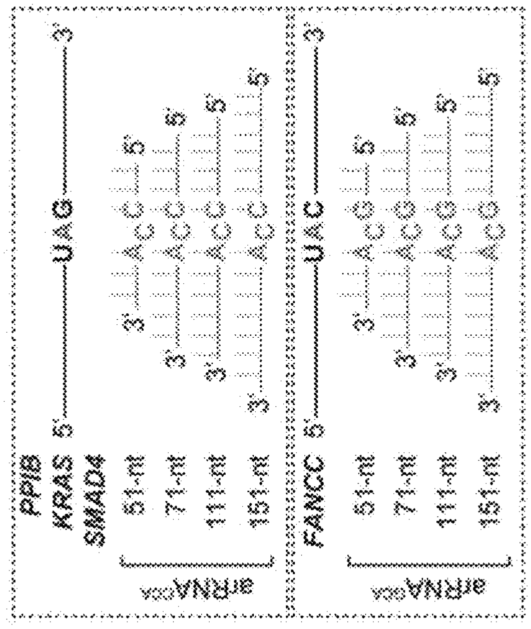
Figure 17C:
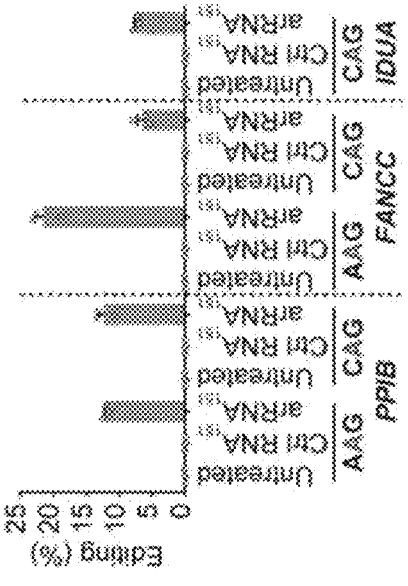

| Name | Sequence (5' -> 3') | Source |
|---|---|---|
| Ctrl RNA$_{111}$ | Uaccgcuacagccacgcugauuucagcuauaccugcccgguauaaagggacguucacaccgc<br>gauguucucugcuggggaauugcgcgauauucaggauuaaaagaagugc<br>(SEQ ID NO: 140) | FIG. 17 |
| Ctrl RNA$_{151}$ | Acuacaguugcuccgauauuuaggcuacgucaauaggcacuaacuuauuggcgcuggugaac<br>ggacuucccucucgaguaccagaagaugacuacaaaacuccuuuccauugcgaguaucggagu<br>cuggcucaguuuggccagggaggcacu<br>(SEQ ID NO: 141) | |
| arRNA$_{51}$-PPIB | cggaagagggugggggccgcgguggcCagggagccggcgccgccacgcgcgg<br>(SEQ ID NO: 142) | FIG. 17B |
| arRNA$_{71}$-PPIB | cagcugaggccggaagagggugggggccgcgguggcCagggagccggcgccgccacgcgcggg<br>ugggggga<br>(SEQ ID NO: 143) | |
| arRNA$_{111}$-PPIB | ggaggcgaaagcagcccggacagcugaggccggaagagggugggggccgcgguggcCagggag<br>ccggcgccgccacgcgcgggugggggggacugggguugcucgcgggcuc<br>(SEQ ID NO: 144) | |
| arRNA$_{151}$-PPIB | gaggcgcagcauccacaggcggaggcgaaagcagcccggacagcugaggccggaagagggug<br>gggccgcgguggcCagggagccggcgccgccacgcgcgggugggggggacugggguugcucg<br>cgggcuccgggcgggcggcgggcgccg<br>(SEQ ID NO: 145) | |
| arRNA$_{51}$-KRAS | ucuugccuacgccaccagcuccaacCaccacaaguuuauauucagucauuu<br>(SEQ ID NO: 146) | |
| arRNA$_{71}$-KRAS | gucaaggcacucuugccuacgccaccagcuccaacCaccacaaguuuauauucagucauuuu<br>cagcaggcc | |
| arRNA$_{111}$-KRAS | GauucugaauuagcuguaucgucaaggcacucuugccuacgccaccagcuccaacCaccaca<br>aguuuauauucagucauuuucagcaggccucucucccgcaccugggagc<br>(SEQ ID NO: 147) | |
| arRNA$_{151}$-KRAS | aucauauucguccacaaaaugauucugaauuagcuguaucgucaaggcacucuugccuacgc<br>caccagcuccaacCaccacaaguuuauauucagucauuuucagcaggccucucucccgcacc<br>ugggagccgcugagccucuggccccgc<br>(SEQ ID NO: 148) | |
| arRNA$_{51}$-SMAD4 | ucggcaugguaugaaguacuucgucCaggagcuggagggcccgguguaagu<br>(SEQ ID NO: 149) | |
| arRNA$_{71}$-SMAD4 | gggucugcaaucggcaugguaugaaguacuucgucCaggagcuggagggcccgguguaagug<br>aauuucaau<br>(SEQ ID NO: 150) | |
| arRNA$_{111}$-SMAD4 | gaccucagucuaaagguuguggggucugcaaucggcaugguaugaaguacuucgucCaggagc<br>uggagggcccgguguaagugaauuucaauccagcaagguguuucuuuga<br>(SEQ ID NO: 151) | |
| arRNA$_{151}$-SMAD4 | uaagggccccaacgguaaaagaccucagucuaaagguuguggggucugcaaucggcaugguau<br>gaaguacuucgucCaggagcuggagggcccgguguaagugaauuucaauccagcaagguguu<br>ucuuugaugcucugucuugguaaucc<br>(SEQ ID NO: 152) | |
| arRNA$_{51}$-FANCC<br>(TAC site) | ugggggguucggcugccgacaucagCaauugcucugccaccaucucagccc<br>(SEQ ID NO: 153) | |
| arRNA$_{71}$-FANCC<br>(TAC site) | agcagggccgugggggguucggcugccgacaucagCaauugcucugccaccaucucagccca<br>uccuccgaa<br>(SEQ ID NO: 154) | |
| arRNA$_{111}$-FANCC<br>(TAC site) | aguagaaggccaagagccacagcagggccgugggggguucggcugccgacaucagCaauugc<br>ucugccaccaucucagcccauccuccgaagugaaugaacaggaaccagc<br>(SEQ ID NO: 155) | |
| arRNA$_{151}$-FANCC<br>(TAC site) | ccucccaucacgggggccguaguagaaggccaagagccacagcagggccgugggggguucgg<br>cugccgacaucagCaauugcucugccaccaucucagcccauccuccgaagugaaugaacagg<br>aaccagcucucaaagggaccuccgcag<br>(SEQ ID NO: 156) | |
| arRNA$_{151}$-PPIB<br>(AAG site) | gccaaacaccacatgcttgccatctagccaggctgtcttgactgtcgtgatgaagaactggg<br>agccgttggtgtcCttgcctgcgttggccatgctcacccagccaggcccgtagtgcttcagt<br>ttgaagttctcatcggggaagcgctca<br>(SEQ ID NO: 157) | FIG. 17C<br>FIG. 17D |
| arRNA$_{151}$-PPIB<br>(CAG site) | gggagtgggtccgctccaccagatgccagcaccggggccagtgcagctcagagccctgtggc<br>ggactacagggccCgcacagacggtcactcaaagaaagatgtccctgtgccctactccttgg<br>cgatggcaaagggcttctccacctcga<br>(SEQ ID NO: 158) | |
| arRNA$_{151}$-FANCC<br>(AAG site) | tgcattttgtaaaatagatactagcagattgtcccaagatgtgtacagctcattctcacagc<br>ccagcgagggcacCtactccacaaatgcgtggccacaggtcatcacctgtcctgtggccctg<br>gcgagcctgatccctcacgccgggcac<br>(SEQ ID NO: 159) | |
| arRNA$_{151}$-FANCC<br>(CAG site) | gctcattctcacagcccagcgagggcacttactccacaaatgcgtggccacaggtcatcacc<br>tgtcctgtggcccCggcgagcctgatccctcacgccgggcacccacacggcctgcgtgcctt<br>ctagacttgagttcgcagctctttaag<br>(SEQ ID NO: 160) | |
| arRNA$_{151}$-IDUA<br>(CAG site) | tcggccgggccctgggggcggtgggcgctggccaggacgcccaccgtgtggttgctgtccag<br>gacggtcccggccCgcgacacttcggcccagagctgctcctcatccagcagcgccagcagcc<br>ccatggccgtgagcaccggcttgcgca<br>(SEQ ID NO: 161) | |

TABLE 3-continued

Figures 17E, 17G, 17H, 17I:
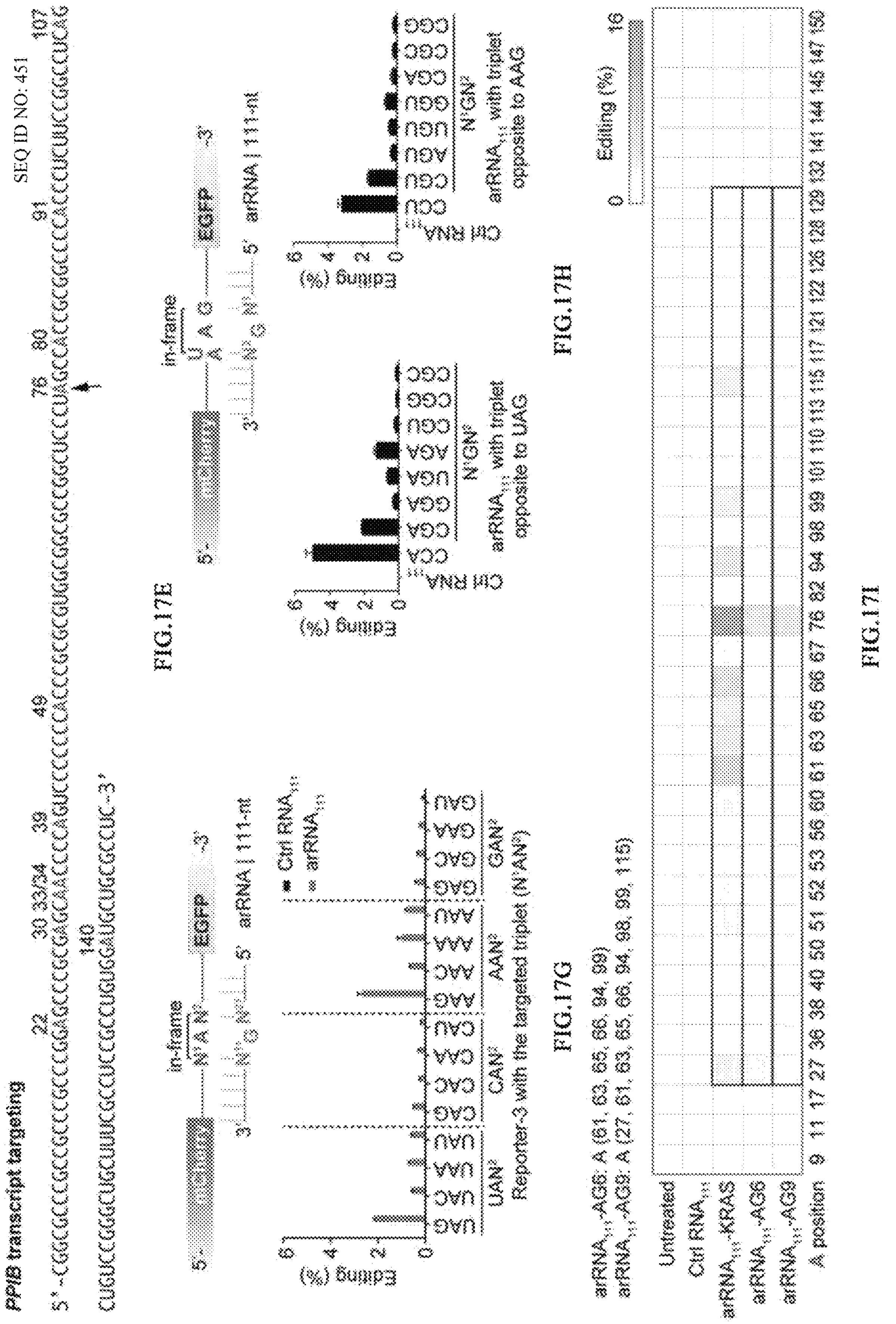

| Name | Sequence (5' -> 3') | Source |
|---|---|---|
| arRNA$_{111}$-TARDBP | ugaccagucuuaagaucuuucuugaccugcaccauaagaacuucuccaaagguacCaaaaua<br>cucuuucagguccuguucgguuguuuuccaugggagacccaacacuauu<br>(SEQ ID NO: 162) | |
| arRNA$_{111}$-CGA-<br>Reporter-3 (UAG) | gaugggcaccaccccggugaacagcuccucgcccuugcucacuggcagagcccucGagcauc<br>gcgagcaggcgcugccuccuccgcccugcagcuuguacagcucguccau<br>(SEQ ID NO: 163) | FIG. 17G |
| arRNA$_{111}$GA-<br>Reporter-3 (UAC) | gaugggcaccaccccggugaacagcuccucgcccuugcucacuggcagagcccugGagcauc<br>gcgagcaggcgcugccuccuccgcccugcagcuuguacagcucguccau<br>(SEQ ID NO: 164) | |
| arRNA$_{111}$-UGA-<br>Reporter-3 (UAA) | gaugggcaccaccccggugaacagcuccucgcccuugcucacuggcagagcccuuGagcauc<br>gcgagcaggcgcugccuccuccgcccugcagcuuguacagcucguccau<br>(SEQ ID NO: 165) | |
| arRNA$_{111}$-AGA-<br>Reporter-3 (UAU) | gaugggcaccaccccggugaacagcuccucgcccuugcucacuggcagagcccuaGagcauc<br>gcgagcaggcgcugccuccuccgcccugcagcuuguacagcucguccau<br>(SEQ ID NO: 166) | |
| arRNA$_{111}$-CGG-<br>Reporter-3 (CAG) | gaugggcaccaccccggugaacagcuccucgcccuugcucacuggcagagcccucGggcauc<br>gcgagcaggcgcugccuccuccgcccugcagcuuguacagcucguccau<br>(SEQ ID NO: 167) | |
| arRNA$_{111}$-GGG-<br>Reporter-3 (CAC) | gaugggcaccaccccggugaacagcuccucgcccuugcucacuggcagagcccugGggcauc<br>gcgagcaggcgcugccuccuccgcccugcagcuuguacagcucguccau<br>(SEQ ID NO: 168) | |
| arRNA$_{111}$-UGG-<br>Reporter-3 (CAA) | gaugggcaccaccccggugaacagcuccucgcccuugcucacuggcagagcccuuGggcauc<br>gcgagcaggcgcugccuccuccgcccugcagcuuguacagcucguccau<br>(SEQ ID NO: 169) | |
| arRNA$_{111}$-AGG-<br>Reporter-3 (CAU) | gaugggcaccaccccggugaacagcuccucgcccuugcucacuggcagagcccuaGggcauc<br>gcgagcaggcgcugccuccuccgcccugcagcuuguacagcucguccau<br>(SEQ ID NO: 170) | |
| arRNA$_{111}$-CGU-<br>Reporter-3 (AAG) | gaugggcaccaccccggugaacagcuccucgcccuugcucacuggcagagcccucGugcauc<br>gcgagcaggcgcugccuccuccgcccugcagcuuguacagcucguccau<br>(SEQ ID NO: 171) | |
| arRNA$_{111}$-GGU-<br>Reporter-3 (AAC) | gaugggcaccaccccggugaacagcuccucgcccuugcucacuggcagagcccugGugcauc<br>gcgagcaggcgcugccuccuccgcccugcagcuuguacagcucguccau<br>(SEQ ID NO: 172) | |
| arRNA$_{111}$-AGU-<br>Reporter-3 (AAA) | gaugggcaccaccccggugaacagcuccucgcccuugcucacuggcagagcccuaGugcauc<br>gcgagcaggcgcugccuccuccgcccugcagcuuguacagcucguccau<br>(SEQ ID NO: 173) | |
| arRNA$_{111}$-UGU-<br>Reporter-3 (AAU) | gaugggcaccaccccggugaacagcuccucgcccuugcucacuggcagagcccuuGugcauc<br>gcgagcaggcgcugccuccuccgcccugcagcuuguacagcucguccau<br>(SEQ ID NO: 174) | |
| arRNA$_{111}$-CGC-<br>Reporter-3 (GAG) | gaugggcaccaccccggugaacagcuccucgcccuugcucacuggcagagcccucGcgcauc<br>gcgagcaggcgcugccuccuccgcccugcagcuuguacagcucguccau<br>(SEQ ID NO: 175) | |
| arRNA$_{111}$-GGC-<br>Reporter-3 (GAC) | gaugggcaccaccccggugaacagcuccucgcccuugcucacuggcagagcccugGcgcauc<br>gcgagcaggcgcugccuccuccgcccugcagcuuguacagcucguccau<br>(SEQ ID NO: 176) | |
| arRNA$_{111}$-UGC-<br>Reporter-3 (GAA) | gaugggcaccaccccggugaacagcuccucgcccuugcucacuggcagagcccuuGcgcauc<br>gcgagcaggcgcugccuccuccgcccugcagcuuguacagcucguccau<br>(SEQ ID NO: 177) | |
| arRNA$_{111}$-AGC-<br>Reporter-3 (GAU) | gaugggcaccaccccggugaacagcuccucgcccuugcucacuggcagagcccuaGcgcauc<br>gcgagcaggcgcugccuccuccgcccugcagcuuguacagcucguccau<br>(SEQ ID NO: 178) | |
| arRNA$_{111}$-CGA-<br>Reporter-3 (UAG) | gaugggcaccaccccggugaacagcuccucgcccuugcucacuggcagagcccucGagcauc<br>gcgagcaggcgcugccuccuccgcccugcagcuuguacagcucguccau<br>(SEQ ID NO: 179) | FIG. 17H |
| arRNA$_{111}$-GGA-<br>Reporter-3 (UAG) | gaugggcaccaccccggugaacagcuccucgcccuugcucacuggcagagcccuGGagcauc<br>gcgagcaggcgcugccuccuccgcccugcagcuuguacagcucguccau<br>(SEQ ID NO: 180) | |
| arRNA$_{111}$-UGA-<br>Reporter-3 (UAG) | gaugggcaccaccccggugaacagcuccucgcccuugcucacuggcagagcccuUGagcauc<br>gcgagcaggcgcugccuccuccgcccugcagcuuguacagcucguccau<br>(SEQ ID NO: 181) | |
| arRNA$_{111}$-AGA-<br>Reporter-3 (UAG) | gaugggcaccaccccggugaacagcuccucgcccuugcucacuggcagagcccuAGagcauc<br>gcgagcaggcgcugccuccuccgcccugcagcuuguacagcucguccau<br>(SEQ ID NO: 182) | |
| arRNA$_{111}$-CGU-<br>Reporter-3 (UAG) | gaugggcaccaccccggugaacagcuccucgcccuugcucacuggcagagcccucGUgcauc<br>gcgagcaggcgcugccuccuccgcccugcagcuuguacagcucguccau<br>(SEQ ID NO: 183) | |
| arRNA$_{111}$-CGG-<br>Reporter-3 (UAG) | gaugggcaccaccccggugaacagcuccucgcccuugcucacuggcagagcccucGGgcauc<br>gcgagcaggcgcugccuccuccgcccugcagcuuguacagcucguccau<br>(SEQ ID NO: 184) | |
| arRNA$_{111}$-CGC-<br>Reporter-3 (UAG) | gaugggcaccaccccggugaacagcuccucgcccuugcucacuggcagagcccucGCgcauc<br>gcgagcaggcgcugccuccuccgcccugcagcuuguacagcucguccau<br>(SEQ ID NO: 185) | |
| arRNA$_{111}$-CGU-<br>Reporter-3 (AAG) | gaugggcaccaccccggugaacagcuccucgcccuugcucacuggcagagcccucGugcauc<br>gcgagcaggcgcugccuccuccgcccugcagcuuguacagcucguccau<br>(SEQ ID NO: 186) | |

TABLE 3-continued

Figure 26:
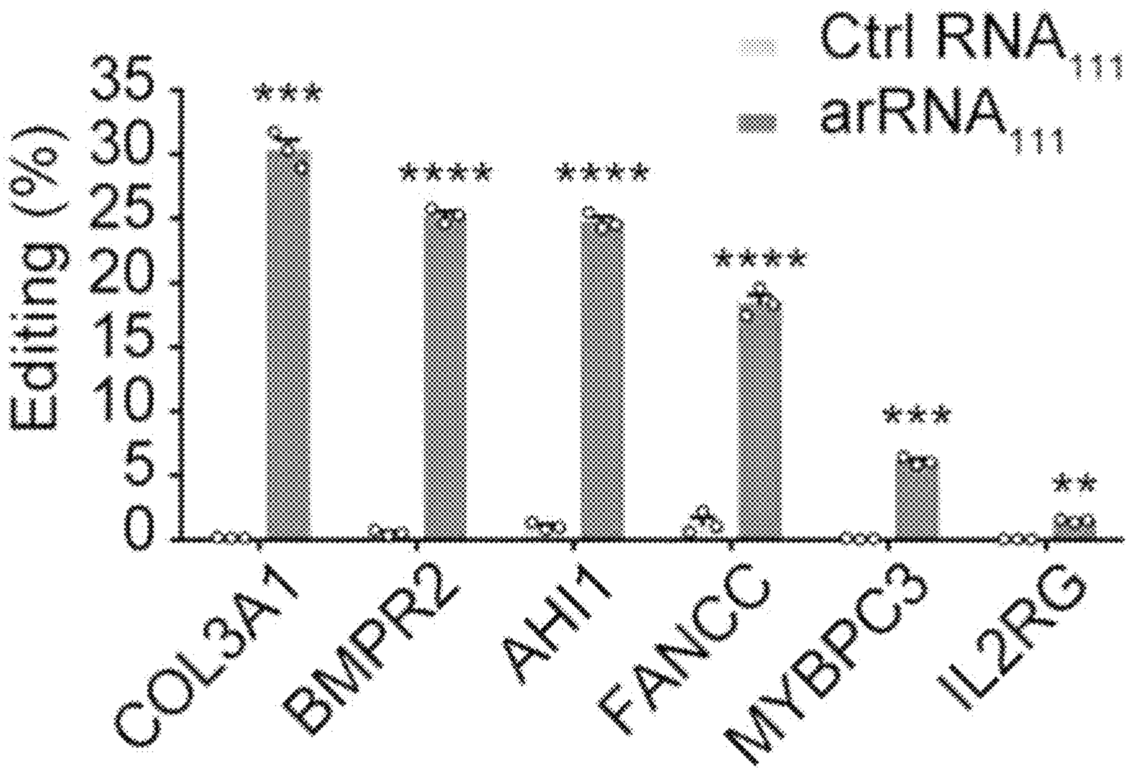
FIG. 26 shows correction of pathogenic mutations by an exemplary LEAPER method. A to I correction of disease-relevant G>A mutation from ClinVar data by the corresponding 111-nt arRNA, targeting clinical-related mutations from six pathogenic genes as indicated (FIG. 25 and the tables of the sequences of arRNAs and control RNAs and disease-related cDNAs below). Data are presented as the mean±s.e.m. (n=3); unpaired two-sided Student's t-test, *P<0.05; P<0.01; *P<0.001; ****P<0.0001; ns, not significant.

| Name | Sequence (5' -> 3') | Source |
|---|---|---|
| arRNA$_{111}$-GGU-<br>Reporter-3 (AAG) | gaugggcaccaccccggugaacagcuccucgcccuugcucacuggcagagcccuGGugcauc<br>gcgagcaggcgcugccuccuccgcccugcagcuuguacagcucguccau<br>(SEQ ID NO: 187) | |
| arRNA$_{111}$-UGU-<br>Reporter-3 (AAG) | gaugggcaccaccccggugaacagcuccucgcccuugcucacuggcagagcccuUGugcauc<br>gcgagcaggcgcugccuccuccgcccugcagcuuguacagcucguccau<br>(SEQ ID NO: 188) | |
| arRNA$_{111}$-AGU-<br>Reporter-3 (AAG) | gaugggcaccaccccggugaacagcuccucgcccuugcucacuggcagagcccuAGugcauc<br>gcgagcaggcgcugccuccuccgcccugcagcuuguacagcucguccau<br>(SEQ ID NO: 189) | |
| arRNA$_{111}$-CGA-<br>Reporter-3 (AAG) | gaugggcaccaccccggugaacagcuccucgcccuugcucacuggcagagcccucGAgcauc<br>gcgagcaggcgcugccuccuccgcccugcagcuuguacagcucguccau<br>(SEQ ID NO: 190) | |
| arRNA$_{111}$-CGC-<br>Reporter-3 (AAG) | gaugggcaccaccccggugaacagcuccucgcccuugcucacuggcagagcccucGCgcauc<br>gcgagcaggcgcugccuccuccgcccugcagcuuguacagcucguccau<br>(SEQ ID NO: 191) | |
| arRNA$_{111}$-CGG-<br>Reporter-3 (AAG) | gaugggcaccaccccggugaacagcuccucgcccuugcucacuggcagagcccucGGgcauc<br>gcgagcaggcgcugccuccuccgcccugcagcuuguacagcucguccau<br>(SEQ ID NO: 192) | |
| arRNA$_{111}$-KRAS-AG6 | gauucugaauuagcuguaucgucaaggcacucgugccgacgccaccagcuccaacCaccaca<br>aguggagagucagucauuuucagcaggccucucucccgcaccugggagc<br>(SEQ ID NO: 193) | FIG. 17I |
| arRNA$_{111}$-KRAS-AG9 | gauucugaauuagcuggaucgucaaggcacucgggccgacgccaccagcuccaacCaccaca<br>aguggagagucagucauuuucagcaggccucucucccgcaccggggagc<br>(SEQ ID NO: 194) | |
| arRNA$_{111}$-TP53 | gggagcagccucuggcauucugggagcuucaucuggaccugggucuucagugaacCauuguu<br>caauaucguccggggacagcaucaaaucauccauugcuugggacggcaa<br>(SEQ ID NO: 195) | FIG. 23 |
| arRNA$_{111}$-TP53-AG1 | gggagcagccucuggcauucugggagcuucaucuggaccugggucuucagugaacCauuguu<br>caagaucguccggggacagcaucaaaucauccauugcuugggacggcaa<br>(SEQ ID NO: 196) | |
| arRNA$_{111}$-TP53-AG4 | gggagcagccucuggcagucggggagcuucaucuggaccugggucuucagugaacCauuguu<br>caagaucguccggggacagcaucaaaucauccagugcuugggacggcaa<br>(SEQ ID NO: 197) | |
| arRNA$_{111}$-COL3A1 | cauauuacagaauaccuugauagcauccaauuugcauccuugguuagggucaaccCaguauu<br>cuccacucuugaguucaggauggcagaauuucaggucucugcaguuucu<br>SEQ ID NO: 198) | FIG. 26 |
| arRNA$_{111}$-BMPR2 | gugaagauaagccaguccucuaguaacagaaugagcaagacggcaagagcuuaccCagucac<br>uuguguggagacuuaaauacuugcauaaagauccauugggauaguacuc<br>(SEQ ID NO: 199) | |
| arRNA$_{111}$-AHI1 | gugaacgucaaacugucggaccaauauggcagaaucuucucucaucucaacuuucCauaucc<br>guaucauggaaucauagcauccuguaacuacuagcucucuuacagcugg<br>(SEQ ID NO: 200) | |
| arRNA$_{111}$-FANCC<br>(Site 2) | gccaaugaucucgugaguuaucucagcagugugagccaucagggugaugacauccCaggcga<br>ucguguggccuccaggagcccagagcaggaaguugaggagaaggugccu<br>(SEQ ID NO: 201) | |
| arRNA$_{111}$-MYBPC3 | caagacggugaaccacuccauggucuucuugucggcuuucugcacuguguaccccCagagcu<br>ccguguugccgacauccugggguggcuuccacuccagagccacauuaag<br>(SEQ ID NO: 202) | |
| arRNA$_{111}$-1L2RG | aggauucucuuuugaaguauugcucccccaguggauuggguggcuccauucacucCaaugcu<br>gagcacuuccacagagugggguuaaagcggcuccgaacacgaaacgugua<br>(SEQ ID NO: 203) | |
| arRNA$_{111}$-IDUA-V1 | gacgcccaccgugugguugcuguccaggacggucccggccugcgacacuucggccCagagcu<br>gcuccucauccagcagcgccagcagccccauggccgugagcaccggcuu<br>(SEQ ID NO: 204) | FIG. 29 |
| arRNA$_{111}$-IDUA-V2 | gacgcccaccgugugguugcuguccaggacggucccggccugcgacacuucggccCagagcu<br>gcuccucaucugcggggcgggggggggccgucgccgcgugggggucguug<br>(SEQ ID NO: 205) | |

Figure 11B:
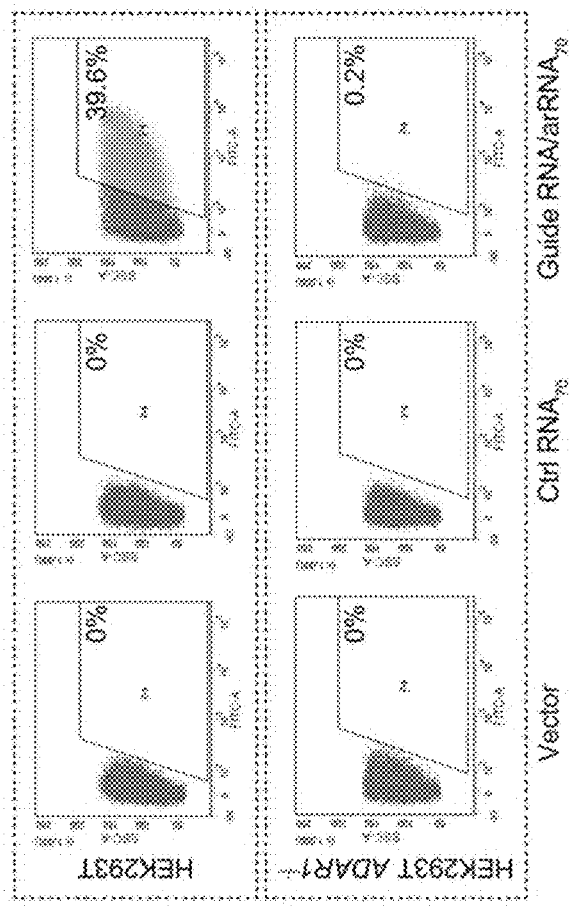

It turned out that this linear guide RNA induced strong EGFP expression in close to 40% of total cells harboring the Reporter-1 (FIG. 11B, upper). Because endogenous ADAR proteins could edit double-stranded RNA (dsRNA) substrates[12], we reasoned that the long guide RNAs could anneal with the target transcripts to form dsRNA substrates that in turn recruit endogenous ADAR proteins for targeted editing. We thus designated such guide RNA as arRNA (ADAR-recruiting RNA).

Figure 11C:
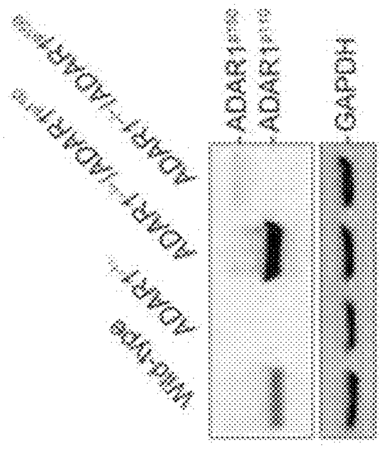
Figure 11D:
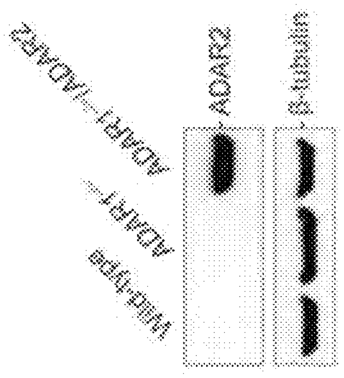
Figure 11E:
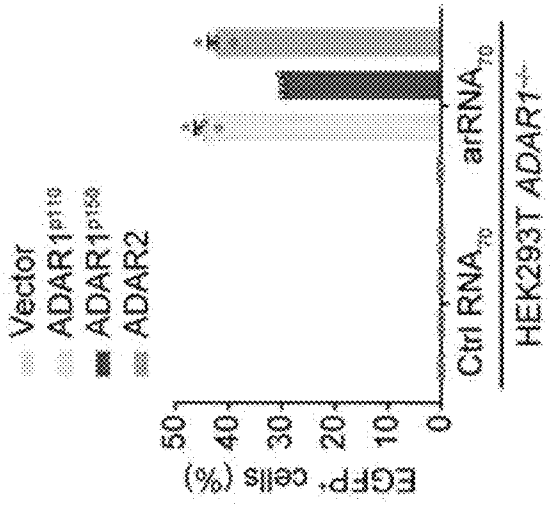
Figure 11F:
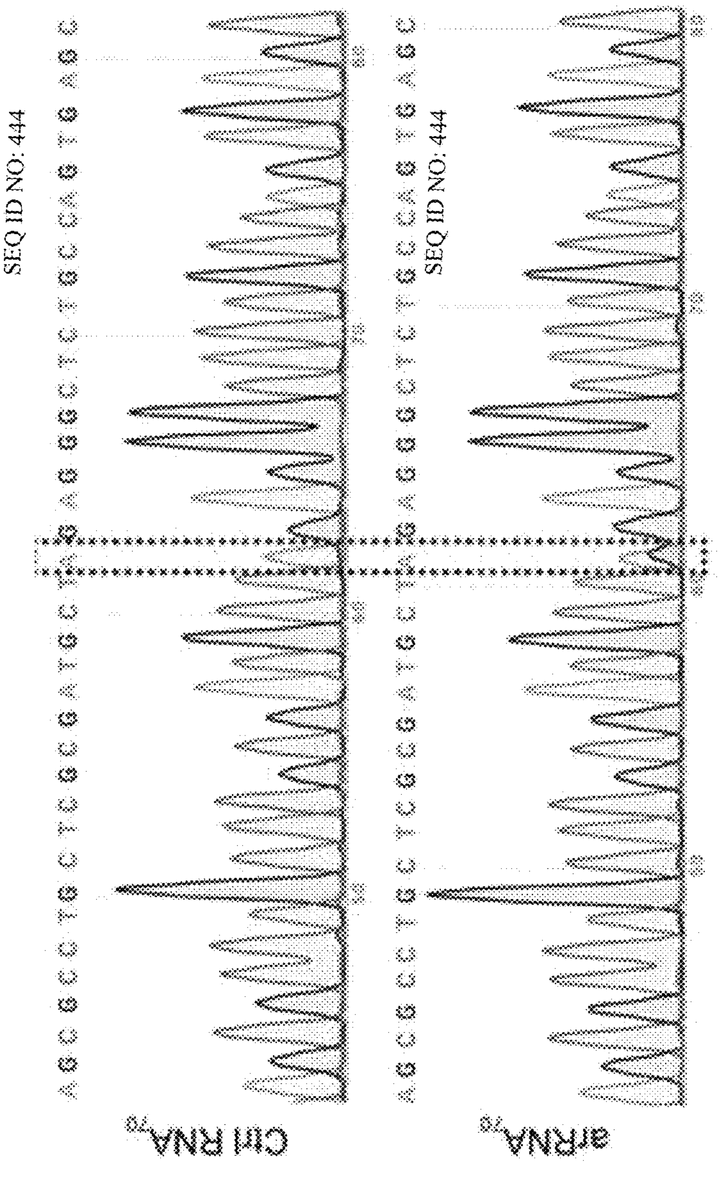
Figure 11G:
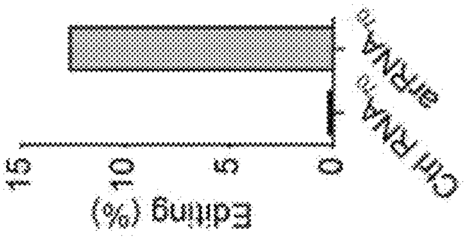

To verify if endogenous ADAR proteins are indeed responsible for above observation, we set out to examine the arRNA-mediated RNA editing in ADAR-deficient cells. Since ADAR2 mRNA was barely detectable in HEK293T cells (FIG. 12A), we generated HEK293T ADAR1$^{-/-}$ cells, rendering this cell line deficient in both ADAR1 and ADAR2 (FIG. 11C, d). Indeed, the depletion of ADAR1 abrogated arRNA$_{70}$-induced EGFP signals (FIG. 11B, lower). Moreover, exogenous expression of ADAR1$^{p110}$, ADAR1$^{p150}$ or ADAR2 in HEK293T ADAR1$^{-/-}$ cells (FIG. 11C, d) successfully rescued the loss of EGFP induction by arRNA$_{70}$ (FIG. 11E, FIG. 12B), demonstrating that arRNA-induced EGFP reporter expression solely depended on native ADAR1, whose activity could be reconstituted by its either isoforms (p110 and p150) or ADAR2. Sanger sequencing analysis on the $arRNA_{70}$-targeting region showed an A/G overlapping peak at the predicted adenosine site within UAG, indicating a significant A to I (G) conversion (FIG. 11F). The next-generation sequencing (NGS) further confirmed that the A to I conversion rate was about 13% of total reporter transcripts (FIG. 11G). The quantitative PCR analysis showed that $arRNA_{70}$ did not reduce the expression of targeted transcripts (FIG. 13), ruling out the possible RNAi effect of the arRNA. Collectively, our data demonstrated that the arRNA is capable of generating significant level of editing on the targeted transcripts through the engineered A-C mismatch.

Example 7. LEAPER Enables RNA Editing in Multiple Cell Lines

Figure 14A:
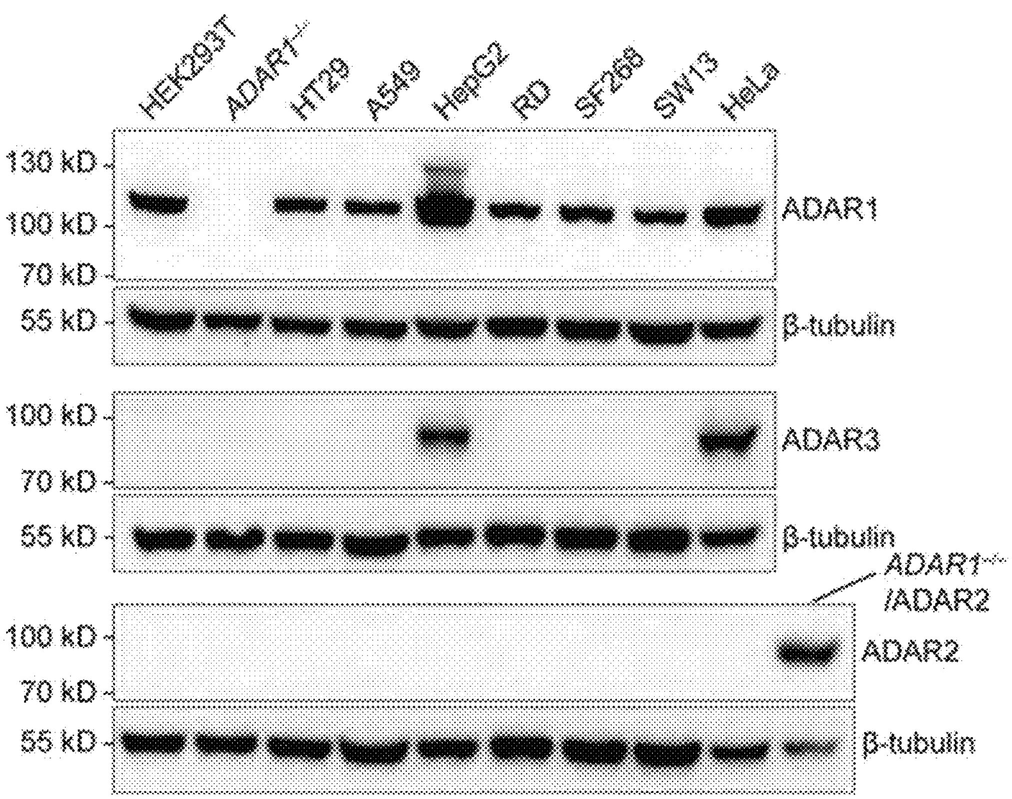
FIGS. 14A-14D show targeted RNA editing with an exemplary LEAPER method in multiple cell lines.
Figure 14B:
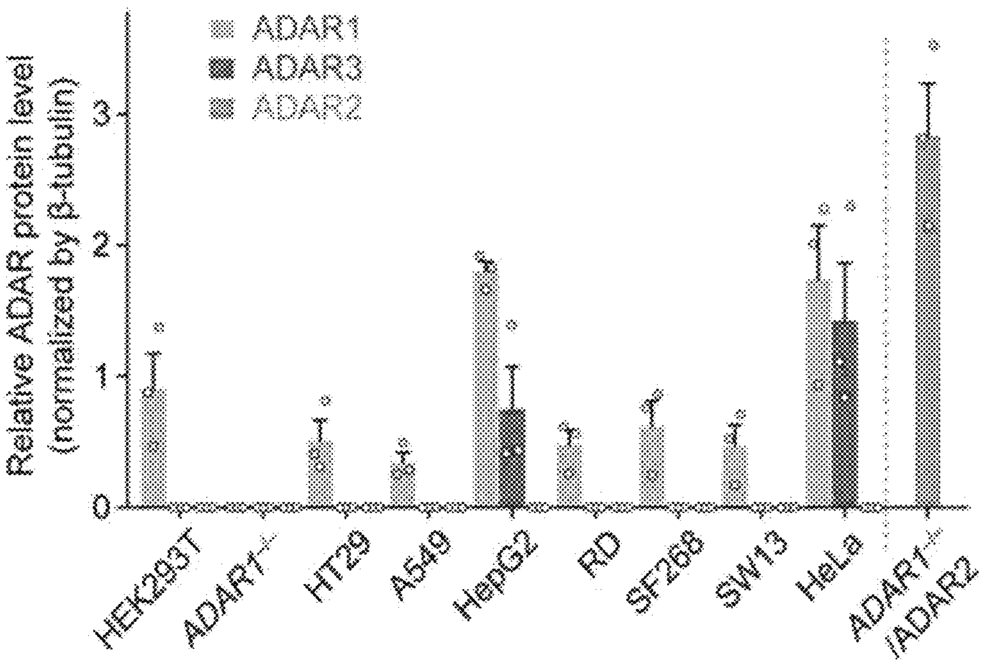

Because the expression of endogenous ADAR proteins is a prerequisite for LEAPER-mediated RNA editing, we tested the performance of LEAPER in a panel of cell lines originated from distinct tissues, including HT29, A549, HepG2, RD, SF268, SW13 and HeLa. We first examined the endogenous expression of all three kinds of ADAR proteins using Western blotting analyses. ADAR1 was highly expressed in all tested cell lines, and its identity in the Western blots was confirmed by the negative control, HEK293T ADAR-1 line (FIG. 14A, b). ADAR3 was detected only in HepG2 and HeLa cells (FIG. 14A, b). ADAR2 was non-detectable in any cells, a result that was not due to the failure of Western blotting because ADAR2 protein could be detected from ADAR2-overexpressing HEK293T cells (FIG. 14A, b). These findings are in consistent with previous reports that ADAR1 is ubiquitously expressed, while the expressions of ADAR2 and ADAR3 are restricted to certain tissues[11].

We then set out to test the editing efficiencies of a re-designed 71-nt arRNA ($arRNA_{71}$) targeting the Reporter-1 (FIG. 15A and Sequences of arRNAs and control RNAs used in this study listed above) in these cell lines.

Figure 14C:
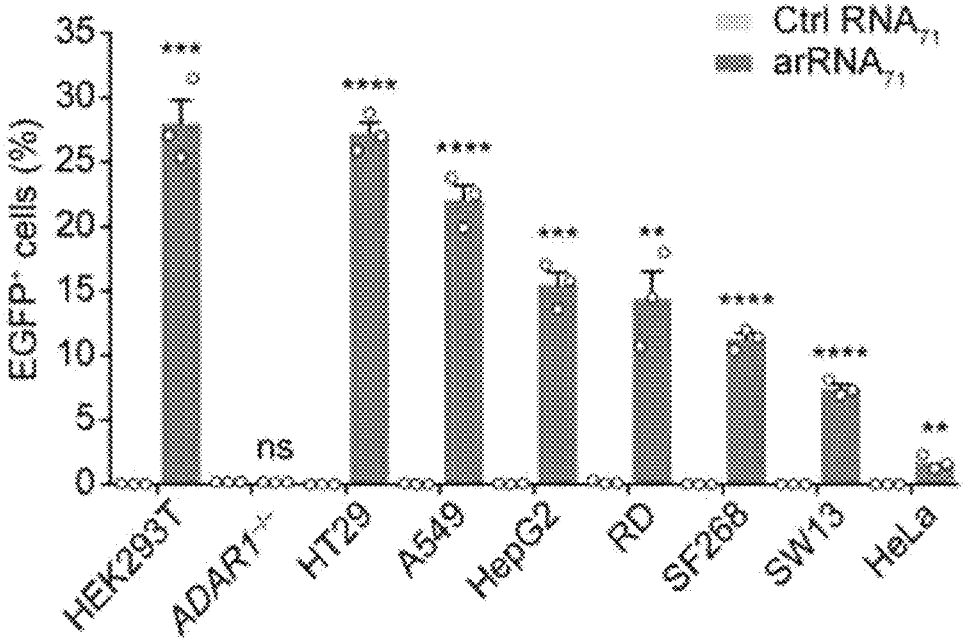
Figure 14D:
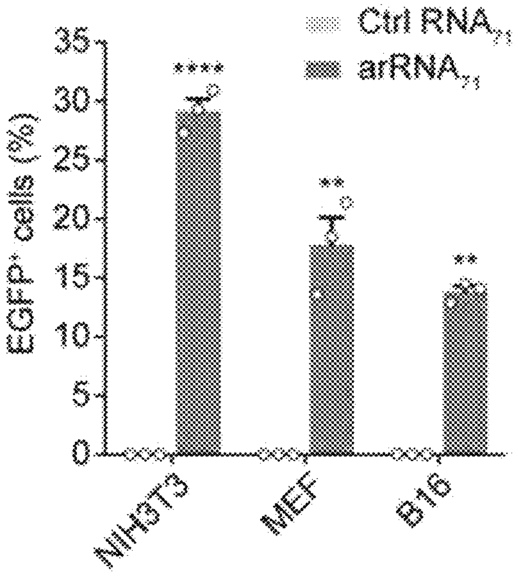

LEAPER worked in all tested cells for this $arRNA_{71}$, albeit with varying efficiencies (FIG. 14C). These results were in agreement with the prior report that the ADAR1/2 protein levels correlate with the RNA editing yield[42], with the exception of HepG2 and HeLa cells. The suboptimal correlations of editing efficiencies with ADAR1 levels were likely due to the abundant ADAR3 expressions in these two lines (FIG. 14A, b) because it has been reported that ADAR3 plays an inhibitory role in RNA editing. Importantly, LEAPER also worked in three different cell lines of mouse origin (NIH3T3, Mouse Embryonic Fibroblast (MEF) and B16) (FIG. 14D), paving the way for testing its therapeutics potential through animal and disease models. Collectively, we conclude that LEAPER is a versatile tool for wide-spectrum of cell types, and for different organisms.

Example 8. Characterization and Optimization of LEAPER

To better characterize and optimize LEAPER, we investigated the choices of nucleotide opposite to the adenosine within the UAG triplet of the targeted transcript. In HEK293T cells, Reporter-I-targeting $arRNA_{71}$ showed variable editing efficiencies with a changed triplet (5'-CNA, N denotes one of A/U/C/G) opposite to the targeted UAG (Sequences of arRNAs and control RNAs used in this study listed above). A-C mismatch resulted in the highest editing efficiency, and the A-G mismatch yielded the least but evident edits (FIG. 16A). We then investigated the preference of nucleotides flanking the A-C mismatch in arRNA. We tested all 16 combinations of 5' and 3' neighbor sites surrounding the cytidine ($5'-N^1CN^2$) (Sequences of arRNAs and control RNAs used in this study listed above), and found that the 3' neighboring adenosine was required for the efficient editing, while adenosine is the least favorable nucleotide at the 5' site (FIG. 16B, c). We thus concluded that CCA motif on the arRNA confers the highest editing efficiency targeting the UAG site. It is worthwhile to note that the 3' neighboring guanosine ($5'-N^1CG$) in arRNA showed a dramatic inhibitory effect (FIG. 16B, c).

Figures 15A, 15B, 15C:
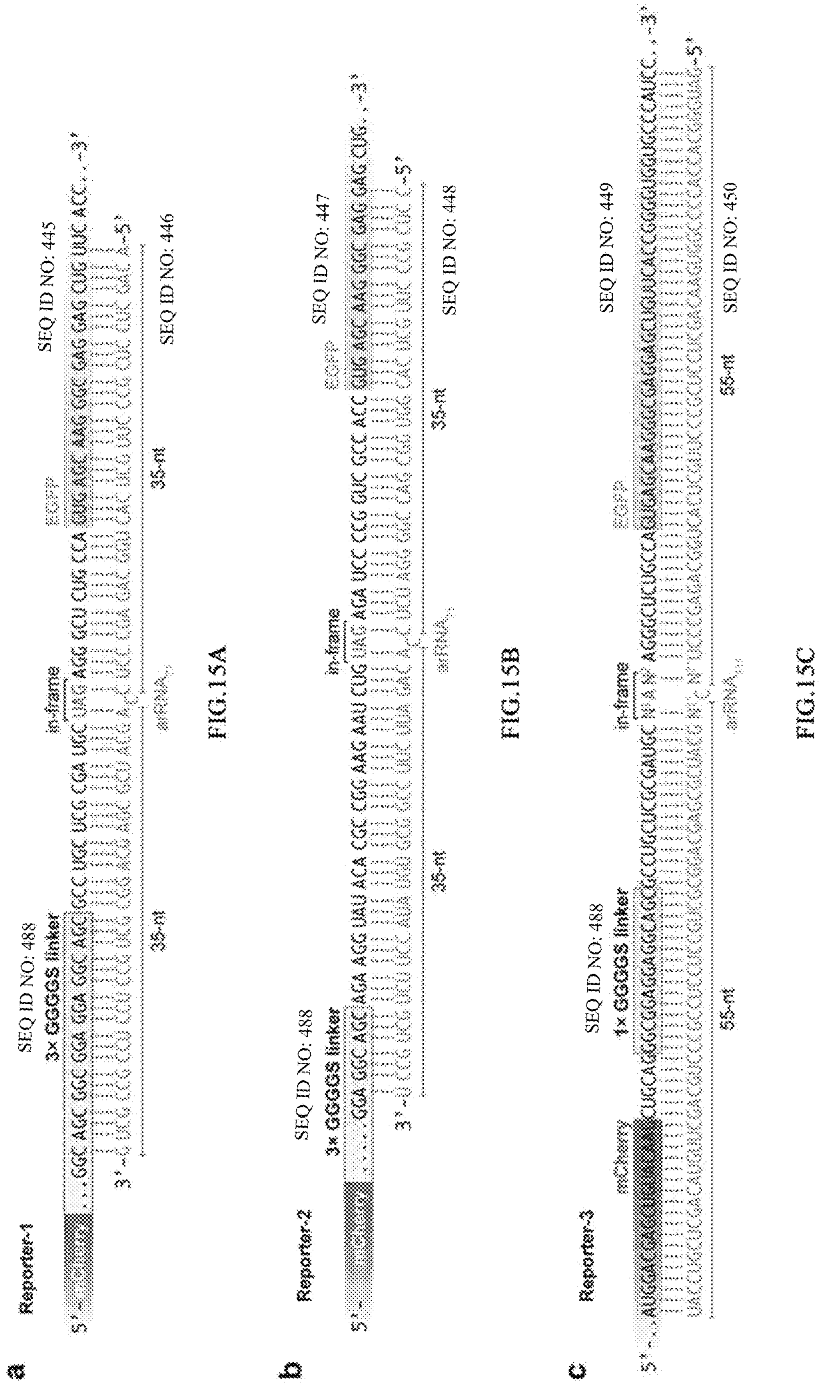
FIGS. 15A-15C show schematics of Reporter-1 (FIG. 15A), -2 (FIG. 15B), and -3 (FIG. 15C), as well as their corresponding arRNAs.

Length of RNA appeared relevant to arRNA efficiency in directing the editing on the targeted transcripts (FIG. 10C), consistent with a previous report[42]. To fully understand this effect, we tested arRNAs with variable lengths targeting two different reporter transcripts—Reporter-1 and Reporter-2 (FIG. 15A, b). For either reporter targeting, arRNAs of 10 different sizes were designed and tested, ranging from 31-nt to 211-nt, with CCA triplet (for UAG targeting) right in the middle (Sequences of arRNAs and control RNAs used in this study listed above). Based on the reporter EGFP activities, the length of arRNA correlated positively with the editing efficiency, for both reporters, peaking at 111- to 191-nt (FIG. 16D). Although one $arRNA_{51}$ appeared working, 71-nt was the minimal length for arRNA to work for both reporters (FIG. 16D).

Next, we investigated the effect of the A-C mismatch position within an arRNA on editing efficiency. We fixed the lengths of all arRNAs for testing to 71-nt, and slided the UAG-targeting ACC triplet from 5' to 3' within arRNAs (Sequences of arRNAs and control RNAs used in this study listed above). It turned out that placing the A-C mismatch in the middle region resulted in high editing yield, and arRNAs with the mismatch sites close to the 3' end outperformed those close to the 5' end in both reporters (FIG. 16E). For convenience, we placed the A-C mismatch at the center of arRNAs for all of our subsequent studies.

We also tested the targeting flexibility of LEAPER and tried to determine whether UAG on target is the only motif subjected to RNA editing. For all 16 triplet combinations ($5'-N^1AN^2$) on Reporter-3 (FIG. 15C), we used the corresponding arRNAs with the fixed lengths (111-nt) and ensured the perfect sequencing match for arRNA and the reporter except for the editing site (A-C mismatch) (FIG. 16F and Sequences of arRNAs and control RNAs used in this study listed above). NGS results showed that all $N^1AN^2$ motifs could be edited. The $UAN^2$ and $GAN^2$ are the most and the least preferable motifs, respectively (FIG. 16F, g). Collectively, the nearest neighbor preference of the target adenosine is 5' U>C≈A>G and 3' G>C>A≈U (FIG. 16G).

Example 9. Editing Endogenous Transcripts Using LEAPER

Figure 18B:
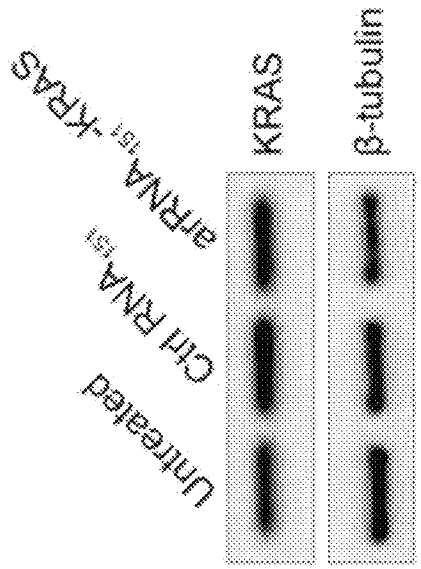
FIGS. 18A-18B show effects of exemplary LEAPER methods on the expression levels of targeted transcripts and protein products.

Next, we examined if LEAPER could enable effective editing on endogenous transcripts. Using arRNAs of different lengths, we targeted the UAG motifs in the transcripts of PPIB, KRAS and SMAD4 genes, and an UAC motif in FANCC gene transcript (FIG. 17A, Sequences of arRNAs and control RNAs used in this study listed above). Encouragingly, targeted adenosine sites in all four transcripts were edited by their corresponding arRNAs with all four sizes, albeit with variable efficiencies according to NGS results (FIG. 17B). In consistent with our prior observation, longer arRNAs tended to yield higher editing rates. Of note, the 151-nt $arRNA^{PPIB}$ edited ~50% of total transcripts of PPIB gene (FIG. 17B). No arRNAs showed RNAi effects on their targeted transcripts (FIG. 18A) or ultimate protein level (e.g. KRAS, FIG. 18B). Besides, LEAPER is able to achieve desirable editing rate on non-UAN sites (FIG. 17C and Sequences of arRNAs and control RNAs used in this study listed above), showing the flexibility of LEAPER on editing endogenous transcripts. To further explore the power of LEAPER, we tested whether it could simultaneously target multiple sites. We observed multiplex editing of both TARDBP and FANCC transcripts by co-expression of two arRNAs (Sequences of arRNAs and control RNAs used in this study listed above), with the efficiency even higher than those with individual arRNAs (FIG. 17D), indicating that LEAPER is well suited for editing multiple targets in parallel.

Figure 19A:
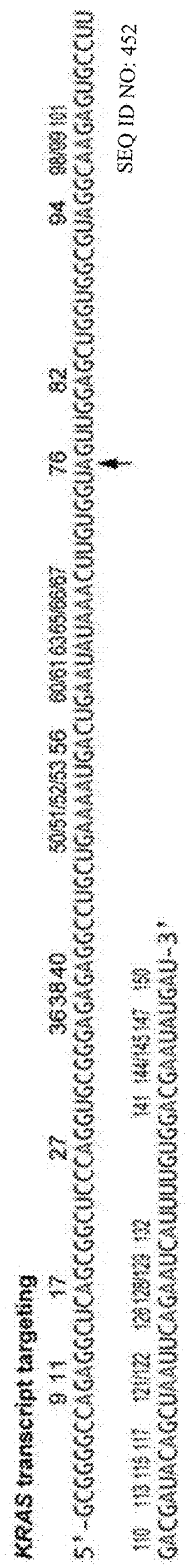
Figure 19B:
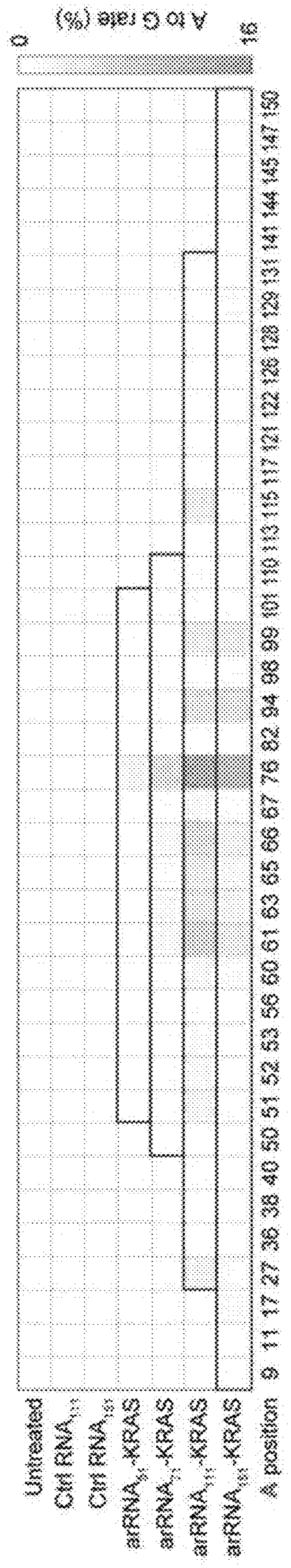
Figure 19C:
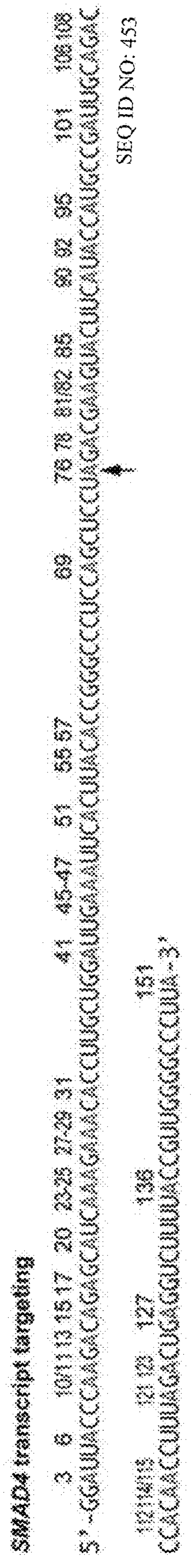

It is noteworthy that ADAR1/2 tend to promiscuously deaminate multiple adenosines in an RNA duplex[44] and the A-C mismatch is not the only motif to guide the A-to-I switch (FIG. 16A). It is therefore reasonable to assume that all adenosines on target transcripts within the arRNA coverages are subjected to variable levels of editing, major sources of unwanted modifications. The longer the arRNA, the higher the possibility of such off-targets. We therefore examined all adenosine sites within the arRNA covering regions in these targeted transcripts. For PPIB transcripts, very little off-target editing was observed throughout the sequencing window for variable sizes of arRNAs (FIG. 17E, f). However, in the cases of targeting KRAS, SMAD4 and FANCC genes, multiple off-target edits were detected (FIG. 19A-f). For KRAS in particular, 11 out of 30 adenosines underwent substantial A to I conversions in the sequencing window of $arRNA_{111}$ (FIG. 19A, b).

We next attempted to develop strategies to minimize such unwanted off-target effects. Because an A-G mismatch suppressed editing for UAG targeting (FIG. 16A), we postulated that pairing a guanosine with a non-targeting adenosine might reduce undesirable editing. We then tested the effect of the A-G mismatch on adenosine in all possible triplet combinations (5'-$N^1AN^2$) as in Reporter-3 (FIG. 15C and Sequences of arRNAs and control RNAs used in this study listed above). A-G mismatch indeed decreased the editing on adenosine in all tested targets, except for UAG or AAG targeting (~2%) (FIG. 17G), in comparison with A-C mismatch (FIG. 16F). To further reduce editing rates at unwanted sites, we went on testing the effect of two consecutive mismatches. It turned out that the additional mismatch at the 3' end nucleotide of the triplet opposite to either UAG or AAG, abolished its corresponding adenosine editing (FIG. 17H and Sequences of arRNAs and control RNAs used in this study listed above). In light of these findings, we attempted to apply this rule to reduce off-targets in KRAS transcripts (FIG. 19A). We first designed an arRNA ($arRNA_{111}$-AG6) that created A-G mismatches on all "editing-prone" motifs covered by $arRNA_{111}$ (FIG. 17I, FIG. 19A and Sequences of arRNAs and control RNAs used in this study listed above), including AAU (the $61^{st}$), UAU (the $63^{rd}$), UAA (the $65^{th}$), AAA (the $66^{th}$), UAG (the $94^{th}$) and AAG (the $99^{th}$). This $arRNA_{111}$-AG6 eliminated most of the off-target editing, while maintained an on-target editing rate of ~5%. In consistent with the findings in FIG. 17G, the single A-G mismatch could not completely minimize editing in AAG motif ($99^{th}$) (FIG. 17I and FIG. 19A). We then added more mismatches on $arRNA_{111}$-AG6, including a dual mismatch (5'-CGG opposite to the targeted motif 5'-AAG), plus three additional A-G mismatches to mitigate editing on the $27^{th}$, $98^{th}$ and the $115^{th}$ adenosines ($arRNA_{111}$-AG9) (Sequences of arRNAs and control RNAs used in this study listed above). Consequently, we achieved a much improved specificity for editing, without additional loss of editing rate on the targeted site (A76) (FIG. 17I). In summary, engineered LEAPER incorporating additional rules enables efficient and more precise RNA editing on endogenous transcripts.

Example 10. RNA Editing Specificity of LEAPER

Figure 20B:
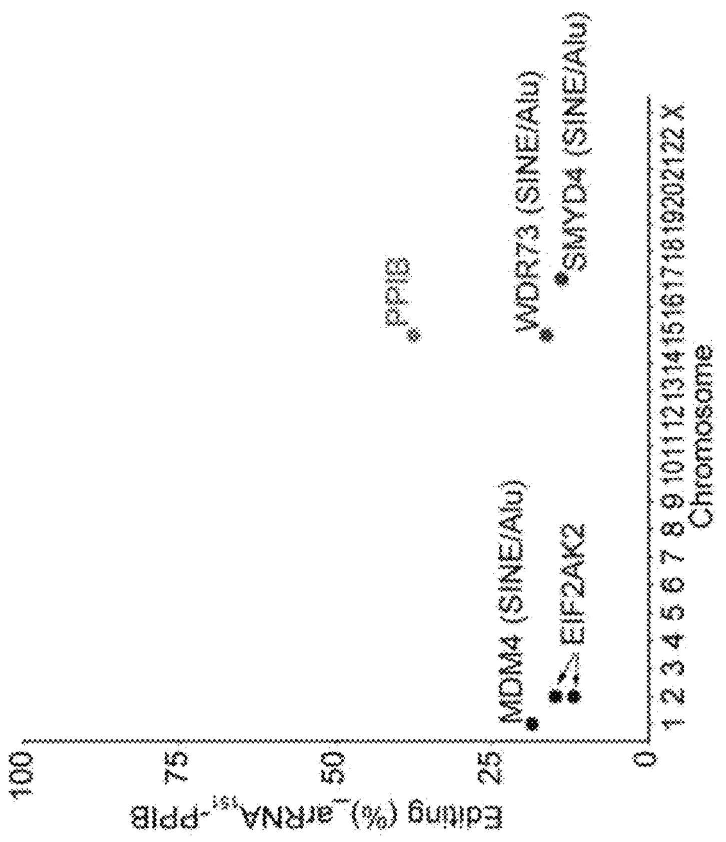
FIGS. 20A-20D show transcriptome-wide specificity of RNA editing by LEAPER.
Figure 20A:
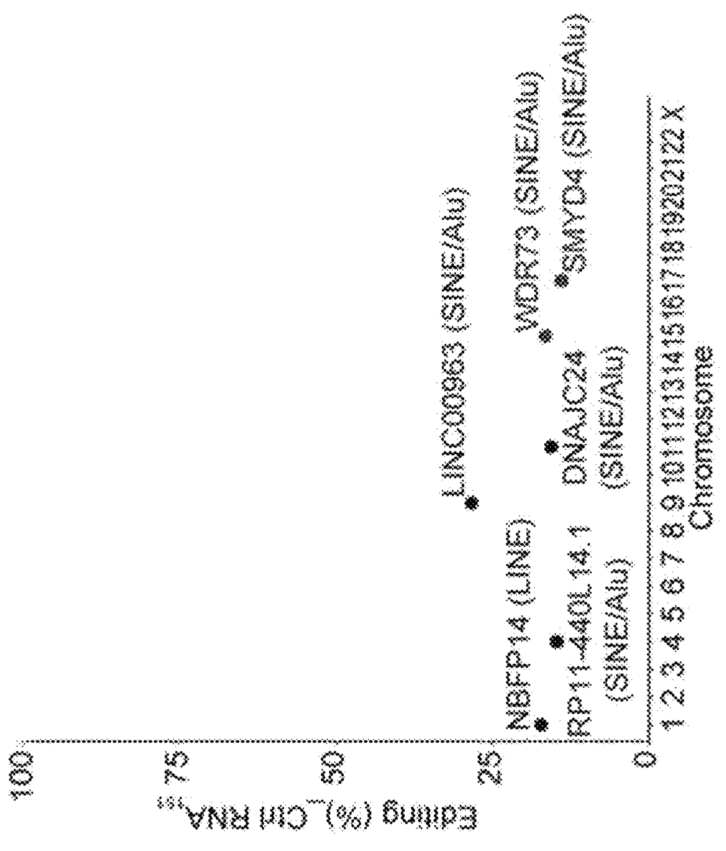
Figure 20D:
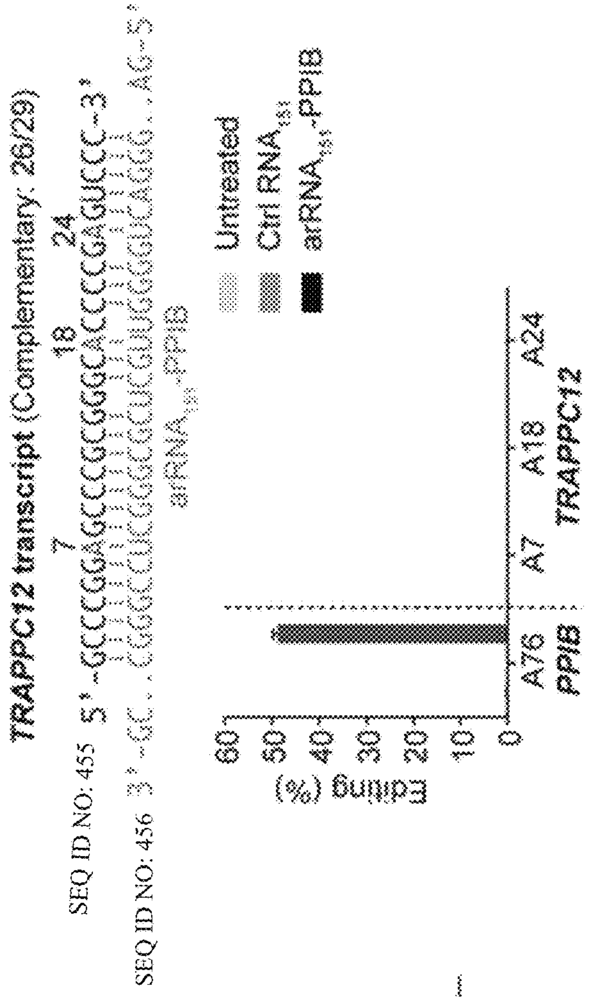
Figure 20C:
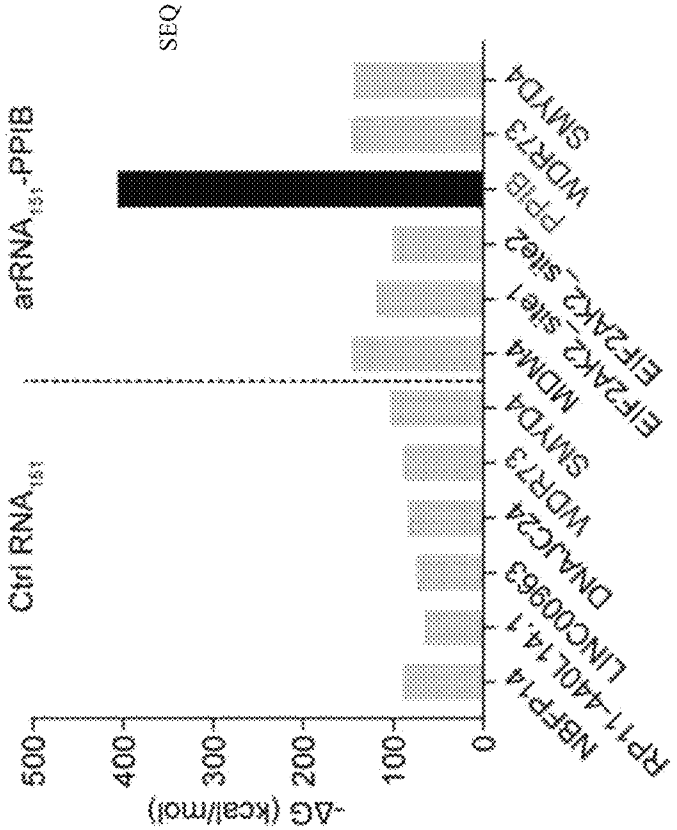
Figure 21B:
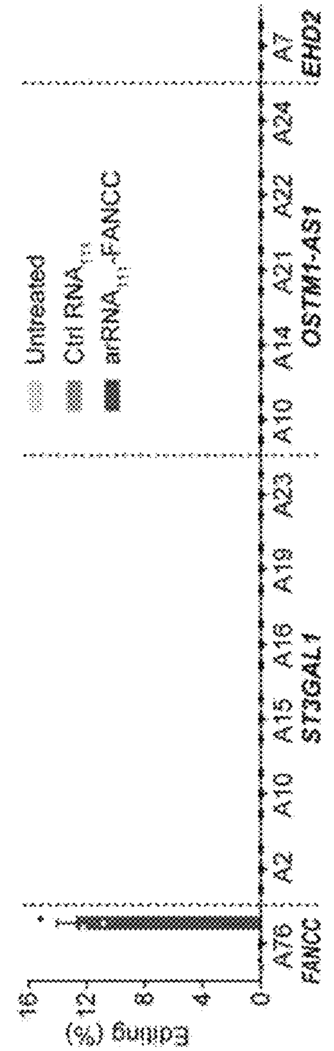
FIGS. 21A-21B show evaluation of potential off-targets.
Figure 21A:

In addition to the possible off-target effects within the arRNA-covered dsRNA region, we were also concerned about the potential off-target effects on other transcripts through partial base pairing of arRNA. We then performed a transcriptome-wide RNA-sequencing analysis to evaluate the global off-target effects of LEAPER. Cells were transfected with a Ctrl RNA151 or a PPIB-specific arRNA (arRNA151-PPIB) expressing plasmids before subjected to RNA-seq analysis. We identified six potential off-targets in the Ctrl RNA151 group (FIG. 20A) and five in the $arRNA_{151}$-PPIB group (FIG. 20B), and the PPIB on-target rate based on NGS analysis was ~37% (FIG. 20B). Further analysis revealed that all sites, except for the two sites from EIF2AK2 transcripts, were located in either SINE (Alu) or LINE regions (FIG. 20A, b), both are prone to ADAR-mediated editing[45], suggesting that these off-targets may not be derived from pairing between the target transcripts and the arRNA or control RNA. Of note, two off-targeting transcripts, WDR73 and SMYD4, appeared in both groups, suggesting they are unlikely sequence-dependent RNA editing. Indeed, minimum free energy analysis suggested that all these possible off-target transcripts failed to form a stable duplex with either Ctrl $RNA_{151}$ or $arRNA_{151}$-PPIB (FIG. 20C). To further test if arRNA generates sequence-dependent off-targets, we selected potential off-target sites by comparing sequence similarity using NCBI BLAST for both $arRNA_{151}$-PPIB and $arRNA_{111}$-FANCC. TRAPPC12 transcripts for $arRNA_{151}$-PPIB and three sites in the ST3GAL1, OSTM1-AS1 and EHD2 transcripts for $arRNA_{111}$-FANCC were top candidates (FIG. 20D and FIG. 21A). NGS analysis revealed that no editing could be detected in any of these predicted off-target sites (FIG. 20D and FIG. 21B). These results indicate that LEAPER empowers efficient editing at the targeted site, while maintaining transcriptome-wide specificity without detectable sequence-dependent off-target edits.

Example 11. Safety Assessment of LEAPER in Mammalian Cells

Figure 22A:
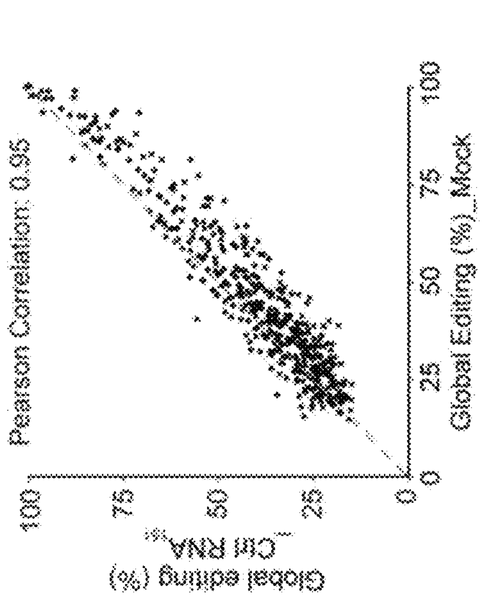
FIGS. 22A-22F show safety evaluation of applying exemplary LEAPER methods in mammalian cells.
Figure 22B:
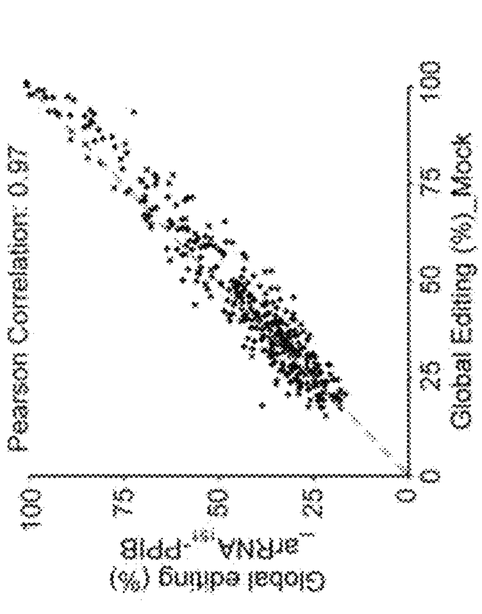

Because arRNAs rely on endogenous ADAR proteins for editing on target transcripts, we wondered if the addition of exogenous arRNAs affects native RNA editing events by occupying too much of ADAR1 or ADAR2 proteins. Therefore, we analyzed the A-to-I RNA editing sites shared by mock group and $arRNA_{151}$-PPIB group from the transcriptome-wide RNA-sequencing results, and the comparison between the mock group and Ctrl $RNA_{151}$ group was also analyzed. Neither Ctrl $RNA_{151}$ group nor $arRNA_{151}$-PPIB group showed a significant difference compared to the mock group (FIG. 22A, B), indicating that LEAPER had little impact on the normal function of endogenous ADAR1 to catalyze the native A-to-I editing events.

Figure 22C:
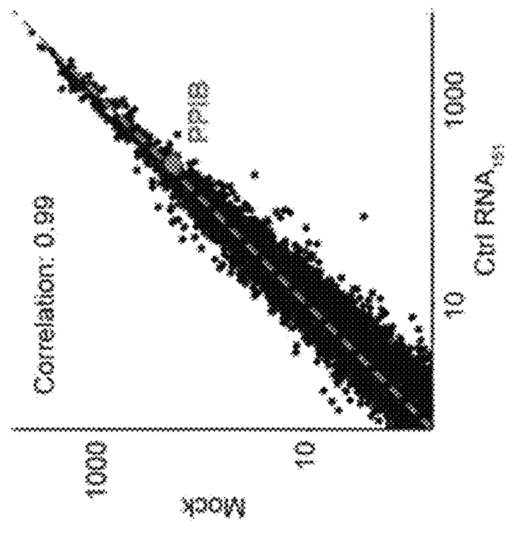
Figure 22D:
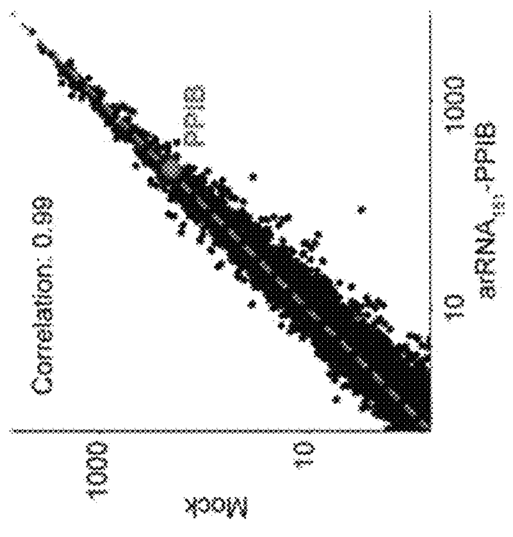

Meanwhile, we performed differential gene expression analysis using RNA-seq data to verify whether arRNA affects global gene expression. We found that neither Ctrl $RNA_{151}$ nor $arRNA_{151}$-PPIB affected the global gene expression in comparison with the mock group (FIG. 22C, D). In consistent with our prior observation (FIG. 18A), arRNAs did not show any RNAi effect on the expression of PPIB (FIG. 22C, D).

Figure 22E:
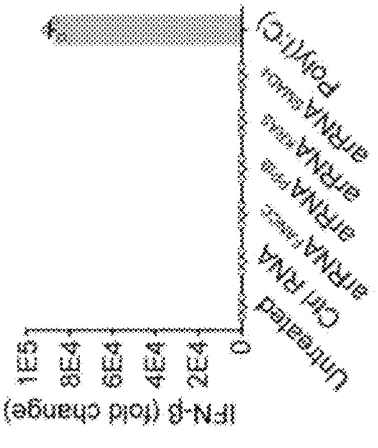
Figure 22F:
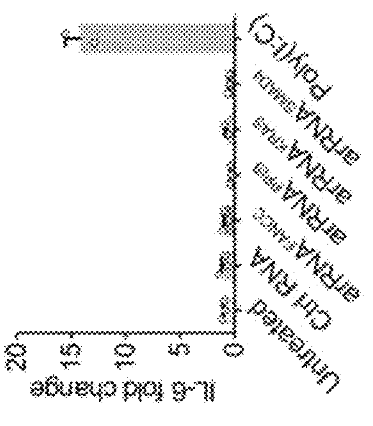

Considering that the arRNA forms RNA duplex with the target transcript and that RNA duplex might elicit innate immune response, we investigated if the introduction of arRNA has such an effect. To test this, we selected arRNAs targeting four gene transcripts that had been proven effective. We did not observe any mRNA induction of interferon-β (IFN-β) (FIG. 22E) or interleukin-6 (IL-6) (FIG. 22F), which are two hallmarks of innate immune activation. As a positive control, a synthetic analog of double-stranded RNA—poly(I:C) induced strong IFN-β and IL-6 expression (FIG. 22E, f). LEAPER does not seem to induce immunogenicity in target cells, a feature important for safe therapeutics.

Example 12. Recovery of Transcriptional Regulatory Activity of p53 by LEAPER

Figure 23A:
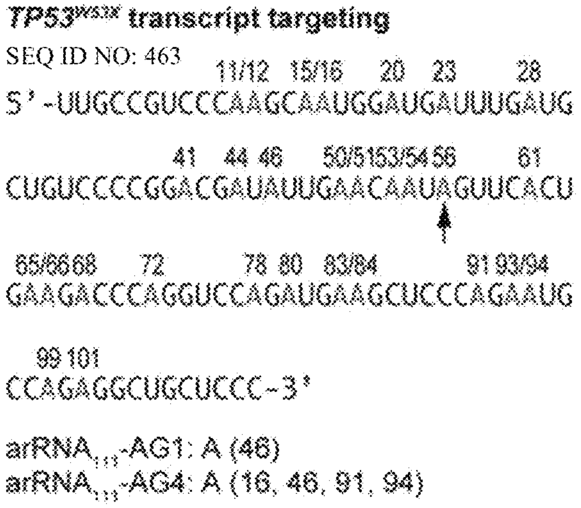
FIGS. 23A-23D show recovery of transcriptional regulatory activity of mutant TP53W53X by LEAPER.
Figure 23C:
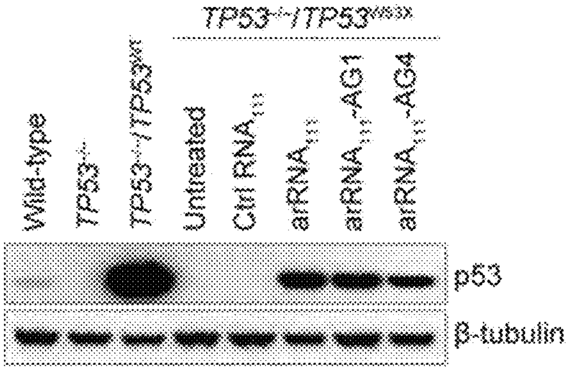
Figure 23B:
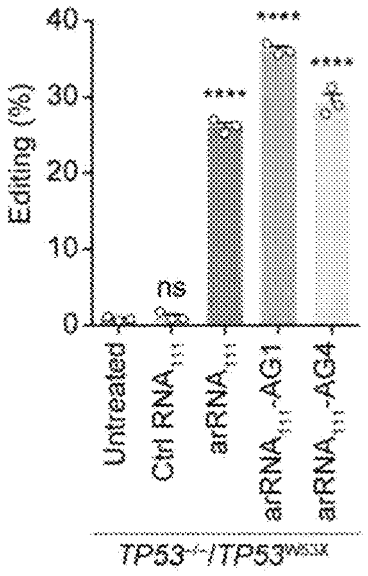
Figure 24:
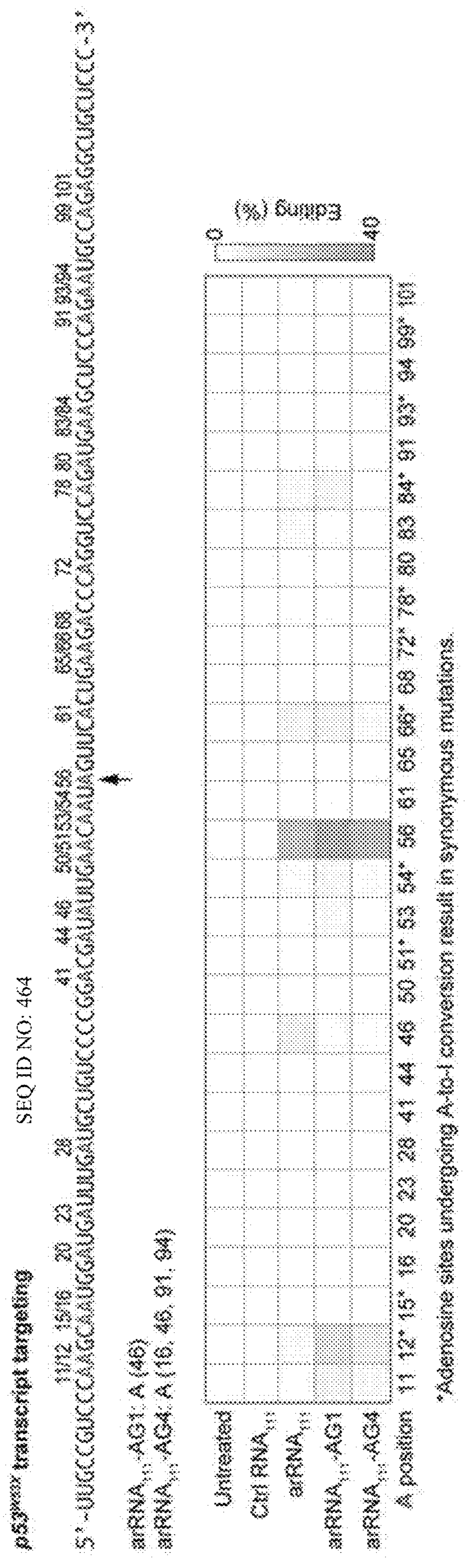
FIG. 24 shows editing of mutant TP53W53X transcripts by an exemplary LEAPER method. Top, schematic of the TP53 transcript sequence covered by the 111-nt arRNAs. The arrow indicates the targeted adenosine. All adenosines were marked in red. Bottom, a heatmap of editing rate on adenosines covered by indicated arRNAs in the TP53 transcript.

Now that we have established a novel method for RNA editing without the necessity of introducing foreign proteins, we attempted to demonstrate its therapeutic utility. We first targeted the tumor suppressor gene TP53, which is known to play a vital role in the maintenance of cellular homeostasis, but undergo frequent mutations in >50% of human cancers[46]. The c.158G>A mutation in TP53 is a clinically-relevant nonsense mutation (Trp53Ter), resulting in a non-functional truncated protein[46]. We designed one $arRNA_{111}$ and two alternative arRNAs ($arRNA_{111}$-AG1 and $arRNA_{111}$-AG4) (Sequences of arRNAs and control RNAs used in this study listed above), all targeting $TP53^{W53X}$ transcripts (FIG. 23A), with the latter two being designed to minimize potential off-targets. We generated HEK293T $TP53^{-/-}$ cell line to eliminate the effects of native p53 protein. All three forms of $TP53^{W53X}$-targeting arRNAs converted ~25-35% of $TP53^{W53X}$ transcripts on the mutated adenosine site (FIG. 23B), with variable reductions of unwanted edits for $arRNA_{111}$-AG1 and $arRNA_{111}$-AG4 (FIG. 24). Western blot showed that $arRNA_{111}$, $arRNA_{111}$-AG1 and $arRNA_{111}$-AG4 could all rescue the production of full-length p53 protein based on the $TP53^{W53X}$ transcripts in HEK293T $TP53^{-/-}$ cells, while the Ctrl $RNA_{111}$ could not (FIG. 23C).

Figure 23D:
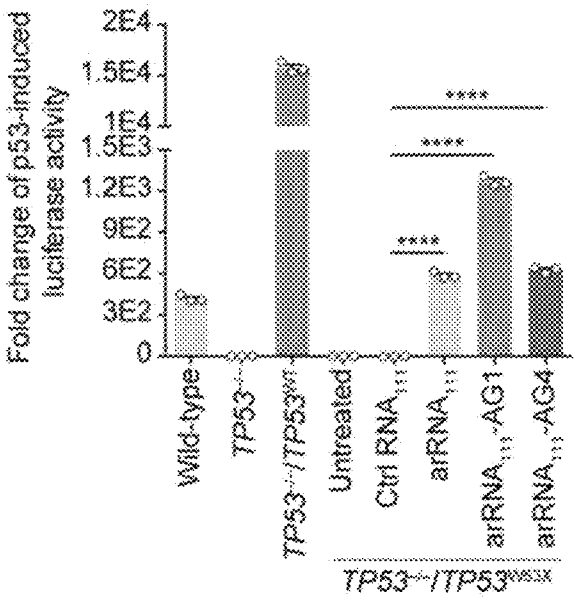

To verify whether the repaired p53 proteins are fully functional, we tested the transcriptional regulatory activity of p53 with a p53-luciferase cis-reporting system[47,48]. All three versions of arRNAs could restore p53 activity, and the optimized version $arRNA_{111}$-AG1 performed the best (FIG. 23D). In conclusion, we demonstrated that LEAPER is capable of repairing the cancer-relevant pre-mature stop codon of TP53 and restoring its function.

Example 13. Corrections of Pathogenic Mutations by LEAPER

Figure 25:
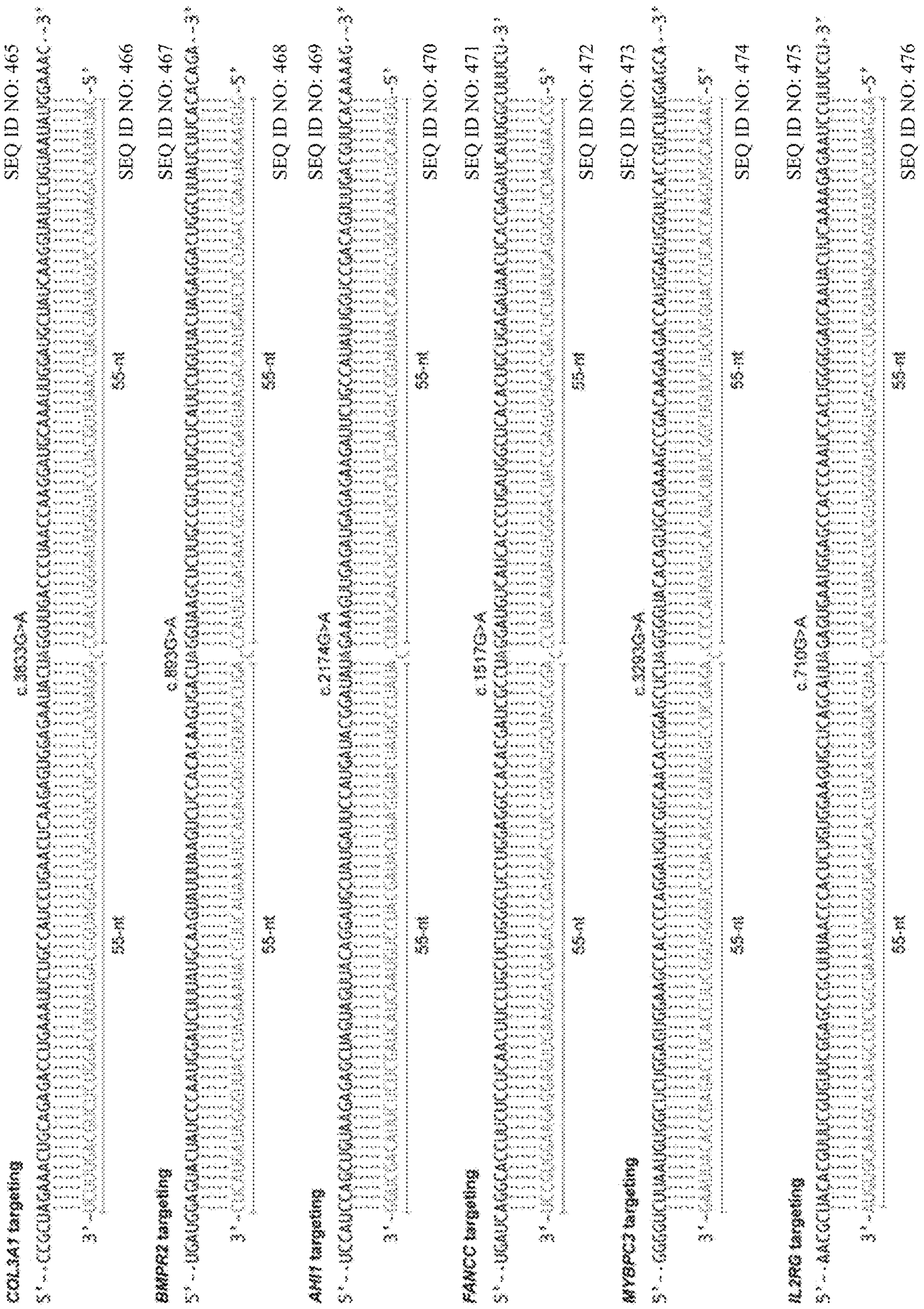
FIG. 25 shows a schematic representation of the selected disease-relevant cDNA containing G to A mutation from ClinVar data and the corresponding 111-nt arRNA.

We next investigated whether LEAPER could be used to correct more pathogenic mutations. Aiming at clinically relevant mutations from six pathogenic genes, COL3A1 of Ehlers-Danlos syndrome, BMPR2 of Primary pulmonary hypertension, AHI1 of Joubert syndrome, FANCC of Fanconi anemia, MYBPC3 of Primary familial hypertrophic cardiomyopathy and IL2RG of X-linked severe combined immunodeficiency, we designed 111-nt arRNAs for each of these genes carrying corresponding pathogenic G>A mutations (FIG. 25 and Sequences of arRNAs and control RNAs used in this study listed above, and the disease-relevant cDNAs used in this study are shown in Table 4).

TABLE 4

Disease-related cDNAs used in this study

| Candidate | Disease | Mutant Adenosine |
|---|---|---|
| NM_000090.3 (COL3A1) | Ehlers-Danlos syndrome, type 4 | c.3833G > A (p.Trp1278Ter) |
| NM_001204.6 (BMIT2) | Primary pulmonary hypertension | c.893G > A (p.Trp298Ter) |
| NM_017651.4 (AHH) | Joubert syndrome 3 | c.2174G > A (p.Trp725Ter) |
| NM_000136.2 (FANCC) | Fanconi anemia, complementation group C | c.1517G > A (p.Trp506Ter) |
| NM_000256.3 (MYBPC3) | Primary familial hypertrophic cardiomyopathy | c.3293G > A (p.Trp1098Ter) |
| NM_000206.2 (IL2RG) | X-linked severe combined immunodeficiency | c.710G > A (p.Trp237Ter) |

By co-expressing arRNA/cDNA pairs in HEK293T cells, we identified significant amounts of target transcripts with A>G corrections in all tests (FIG. 24). Because G>A mutations account for nearly half of known disease-causing point mutations in humans[10,49], the A>G conversion by LEAPER may offer immense opportunities for therapeutics.

Example 14. RNA Editing in Multiple Human Primary Cells by LEAPER

Figure 27A:
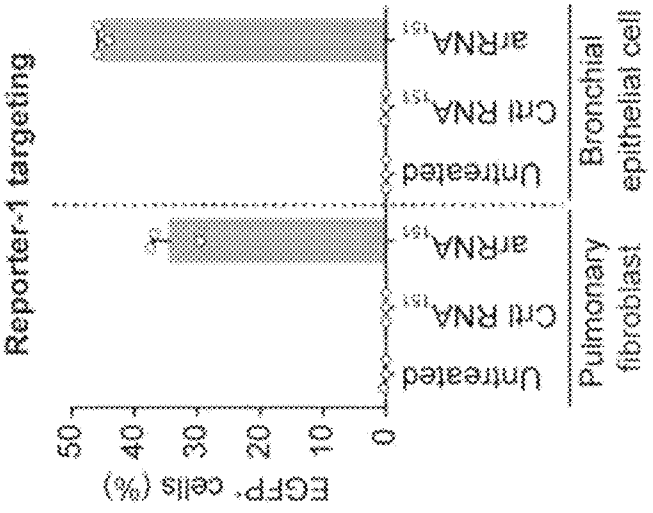
FIGS. 27A-27C show RNA editing in multiple human primary cells by exemplary LEAPER methods.
Figure 27B:
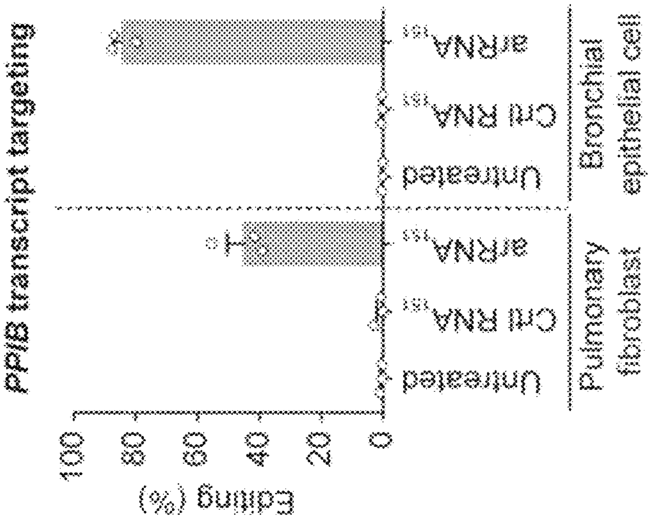
Figure 27C:
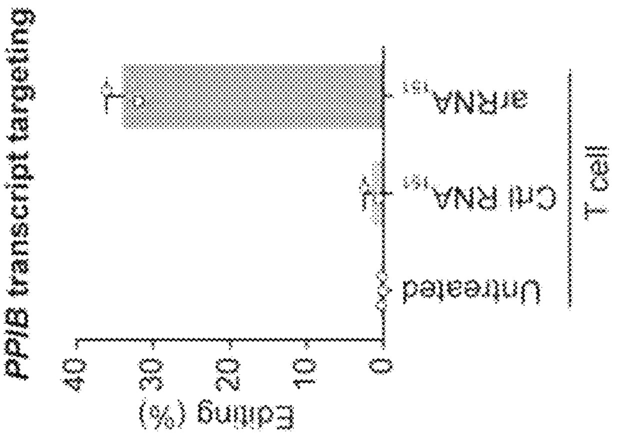

To further explore the clinical utility of LEAPER, we set out to test the method in multiple human primary cells. First, we tested LEAPER in human primary pulmonary fibroblasts and human primary bronchial epithelial cells with 151-nt arRNA (Sequences of arRNAs and control RNAs used in this study listed above) to edit the Reporter-1 (FIG. 15A). 35-45% of EGFP positive cells could be obtained by LEAPER in both human primary cells (FIG. 27A). We then tested LEAPER in editing endogenous gene PPIB in these two primary cells and human primary T cells, and found that $arRNA_{151}$-PPIB could achieve >40%, >80% and >30% of editing rates in human primary pulmonary fibroblasts, primary bronchial epithelial cells (FIG. 27B) and primary T cells (FIG. 27C), respectively. The high editing efficiency of LEAPER in human primary cells is particularly encouraging for its potential application in therapeutics.

Example 15. Efficient Editing by Lentiviral Expression and Chemical Synthesis of arRNAs We then investigated if LEAPER could be delivered by more clinically-relevant methods. We first tested the effect of arRNA through lentivirus-based expression. Reporter-1-targeting $arRNA_{151}$ induced strong EGFP expression in more than 40% of total cells harboring the Reporter-I in HEK293T cells 2 days post infection (dpi). At 8 dpi, the EGFP ratio maintained at a comparable level of -38% (FIG. 28A and Sequences of arRNAs and control RNAs used in this study listed above), suggesting that LEAPER could be tailored to therapeutics that require continuous administration. For native gene editing, we delivered PPIB-targeting $arRNA_{151}$ through lentiviral transduction in HEK293T cells and observed over 6% of target editing at 6 dpi (FIG. 28B).

We next tested synthesized arRNA oligonucleotides and electroporation delivery method for LEAPER. The 111-nt arRNA targeting PPIB transcripts as well as Ctrl RNA were chemically synthesized with 2'-O-methylation and phosphorothioate linkage at the first three and last three nucleotides of arRNAs (FIG. 28C). After introduced into T cells through electroporation, $arRNA_{111}$-PPIB oligos achieved ~20% of editing on PPIB transcripts (FIG. 28D), indicating that LEAPER holds promise for the development of oligonucleotide drugs.

Figure 29A:
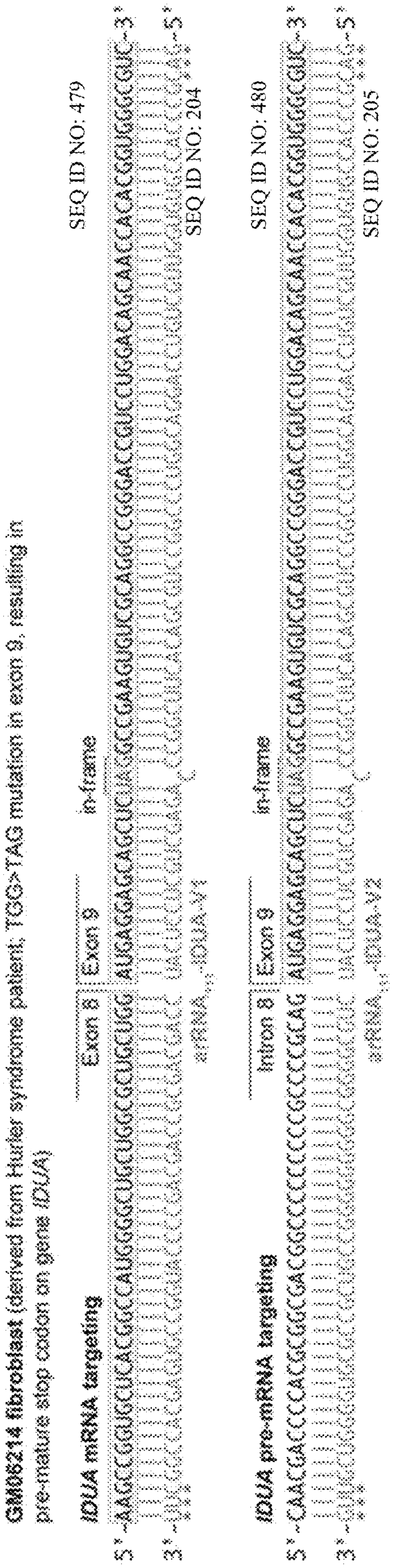
FIGS. 29A-29E show restoration of α-L-iduronidase activity in Hurler syndrome patient-derived primary fibroblast by an exemplary LEAPER method.
Figure 29B:
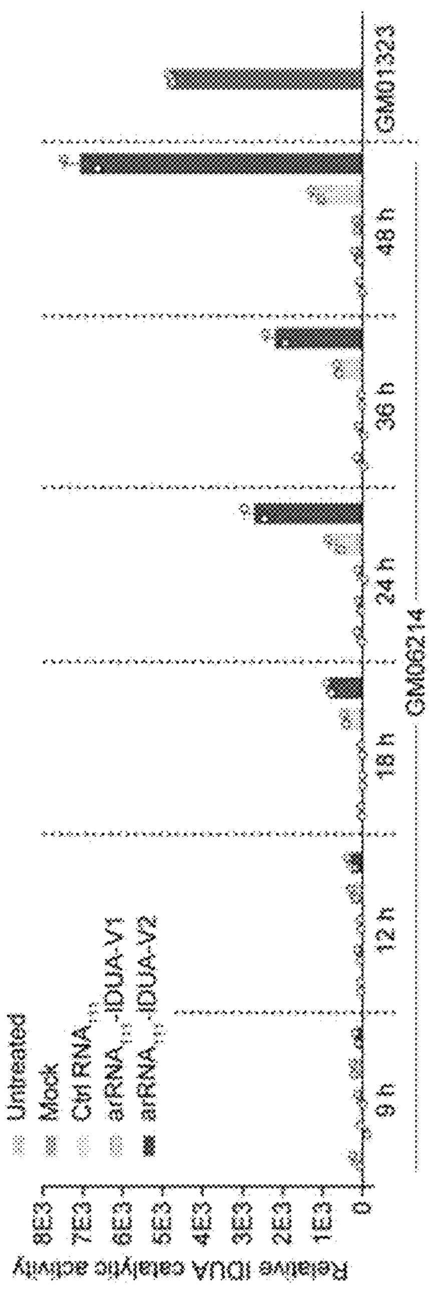

Example 16. Restoration of α-L-Iduronidase Activity in Hurler Syndrome Patient-Derived Primary Fibroblast by LEAPER Finally, we examined the potential of LEAPER in treating a monogenic disease—Hurler syndrome, the most severe subtype of Mucopolysaccharidosis type I (MPS I) due to the deficiency of α-L-iduronidase (IDUA), alysosomal metabolic enzyme responsible for the degradation of mucopolysaccharides[50]. We chose a primary fibroblast GM06214 that was originally isolated from Hurler syndrome patient. The GM06214 cells contain a homozygous TGG>TAG mutation in exon 9 of the IDUA gene, resulting in a Trp402Ter mutation in the protein. We designed two versions of arRNAs by synthesized RNA oligonucleotides with chemical modifications of 2'-O-methylations and internucleotide phosphorothioate linkages in the first and last 3 nucleotides of the sequences, $arRNA_{111}$-IDUA-V1 and $arRNA_{111}$-IDUA-V2, targeting the mature mRNA and the pre-mRNA of IDUA, respectively (FIG. 29A and Sequences of arRNAs and control RNAs used in this study listed above). After introduction of $arRNA_{111}$-IDUA-V1 or $arRNA_{111}$-IDUA-V2 into GM06214 cells via electroporation, we measured the targeted RNA editing rates via NGS analysis and the catalytic activity of α-L-iduronidase with 4-MU-α-L-iduronidase substrate at different time points. Both $arRNA_{111}$-IDUA-V1 and $arRNA_{111}$-IDUA-V2 significantly restored the IDUA catalytic activity in IDUA-deficient GM06214 cells progressively with time after electroporation, and $arRNA_{111}$-IDUA-V2 performed much better than $arRNA_{111}$-IDUA-V1, while no α-L-iduronidase activity could be detected in three control groups (FIG. 29B).

Figure 29C:
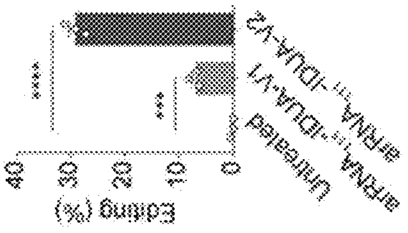
Figure 29D:
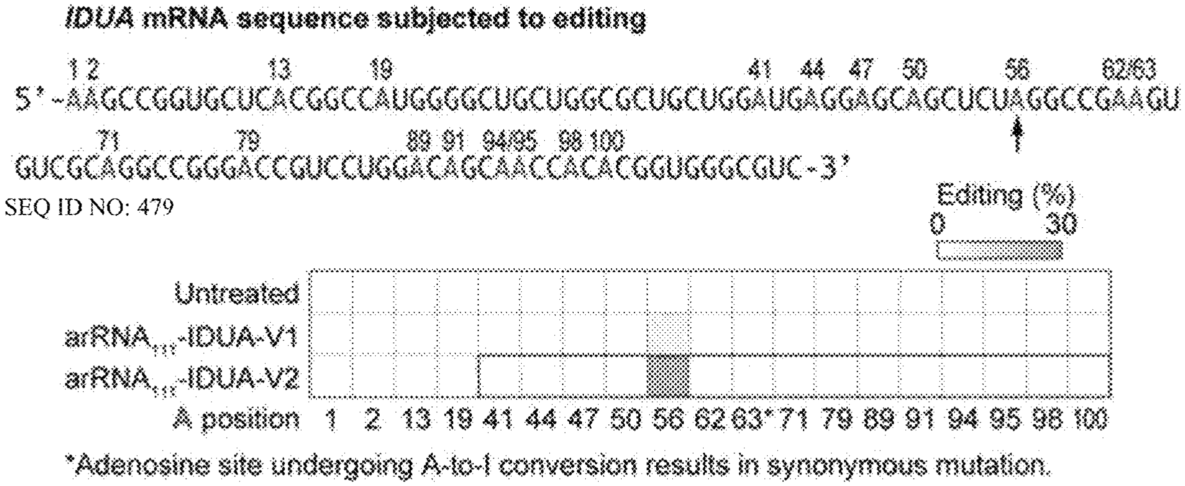
Figure 29E:
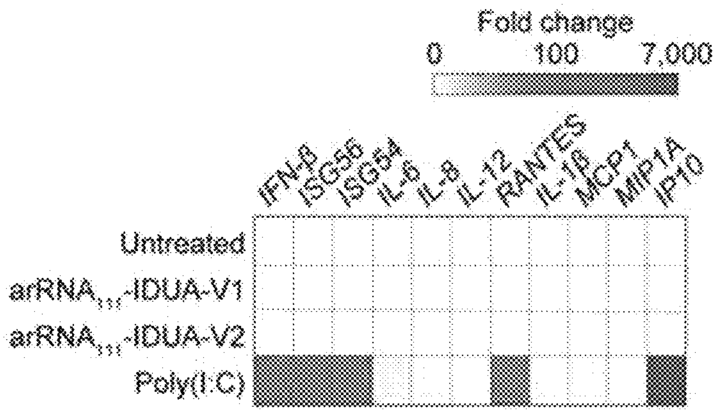

To further evaluate the extent to which the restored IDUA activity in GM06214 by LEAPER relieves the Hurler syndrome, we examined the IDUA activity in GM01323 cells, another primary fibroblasts from patient with Scheie syndrome, a much milder subtype of MPS I than Hurler syndrome due to the remnant IDUA activity resulting from heterozygous genotype on IDUA gene. We found that the catalytic activity of IDUA in GM06214 cells harboring $arRNA_{111}$-IDUA-V2 was higher than GM01323 cells 48 hr post electroporation (FIG. 29B). Consistent with these results, NGS analysis indicated that $arRNA_{111}$-IDUA-V2 converted nearly 30% of A to I editing, a much higher rate than $arRNA_{111}$-IDUA-V1 (FIG. 29C). Further analysis revealed that minimal unwanted edits were detected within the arRNA covered regions of IDUA transcripts (FIG. 29D). Importantly, LEAPER did not trigger immune responses in primary cells as we demonstrated that, unlike the RNA duplex poly(I:C) serving as a positive control, neither $arRNA_{111}$-IDUA-V1 nor $arRNA_{111}$-IDUA-V2 induced expressions of a panel of genes involved in type-I interferon and pro-inflammatory responses (FIG. 29E). These results showed the therapeutic potential of LEAPER in targeting certain monogenetic diseases.

Example 17. Detection of GM06214 Mutant Genotype

GM06214 cells was cultured in a fibroblast culture medium (ScienCell, FM medium, Cat. No. 2301) containing 15% serum and 1% fibroblast growth additive (ScienCell, GFS, Cat. No. 2301), in an incubator of 37° C. and 5% $CO_2$, for 2-3 days. When cells are 90% confluent, they are digested with 0.25% trypsin, then the digestion is terminated by fibroblast culture medium containing 15% serum. DNA extraction was performed using a TianGene® (TIANGEN Biotech (Beijing) Co., Ltd.) cell DNA extraction kit (Cat. No. DP304-03) according to the operating instructions.

Figure 34:
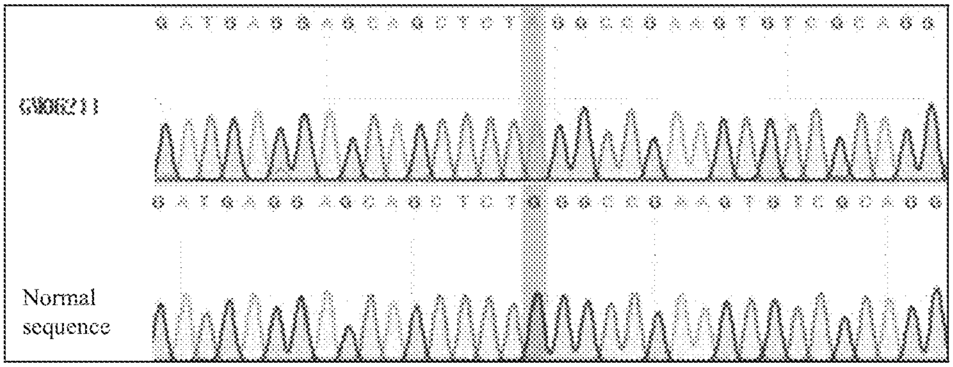
FIG. 34 shows the detected genotype of IDUA in GM06214 cells. A C1205 G>A mutation was in the genome.

Primers for sequences upstream and downstream of the IDUA mutation site was designed using NCBI-Primer blast (website: https://www.ncbi.nlm.nih.gov/tools/primer-blast/). SEQ ID NO:304: CGCTTCCAGGTCAACAACAC (forward primer hIDUA-F1); SEQ ID NO 305: CTCGCGTAGATCAGCACCG (reverse primer hIDUA-R1). A PCR was performed, and the PCR products were subjected to Sanger sequencing. As shown in FIG. 34, the mutation of the cells was confirmed to be a G to A mutation which results in the disease.

Example 18. Test of GM06214 Cell Transfection Conditions

Figure 35:
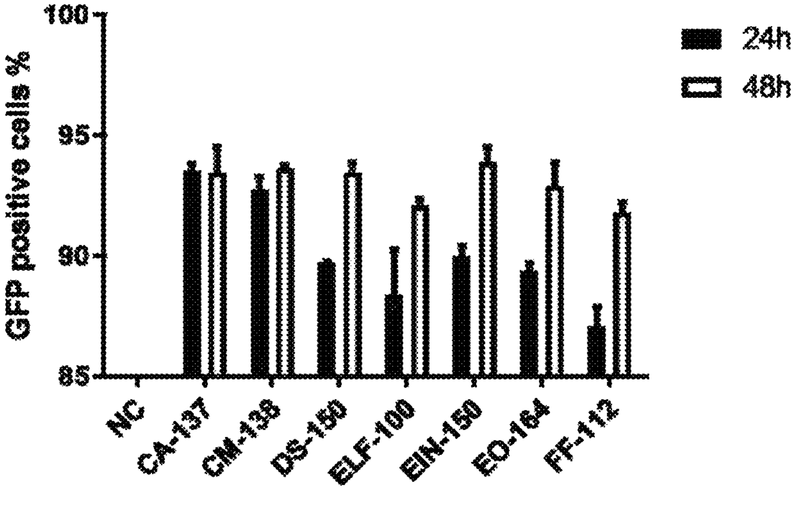
FIG. 35 shows the test result of electrotransfection conditions of cells.

GM06214 cells were digest when the GM06214 at 90% confluency, and were counted after the terminating of digestion. For electrotransfection, 6 million cells were resuspend with 400 ul of pre-mixed electrotransfection solution (Lonza, Cat. No. V4XP-3024), and added with 20 ug of GFP plasmid (Lonza, Cat. No. V4XP-3024). After mixing, 20 ul of the suspension is taken as an electrotrasfection system for the test of each of the 8 conditions, comprising 7 test electrotransfection conditions (see FIG. 35) and one negative control, using a Lonza Nucleofector™ instrument. The test of each condition is duplicated. After electrotransfection, the cells are rapidly transferred into 2 ml fibroblast culture medium (ScienCell, FM medium, Cat. No. 2301) containing 15% serum. Cells of each condition were plated into 2 wells (6 well culture plates) and cultured in an incubator of 5% $CO_2$ and 37° C. 24 hours after electrotransfection, cells in one of the 2 wells of each electrotransfection condition were digested, and the proportion of GFP-positive cells was measured by flow cytometry. 48 hours after electrotransfection, the cells in the other well of the 2 wells of each electrotransfection condition are digested, and the proportion of GFP-positive cells was measured by flow cytometry. The optimal electrotransfection conditions for the cells are CA-137 conditions, as shown in FIG. 35.

Example 19. Detection of IDUA Enzyme Activity and A to G Mutation Rate

The oligo dRNAs are designed and synthesized for targeting the sequence with the mutation site of the pre-mRNA and mature RNA transcribed from IDUA gene. The sequence of the dRNAs are shown as follows. All the dRNA sequences were modified in CM0 pattern (2'-O-methylations were in the first and last 3 nucleotides of the sequences and the first and last 3 internucleotide linkages in the sequences were phosphorothioated).

```
SEQ ID NO 204:
gacgcccaccgugugguugcuguccaggacggucccggcc

ugcgacacuucggcccagagcugcuccucauccagcagcg

ccagcagccccauggccgugagcaccggcuu
(Pre-55nt-c-55nt);

SEQ ID NO 205:
gacgcccaccgugugguugcuguccaggacggucccggcc

ugcgacacuucggcccagagcugcuccucaucugcggggc

gggggggggccgucgccgcguggggucguug
(m-55nt-c-55nt);

SEQ ID NO 341:
uaccgcuacagccacgcugauuucagcuauaccugcccgg

uauaaagggacguucacaccggauguucucccgcggggaua

ucgcgauauucaggauuaaaagaagugc
(Random-111nt).
```

Wherein the base corresponding to the mutated base in the synthesized dRNA is a C, which forms an A-C mismatch with the mutated base when binding. The length of the synthesized dRNA is preferably 111 nt. The cells were electrotransfected using the optimal electrotransfection condition obtained in Example 2. 48 hours after electrotransfection, the cells were collected for enzyme activity determination and A to G mutation rate detection.

Determination of A to G Mutation Rate:

The designed dRNA was dissolved to the required concentration in RNase-free water (TransGene Biotech, Cat. No. GI201-01) and stored at −80° C. Cells were digested when the GM06214 cells grow to about 90% confluence and counted after the terminating of the digestion. 1 million cells and 200 pmol of dRNA were mixed and diluted to 100 μl, and then electrotransfected under the condition of CA-137. 48 hours after electrotransfection, cells were counted and their viability was measured. The cells were transferred to a RNase-free centrifuge tube and centrifuged. The supernatant was discarded. RNA was extracted using a QIAGEN RNA extraction kit (QIAGEN, Cat. No. 74134). According to the instructions, 0.35 ml of Buffer RLT Plus was mixed with $5\times10^5$ cells (if the RNA is directly extracted from frozen cells, it is recommended that cells be washed with PBS once) by pipetting. The cell lysate was transferred to the gDNA Eliminator spin column and centrifuged at ≥8000 g for 30 s. The column was discarded and the liquid was remained. The same volume of 70% ethanol as the liquid was added. Immediately after mixing, the mixture was transferred to the RNeasyMinElute spin column and centrifuged at ≥8000 g for 15 sand the waste liquid was discarded. 700 μl of Buffer RW1 was added to the RNeasyMinElute spin column and centrifuged at ≥8000 g for 15 s. Waste solution was discarded and 500 μl of Buffer RPE was added, and then the RNeasyMinElute spin column was centrifuge at ≥8000 g for 15 s. Waste solution was discarded and 500 μl of 80% ethanol was added, and then the RNeasyMinElute spin column was centrifuged at ≥8000 g for 2 minutes. Waste solution was discarded. The RNeasyMinElute spin column was placed into a new 2 ml collection column and centrifuged with the lid at maximum speed for 5 minutes to dry the column. The RNeasyMinElute spin column was placed into a new 1.5 ml collection column and 14 μl of RNase-free water was added dropwise to the center of the column membrane, then the columns are centrifuged at maximum speed for 1 minute to elute the RNA.

The concentration of the extracted RNA was determined by Nanodrop (Thermo, Nanodrop2000), and 1 μg of RNA was used for reverse transcription (Thermo, reverse transcriptase, Cat. No. 28025013). The reverse transcription system was shown in Table 5-6. After incubation at 65° C. for 5 minutes, the reverse transcription system was immediately cooled in an ice bath. Incubation was continued at 37° C. for 50 minutes. Reverse transcriptase was inactivated at 70° C. for 15 minutes. PCR was performed under the conditions shown in Table 7. After PCR, 2 ul of the PCR product was taken for agarose gel electrophoresis. According to the results of the electrophoresis, the concentration of the PCR product and whether the band size is correct is determined. After purification, the PCR products were used to preparing the library which was sent for next-generation sequencing.

TABLE 5

Reverse transcription system-1

| | Volume (ul) |
|---|---|
| Total RNA (1 ug) | X |
| Oligo dT | 1 |
| 10 nM dNTP | 1 |
| RNase-Free Water | 10-X |
| Total volume | 12 |

65° C., 5 min, and immediately transferring to the ice

TABLE 6

Reverse transcription system-2

| | Volume (ul) |
|---|---|
| The product from Table 5 | 12 ul |
| 5 × First-Strand Buffer | 4 |
| 0.1 M DTT | 2 |
| RNaseOUT ™ Recombinant Ribonuclease Inhibitor | 1 |
| M-MLV | 1 |
| Total volume | 20 |

TABLE 7

PCR conditions

| Steps | Time | Cycle |
|---|---|---|
| 98° C. | 2 min | 1 cycle |
| 98° C. | 15 s | 28-35 cycle |
| 63° C. | 30 s | |
| 72° C. | 15 s | |
| 72° C. | 2 min | 1 cycle |

Enzyme Activity Assay in this Example

GM06214 cells were digested, centrifuged, and resuspended in 28 ul of 1×PBS containing 0.1% Triton X-100 and lysed on ice for 30 minutes. Then 25 ul of cell lysate was added to 25 ul of substrate containing 190 m 4-methylumbelliferyl-α-L-iduronidase (Cayman, 2A-19543-500, Dissolved in 0.4 M sodium formate buffer containing 0.2% Triton X-100, pH 3.5) and incubated in the dark at 37° C. for 90 minutes. 200 ul 0.5M NaOH/Glycine solution (Beijing Chemical Works, NAOH, Cat. No. AR500G; Solarbio, Glycine, Cat. No. G8200), pH 10.3, was added to inactivate the catalytic reaction. After centrifuging at 4° C. for 2 minutes, its supernatant was transferred to a 96-well plate for the determination of fluorescence values using Infinite M200 instrument (TECAN). The wavelength of the excitation light was 365 nm and 450 nm. The fluorescence represents the enzyme activity which in the figures is expressed as a multiple of the enzyme activity in GM01323.

Figure 36A:
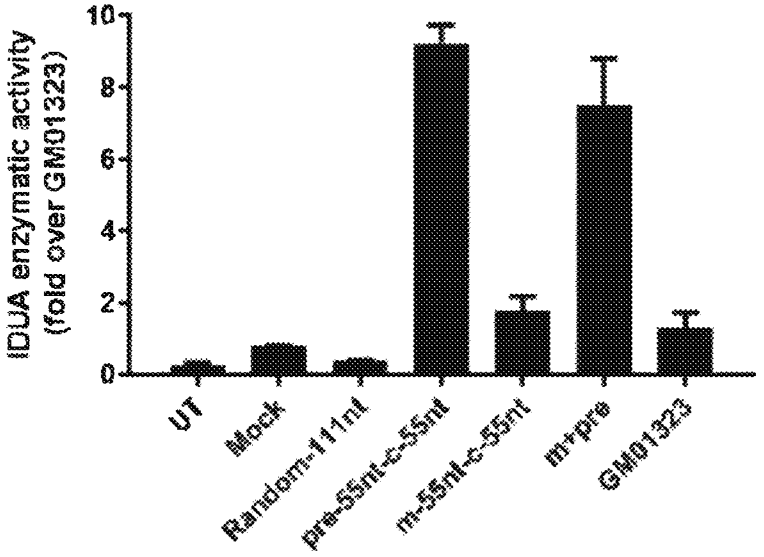
FIGS. 36A-36B show enzyme activity of IDUA (FIG. 36A) and rate of desired mutation (FIG. 36B) in cells transfected with dRNAs designed to target IDUA pre-mRNA and mRNA using electroporation, respectively.
Figure 36B:
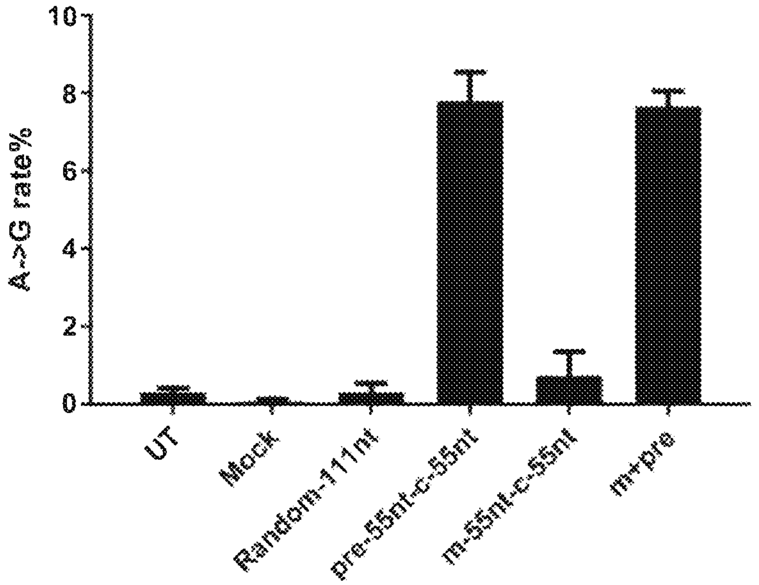

As shown in FIGS. 36A-36B, the results were that dRNA targeting pre-mRNA leading to significantly higher enzyme activity and A to G mutation rate than those targeting mature-mRNA. Therefore, the dRNAs used in the following examples are targeted to pre-mRNA.

Figure 37A:
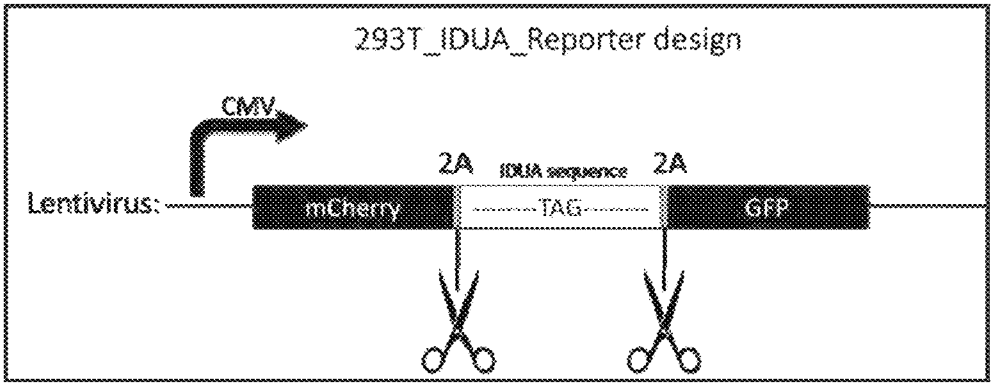
FIGS. 37A-37B show the test using IDUA-reporter.
Figure 37B:
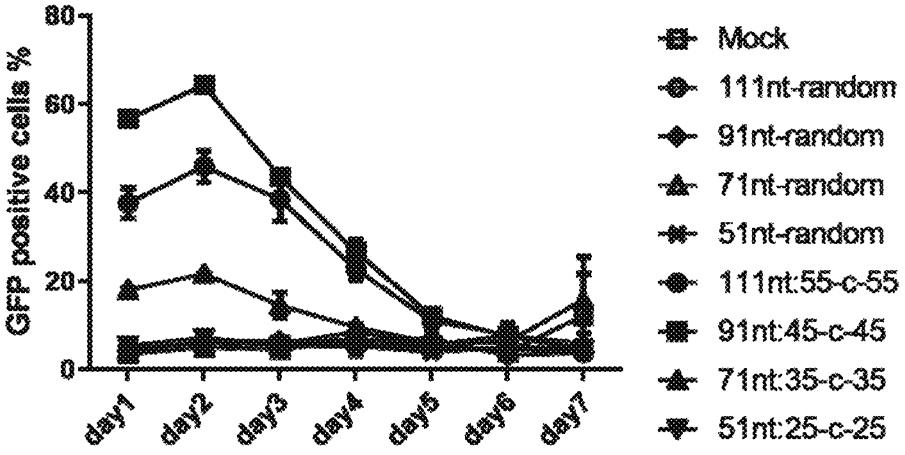

Example 20. Detection of Editing Efficiency in IDUA-Reporter Cell Line after Electrotransfection of Chemically Modified dRNA As shown in FIG. 37A, a plasmid was constructed by inserting a sequence with an IDUA mutation site flanked with about 100 bp on each side, respectively, between the sequences expressing mCherry and GFP proteins on the lentiviral plasmid. The constructed plasmids were packaged into viruses used to infect 293T cells later. After integration into the genome, IDUA-reporter monoclonal cells were selected. Because the monoclonal cells were affected by the TAG stop codon of the IDUA mutation site in the inserted sequence, they only expressed the mCherry protein. When the cells are edited by dRNA, the GFP behind TAG which has then been mutated to TGG can express normally. Thus, the expression of GFP was viewed as the editing efficiency of dRNA in cells. 4 preferable dRNAs with different lengths from 51 nt to 111 nt were designed, as shown in Table 8 below. All the dRNA sequences were modified in CM0 pattern. Cells were electrotransfected with dRNAs of different lengths under the conditions of electrotransfection in Example 18. On each day from the 1th day to the 7th day after the transfection, the editing efficiency was preliminarily evaluated by determining the ratio of GFP in the cells. As shown in FIG. 37B, the peak of editing efficiency appeared on the second day (48 h). The sequence with the highest editing efficiency was 91 nt: 45-c-45 which is higher than that of 111 nt: 55-c-55. Accordingly, it's not in all cases that the longer the dRNA, the higher the editing efficiency. Besides, the editing efficiency of dRNAs of 51 nt was very low.

TABLE 8

| | |
|---|---|
| hint-random | SEQ ID NO: 140: uaccgcuacagccacgcugauuucagcuauaccugcccgguauaaagggacguucacaccgcgauguucucugcuggggaauugcgcgauauucaggauuaaaagaagugc |
| 91nt-ramdom | SEQ ID NO: 342: uaauccugaauaucgcgcaauuccccagcagagaacaucgcggugugaacgucccuuuauaccgggcagguauagcugaaaucagcguggc |
| 71nt-random | SEQ ID NO: 343: uuucagcuauaccugcccgguauaaagggacguucacaccgcgauguucucugcuggggaauugcgcgaua |
| 51nt-random | SEQ ID NO 8: uuccccagcagagaacaucgcggugugaacgucccuuuauaccgggcaggu |

TABLE 8-continued

| | |
|---|---|
| 55nt-c-55nt | SEQ ID NO: 205: gacgcccaccgugugguugcuguccaggacggucccggccugcgacacuucggcccagagcugcuccucaucugcggggcgggggggggccgucgccgcgugggggucguug |
| 45nt-c-45nt | SEQ ID NO: 344: gugugguugcuguccaggacggucccggccugcgacacuucggcccagagcugcuccucaucugcggggcgggggggggccgucgccgcgu |
| 35nt-c-35nt | SEQ ID NO: 345: uguccaggacggucccggccugcgacacuucggcccagagcugcuccucaucugcggggcgggggggggcc |
| 25nt-c-25nt | SEQ ID NO: 346: ggucccggccugcgacacuucggcccagagcugcuccucaucugcggggcg |

Figure 38A:
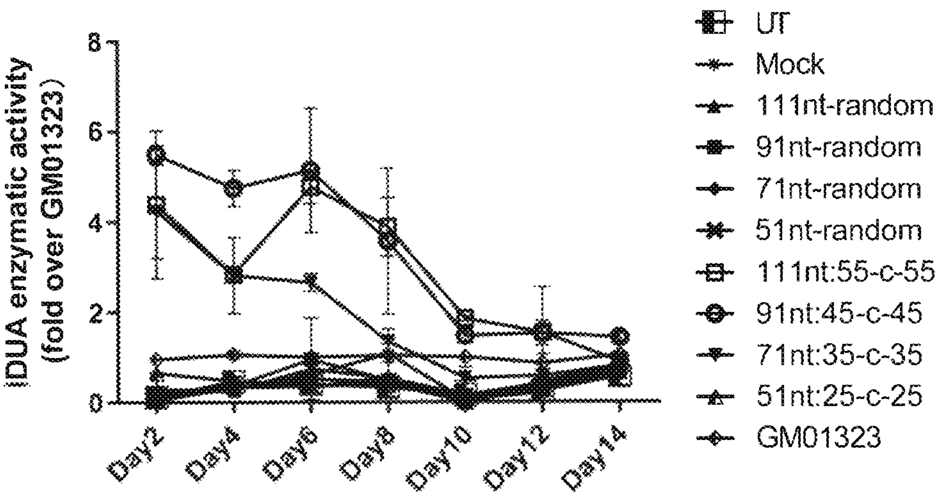
FIGS. 38A-38B show the enzyme activity (FIG. 38A) and editing efficiency (FIG. 38B) determined at different time points in GM06214 cells electrotransfected with dRNAs of different lengths (symmetric truncations).
Figure 38B:
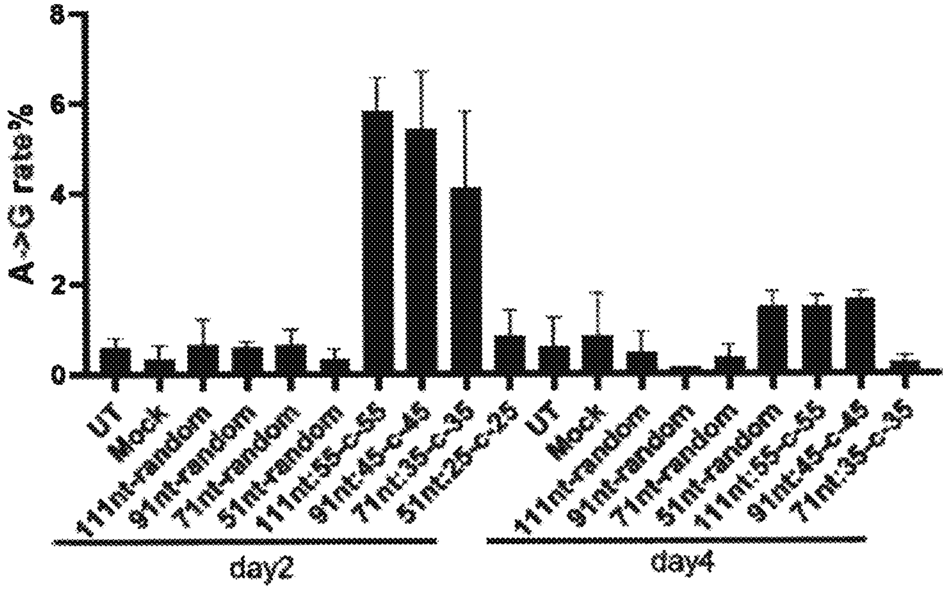

Example 21. Determination of the Intracellular IDUA Enzyme Activity and RNA Editing Efficiency in GM06214 Cells at Different Time Points after Transfection with Chemically Modified dRNAs of Different Lengths The conditions in Example 18 (see Table 7) for electrotransfecting dRNAs of different lengths into GM06214 cells and the methods in Example 19 for determining enzyme activity and editing efficiency were used. On the 2th, 4th, 6th, 8th, $10^{th}$, $12^{th}$ and $14^{th}$ after the electrotransfection, the intracellular enzyme activity was tested. And on the 2th and $4^{th}$ day, the efficiency of RNA editing in the cells was tested. As shown in FIG. 38A, 91 nt: 45-c-45 led to the highest enzyme activity, and the IDUA enzyme activity had been maintained at a high level till the 6th day after electrotransfection. In FIG. 38B, dRNA of 91 nt and dRNA of 111 nt presented roughly the same editing efficiency. Again, the dRNA of 51 nt showed a low editing efficiency.

Example 22. Screening for Preferable Sequences of Chemically Modified dRNAs

Figure 39A:
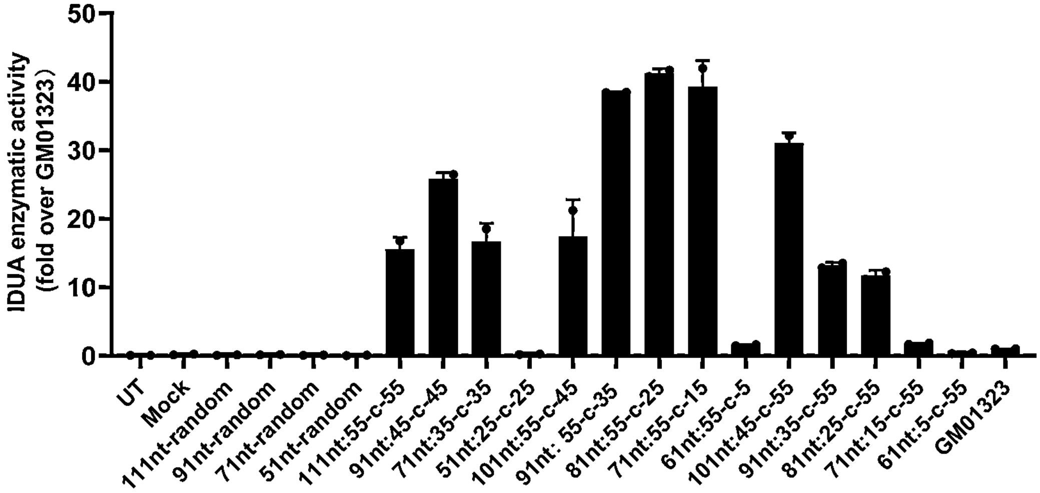
FIGS. 39A-39B show the determined IDUA enzyme activity (FIG. 39A) and A to G mutation rate (FIG. 39B) in cells transfected with different dRNAs (symmetrical truncations, 3' terminal truncations and 5' terminal truncations) using Lipofectamine RNAiMAX.
Figure 39B:
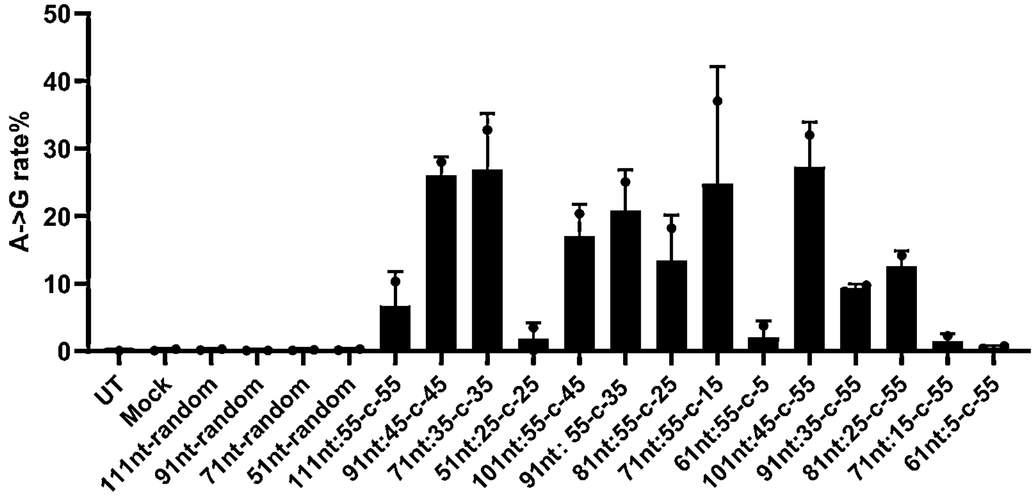

Through literature research, we believe electrotransfection is not suitable for disease treatment in the future. Therefore, we turned electrotransfection to Lipofectamine RNAiMAX (Invitrogen, Cat. No. 13778-150) for transfecting dRNA into cells. It turned out that the Lipofectamine RNAiMAX has a higher transfection efficiency than that of electrotransfection. The sequence was first truncated on both termini at the same time, and then one terminus of the sequence is fixed and the other terminus was truncated. In this way, 14 dRNAs and 4 random sequences of equal length are obtained, as shown in Table 9 below. All the dRNA sequences were modified in CM0 pattern. As shown in FIG. 39, the IDUA enzyme activity (FIG. 39A, using the method described in Example 19) and RNA editing efficiency (FIG. 39B, using NGS) were determined 48 hours after transfection. The IDUA enzyme activities and RNA editing efficiencies led by 8 nt: 55-c-25 (SEQ ID NO 24) and 71 nt: 55-c-15 (SEQ ID NO 25) turned out to be higher than that led by the other dRNAs. An dRNA with a shorter 3' terminus and a longer 5' terminus always had a higher efficiency. In addition, it seems that the editing efficiency of dRNA decreased dramatically when its length was reduced to 61 nt or less, no matter how the 3' or 5' terminus changed.

TABLE 9

| | |
|---|---|
| 111nt-random | SEQ ID NO: 140: uaccgcuacagccacgcugauuucagcuauaccugcccgguauaaagggacguucacaccgcgauguucucugcuggggaauugcgcgauauucaggauuaaaagaagugc |
| 91nt-random | SEQ ID NO: 342: uaauccugaauaucgcgcaauuccccagcagagaacaucgcggugugaacgucccuuuauaccgggcagguauagcugaaaucagcguggc |
| 71nt-random | SEQ ID NO: 343: uuucagcuauaccugcccgguauaaagggacguucacaccgcgauguucucugcuggggaauugcgcgaua |
| 51nt-random | SEQ ID NO 8: uuccccagcagagaacaucgcggugugaacgucccuuuauaccgggcaggu |
| 55nt-c-55nt | SEQ ID NO: 205: gacgcccaccgugugguugcuguccaggacggucccggccugcgacacuucggcccagagcugcuccucaucugcggggcgggggggggccgucgccgc |
| 45nt-c-45nt | SEQ ID NO: 344: gugugguugcuguccaggacggucccggccugcgacacuucggcccagagcugcuccucaucugcggggcgggggggggccgcugccgcgu |
| 35nt-c-35nt | SEQ ID NO: 345: uguccaggacggucccggccugcgacacuucggcccagagcugcuccucaucugcggggcgggggggggcc |
| 25nt-c-25nt | SEQ ID NO: 346: ggucccggccugcgacacuucggcccagagcugcuccucaucugcggggcg |
| 55nt-c-45nt | SEQ ID NO: 347: gacgcccaccgugugguugcuguccaggacggucccggccugcgacacuucggcccagagcugcuccucaucugcggggcgggggggggccgucgccgcgu |
| 55nt-c-35nt | SEQ ID NO: 348: gacgcccaccgugugguugcuguccaggacggucccggccugcgacacuucggcccagagcugcuccucaucugcggggcgggggggggcc |
| 55nt-c-25nt | SEQ ID NO: 349: gacgcccaccgugugguugcuguccaggacggucccggccugcgacacuucggcccagagcugcuccucaucugcggggcg |
| 55nt-c-15nt | SEQ ID NO: 350: gacgcccaccgugugguugcuguccaggacggucccggccugcgacacuucggcccagagcugcuccucau |
| 55nt-c-5nt | SEQ ID NO: 351: gacgcccaccgugugguugcuguccaggacggucccggccugcgacacuucggcccagagc |
| 45nt-c-55nt | SEQ ID NO: 352: gugugguugcuguccaggacggucccggccugcgacacuucggcccagagcugcuccucaucugcggggcgggggggggccgucgccgcguggggucguug |
| 35nt-c-55nt | SEQ ID NO: 353: uguccaggacggucccggccugcgacacuucggcccagagcugcuccucaucugcggggcgggggggggccgucgccgcguggggucguug |
| 25nt-c-55nt | SEQ ID NO: 354: ggucccggccugcgacacuucggcccagagcugcuccucaucugcggggcgggggggggccgucgccgcguggggucguug |
| 15nt-c-55nt | SEQ ID NO: 355: ugcgacacuucggcccagagcugcuccucaucugcggggcgggggggggccgucgccgcguggggucguug |
| 5nt-c-55nt | SEQ ID NO: 356: cggcccagagcugcuccucaucugcggggcgggggggggccgucgccgcguggggucguug |

Figure 40A:
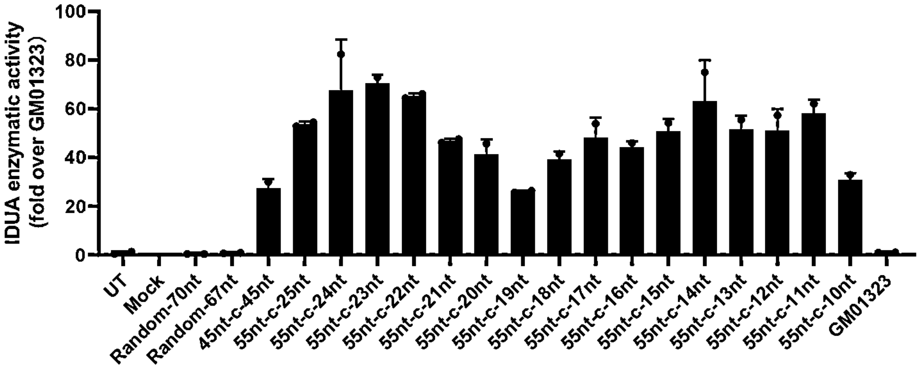
FIGS. 40A-40B show the comparison of enzyme activities in GM06214 cells transfected with dRNAs of different lengths using Lipofectamine RNAiMAX.
Figure 40B:
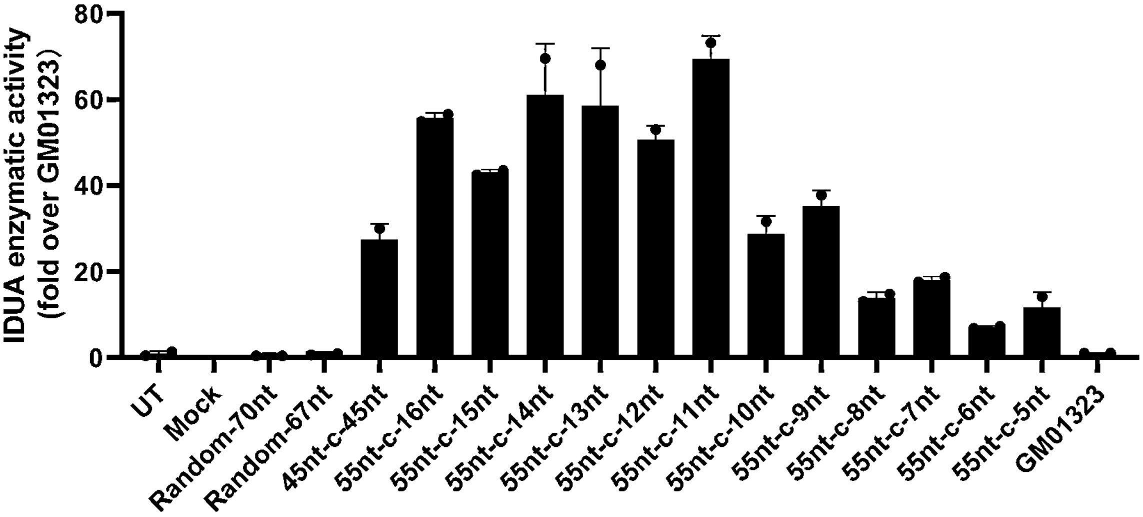

Example 23. Determination of the Optional Length of the 3' Terminus of Chemically Modified dRNA In Example 22, higher IDUA enzyme activity and editing efficiency were detected in cells edited by dRNAs with 81 nt: 55-c-25 and 71 nt: 55-c-15 sequences. In order to find out the shortest and optimal length of the 3' terminus, the sequence at 3' terminus of was truncated from 25 nt (81 nt: 55-c-25) to 5 nt (61 nt: 55-c-5), as shown in Table 10. All the dRNA sequences were modified in CM0 pattern. Two IDUA enzyme activity assays were conducted on cells separately transfected with dRNAs from 81 nt: 55-c-25 to 66 nt: 55-c-10 (FIG. 40A) and cells separately transfected with dRNAs from 72 nt: 55-c-16 to 61 nt: 55-c-5 (FIG. 40B). The dRNAs with the 3' terminus lengths from 25 nt to 9 nt easily raised the enzymatic activity in GM06214 cells to more than 20 times of that in GM0123 cells. Accordingly, the optimal length of the 3' terminus was 25 nt-7 nt. Besides, compared to 45 nt-c-45 nt having equal length of 3' and 5' termini, the dRNAs with shorter 3' termini always had higher editing efficiency.

The IDUA enzyme activity assay used herein is described as below. One day before transfection, $3\times10^5$ cells per well were plated in a 6-well plate. Medium was refreshed on the day of transfection. 48 hrs after transfection using 20 nM Lipofectamine RNAiMAX reagent, GM06214 cells were digested, centrifuged, and resuspended in 33 ul of 1×PBS containing 0.1% Triton X-100 and lysed on ice for 30 minutes. Then the lysate was centrifuged at 4° C. for 2 min. 25 ul of cell lysate was added to 25 ul of substrate containing 190 μm 4-methylumbelliferyl-α-L-iduronidase (Glycosynth, 44076) dissolved in 0.4 M sodium formate buffer containing 0.2% Triton X-100 (pH 3.5) and incubated in the dark at 37° C. for 30 minutes. 200 ul 0.5M NaOH/Glycine solution (Beijing Chemical Works, NAOH, Cat. No. AR500G; Solarbio, Glycine, Cat. No. G8200), pH 10.3, was added to inactivate the catalytic reaction. All of its supernatant was detected using Infinite M200 instrument (TECAN). The wavelength of the excitation light was 365 nm and 450 nm. The enzyme activity is expressed as a multiple of the enzyme activity in GM01323.

TABLE 10

| | |
|---|---|
| 55nt-c-25nt | SEQ ID NO: 349: gacgcccaccgugugguugcuguccaggacggucccggccugcgacacuucggcccagagcugcuccucaucugcggggcg |
| 55nt-c-24nt | SEQ ID NO: 357: gacgcccaccgugugguugcuguccaggacggucccggccugcgacacuucggcccagagcugcuccucaucugcggggc |
| 55nt-c-23nt | SEQ ID NO: 358: gacgcccaccgugugguugcuguccaggacggucccggccugcgacacuucggcccagagcugcuccucaucugcgggg |
| 55nt-c-22nt | SEQ ID NO: 359: gacgcccaccgugugguugcuguccaggacggucccggccugcgacacuucggcccagagcugcuccucaucugcggg |
| 55nt-c-21nt | SEQ ID NO: 360: gacgcccaccgugugguugcuguccaggacggucccggccugcgacacuucggcccagagcugcuccucaucugcgg |
| 55nt-c-20nt | SEQ ID NO: 361: gacgcccaccgugugguugcuguccaggacggucccggccugcgacacuucggcccagagcugcuccucaucugcg |
| 55nt-c-19nt | SEQ ID NO: 362: gacgcccaccgugugguugcuguccaggacggucccggccugcgacacuucggcccagagcugcuccucaucugc |
| 55nt-c-18nt | SEQ ID NO: 363: gacgcccaccgugugguugcuguccaggacggucccggccugcgacacuucggcccagagcugcuccucaucug |

TABLE 10-continued

| | |
|---|---|
| 55nt-c-17nt | SEQ ID NO: 364: gacgcccaccgugugguugcuguccaggacggucccggccu gcgacacuucggcccagagcugcuccucaucu |
| 55nt-c-16nt | SEQ ID NO: 365: gacgcccaccgugugguugcuguccaggacggucccggccu gcgacacuucggcccagagcugcuccucauc |
| 55nt-c-15nt | SEQ ID NO: 350: gacgcccaccgugugguugcuguccaggacggucccggccu gcgacacuucggcccagagcugcuccucau |
| 55nt-c-14nt | SEQ ID NO: 366: gacgcccaccgugugguugcuguccaggacggucccggccu gcgacacuucggcccagagcugcuccuca |
| 55nt-c-13nt | SEQ ID NO: 367: gacgcccaccgugugguugcuguccaggacggucccggccu gcgacacuucggcccagagcugcuccuc |
| 55nt-c-12nt | SEQ ID NO: 368: gacgcccaccgugugguugcuguccaggacggucccggccu gcgacacuucggcccagagcugcuccu |
| 55nt-c-11nt | SEQ ID NO: 369: gacgcccaccgugugguugcuguccaggacggucccggccu gcgacacuucggcccagagcugcucc |
| 55nt-c-10nt | SEQ ID NO: 370: gacgcccaccgugugguugcuguccaggacggucccggccu gcgacacuucggcccagagcugcuc |
| 55nt-c-9nt | SEQ ID NO: 371: gacgcccaccgugugguugcuguccaggacggucccggccu gcgacacuucggcccagagcugcu |
| 55nt-c-8nt | SEQ ID NO: 372: gacgcccaccgugugguugcuguccaggacggucccggccu gcgacacuucggcccagagcugc |
| 55nt-c-7nt | SEQ ID NO: 373: gacgcccaccgugugguugcuguccaggacggucccggccu gcgacacuucggcccagagcug |
| 55nt-c-6nt | SEQ ID NO: 374: gacgcccaccgugugguugcuguccaggacggucccggccu gcgacacuucggcccagagcu |
| 55nt-c-5nt | SEQ ID NO: 375: gacgcccaccgugugguugcuguccaggacggucccggccu gcgacacuucggcccagagc |
| random-70nt | SEQ ID NO: 376: uaccgcuacagccacgcugauuucagcuauaccugcccggu auaaagggacguucacaccgcgauguucu |
| random-67nt | SEQ ID NO: 377: uaccgcuacagccacgcugauuucagcuauaccugcccggu auaaagggacguucacaccgcgaug |

Figure 41:
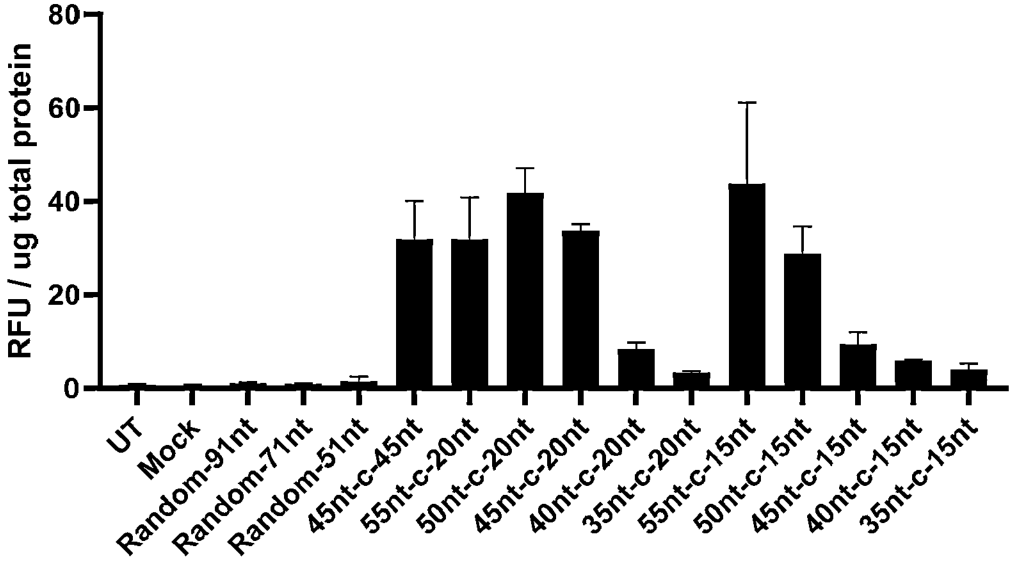
FIG. 41 shows the comparison of enzyme activities in GM06214 cells transfected with dRNAs of different lengths (the length of 3' terminus was fixed to 15 nt or 20 nt, while the length of the 5' terminus was gradually reduced) using Lipofectamine RNAiMAX.

Example 24. Determination of the Optional Length of 5' Terminus of Chemically Modified dRNA when the Length of its 3' Terminus was Fixed The truncation of 5' terminus was separately conducted on dRNAs of two different lengths: 76 nt: 55-c-20 and 71 nt: 55-c-15. With the fixed length of 3' terminus, their 5' termini were gradually truncated, as shown in Table 11. All the dRNA sequences were modified in CM0 pattern. According to the result of IDUA enzyme activity assay, cells transfected with dRNAs with 5' terminals between 55 nt and 45 nt had higher IDUA enzyme activity, as shown in FIG. 41. Lipofectaine RNAiMAX was used in the transfection. In accordance with FIG. 39, when the length was reduced to less than 61 nt, the editing efficiency of dRNAs, even those with unequal lengths of 3' and 5' termini, decreased dramatically.

TABLE 11

| | |
|---|---|
| 55nt-c-20nt | SEQ ID NO: 361: gacgcccaccgugugguugcuguccaggacggucccggccugc gacacuucggcccagagcugcuccucaucugcg |
| 50nt-c-20nt | SEQ ID NO: 378: ccaccgugugguugcuguccaggacggucccggccugcgacac uucggcccagagcugcuccucaucugcg |
| 45nt-c-20nt | SEQ ID NO: 379: gugugguugcuguccaggacggucccggccugcgacacuucgg cccagagcugcuccucaucugcg |
| 40nt-c-20nt | SEQ ID NO: 380: guugcuguccaggacggucccggccugcgacacuucggcccag agcugcuccucaucugcg |
| 35nt-c-20nt | SEQ ID NO: 381: uguccaggacggucccggccugcgacacuucggcccagagcug cuccucaucugcg |
| 55nt-c-15nt | SEQ ID NO: 350: gacgcccaccgugugguugcuguccaggacggucccggccugc gacacuucggcccagagcugcuccucau |
| 50nt-c-15nt | SEQ ID NO: 382: ccaccgugugguugcuguccaggacggucccggccugcgacac uucggcccagagcugcuccucau |
| 45nt-c-15nt | SEQ ID NO: 383: gugugguugcuguccaggacggucccggccugcgacacuucgg cccagagcugcuccucau |
| 40nt-c-15nt | SEQ ID NO: 384: guugcuguccaggacggucccggccugcgacacuucggcccag agcugcuccucau |
| 35nt-c-15nt | SEQ ID NO: 385: uguccaggacggucccggccugcgacacuucggcccagagcug cuccucau |

Figure 42:
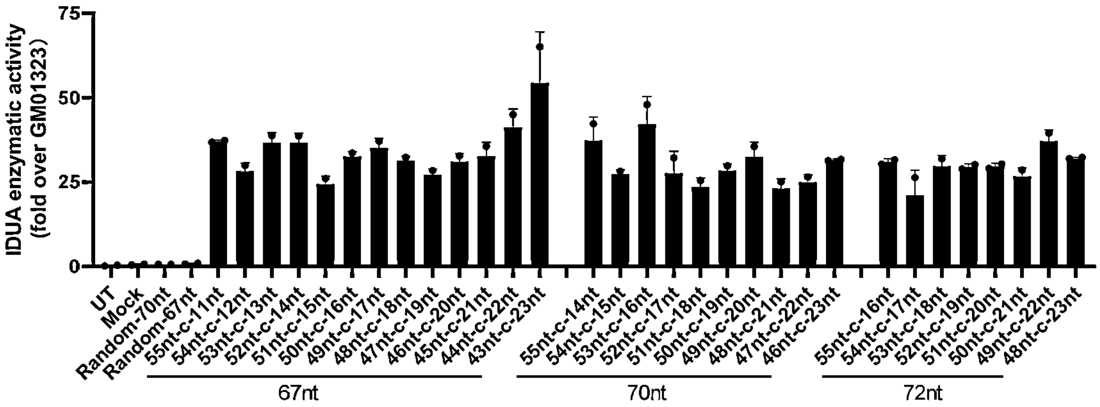
FIG. 42 shows the comparison of enzyme activities in GM06214 cells transfected with 3 groups of dRNAs using Lipofectamine RNAiMAX. For the dRNAs in each group, the distance from the targeting nucleotide to 5' end is different. This figure also shows the low editing efficiency of dRNAs which are less than 60 nt.
Figure 43A:
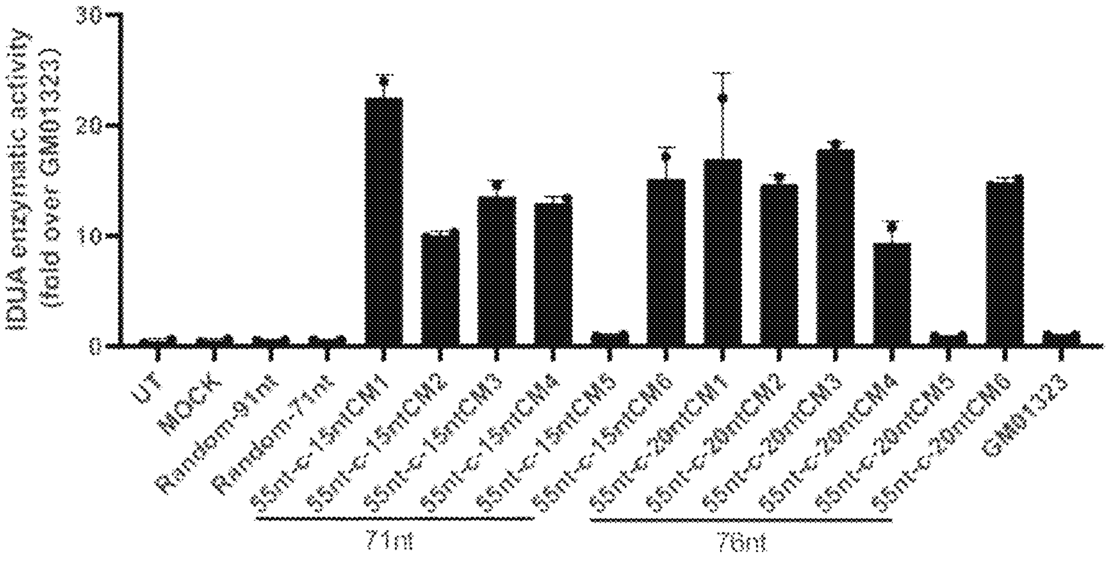
FIGS. 43A-43B show the editing efficiency of 71 nt and 76 nt dRNAs with different chemical modifications.
Figure 43B:
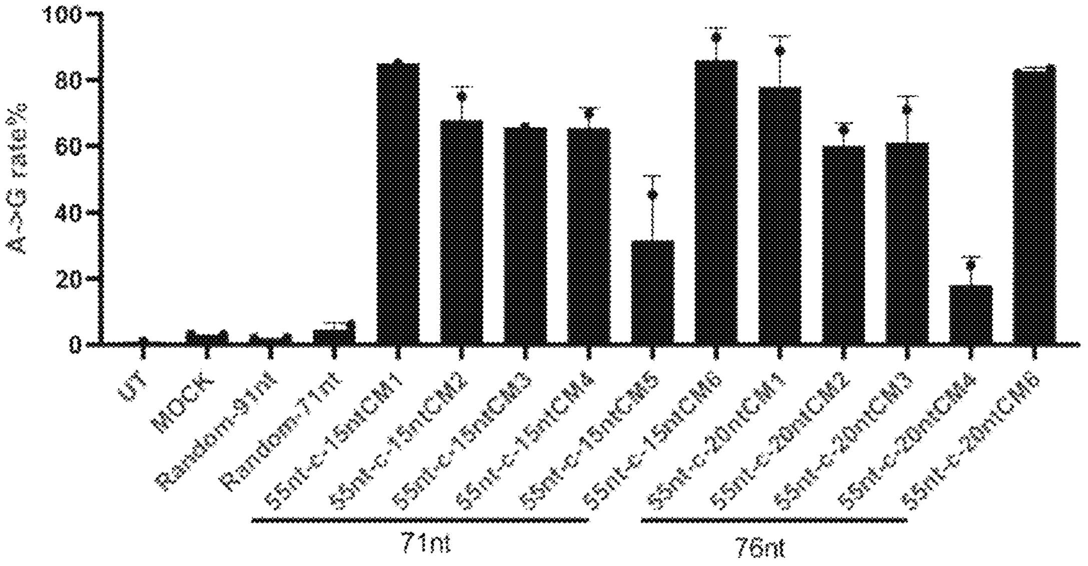

Example 27. Determination of the Relation Between the Targeting Nucleotide Location and the Editing Efficiency of Chemically Modified dRNAs to the IDUA Mutation Site According to the data above, the editing efficiency of dRNA is related to the length and the location of the targeting nucleotide on the dRNA. Usually, the closer the targeting nucleotide is to the 5' end, the lower the editing efficiency is. Thus, in this example, 3 groups of dRNAs of 3 fixed lengths were designed. dRNAs in each group were designed by gradually moving the targeting nucleotide from the middle of the sequence toward the 5' end. Structures that are not easy to synthesize are avoided. Sequences are shown in Table 12. All the dRNA sequences were modified in CM0 pattern. The dRNAs were transfected into GM06214 cells using Lipofectamine RNAiMAX. 48 hrs later, the cells were harvested and the enzyme activities were tested according to the methods described in Example 23. According to the data shown in FIG. 42, at least when the total length of dRNA was fixed to 67 nt, 70 nt or 72 nt, the location change of the targeting nucleotide didn't seem to affect the enzyme activity which represented the editing efficiency.

TABLE 12

| Length | Location of C | Sequence No. | Sequence |
|---|---|---|---|
| 67 nt sliding | 55nt-c-11nt | SEQ ID NO: 369 | gacgcccaccgugugguugcuguccaggacggucccggccugcgacacuucggcccagagcugcucc |
| | 54nt-c-12nt | SEQ ID NO: 386 | acgcccaccgugugguugcuguccaggacggucccggccugcgacacuucggcccagagcugcuccu |
| | 53nt-c-13nt | SEQ ID NO: 387 | cgcccaccgugugguugcuguccaggacggucccggccugcgacacuucggcccagagcugcuccuc |
| | 52nt-c-14nt | SEQ ID NO: 388 | gcccaccgugugguugcuguccaggacggucccggccugcgacacuucggcccagagcugcuccuca |
| | 51nt-c-15nt | SEQ ID NO: 389 | cccaccgugugguugcuguccaggacggucccggccugcgacacuucggcccagagcugcuccucau |
| | 50nt-c-16nt | SEQ ID NO: 390 | ccaccgugugguugcuguccaggacggucccggccugcgacacuucggcccagagcugcuccucauc |
| | 49nt-c-17nt | SEQ ID NO: 391 | caccgugugguugcuguccaggacggucccggccugcgacacuucggcccagagcugcuccucaucu |
| | 48nt-c-18nt | SEQ ID NO: 392 | accgugugguugcuguccaggacggucccggccugcgacacuucggcccagagcugcuccucaucug |
| | 47nt-c-19nt | SEQ ID NO: 393 | ccgugugguugcuguccaggacggucccggccugcgacacuucggcccagagcugcuccucaucugc |
| | 46nt-c-20nt | SEQ ID NO: 394 | cgugugguugcuguccaggacggucccggccugcgacacuucggcccagagcugcuccucaucugcg |
| | 45nt-c-21nt | SEQ ID NO: 395 | gugugguugcuguccaggacggucccggccugcgacacuucggcccagagcugcuccucaucugcgg |
| | 44nt-c-22nt | SEQ ID NO: 396 | ugugguugcuguccaggacggucccggccugcgacacuucggcccagagcugcuccucaucugcggg |
| | 43nt-c-23nt | SEQ ID NO: 397 | gugguugcuguccaggacggucccggccugcgacacuucggcccagagcugcuccucaucugcgggg |
| 70 nt sliding | 55nt-c-14nt | SEQ ID NO: 366 | gacgcccaccgugugguugcuguccaggacggucccggccugcgacacuucggcccagagcugcuccuca |
| | 54nt-c-15nt | SEQ ID NO: 398 | acgcccaccgugugguugcuguccaggacggucccggccugcgacacuucggcccagagcugcuccucau |

TABLE 12-continued

| Length | Location of C | Sequence No. | Sequence |
|---|---|---|---|
| | 53nt-c-16nt | SEQ ID NO: 399 | cgcccaccgugugguugcuguccaggacggucccggccugcgacacuucggcccagagcugcuccucauc |
| | 52nt-c-17nt | SEQ ID NO: 400 | gcccaccgugugguugcuguccaggacggucccggccugcgacacuucggcccagagcugcuccucaucu |
| | 51nt-c-18nt | SEQ ID NO: 401 | cccaccgugugguugcuguccaggacggucccggccugcgacacuucggcccagagcugcuccucaucug |
| | 50nt-c-19nt | SEQ ID NO: 402 | ccaccgugugguugcuguccaggacggucccggccugcgacacuucggcccagagcugcuccucaucugc |
| | 49nt-c-20nt | SEQ ID NO: 403 | caccgugugguugcuguccaggacggucccggccugcgacacuucggcccagagcugcuccucaucugcg |
| | 48nt-c-21nt | SEQ ID NO: 404 | accgugugguugcuguccaggacggucccggccugcgacacuucggcccagagcugcuccucaucugcgg |
| | 47nt-c-22nt | SEQ ID NO: 405 | ccgugugguugcuguccaggacggucccggccugcgacacuucggcccagagcugcuccucaucugcggg |
| | 46nt-c-23nt | SEQ ID NO: 406 | cgugugguugcuguccaggacggucccggccugcgacacuucggcccagagcugcuccucaucugcgggg |
| 72 nt sliding | 55nt-c-16nt | SEQ ID NO: 365 | gacgcccaccgugugguugcuguccaggacggucccggccugcgacacuucggcccagagcugcuccucauc |
| | 54nt-c-17nt | SEQ ID NO: 407 | acgcccaccgugugguugcuguccaggacggucccggccugcgacacuucggcccagagcugcuccucaucu |
| | 53nt-c-18nl | SEQ ID NO: 408 | cgcccaccgugugguugcuguccaggacggucccggccugcgacacuucggcccagagcugcuccucaucug |
| | 52nt-c-19nt | SEQ ID NO: 409 | gcccaccgugugguugcuguccaggacggucccggccugcgacacuucggcccagagcugcuccucaucugc |
| | 51nt-c-20nt | SEQ ID NO: 410 | cccaccgugugguugcuguccaggacggucccggccugcgacacuucggcccagagcugcuccucaucugcg |
| | 50nt-c-21nt | SEQ ID NO: 411 | ccaccgugugguugcuguccaggacggucccggccugcgacacuucggcccagagcugcuccucaucugcgg |
| | 49nt-c-22nt | SEQ ID NO: 412 | caccgugugguugcuguccaggacggucccggccugcgacacuucggcccagagcugcuccucaucugcggg |

TABLE 12-continued

| Length | Location of C | Sequence No. | Sequence |
|---|---|---|---|
| | 48nt-c-23nt | SEQ ID NO: 413 | accgugugguugcuguccag gacggucccggccugcgaca cuucggcccagagcugcucc ucaucugcgggg |

Example 28. Effect of Chemical Modification on Editing Efficiency of dRNA

Chemical modifications of synthesized RNA increase RNA stability and reduce off-target potential. The relatively common chemical modifications of RNA are 2'-O-methylation (2'-O-Me) and phosphorothioate linkage. The dRNAs with different combinations of lengths: 71 nt or 76 nt and chemical modifications were shown in Table 13. GM06214 cells were transfected with the different dRNAs using Lipofectamine RNAiMAX for the editing of intracellular IDUA. Cells were collected 48 hours after transfection, and IDUA enzyme activity were determined using the method shown in Example 23. According to the results shown in FIG. 42A, all the modifications led to excellent enzyme activities, except for CM5 (the 5th modification: all nucleotides, except for the targeting nucleotide and 5 nt on each side of it, were modified by 2'-OMe). The modification on the targeting nucleotide or the two nucleotides most adjacent to it didn't reduce the editing efficiency.

The editing efficiency was further determined by counting the A to G substitution rate. The method was described as below: A sequence comprising the target adenosine in IDUA gene of GM06214 cells is CTAG, which is mutated to CTGG after RNA editing using dRNAs. CTAG is the recognition site of restriction enzyme BfaI. Thus, a successful A to G substitution doesn't result in a digestion by BfaI, while the wild type does. After editing, RNA of GM06214 cells were extracted and reverse transcribed into cDNA. PCR were conducted using the cDNA. Primers were hIDUA-62F: CCTTCCTGAGCTACCACCCG (SEQ ID NO: 415) and hIDUA-62R: CCAGGGCTCGAACTCGGTAG (SEQ ID NO: 416). After PCR, the product was purified and incubated with BfaI (NEB, Cat. No. R0568L). The A to G substitution rate, or the editing efficiency was determined using agarose gel electrophoresis. The result was expressed as the percentage of the uncut sections (with A to G substitution) to the total nucleic acid in the PCR product, calculated using the gray values of the gel electrophoresis image. The result was shown in FIG. 42B. It was similar to the result of enzyme activity assay in FIG. 42A.

TABLE 13

| Name | Length | Modification pattern | Sequence |
|---|---|---|---|
| HIV2-76-CM1 | 55nt-c-20nt | CM1: Modifications in CM0 and all U: are with 2'-OME | Gm*Am*Cm*G-C-C-C-A-C-C-G-Um-G-Um-G-G-Um-Um-G-C-Um-G-Um-C-C-A-G-G-A-C-G-G-Um-C-C-C-G-G-C-C-Um-G-C-G-A-C-A-C-Um-Um-C-G-G-C-C-C-A-G-A-G-C-Um-G-C-Um-C-C-Um-C-A-Um-C-Um*Gm*Cm*Gm (SEQ ID NO: 361) |
| HIV2-76-CM2 | 55nt-c-20nt | CM2: Modifications in CM1 and the targeting triplet is CCAm | Gm*Am*Cm*G-C-C-C-A-C-C-G-Um-G-Um-G-G-Um-Um-G-C-Um-G-Um-C-C-A-G-G-A-C-G-G-Um-C-C-C-G-G-C-C-Um-G-C-G-A-C-A-C-Um-Um-C-G-G-C-C-C-Am-G-A-G-Um-G-C-Um-C-C-Um-C-A-Um-C-Um*Gm*Cm*Gm (SEQ ID NO: 361) |
| HIV2-76-CM3 | 55nt-c-20nt | CM3: Modifications in CM1 and the targeting triplet is CmCA | Gm*Am*Cm*G-C-C-C-A-C-C-G-Um-G-Um-G-G-Um-Um-G-C-Um-G-Um-C-C-A-G-G-A-C-G-G-Um-C-C-C-G-G-C-C-Um-G-C-G-A-C-A-C-Um-Um-C-G-G-C-Cm-C-A-G-A-G-C-Um-G-C-Um-C-C-Um-C-A-Um-C-Um*Gm*Cm*Gm (SEQ ID NO: 361) |
| HIV2-76-CM4 | 55nt-c-20nt | CM4: Modifications in CM1 and the targeting triplet is c*C*A* | Gm*Am*Cm*G-C-C-C-A-C-C-G-Um-G-Um-G-G-Um-Um-G-C-Um-G-Um-C-C-A-G-G-A-C-G-G-Um-C-C-C-G-G-C-C-Um-G-C-G-A-C-A-C-Um-Um-C-G-G-C-Cm-C-A-G-A-G-C-Um-G-C-Um-C-C-Um-C-A-Um-C-Um*Gm*Cm*Gm (SEQ ID NO: 361) |
| HIV2-76-CM5 | 55nt-c-20nt | CM5: Modifications in CM1 and all nucleotides with 2'-OMe, except for the targeting nucleotide and 5nt on each side of it | Gm*Am*Cm*Gm-Cm-Cm-Cm-Am-Cm-Cm-Gm-Um-Gm-Um-Gm-Gm-Um-Um-Gm-Cm-Um-Gm-Um-Cm-Cm-Am-Gm-Gm-Am-Cm-Gm-Gm-Um-Cm-Cm-CM-Gm-Gm-Cm-Cm-Um-Gm-Cm-Gm-Am-Cm-Am-Cm-Um-Um-C-G-G-C-C-C-A-G-A-G-C-Um-Gm-Cm-Um-CM-Cm-Um-Cm-Am-Um-Cm-Um*Gm*Cm*Gm (SEQ ID NO: 361) |
| HIV2-76-CM6 | 55nt-c-20nt | CM6: 5 terminal bases at each terminus are with 2'-OMe, and the first and last 5 internucleotide linkages were phosphorothioated | Gm*Am*Cm*Gm*Cm*C-C-A-C-C-G-U-G-U-G-G-U-U-G-C-U-G-U-C-C-A-G-G-A-C-G-G-U-C-C-C-G-G-C-C-U-G-C-G-A-C-A-C-U-U*Cm*Um*Gm*Cm*Gm (SEQ ID NO: 361) |

TABLE 13-continued

| Name | Length | Modification pattern | Sequence |
|---|---|---|---|
| HIV2-71-CM1 | 55nt-c-15nt | CM1: Modifications in CM0 and all U: are with 2'-OMe | Gm*Am*Cm*G-C-C-C-A-C-C-G-Um-G-Um-G-G-Um-Um-G-C-Um-G-Um-C-C-A-G-G-A-C-G-G-Um-C-C-C-G-G-C-C-Um-G-C-G-A-C-A-C-Um-Um-C-G-G-C-C-C-A-G-A-G-C-Um-G-C-Um-C-C-Um*Cm*Am*Um (SEQ ID NO: 350) |
| HIV2-71-CM2 | 55nt-c-15nt | CM2: Modifications in CM1 and the targeting triplet is CCAm | Gm*Am*Cm*G-C-C-C-A-C-C-G-Um-G-Um-G-G-Um-Um-G-C-Um-G-Um-C-C-A-G-G-A-C-G-G-Um-C-C-C-G-G-C-C-Um-G-C-G-A-C-A-C-Um-Um-C-G-G-C-C-C-A-G-A-G-C-Um-G-C-Um-C-C-Um*Cm*Am*Um (SEQ ID NO: 350) |
| HIV2-71-CM3 | 55nt-c-15nt | CM3: Modifications in CM1 and the targeting triplet is CmCA | Gm*Am*Cm*G-C-C-C-A-C-C-G-Um-G-Um-G-G-Um-Um-G-C-Um-G-Um-C-C-A-G-G-A-C-G-G-Um-C-C-C-G-G-C-C-Um-G-C-G-A-C-A-C-Um-Um-C-G-G-C-C-C-A-G-A-G-C-Um-G-C-Um-C-C-Um*Cm*Am*Um (SEQ ID NO: 350) |
| HIV2-71-CM4 | 55nt-c-15nt | CM4: Modifications in CM1 and the targeting triplet is C*C*A* | Gm*Am*Cm*G-C-C-C-A-C-C-G-Um-G-Um-G-G-Um-Um-G-C-Um-G-Um-C-C-A-G-G-A-C-G-G-Um-C-C-C-G-G-C-C-Um-G-C-G-A-C-A-C-Um-Um-C-G-G-C-C-C-A-G-A-G-C-Um-G-C-Um-C-C-Um*Cm*Am*Um (SEQ ID NO: 350) |
| HIV2-71-CM5 | 55nt-c-15nt | CM5: Modifications in CM1 and all nucleotides are with 2'-OMe, except for the targeting nucleotide and 5nt on each side of it | Gm*Am*Cm*Gm*-Cm-Cm-Cm-Am-Cm-Cm-Gm-Um-Gm-Um-Gm-Gm-Um-Um-Gm-Cm-Um-Gm-Um-Cm-Cm-Am-Gm-Gm-Am-Cm-Gm-Gm-Um-Cm-CM-CM-Gm-Gm-Cm-CM-Um-Gm-Cm-Gm-Am-Cm-Am-Cm-Um-Um-C-G-G-C-C-C-A-G-A-G-C-Um-Gm-Cm-Um-Cm-Cm-Um*Cm*Am*Um (SEQ ID NO: 350) |
| HIV2-71-CM6 | 55nt-c-15nt | CM6: 5 termianl bases at each terminus are with 2'-OMe and the first and last 5 internucleotide linkages were phosphorothioated | Gm*Am*Cm*Gm*Cm*C-C-A-C-C-G-U-G-U-G-G-U-U-G-C-U-G-U-C-C-A-G-G-A-C-G-G-U-C-C-C-G-G-C-C-U-G-C-G-A-C-A-C-U-U-C-G-G-C-C-C-A-G-A-G-C-U-G-C-U-C*Cm*Um*Cm*Am*Um (SEQ ID NO: 350) |

Note:
"m" refers to 2'-O-Me on the ribose of the nuclcotide "*" refers to phosphorothiate linkage.

Example 29. Further Verification of the Modification Pattern

Figure 44:
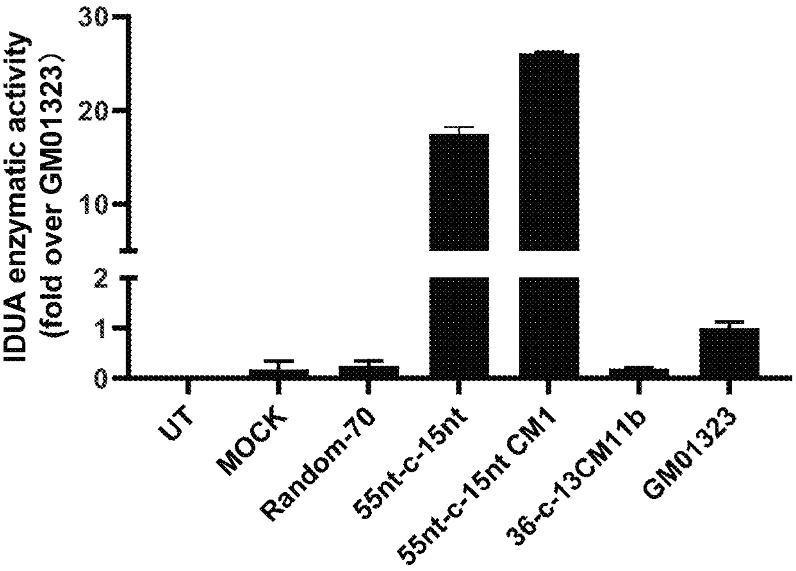
FIG. 44 shows the comparison of enzyme activities in cells transfected with dRNAs in this invention and a preferable RNA for exogenous enzyme independent RNA base editing in the prior art.

The modification pattern of CM1 was tested on another sequence. A preferable modification pattern in a prior art was used as a control. As shown in table 14, 55 nt-c-15 nt-CM1 was the test sequence, and 36 nt-c-13 nt-CM11 was a positive control, in which, all the nucleotides, except for the editing triplet "CCA", are modified with 2'-O-Me, and the first and last 4 internucleotide linkages were phosphorothioated. In addition, 36 nt-c-13 nt-CM11 was only 51 nt, which is not a preferable length in this invention but a preferable length in the prior art. 48 hours after the transfection of the dRNAs into GM06214 cells using Lipofectamine RNAiMAX, IDUA enzyme activity was detected using the method shown in Example 23. As shown in FIG. 44, 55 nt-c-15 nt-CMT had a significantly higher editing efficiency than that of 36 nt-c-13 nt-CMT11.

TABLE 14

| Name | Modification pattern | Sequence |
|---|---|---|
| 55nt-c-15nt-CM1 | CM1 | Gm*Am*CM*G-C-C-C-A-C-C-G-Um-G-Um-G-G-Um-Um-G-C-Um-G-Um-C-C-A-G-G-A-C-G-G-Um-C-C-C-G-G-C-C-Um-G-C-G-A-C-A-C-Um-Um-C-G-G-C-C-C-A-G-A-G-C-Um-G-C-Um-C-C-Um*Cm*Am*Um (SEQ ID NO: 366) |
| 36nt-c-13nt-CM11 | CM11: All nucleotides, except for the targeting tripletCroCroAro, are modified with 2'-O-Me, the first and last 4 internucle-otide linkages were phosphorothioated | Cm*Um*Gm*Um*Cm-Cm-Am-Gm-Gm-Am-Cm-Gm-Gm-Um-Cm-Cm-Cm-Gm-Gm-Cm-Cm-Um-Gm-Cm-Gm-Am-Cm-Am-Cm-Um-Um-Cm-Gm-Gm-Cm-C-C-A-Gm-Am-Gm-Cm-Um-Gm-Cm-Um*Cm*Cm*Um*Cm (SEQ ID NO: 414) |

Note:
"m" refers to 2'-O-Me on the ribose of the nuclcotide "*" refers to phosphorothiate linkage.

Example 30. Further Test of the dRNAs in Other Cells

Figure 45A:
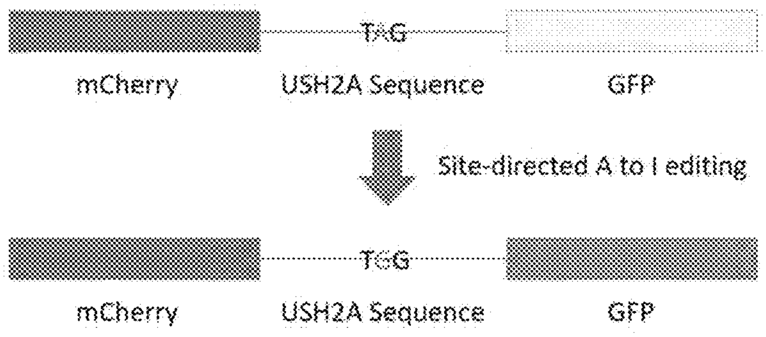
FIGS. 45A-45D show the RNA editing result of the mutation in USH2A model (c.11864 G>A, p. Trp3955*) using the chemically modified dRNAs of this invention. MFI and % GFP represent the editing efficiency.

This example focused on the repair of USH2A c.11864 G>A (p.Trp3955*) mutation using LEAPER technology. The reporter system designed in this example is shown in FIG. 45A. In the case of USH2A c.11864 G>A (p.Trp3955*, the normal TGG sequence was mutated to TAG which is a stop codon. Thus, translation of the mutated mRNA will be terminated early at this TAG. The 293T (293T cells from C. Zhang's laboratory, Peking University) reporter system is a lentiviral vector, and the mRNA shown in FIG. 45A above is driven by a CMV promoter. The system comprises the following parts: 1) mCherry red fluorescent protein, which can be stably expressed, 2) the mutation site of USH2A gene and the adjacent 100 base pairs on both sides. 3) GFP green fluorescent protein. When the mutation site is successfully edited, the TAG codon is converted TIG, which allows translation to continue, and the GFP after the USH2A sequence can be translated normally. Thus, the expression of GFP represents the editing efficiency.

The dRNA were synthesized in vitro, and all the dRNA sequences used in this example were shown in Table 15. All the dRNA sequences were modified in CM0 pattern. The specific steps of the test were as follows:

293T reporter cells were cultured in DMEM (Hyclone SH30243.01) with 10% FBS (Vistech, SE100-011). When confluent, cells were transferred into 12 well plates at 15,000 cells/well. The time is recorded as 0 hr.

At 24 hr, 293T cells in each well were transfected with 12.5 pmol of dRNA using Lipofectamine RNAiMAX reagent (Invitrogen 13778150). Transfection protocol was provided in the product manual.

At 72 hr, cells in each well were digested with trypsin (Invitrogen, 13778-150), and the intensity of FITC (Fluorescein isothiocyanate) was detected using a flow cytometer.

Figure 45B:
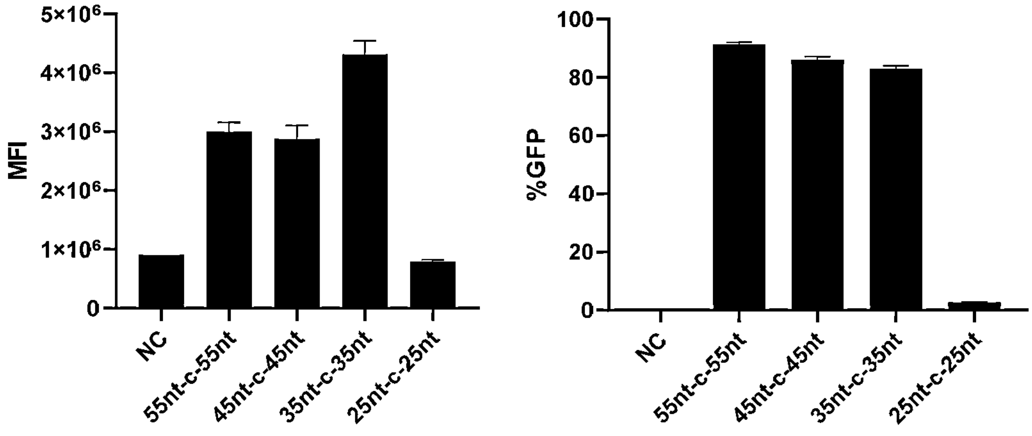

As shown in FIG. 45B, cells were he editing efficiency of dRNAs with 3' and 5' termini of equal length. NC represents the control cells without dRNA transfection. In accordance with the above examples, the GFP positive ratio of the cells transfected with dRNAs of 1 Int, 91 nt and 71 nt exceed 90%, while cells transfected with 51 nt dRNA resulted in a very low GFP positive ratio. From the data of MFI (mean fluorescence intensity) on the left, the 111 nt dRNA led to the highest fluorescence intensity.

Figure 45C:
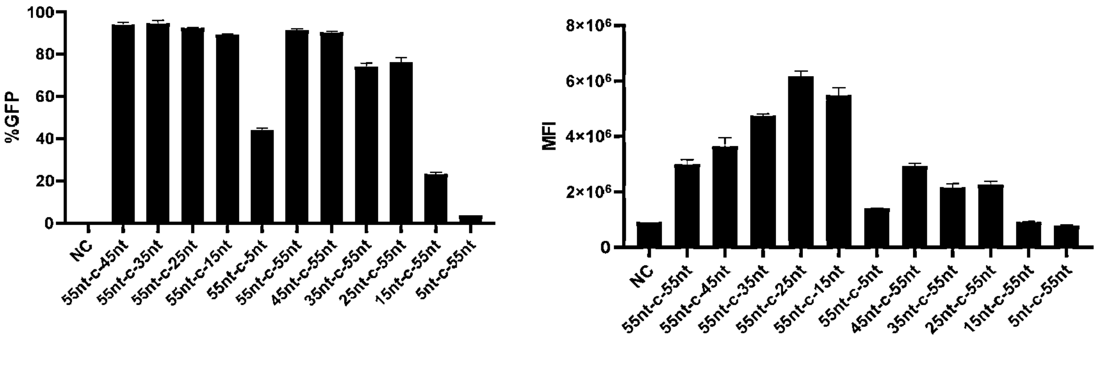
Figure 45D:
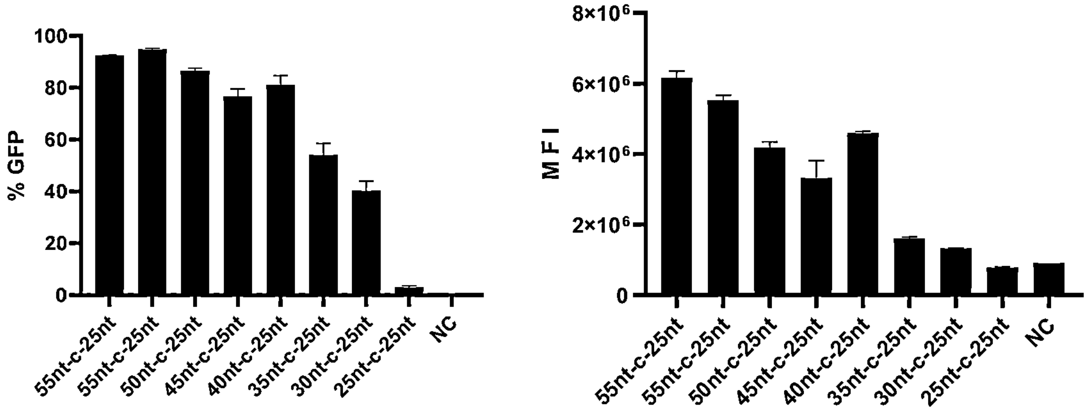

As shown in FIG. 45C, dRNAs with 3' and 5' termini of different lengths and a 111 nt dRNA with equal 3' and 5' termini were transfected into cells, separately. As used in this example, the dRNA with a 55 nt 5' terminus has a 3' terminus of 55 nt, 45 nt, 35 nt, 25 nt, or 5 nt. Similarly, the dRNA with a 55 nt 3' terminus has a 5' terminus of 55 nt, 45 nt, 35 nt, 25 nt, or 5 nt. According to the result in FIG. 45C, the editing efficiency decreased dramatically when the length of dRNA was reduced to 61 nt, while the longer dRNAs had obviously higher editing efficiency. Among them, dRNA 55 nt-c-25 nt had the highest editing efficiency. Thus, the 3' terminus was fixed to 25 nt, and dRNAs with 5' termini of different lengths from 55 nt to 25 nt. The result of cells transfected with these dRNAs was shown in FIG. 45D. Two 55 nt-c-25 nt dRNAs were from 2 different batches. It was obvious that the shorter the 5' terminus, the lower the editing efficiency. In addition, result in FIG. 45D once again indicated that, to ensure the editing efficiency, the length of dRNA is preferably not to be less than 61 nt.

TABLE 15

| Length | Sequence No. | Sequence |
|---|---|---|
| 55nt-C-55nt | SEQ ID NO: 417 | agcccaaggagcuggaaaaucuugagguggagcuuccagaguuuguguuaaugaccacagacucuccacugaacccuuggaguuacaggcucugacccgauauucguagag |
| 45nt-C-45nt | SEQ ID NO: 418 | gcuggaaaaucuugagguggagcuuccagaguuuguguuaaugaccacagacucuccacugaacccuuggaguuacaggcucugacccgau |
| 35nt-C-35nt | SEQ ID NO: 419 | cuugagguggagcuuccagaguuuguguuaaugaccacagacucuccacugaacccuuacaggcu |
| 25nt-C-35nt | SEQ ID NO: 420 | agcuuccagaguuuguguuaaugaccacagacucuccacugaacccuugga |
| 55nt-C-45nt | SEQ ID NO: 421 | agcccaaggagcuggaaaaucuugagguggagcuuccagaguuuguguuaaugaccacagacucuccacugaacccuuggaguuacaggcucugacccgau |
| 55nt-C-35nt | SEQ ID NO: 422 | agcccaaggagcuggaaaaucuugagguggagcuuccagaguuuguguuaaugaccacagacucuccacugaacccuuggaguuacaggcu |
| 55nt-C-25nt | SEQ ID NO: 423 | agcccaaggagcuggaaaaucuugagguggagcuuccagaguuuguguuaaugaccacagacucuccacugaacccuugga |
| 55nt-C-15nt | SEQ ID NO: 424 | agcccaaggagcuggaaaaucuugagguggagcuuccagaguuuguguuaaugaccacagacucuccacug |
| 55nt-C-5nt | SEQ ID NO: 425 | agcccaaggagcuggaaaaucuugagguggagcuuccagaguuuguguuaaugaccacaga |
| 45nt-C-55nt | SEQ ID NO: 426 | gcuggaaaaucuugagguggagcuuccagaguuuguguuaaugaccacagacucuccacugaacccuuggaguuacaggcucugacccgauauucguagag |
| 35nt-C-55nt | SEQ ID NO: 427 | cuugagguggagcuuccagaguuuguguuaaugaccacagacucuccacugaacccuuggaguuacaggcucugacccgauauucguagag |
| 25nt-C-55nt | SEQ ID NO: 428 | agcuuccagaguuuguguuaaugaccacagacucuccacugaacccuuggaguuacaggcucugacccgauauucguagag |
| 15nt-C-55nt | SEQ ID NO: 429 | guuuguguuaaugaccacagacucuccacugaacccuuggaguuacaggcucugacccgauauucguagag |

TABLE 15-continued

| Length | Sequence No. | Sequence |
|---|---|---|
| 5nt-C-55nt | SEQ ID NO: 430 | augaccacagacucuccacugaacccuuggaguuacaggcucugacccgauauucgua-gag |
| 50nt-C-25nt | SEQ ID NO: 431 | aaggagcuggaaaaucuugagguggagcuuccagaguuuguguuaaugaccacagacucu ccacugaacccuugga |
| 45nt-C-25nt | SEQ ID NO: 432 | gcuggaaaaucuugagguggagcuuccagaguuuguguuaaugaccacagacucuccacu gaacccuugga |
| 40-C-25nt | SEQ ID NO: 433 | aaaaucuugagguggagcuuccagaguuuguguuaaugaccacagacucuccacugaacc cuugga |
| 35nt-C-25nt | SEQ ID NO: 434 | cuugagguggagcuuccagaguuuguguuaaugaccacagacucuccacugaaccc-uugga |
| 30-C-25nt | SEQ ID NO: 435 | gguggagcuuccagaguuuguguuaaugaccacagacucuccacugaacccuugga |

ADAR1(p110)cDNA (SEQ ID NO: 332)

5'-atggccgagatcaaggagaaaatctgcgac tatctcttcaatgtgtctgactcctctgccctgaa tttggctaaaaatattggccttaccaaggcccgag atataaatgctgtgctaattgacatggaaaggcag ggggatgtctatagacaagggacaacccctcccat atggcatttgacagacaagaagcgagagaggatgc aaatcaagagaaatacgaacagtgttcctgaaacc gctccagctgcaatccctgagaccaaaagaaacgc agagttcctcacctgtaatatacccacatcaaatg cctcaaataacatggtaaccacagaaaaagtggag aatgggcaggaacctgtcataaagttagaaaacag gcaagaggccagaccagaaccagcaagactgaaac cacctgttcattacaatggcccctcaaaagcaggg tatgttgactttgaaaatggccagtgggccacaga tgacatcccagatgacttgaatagtatccgcgcag caccaggtgagtttcgagccatcatggagatgccc tccttctacagtcatggcttgccacggtgttcacc ctacaagaaactgacagagtgccagctgaagaacc ccatcagcgggctgttagaatatgcccagttcgct agtcaaacctgtgagttcaacatgatagagcagag tggaccaccccatgaacctcgatttaaattccagg ttgtcatcaatggccgagagtttcccccagctgaa gctggaagcaagaaagtggccaagcaggatgcagc tatgaaagccatgacaattctgctagaggaagcca aagccaaggacagtggaaaatcagaagaatcatcc cactattccacagagaaagaatcagagaagactgc agagtcccagacccccaccccttcagccacatcct tcttttctgggaagagccccgtcaccacactgctt -continued gagtgtatgcacaaattggggaactcctgcgaatt ccgtctcctgtccaaagaaggccctgcccatgaac ccaagttccaatactgtgttgcagtgggagcccaa actttccccagtgtgagtgctcccagcaagaaagt ggcaaagcagatggccgcagaggaagccatgaagg ccctgcatggggaggcgaccaactccatggcttct gataaccagcctgaaggtatgatctcagagtcact tgataacttggaatccatgatgcccaacaaggtca ggaagattggcgagctcgtgagatacctgaacacc aaccctgtgggtggcctttttggagtacgcccgctc ccatggctttgctgctgaattcaagttggtcgacc agtccggacctcctcacgagcccaagttcgtttac caagcaaaagttgggggtcgctggttcccagccgt ctgcgcacacagcaagaagcaaggcaagcaggaag cagcagatgcggctctccgtgtcttgattggggag aacgagaaggcagaacgcatgggtttcacagaggt aaccccagtgacaggggccagtctcagaagaacta tgctcctcctctcaaggtccccagaagcacagcca aagacactccctctcactggcagcaccttccatga ccagatagccatgctgagccaccggtgcttcaaca ctctgactaacagcttccagccctccttgctcggc cgcaagattctggccgccatcattatgaaaaaaga ctctgaggacatgggtgtcgtcgtcagcttgggaa cagggaatcgctgtgtaaaaggagattctctcagc ctaaaaggagaaactgtcaatgactgccatgcaga aataatctcccggagaggcttcatcaggtttctct acagtgagttaatgaaatacaactcccagactgcg aaggatagtatatttgaacctgctaagggaggaga aaagctccaaataaaaaagactgtgtcattccatc tgtatatcagcactgctccgtgtggagatggcgcc ctctttgacaagtcctgcagcgaccgtgctatgga aagcacagaatcccgccactaccctgtcttcgaga atcccaaacaaggaaagctccgcaccaaggtggag aacggagaaggcacaatccctgtggaatccagtga cattgtgcctacgtgggatggcattcggctcgggg agagactccgtaccatgtcctgtagtgacaaaatc ctacgctggaacgtgctgggcctgcaaggggcact gttgacccacttcctgcagcccatttatctcaaat ctgtcacattgggttaccttttcagccaagggcat ctgacccgtgctatttgctgtcgtgtgacaagaga tgggagtgcatttgaggatggactacgacatccct ttattgtcaaccaccccaaggttggcagagtcagc atatatgattccaaaaggcaatccgggaagactaa ggagacaagcgtcaactggtgtctggctgatggct atgacctggagatcctggacggtaccagaggcact gtggatgggccacggaatgaattgtcccgggtctc caaaaagaacatttttcttctatttaagaagctct gctccttccgttaccgcagggatctactgagactc tcctatggtgaggccaagaaagctgcccgtgacta cgagacggccaagaactacttcaaaaaaggcctga aggatatgggctatgggaactggattagcaaaccc caggaggaaaagaacttttatctctgcccagta gattacaaggatgacgacgataag(Flag tag)

TAG-3'

ADAR1(p150) cDNA (SEQ ID NO: 333)

5'atgaatccgcggcaggggtattccctcagcgga tactacacccatccatttcaaggctatgagcacag acagctcagataccagcagcctgggccaggatctt cccccagtagtttcctgcttaagcaaatagaattt ctcaaggggcagctcccagaagcaccggtgattgg aaagcagacaccgtcactgccaccttccctcccag gactccggccaaggtttccagtactacttgcctcc agtaccagaggcaggcaagtggacatcaggggtgt ccccaggggcgtgcatctcggaagtcaggggctcc agagagggttccagcatccttcaccacgtggcagg agtctgccacagagaggtgttgattgcctttcctc acatttccaggaactgagtatctaccaagatcagg aacaaaggatcttaaagttcctggaagagcttggg gaagggaaggccaccacagcacatgatctgtctgg gaaacttgggactccgaagaaagaaatcaatcgag ttttatactccctggcaaagaagggcaagctacag aaagaggcaggaacacccccttttgtggaaaatcgc ggtctccactcaggcttggaaccagcacagcggag tggtaagaccagacggtcatagccaaggagcccca aactcagacccgagtttggaaccggaagacagaaa ctccacatctgtctcagaagatcttcttgagcctt ttattgcagtctcagctcaggcttggaaccagcac agcggagtggtaagaccagacagtcatagccaagg atccccaaactcagacccaggtttggaacctgaag acagcaactccacatctgccttggaagatcctctt gagtttttagacatggccgagatcaaggagaaaat ctgcgactatctcttcaatgtgtctgactcctctg ccctgaatttggctaaaaatattggccttaccaag gcccgagatataaatgctgtgctaattgacatgga aaggcagggggatgtctatagacaagggacaaccc ctcccatatggcatttgacagacaagaagcgagag aggatgcaaatcaagagaaatacgaacagtgttcc tgaaaccgctccagctgcaatccctgagaccaaaa gaaacgcagagttcctcacctgtaatatacccaca tcaaatgcctcaaataacatggtaaccacagaaaa agtggagaatgggcaggaacctgtcataaagttag aaaacaggcaagaggccagaccagaaccagcaaga ctgaaaccacctgttcattacaatggcccctcaaa agcagggtatgttgactttgaaaatggccagtggg ccacagatgacatcccagatgacttgaatagtatc cgcgcagcaccaggtgagtttcgagccatcatgga gatgccctccttctacagtcatggcttgccacggt gttcaccctacaagaaactgacagagtgccagctg aagaaccccatcagcgggctgttagaatatgccca gttcgctagtcaaacctgtgagttcaacatgatag agcagagtggaccaccccatgaacctcgatttaaa ttccaggttgtcatcaatggccgagagtttccccc agctgaagctggaagcaagaaagtggccaagcagg atgcagctatgaaagccatgacaattctgctagag gaagccaaagccaaggacagtggaaaatcagaaga atcatcccactattccacagagaaagaatcagaga agactgcagagtcccagacccccaccccttcagcc acatccttcttttctgggaagagccccgtcaccac actgcttgagtgtatgcacaaattggggaactcct -continued gcgaattccgtctcctgtccaaagaaggccctgcc catgaacccaagttccaatactgtgttgcagtggg agcccaaactttccccagtgtgagtgctcccagca agaaagtggcaaagcagatggccgcagaggaagcc atgaaggccctgcatggggaggcgaccaactccat ggcttctgataaccagcctgaaggtatgatctcag agtcacttgataacttggaatccatgatgcccaac aaggtcaggaagattggcgagctcgtgagatacct gaacaccaaccctgtgggtggccttttggagtacg cccgctcccatggcmgctgctgaattcaagttggt cgaccagtccggacctcctcacgagcccaagttcg tttaccaagcaaaagttgggggtcgctggttccca gccgtctgcgcacacagcaagaagcaaggcaagca ggaagcagcagatgcggctctccgtgtcttgattg gggagaacgagaaggcagaacgcatgggtttcaca gaggtaaccccagtgacaggggccagtctcagaag aactatgctcctcctctcaaggtccccagaagcac agccaaagacactccctctcactggcagcaccttc catgaccagatagccatgctgagccaccggtgctt caacactctgactaacagcttccagccctccttgc tcggccgcaagattctggccgccatcattatgaaa aaagactctgaggacatgggtgtcgtcgtcagctt gggaacagggaatcgctgtgtaaaaggagattctc tcagcctaaaaggagaaactgtcaatgactgccat gcagaaataatctcccggagaggcttcatcaggtt tctctacagtgagttaatgaaatacaactcccaga ctgcgaaggatagtatatttgaacctgctaaggga ggagaaaagctccaaataaaaaagactgtgtcatt ccatctgtatatcagcactgctccgtgtggagatg gcgccctctttgacaagtcctgcagcgaccgtgct atggaaagcacagaatcccgccactaccctgtcTT cgagaatcccaaacaaggaaagctccgcaccaagg tggagaacggagaaggcacaatccctgtggaatcc agtgacattgtgcctacgtgggatggcattcggct cggggagagactccgtaccatgtcctgtagtgaca aaatcctacgctggaacgtgctgggcctgcaaggg gcactgttgacccacttectgcagcccatttatct caaatctgtcacattgggttaccttttcagccaag ggcatctgacccgtgctatttgctgtcgtgtgaca agagatgggagtgcatttgaggatggactacgaca tcccttattgtcaaccaccccaaggttggcagag -continued tcagcatatatgattccaaaaggcaatccgggaag actaaggagacaagcgtcaactggtgtctggctga tggctatgacctggagatcctggacggtaccagag gcactgtggatgggccacggaatgaattgtcccgg gtctccaaaaagaacatttttcttctatttaagaa gctctgctccttccgttaccgcagggatctactga gactctcctatggtgaggccaagaaagctgcccgt gactacgagacggccaagaactacttcaaaaaagg cctgaaggatatgggctatgggaactggattagca aaccccaggaggaaaagaacttttatctctgccca gta <u>gattacaaggatgacgacgataag</u>

<u>(Flag tag)</u> TAG-3'

ADAR2 cDNA (seq id no: 334)

5'-atggatatagaagatgaagaaaacatgagtt ccagcagcactgatgtgaaggaaaaccgcaatctg gacaacgtgtcccccaaggatggcagcacacctgg gcctggcgagggctctcagctctccaatgggggtg gtggtggccccggcagaaagcggcccctggaggag ggcagcaatggccactccaagtaccgcctgaagaa aaggaggaaaacaccagggcccgtcctccccaaga acgccctgatgcagctgaatgagatcaagcctggt ttgcagtacacactcctgtcccagactgggcccgt gcacgcgcctttgtttgtcatgtctgtggaggtga atggccaggtttttgagggctctggtcccacaaag aaaaaggcaaaactccatgctgctgagaaggcctt gaggtctttcgttcagtttcctaatgcctctgagg cccacctggccatggggaggaccctgtctgtcaac acggacttcacatctgaccaggccgacttccctga cacgctcttcaatggttttgaaactcctgacaagg cggagcctcccttttacgtgggctccaatggggat gactccttcagttccagcggggacctcagcttgtc tgcttccccggtgcctgccagcctagcccagcctc ctctccctgccttaccaccattcccacccccgagt gggaagaatcccgtgatgatcttgaacgaactgcg cccaggactcaagtatgacttcctctccgagagcg gggagagccatgccaagagcttcgtcatgtctgtg gtcgtggatggtcagttctttgaaggctcggggag aaacaagaagcttgccaaggcccgggctgcgcagt ctgccctggccgccatttttaacttgcacttggat cagacgccatctcgccagcctattcccagtgaggg -continued tcttcagctgcatttaccgcaggttttagctgacg ctgtctcacgcctggtcctgggtaagtttggtgac ctgaccgacaacttctcctcccctcacgctcgcag aaaagtgctggctggagtcgtcatgacaacaggca cagatgttaaagatgccaaggtgataagtgtttct acaggaacaaaatgtattaatggtgaatacatgag tgatcgtggccttgcattaaatgactgccatgcag aaataatatctcggagatccttgctcagatttctt tatacacaacttgagctttacttaaataacaaaga tgatcaaaaaagatccatctttcagaaatcagagc gagggggtttaggctgaaggagaatgtccagttt catctgtacatcagcacctctccctgtggagatgc cagaatcttctcaccacatgagccaatcctggaag aaccagcagatagacacccaaatcgtaaagcaaga ggacagctacggaccaaaatagagtctggtgaggg gacgattccagtgcgctccaatgcgagcatccaaa cgtgggacggggtgctgcaaggggagcggctgctc accatgtcctgcagtgacaagattgcacgctggaa cgtggtgggcatccagggatccctgctcagcattt tcgtggagcccatttacttctcgagcatcatcctg ggcagcctttaccacggggaccacctttccagggc catgtaccagcggatctccaacatagaggacctgc cacctctctacaccctcaacaagcctttgctcagt ggcatcagcaatgcagaagcacggcagccagggaa ggcccccaacttcagtgtcaactggacggtaggcg actccgctattgaggtcatcaacgccacgactggg aaggatgagctgggccgcgcgtcccgcctgtgtaa gcacgcgttgtactgtcgctggatgcgtgtgcacg gcaaggttccctcccacttactacgctccaagatt accaaacccaacgtgtaccatgagtccaagctggc ggcaaaggagtaccaggccgccaaggcgcgtctgt tcacagccttcatcaaggcggggctgggggcctgg gtggagaagcccaccgagcaggaccagttctcact cacgcccgattttcaaggatgacgacgataag (flag tag) tag-3'

Coding sequence (CDS) of the disease-relevant genes
COL3A1

(SEQ ID NO: 335)

5'-gctcctggactgatgggagcccggggtcct ccaggaccagccggtgctaatggtgctcctggact gcgaggtggtgcaggtgagcctggtaagaatggtg ccaaaggagagcccggaccacgtggtgaacgcggt -continued gaggctggtattccaggtgttccaggagctaaagg cgaagatggcaaggatggatcacctggagaacctg gtgcaaatgggcttccaggagctgcaggagaaagg ggtgcccctgggttccgaggacctgctggaccaaa tggcatcccaggagaaaagggtcctgctggagagc gtggtgctccaggccctgcagggcccagaggagct gctggagaacctggcagagatggcgtccctggagg tccaggaatgaggggcatgcccggaagtccaggag gaccaggaagtgatgggaaaccagggcctcccgga agtcaaggagaaagtggtcgaccaggtcctcctgg gccatctggtccccgaggtcagcctggtgtcatgg gcttccccggtcctaaaggaaatgatggtgctcct ggtaagaatggagaacgaggtggccctggaggacc tggccctcagggtcctcctggaaagaatggtgaaa ctggacctcagggacccccagggcctactgggcct ggtggtgacaaaggagacacaggacccccctggtcc acaaggattacaaggcttgcctggtacaggtggtc ctccaggagaaaatggaaaacctggggaaccaggt ccaaagggtgatgccggtgcacctggagctccagg aggcaagggtgatgctggtgcccctggtgaacgtg gacctcctggattggcaggggccccaggacttaga ggtggagctggtccccctggtcccgaaggaggaaa gggtgctgctggtcctcctgggccacctggtgctg ctggtactcctggtctgcaaggaatgcctggagaa agaggaggtcttggaagtcctggtccaaagggtga caagggtgaaccaggcggtccaggtgctgatggtg tcccagggaaagatggcccaaggggtcctactggt cctattggtcctcctggcccagctggccagcctgg agataagggtgaaggtggtgcccccggacttccag gtatagctggacctcgtggtagccctggtgagaga ggtgaaactggccctccaggacctgctggtttccc tggtgctcctggacagaatggtgaacctggtggta aaggagaaagaggggctccgggtgagaaaggtgaa ggaggccctcctggagttgcaggacccccctggagg ttctggacctgctggtcctcctggtccccaaggtg tcaaaggtgaacgtggcagtcctggtggacctggt gctgctggcttccctggtgctcgtggtcttcctgg tcctcctggtagtaatggtaacccaggacccccag gtcccagcggttctccaggcaaggatgggcccca ggtcctgcgggtaacactggtgctcctggcagccc -continued tggagtgtctggaccaaaaggtgatgctggccaac caggagagaagggatcgcctggtgcccagggccca ccaggagctccaggcccacttgggattgctgggat cactggagcacggggtcttgcaggaccaccaggca tgccaggtcctaggggaagccctggccctcagggt gtcaagggtgaaagtgggaaaccaggagctaacgg tctcagtggagaacgtggtccccctggaccccagg gtcttcctggtctggctggtacagctggtgaacct ggaagagatggaaaccctggatcagatggtcttcc aggccgagatggatctcctggtggcaagggtgatc gtggtgaaaatggctctcctggtgcccctggcgct cctggtcatccaggcccacctggtcctgtcggtcc agctggaaagagtggtgacagaggagaaagtggcc ctgctggccctgctggtgctcccggtcctgctggt tcccgaggtgctcctggtcctcaaggcccacgtgg tgacaaaggtgaaacaggtgaacgtggagctgctg gcatcaaaggacatcgaggattccctggtaatcca ggtgccccaggttctccaggccctgctggtcagca gggtgcaatcggcagtccaggacctgcaggcccca gaggacctgttggacccagtggacctcctggcaaa gatggaaccagtggacatccaggtcccattggacc accagggcctcgaggtaacagaggtgaaagaggat ctgagggctccccaggccacccagggcaaccaggc cctcctggacctcctggtgcccctggtccttgctg tggtggtgttggagccgctgccattgctgggattg gaggtgaaaaagctggcggttttgccccgtattat ggagatgaaccaatggatttcaaaatcaacaccga tgagattatgacttcactcaagtctgttaatggac aaatagaaagcctcattagtcctgatggttctcgt aaaaaccccgctagaaactgcagagacctgaaatt ctgccatcctgaactcaagagtggagaatactggg ttgaccctaaccaaggatgcaaattggatgctatc aaggtattctgtaatatggaaactggggaaacatg cataagtgccaatcctttgaatgttccacggaaac actggtggacagattctagtgctgagaagaaacac gtttggtttggagagtccatggatggtggttttca gtttagctacggcaatcctgaacttcctgaagatg tccttgatgtgcagctggcattccttcgacttctc tccagccgagcttcccagaacatcacatatcactg caaaaatagcattgcatacatggatcaggccagtg gaaatgtaaagaaggccctgaagctgatggggtca -continued aatgaaggtgaattcaaggctgaaggaaatagcaa attcacctacacagttctggaggatggttgcacga aacacactggggaatggagcaaaacagtctttgaa tatcgaacacgcaaggctgtgagactacctattgt agatattgcaccctatgacattggtggtcctgatc aagaatttggtgtggacgttggccctgtttgcttt ttataa-3'

BMPR2

(SEQ ID NO: 336)

5'-atgacttcctcgctgcagcggccctggcggg tgccctggctaccatggaccatcctgctggtcagc gctgcggctgcttcgcagaatcaagaacggctatg tgcgtttaaagatccgtatcagcaagaccttggga taggtgagagtagaatctctcatgaaaatgggaca atattatgctcgaaaggtagcacctgctatggcct ttgggagaaatcaaaaggggacataaatcttgtaa aacaaggatgttggtctcacattggagatccccaa gagtgtcactatgaagaatgtgtagtaactaccac tcctccctcaattcagaatggaacataccgtttct gctgttgtagcacagatttatgtaatgtcaacttt actgagaattttccacctcctgacacaacaccact cagtccacctcattcatttaaccgagatgagacaa taatcattgctttggcatcagtctctgtattagct gttttgatagttgccttatgctttggatacagaat gttgacaggagaccgtaaacaaggtcttcacagta tgaacatgatggaggcagcagcatccgaaccctct cttgatctagataatctgaaactgttggagctgat tggccgaggtcgatatggagcagtatataaaggct ccggatgagcgtccagttgctgtaaaagtgttttc ctttgcaaaccgtcagaattttatcaacgaaaaga acatttacagagtgcctttgatggaacatgacaac attgcccgctttatagttggagatgagagagtcac tgcagatggacgcatggaatatttgcttgtgatgg agtactatcccaatggatctttatgcaagtattta agtctccacacaagtgactgggtaagctcttgccg tcttgctcattctgttactagaggactggcttatc ttcacacagaattaccacgaggagatcattataaa cctgcaatttcccatcgagatttaaacagcagaaa tgtcctagtgaaaaatgatggaacctgtgttatta gtgactttggactgtccatgaggctgactggaaat agactggtgcgcccaggggaggaagataatgcagc -continued cataagcgaggttggcactatcagatatatggcac cagaagtgctagaaggagctgtgaacttgagggac tgtgaatcagctttgaaacaagtagacatgtatgc tcttggactaatctattgggagatatttatgagat gtacagacctcttcccaggggaatccgtaccagag taccagatggcttttcagacagaggttggaaacca tcccacttttgaggatatgcaggttctcgtgtcta gggaaaaacagagacccaagttcccagaagcctgg aaagaaaatagcctggcagtgaggtcactcaagga gacaatcgaagactgttgggaccaggatgcagagg ctcggcttactgcacagtgtgctgaggaaaggatg gctgaacttatgatgatttgggaaagaaacaaatc tgtgagcccaacagtcaatccaatgtctactgcta tgcagaatgaacgcaacctgtcacataataggcgt gtgccaaaaattggtccttatccagattattcttc ctcctcatacattgaagactctatccatcatactg acagcatcgtgaagaatatttcctctgagcattct atgtccagcacacctttgactataggggaaaaaaa ccgaaattcaattaactatgaacgacagcaagcac aagctcgaatccccagccctgaaacaagtgtcacc agcctctccaccaacacaacaaccacaaacaccac aggactcacgccaagtactggcatgactactatat ctgagatgccatacccagatgaaacaaatctgcat accacaaatgttgcacagtcaattgggccaacccc tgtctgcttacagctgacagaagaagacttggaaa ccaacaagctagacccaaaagaagttgataagaac ctcaaggaaagctctgatgagaatctcatggagca ctctcttaaacagttcagtggcccagacccactga gcagtactagttctagcttgctttacccactcata aaacttgcagtagaagcaactggacagcaggactt cacacagactgcaaatggccaagcatgtttgattc ctgatgttctgcctactcagatctatcctctcccc aagcagcagaaccttcccaagagacctactagttt gcctttgaacaccaaaaattcaacaaaagagcccc ggctaaaatttggcagcaagcacaaatcaaacttg aaacaagtcgaaactggagttgccaagatgaatac aatcaatgcagcagaacctcatgtggtgacagtca ccatgaatggtgtggcaggtagaaaccacagtgtt aactcccatgctgccacaacccaatatgccaatgg gacagtactatctggccaaacaaccaacatagtga cacatagggcccaagaaatgttgcagaatcagttt -continued attggtgaggacacccggctgaatattaattccag tcctgatgagcatgagcctttactgagacgagagc aacaagctggccatgatgaaggtgttctggatcgt cttgtggacaggagggaacggccactagaaggtgg ccgaactaattccaataacaacaacagcaatccat gttcagaacaagatgttcttgcacagggtgttcca agcacagcagcagatcctgggccatcaaagcccag aagagcacagaggcctaattctctggatctttcag ccacaaatgtcctggatggcagcagtatacagata ggtgagtcaacacaagatggcaaatcaggatcagg tgaaaagatcaagaaacgtgtgaaaactccctatt ctcttaagcggtggcgcccctccacctgggtcatc tccactgaatcgctggactgtgaagtcaacaataa tggcagtaacagggcagttcattccaaatccagca ctgctgtttaccttgcagaaggaggcactgctaca accatggtgtctaaagatataggaatgaactgtct gtga-3'

AHI1

(SEQ ID NO: 337)

5'-atgcctacagctgagagtgaagcaaaagta aaaaccaaagttcgctttgaagaattgcttaagac ccacagtgatctaatgcgtgaaaagaaaaaactga agaaaaaacttgtcaggtctgaagaaaacatctca cctgacactattagaagcaatcttcactatatgaa agaaactacaagtgatgatcccgacactattagaa gcaatcttccccatattaaagaaactacaagtgat gatgtaagtgctgctaacactaacaacctgaagaa gagcacgagagtcactaaaaacaaattgaggaaca cacagttagcaactgaaaatcctaatggtgatgct agtgtagaggaagacaaacaaggaaagccaaataa aaaggtgataaagacggtgccccagttgactacac aagacctgaaaccggaaactcctgagaataaggtt gattctacacaccagaaaacacatacaaagccaca gccaggcgttgatcatcagaaaagtgagaaggcaa atgagggaagagaagagactgatttagaagaggat gaagaattgatgcaagcatatcagtgccatgtaac tgaagaaatggcaaaggagattaagaggaaaataa gaaagaaactgaaagaacagttgacttactttccc tcagatactttattccatgatgacaaactaagcag tgaaaaaaggaaaaagaaaaaggaagttccagtct tctctaaagctgaaacaagtacattgaccatctct -continued ggtgacacagttgaaggtgaacaaaagaaagaatc
ttcagttagatcagtttcttcagattctcatcaag
atgatgaaataagctcaatggaacaaagcacagaa
gacagcatgcaagatgatacaaaacctaaaccaaa
aaaaacaaaaaagaagactaaagcagttgcagata
ataatgaagatgttgatggtgatggtgttcatgaa
ataacaagccgagatagcccggtttatcccaaatg
ttgcttgatgatgaccttgtcttgggagttacatt
caccgaactgatagacttaagtcagattttatgat
ttctcacccaatggtaaaaattcatgtggttgatg
agcatactggtcaatatgtcaagaaagatgatagt
ggacggcctgtttcatcttactatgaaaaagagaa
tgtggattatattcttcctattatgacccagccat
atgattttaaacagttaaaatcaagacttccagag
tgggaagaacaaattgtatttaatgaaaattttcc
ctatttgcttcgaggctctgatgagagtcctaaag
tcatcctgtcttgagatcttgatttcttaagcgtg
gatgaaattaagaataattctgaggttcaaaacca
agaatgtggcttcggaaaattgcctgggcattcta
agcttctgggagccaatggaaatgcaaacatcaac
tcaaaacttcgcttgcagctatattacccacctac
taagcctcgatccccataagtgttgttgaggcatt
tgaatggtggtcaaaatgtccaagaaatcattacc
catcaacactgtacgtaactgtaagaggactgaaa
gttccagactgtataaagccatcttaccgctctat
gatggctcttcaggaggaaaaaggtaaaccagtgc
attgtgaacgtcaccatgagtcaagctcagtagac
acagaacctggattagaagagtcaaaggaagtaat
aaagtggaaacgactccctgggcaggcttgccgta
tcccaaacaaacacctcttctcactaaatgcagga
gaacgaggatgtttttgtcttgatttctcccacaa
tggaagaatattagcagcagcttgtgccagccggg
atggatatccaattattttatatgaaattccttct
ggacgtttcatgagagaattgtgtggccacctcaa
tatcatttatgatctttcctggtcaaaagatgatc
actacatccttacttcatcatctgatggcactgcc
aggatatggaaaaatgaaataaacaatacaaatac
tttcagagttttacctcatccttcttttgtttaca
cggctaaattccatccagctgtaagagagctagta
gttacaggatgctatgattccatgatacggatatg
gaaagttgagatgagagaagattctgccatattgg -continued tccgacagtttgacgttcacaaaagttttatcaac
tcactttgttttgatactgaaggtcatcatatgta
ttcaggagattgtacaggggtgattgttgtttgga
atacctatgtcaagattaatgatttggaacattca
gtgcaccactggactataaataaggaaattaaaga
aactgagtttaagggaattccaataagttatttgg
agattcatcccaatggaaaacgtttgttaatccat
accaaagacagtactttgagaattatggatctccg
gatattagtagcaaggaagtttgtaggagcagcaa
attatcgggagaagattcatagtactttgactcca
tgtgggacttttctgtttgctggaagtgaggatgg
tatagtgtatgtttggaacccagaaacaggagaac
aagtagccatgtattctgacttgccattcaagtca
cccattcgagacatttcttatcatccatttgaaaa
tatggttgcattctgtgcattgggcaaaatgagcc
aatcttctgtatatttacgatttccatgttgccca
gcaggaggctgaaatgttcaaacgctacaatggaa
catttccattacctggaatacaccaaagtcaagat
gccctatgtacctgtccaaaactaccccatcaagg
ctcttttcagattgatgaatttgtccacactgaaa
gttcttcaacgaagatgcagctagtaaaacagagg
cttgaaactgtcacagaggtgatacgttcctgtgc
tgcaaaagtcaacaaaaatctctcatttacttcac
caccagcagtttcctcacaacagtctaagttaaag
cagtcaaacatgctgaccgctcaagagattctaca
tcagtttggtttcactcagaccgggattatcagca
tagaaagaaagccttgtaaccatcaggtagataca
gcaccaacggtagtggctctttatgactacacagc
gaatcgatcagatgaactaaccatccatcgcggag
acatatccgagtgttttcaaagataatgaagactg
gtggtatggcagcataggaaagggacaggaaggtt
atttccagctaatcatgtggctagtgaaacactgt
atcaagaactgcctcctgagataaaggagcgatcc
cctcctttaagccctgaggaaaaaactaaaataga
aaaatctccagctcctcaaaagcaatcaatcaata
agaacaagtcccaggacttcagactaggctcagaa
tctatgacacattctgaaatgagaaaagaacagag
ccatgaggaccaaggacacataatggatacacgga
tgaggaagaacaagcaagcaggcagaaaagtcact
ctaatagagta-3'

FANCC (SEQ ID NO: 338)

5'-atggctcaagattcagtagatctttcttgtga
ttatcagttttggatgcagaagctttctgtatggg
atcaggcttccactttggaaacccagcaagacacc
tgtcttcacgtggctcagtccaggagttcctaagg
aagatgtatgaagccttgaaagagatggattctaa
tacagtcatgaaagattccccacaatggtcaactg
ttggcaaaagcttgttggaatccttttattttagc
atatgatgaaagccaaaaaattdaatatggtgctt
atgttgtctaattaacaaagaaccacagaattctg
gacaatcaaaacttaactcctggatacagggtgta
ttatctcatatactttcagcactcagatttgataa
agaagttgctcttttcactcaaggtcttgggtatg
cacctatagattactatcctggtttgcttaaaaat
atggttttatcattagcgtctgaactcagagagaa
tcatcttaatggatttaacactcaaaggcgaatgg
ctcccgagcgagtggcgtccctgtcacgagtttgt
gtcccacttattaccctgacagatgttgacccccct
ggtggaggctctcctcatctgtcatggacgtgaac
ctcaggaaatcctccagccagagttctttgaggct
gtaaacgaggccattttgctgaagaagatttctct
ccccatgtcagctgtagtctgcctctggcttcggc
accttcccagccttgaaaaagcaatgctgcatctt
tttgaaaagctaatctccagtgagagaaattgtct
gagaaggatcgaatgctttataaaagattcatcgc
tgcctcaagcagcctgccaocctgccatattccgg
gttgttgatgagatgttcaggtgtgcactcctgga
aaccgatggggccctggaaatcatagccactattc
aggtgtttacgcagtgctttgtagaagctctggag
aaagcaagcaagcagctgcggttgcactcaagacc
tactttccttacacttctccatctcttgccatggt
gctgctgcaagaccctcaagatatccctcggggac
actggctccagacactgaagcatatttctgaactg
ctcagagaagcagttgaagaccagactcatgggtc
ctgcggaggtccctttgagagctggttcctgttca
ttcacttcggaggatgggctgagatggtggcagag
caattactgatgtcggcagccgaaccccccacggc
cctgctgtggctcttggccttctactacggccccc
gtgatgggaggcagcagagagcacagactatggtc
caggtgaaggccgtgctgggccacctcctggcaat
gtccagaagcagcagcctctcagcccaggacctgc agacggtagcaggacagggcacagacacagacctc
agagctcctgcacaacagctgatcaggcaccttct
cctcaacttcctgctctgggctcctggaggccaca
cgatcgcctgggatgtcatcaccctgatggctcac
actgctgagataactcacgagatcattggctttct
tgaccagaccttgtacagatggaatcgtcttggca
ttgaaagccctagatcagaaaaactggcccgagag
ctccttaaagagctgcgaactcaagtctag-3'

MYBPC3

(SEQ ID NO: 339)

5'-atgcctgagccggggaagaagccagtctcagc
ttttagcaagaagccacggtcagtggaagtggccg
caggcagccctgccgtgttcgaggccgagacagag
cgggcaggagtgaaggtgcgctggcagcgcggagg
cagtgacatcagcgccagcaacaagtacggcctgg
ccacagagggcacacggcatacgctgacagtgcgg
gaagtgggccctgccgaccagggatcttacgcagt
cattgctggctcctccaaggtcaagttcgacctca
aggtcatagaggcagagaaggcagagcccatgctg
gcccctgcccctgcccctgctgaggccactggagc
ccctggagaagccccggccccagccgctgagctgg
gagaaagtgccccaagtcccaaagggtcaagctca
gcagctctcaatggtcctacccctggagcccccga
tgaccccattggcctcttcgtgatgcggccacagg
atggcgaggtgaccgtgggtggcagcatcaccttc
tcagcccgcgtggccggcgccagcctcctgaagcc
gcctgtggtcaagtggttcaagggcaaatgggtgg
acctgagcagcaaggtgggccagcacctgcagctg
cacgacagctacgaccgcgccagcaaggtctatct
gttcgagctgcacatcaccgatgcccagcctgcct
tcactggcagctaccgctgtgaggtgtccaccaag
gacaaatttgactgctccaacttcaatctcactgt
ccacgaggccatgggcaccggagacctggacctcc
tatcagccttccgccgcacgagcctggctggaggt
ggtcggcggatcagtgatagccatgaggacactgg
gattctggacttcagctcactgctgaaaaagagag
acagtttccggaccccgagggactcgaagctggag
gcaccagcagaggaggacgtgtgggagatcctacg
gcaggcacccccatctgagtacgagcgcatcgcct
tccagtacggcgtcactgacctgcgcggcatgcta
aagaggctcaagggcatgaggcgcgatgagaagaa -continued gagcacagcctttcagaagaagctggagccggcct
accaggtgagcaaaggccacaagatccggctgacc
gtggaactggctgaccatgacgctgaggtcaaatg
gctcaagaatggccaggagatccagatgagcggca
gcaagtacatctttgagtccatcggtgccaagcgt
accctgaccatcagccagtgctcattggcggacga
cgcagcctaccagtgcgtggtgggtggcgagaagt
gtagcacggagctctttgtgaaagagccccctgtg
ctcatcacgcgccccttggaggaccagctggtgat
ggtggggcagcgggtggagtttgagtgtgaagtat
cggaggagggggcgcaagtcaaatggctgaaggac
ggggtggagctgacccgggaggagaccttcaaata
ccggttcaagaaggacgggcagagacaccacctga
tcatcaacgaggccatgctggaggacgcggggcac
tatgcactgtgcactagcggggggccaggcgctggc
tgagctcattgtgcaggaaaagaagctggaggtgt
accagagcatcgcagacctgatggtgggcgcaaag
gaccaggcggtgttcaaatgtgaggtctcagatga
gaatgttcggggtgtgtggctgaagaatgggaagg
agctggtgcccgacagccgcataaaggtgtcccac
atcgggcgggtccacaaactgaccattgacgacgt
cacacctgccgacgaggctgactacagctttgtgc
ccgagggcttcgcctgcaacctgtcagccaagctc
cacUcatggaggtcaagattgacttcgtacccagg
caggaacctcccaagatccacctggactgcccagg
ccgcataccagacaccattgtggttgtagctggaa
ataagctacgtctggacgtccctatctctggggac
cctgctcccactgtgatctggcagaaggctatcac
gcaggggaataaggccccagccaggccagccccag
atgccccagaggacacaggtgacagcgatgagtgg
gtgtttgacaagaagctgctgtgtgagaccgaggg
ccgggtccgcgtggagaccaccaaggaccgcagca
tcttcacggtcgaggggggcagagaaggaagatgag
ggcgtctacacggtcacagtgaagaaccctgtggg
cgaggaccaggtcaacctcacagtcaaggtcatcg
acgtgccagacgcacctgcggcccccaagatcagc
aacgtgggagaggactcctgcacagtacagtggga
gccgcctgcctacgatggcgggcagcccatcctgg
gctacatcctggagcgcaagaagaagaagagctac
cggtggatgcggctgaacttcgacctgattcagga
gctgagtcatgaagcgcggcgcatgatcgagggcg -continued tggtgtacgagatgcgcgtctacgcggtcaacgcc
atcggcatgtccaggcccagccctgcctcccagcc
cttcatgcctatcggtccccccagcgaacccaccc
acctggcagtagaggacgtctctgacaccacggtc
tccctcaagtggcggcccccagagcgcgtgggagc
aggaggcctggatggctacagcgtggagtactgcc
cagagggctgctcagagtgggtggctgccctgcag
gggctgacagagcacacatcgatactggtgaagga
cctgcccacgggggcccggctgcttttccgagtgc
gggcacacaatatggcagggcctggagcccctgtt
accaccacggagccggtgacagtgcaggagatcct
gcaacggccacggcttcagctgcccaggcacctgc
gccagaccattcagaagaaggtcggggagcctgtg
aaccttctcatccctttccagggcaagccccggcc
tcaggtgacctggaccaaagaggggcagcccctgg
caggcgaggaggtgagcatccgcaacagccccaca
gacaccatcctgttcatccgggccgctcgccgcgt
gcattcaggcacttaccaggtgacggtgcgcattg
agaacatggaggacaaggccacgctggtgctgcag
gttgttgacaagccaagtcctccccaggatctccg
ggtgactgacgcctggggtcttaatgtggctctgg
agtggaagccaccccaggatgtcggcaacacggag
ctctggggggtacacagtgcagaaagccgacaagaa
gaccatggagtggttcaccgtcttggagcattacc
gccgcacccactgcgtggtgccagagctcatcatt
ggcaatggctactacttccgcgtcttcagccagaa
tatggttggctttagtgacagagcggccaccacca
aggagcccgtctttatccccagaccaggcatcacc
tatgagccacccaactataaggccctggacttctc
cgaggccccaagcttcacccagcccctggtgaacc
gctcggtcatcgcgggctacactgctatgctctgc
tgtgctgtccggggtagccccaagcccaagatttc
ctggttcaagaatggcctggacctgggagaagacg
cccgcttccgcatgttcagcaagcagggagtgttg
actctggagattagaaagccctgcccctttgacgg
gggcatctatgtctgcagggccaccaacttacagg
gcgaggcacggtgtgagtgccgcctggaggtgcga
gtgcctcagtga-3'

-continued

```
IL2RG
 (SEQ ID NO: 340)
5'-atgttgaagccatcattaccattcacatccct

cttattcctgcagctgcccctgctgggagtggggc

tgaacacgacaattctgacgcccaatgggaatgaa

gacaccacagctgatttcttcctgaccactatgcc

cactgactccctcagtgtttccactctgcccctcc

cagaggttcagtgttttgtgttcaatgtcgagtac

atgaattgcacttggaacagcagctctgagcccca

gcctaccaacctcactctgcattattggtacaaga

actcggataatgataaagtccagaagtgcagccac

tatctattctctgaagaaatcacttctggctgtca

gttgcaaaaaaaggagatccacctctaccaaacat

ttgttgttcagctccaggacccacgggaacccagg

agacaggccacacagatgctaaaactgcagaatct

ggtgatcccctgggctccagagaacctaacacttc

acaaactgagtgaatcccagctagaactgaactgg

aacaacagattcttgaaccactgtttggagcactt

ggtgcagtaccggactgactgggaccacagctgga

ctgaacaatcagtggattatagacataagttctcc

ttgcctagtgtggatgggcagaaacgctacacgtt

tcgtgttcggagccgctttaacccactctgtggaa

gtgctcagcattggagtgaatggagccacccaatc

cactgggggagcaatacttcaaaagagaatccttt

cctgtttgcattggaagccgtggttatctctgttg

gctccatgggattgattatcagccttctctgtgtg

tatttctggctggaacggacgatgccccgaattcc

caccctgaagaacctagaggatcttgttactgaat

accacgggaacttttcggcctggagtggtgtgtct

aagggactggctgagstgtctgcagccagactaca

gtgaacgactctgcctcgtcagtgagattcccca

aaaggaggggcccttggggaggggcctggggcctc

cccatgcaaccagcatagcccctactgggcccccc

catgttacaccctaaagcctgaaacctga-3'
```

Discussion

Genome editing technologies are revolutionizing biomedical research. Highly active nucleases, such as zinc finger nucleases (ZFNs)[1], transcription activator-like effector nucleases (TALENs)[2-4], and Cas proteins of CRISPR (Clustered Regularly Interspaced Short Palindromic Repeats) system[5-7] have been successfully engineered to manipulate the genome in a myriad of organisms. Recently, deaminases have been harnessed to precisely change the genetic code without breaking double-stranded DNA. By coupling a cytidine or an adenosine deaminase with the CRISPR-Cas9 system, researchers created programmable base editors that enable the conversion of C·G to T·A or A·T to G·C in genomic DNA[8-10], offering novel opportunities for correcting disease-causing mutations.

Aside from DNA, RNA is an attractive target for genetic correction because RNA modification could alter the protein function without generating any permanent changes to the genome. The ADAR adenosine deaminases are currently exploited to achieve precise base editing on RNAs. Three kinds of ADAR proteins have been identified in mammals, ADAR1 (isoforms p110 and p150), ADAR2 and ADAR3 (catalytic inactive)[11,12], whose substrates are double-stranded RNAs, in which an adenosine (A) mismatched with a cytosine (C) is preferentially deaminated to inosine (I). Inosine is believed to mimic guanosine (G) during translation[13,14]. To achieve targeted RNA editing, the ADAR protein or its catalytic domain was fused with a λN peptide[15-17], a SNAP-tag[18-22] or a Cas protein (dCas13b)[23], and a guide RNA was designed to recruit the chimeric ADAR protein to the specific site. Alternatively, overexpressing ADAR1 or ADAR2 proteins together with an R/G motif-bearing guide RNA was also reported to enable targeted RNA editing[24-27].

All these reported nucleic acid editing methods in mammalian system rely on ectopic expression of two components: an enzyme and a guide RNA. Although these binary systems work efficiently in most studies, some inherent obstacles limit their broad applications, especially in therapies. Because the most effective in vivo delivery for gene therapy is through viral vectors[28], and the highly desirable adeno-associated virus (AAV) vectors are limited with cargo size (~4.5 kb), making it challenging for accommodating both the protein and the guide RNA[29,30]. Over-expression of ADAR1 has recently been reported to confer oncogenicity in multiple myelomas due to aberrant hyper-editing on RNAs[31], and to generate substantial global off-targeting edits[32]. In addition, ectopic expression of proteins or their domains of non-human origin has potential risk of eliciting immunogenicity[30,33]. Moreover, pre-existing adaptive immunity and p53-mediated DNA damage response may compromise the efficacy of the therapeutic protein, such as Cas9[34-38]. Although it has been attempted to utilize endogenous mechanism for RNA editing, this was tried only by injecting pre-assembled target transcript:RNA duplex into *Xenopus* embryos[39]. Alternative technologies for robust nucleic acid editing that don't rely on ectopic expression of proteins are much needed. Here, we developed a novel approach that leverages endogenous ADAR for RNA editing. We showed that expressing a deliberately designed guide RNA enables efficient and precise editing on endogenous RNAs, and corrects pathogenic mutations. This unary nucleic acid editing platform may open new avenues for therapeutics and research.

In particular, we showed that expression of a linear arRNA with adequate length is capable of guiding endogenous ADAR proteins to edit adenosine to inosine on the targeted transcripts. This system, referred to as LEAPER, utilizes endogenous ADAR proteins to achieve programmable nucleic acid editing, thus possessing advantages over existing approaches.

Figure 18A:
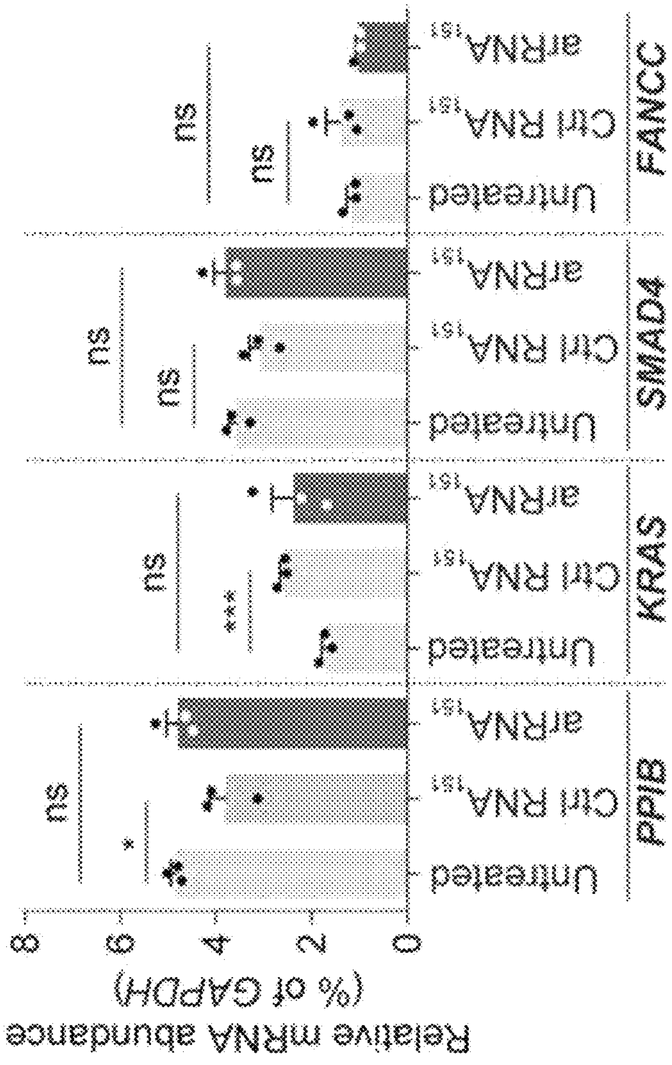

The rare quality of LEAPER is its simplicity because it only relies on a small size of RNA molecule to direct the endogenous proteins for RNA editing. This is reminiscent of RNAi, in which a small dsRNA could invoke native mechanism for targeted RNA degradation[51]. Because of the small size, arRNA could be readily delivered by a variety of viral and non-viral vehicles. Different from RNAi, LEAPER catalyzes the precise A to I switch without generating cutting or degradation of targeted transcripts (FIG. 18A). Although the length requirement for arRNA is longer than RNAi, it neither induces immune-stimulatory effects at the cellular level (FIG. 22E, f and FIG. 29E) nor affects the function of endogenous ADAR proteins (FIG. 22A, b), making it a safe strategy for RNA targeting. Remarkably, it has been reported that ectopic expression of ADAR proteins or their catalytic domains induces substantial global off-target edits[32] and possibly triggers cancer[31].

Recently, several groups reported that cytosine base editor could generate substantial off-target single-nucleotide variants in mouse embryos, rice or human cell lines due to the expression of an effector protein, which illustrates the advantage of LEAPER for potential therapeutic application[22-54]. Gratifyingly, LEAPER empowers efficient editing while elicits rare global off-target editing (FIG. 20 and FIG. 21). In addition, LEAPER could minimize potential immunogenicity or surmount delivery obstacles commonly shared by other methods that require the introduction of foreign proteins.

For LEAPER, we would recommend using arRNA with a minimal size above 70-nt to achieve desirable activity. In the native context, ADAR proteins non-specifically edit Alu repeats which have a duplex of more than 300-nt[55]. Of note, Alu repeats form stable intramolecular duplex, while the LEAPER results in an intermolecular duplex between arRNA and mRNA or pre-mRNA, which is supposed to be less stable and more difficult to form. Therefore, we hypothesized that an RNA duplex longer than 70-nt is stoichiometrically important for recruiting or docking ADAR proteins for effective editing. Indeed, longer arRNA resulted in higher editing yield in both ectopically expressed reporters and endogenous transcripts (FIG. 16D and FIG. 17B). However, because ADAR proteins promiscuously deaminate adenosine base in the RNA duplex, longer arRNA may incur more off-targets within the targeting window.

While LEAPER could effectively target native transcripts, their editing efficiencies and off-target rates varied. For PPIB transcript-targeting, we could convert 50% of targeted adenosine to inosine without evident off-targets within the covering windows (FIG. 17B, f). The off-targets became more severe for other transcripts. We have managed to reduce off-targets such as introducing A-G mismatches or consecutive mismatches to repress undesired editing. However, too many mismatches could decrease on-target efficiency. Weighing up the efficiency and potential off-targets, we would recommend arRNA with the length ranging from 100- to 150-nt for editing on endogenous transcripts. If there is a choice, it's better to select regions with less adenosine to minimize the chance of unwanted edits. Encouragingly, we have not detected any off-targets outside of the arRNA-targeted-transcript duplexes (FIG. 20).

We have optimized the design of the arRNA to achieve improved editing efficiency and demonstrated that LEAPER could be harnessed to manipulate gene function or correct pathogenic mutation. We have also shown that LEAPER is not limited to only work on UAG, instead that it works with possibly any adenosine regardless of its flanking nucleotides (FIG. 16F, g and FIG. 17C). Such flexibility is advantageous for potential therapeutic correction of genetic diseases caused by certain single point mutations. Interestingly, in editing the IDUA transcripts, the arRNA targeting pre-mRNA is more effective than that targeting mature RNA, indicating that nuclei are the main sites of action for ADAR proteins and LEAPER could be leveraged to manipulate splicing by modifying splice sites within pre-mRNAs. What's more, LEAPER has demonstrated high efficiency for simultaneously targeting multiple gene transcripts (FIG. 17D). This multiplexing capability of LEAPER might be developed to cure certain polygenetic diseases in the future.

It is beneficial to perform genetic correction at the RNA level. First, editing on targeted transcripts would not permanently change the genome or transcriptome repertoire, making RNA editing approaches safer for therapeutics than means of genome editing. In addition, transient editing is well suited for temporal control of treating diseases caused by occasional changes in a specific state. Second, LEAPER and other RNA editing methods would not introduce DSB on the genome, avoiding the risk of generating undesirable deletions of large DNA fragments[37]. DNA base editing methods adopting nickase Cas9 could still generate indels in the genome[8]. Furthermore, independent of native DNA repair machinery, LEAPER should also work in post-mitosis cells such as cerebellum cells with high expression of ADAR2[11].

Figure 7A:
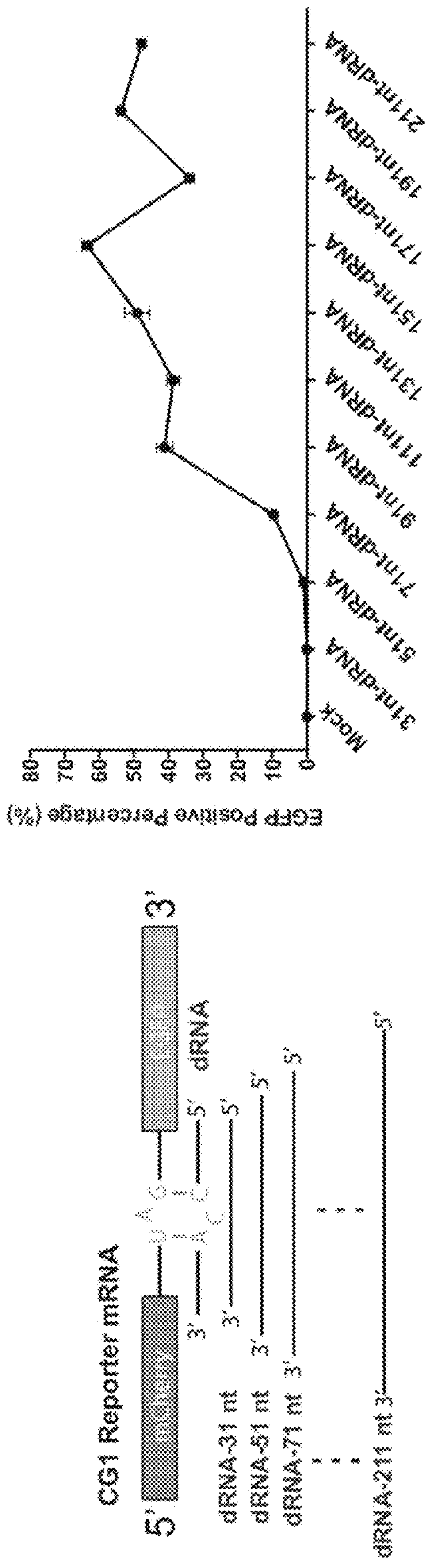
FIGS. 7A-7C shows optimization of dRNAs.
Figure 7B:
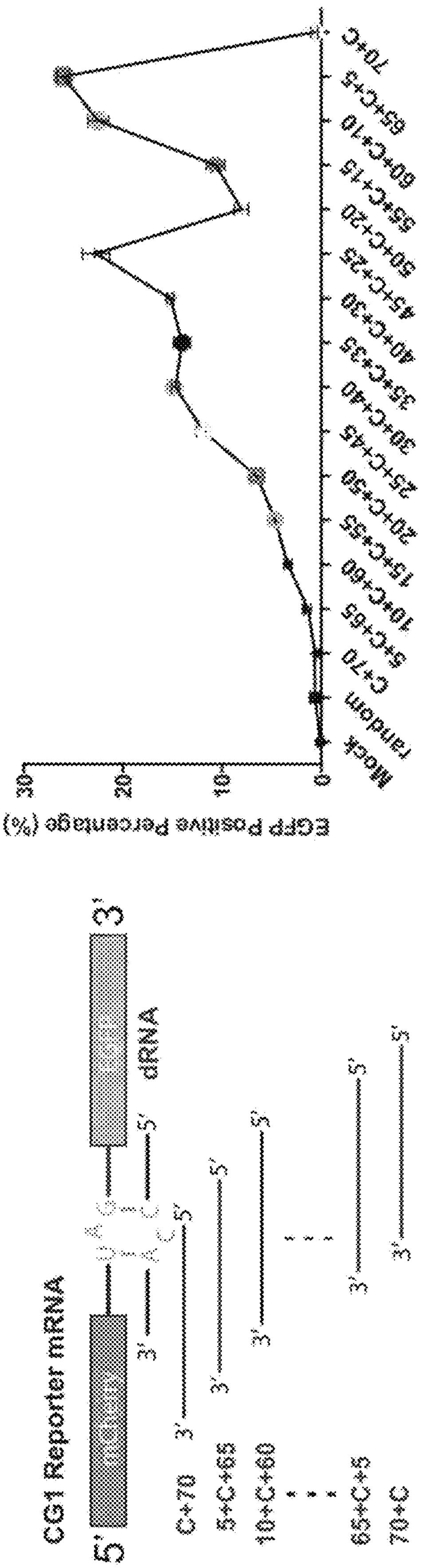
Figure 7C:
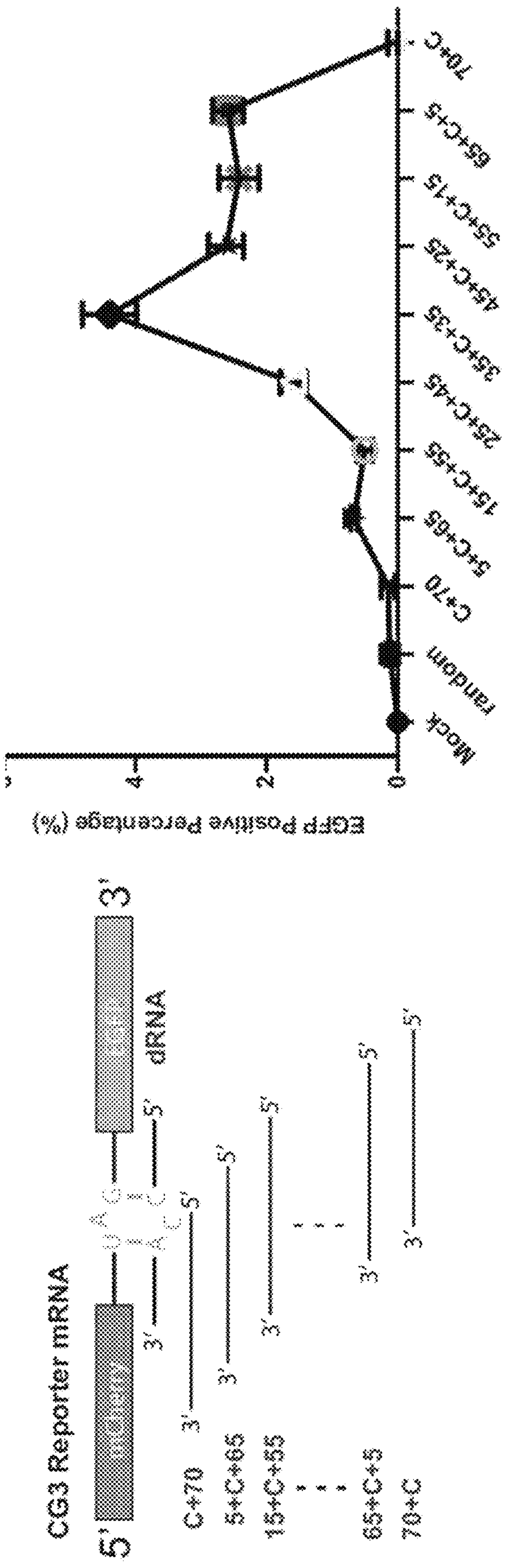

We have demonstrated that LEAPER could apply to a broad spectrum of cell types such as human cell lines (FIG. 14C), mouse cell lines (FIG. 14D) and human primary cells including primary T cells (FIG. 27 and FIG. 28D). Efficient editing through lentiviral delivery or synthesized oligo provides increased potential for therapeutic development (FIG. 28). Moreover, LEAPER could produce phenotypic or physiological changes in varieties of applications including recovering the transcriptional regulatory activity of p53 (FIG. 7), correcting pathogenic mutations (FIG. 26), and restoring the α-L-iduronidase activity in Hurler syndrome patient-derived primary fibroblasts (FIG. 29). It can thus be envisaged that LEAPER has enormous potential in disease treatment.

Stafforst and colleagues reported a new and seemingly similar RNA editing method, named RESTORE, which works through recruiting endogenous ADARs using synthetic antisense oligonucleotides[56]. The fundamental difference between RESTORE and LEAPER lies in the distinct nature of the guide RNA for recruiting endogenous ADAR. The guide RNA of RESTORE is limited to chemosynthetic antisense oligonucleotides (ASO) depending on complex chemical modification, while arRNA of LEAPER can be generated in a variety of ways, chemical synthesis and expression from viral or non-viral vectors (FIG. 28 and FIG. 29). Importantly, being heavily chemically modified, ASOs is restricted to act transiently in disease treatment. In contrast, arRNA could be produced through expression, a feature particularly important for the purpose of constant editing.

Figure 12B:
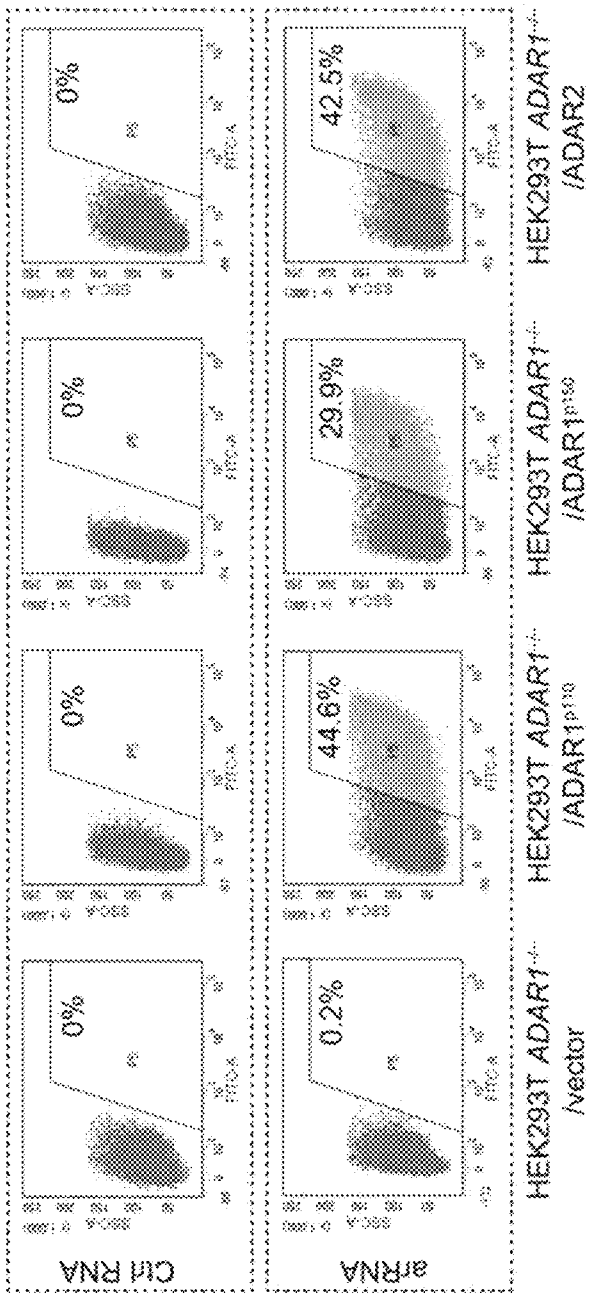
FIGS. 12A-12B show mRNA expression level of ADAR1/ADAR2 and arRNA-mediated RNA editing.
Figure 12A:
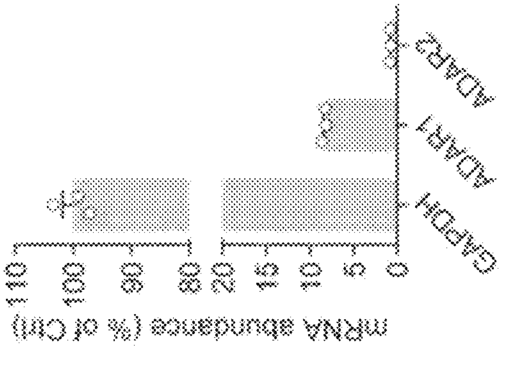
Figure 13:
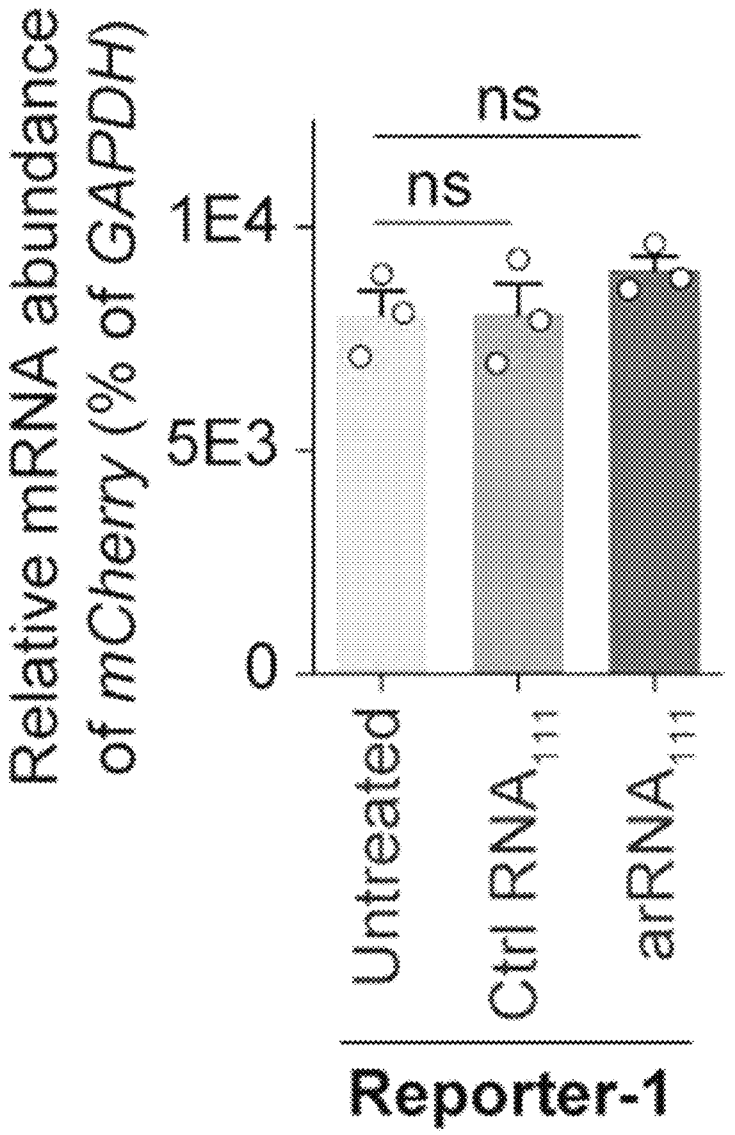
FIG. 13 shows quantitative PCR results demonstrating the effects of an exemplary LEAPER method on the expression levels of targeted Reporter-1 transcripts by 111-nt arRNA or control RNA in HEK293T cells. Data are presented as the mean±s.e.m. (n=3); unpaired two-sided Student's t-test, ns, not significant.

There are still rooms for improvements regarding LEAPER's efficiency and specificity. Because LEAPER relies on the endogenous ADAR, the expression level of ADAR proteins in target cells is one of the determinants for successful editing. According to previous report[17] and our observations (FIG. 14A, b), the $ADAR1^{p110}$ is ubiquitously expressed across tissues, assuring the broad applicability of LEAPER. The $ADAR1^{p150}$ is an interferon-inducible isoform[58], and has proven to be functional in LEAPER (FIG. 11E, FIG. 12B). Thus, co-transfection of interferon stimulatory RNAs with the arRNA might further improve editing efficiency under certain circumstances. Alternatively, as ADAR3 plays inhibitory roles, inhibition of ADAR3 might enhance editing efficiency in ADAR3-expressing cells. Moreover, additional modification of arRNA might increase its editing efficiency. For instance, arRNA fused with certain ADAR-recruiting scaffold may increase local ADAR protein concentration and consequently boost editing yield. So far, we could only leverage endogenous ADAR1/2 proteins for the A to I base conversion. It is exciting to explore whether more native mechanisms could be harnessed similarly for the modification of genetic elements, especially to realize potent nucleic acid editing.

Altogether, we provided a proof of principle that the endogenous machinery in cells could be co-opted to edit RNA transcripts. We demonstrated that LEAPER is a simple, efficient and safe system, shedding light on a novel path for gene editing-based therapeutics and research.

REFERENCES

1 Porteus, M. H. & Carroll, D. Gene targeting using zinc finger nucleases. Nat Biotechnol 23, 967-973 (2005).
2 Boch, J. et al. Breaking the code of DNA binding specificity of TAL-type III effectors. Science 326, 1509-1512 (2009).
3 Moscou, M. J. & Bogdanove, A. J. A simple cipher governs DNA recognition by TAL effectors. Science 326, 1501 (2009).
4 Miller, J. C. et al. A TALE nuclease architecture for efficient genome editing. Nat Biotechnol 29, 143-148 (2011).
5 Jinek, M. et al. A programmable dual-RNA-guided DNA endonuclease in adaptive bacterial immunity. Science 337, 816-821 (2012).
6 Cong, L. et al. Multiplex genome engineering using CRISPR/Cas systems. Science 339, 819-823 (2013).
7 Mali, P. et al. RNA-guided human genome engineering via Cas9. Science 339, 823-826 (2013).
8 Komor, A. C., Kim, Y. B., Packer, M. S., Zuris, J. A. & Liu, D. R. Programmable editing of a target base in genomic DNA without double-stranded DNA cleavage. Nature 533, 420-424 (2016).
9 Ma, Y. et al. Targeted AID-mediated mutagenesis (TAM) enables efficient genomic diversification in mammalian cells. Nat Methods 13, 1029-1035 (2016).
10 Gaudelli, N. M. et al. Programmable base editing of A*T to G*C in genomic DNA without DNA cleavage. Nature 551, 464-471 (2017).
11 Tan, M. H. et al. Dynamic landscape and regulation of RNA editing in mammals. Nature 550, 249-254 (2017).
12 Nishikura, K. Functions and regulation of RNA editing by ADAR deaminases. Annu Rev Biochem 79, 321-349 (2010).
13 Bass, B. L. & Weintraub, H. An unwinding activity that covalently modifies its double-stranded RNA substrate. Cell 55, 1089-1098 (1988).
14 Wong, S. K., Sato, S. & Lazinski, D. W. Substrate recognition by ADAR1 and ADAR2. RNA 7, 846-858 (2001).
15 Montiel-Gonzalez, M. F., Vallecillo-Viejo, I., Yudowski, G. A. & Rosenthal, J. J. Correction of mutations within the cystic fibrosis transmembrane conductance regulator by site-directed RNA editing. Proc Natl Acad Sci USA 110, 18285-18290 (2013).
16 Sinnamon, J. R. et al. Site-directed RNA repair of endogenous Mecp2 RNA in neurons. Proc Natl Acad Sci USA 114, E9395-E9402 (2017).
17 Montiel-Gonzalez, M. F., Vallecillo-Viejo, I. C. & Rosenthal, J. J. An efficient system for selectively altering genetic information within mRNAs. Nucleic Acids Res 44, e157 (2016).
18 Hanswillemenke, A., Kuzdere, T., Vogel, P., Jekely, G. & Stafforst, T. Site-Directed RNA Editing in Vivo Can Be Triggered by the Light-Driven Assembly of an Artificial Riboprotein. J Am Chem Soc 137, 15875-15881 (2015).
19 Schneider, M. F., Wettengel, J., Hoffmann, P. C. & Stafforst, T. Optimal guide RNAs for re-directing deaminase activity of hADAR1 and hADAR2 in trans. Nucleic Acids Res 42, e87 (2014).
20 Vogel, P., Hanswillemenke, A. & Stafforst, T. Switching Protein Localization by Site-Directed RNA Editing under Control of Light. ACS synthetic biology 6, 1642-1649 (2017).
21 Vogel, P., Schneider, M. F., Wettengel, J. & Stafforst, T. Improving site-directed RNA editing in vitro and in cell culture by chemical modification of the guideRNA. Angewandte Chemie 53, 6267-6271 (2014).
22 Vogel, P. et al. Efficient and precise editing of endogenous transcripts with SNAP-tagged ADARs. Nat Methods 15, 535-538 (2018).
23 Cox, D. B. T. et al. RNA editing with CRISPR-Cas13. Science 358, 1019-1027 (2017).
24 Fukuda, M. et al. Construction of a guide-RNA for site-directed RNA mutagenesis utilising intracellular A-to-I RNA editing. Scientific reports 7, 41478 (2017).
25 Wettengel, J., Reautschnig, P., Geisler, S., Kahle, P. J. & Stafforst, T. Harnessing human ADAR2 for RNA repair—Recoding a PINKI mutation rescues mitophagy. Nucleic Acids Res 45, 2797-2808 (2017).
26 Heep, M., Mach, P., Reautschnig, P., Wettengel, J. & Stafforst, T. Applying Human ADAR1p110 and ADAR1p150 for Site-Directed RNA Editing-G/C Substitution Stabilizes GuideRNAs against Editing. Genes (Basel) 8 (2017).
27 Katrekar, D. et al. In vivo RNA editing of point mutations via RNA-guided adenosine deaminases. Nat Methods 16, 239-242 (2019).
28 Yin, H., Kauffman, K. J. & Anderson, D. G. Delivery technologies for genome editing. Nat Rev Drug Discov 16, 387-399 (2017).
29 Platt, R. J. et al. CRISPR-Cas9 knockin mice for genome editing and cancer modeling. Cell 159, 440-455 (2014). Chew, W. L. et al. A multifunctional AAV-CRISPR-Cas9 and its host response. Nat Methods 13, 868-874 (2016).
31 Teoh, P. J. et al. Aberrant hyperediting of the myeloma transcriptome by ADAR1 confers oncogenicity and is a marker of poor prognosis. Blood 132, 1304-1317 (2018).
32 Vallecillo-Viejo, I. C., Liscovitch-Brauer, N., Montiel-Gonzalez, M. F., Eisenberg, E. & Rosenthal, J. J. C. Abundant off-target edits from site-directed RNA editing can be reduced by nuclear localization of the editing enzyme. RNA biology 15, 104-114 (2018).
33 Mays, L. E. & Wilson, J. M. The complex and evolving story of T cell activation to AAV vector-encoded transgene products. Mol Ther 19, 16-27 (2011).
34 Wagner, D. L. et al. High prevalence of *Streptococcus pyogenes* Cas9-reactive T cells within the adult human population. Nat Med 25, 242-248 (2019).
35 Simhadri, V. L. et al. Prevalence of Pre-existing Antibodies to CRISPR-Associated Nuclease Cas9 in the USA Population. Mol Ther Methods Clin Dev 10, 105-112 (2018).
36 Charlesworth, C. T. et al. Identification of preexisting adaptive immunity to Cas9 proteins in humans. Nat Med 25, 249-254 (2019).
37 Haapaniemi, E., Botla, S., Persson, J., Schmierer, B. & Taipale, J. CRISPR-Cas9 genome editing induces a p53-mediated DNA damage response. Nat Med 24, 927-930 (2018).
38 Ihry, R. J. et al. p53 inhibits CRISPR-Cas9 engineering in human pluripotent stem cells. Nat Med 24, 939-946 (2018).

39 Woolf, T. M., Chase, J. M. & Stinchcomb, D. T. Toward the therapeutic editing of mutated RNA sequences. Proc Natl Acad Sci USA 92, 8298-8302 (1995).

40 Zheng, Y., Lorenzo, C. & Beal, P. A. DNA editing in DNA/RNA hybrids by adenosine deaminases that act on RNA. Nucleic Acids Res 45, 3369-3377 (2017).

41 Abudayyeh, O. O. et al. C2c2 is a single-component programmable RNA-guided RNA-targeting CRISPR effector. Science 353, aaf5573 (2016).

42 Daniel, C., Widmark, A., Rigardt, D. & Ohman, M. Editing inducer elements increases A-to-I editing efficiency in the mammalian transcriptome. Genome Biol 18, 195 (2017).

43 Chen, C. X. et al. A third member of the RNA-specific adenosine deaminase gene family, ADAR3, contains both single- and double-stranded RNA binding domains. RNA 6, 755-767 (2000).

44 Savva, Y. A., Rieder, L. E. & Reenan, R. A. The ADAR protein family. Genome Biol 13, 252 (2012).

45 Nishikura, K. A-to-I editing of coding and non-coding RNAs by ADARs. Nat Rev Mol Cell Biol 17, 83-96 (2016).

46 Floquet, C., Deforges, J., Rousset, J. P. & Bidou, L. Rescue of non-sense mutated p53 tumor suppressor gene by aminoglycosides. Nucleic Acids Res 39, 3350-3362 (2011).

47 Kern, S. E. et al. Identification of p53 as a sequence-specific DNA-binding protein. Science 252, 1708-1711 (1991).

48 Doubrovin, M. et al. Imaging transcriptional regulation of p53-dependent genes with positron emission tomography in vivo. Proc Natl Acad Sci USA 98, 9300-9305 (2001).

49 Landrum, M. J. et al. ClinVar: public archive of interpretations of clinically relevant variants. Nucleic Acids Res 44, D862-868 (2016).

50 Ou, L. et al. ZFN-Mediated In Vivo Genome Editing Corrects Murine Hurler Syndrome. Mol Ther 27, 178-187 (2019).

51 Fire, A. et al. Potent and specific genetic interference by double-stranded RNA in *Caenorhabditis elegans*. Nature 391, 806-811 (1998).

52 Zuo, E. et al. Cytosine base editor generates substantial off-target single-nucleotide variants in mouse embryos. Science (2019).

53 Jin, S. et al. Cytosine, but not adenine, base editors induce genome-wide off-target mutations in rice. Science (2019).

54 Kim, D., Kim, D. E., Lee, G., Cho, S. I. & Kim, J. S. Genome-wide target specificity of CRISPR RNA-guided adenine base editors. Nat Biotechnol 37, 430-435 (2019).

55 Levanon, E. Y. et al. Systematic identification of abundant A-to-I editing sites in the human transcriptome. Nat Biotechnol 22, 1001-1005 (2004).

56 Merkle, T. et al. Precise RNA editing by recruiting endogenous ADARs with antisense oligonucleotides. Nat Biotechnol 37, 133-138 (2019).

57 Wagner, R. W. et al. Double-stranded RNA unwinding and modifying activity is detected ubiquitously in primary tissues and cell lines. Mol Cell Biol 10, 5586-5590 (1990).

58 Patterson, J. B. & Samuel, C. E. Expression and regulation by interferon of a double-stranded-RNA-specific adenosine deaminase from human cells: evidence for two forms of the deaminase. Mol Cell Biol 15, 5376-5388 (1995).

59 Gibson, D. G. et al. Enzymatic assembly of DNA molecules up to several hundred kilobases. Nat Methods 6, 343-345 (2009).

60 Zhou, Y., Zhang, H. & Wei, W. Simultaneous generation of multi-gene knockouts in human cells. FEBS Lett 590, 4343-4353 (2016).

61 Dobin, A. et al. STAR: ultrafast universal RNA-seq aligner. Bioinformatics 29, 15-21 (2013).

62 Van der Auwera, G. A. et al. From FastQ data to high confidence variant calls: the Genome Analysis Toolkit best practices pipeline. Curr Protoc Bioinformatics 43, 11 10 11-33 (2013).

63 Wang, K., Li, M. & Hakonarson, H. ANNOVAR: functional annotation of genetic variants from high-throughput sequencing data. Nucleic Acids Res 38, e164 (2010).

64 Genomes Project, C. et al. An integrated map of genetic variation from 1,092 human genomes. Nature 491, 56-65 (2012).

65 Pertea, M., Kim, D., Pertea, G. M., Leek, J. T. & Salzberg, S. L. Transcript-level expression analysis of RNA-seq experiments with HISAT, StringTie and Ballgown. Nat Protoc 11, 1650-1667 (2016).

SEQUENCE LISTING

SEQUENCE LISTING

| SEQ ID NO: | Sequence |
|---|---|
| 436 | GGAGGCAGCGGCGGAGGAGGCAGCGCCUGCUCGCGAUGCUAGAGGGCUCUGCCAGUGAGC AAGGGCGAGGAGCUGUUCACC |
| 437 | CGGCGCCCGCCGCCCGCCCGGAGCCCGCGAGCAACCCCAGUCCCCCCCACCCGCGCGUGGC GGCGCCGGCUCCCUAGCCACCGCGGCCCCACCCUCUUCCGGCCUCAGCUGUCCGGGCUGCU UUCGCCUCCGCCUGUGGAUGCUGCGCCTC |
| 438 | GCUCCCAGGUGCGGGAGAGAGGCCUGCUGAAAAUGACUGAAUAUAAACUUGUGGUAGUU GGAGCUGGUGGCGUAGGCAAGAGUGCCUUGACGAUACAGCUAAUUCAGAAUC |
| 439 | CCACCTGTTCATTACAATGGCCCCTCAAAATGAAAATGGCCAG |
| 440 | GACCGGTAAAAGTTTCAGTTGTATGGGACGAAAACTCCCCGGTAACATTACTTGTCCACC |
| 441 | CCACCTGTTCATTACAATGGCCCCTCAAAAAGCAGGGTATGTTGACTTTGAAAATGGCCAG |
| 442 | AGCGCCTGCTCGCGATGCTAGAGGGCTCTGCCAGTGAGC |

-continued

| SEQUENCE LISTING | |
|---|---|
| SEQ ID NO: | Sequence |
| 443 | AGCGGCGGAGGAGGCAGCGCCUGCUCGCGAUGCUAGAGGGCUCUGCCAGUGAGCAAGGGC GAGGAGCUGUUCACC |
| 444 | AGCGCCTGCTCGCGATGCTAGAGGGCTCTGCCAGTGAGC |
| 445 | GGCAGCGGCGGAGGAGGCAGCGCCUGCUCGCGAUGCUAGAGGGCUCUGCCAGUGAGCAAG GGCGAGGAGCUGUUCACC |
| 446 | ACAGCUCCUCGCCCUUGCUCACUGGCAGAGCCCUCCAGCAUCGCGAGCAGGCGCUGCCUCC UCCGCCGCUG |
| 447 | GGAGGCAGCAGAAGGUAUACACGCCGGAAGAAUCUGUAGAGAUCCCCGGUCGCCACCGUG AGCAAGGGCGAGGAGCUG |
| 448 | CCUCGCCCUUGCUCACGGUGGCGACCGGGGAUCUCCACAGAUUCUUCCGGCGUGUAUACC UUCUGCUGCCU |
| 449 | AUGGACGAGCUGUACAAGCUGCAGGGCGGAGGAGGCAGCGCCUGCUCGCGAUGCNANAGG GCUCUGCCAGUGAGCAAGGGCGAGGAGCUGUUCACCGGGGUGGUGCCCAUCC |
| 450 | GAUGGGCACCACCCCGGUGAACAGCUCCUCGCCCUUGCUCACUGGCAGAGCCCUNCNGCA UCGCGAGCAGGCGCUGCCUCCUCCGCCCUGCAGCUUGUACAGCUCGUCCAU |
| 451 | CGGCGCCCGCCGCCCGCCCGGAGCCCGCGAGCAACCCCAGUCCCCCCCACCCGCGCGUGGC GGCGCCGGCUCCCUAGCCACCGCGGCCCCACCCUCUUCCGGCCUCAGCUGUCCGGGCUGCU UUCGCCUCCGCCUGUGGAUGCUGCGCCUC |
| 452 | GCGGGGCCAGAGGCUCAGCGGCUCCCAGGUGCGGGAGAGAGGCCUGCUGAAAAUGACUGA AUAUAAACUUGUGGUAGUUGGAGCUGGUGGCGUAGGCAAGAGUGCCUUGACGAUACAGC UAAUUCAGAAUCAUUUUGUGGACGAAUAUGAU |
| 453 | GGAUUACCCAAGACAGAGCAUCAAAGAAACACCUUGCUGGAUUGAAAUUCACUUACACCG GGCCCUCCAGCUCCUAGACGAAGUACUUCAUACCAUGCCGAUUGCAGACCCACAACCUUU AGACUGAGGUCUUUUACCGUUGGGGCCCUUA |
| 454 | CUGCGGAGGUCCCUUUGAGAGCUGGUUCCUGUUCAUUCACUUCGGAGGAUGGGCUGAGA UGGUGGCAGAGCAAUUACUGAUGUCGGCAGCCGAACCCCCCACGGCCCUGCUGUGGCUCU UGGCCUUCUACUACGGCCCCCGUGAUGGGAGG |
| 455 | GCCCGGAGCCCGCGGGCACCCCGAGUCCC |
| 456 | GGGACUGGGGUUGCUCGCGGGCUCCGGGC |
| 457 | GAUGUUGGCAGCCGAACCACCCAC |
| 458 | GUGGGGGGUUCGGCUGCCGACAUC |
| 459 | UUCCUGUUCAUUCACUUUGGAAGA |
| 460 | UCCUCCGAAGUGAAUGAACAGGAA |
| 461 | CCUCCCAUGGCCCUGCUGUGGCUC |
| 462 | GAGCCACAGCAGGGCCGUGGGGGG |
| 463 | UUGCCGUCCCAAGCAAUGGAUGAUUUGAUGCUGUCCCCGGACGAUAUUGAACAAUAGUUC ACUGAAGACCCAGGUCCAGAUGAAGCUCCCAGAAUGCCAGAGGCUGCUCCC |
| 464 | UUGCCGUCCCAAGCAAUGGAUGAUUUGAUGCUGUCCCCGGACGAUAUUGAACAAUAGUUC ACUGAAGACCCAGGUCCAGAUGAAGCUCCCAGAAUGCCAGAGGCUGCUCCC |
| 465 | CCGCUAGAAACUGCAGAGACCUGAAAUUCUGCCAUCCUGAACUCAAGAGUGGAGAAUACU AGGUUGACCCUAACCAAGGAUGCAAAUUGGAUGCUAUCAAGGUAUUCUGUAAUAUGGAA AC |
| 466 | CAUAUUACAGAAUACCUUGAUAGCAUCCAAUUUGCAUCCUUGGUUAGGGUCAACCCAGUA UUCUCCACUCUUGAGUUCAGGAUGGCAGAAUUUCAGGUCUCUGCAGUUUCU |
| 467 | UGAUGGAGUACUAUCCCAAUGGAUCUUUAUGCAAGUAUUUAAGUCUCCACACAAGUGAC UAGGUAAGCUCUUGCCGUCUUGCUCAUUCUGUUACUAGAGGACUGGCUUAUCUUCACACA GA |

-continued

SEQUENCE LISTING

| SEQ ID NO: | Sequence |
|---|---|
| 468 | GUGAAGAUAAGCCAGUCCUCUAGUAACAGAAUGAGCAAGACGGCAAGAGCUUACCCAGUC ACUUGUGUGGAGACUUAAAUACUUGCAUAAAGAUCCAUUGGGAUAGUACUC |
| 469 | UCCAUCCAGCUGUAAGAGAGCUAGUAGUUACAGGAUGCUAUGAUUCCAUGAUACGGAUA UAGAAAGUUGAGAUGAGAGAAGAUUCUGCCAUAUUGGUCCGACAGUUUGACGUUCACAA AAG |
| 470 | GUGAACGUCAAACUGUCGGACCAAUAUGGCAGAAUCUUCUCUCAUCUCAACUUUCCAUAU CCGUAUCAUGGAAUCAUAGCAUCCUGUAACUACUAGCUCUCUUACAGCUGG |
| 471 | UGAUCAGGCACCUUCUCCUCAACUUCCUGCUCUGGGCUCCUGGAGGCCACACGAUCGCCU AGGAUGUCAUCACCCUGAUGGCUCACACUGCUGAGAUAACUCACGAGAUCAUUGGCUUUC U |
| 472 | GCCAAUGAUCUCGUGAGUUAUCUCAGCAGUGUGAGCCAUCAGGGUGAUGACAUCCCAGGC GAUCGUGUGGCCUCCAGGAGCCCAGAGCAGGAAGUUGAGGAGAAGGUGCCU |
| 473 | GGGGUCUUAAUGUGGCUCUGGAGUGGAAGCCACCCCAGGAUGUCGGCAACACGGAGCUCU AGGGGUACACAGUGCAGAAAGCCGACAAGAAGACCAUGGAGUGGUUCACCGUCUUGGAG CA |
| 474 | CAAGACGGUGAACCACUCCAUGGUCUUCUUGUCGGCUUUCUGCACUGUGUACCCCCAGAG CUCCGUGUUGCCGACAUCCUGGGGUGGCUUCCACUCCAGAGCCACAUUAAG |
| 475 | AACGCUACACGUUUCGUGUUCGGAGCCGCUUUAACCCACUCUGUGGAAGUGCUCAGCAUU AGAGUGAAUGGAGCCACCCAAUCCACUGGGGGAGCAAUACUUCAAAAGAGAAUCCUUUCC U |
| 476 | AGGAUUCUCUUUUGAAGUAUUGCUCCCCCAGUGGAUUGGGUGGCUCCAUUCACUCCAAUG CUGAGCACUUCCACAGAGUGGGUUAAAGCGGCUCCGAACACGAAACGUGUA |
| 477 | GAGCCCGCGAGCAACCCCAGUCCCCCCACCCGCGCGUGGCGGCGCCGGCUCCCUAGCCAC CGCGGCCCCACCCUCUUCCGGCCUCAGCUGUCCGGGCUGCUUUCGCCUCC |
| 478 | CCAGGCGAAAGCAGCCCGGACAGCUGAGGCCGGAAGAGGGUGGGGCCGCGGUGGCCAGGG AGCCGGCGCCGCCACGCGCGGGUGGGGGGACUGGGGUUGCUCGCGGGCUC |
| 479 | AAGCCGGUGCUCACGGCCAUGGGGCUGCUGGCGCUGCUGGAUGAGGAGCAGCUCUAGGCC GAAGUGUCGCAGGCCGGGACCGUCCUGGACAGCAACCACACGGUGGGCGUC |
| 480 | CAACGACCCCACGCGGCGACGGCCCCCCCCGCCCCGCAGAUGAGGAGCAGCUCUAGGCCG AAGUGUCGCAGGCCGGGACCGUCCUGGACAGCAACCACACGGUGGGCGUC |
| 481 | GGSGGGGSACSRCX |
| 482 | ELFTVSKGEELFT |
| 483 | ATGGTGGATTACAAGGATGACGACGATAAGATGAAAGTGACGAAGGTAGGAGGCATTTCGCA TAAGAAGTACACGTCCGAAGGCCGCTTAGTGAAGTCAGAATCGGAAGAAAATCGCACAGAC GAACGTCTGTCGGCGTTGCTTAATATGCGCCTTGACATGTATATCAAGAATCCCAGCAGCACGG AAACCAAGGAAAATCAAAAACGCATTGGGAAATTAAAGAAATTCTTCTCAAACAAAATGGTC TATCTTAAAGACAATACCTTGAGTTTGAAGAATGGAAAAAGGAGAACATTGATCGTGAGTAT TCTGAGACTGACATCCTTGAGAGCGATGTCCGTGACAAGAAAAACTTCGCCGTGTTGAAAAA GATCTATCTGAATGAAAACGTGAACTCGGAGGAATTGGAAGTTTTTCGTAACGACATTAAGAA GAAACTGAACAAAATCAACAGCCTGAAGTACTCATTTGAAAAGAATAAGGCGAATTATCAAA AGATTAATGAGAATAACATCGAGAAGGTTGAAGGTAAGTCAAAGCGTAACATTATTTACGATT ATTATCGTGAGTCAGCGAAACGTGACGCTTATGTAAGCAATGTGAAAGAAGCCTTTGATAAGC TTTACAAGGAAGAGGACATTGCAAAACTTGTTCTTGAAATTGAGAACCTTACGAAGTTAGAG AAATACAAGATTCGCGAGTTCTACCACGAAATTATTGGACGTAAGAATGACAAGGAAAACTTT GCAAAAATCATCTACGAAGAAATCCAGAATGTTAATAACATGAAAGAGTTGATCGAGAAGGTA CCGGACATGAGTGAGTTGAAAAAGAGCCAAGTATTTTACAAGTATTACTTAGACAAAGAAGA GTTGAACGACAAGAACATCAAATACGCGTTTTGTCATTTCGTGGAAATCGAAATGAGTCAGTT GCTGAAGAACTACGTATATAAGCGCTTAAGTAATATCTCGAATGACAAAATTAAGCGTATCTTT GAATACCAGAACTTGAAAAAATTGATCGAAAATAAGCTGTTAAACAAACTTGACACGTACGTC CGTAATTGTGGAAAGTATAATTATTATTTGCAAGACGGCGAAATTGCCACTTCAGATTTCATCG CCCGCAACCGTCAGAATGAAGCGTTTCTTCGCAACATCATTGGGGTGTCATCTGTGGCCTACT TTTCTCTTCGCAACATTCTTGAAACGGAGAACGAGAATGATATTACTGGGCGTATGCGCGGCA AAACAGTTAAGAACAATAAAGGTGAAGAGAAGTACGTGTCCGGAGAAGTTGATAAGATCTAT AATGAAAATAAGAAGAACGAGGTTAAGGAGAACTTAAAAATGTTCTATTCGTACGATTTCAAT ATGGACAACAAGAATGAAATCGAAGATTTCTTCGCCAACATCGACGAGGCGATTTCTTCCATC GCTCACGGTATTGTCGCCTTCAACTTGGAATTAGAAGGTAAGGATATCTTTGCGTTCAAGAAC ATTGCGCCATCCGAAATCTCAAAGAAGATGTTTCAGAATGAGATTAACGAGAAAAAACTGAA ATTGAAGATCTTTCGTCAACTGAACTCTGCCAACGTGTTCCGCTATCTCGAAAAGTATAAAATT |

-continued

| SEQUENCE LISTING | |
|---|---|
| SEQ ID NO: | Sequence |
| | CTGAATTACCTTAAACGTACACGCTTCGAGTTTGTCAATAAAAATATCCCATTCGTCCCGTCTT<br>TCACCAAATTATATTCGCGCATTGATGACCTGAAGAATAGTCTTGGGATTTACTGGAAAACTCC<br>GAAAACAAACGACGACAATAAGACTAAGGAGATTATTGATGCCCAAATCTATTTGCTTAAAAA<br>CATCTATTACGGGGAGTTCCTGAATTATTTCATGTCGAACAATGGTAATTTCTTTGAGATTTCTA<br>AAGAAATCATCGAATTGAACAAGAACGATAAACGCAACTTAAAGACTGGGTTTTACAAGCTG<br>CAAAAGTTTGAAGACATCCAGGAGAAGATTCCAAAGGAATACTTGGCGAATATCCAGTCCCT<br>GTACATGATTAATGCCGGTAATCAGGACGAAGAAGAAAAGGACACTTATATTGATTTCATTCAA<br>AAGATCTTCTTAAAGGGATTTATGACGTATCTTGCTAATAACGGTCGTTTAAGTCTGATTTACAT<br>CGGCTCGGATGAAGAAACAAATACGTCATTAGCAGAAAAGAAGCAAGAGTTTGACAAGTTCT<br>TGAAGAAGTACGAGCAGAACAATAATATCAAGATCCCCTATGAGATCAATGAATTCCTGCGTG<br>AGATCAAACTGGGAAACATCCTGAAGTATACTGAGCGTTTAAACATGTTCTACCTTATCTTAAA<br>GCTTTTGAATCACAAGGAGCTGACAAATCTGAAGGGTAGTCTTGAAAAATATCAGTCTGCCAA<br>TAAGGAAGAAGCGTTCTCTGACCAATTGGAGTTAATTAACCTGCTTAACCTTGACAACAACCG<br>CGTGACGGAAGACTTCGAATTAGAGGCCGACGAGATTGGAAAATTTCTTGATTTCAATGGCAA<br>CAAAGTTAAGGATAACAAGGAACTGAAAAAGTTCGATACAAACAAGATCTACTTTGACGGCG<br>AGAACATTATCAAACACCGTGCCTTCTACAATATTAAGAAATATGGCATGTTAAACTTACTGGA<br>GAAAATTGCCGACAAGGCTGGATACAAGATCTCGATCGAAGAGCTGAAGAAATACTCCAATA<br>AAAAGAATGAGATCGAGAAGAACCATAAGATGCAGGAAAATCTGCACCGCAAATACGCTCGT<br>CCCCGTAAAGACGAGAAGTTTACAGATGAGGACTATGAAAGTTACAAGCAAGCTATTGAGAA<br>TATTGAGGAGTACACCCACCTTAAGAACAAGGTAGAATTCAATGAGCTGAATTTACTGCAGGG<br>CCTGTTGCTGCGCATTTTACATCGTTTAGTCGGATATACCTCAATTTGGGAACGCGATCTGCGC<br>TTCCGCCTTAAAGGTGAGTTCCCAGAAAACCAATACATCGAAGAGATCTTCAACTTTGAAAAT<br>AAGAAGAACGTGAAGTACAAAGGGGGTCAGATTGTAGAGAAATACATTAAATTCTACAAGGA<br>ATTACATCAAAATGATGAAGTTAAGATCAACAAGTACAGTTCCGCGAATATCAAGGTGTTGAA<br>GCAAGAAAAGAAGGACCTTTATATTGCTAATTACATCGCCGCATTCAATTATATTCCTCACGCC<br>GAGATCTCACTGCTGGAAGTCCTTGAAAATTTGCGTAAATTGCTGTCCTACGATCGCAAACTG<br>AAAAATGCCGTAATGAAATCAGTAGTTGATATCCTTAAGGAGTATGGTTTTGTAGCCACATTCA<br>AAATCGGGGCGGACAAGAAGATCGGTATTCAGACACTGGAGAGCGAAAAAATCGTGCATCTT<br>AAGAATCTTAAGAAGAAGAAGTTAATGACTGACCGCAATTCCGAGGAACTTTGCAAATTGGT<br>GAAGATTATGTTTGAATACAAAATGGAAGAGAAAAAGTCTGAAAACGGCGCGCCAGGCGGA<br>GGAGGCAGCGGCGGAGGAGGCAGCCTCCTCCTCTCAAGGTCCCCAGAAGCACAGCCAAAGA<br>CACTCCCTCTCACTGGCAGCACCTTCCATGACCAGATAGCCATGCTGAGCCACCGGTGCTTCA<br>ACACTCTGACTAACAGCTTCCAGCCCTCCTTGCTCGGCCGCAAGATTCTGGCCGCCATCATTAT<br>GAAAAAAGACTCTGAGGACATGGGTGTCGTCGTCAGCTTGGGAACAGGGAATCGCTGTGTAA<br>AAGGAGATTCTCTCAGCCTAAAAGGAGAAACTGTCAATGACTGCCATGCAGAAATAATCTCCC<br>GGAGAGGCTTCATCAGGTTTCTCTACAGTGAGTTAATGAAATACAACTCCCAGACTGCGAAGG<br>ATAGTATATTTGAACCTGCTAAGGGAGGAGAAAAGCTCCAAATAAAAAAGACTGTGTCATTCC<br>ATCTGTATATCAGCACTGCTCCGTGTGGAGATGGCGCCCTCTTTGACAAGTCCTGCAGCGACC<br>GTGCTATGGAAAGCACAGAATCCCGCCACTACCCTGTCTTCGAGAATCCCAAACAAGGAAAG<br>CTCCGCACCAAGGTGGAGAACGGACAAGGCACAATCCCTGTGGAATCCAGTGACATTGTGCC<br>TACGTGGGATGGCATTCGGCTCGGGGAGAGACTCCGTACCATGTCCTGTAGTGACAAAATCCT<br>ACGCTGGAACGTGCTGGGCCTGCAAGGGGCACTGTTGACCCACTTCCTGCAGCCCATTTATCT<br>CAAATCTGTCACATTGGGTTACCTTTTCAGCCAAGGGCATCTGACCCGTGCTATTTGCTGTCGT<br>GTGACAAGAGATGGGAGTGCATTTGAGGATGGACTACGACATCCCTTTATTGTCAACCACCCC<br>AAGGTTGGCAGAGTCAGCATATATGATTCCAAAAGGCAATCCGGGAAGACTAAGGAGACAAG<br>CGTCAACTGGTGTCTGGCTGATGGCTATGACCTGGAGATCCTGGACGGTACCAGAGGCACTGT<br>GGATGGGCCACGGAATGAATTGTCCCGGGTCTCCAAAAAGAACATTTTTCTTCTATTTAAGAA<br>GCTCTGCTCCTTCCGTTACCGCAGGGATCTACTGAGACTCTCCTATGGTGAGGCCAAGAAAGC<br>TGCCCGTGACTACGAGACGGCCAAGAACTACTTCAAAAAGGCCTGAAGGATATGGGCTATG<br>GGAACTGGATTAGCAAACCCCAGGAGGAAAAGAACTTTTATCTCTGCCCAGTATAG |
| 484 | CGATAAGCTTGGGAGTTCCGCGTTACATAACTTACGGTAAATGGCCCGCCTGGCTGACCGCCC<br>AACGACCCCCGCCCATTGACGTCAATAATGACGTATGTTCCCATAGTAACGCCAATAGGGACTT<br>TCCATTGACGTCAATGGGTGGAGTATTTACGGTAAACTGCCCACTTGGCAGTACATCAAGTGT<br>ATCATATGCCAAGTACGCCCCCTATTGACGTCAATGACGGTAAATGGCCCGCCTGGCATTATGC<br>CCAGTACATGACCTTATGGGACTTTCCTACTTGGCAGTACATCTACGTATTAGTCATCGCTATTA<br>CCATGGTGATGCGGTTTTGGCAGTACATCAATGGGCGTGGATAGCGGTTTGACTCACGGGGAT<br>TTCCAAGTCTCCACCCCATTGACGTCAATGGGAGTTTGTTTTGGCACCAAAATCAACGGGACT<br>TTCCAAAATGTCGTAACAACTCCGCCCCATTGACGCAAATGGGCGGTAGGCGTGTACGGTGG<br>GAGGTCTATATAAGCAGAGCTCGTTTAGTGAACCGTCAGATCGCCTGGAGACGCCATCCACGC<br>TGTTTTGACCTCCATAGAAGACACCGACTCTAGAGGATCCGGACTAGTTTACCGGTGGGGCC<br>CCCGGCGCGCCGGTGTACACCCTGCAGGGGTTTAAACCCACGCGTCGACCAGTGGTCGACCC<br>TGTGGAATGTGTGTCAGTTAGGGTGTGGAAAGTCCCCAGGCTCCCCAGCAGGCAGAAGTATG<br>CAAAGCATGCATCTCAATTAGTCAGCAACCAGGTGTGGAAAGTCCCCAGGCTCCCCAGCAGG<br>CAGAAGTATGCAAAGCATGCATCTCAATTAGTCAGCAACCATAGTCCCGCCCCTAACTCCGCC<br>CATCCCGCCCCTAACTCCGCCCAGTTCCGCCCATTCTCCGCCCCATGGCTGACTAATTTTTTT<br>ATTTATGCAGAGGCCGAGGCCGCCTCGGCCTCTGAGCTATTCCAGAAGTAGTGAGGAGGCTTT<br>TTTGGAGGCCTAGGCTTTTGCAAAAAGCTATCGCTAGCTCGAGATGGTGAGCAAGGGCGAGG<br>AGGATAACATGGCCATCATCAAGGAGTTCATGCGCTTCAAGGTGCACATGGAGGGCTCCGTGA<br>ACGGCCACGAGTTCGAGATCGAGGGCGAGGGCGAGGGCCGCCCCTACGAGGGCACCCAGAC<br>CGCCAAGCTGAAGGTGACCAAGGGTGGCCCCCTGCCCTTCGCCTGGGACATCCTGTCCCCTC<br>AGTTCATGTACGGCTCCAAGGCCTACGTGAAGCACCCCGCCGACATCCCCGACTACTTGAAGC<br>TGTCCTTCCCCGAGGGCTTCAAGTGGGAGCGCGTGATGAACTTCGAGGACGGCGGCGTGGTG<br>ACCGTGACCCAGGACTCCTCCCTGCAGGACGGCGAGTTCATCTACAAGGTGAAGCTGCGCGG |

-continued

SEQUENCE LISTING

| SEQ ID NO: | Sequence |
|---|---|
| | CACCAACTTCCCCTCCGACGGCCCCGTAATGCAGAAGAAGACCATGGGCTGGGAGGCCTCCT<br>CCGAGCGGATGTACCCCGAGGACGGCGCCCTGAAGGGCGAGATCAAGCAGAGGCTGAAGCT<br>GAAGGACGGCGGCCACTACGACGCTGAGGTCAAGACCACCTACAAGGCCAAGAAGCCCGTG<br>CAGCTGCCCGGCGCCTACAACGTCAACATCAAGTTGGACATCACCTCCCACAACGAGGACTA<br>CACCATCGTGGAACAGTACGAACGCGCCGAGGGCCGCCACTCCACCGGCGGCATGGACGAG<br>CTGTACAAGTAAGCTAAGCACTTCGTGGCCGAGGAGCAGGACTGAGAATTCCAGTCGACAAT<br>CAACCTCTGGATTACAAAATTTGTGAAAGATTGACTGGTATTCTTAACTATGTTGCTCCTTTTAC<br>GCTATGTGGATACGCTGCTTTAATGCCTTTGTATCATGCTATTGCTTCCCGTATGGCTTTCATTTT<br>CTCCTCCTTGTATAAATCCTGGTTGCTGTCTCTTTATGAGGAGTTGTGGCCCGTTGTCAGGCAA<br>CGTGGCGTGGTGTGCACTGTGTTTGCTGACGCAACCCCCACTGGTTGGGGCATTGCCACCAC<br>CTGTCAGCTCCTTTCCGGGACTTTCGCTTTCCCCCTCCCTATTGCCACGGCGGAACTCATCGCC<br>GCCTGCCTTGCCCGCTGCTGGACAGGGGCTCGGCTGTTGGGCACTGACAATTCCGTGGTGTT<br>GTCGGGGAAGCTGACGTCCTTTCCATGGCTGCTCGCCTGTGTTGCCACCTGGATTCTGCGCGG<br>GACGTCCTTCTGCTACGTCCCTTCGGCCCTCAATCCAGCGGACCTTCCTTCCCGCGGCCTGCT<br>GCCGGCTCTGCGGCCTCTTCCGCGTCTTCGCCTTCGCCCTCAGACGAGTCGGATCTCCCTTTG<br>GGCCGCCTCCCCGCCTGGAATTCGAGCTCGGTACCTTTAAGACCAATGACTTACAAGGCAGCT<br>GTAGATCTTAGCCACTTTTTAAAAGAAAAGGGGGGACTGGAAGGGCTAATTCACTCCCAACG<br>AAGACAAGATCTGCTTTTTGCTTGTACTGGGTCTCTCTGGTTAGACCAGATCTGAGCCTGGGA<br>GCTCTCTGGCTAACTAGGGAACCCACTGCTTAAGCCTCAATAAAGCTTGCCTTGAGTGCTTCA<br>AGTAGTGTGTGCCCGTCTGTTGTGTGACTCTGGTAACTAGAGATCCCTCAGACCCTTTTAGTC<br>AGTGTGGAAAATCTCTAGCAGTAGTAGTTCATGTCATCTTATTATTCAGTATTTATAACTTGCAA<br>AGAAATGAATATCAGAGAGTGAGAGGAACTTGTTTATTGCAGCTTATAATGGTTACAAATAAA<br>GCAATAGCATCACAAATTTCACAAATAAAGCATTTTTTTCACTGCATTCTAGTTGTGGTTTGTC<br>CAAACTCATCAATGTATCTTATCATGTCTGGCTCTAGCTATCCCGCCCCTA |
| 485 | GAGGGCCTATTTCCCATGATTCCTTCATATTTGCATATACGATACAAGGCTGTTAGAGAGATAAT<br>TAGAATTAATTTGACTGTAAACACAAAGATATTAGTACAAAATACGTGACGTAGAAAGTAATAA<br>TTTCTTGGGTAGTTTGCAGTTTTAAAATTATGTTTTAAAATGGACTATCATATGCTTACCGTAAC<br>TTGAAAGTATTTCGATTTCTTGGCTTTATATATCTTGTGGAAAGGACGAAACACCGAGAGACGC<br>TGGCTTATCGAAATTAATACGACTCACTATAGGGAGACCCAAGCTGGCTAGTTAAGCTATCAAC<br>AAGTTTGTACAAAAAAGCTGAACGAGAAACGTAAAATGATATAAATATCAATATATTAAATTAG<br>ATTTTGCATAAAAAACAGACTACATAATACTGTAAAACACAACATATCCAGTCACTATGAATCA<br>ACTACTTAGATGGTATTAGTGACCTGTAGTCGACCGACAGCCTTCCAAATGTTCTTCGGGTGAT<br>GCTGCCAACTTAGTCGACCGACAGCCTTCCAAATGTTCTTCTCAAACGGAATCGTCGTATCCA<br>GCCTACTCGCTATTGTCCTCAATGCCGTATTAAATCATAAAAAGAAATAAGAAAAAGAGGTGC<br>GAGCCTCTTTTTTGTGTGACAAAATAAAAACATCTACCTATTCATATACGCTAGTGTCATAGTCC<br>TGAAAATCATCTGCATCAAGAACAATTTCACAACTCTTATACTTTTCTCTTACAAGTCGTTCGG<br>CTTCATCTGGATTTTCAGCCTCTATACTTACTAAACGTGATAAAGTTTCTGTAATTTCTACTGTAT<br>CGACCTGCAGACTGGCTGTGTATAAGGGAGCCTGACATTTATATTCCCCAGAACATCAGGTTA<br>ATGGCGTTTTTGATGTCATTTTCGCGGTGGCTGAGATCAGCCACTTCTTCCCCGATAACGGAGA<br>CCGGCACACTGGCCATATCGGTGGTCATCATGCGCCAGCTTTCATCCCCGATATGCACCACCGG<br>GTAAAGTTCACGGGAGACTTTATCTGACAGCAGACGTGCACTGGCCAGGGGGATCACCATCC<br>GTCGCCCGGGCGTGTCAATAATATCACTCTGTACATCCACAAACAGACGATAACGGCTCTCTC<br>TTTTATAGGTGTAAACCTTAAACTGCATTTCACCAGCCCCTGTTCTCGTCAGCAAAAGAGCCG<br>TTCATTTCAATAAACCGGGCGACCTCAGCCATCCCTTCCTGATTTTCCGCTTTCCAGCGTTCGG<br>CACGCAGACGACGGGCTTCATTCTGCATGGTTGTGCTTACCAGACCGGAGATATTGACATCAT<br>ATATGCCTTGAGCAACTGATAGCTGTCGCTGTCAACTGTCACTGTAATACGCTGCTTCATAGCA<br>TACCTCTTTTTGACATACTTCGGGTATACATATCAGTATATATTCTTATACCGCAAAAATCAGCGC<br>GCAAATACGCATACTGTTATCTGGCTTTTAGTAAGCCGGATCCACGCGGCGTTTACGCCCCCC<br>TGCCACTCATCGCAGTACTGTTGTAATTCATTAAGCATTCTGCCGACATGGAAGCCATCACAAA<br>CGGCATGATGAACCTGAATCGCCAGCGGCATCAGCACCTTGTCGCCTTGCGTATAATATTTGCC<br>CATGGTGAAAACGGGGGCGAAGAAGTTGTCCATATTGGCCACGTTTAAATCAAAACTGGTGA<br>AACTCACCCAGGGATTGGCTGAGACGAAAAACATATTCTCAATAAACCCTTTAGGGAAATAGG<br>CCAGGTTTTCACCGTAACACGCCACATCTTGCGAATATATGTGTAGAAACTGCCGGAAATCGT<br>CGTGGTATTCACTCCAGAGCGATGAAAACGTTTCAGTTTGCTCATGGAAAACGGTGTAACAAG<br>GGTGAACACTATCCCATATCACCAGCTCACCGTCTTTCATTGCCATACGGAATTCCGGATGAGC<br>ATTCATCAGGCGGGCAAGAATGTGAATAAAGGCCGGATAAAACTTGTGCTTATTTTTCTTTACG<br>GTCTTTAAAAAGGCCGTAATATCCAGCTGAACGGTCTGGTTATAGGTACATTGAGCAACTGAC<br>TGAAATGCCTCAAAATGTTCTTTACGATGCCATTGGGATATATCAACGGTGGTATATCCAGTGAT<br>TTTTTTCTCCATTTTAGCTTCCTTAGCTCCTGAAAATCTCGATAACTCAAAAAATACGCCCGGT<br>AGTGATCTTATTTCATTATGGTGAAAGTTGGAACCTCTTACGTGCCGATCAACGTCTCATTTTC<br>GCCAAAAGTTGGCCCAGGGCTTCCCGGTATCAACAGGGACACCAGGATTTATTTATTCTGCGA<br>AGTGATCTTCCGTCACAGGTATTTATTCGGCGCAAAGTGCGTCGGGTGATGCTGCCAACTTAG<br>TCGACTACAGGTCACTAATACCATCTAAGTAGTTGATTCATAGTGACTGGATATGTTGTGTTTTA<br>CAGTATTATGTAGTCTGTTTTTTATGCAAAATCTAATTTAATATATTGATATTTATATCATTTTAC<br>GTTTCTCGTTCAGCTTTCTTGTACAAAGTGGTTGATCTAGAGGGCCCGCGGTTCGAACGTCTCTT<br>GATCATATGGCGCGCCCTCGAGGTCGACGGTATCGATAAGCTCGCTTCACGAGATTCCAGCAG<br>GTCGAGGGACCTAATAACTTCGTATAGCATACATTATACGAAGTTATATTAAGGGTTCCAAGCTT<br>AAGCGGCCGCGTGGATAACCGTATTACCGCCATGCATTAGTTATTAATAGTAATCAATTACGGG<br>GTCATTAGTTCATAGCCCATATATGGAGTTCCGCGTTACATAACTTACGGTAAATGGCCCGCCTG<br>GCTGACCGCCCAACGACCCCCGCCCATTGACGTCAATAATGACGTATGTTCCCATAGTAACGC<br>CAATAGGGACTTTCCATTGACGTCAATGGGTGGAGTATTTACGGTAAACTGCCCACTTGGCAG<br>TACATCAAGTGTATCATATGCCAAGTACGCCCCCTATTGACGTCAATGACGGTAAATGGCCCGC<br>CTGGCATTATGCCCAGTACATGACCTTATGGGACTTTCCTACTTGGCAGTACATCTACGTATTAG |

-continued

SEQUENCE LISTING

| SEQ ID NO: | Sequence |
|---|---|
| | TCATCGCTATTACCATGGTGATGCGGTTTTGGCAGTACATCAATGGGCGTGGATAGCGGTTTGA CTCACGGGGATTTCCAAGTCTCCACCCCATTGACGTCAATGGGAGTTTGTTTTGGCACCAAAA TCAACGGGACTTTCCAAAATGTCGTAACAACTCCGCCCCATTGACGCAAATGGGCGGTAGGC GTGTACGGTGGGAGGTCTATATAAGCAGAGCTGGTTTAGTGAACCGTCAGATCCGCTAGCGCC ACCATGAGCGAGCTGATTAAGGAGAACATGCACATGAAGCTGTACATGGAGGGCACCGTGGA CAACCATCACTTCAAGTGCACATCCGAGGGCGAAGGCAAGCCCTACGAGGGCACCCAGACC ATGAGAATCAAGGTGGTCGAGGGCGGCCCTCTCCCCTTCGCCTTCGACATCCTGGCTACTAGC TTCCTCTACGGCAGCAAGACCTTCATCAACCACACCCAGGGCATCCCCGACTTCTTCAAGCAG TCCTTCCCTGAGGGCTTCACATGGGAGAGAGTCACCACATACGAAGACGGGGGCGTGCTGAC CGCTACCCAGGACACCAGCCTCCAGGACGGCTGCCTCATCTACAACGTCAAGATCAGAGGGG TGAACTTCACATCCAACGGCCCTGTGATGCAGAAGAAAACACTCGGCTGGGAGGCCTTCACC GAGACTCTGTACCCCGCTGACGGCGGCCTGGAAGGCAGAAACGACATGGCCCTGAAGCTCGT GGGCGGGAGCCATCTGATCGCAAACATCAAGACCACATATAGATCCAAGAAACCCGCTAAGA ACCTCAAGATGCCTGGCGTCTACTATGTGGACTACAGACTGGAAAGAATCAAGGAGGCCAAC AACGAGACCTACGTCGAGCAGCACGAGGTGGCAGTGGCCAGATACTGCGACCTCCCTAGCAA ACTGGGGCACAAACTCAATTAA |
| 486 | GATGAGGAGCAGCTCTAGGCCGAAGTGTCGCAGG |
| 487 | GATGAGGAGCAGCTCTGGGCCGAAGTGTCGCAGG |
| 488 | GGGGS |
| 489 | UGAACAGCUCCUCGCCCUUGCUCUCUGGCAGAGCCCUCCAGCAUCGCGAGCAGGCGCUGC CUCCUCCGCC |
| 490 | UGAACAGCUCCUCGCCCUUGCUCACUGGCAGAGCCCUCCAGCAUCGC |
| 491 | CUCCUCGCCCUUGCUCACUGGCAGAGCCCUCCAGCAUCGC |
| 492 | CUCCUCGCCCUUGCUCACUGGCAGAGCCCUCCAGC |
| 493 | CCCUUGCUCACUGGCAGAGCCCUCCAGC |
| 494 | CUCACUGGCAGAGCCCUCCAGC |
| 495 | GCAGAGCCCUCCAGC |
| 496 | CTGCAGGGCGGAGGAGGCAGCGCCTGCTCGCGATGCTAGAGGGCTCTGCCA |

The invention claimed is:

1. A deaminase-recruiting RNA (dRNA) of about 60 to about 200 nucleotides, wherein:

a) the dRNA comprises a complementary RNA sequence capable of hybridizing to a target RNA, wherein the dRNA does not comprise an adenosine deaminases acting on RNA (ADAR)-recruiting domain capable of forming an intramolecular stem loop structure for binding an ADAR enzyme;

b) the dRNA is capable of recruiting a deaminase, a construct comprising a deaminase, or a construct comprising a catalytic domain of a deaminase, to deaminate a target adenosine in the target RNA; and c) the dRNA comprises one or more chemical modifications;

wherein the complementary RNA sequence comprises a cytidine, an adenosine, or a uridine directly opposite to a target adenosine in the target RNA;

wherein the cytidine, adenosine, or uridine directly opposite to the target adenosine locates at least about 7 nucleotides away from the 3' end of the complementary RNA sequence, and at least about 25 nucleotides away from the 5' end of the complementary RNA sequence; and wherein the length of the 5' sequence within the complementary RNA sequence flanking the cytidine, adenosine, or uridine directly opposite to the target adenosine is longer than the length of the 3' sequence within the complementary RNA sequence.

2. The dRNA of claim 1, wherein the dRNA is longer than about any of 60 nt, 65 nt, 70 nt, 80 nt, 90 nt, 100 nt, or 110 nt.

3. The dRNA of claim 1, comprising one or more mismatches, wobbles, and/or bulges within the complementary RNA sequence.

4. The dRNA of claim 1, comprising a cytidine directly opposite to the target adenosine in the target RNA.

5. The dRNA of claim 1, wherein the complementary RNA sequence comprises one or more guanosines each opposite to a non-target adenosine in the target RNA.

6. The dRNA of claim 1, wherein the complementary RNA sequence comprises two or more consecutive mismatch nucleotides opposite to a non-target adenosine in the target RNA.

7. The dRNA of claim 1, wherein the target adenosine is in a three-base motif of UAG, and wherein the dRNA comprises an adenosine directly opposite to the uridine in the three-base motif, a cytidine directly opposite to the target adenosine, and a cytidine, guanosine, or uridine directly opposite to the guanosine in the three-base motif.

8. The dRNA of claim 7, wherein the dRNA comprises a 5'-CCA-3' directly opposite to the three-base motif of UAG.

9. The dRNA of claim 1, wherein the chemical modification comprises phosphorothioate linkage.

10. The dRNA of claim 1, wherein the chemical modification comprises 2'-O-methylation.

11. The dRNA of claim 10, wherein the chemical modification comprises a 2'-O-methylation in the first and last 1-5 nucleotides.

12. The dRNA of claim 9, wherein the chemical modification comprises a 3'-phosphorothioation in the 5' and/or 3' most adjacent nucleotides with respect to the nucleotide opposite to the target adenosine.

13. The dRNA of claim 1, wherein the chemical modification is selected from the group consisting of:

1) 2'-O-methylations in the first and last 3 nucleotides and/or phosphorothioations in the first and last 3 internucleotide linkages;
2) i) 2'-O-methylations in the first and last 3 nucleotides and/or phosphorothioations in the first and last 3 internucleotide linkages, and ii) 2'-O-methylations in a single, multiple, or all uridines;
3) i) 2'-O-methylations in the first and last 3 nucleotides, ii) phosphorothioations in the first and last 3 internucleotide linkages, iii) 2'-O-methylations in a single, multiple, or all uridines, and iv) a modification in the nucleotide opposite to the target adenosine, and/or in the 5' and/or 3' most adjacent nucleotides of the nucleotide opposite to the target adenosine;
4) i) 2'-O-methylations in the first and last 3 nucleotides, ii) phosphorothioations in the first and last 3 internucleotide linkages, iii) 2'-O-methylations in a single, multiple, or all uridines, and iv) a 2'-O-methylation in the nucleotide most adjacent to the 3' terminus and/or 5' terminus of the nucleotide opposite to the target adenosine;
5) i) 2'-O-methylations in the first and last 3 nucleotides, ii) phosphorothioations in the first and last 3 internucleotide linkages, iii) 2'-O-methylations in a single, multiple, or all uridines, and iv) a phosphorothioate linkage in the nucleotide opposite to the target adenosine and/or in the 5' and/or 3' most adjacent nucleotides of the nucleotide opposite to the target adenosine; and
6) 2'-O-methylations in the first and last 1-5 nucleotides and/or phosphorothioations in the first and last 1-5 internucleotide linkages.

14. A construct comprising or encoding a dRNA of claim 1.

15. A method for editing a target RNA in a host cell, comprising introducing a dRNA of claim 1 into the host cell.

16. The method of claim 15, comprising introducing a plurality of the dRNAs each targeting a different target RNA.

* * * * *

SEQUENCE LISTING

<160> NUMBER OF SEQ ID NOS: 496

<210> SEQ ID NO 1
<211> LENGTH: 708
<212> TYPE: DNA
<213> ORGANISM: Artificial Sequence
<220> FEATURE:
<223> OTHER INFORMATION: dRNA/arRNA

<400> SEQUENCE: 1

```
atggtgagca agggcgagga ggataacatg gccatcatca aggagttcat gcgcttcaag      60

gtgcacatgg agggctccgt gaacggccac gagttcgaga tcgagggcga gggcgagggc     120

cgcccctacg agggcaccca gaccgccaag ctgaaggtga ccaagggtgg cccctgccc      180

ttcgcctggg acatcctgtc ccctcagttc atgtacggct ccaaggccta cgtgaagcac     240

cccgccgaca tccccgacta cttgaagctg tccttccccg agggcttcaa gtgggagcgc     300

gtgatgaact tcgaggacgg cggcgtggtg accgtgaccc aggactcctc cctgcaggac     360

ggcgagttca tctacaaggt gaagctgcgc ggcaccaact tcccctccga cggccccgta     420

atgcagaaga agaccatggg ctgggaggcc tcctccgagc ggatgtaccc cgaggacggc     480

gccctgaagg gcgagatcaa gcagaggctg aagctgaagg acggcggcca ctacgacgct     540
```

```
gaggtcaaga ccacctacaa ggccaagaag cccgtgcagc tgcccggcgc ctacaacgtc    600

aacatcaagt tggacatcac ctcccacaac gaggactaca ccatcgtgga acagtacgaa    660

cgcgccgagg gccgccactc caccggcggc atggacgagc tgtacaag                 708


<210> SEQ ID NO 2
<211> LENGTH: 99
<212> TYPE: DNA
<213> ORGANISM: Artificial Sequence
<220> FEATURE:
<223> OTHER INFORMATION: dRNA/arRNA

<400> SEQUENCE: 2

ctgcagggcg gaggaggcag cggcggagga ggcagcggcg gaggaggcag cagaaggtat     60

acacgccgga agaatctgta gagatccccg gtcgccacc                            99


<210> SEQ ID NO 3
<211> LENGTH: 717
<212> TYPE: DNA
<213> ORGANISM: Artificial Sequence
<220> FEATURE:
<223> OTHER INFORMATION: dRNA/arRNA

<400> SEQUENCE: 3

gtgagcaagg gcgaggagct gttcaccggg gtggtgccca tcctggtcga gctggacggc     60

gacgtaaacg gccacaagtt cagcgtgtcc ggcgagggcg agggcgatgc cacctacggc    120

aagctgaccc tgaagttcat ctgcaccacc ggcaagctgc ccgtgccctg gcccaccctc    180

gtgaccaccc tgacctacgg cgtgcagtgc ttcagccgct accccgacca catgaagcag    240

cacgacttct tcaagtccgc catgcccgaa ggctacgtcc aggagcgcac catcttcttc    300

aaggacgacg gcaactacaa gacccgcgcc gaggtgaagt tcgagggcga caccctggtg    360

aaccgcatcg agctgaaggg catcgacttc aaggaggacg gcaacatcct ggggcacaag    420

ctggagtaca actacaacag ccacaacgtc tatatcatgg ccgacaagca gaagaacggc    480

atcaaggtga acttcaagat ccgccacaac atcgaggacg gcagcgtgca gctcgccgac    540

cactaccagc agaacacccc catcggcgac ggccccgtgc tgctgcccga caaccactac    600

ctgagcaccc agtccgccct gagcaaagac cccaacgaga agcgcgatca catggtcctg    660

ctggagttcg tgaccgccgc cgggatcact ctcggcatgg acgagctgta caagtaa       717


<210> SEQ ID NO 4
<211> LENGTH: 81
<212> TYPE: DNA
<213> ORGANISM: Artificial Sequence
<220> FEATURE:
<223> OTHER INFORMATION: dRNA/arRNA

<400> SEQUENCE: 4

ctgcagggcg gaggaggcag cggcggagga ggcagcggcg gaggaggcag cgcctgctcg     60

cgatgctaga gggctctgcc a                                               81


<210> SEQ ID NO 5
<211> LENGTH: 50
<212> TYPE: DNA
<213> ORGANISM: Artificial Sequence
<220> FEATURE:
<223> OTHER INFORMATION: dRNA/arRNA

<400> SEQUENCE: 5
```

ctgcagggcg gaggaggcag cgcctgctcg cgatgctaga gggctctgcc 50

<210> SEQ ID NO 6
<211> LENGTH: 101
<212> TYPE: RNA
<213> ORGANISM: Artificial Sequence
<220> FEATURE:
<223> OTHER INFORMATION: dRNA/arRNA

<400> SEQUENCE: 6
ggaccacccc aaaaaugaau auaaccaaaa cugaacagcu ccucgcccuu gcucacuggc 60
agagcccucc agcaucgcga gcaggcgcug ccuccuccgc c 101

<210> SEQ ID NO 7
<211> LENGTH: 70
<212> TYPE: RNA
<213> ORGANISM: Artificial Sequence
<220> FEATURE:
<223> OTHER INFORMATION: dRNA/arRNA

<400> SEQUENCE: 7
aaaccgaggg aucauagggg acugaaucca ccauucuucu cccaaucccu gcaacuccuu 60
cuuccccugc 70

<210> SEQ ID NO 8
<211> LENGTH: 70
<212> TYPE: RNA
<213> ORGANISM: Artificial Sequence
<220> FEATURE:
<223> OTHER INFORMATION: dRNA/arRNA

<400> SEQUENCE: 8
ugaacagcuc cucgcccuug cucacuggca gagcccucca gcaucgcgag caggcgcugc 60
cuccuccgcc 70

<210> SEQ ID NO 9
<211> LENGTH: 111
<212> TYPE: DNA
<213> ORGANISM: Artificial Sequence
<220> FEATURE:
<223> OTHER INFORMATION: dRNA/arRNA

<400> SEQUENCE: 9
atggacgagc tgtacaagct gcagggcgga ggaggcagcg cctgctcgcg atgctatagg 60
gctctgccag tgagcaaggg cgaggagctg ttcaccgggg tggtgcccat c 111

<210> SEQ ID NO 10
<211> LENGTH: 111
<212> TYPE: DNA
<213> ORGANISM: Artificial Sequence
<220> FEATURE:
<223> OTHER INFORMATION: dRNA/arRNA

<400> SEQUENCE: 10
atggacgagc tgtacaagct gcagggcgga ggaggcagcg cctgctcgcg atgctaaagg 60
gctctgccag tgagcaaggg cgaggagctg ttcaccgggg tggtgcccat c 111

<210> SEQ ID NO 11
<211> LENGTH: 111
<212> TYPE: DNA
<213> ORGANISM: Artificial Sequence
<220> FEATURE:
<223> OTHER INFORMATION: dRNA/arRNA

<400> SEQUENCE: 11
atggacgagc tgtacaagct gcagggcgga ggaggcagcg cctgctcgcg atgctacagg 60
gctctgccag tgagcaaggg cgaggagctg ttcaccgggg tggtgcccat c 111

<210> SEQ ID NO 12
<211> LENGTH: 111
<212> TYPE: DNA
<213> ORGANISM: Artificial Sequence
<220> FEATURE:
<223> OTHER INFORMATION: dRNA/arRNA

<400> SEQUENCE: 12
atggacgagc tgtacaagct gcagggcgga ggaggcagcg cctgctcgcg atgctagagg 60
gctctgccag tgagcaaggg cgaggagctg ttcaccgggg tggtgcccat c 111

<210> SEQ ID NO 13
<211> LENGTH: 111
<212> TYPE: DNA
<213> ORGANISM: Artificial Sequence
<220> FEATURE:
<223> OTHER INFORMATION: dRNA/arRNA

<400> SEQUENCE: 13
atggacgagc tgtacaagct gcagggcgga ggaggcagcg cctgctcgcg atgcaatagg 60
gctctgccag tgagcaaggg cgaggagctg ttcaccgggg tggtgcccat c 111

<210> SEQ ID NO 14
<211> LENGTH: 111
<212> TYPE: DNA
<213> ORGANISM: Artificial Sequence
<220> FEATURE:
<223> OTHER INFORMATION: dRNA/arRNA

<400> SEQUENCE: 14
atggacgagc tgtacaagct gcagggcgga ggaggcagcg cctgctcgcg atgcaaaagg 60
gctctgccag tgagcaaggg cgaggagctg ttcaccgggg tggtgcccat c 111

<210> SEQ ID NO 15
<211> LENGTH: 111
<212> TYPE: DNA
<213> ORGANISM: Artificial Sequence
<220> FEATURE:
<223> OTHER INFORMATION: dRNA/arRNA

<400> SEQUENCE: 15
atggacgagc tgtacaagct gcagggcgga ggaggcagcg cctgctcgcg atgcaacagg 60
gctctgccag tgagcaaggg cgaggagctg ttcaccgggg tggtgcccat c 111

<210> SEQ ID NO 16
<211> LENGTH: 111
<212> TYPE: DNA
<213> ORGANISM: Artificial Sequence
<220> FEATURE:
<223> OTHER INFORMATION: dRNA/arRNA

<400> SEQUENCE: 16
atggacgagc tgtacaagct gcagggcgga ggaggcagcg cctgctcgcg atgcaagagg 60
gctctgccag tgagcaaggg cgaggagctg ttcaccgggg tggtgcccat c 111

<210> SEQ ID NO 17

<211> LENGTH: 111
<212> TYPE: DNA
<213> ORGANISM: Artificial Sequence
<220> FEATURE:
<223> OTHER INFORMATION: dRNA/arRNA

<400> SEQUENCE: 17
atggacgagc tgtacaagct gcagggcgga ggaggcagcg cctgctcgcg atgccatagg 60
gctctgccag tgagcaaggg cgaggagctg ttcaccgggg tggtgcccat c 111

<210> SEQ ID NO 18
<211> LENGTH: 111
<212> TYPE: DNA
<213> ORGANISM: Artificial Sequence
<220> FEATURE:
<223> OTHER INFORMATION: dRNA/arRNA

<400> SEQUENCE: 18
atggacgagc tgtacaagct gcagggcgga ggaggcagcg cctgctcgcg atgccaaagg 60
gctctgccag tgagcaaggg cgaggagctg ttcaccgggg tggtgcccat c 111

<210> SEQ ID NO 19
<211> LENGTH: 111
<212> TYPE: DNA
<213> ORGANISM: Artificial Sequence
<220> FEATURE:
<223> OTHER INFORMATION: dRNA/arRNA

<400> SEQUENCE: 19
atggacgagc tgtacaagct gcagggcgga ggaggcagcg cctgctcgcg atgccacagg 60
gctctgccag tgagcaaggg cgaggagctg ttcaccgggg tggtgcccat c 111

<210> SEQ ID NO 20
<211> LENGTH: 111
<212> TYPE: DNA
<213> ORGANISM: Artificial Sequence
<220> FEATURE:
<223> OTHER INFORMATION: dRNA/arRNA

<400> SEQUENCE: 20
atggacgagc tgtacaagct gcagggcgga ggaggcagcg cctgctcgcg atgccagagg 60
gctctgccag tgagcaaggg cgaggagctg ttcaccgggg tggtgcccat c 111

<210> SEQ ID NO 21
<211> LENGTH: 111
<212> TYPE: DNA
<213> ORGANISM: Artificial Sequence
<220> FEATURE:
<223> OTHER INFORMATION: dRNA/arRNA

<400> SEQUENCE: 21
atggacgagc tgtacaagct gcagggcgga ggaggcagcg cctgctcgcg atgcgatagg 60
gctctgccag tgagcaaggg cgaggagctg ttcaccgggg tggtgcccat c 111

<210> SEQ ID NO 22
<211> LENGTH: 111
<212> TYPE: DNA
<213> ORGANISM: Artificial Sequence
<220> FEATURE:
<223> OTHER INFORMATION: dRNA/arRNA

<400> SEQUENCE: 22
atggacgagc tgtacaagct gcagggcgga ggaggcagcg cctgctcgcg atgcgaaagg 60
gctctgccag tgagcaaggg cgaggagctg ttcaccgggg tggtgcccat c 111

<210> SEQ ID NO 23
<211> LENGTH: 111
<212> TYPE: DNA
<213> ORGANISM: Artificial Sequence
<220> FEATURE:
<223> OTHER INFORMATION: dRNA/arRNA

<400> SEQUENCE: 23
atggacgagc tgtacaagct gcagggcgga ggaggcagcg cctgctcgcg atgcgacagg 60
gctctgccag tgagcaaggg cgaggagctg ttcaccgggg tggtgcccat c 111

<210> SEQ ID NO 24
<211> LENGTH: 111
<212> TYPE: DNA
<213> ORGANISM: Artificial Sequence
<220> FEATURE:
<223> OTHER INFORMATION: dRNA/arRNA

<400> SEQUENCE: 24
atggacgagc tgtacaagct gcagggcgga ggaggcagcg cctgctcgcg atgcgagagg 60
gctctgccag tgagcaaggg cgaggagctg ttcaccgggg tggtgcccat c 111

<210> SEQ ID NO 25
<211> LENGTH: 91
<212> TYPE: RNA
<213> ORGANISM: Artificial Sequence
<220> FEATURE:
<223> OTHER INFORMATION: dRNA/arRNA

<400> SEQUENCE: 25
uagcuguauc gucaaggcac ucuugccuac gccaccagcu ccaaccacca caaguuuaua 60
uucagucauu uucagcaggc cucucucccg c 91

<210> SEQ ID NO 26
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 26
gauucugaau uagcuguauc gucaaggcac ucuugccuac gccaccagcu ccaacuacca 60
caaguuuaua uucagucauu uucagcaggc cucucucccg caccugggag c 111

<210> SEQ ID NO 27
<211> LENGTH: 131
<212> TYPE: RNA
<213> ORGANISM: Artificial Sequence
<220> FEATURE:
<223> OTHER INFORMATION: dRNA/arRNA

<400> SEQUENCE: 27
uccacaaaau gauucugaau uagcuguauc gucaaggcac ucuugccuac gccaccagcu 60
ccaacuacca caaguuuaua uucagucauu uucagcaggc cucucucccg caccugggag 120
ccgcugagcc u 131

<210> SEQ ID NO 28
<211> LENGTH: 151
<212> TYPE: RNA

<213> ORGANISM: Artificial Sequence
<220> FEATURE:
<223> OTHER INFORMATION: dRNA/arRNA

<400> SEQUENCE: 28
aucauauucg uccacaaaau gauucugaau uagcuguauc gucaaggcac ucuugccuac 60
gccaccagcu ccaaccacca caaguuuaua uucagucauu uucagcaggc cucucucccg 120
caccugggag ccgcugagcc ucuggccccg c 151

<210> SEQ ID NO 29
<211> LENGTH: 171
<212> TYPE: RNA
<213> ORGANISM: Artificial Sequence
<220> FEATURE:
<223> OTHER INFORMATION: dRNA/arRNA

<400> SEQUENCE: 29
cuauuguugg aucauauucg uccacaaaau gauucugaau uagcuguauc gucaaggcac 60
ucuugccuac gccaccagcu ccaaccacca caaguuuaua uucagucauu uucagcaggc 120
cucucucccg caccugggag ccgcugagcc ucuggccccg ccgccgccuu c 171

<210> SEQ ID NO 30
<211> LENGTH: 191
<212> TYPE: RNA
<213> ORGANISM: Artificial Sequence
<220> FEATURE:
<223> OTHER INFORMATION: dRNA/arRNA

<400> SEQUENCE: 30
uaggaauccu cuauuguugg aucauauucg uccacaaaau gauucugaau uagcuguauc 60
gucaaggcac ucuugccuac gccaccagcu ccaaccacca caaguuuaua uucagucauu 120
uucagcaggc cucucucccg caccugggag ccgcugagcc ucuggccccg ccgccgccuu 180
cagugccugc g 191

<210> SEQ ID NO 31
<211> LENGTH: 151
<212> TYPE: RNA
<213> ORGANISM: Artificial Sequence
<220> FEATURE:
<223> OTHER INFORMATION: dRNA/arRNA

<400> SEQUENCE: 31
gaggcgcagc auccacaggc ggaggcgaaa gcagcccgga cagcugaggc cggaagaggg 60
uggggccgcg guggccaggg agccggcgcc gccacgcgcg gguggggggg acuggggguug 120 cucgcgggcu ccgggcgggc ggcgggcgcc g 151

<210> SEQ ID NO 32
<211> LENGTH: 151
<212> TYPE: RNA
<213> ORGANISM: Artificial Sequence
<220> FEATURE:
<223> OTHER INFORMATION: dRNA/arRNA

<400> SEQUENCE: 32
uccuguagcu aaggccacaa aauuauccac uguuuuugga acagucuuuc cgaagagacc 60
aaagaucacc cggcccacau cuucaucucc aauucguagg ucaaaauaca ccuugacggu 120
gacuuugggc cccuucuucu ucucaucggc c 151

```
<210> SEQ ID NO 33
<211> LENGTH: 151
<212> TYPE: RNA
<213> ORGANISM: Artificial Sequence
<220> FEATURE:
<223> OTHER INFORMATION: dRNA/arRNA

<400> SEQUENCE: 33

gcccuggauc augaaguccu ugauuacacg auggaauuug cuguuuuugu agccaaaucc     60

uuucucuccu guagccaagg ccacaaaauu auccacuguu uuuggaacag ucuuuccgaa    120

gagaccaaag aucacccggc cuacaucuuc a                                   151


<210> SEQ ID NO 34
<211> LENGTH: 72
<212> TYPE: RNA
<213> ORGANISM: Artificial Sequence
<220> FEATURE:
<223> OTHER INFORMATION: dRNA/arRNA

<400> SEQUENCE: 34

gcgcaaguua gguuuuguca agaaagggug uaacgcaacc aagucauagu ccgccuagaa     60

gcauuugcgg ug                                                         72


<210> SEQ ID NO 35
<211> LENGTH: 131
<212> TYPE: RNA
<213> ORGANISM: Artificial Sequence
<220> FEATURE:
<223> OTHER INFORMATION: dRNA/arRNA

<400> SEQUENCE: 35

gccaugccaa ucucaucuug uuuucugcgc aaguuagguu uugucaagaa agggguguaac     60

gcaaccaagu cauaguccgc cuagaagcau uugcggugga cgauggaggg gccggacucg    120

ucauacuccu g                                                         131


<210> SEQ ID NO 36
<211> LENGTH: 70
<212> TYPE: RNA
<213> ORGANISM: Artificial Sequence
<220> FEATURE:
<223> OTHER INFORMATION: dRNA/arRNA

<400> SEQUENCE: 36

ggacuuccug uaacaacgca ucucauauuu ggaaugacca uuaaaaaaac aacaaugugc     60

aaucaaaguc                                                            70


<210> SEQ ID NO 37
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 37

caaggugcgg cuccggcccc ucccucuuc aaggggucca cauggcaacu gugaggaggg     60

gagauucagu g                                                          71


<210> SEQ ID NO 38
<211> LENGTH: 91
<212> TYPE: RNA
<213> ORGANISM: Artificial Sequence
<220> FEATURE:
```

<223> OTHER INFORMATION: dRNA/arRNA

<400> SEQUENCE: 38
uagcuguauc gucaaggcac ucgugccgac gccaccagcu ccaaccacca caaggggaga 60
gucagucagg gucagcaggc cucucucccg c 91

<210> SEQ ID NO 39
<211> LENGTH: 91
<212> TYPE: RNA
<213> ORGANISM: Artificial Sequence
<220> FEATURE:
<223> OTHER INFORMATION: dRNA/arRNA

<400> SEQUENCE: 39
uagcuguauc gucaaggcac ucuugccgac gccaccagcu ccaaccacca caaguguaua 60
gucagucauu uucagcaggc cucucucccg c 91

<210> SEQ ID NO 40
<211> LENGTH: 91
<212> TYPE: RNA
<213> ORGANISM: Artificial Sequence
<220> FEATURE:
<223> OTHER INFORMATION: dRNA/arRNA

<400> SEQUENCE: 40
uagcuggauc gucaaggcac ucgugccgac gccaccagcu ccaaccacca caaggggaga 60
ggcagucagg gucagcaggc cucucucccg c 91

<210> SEQ ID NO 41
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 41
gauucugaau uagcuguauc gucaaggcac ucuugccgac gccaccagcu ccaaccacca 60
caaguguaua gucagucauu uucagcaggc cucucucccg caccugggag c 111

<210> SEQ ID NO 42
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 42
gauucugaau uagcuguauc gucaaggcac ucgugccgac gccaccagcu ccaaccacca 60
caaguggaga gucagucauu uucagcaggc cucucucccg caccugggag c 111

<210> SEQ ID NO 43
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 43
gauucugaau uagcuguauc gucaaggcac ucgugccgac gccaccagcu ccaaccacca 60
caaggggaga gucagucagg gucagcaggc cucucucccg caccugggag c 111

<210> SEQ ID NO 44
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 44
gcuccccggu gcgggagaga ggccugcuga cccugacugc cucuccccuu guggugguug 60
gagcuggugg cgucggcacg agugccuuga cgauccagcu aauucagaau c 111

<210> SEQ ID NO 45
<211> LENGTH: 71
<212> TYPE: DNA
<213> ORGANISM: Artificial Sequence
<220> FEATURE:
<223> OTHER INFORMATION: dRNA/arRNA

<400> SEQUENCE: 45
tctcagtcca atgtatggtc cgagcacaag ctctaatcaa agtccgcggg tgtagaccgg 60
ttgccatagg a 71

<210> SEQ ID NO 46
<211> LENGTH: 31
<212> TYPE: RNA
<213> ORGANISM: Artificial Sequence
<220> FEATURE:
<223> OTHER INFORMATION: dRNA/arRNA

<400> SEQUENCE: 46
ggaccacccc aaaaaugaag gggacuaaaa c 31

<210> SEQ ID NO 47
<211> LENGTH: 70
<212> TYPE: RNA
<213> ORGANISM: Artificial Sequence
<220> FEATURE:
<223> OTHER INFORMATION: dRNA/arRNA

<400> SEQUENCE: 47
aaaccgaggg aucauagggg acugaaucca ccauucuucu cccaaucccu gcaacuccuu 60
cuuccccugc 70

<210> SEQ ID NO 48
<211> LENGTH: 14
<212> TYPE: RNA
<213> ORGANISM: Artificial Sequence
<220> FEATURE:
<223> OTHER INFORMATION: dRNA/arRNA

<400> SEQUENCE: 48
gcagagccuc cagc 14

<210> SEQ ID NO 49
<211> LENGTH: 21
<212> TYPE: RNA
<213> ORGANISM: Artificial Sequence
<220> FEATURE:
<223> OTHER INFORMATION: dRNA/arRNA

<400> SEQUENCE: 49
cucacuggca gagccuccag c 21

<210> SEQ ID NO 50

-continued

<211> LENGTH: 27
<212> TYPE: RNA
<213> ORGANISM: Artificial Sequence
<220> FEATURE:
<223> OTHER INFORMATION: dRNA/arRNA

<400> SEQUENCE: 50
cccuugcuca cuggcagagc cuccagc 27

<210> SEQ ID NO 51
<211> LENGTH: 33
<212> TYPE: RNA
<213> ORGANISM: Artificial Sequence
<220> FEATURE:
<223> OTHER INFORMATION: dRNA/arRNA

<400> SEQUENCE: 51
cucucgcccu ugcucacugg cagagccucc agc 33

<210> SEQ ID NO 52
<211> LENGTH: 38
<212> TYPE: RNA
<213> ORGANISM: Artificial Sequence
<220> FEATURE:
<223> OTHER INFORMATION: dRNA/arRNA

<400> SEQUENCE: 52
cucucgcccu ugcucacugg cagagccucc agcaucgc 38

<210> SEQ ID NO 53
<211> LENGTH: 45
<212> TYPE: RNA
<213> ORGANISM: Artificial Sequence
<220> FEATURE:
<223> OTHER INFORMATION: dRNA/arRNA

<400> SEQUENCE: 53
ugaacagcuc ucgcccuugc ucacuggcag agccuccagc aucgc 45

<210> SEQ ID NO 54
<211> LENGTH: 70
<212> TYPE: RNA
<213> ORGANISM: Artificial Sequence
<220> FEATURE:
<223> OTHER INFORMATION: dRNA/arRNA

<400> SEQUENCE: 54
ugaacagcuc cucgcccuug cucacuggca gagcccucca gcaucgcgag caggcgcugc 60
cuccuccgcc 70

<210> SEQ ID NO 55
<211> LENGTH: 70
<212> TYPE: RNA
<213> ORGANISM: Artificial Sequence
<220> FEATURE:
<223> OTHER INFORMATION: dRNA/arRNA

<400> SEQUENCE: 55
aaaccgaggg aucauagggg acugaaucca ccauucuucu cccaaucccu gcaacuccuu 60
cuuccccugc 70

<210> SEQ ID NO 56
<211> LENGTH: 70
<212> TYPE: RNA
<213> ORGANISM: Artificial Sequence
<220> FEATURE:
<223> OTHER INFORMATION: dRNA/arRNA

<400> SEQUENCE: 56
ugaacagcuc cucgcccuug cucacuggca gagcccucca gcaucgcgag caggcgcugc 60
cuccuccgcc 70

<210> SEQ ID NO 57
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 57
ucucagucca auguaugguc cgagcacaag cucuaaucaa aguccgcggg uguagaccgg 60
uugccauagg a 71

<210> SEQ ID NO 58
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 58
acagcuccuc gcccuugcuc acuggcagag cccuccagca ucgcgagcag gcgcugccuc 60
cuccgccgcu g 71

<210> SEQ ID NO 59
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 59
acagcuccuc gcccuugcuc acuggcagag cccucaagca ucgcgagcag gcgcugccuc 60
cuccgccgcu g 71

<210> SEQ ID NO 60
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 60
acagcuccuc gcccuugcuc acuggcagag cccucuagca ucgcgagcag gcgcugccuc 60
cuccgccgcu g 71

<210> SEQ ID NO 61
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 61
acagcuccuc gcccuugcuc acuggcagag cccucgagca ucgcgagcag gcgcugccuc 60
cuccgccgcu g 71

<210> SEQ ID NO 62
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 62
acagcuccuc gcccuugcuc acuggcagag cccugcagca ucgcgagcag gcgcugccuc 60
cuccgccgcu g 71

<210> SEQ ID NO 63
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 63
acagcuccuc gcccuugcuc acuggcagag cccuucagca ucgcgagcag gcgcugccuc 60
cuccgccgcu g 71

<210> SEQ ID NO 64
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 64
acagcuccuc gcccuugcuc acuggcagag cccuacagca ucgcgagcag gcgcugccuc 60
cuccgccgcu g 71

<210> SEQ ID NO 65
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 65
acagcuccuc gcccuugcuc acuggcagag cccuccugca ucgcgagcag gcgcugccuc 60
cuccgccgcu g 71

<210> SEQ ID NO 66
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 66
acagcuccuc gcccuugcuc acuggcagag cccugcugca ucgcgagcag gcgcugccuc 60
cuccgccgcu g 71

<210> SEQ ID NO 67
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 67
acagcuccuc gcccuugcuc acuggcagag cccuucugca ucgcgagcag gcgcugccuc 60
cuccgccgcu g 71

<210> SEQ ID NO 68
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 68
acagcuccuc gcccuugcuc acuggcagag cccuacugca ucgcgagcag gcgcugccuc 60
cuccgccgcu g 71

<210> SEQ ID NO 69
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 69
acagcuccuc gcccuugcuc acuggcagag cccucccgca ucgcgagcag gcgcugccuc 60
cuccgccgcu g 71

<210> SEQ ID NO 70
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 70
acagcuccuc gcccuugcuc acuggcagag cccugccgca ucgcgagcag gcgcugccuc 60
cuccgccgcu g 71

<210> SEQ ID NO 71
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 71
acagcuccuc gcccuugcuc acuggcagag cccuuccgca ucgcgagcag gcgcugccuc 60
cuccgccgcu g 71

<210> SEQ ID NO 72
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 72
acagcuccuc gcccuugcuc acuggcagag cccuaccgca ucgcgagcag gcgcugccuc 60
cuccgccgcu g 71

<210> SEQ ID NO 73
<211> LENGTH: 71
<212> TYPE: RNA

<213> ORGANISM: Artificial Sequence
<220> FEATURE:
<223> OTHER INFORMATION: dRNA/arRNA

<400> SEQUENCE: 73
acagcuccuc gcccuugcuc acuggcagag cccuccggca ucgcgagcag gcgcugccuc 60
cuccgccgcu g 71

<210> SEQ ID NO 74
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 74
acagcuccuc gcccuugcuc acuggcagag cccugcugca ucgcgagcag gcgcugccuc 60
cuccgccgcu g 71

<210> SEQ ID NO 75
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 75
acagcuccuc gcccuugcuc acuggcagag cccuucggca ucgcgagcag gcgcugccuc 60
cuccgccgcu g 71

<210> SEQ ID NO 76
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 76
acagcuccuc gcccuugcuc acuggcagag cccuacggca ucgcgagcag gcgcugccuc 60
cuccgccgcu g 71

<210> SEQ ID NO 77
<211> LENGTH: 31
<212> TYPE: RNA
<213> ORGANISM: Artificial Sequence
<220> FEATURE:
<223> OTHER INFORMATION: dRNA/arRNA

<400> SEQUENCE: 77
acuggcagag cccuccagca ucgcgagcag g 31

<210> SEQ ID NO 78
<211> LENGTH: 51
<212> TYPE: RNA
<213> ORGANISM: Artificial Sequence
<220> FEATURE:
<223> OTHER INFORMATION: dRNA/arRNA

<400> SEQUENCE: 78
gcccuugcuc acuggcagag cccuccagca ucgcgagcag gcgcugccuc c 51

<210> SEQ ID NO 79
<211> LENGTH: 71

-continued

<212> TYPE: RNA
<213> ORGANISM: Artificial Sequence
<220> FEATURE:
<223> OTHER INFORMATION: dRNA/arRNA

<400> SEQUENCE: 79
acagcuccuc gcccuugcuc acuggcagag cccuccagca ucgcgagcag gcgcugccuc 60
cuccgccgcu g 71

<210> SEQ ID NO 80
<211> LENGTH: 91
<212> TYPE: RNA
<213> ORGANISM: Artificial Sequence
<220> FEATURE:
<223> OTHER INFORMATION: dRNA/arRNA

<400> SEQUENCE: 80
accccgguga acagcuccuc gcccuugcuc acuggcagag cccuccagca ucgcgagcag 60
gcgcugccuc cuccgccgcu gccuccuccg c 91

<210> SEQ ID NO 81
<211> LENGTH: 131
<212> TYPE: RNA
<213> ORGANISM: Artificial Sequence
<220> FEATURE:
<223> OTHER INFORMATION: dRNA/arRNA

<400> SEQUENCE: 81
gcucgaccag gaugggcacc accccgguga acagcuccuc gcccuugcuc acuggcagag 60
cccuccagca ucgcgagcag gcgcugccuc cuccgccgcu gccuccuccg ccgcugccuc 120
cuccgcccug c 131

<210> SEQ ID NO 82
<211> LENGTH: 151
<212> TYPE: RNA
<213> ORGANISM: Artificial Sequence
<220> FEATURE:
<223> OTHER INFORMATION: dRNA/arRNA

<400> SEQUENCE: 82
ucgccgucca gcucgaccag gaugggcacc accccgguga acagcuccuc gcccuugcuc 60
acuggcagag cccuccagca ucgcgagcag gcgcugccuc cuccgccgcu gccuccuccg 120
ccgcugccuc cuccgcccug cagcuuguac a 151

<210> SEQ ID NO 83
<211> LENGTH: 171
<212> TYPE: RNA
<213> ORGANISM: Artificial Sequence
<220> FEATURE:
<223> OTHER INFORMATION: dRNA/arRNA

<400> SEQUENCE: 83
gccguuuacg ucgccgucca gcucgaccag gaugggcacc accccgguga acagcuccuc 60
gcccuugcuc acuggcagag cccuccagca ucgcgagcag gcgcugccuc cuccgccgcu 120
gccuccuccg ccgcugccuc cuccgcccug cagcuuguac agcucgucca u 171

<210> SEQ ID NO 84
<211> LENGTH: 191
<212> TYPE: RNA
<213> ORGANISM: Artificial Sequence
<220> FEATURE:

-continued

<223> OTHER INFORMATION: dRNA/arRNA

<400> SEQUENCE: 84
ugaacuugug gccguuuacg ucgccgucca gcucgaccag gaugggcacc accccgguga 60
acagcuccuc gcccuugcuc acuggcagag cccuccagca ucgcgagcag gcgcugccuc 120
cuccgccgcu gccuccuccg ccgcugccuc cuccgcccug cagcuuguac agcucgucca 180
ugccgccggu g 191

<210> SEQ ID NO 85
<211> LENGTH: 211
<212> TYPE: RNA
<213> ORGANISM: Artificial Sequence
<220> FEATURE:
<223> OTHER INFORMATION: dRNA/arRNA

<400> SEQUENCE: 85
ccggacacgc ugaacuugug gccguuuacg ucgccgucca gcucgaccag gaugggcacc 60
accccgguga acagcuccuc gcccuugcuc acuggcagag cccuccagca ucgcgagcag 120
gcgcugccuc cuccgccgcu gccuccuccg ccgcugccuc cuccgcccug cagcuuguac 180
agcucgucca ugccgccggu ggaguggcgg c 211

<210> SEQ ID NO 86
<211> LENGTH: 31
<212> TYPE: RNA
<213> ORGANISM: Artificial Sequence
<220> FEATURE:
<223> OTHER INFORMATION: dRNA/arRNA

<400> SEQUENCE: 86
gcgaccgggg aucuccacag auucuuccgg c 31

<210> SEQ ID NO 87
<211> LENGTH: 51
<212> TYPE: RNA
<213> ORGANISM: Artificial Sequence
<220> FEATURE:
<223> OTHER INFORMATION: dRNA/arRNA

<400> SEQUENCE: 87
gcucacggug gcgaccgggg aucuccacag auucuuccgg cguguauacc u 51

<210> SEQ ID NO 88
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 88
ccucgcccuu gcucacggug gcgaccgggg aucuccacag auucuuccgg cguguauacc 60
uucugcugcc u 71

<210> SEQ ID NO 89
<211> LENGTH: 91
<212> TYPE: RNA
<213> ORGANISM: Artificial Sequence
<220> FEATURE:
<223> OTHER INFORMATION: dRNA/arRNA

<400> SEQUENCE: 89
gugaacagcu ccucgcccuu gcucacggug gcgaccgggg aucuccacag auucuuccgg 60
cguguauacc uucugcugcc uccuccgccg c 91

<210> SEQ ID NO 90
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 90
caccaccccg gugaacagcu ccucgcccuu gcucacggug gcgaccgggg aucuccacag 60
auucuuccgg cguguauacc uucugcugcc uccuccgccg cugccuccuc c 111

<210> SEQ ID NO 91
<211> LENGTH: 131
<212> TYPE: RNA
<213> ORGANISM: Artificial Sequence
<220> FEATURE:
<223> OTHER INFORMATION: dRNA/arRNA

<400> SEQUENCE: 91
ccaggauggg caccaccccg gugaacagcu ccucgcccuu gcucacggug gcgaccgggg 60
aucuccacag auucuuccgg cguguauacc uucugcugcc uccuccgccg cugccuccuc 120
cgccgcugcc u 131

<210> SEQ ID NO 92
<211> LENGTH: 151
<212> TYPE: RNA
<213> ORGANISM: Artificial Sequence
<220> FEATURE:
<223> OTHER INFORMATION: dRNA/arRNA

<400> SEQUENCE: 92
uccagcucga ccaggauggg caccaccccg gugaacagcu ccucgcccuu gcucacggug 60
gcgaccgggg aucuccacag auucuuccgg cguguauacc uucugcugcc uccuccgccg 120
cugccuccuc cgccgcugcc uccuccgccc u 151

<210> SEQ ID NO 93
<211> LENGTH: 171
<212> TYPE: RNA
<213> ORGANISM: Artificial Sequence
<220> FEATURE:
<223> OTHER INFORMATION: dRNA/arRNA

<400> SEQUENCE: 93
cggcgacgua uccagcucga ccaggauggg caccaccccg gugaacagcu ccucgcccuu 60
gcucacggug gcgaccgggg aucuccacag auucuuccgg cguguauacc uucugcugcc 120
uccuccgccg cugccuccuc cgccgcugcc uccuccgccc ugcagcuugu a 171

<210> SEQ ID NO 94
<211> LENGTH: 191
<212> TYPE: RNA
<213> ORGANISM: Artificial Sequence
<220> FEATURE:
<223> OTHER INFORMATION: dRNA/arRNA

<400> SEQUENCE: 94
uguggccguu uacgucgccg uccagcucga ccaggauggg caccaccccg gugaacagcu 60
ccucgcccuu gcucacggug gcgaccgggg aucuccacag auucuuccgg cguguauacc 120
uucugcugcc uccuccgccg cugccuccuc cgccgcugcc uccuccgccc ugcagcuugu 180
acagcucguc c 191

<210> SEQ ID NO 95
<211> LENGTH: 211
<212> TYPE: RNA
<213> ORGANISM: Artificial Sequence
<220> FEATURE:
<223> OTHER INFORMATION: dRNA/arRNA

<400> SEQUENCE: 95
acgcugaacu uguggccguu uacgucgccg uccagcucga ccaggauggg caccaccccg 60
gugaacagcu ccucgcccuu gcucacggug gcgaccgggg aucuccacag auucuuccgg 120
cguguauacc uucugcugcc uccuccgccg cugccuccuc cgccgcugcc uccuccgccc 180
ugcagcuugu acagcucguc caugccgccg g 211

<210> SEQ ID NO 96
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 96
cagcaucgcg agcaggcgcu gccuccuccg ccgcugccuc cuccgccgcu gccuccuccg 60
cccugcagcu u 71

<210> SEQ ID NO 97
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 97
cccuccagca ucgcgagcag gcgcugccuc cuccgccgcu gccuccuccg ccgcugccuc 60
cuccgcccug c 71

<210> SEQ ID NO 98
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 98
cagagcccuc cagcaucgcg agcaggcgcu gccuccuccg ccgcugccuc cuccgccgcu 60
gccuccuccg c 71

<210> SEQ ID NO 99
<211> LENGTH: 72
<212> TYPE: RNA
<213> ORGANISM: Artificial Sequence
<220> FEATURE:
<223> OTHER INFORMATION: dRNA/arRNA

<400> SEQUENCE: 99
acuggcagag cccucccagc aucgcgagca ggcgcugccu ccuccgccgc ugccuccucc 60
gccgcugccu cc 72

<210> SEQ ID NO 100
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 100
ugcucacugg cagagcccuc cagcaucgcg agcaggcgcu gccuccuccg ccgcugccuc 60
cuccgccgcu g 71

<210> SEQ ID NO 101
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 101
gcccuugcuc acuggcagag cccuccagca ucgcgagcag gcgcugccuc cuccgccgcu 60
gccuccuccg c 71

<210> SEQ ID NO 102
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 102
uccucgcccu ugcucacugg cagagcccuc cagcaucgcg agcaggcgcu gccuccuccg 60
ccgcugccuc c 71

<210> SEQ ID NO 103
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 103
ggugaacagc uccucgcccu ugcucacugg cagagcccuc cagcaucgcg agcaggcgcu 60
gccuccuccg c 71

<210> SEQ ID NO 104
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 104
accccgguga acagcuccuc gcccuugcuc acuggcagag cccuccagca ucgcgagcag 60
gcgcugccuc c 71

<210> SEQ ID NO 105
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 105
gcaccacccc ggugaacagc uccucgcccu ugcucacugg cagagcccuc cagcaucgcg 60
agcaggcgcu g 71

<210> SEQ ID NO 106
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 106
gaugggcacc accccgguga acagcuccuc gcccuugcuc acuggcagag cccuccagca 60
ucgcgagcag g 71

<210> SEQ ID NO 107
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 107
accaggaugg gcaccacccc ggugaacagc uccucgcccu ugcucacugg cagagcccuc 60
cagcaucgcg a 71

<210> SEQ ID NO 108
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 108
gcucgaccag gaugggcacc accccgguga acagcuccuc gcccuugcuc acuggcagag 60
cccuccagca u 71

<210> SEQ ID NO 109
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 109
guccagcucg accaggaugg gcaccacccc ggugaacagc uccucgcccu ugcucacugg 60
cagagcccuc c 71

<210> SEQ ID NO 110
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 110
cacagauucu uccggcgugu auaccuucug cugccuccuc cgccgcugcc uccuccgccg 60
cugccuccuc c 71

<210> SEQ ID NO 111
<211> LENGTH: 71
<212> TYPE: RNA
<213> ORGANISM: Artificial Sequence

```
<220> FEATURE:
<223> OTHER INFORMATION: dRNA/arRNA

<400> SEQUENCE: 111

aucuccacag auucuuccgg cguguauacc uucugcugcc uccuccgccg cugccuccuc    60

cgccgcugcc u                                                        71

<210> SEQ ID NO 112
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 112

cggggaucuc cacagauucu uccggcgugu auaccuucug cugccuccuc cgccgcugcc    60

uccuccgccg c                                                        71

<210> SEQ ID NO 113
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 113

gcgaccgggg aucuccacag auucuuccgg cguguauacc uucugcugcc uccuccgccg    60

cugccuccuc c                                                        71

<210> SEQ ID NO 114
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 114

cgguggcgac cggggaucuc cacagauucu uccggcgugu auaccuucug cugccuccuc    60

cgccgcugcc u                                                        71

<210> SEQ ID NO 115
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 115

gcucacggug gcgaccgggg aucuccacag auucuuccgg cguguauacc uucugcugcc    60

uccuccgccg c                                                        71

<210> SEQ ID NO 116
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 116

cccuugcuca cgguggcgac cggggaucuc cacagauucu uccggcgugu auaccuucug    60

cugccuccuc c                                                        71
```

<210> SEQ ID NO 117
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 117
cagcuccucg cccuugcuca cgguggcgac cggggaucuc cacagauucu uccggcgugu 60
auaccuucug c 71

<210> SEQ ID NO 118
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 118
gugaacagcu ccucgcccuu gcucacggug gcgaccgggg aucuccacag auucuuccgg 60
cguguauacc u 71

<210> SEQ ID NO 119
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 119
ccccggugaa cagcuccucg cccuugcuca cgguggcgac cggggaucuc cacagauucu 60
uccggcgugu a 71

<210> SEQ ID NO 120
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 120
caccaccccg gugaacagcu ccucgcccuu gcucacggug gcgaccgggg aucuccacag 60
auucuuccgg c 71

<210> SEQ ID NO 121
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 121
augggcacca ccccggugaa cagcuccucg cccuugcuca cgguggcgac cggggaucuc 60
cacagauucu u 71

<210> SEQ ID NO 122
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 122

```
ccaggauggg caccaccccg gugaacagcu ccucgcccuu gcucacggug gcgaccgggg    60

aucuccacag a                                                         71

<210> SEQ ID NO 123
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 123

cucgaccagg augggcacca ccccggugaa cagcuccucg cccuugcuca cgguggcgac    60

cggggaucuc c                                                         71

<210> SEQ ID NO 124
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 124

gaugggcacc accccgguga acagcuccuc gcccuugcuc acuggcagag cccuccagca    60

ucgcgagcag gcgcugccuc cuccgcccug cagcuuguac agcucgucca u            111

<210> SEQ ID NO 125
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 125

gaugggcacc accccgguga acagcuccuc gcccuugcuc acuggcagag cccugcagca    60

ucgcgagcag gcgcugccuc cuccgcccug cagcuuguac agcucgucca u            111

<210> SEQ ID NO 126
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 126

gaugggcacc accccgguga acagcuccuc gcccuugcuc acuggcagag cccuucagca    60

ucgcgagcag gcgcugccuc cuccgcccug cagcuuguac agcucgucca u            111

<210> SEQ ID NO 127
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 127

gaugggcacc accccgguga acagcuccuc gcccuugcuc acuggcagag cccuacagca    60

ucgcgagcag gcgcugccuc cuccgcccug cagcuuguac agcucgucca u            111

<210> SEQ ID NO 128
<211> LENGTH: 111
<212> TYPE: RNA
```

<213> ORGANISM: Artificial Sequence
<220> FEATURE:
<223> OTHER INFORMATION: dRNA/arRNA

<400> SEQUENCE: 128
gaugggcacc accccggguga acagcuccuc gcccuugcuc acuggcagag cccuccggca 60
ucgcgagcag gcgcugccuc cuccgcccug cagcuuguac agcucgucca u 111

<210> SEQ ID NO 129
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 129
gaugggcacc accccgguga acagcuccuc gcccuugcuc acuggcagag cccugcggca 60
ucgcgagcag gcgcugccuc cuccgcccug cagcuuguac agcucgucca u 111

<210> SEQ ID NO 130
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 130
gaugggcacc accccgguga acagcuccuc gcccuugcuc acuggcagag cccuucggca 60
ucgcgagcag gcgcugccuc cuccgcccug cagcuuguac agcucgucca u 111

<210> SEQ ID NO 131
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 131
gaugggcacc accccgguga acagcuccuc gcccuugcuc acuggcagag cccuacggca 60
ucgcgagcag gcgcugccuc cuccgcccug cagcuuguac agcucgucca u 111

<210> SEQ ID NO 132
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 132
gaugggcacc accccgguga acagcuccuc gcccuugcuc acuggcagag cccuccugca 60
ucgcgagcag gcgcugccuc cuccgcccug cagcuuguac agcucgucca u 111

<210> SEQ ID NO 133
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 133
gaugggcacc accccgguga acagcuccuc gcccuugcuc acuggcagag cccugcugca 60
ucgcgagcag gcgcugccuc cuccgcccug cagcuuguac agcucgucca u 111

```
<210> SEQ ID NO 134
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 134

gaugggcacc accccgguga acagcuccuc gcccuugcuc acuggcagag cccuacugca      60

ucgcgagcag gcgcugccuc cuccgcccug cagcuuguac agcucgucca u              111

<210> SEQ ID NO 135
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 135

gaugggcacc accccgguga acagcuccuc gcccuugcuc acuggcagag cccuucugca      60

ucgcgagcag gcgcugccuc cuccgcccug cagcuuguac agcucgucca u              111

<210> SEQ ID NO 136
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 136

gaugggcacc accccgguga acagcuccuc gcccuugcuc acuggcagag cccucccgca      60

ucgcgagcag gcgcugccuc cuccgcccug cagcuuguac agcucgucca u              111

<210> SEQ ID NO 137
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 137

gaugggcacc accccgguga acagcuccuc gcccuugcuc acuggcagag cccugccgca      60

ucgcgagcag gcgcugccuc cuccgcccug cagcuuguac agcucgucca u              111

<210> SEQ ID NO 138
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 138

gaugggcacc accccgguga acagcuccuc gcccuugcuc acuggcagag cccuuccgca      60

ucgcgagcag gcgcugccuc cuccgcccug cagcuuguac agcucgucca u              111

<210> SEQ ID NO 139
<211> LENGTH: 111
<212> TYPE: RNA
<213> ORGANISM: Artificial Sequence
<220> FEATURE:
<223> OTHER INFORMATION: dRNA/arRNA
```

<400> SEQUENCE: 139
gaugggcacc accccgguga acagcuccuc gcccuugcuc acuggcagag cccuaccgca 60
ucgcgagcag gcgcugccuc cuccgcccug cagcuuguac agcucgucca u 111

<210> SEQ ID NO 140
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 140
uaccgcuaca gccacgcuga uuucagcuau accugcccgg uauaaaggga cguucacacc 60
gcgauguucu cugcugggga auugcgcgau auucaggauu aaaagaagug c 111

<210> SEQ ID NO 141
<211> LENGTH: 151
<212> TYPE: RNA
<213> ORGANISM: Artificial Sequence
<220> FEATURE:
<223> OTHER INFORMATION: dRNA/arRNA

<400> SEQUENCE: 141
acuacaguug cuccgauauu uaggcuacgu caauaggcac uaacuuauug gcgcugguga 60
acggacuucc ucucgaguac cagaagauga cuacaaaacu ccuuuccauu gcgaguaucg 120
gagucuggcu caguuuggcc agggaggcac u 151

<210> SEQ ID NO 142
<211> LENGTH: 51
<212> TYPE: RNA
<213> ORGANISM: Artificial Sequence
<220> FEATURE:
<223> OTHER INFORMATION: dRNA/arRNA

<400> SEQUENCE: 142
cggaagaggg uggggccgcg guggccaggg agccggcgcc gccacgcgcg g 51

<210> SEQ ID NO 143
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 143
cagcugaggc cggaagaggg uggggccgcg guggccaggg agccggcgcc gccacgcgcg 60 ggugggggggg a 71

<210> SEQ ID NO 144
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 144
ggaggcgaaa gcagcccgga cagcugaggc cggaagaggg uggggccgcg guggccaggg 60
agccggcgcc gccacgcgcg ggugggggggg acugggguug cucgcgggcu c 111

<210> SEQ ID NO 145
<211> LENGTH: 151

-continued

<212> TYPE: RNA
<213> ORGANISM: Artificial Sequence
<220> FEATURE:
<223> OTHER INFORMATION: dRNA/arRNA

<400> SEQUENCE: 145
gaggcgcagc auccacaggc ggaggcgaaa gcagcccgga cagcugaggc cggaagaggg 60
uggggccgcg guggccaggg agccggcgcc gccacgcgcg ggugggggg acugggguug 120 cucgcgggcu ccgggcgggc ggcgggcgcc g 151

<210> SEQ ID NO 146
<211> LENGTH: 51
<212> TYPE: RNA
<213> ORGANISM: Artificial Sequence
<220> FEATURE:
<223> OTHER INFORMATION: dRNA/arRNA

<400> SEQUENCE: 146
ucuugccuac gccaccagcu ccaaccacca caaguuuaua uucagucauu u 51

<210> SEQ ID NO 147
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 147
gauucugaau uagcuguauc gucaaggcac ucuugccuac gccaccagcu ccaaccacca 60
caaguuuaua uucagucauu uucagcaggc cucucucccg caccugggag c 111

<210> SEQ ID NO 148
<211> LENGTH: 151
<212> TYPE: RNA
<213> ORGANISM: Artificial Sequence
<220> FEATURE:
<223> OTHER INFORMATION: dRNA/arRNA

<400> SEQUENCE: 148
aucauauucg uccacaaaau gauucugaau uagcuguauc gucaaggcac ucuugccuac 60
gccaccagcu ccaaccacca caaguuuaua uucagucauu uucagcaggc cucucucccg 120
caccugggag ccgcugagcc ucuggccccg c 151

<210> SEQ ID NO 149
<211> LENGTH: 51
<212> TYPE: RNA
<213> ORGANISM: Artificial Sequence
<220> FEATURE:
<223> OTHER INFORMATION: dRNA/arRNA

<400> SEQUENCE: 149
ucggcauggu augaaguacu ucguccagga gcuggagggc ccgguguaag u 51

<210> SEQ ID NO 150
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 150
gggucugcaa ucggcauggu augaaguacu ucguccagga gcuggagggc ccgguguaag 60
ugaauuucaa u 71

<210> SEQ ID NO 151
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 151
gaccucaguc uaaagguugu gggucugcaa ucggcauggu augaaguacu ucguccagga 60
gcuggagggc ccgguguaag ugaauuucaa uccagcaagg uguuucuuug a 111

<210> SEQ ID NO 152
<211> LENGTH: 151
<212> TYPE: RNA
<213> ORGANISM: Artificial Sequence
<220> FEATURE:
<223> OTHER INFORMATION: dRNA/arRNA

<400> SEQUENCE: 152
uaagggcccc aacgguaaaa gaccucaguc uaaagguugu gggucugcaa ucggcauggu 60
augaaguacu ucguccagga gcuggagggc ccgguguaag ugaauuucaa uccagcaagg 120
uguuucuuug augcucuguc uuggguaauc c 151

<210> SEQ ID NO 153
<211> LENGTH: 51
<212> TYPE: RNA
<213> ORGANISM: Artificial Sequence
<220> FEATURE:
<223> OTHER INFORMATION: dRNA/arRNA

<400> SEQUENCE: 153
ugggggguuc ggcugccgac aucagcaauu gcucugccac caucucagcc c 51

<210> SEQ ID NO 154
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 154
agcagggccg ugggggguuc ggcugccgac aucagcaauu gcucugccac caucucagcc 60
cauccuccga a 71

<210> SEQ ID NO 155
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 155
aguagaaggc caagagccac agcagggccg ugggggguuc ggcugccgac aucagcaauu 60
gcucugccac caucucagcc cauccuccga agugaaugaa caggaaccag c 111

<210> SEQ ID NO 156
<211> LENGTH: 151
<212> TYPE: RNA
<213> ORGANISM: Artificial Sequence
<220> FEATURE:
<223> OTHER INFORMATION: dRNA/arRNA

<400> SEQUENCE: 156
ccucccauca cgggggccgu aguagaaggc caagagccac agcagggccg ugggggguuc 60
ggcugccgac aucagcaauu gcucugccac caucucagcc cauccuccga agugaaugaa 120
caggaaccag cucucaaagg gaccuccgca g 151

<210> SEQ ID NO 157
<211> LENGTH: 151
<212> TYPE: DNA
<213> ORGANISM: Artificial Sequence
<220> FEATURE:
<223> OTHER INFORMATION: dRNA/arRNA

<400> SEQUENCE: 157
gccaaacacc acatgcttgc catctagcca ggctgtcttg actgtcgtga tgaagaactg 60
ggagccgttg gtgtccttgc ctgcgttggc catgctcacc cagccaggcc cgtagtgctt 120
cagtttgaag ttctcatcgg ggaagcgctc a 151

<210> SEQ ID NO 158
<211> LENGTH: 151
<212> TYPE: DNA
<213> ORGANISM: Artificial Sequence
<220> FEATURE:
<223> OTHER INFORMATION: dRNA/arRNA

<400> SEQUENCE: 158
gggagtgggt ccgctccacc agatgccagc accggggcca gtgcagctca gagccctgtg 60
gcggactaca gggcccgcac agacggtcac tcaaagaaag atgtccctgt gccctactcc 120
ttggcgatgg caaagggctt ctccacctcg a 151

<210> SEQ ID NO 159
<211> LENGTH: 151
<212> TYPE: DNA
<213> ORGANISM: Artificial Sequence
<220> FEATURE:
<223> OTHER INFORMATION: dRNA/arRNA

<400> SEQUENCE: 159
tgcattttgt aaaatagata ctagcagatt gtcccaagat gtgtacagct cattctcaca 60
gcccagcgag ggcacctact ccacaaatgc gtggccacag gtcatcacct gtcctgtggc 120
cctggcgagc ctgatccctc acgccgggca c 151

<210> SEQ ID NO 160
<211> LENGTH: 151
<212> TYPE: DNA
<213> ORGANISM: Artificial Sequence
<220> FEATURE:
<223> OTHER INFORMATION: dRNA/arRNA

<400> SEQUENCE: 160
gctcattctc acagcccagc gagggcactt actccacaaa tgcgtggcca caggtcatca 60
cctgtcctgt ggccccggcg agcctgatcc ctcacgccgg gcacccacac ggcctgcgtg 120
ccttctagac ttgagttcgc agctctttaa g 151

<210> SEQ ID NO 161
<211> LENGTH: 151
<212> TYPE: DNA
<213> ORGANISM: Artificial Sequence
<220> FEATURE:

<223> OTHER INFORMATION: dRNA/arRNA

<400> SEQUENCE: 161

| tcggccgggc cctgggggcg gtgggcgctg gccaggacgc ccaccgtgtg gttgctgtcc | 60 |
| aggacggtcc cggcccgcga cacttcggcc cagagctgct cctcatccag cagcgccagc | 120 |
| agccccatgg ccgtgagcac cggcttgcgc a | 151 |

<210> SEQ ID NO 162
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 162

| ugaccagucu uaagaucuuu cuugaccugc accauaagaa cuucuccaaa gguaccaaaa | 60 |
| uacucuuuca gguccuguuc gguuguuuuc caugggagac ccaacacuau u | 111 |

<210> SEQ ID NO 163
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 163

| gaugggcacc accccgguga acagcuccuc gcccuugcuc acuggcagag cccucgagca | 60 |
| ucgcgagcag gcgcugccuc cuccgcccug cagcuuguac agcucgucca u | 111 |

<210> SEQ ID NO 164
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 164

| gaugggcacc accccgguga acagcuccuc gcccuugcuc acuggcagag cccuggagca | 60 |
| ucgcgagcag gcgcugccuc cuccgcccug cagcuuguac agcucgucca u | 111 |

<210> SEQ ID NO 165
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 165

| gaugggcacc accccgguga acagcuccuc gcccuugcuc acuggcagag cccuugagca | 60 |
| ucgcgagcag gcgcugccuc cuccgcccug cagcuuguac agcucgucca u | 111 |

<210> SEQ ID NO 166
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 166

| gaugggcacc accccgguga acagcuccuc gcccuugcuc acuggcagag cccuagagca | 60 |
| ucgcgagcag gcgcugccuc cuccgcccug cagcuuguac agcucgucca u | 111 |

<210> SEQ ID NO 167
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 167
gaugggcacc accccgguga acagcuccuc gcccuugcuc acuggcagag cccucgggca     60
ucgcgagcag gcgcugccuc cuccgcccug cagcuuguac agcucgucca u            111

<210> SEQ ID NO 168
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 168
gaugggcacc accccgguga acagcuccuc gcccuugcuc acuggcagag cccuggggca     60
ucgcgagcag gcgcugccuc cuccgcccug cagcuuguac agcucgucca u            111

<210> SEQ ID NO 169
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 169
gaugggcacc accccgguga acagcuccuc gcccuugcuc acuggcagag cccuugggca     60
ucgcgagcag gcgcugccuc cuccgcccug cagcuuguac agcucgucca u            111

<210> SEQ ID NO 170
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 170
gaugggcacc accccgguga acagcuccuc gcccuugcuc acuggcagag cccuagggca     60
ucgcgagcag gcgcugccuc cuccgcccug cagcuuguac agcucgucca u            111

<210> SEQ ID NO 171
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 171
gaugggcacc accccgguga acagcuccuc gcccuugcuc acuggcagag cccucgugca     60
ucgcgagcag gcgcugccuc cuccgcccug cagcuuguac agcucgucca u            111

<210> SEQ ID NO 172
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 172
gaugggcacc accccgguga acagcuccuc gcccuugcuc acuggcagag cccuggugca 60
ucgcgagcag gcgcugccuc cuccgcccug cagcuuguac agcucgucca u 111

<210> SEQ ID NO 173
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 173
gaugggcacc accccgguga acagcuccuc gcccuugcuc acuggcagag cccuagugca 60
ucgcgagcag gcgcugccuc cuccgcccug cagcuuguac agcucgucca u 111

<210> SEQ ID NO 174
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 174
gaugggcacc accccgguga acagcuccuc gcccuugcuc acuggcagag cccuugugca 60
ucgcgagcag gcgcugccuc cuccgcccug cagcuuguac agcucgucca u 111

<210> SEQ ID NO 175
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 175
gaugggcacc accccgguga acagcuccuc gcccuugcuc acuggcagag cccucgcgca 60
ucgcgagcag gcgcugccuc cuccgcccug cagcuuguac agcucgucca u 111

<210> SEQ ID NO 176
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 176
gaugggcacc accccgguga acagcuccuc gcccuugcuc acuggcagag cccuggcgca 60
ucgcgagcag gcgcugccuc cuccgcccug cagcuuguac agcucgucca u 111

<210> SEQ ID NO 177
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 177
gaugggcacc accccgguga acagcuccuc gcccuugcuc acuggcagag cccuugcgca 60
ucgcgagcag gcgcugccuc cuccgcccug cagcuuguac agcucgucca u 111

<210> SEQ ID NO 178
<211> LENGTH: 111

<212> TYPE: RNA
<213> ORGANISM: Artificial Sequence
<220> FEATURE:
<223> OTHER INFORMATION: dRNA/arRNA

<400> SEQUENCE: 178
gaugggcacc accccgguga acagcuccuc gcccuugcuc acuggcagag cccuagcgca 60
ucgcgagcag gcgcugccuc cuccgcccug cagcuuguac agcucgucca u 111

<210> SEQ ID NO 179
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 179
gaugggcacc accccgguga acagcuccuc gcccuugcuc acuggcagag cccucgagca 60
ucgcgagcag gcgcugccuc cuccgcccug cagcuuguac agcucgucca u 111

<210> SEQ ID NO 180
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 180
gaugggcacc accccgguga acagcuccuc gcccuugcuc acuggcagag cccuggagca 60
ucgcgagcag gcgcugccuc cuccgcccug cagcuuguac agcucgucca u 111

<210> SEQ ID NO 181
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 181
gaugggcacc accccgguga acagcuccuc gcccuugcuc acuggcagag cccuugagca 60
ucgcgagcag gcgcugccuc cuccgcccug cagcuuguac agcucgucca u 111

<210> SEQ ID NO 182
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 182
gaugggcacc accccgguga acagcuccuc gcccuugcuc acuggcagag cccuagagca 60
ucgcgagcag gcgcugccuc cuccgcccug cagcuuguac agcucgucca u 111

<210> SEQ ID NO 183
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 183
gaugggcacc accccgguga acagcuccuc gcccuugcuc acuggcagag cccucgugca 60
ucgcgagcag gcgcugccuc cuccgcccug cagcuuguac agcucgucca u 111

<210> SEQ ID NO 184
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 184
gaugggcacc accccgguga acagcuccuc gcccuugcuc acuggcagag cccucgggca 60
ucgcgagcag gcgcugccuc cuccgcccug cagcuuguac agcucgucca u 111

<210> SEQ ID NO 185
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 185
gaugggcacc accccgguga acagcuccuc gcccuugcuc acuggcagag cccucgcgca 60
ucgcgagcag gcgcugccuc cuccgcccug cagcuuguac agcucgucca u 111

<210> SEQ ID NO 186
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 186
gaugggcacc accccgguga acagcuccuc gcccuugcuc acuggcagag cccucgugca 60
ucgcgagcag gcgcugccuc cuccgcccug cagcuuguac agcucgucca u 111

<210> SEQ ID NO 187
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 187
gaugggcacc accccgguga acagcuccuc gcccuugcuc acuggcagag cccuggugca 60
ucgcgagcag gcgcugccuc cuccgcccug cagcuuguac agcucgucca u 111

<210> SEQ ID NO 188
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 188
gaugggcacc accccgguga acagcuccuc gcccuugcuc acuggcagag cccuugugca 60
ucgcgagcag gcgcugccuc cuccgcccug cagcuuguac agcucgucca u 111

<210> SEQ ID NO 189
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 189
gaugggcacc accccgguga acagcuccuc gcccuugcuc acuggcagag cccuagugca 60
ucgcgagcag gcgcugccuc cuccgcccug cagcuuguac agcucgucca u 111

<210> SEQ ID NO 190
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 190
gaugggcacc accccgguga acagcuccuc gcccuugcuc acuggcagag cccucgagca 60
ucgcgagcag gcgcugccuc cuccgcccug cagcuuguac agcucgucca u 111

<210> SEQ ID NO 191
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 191
gaugggcacc accccgguga acagcuccuc gcccuugcuc acuggcagag cccucgcgca 60
ucgcgagcag gcgcugccuc cuccgcccug cagcuuguac agcucgucca u 111

<210> SEQ ID NO 192
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 192
gaugggcacc accccgguga acagcuccuc gcccuugcuc acuggcagag cccucgggca 60
ucgcgagcag gcgcugccuc cuccgcccug cagcuuguac agcucgucca u 111

<210> SEQ ID NO 193
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 193
gauucugaau uagcuguauc gucaaggcac ucgugccgac gccaccagcu ccaaccacca 60
caaguggaga gucagucauu uucagcaggc cucucucccg caccugggag c 111

<210> SEQ ID NO 194
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 194
gauucugaau uagcuggauc gucaaggcac ucgggccgac gccaccagcu ccaaccacca 60
caaguggaga gucagucauu uucagcaggc cucucucccg caccggggag c 111

<210> SEQ ID NO 195

<211> LENGTH: 111
<212> TYPE: RNA
<213> ORGANISM: Artificial Sequence
<220> FEATURE:
<223> OTHER INFORMATION: dRNA/arRNA

<400> SEQUENCE: 195
gggagcagcc ucuggcauuc ugggagcuuc aucuggaccu gggucuucag ugaaccauug 60
uucaauaucg uccggggaca gcaucaaauc auccauugcu ugggacggca a 111

<210> SEQ ID NO 196
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 196
gggagcagcc ucuggcauuc ugggagcuuc aucuggaccu gggucuucag ugaaccauug 60
uucaagaucg uccggggaca gcaucaaauc auccauugcu ugggacggca a 111

<210> SEQ ID NO 197
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 197
gggagcagcc ucuggcaguc ggggagcuuc aucuggaccu gggucuucag ugaaccauug 60
uucaagaucg uccggggaca gcaucaaauc auccagugcu ugggacggca a 111

<210> SEQ ID NO 198
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 198
cauauuacag aauaccuuga uagcauccaa uuugcauccu ugguuagggu caacccagua 60
uucuccacuc uugaguucag gauggcagaa uuucaggucu cugcaguuuc u 111

<210> SEQ ID NO 199
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 199
gugaagauaa gccaguccuc uaguaacaga augagcaaga cggcaagagc uuacccaguc 60
acuugugugg agacuuaaau acuugcauaa agauccauug ggauaguacu c 111

<210> SEQ ID NO 200
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 200
gugaacguca aacugucgga ccaauauggc agaaucuucu cucaucucaa cuuuccauau 60
ccguaucaug gaaucauagc auccuguaac uacuagcucu cuuacagcug g 111

<210> SEQ ID NO 201
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 201
gccaaugauc ucgugaguua ucucagcagu gugagccauc agggugauga caucccaggc 60
gaucgugugg ccuccaggag cccagagcag gaaguugagg agaaggugcc u 111

<210> SEQ ID NO 202
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 202
caagacggug aaccacucca uggucuucuu gucggcuuuc ugcacugugu acccccagag 60
cuccguguug ccgacauccu gggguggcuu ccacuccaga gccacauuaa g 111

<210> SEQ ID NO 203
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 203
aggauucucu uuugaaguau ugcuccccca guggauuggg uggcuccauu cacuccaaug 60
cugagcacuu ccacagagug gguuaaagcg gcuccgaaca cgaaacgugu a 111

<210> SEQ ID NO 204
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 204
gacgcccacc gugugguugc uguccaggac ggucccggcc ugcgacacuu cggcccagag 60
cugcuccuca uccagcagcg ccagcagccc cauggccgug agcaccggcu u 111

<210> SEQ ID NO 205
<211> LENGTH: 111
<212> TYPE: RNA
<213> ORGANISM: Artificial Sequence
<220> FEATURE:
<223> OTHER INFORMATION: dRNA/arRNA

<400> SEQUENCE: 205
gacgcccacc gugugguugc uguccaggac ggucccggcc ugcgacacuu cggcccagag 60
cugcuccuca ucugcggggc gggggggggc cgucgccgcg uggggucguu g 111

<210> SEQ ID NO 206
<211> LENGTH: 31
<212> TYPE: DNA
<213> ORGANISM: Artificial Sequence
<220> FEATURE:

<223> OTHER INFORMATION: Primer

<400> SEQUENCE: 206
tataactagt atggtgagca agggcgagga g 31

<210> SEQ ID NO 207
<211> LENGTH: 41
<212> TYPE: DNA
<213> ORGANISM: Artificial Sequence
<220> FEATURE:
<223> OTHER INFORMATION: Primer

<400> SEQUENCE: 207
tatacgtctc atctacagat tcttccggcg tgtatacctt c 41

<210> SEQ ID NO 208
<211> LENGTH: 53
<212> TYPE: DNA
<213> ORGANISM: Artificial Sequence
<220> FEATURE:
<223> OTHER INFORMATION: Primer

<400> SEQUENCE: 208
tatacgtctc atagagatcc ccggtcgcca ccgtgagcaa gggcgaggag ctg 53

<210> SEQ ID NO 209
<211> LENGTH: 36
<212> TYPE: DNA
<213> ORGANISM: Artificial Sequence
<220> FEATURE:
<223> OTHER INFORMATION: Primer

<400> SEQUENCE: 209
tataggcgcg ccttacttgt acagctcgtc catgcc 36

<210> SEQ ID NO 210
<211> LENGTH: 94
<212> TYPE: DNA
<213> ORGANISM: Artificial Sequence
<220> FEATURE:
<223> OTHER INFORMATION: Primer

<400> SEQUENCE: 210
tatacgtctc aaggcgctgc ctcctccgcc gctgcctcct ccgccgctgc ctcctccgcc 60
ctgcagcttg tacagctcgt ccatgccgcc ggtg 94

<210> SEQ ID NO 211
<211> LENGTH: 62
<212> TYPE: DNA
<213> ORGANISM: Artificial Sequence
<220> FEATURE:
<223> OTHER INFORMATION: Primer

<400> SEQUENCE: 211
tatacgtctc agcctgctcg cgatgctaga gggctctgcc agtgagcaag ggcgaggagc 60
tg 62

<210> SEQ ID NO 212
<211> LENGTH: 70
<212> TYPE: DNA
<213> ORGANISM: Artificial Sequence
<220> FEATURE:
<223> OTHER INFORMATION: Primer

<400> SEQUENCE: 212
tataactagt atggtggatt acaaggatga cgacgataag atgaaagtga cgaaggtagg 60
aggcatttcg 70

<210> SEQ ID NO 213
<211> LENGTH: 60
<212> TYPE: DNA
<213> ORGANISM: Artificial Sequence
<220> FEATURE:
<223> OTHER INFORMATION: Primer

<400> SEQUENCE: 213
atatggcgcg ccgttttcag actttttctc ttccattttg tattcaaaca taatcttcac 60

<210> SEQ ID NO 214
<211> LENGTH: 69
<212> TYPE: DNA
<213> ORGANISM: Artificial Sequence
<220> FEATURE:
<223> OTHER INFORMATION: Primer

<400> SEQUENCE: 214
tataggcgcg ccaggcggag gaggcagcgg cggaggaggc agcctcctcc tctcaaggtc 60
cccagaagc 69

<210> SEQ ID NO 215
<211> LENGTH: 64
<212> TYPE: DNA
<213> ORGANISM: Artificial Sequence
<220> FEATURE:
<223> OTHER INFORMATION: Primer

<400> SEQUENCE: 215
tatacctgca ggctacacct tgcgtttttt cttgggtact gggcagagat aaaagttctt 60
ttcc 64

<210> SEQ ID NO 216
<211> LENGTH: 24
<212> TYPE: DNA
<213> ORGANISM: Artificial Sequence
<220> FEATURE:
<223> OTHER INFORMATION: Primer

<400> SEQUENCE: 216
cactccaccg gcggcatgga cgag 24

<210> SEQ ID NO 217
<211> LENGTH: 28
<212> TYPE: DNA
<213> ORGANISM: Artificial Sequence
<220> FEATURE:
<223> OTHER INFORMATION: Primer

<400> SEQUENCE: 217
cacgctgaac ttgtggccgt ttacgtcg 28

<210> SEQ ID NO 218
<211> LENGTH: 40
<212> TYPE: DNA
<213> ORGANISM: Artificial Sequence
<220> FEATURE:
<223> OTHER INFORMATION: Primer

<400> SEQUENCE: 218
tataactagt atgaatccgc ggcaggggta ttccctcagc 40

<210> SEQ ID NO 219
<211> LENGTH: 73
<212> TYPE: DNA
<213> ORGANISM: Artificial Sequence
<220> FEATURE:
<223> OTHER INFORMATION: Primer

<400> SEQUENCE: 219
tataggcgcg ccctacttat cgtcgtcatc cttgtaatct actgggcaga gataaaagtt 60
cttttcctcc tgg 73

<210> SEQ ID NO 220
<211> LENGTH: 42
<212> TYPE: DNA
<213> ORGANISM: Artificial Sequence
<220> FEATURE:
<223> OTHER INFORMATION: Primer

<400> SEQUENCE: 220
tataactagt atggatatag aagatgaaga aaacatgagt tc 42

<210> SEQ ID NO 221
<211> LENGTH: 67
<212> TYPE: DNA
<213> ORGANISM: Artificial Sequence
<220> FEATURE:
<223> OTHER INFORMATION: Primer

<400> SEQUENCE: 221
tataggcgcg ccctacttat cgtcgtcatc cttgtaatcg ggcgtgagtg agaactggtc 60
ctgctcg 67

<210> SEQ ID NO 222
<211> LENGTH: 37
<212> TYPE: DNA
<213> ORGANISM: Artificial Sequence
<220> FEATURE:
<223> OTHER INFORMATION: Primer

<400> SEQUENCE: 222
tataactagt atggccgaga tcaaggagaa aatctgc 37

<210> SEQ ID NO 223
<211> LENGTH: 73
<212> TYPE: DNA
<213> ORGANISM: Artificial Sequence
<220> FEATURE:
<223> OTHER INFORMATION: Primer

<400> SEQUENCE: 223
tataggcgcg ccctacttat cgtcgtcatc cttgtaatct actgggcaga gataaaagtt 60
cttttcctcc tgg 73

<210> SEQ ID NO 224
<211> LENGTH: 19
<212> TYPE: DNA
<213> ORGANISM: Artificial Sequence
<220> FEATURE:
<223> OTHER INFORMATION: Primer

<400> SEQUENCE: 224
cgccatttcg gactgggag 19

<210> SEQ ID NO 225
<211> LENGTH: 25
<212> TYPE: DNA
<213> ORGANISM: Artificial Sequence
<220> FEATURE:
<223> OTHER INFORMATION: Primer

<400> SEQUENCE: 225
agagacaggt ttctccatca attac 25

<210> SEQ ID NO 226
<211> LENGTH: 16
<212> TYPE: DNA
<213> ORGANISM: Artificial Sequence
<220> FEATURE:
<223> OTHER INFORMATION: Primer

<400> SEQUENCE: 226
gagcccgcga gcaacc 16

<210> SEQ ID NO 227
<211> LENGTH: 20
<212> TYPE: DNA
<213> ORGANISM: Artificial Sequence
<220> FEATURE:
<223> OTHER INFORMATION: Primer

<400> SEQUENCE: 227
gcagcaggaa gaagacggac 20

<210> SEQ ID NO 228
<211> LENGTH: 23
<212> TYPE: DNA
<213> ORGANISM: Artificial Sequence
<220> FEATURE:
<223> OTHER INFORMATION: Primer

<400> SEQUENCE: 228
agaagcagtt gaagaccaga ctc 23

<210> SEQ ID NO 229
<211> LENGTH: 20
<212> TYPE: DNA
<213> ORGANISM: Artificial Sequence
<220> FEATURE:
<223> OTHER INFORMATION: Primer

<400> SEQUENCE: 229
ggccttcacc tggaccatag 20

<210> SEQ ID NO 230
<211> LENGTH: 22
<212> TYPE: DNA
<213> ORGANISM: Artificial Sequence
<220> FEATURE:
<223> OTHER INFORMATION: Primer

<400> SEQUENCE: 230
agagaagcag ttgaagacca ga 22

<210> SEQ ID NO 231
<211> LENGTH: 20
<212> TYPE: DNA
<213> ORGANISM: Artificial Sequence
<220> FEATURE:

-continued

<223> OTHER INFORMATION: Primer

<400> SEQUENCE: 231
cggccttcac ctggaccata 20

<210> SEQ ID NO 232
<211> LENGTH: 23
<212> TYPE: DNA
<213> ORGANISM: Artificial Sequence
<220> FEATURE:
<223> OTHER INFORMATION: Primer

<400> SEQUENCE: 232
cagagaagca gttgaagacc aga 23

<210> SEQ ID NO 233
<211> LENGTH: 20
<212> TYPE: DNA
<213> ORGANISM: Artificial Sequence
<220> FEATURE:
<223> OTHER INFORMATION: Primer

<400> SEQUENCE: 233
cggccttcac ctggaccata 20

<210> SEQ ID NO 234
<211> LENGTH: 20
<212> TYPE: DNA
<213> ORGANISM: Artificial Sequence
<220> FEATURE:
<223> OTHER INFORMATION: Primer

<400> SEQUENCE: 234
tttgtgaaag gctggggacc 20

<210> SEQ ID NO 235
<211> LENGTH: 25
<212> TYPE: DNA
<213> ORGANISM: Artificial Sequence
<220> FEATURE:
<223> OTHER INFORMATION: Primer

<400> SEQUENCE: 235
acaggattgt attttgtagt ccacc 25

<210> SEQ ID NO 236
<211> LENGTH: 23
<212> TYPE: DNA
<213> ORGANISM: Artificial Sequence
<220> FEATURE:
<223> OTHER INFORMATION: Primer

<400> SEQUENCE: 236
aggatgagtt ttgtgaaagg ctg 23

<210> SEQ ID NO 237
<211> LENGTH: 24
<212> TYPE: DNA
<213> ORGANISM: Artificial Sequence
<220> FEATURE:
<223> OTHER INFORMATION: Primer

<400> SEQUENCE: 237
attttgtagt ccaccatcct gata 24

<210> SEQ ID NO 238
<211> LENGTH: 22
<212> TYPE: DNA
<213> ORGANISM: Artificial Sequence
<220> FEATURE:
<223> OTHER INFORMATION: Primer

<400> SEQUENCE: 238
gatgagtttt gtgaaaggct gg 22

<210> SEQ ID NO 239
<211> LENGTH: 25
<212> TYPE: DNA
<213> ORGANISM: Artificial Sequence
<220> FEATURE:
<223> OTHER INFORMATION: Primer

<400> SEQUENCE: 239
attttgtagt ccaccatcct gataa 25

<210> SEQ ID NO 240
<211> LENGTH: 20
<212> TYPE: DNA
<213> ORGANISM: Artificial Sequence
<220> FEATURE:
<223> OTHER INFORMATION: Primer

<400> SEQUENCE: 240
cgaagagaac gagaccgcat 20

<210> SEQ ID NO 241
<211> LENGTH: 19
<212> TYPE: DNA
<213> ORGANISM: Artificial Sequence
<220> FEATURE:
<223> OTHER INFORMATION: Primer

<400> SEQUENCE: 241
gaagatggtg cacaccggg 19

<210> SEQ ID NO 242
<211> LENGTH: 22
<212> TYPE: DNA
<213> ORGANISM: Artificial Sequence
<220> FEATURE:
<223> OTHER INFORMATION: Primer

<400> SEQUENCE: 242
gacagatgct tcatcagcag tg 22

<210> SEQ ID NO 243
<211> LENGTH: 21
<212> TYPE: DNA
<213> ORGANISM: Artificial Sequence
<220> FEATURE:
<223> OTHER INFORMATION: Primer

<400> SEQUENCE: 243
cgaacaaagc caaacccctt t 21

<210> SEQ ID NO 244
<211> LENGTH: 25
<212> TYPE: DNA
<213> ORGANISM: Artificial Sequence
<220> FEATURE:
<223> OTHER INFORMATION: Primer

<400> SEQUENCE: 244
tctgttaatg gacaaataga aagcc 25

<210> SEQ ID NO 245
<211> LENGTH: 23
<212> TYPE: DNA
<213> ORGANISM: Artificial Sequence
<220> FEATURE:
<223> OTHER INFORMATION: Primer

<400> SEQUENCE: 245
ggaacattca aaggattggc act 23

<210> SEQ ID NO 246
<211> LENGTH: 20
<212> TYPE: DNA
<213> ORGANISM: Artificial Sequence
<220> FEATURE:
<223> OTHER INFORMATION: Primer

<400> SEQUENCE: 246
agtcactgca gatggacgca 20

<210> SEQ ID NO 247
<211> LENGTH: 22
<212> TYPE: DNA
<213> ORGANISM: Artificial Sequence
<220> FEATURE:
<223> OTHER INFORMATION: Primer

<400> SEQUENCE: 247
atctcgatgg gaaattgcag gt 22

<210> SEQ ID NO 248
<211> LENGTH: 25
<212> TYPE: DNA
<213> ORGANISM: Artificial Sequence
<220> FEATURE:
<223> OTHER INFORMATION: Primer

<400> SEQUENCE: 248
tcagagtttt acctcatcct tcttt 25

<210> SEQ ID NO 249
<211> LENGTH: 25
<212> TYPE: DNA
<213> ORGANISM: Artificial Sequence
<220> FEATURE:
<223> OTHER INFORMATION: Primer

<400> SEQUENCE: 249
cctgaataca tatgatgacc ttcag 25

<210> SEQ ID NO 250
<211> LENGTH: 20
<212> TYPE: DNA
<213> ORGANISM: Artificial Sequence
<220> FEATURE:
<223> OTHER INFORMATION: Primer

<400> SEQUENCE: 250
agggcacaga cacagacctc 20

<210> SEQ ID NO 251
<211> LENGTH: 21

<212> TYPE: DNA
<213> ORGANISM: Artificial Sequence
<220> FEATURE:
<223> OTHER INFORMATION: Primer

<400> SEQUENCE: 251
agggctttca atgccaagac g 21

<210> SEQ ID NO 252
<211> LENGTH: 19
<212> TYPE: DNA
<213> ORGANISM: Artificial Sequence
<220> FEATURE:
<223> OTHER INFORMATION: Primer

<400> SEQUENCE: 252
tgacaagcca agtcctccc 19

<210> SEQ ID NO 253
<211> LENGTH: 21
<212> TYPE: DNA
<213> ORGANISM: Artificial Sequence
<220> FEATURE:
<223> OTHER INFORMATION: Primer

<400> SEQUENCE: 253
attgccaatg atgagctctg g 21

<210> SEQ ID NO 254
<211> LENGTH: 25
<212> TYPE: DNA
<213> ORGANISM: Artificial Sequence
<220> FEATURE:
<223> OTHER INFORMATION: Primer

<400> SEQUENCE: 254
ttatagacat aagttctcct tgcct 25

<210> SEQ ID NO 255
<211> LENGTH: 20
<212> TYPE: DNA
<213> ORGANISM: Artificial Sequence
<220> FEATURE:
<223> OTHER INFORMATION: Primer

<400> SEQUENCE: 255
tcaatcccat ggagccaaca 20

<210> SEQ ID NO 256
<211> LENGTH: 50
<212> TYPE: DNA
<213> ORGANISM: Artificial Sequence
<220> FEATURE:
<223> OTHER INFORMATION: Primer

<400> SEQUENCE: 256
tacacgacgc tcttccgatc ttaagtagag gccgccactc caccggcggc 50

<210> SEQ ID NO 257
<211> LENGTH: 51
<212> TYPE: DNA
<213> ORGANISM: Artificial Sequence
<220> FEATURE:
<223> OTHER INFORMATION: Primer

<400> SEQUENCE: 257
tacacgacgc tcttccgatc tatcatgctt agccgccact ccaccggcgg c 51

<210> SEQ ID NO 258
<211> LENGTH: 52
<212> TYPE: DNA
<213> ORGANISM: Artificial Sequence
<220> FEATURE:
<223> OTHER INFORMATION: dRNA/arRNA

<400> SEQUENCE: 258
tacacgacgc tcttccgatc tgatgcacat ctgccgccac tccaccggcg gc 52

<210> SEQ ID NO 259
<211> LENGTH: 53
<212> TYPE: DNA
<213> ORGANISM: Artificial Sequence
<220> FEATURE:
<223> OTHER INFORMATION: Primer

<400> SEQUENCE: 259
tacacgacgc tcttccgatc tcgattgctc gacgccgcca ctccaccggc ggc 53

<210> SEQ ID NO 260
<211> LENGTH: 54
<212> TYPE: DNA
<213> ORGANISM: Artificial Sequence
<220> FEATURE:
<223> OTHER INFORMATION: Primer

<400> SEQUENCE: 260
tacacgacgc tcttccgatc ttcgatagca attcgccgcc actccaccgg cggc 54

<210> SEQ ID NO 261
<211> LENGTH: 55
<212> TYPE: DNA
<213> ORGANISM: Artificial Sequence
<220> FEATURE:
<223> OTHER INFORMATION: Primer

<400> SEQUENCE: 261
tacacgacgc tcttccgatc tatcgatagt tgcttgccgc cactccaccg gcggc 55

<210> SEQ ID NO 262
<211> LENGTH: 56
<212> TYPE: DNA
<213> ORGANISM: Artificial Sequence
<220> FEATURE:
<223> OTHER INFORMATION: Primer

<400> SEQUENCE: 262
tacacgacgc tcttccgatc tgatcgatcc agttaggccg ccactccacc ggcggc 56

<210> SEQ ID NO 263
<211> LENGTH: 57
<212> TYPE: DNA
<213> ORGANISM: Artificial Sequence
<220> FEATURE:
<223> OTHER INFORMATION: Primer

<400> SEQUENCE: 263
tacacgacgc tcttccgatc tcgatcgatt tgagcctgcc gccactccac cggcggc 57

<210> SEQ ID NO 264
<211> LENGTH: 58
<212> TYPE: DNA
<213> ORGANISM: Artificial Sequence
<220> FEATURE:
<223> OTHER INFORMATION: Primer

<400> SEQUENCE: 264
tacacgacgc tcttccgatc tacgatcgat acacgatcgc cgccactcca ccggcggc 58

<210> SEQ ID NO 265
<211> LENGTH: 59
<212> TYPE: DNA
<213> ORGANISM: Artificial Sequence
<220> FEATURE:
<223> OTHER INFORMATION: Primer

<400> SEQUENCE: 265
tacacgacgc tcttccgatc ttacgatcga tggtccagag ccgccactcc accggcggc 59

<210> SEQ ID NO 266
<211> LENGTH: 50
<212> TYPE: DNA
<213> ORGANISM: Artificial Sequence
<220> FEATURE:
<223> OTHER INFORMATION: Primer

<400> SEQUENCE: 266
agacgtgtgc tcttccgatc ttaagtagag tcgccgtcca gctcgaccag 50

<210> SEQ ID NO 267
<211> LENGTH: 51
<212> TYPE: DNA
<213> ORGANISM: Artificial Sequence
<220> FEATURE:
<223> OTHER INFORMATION: Primer

<400> SEQUENCE: 267
agacgtgtgc tcttccgatc tatcatgctt atcgccgtcc agctcgacca g 51

<210> SEQ ID NO 268
<211> LENGTH: 52
<212> TYPE: DNA
<213> ORGANISM: Artificial Sequence
<220> FEATURE:
<223> OTHER INFORMATION: Primer

<400> SEQUENCE: 268
agacgtgtgc tcttccgatc tgatgcacat cttcgccgtc cagctcgacc ag 52

<210> SEQ ID NO 269
<211> LENGTH: 53
<212> TYPE: DNA
<213> ORGANISM: Artificial Sequence
<220> FEATURE:
<223> OTHER INFORMATION: Primer

<400> SEQUENCE: 269
agacgtgtgc tcttccgatc tcgattgctc gactcgccgt ccagctcgac cag 53

<210> SEQ ID NO 270
<211> LENGTH: 54
<212> TYPE: DNA
<213> ORGANISM: Artificial Sequence
<220> FEATURE:
<223> OTHER INFORMATION: Primer

<400> SEQUENCE: 270
agacgtgtgc tcttccgatc ttcgatagca attctcgccg tccagctcga ccag 54

<210> SEQ ID NO 271
<211> LENGTH: 55
<212> TYPE: DNA
<213> ORGANISM: Artificial Sequence
<220> FEATURE:
<223> OTHER INFORMATION: Primer

<400> SEQUENCE: 271
agacgtgtgc tcttccgatc tatcgatagt tgctttcgcc gtccagctcg accag 55

<210> SEQ ID NO 272
<211> LENGTH: 56
<212> TYPE: DNA
<213> ORGANISM: Artificial Sequence
<220> FEATURE:
<223> OTHER INFORMATION: Primer

<400> SEQUENCE: 272
agacgtgtgc tcttccgatc tgatcgatcc agttagtcgc cgtccagctc gaccag 56

<210> SEQ ID NO 273
<211> LENGTH: 57
<212> TYPE: DNA
<213> ORGANISM: Artificial Sequence
<220> FEATURE:
<223> OTHER INFORMATION: Primer

<400> SEQUENCE: 273
agacgtgtgc tcttccgatc tcgatcgatt tgagccttcg ccgtccagct cgaccag 57

<210> SEQ ID NO 274
<211> LENGTH: 58
<212> TYPE: DNA
<213> ORGANISM: Artificial Sequence
<220> FEATURE:
<223> OTHER INFORMATION: Primer

<400> SEQUENCE: 274
agacgtgtgc tcttccgatc tacgatcgat acacgatctc gccgtccagc tcgaccag 58

<210> SEQ ID NO 275
<211> LENGTH: 59
<212> TYPE: DNA
<213> ORGANISM: Artificial Sequence
<220> FEATURE:
<223> OTHER INFORMATION: Primer

<400> SEQUENCE: 275
agacgtgtgc tcttccgatc ttacgatcga tggtccagat cgccgtccag ctcgaccag 59

<210> SEQ ID NO 276
<211> LENGTH: 18
<212> TYPE: DNA
<213> ORGANISM: Artificial Sequence
<220> FEATURE:
<223> OTHER INFORMATION: Primer

<400> SEQUENCE: 276
ggggaactcg ggcaacct 18

<210> SEQ ID NO 277
<211> LENGTH: 19
<212> TYPE: DNA
<213> ORGANISM: Artificial Sequence
<220> FEATURE:
<223> OTHER INFORMATION: Primer

<400> SEQUENCE: 277
gaatcggatc tgccccgtg 19

<210> SEQ ID NO 278
<211> LENGTH: 19
<212> TYPE: DNA
<213> ORGANISM: Artificial Sequence
<220> FEATURE:
<223> OTHER INFORMATION: Primer

<400> SEQUENCE: 278
catcgaggcc aagctggaa 19

<210> SEQ ID NO 279
<211> LENGTH: 20
<212> TYPE: DNA
<213> ORGANISM: Artificial Sequence
<220> FEATURE:
<223> OTHER INFORMATION: Primer

<400> SEQUENCE: 279
gtagtgagga gggagacccc 20

<210> SEQ ID NO 280
<211> LENGTH: 20
<212> TYPE: DNA
<213> ORGANISM: Artificial Sequence
<220> FEATURE:
<223> OTHER INFORMATION: Primer

<400> SEQUENCE: 280
aagcctcctt ccttccccaa 20

<210> SEQ ID NO 281
<211> LENGTH: 21
<212> TYPE: DNA
<213> ORGANISM: Artificial Sequence
<220> FEATURE:
<223> OTHER INFORMATION: Primer

<400> SEQUENCE: 281
atcgatacac tccctagccc a 21

<210> SEQ ID NO 282
<211> LENGTH: 22
<212> TYPE: DNA
<213> ORGANISM: Artificial Sequence
<220> FEATURE:
<223> OTHER INFORMATION: Primer

<400> SEQUENCE: 282
acaaattcgg tacatcctcg ac 22

<210> SEQ ID NO 283
<211> LENGTH: 21
<212> TYPE: DNA
<213> ORGANISM: Artificial Sequence
<220> FEATURE:
<223> OTHER INFORMATION: Primer

<400> SEQUENCE: 283
ttcagccatc tttggaaggt t 21

<210> SEQ ID NO 284

<211> LENGTH: 20
<212> TYPE: DNA
<213> ORGANISM: Artificial Sequence
<220> FEATURE:
<223> OTHER INFORMATION: Primer

<400> SEQUENCE: 284
acgccgcatt gaccatctat 20

<210> SEQ ID NO 285
<211> LENGTH: 20
<212> TYPE: DNA
<213> ORGANISM: Artificial Sequence
<220> FEATURE:
<223> OTHER INFORMATION: Primer

<400> SEQUENCE: 285
tagccaggag gttctcaaca 20

<210> SEQ ID NO 286
<211> LENGTH: 21
<212> TYPE: DNA
<213> ORGANISM: Artificial Sequence
<220> FEATURE:
<223> OTHER INFORMATION: Primer

<400> SEQUENCE: 286
ggcatggact gtggtcatga g 21

<210> SEQ ID NO 287
<211> LENGTH: 20
<212> TYPE: DNA
<213> ORGANISM: Artificial Sequence
<220> FEATURE:
<223> OTHER INFORMATION: Primer

<400> SEQUENCE: 287
tgcaccacca actgcttagc 20

<210> SEQ ID NO 288
<211> LENGTH: 22
<212> TYPE: DNA
<213> ORGANISM: Artificial Sequence
<220> FEATURE:
<223> OTHER INFORMATION: Primer

<400> SEQUENCE: 288
ccccgtaatg cagaagaaga cc 22

<210> SEQ ID NO 289
<211> LENGTH: 21
<212> TYPE: DNA
<213> ORGANISM: Artificial Sequence
<220> FEATURE:
<223> OTHER INFORMATION: Primer

<400> SEQUENCE: 289
gtccttcagc ttcagcctct g 21

<210> SEQ ID NO 290
<211> LENGTH: 20
<212> TYPE: DNA
<213> ORGANISM: Artificial Sequence
<220> FEATURE:
<223> OTHER INFORMATION: Primer

<400> SEQUENCE: 290
aacgcaacat gaaggtgctc 20

<210> SEQ ID NO 291
<211> LENGTH: 20
<212> TYPE: DNA
<213> ORGANISM: Artificial Sequence
<220> FEATURE:
<223> OTHER INFORMATION: Primer

<400> SEQUENCE: 291
accttgacgg tgactttggg 20

<210> SEQ ID NO 292
<211> LENGTH: 20
<212> TYPE: DNA
<213> ORGANISM: Artificial Sequence
<220> FEATURE:
<223> OTHER INFORMATION: Primer

<400> SEQUENCE: 292
cagtgcaatg agggaccagt 20

<210> SEQ ID NO 293
<211> LENGTH: 24
<212> TYPE: DNA
<213> ORGANISM: Artificial Sequence
<220> FEATURE:
<223> OTHER INFORMATION: Primer

<400> SEQUENCE: 293
aggaccatag gtacatcttc agag 24

<210> SEQ ID NO 294
<211> LENGTH: 22
<212> TYPE: DNA
<213> ORGANISM: Artificial Sequence
<220> FEATURE:
<223> OTHER INFORMATION: Primer

<400> SEQUENCE: 294
cgaacgagtt gtatcacctg ga 22

<210> SEQ ID NO 295
<211> LENGTH: 20
<212> TYPE: DNA
<213> ORGANISM: Artificial Sequence
<220> FEATURE:
<223> OTHER INFORMATION: Primer

<400> SEQUENCE: 295
cgatggctgt ccctcaaagt 20

<210> SEQ ID NO 296
<211> LENGTH: 23
<212> TYPE: DNA
<213> ORGANISM: Artificial Sequence
<220> FEATURE:
<223> OTHER INFORMATION: Primer

<400> SEQUENCE: 296
agttgctctt ttcactcaag gtc 23

<210> SEQ ID NO 297
<211> LENGTH: 21
<212> TYPE: DNA

<213> ORGANISM: Artificial Sequence
<220> FEATURE:
<223> OTHER INFORMATION: Primer

<400> SEQUENCE: 297
ttctctctga gttcagacgc t 21

<210> SEQ ID NO 298
<211> LENGTH: 52
<212> TYPE: DNA
<213> ORGANISM: Artificial Sequence
<220> FEATURE:
<223> OTHER INFORMATION: Primer

<400> SEQUENCE: 298
tacacgacgc tcttccgatc ttaagtagag tggcacagga ggaaagagca tc 52

<210> SEQ ID NO 299
<211> LENGTH: 49
<212> TYPE: DNA
<213> ORGANISM: Artificial Sequence
<220> FEATURE:
<223> OTHER INFORMATION: Primer

<400> SEQUENCE: 299
agacgtgtgc tcttccgatc ttaagtagag gcaccacctc catgccctc 49

<210> SEQ ID NO 300
<211> LENGTH: 49
<212> TYPE: DNA
<213> ORGANISM: Artificial Sequence
<220> FEATURE:
<223> OTHER INFORMATION: Primer

<400> SEQUENCE: 300
tacacgacgc tcttccgatc ttaagtagag catcgcagac tgcggcaag 49

<210> SEQ ID NO 301
<211> LENGTH: 52
<212> TYPE: DNA
<213> ORGANISM: Artificial Sequence
<220> FEATURE:
<223> OTHER INFORMATION: Primer

<400> SEQUENCE: 301
agacgtgtgc tcttccgatc ttaagtagag agtccatggg cctgtggaat gt 52

<210> SEQ ID NO 302
<211> LENGTH: 19
<212> TYPE: DNA
<213> ORGANISM: Artificial Sequence
<220> FEATURE:
<223> OTHER INFORMATION: Primer

<400> SEQUENCE: 302
gaaaaactgg cccgagagc 19

<210> SEQ ID NO 303
<211> LENGTH: 20
<212> TYPE: DNA
<213> ORGANISM: Artificial Sequence
<220> FEATURE:
<223> OTHER INFORMATION: Primer

<400> SEQUENCE: 303
ctgagtctgg gctgagggac 20

<210> SEQ ID NO 304
<211> LENGTH: 20
<212> TYPE: DNA
<213> ORGANISM: Artificial Sequence
<220> FEATURE:
<223> OTHER INFORMATION: Primer

<400> SEQUENCE: 304
cgcttccagg tcaacaacac 20

<210> SEQ ID NO 305
<211> LENGTH: 19
<212> TYPE: DNA
<213> ORGANISM: Artificial Sequence
<220> FEATURE:
<223> OTHER INFORMATION: Primer

<400> SEQUENCE: 305
ctcgcgtaga tcagcaccg 19

<210> SEQ ID NO 306
<211> LENGTH: 21
<212> TYPE: DNA
<213> ORGANISM: Artificial Sequence
<220> FEATURE:
<223> OTHER INFORMATION: Primer

<400> SEQUENCE: 306
cccctctgag tcaggaaaca t 21

<210> SEQ ID NO 307
<211> LENGTH: 19
<212> TYPE: DNA
<213> ORGANISM: Artificial Sequence
<220> FEATURE:
<223> OTHER INFORMATION: Primer

<400> SEQUENCE: 307
gaagatgaca ggggccagg 19

<210> SEQ ID NO 308
<211> LENGTH: 19
<212> TYPE: DNA
<213> ORGANISM: Artificial Sequence
<220> FEATURE:
<223> OTHER INFORMATION: Primer

<400> SEQUENCE: 308
tagcactggc tggaatgag 19

<210> SEQ ID NO 309
<211> LENGTH: 21
<212> TYPE: DNA
<213> ORGANISM: Artificial Sequence
<220> FEATURE:
<223> OTHER INFORMATION: Primer

<400> SEQUENCE: 309
gtttcggagg taacctgtaa g 21

<210> SEQ ID NO 310
<211> LENGTH: 20
<212> TYPE: DNA
<213> ORGANISM: Artificial Sequence
<220> FEATURE:

-continued

<223> OTHER INFORMATION: Primer

<400> SEQUENCE: 310
tacagcaacc atgagtacaa 20

<210> SEQ ID NO 311
<211> LENGTH: 19
<212> TYPE: DNA
<213> ORGANISM: Artificial Sequence
<220> FEATURE:
<223> OTHER INFORMATION: Primer

<400> SEQUENCE: 311
tcaggtgttt cacataggc 19

<210> SEQ ID NO 312
<211> LENGTH: 19
<212> TYPE: DNA
<213> ORGANISM: Artificial Sequence
<220> FEATURE:
<223> OTHER INFORMATION: Primer

<400> SEQUENCE: 312
ctgcaaccat gagtgagaa 19

<210> SEQ ID NO 313
<211> LENGTH: 21
<212> TYPE: DNA
<213> ORGANISM: Artificial Sequence
<220> FEATURE:
<223> OTHER INFORMATION: Primer

<400> SEQUENCE: 313
cctttgaggt gctttagata g 21

<210> SEQ ID NO 314
<211> LENGTH: 19
<212> TYPE: DNA
<213> ORGANISM: Artificial Sequence
<220> FEATURE:
<223> OTHER INFORMATION: Primer

<400> SEQUENCE: 314
gccctgagaa aggagacat 19

<210> SEQ ID NO 315
<211> LENGTH: 24
<212> TYPE: DNA
<213> ORGANISM: Artificial Sequence
<220> FEATURE:
<223> OTHER INFORMATION: Primer

<400> SEQUENCE: 315
ctgttctgga ggtactctag gtat 24

<210> SEQ ID NO 316
<211> LENGTH: 18
<212> TYPE: DNA
<213> ORGANISM: Artificial Sequence
<220> FEATURE:
<223> OTHER INFORMATION: Primer

<400> SEQUENCE: 316
tttgaagagg gctgagaa 18

<210> SEQ ID NO 317
<211> LENGTH: 19
<212> TYPE: DNA
<213> ORGANISM: Artificial Sequence
<220> FEATURE:
<223> OTHER INFORMATION: Primer

<400> SEQUENCE: 317
tgttctggat atttcatgg 19

<210> SEQ ID NO 318
<211> LENGTH: 20
<212> TYPE: DNA
<213> ORGANISM: Artificial Sequence
<220> FEATURE:
<223> OTHER INFORMATION: Primer

<400> SEQUENCE: 318
catctgcctc cccatattcc 20

<210> SEQ ID NO 319
<211> LENGTH: 22
<212> TYPE: DNA
<213> ORGANISM: Artificial Sequence
<220> FEATURE:
<223> OTHER INFORMATION: Primer

<400> SEQUENCE: 319
tccatcctag ctcatctcca aa 22

<210> SEQ ID NO 320
<211> LENGTH: 18
<212> TYPE: DNA
<213> ORGANISM: Artificial Sequence
<220> FEATURE:
<223> OTHER INFORMATION: Primer

<400> SEQUENCE: 320
tgctccagaa ggccagac 18

<210> SEQ ID NO 321
<211> LENGTH: 25
<212> TYPE: DNA
<213> ORGANISM: Artificial Sequence
<220> FEATURE:
<223> OTHER INFORMATION: Primer

<400> SEQUENCE: 321
ttcataaata ctactaaggc acagg 25

<210> SEQ ID NO 322
<211> LENGTH: 21
<212> TYPE: DNA
<213> ORGANISM: Artificial Sequence
<220> FEATURE:
<223> OTHER INFORMATION: Primer

<400> SEQUENCE: 322
acagatgaag tgctccttcc a 21

<210> SEQ ID NO 323
<211> LENGTH: 21
<212> TYPE: DNA
<213> ORGANISM: Artificial Sequence
<220> FEATURE:
<223> OTHER INFORMATION: Primer

<400> SEQUENCE: 323
gtcggagatt cgtagctgga t 21

<210> SEQ ID NO 324
<211> LENGTH: 21
<212> TYPE: DNA
<213> ORGANISM: Artificial Sequence
<220> FEATURE:
<223> OTHER INFORMATION: Primer

<400> SEQUENCE: 324
cattgtggcc aaggagatct g 21

<210> SEQ ID NO 325
<211> LENGTH: 21
<212> TYPE: DNA
<213> ORGANISM: Artificial Sequence
<220> FEATURE:
<223> OTHER INFORMATION: Primer

<400> SEQUENCE: 325
cttcggagtt tgggtttgct t 21

<210> SEQ ID NO 326
<211> LENGTH: 20
<212> TYPE: DNA
<213> ORGANISM: Artificial Sequence
<220> FEATURE:
<223> OTHER INFORMATION: Primer

<400> SEQUENCE: 326
catcacttgc tgctgacacg 20

<210> SEQ ID NO 327
<211> LENGTH: 18
<212> TYPE: DNA
<213> ORGANISM: Artificial Sequence
<220> FEATURE:
<223> OTHER INFORMATION: dRNA/arRNA

<400> SEQUENCE: 327
tgtggaatct gccgggag 18

<210> SEQ ID NO 328
<211> LENGTH: 18
<212> TYPE: DNA
<213> ORGANISM: Artificial Sequence
<220> FEATURE:
<223> OTHER INFORMATION: Primer

<400> SEQUENCE: 328
ctgactctaa gtggcatt 18

<210> SEQ ID NO 329
<211> LENGTH: 18
<212> TYPE: DNA
<213> ORGANISM: Artificial Sequence
<220> FEATURE:
<223> OTHER INFORMATION: dRNA/arRNA

<400> SEQUENCE: 329
tgatggcctt cgattctg 18

<210> SEQ ID NO 330
<211> LENGTH: 23

<212> TYPE: DNA
<213> ORGANISM: Artificial Sequence
<220> FEATURE:
<223> OTHER INFORMATION: dRNA/arRNA

<400> SEQUENCE: 330
cggagtcaac ggatttggtc gta 23

<210> SEQ ID NO 331
<211> LENGTH: 24
<212> TYPE: DNA
<213> ORGANISM: Artificial Sequence
<220> FEATURE:
<223> OTHER INFORMATION: Primer

<400> SEQUENCE: 331
agccttctcc atggtggtga agac 24

<210> SEQ ID NO 332
<211> LENGTH: 2820
<212> TYPE: DNA
<213> ORGANISM: Artificial Sequence
<220> FEATURE:
<223> OTHER INFORMATION: dRNA/arRNA

<400> SEQUENCE: 332
atggccgaga tcaaggagaa aatctgcgac tatctcttca atgtgtctga ctcctctgcc 60
ctgaatttgg ctaaaaatat tggccttacc aaggcccgag atataaatgc tgtgctaatt 120
gacatggaaa ggcaggggga tgtctataga caagggacaa cccctcccat atggcatttg 180
acagacaaga agcgagagag gatgcaaatc aagagaaata cgaacagtgt tcctgaaacc 240
gctccagctg caatccctga gaccaaaaga aacgcagagt tcctcacctg taatataccc 300
acatcaaatg cctcaaataa catggtaacc acagaaaaag tggagaatgg gcaggaacct 360
gtcataaagt tagaaaacag gcaagaggcc agaccagaac cagcaagact gaaaccacct 420
gttcattaca atggcccctc aaaagcaggg tatgttgact ttgaaaatgg ccagtgggcc 480
acagatgaca tcccagatga cttgaatagt atccgcgcag caccaggtga gtttcgagcc 540
atcatggaga tgccctcctt ctacagtcat ggcttgccac ggtgttcacc ctacaagaaa 600
ctgacagagt gccagctgaa gaaccccatc agcgggctgt tagaatatgc ccagttcgct 660
agtcaaacct gtgagttcaa catgatagag cagagtggac caccccatga acctcgattt 720
aaattccagg ttgtcatcaa tggccgagag tttcccccag ctgaagctgg aagcaagaaa 780
gtggccaagc aggatgcagc tatgaaagcc atgacaattc tgctagagga agccaaagcc 840
aaggacagtg gaaaatcaga agaatcatcc cactattcca cagagaaaga atcagagaag 900
actgcagagt cccagacccc caccccttca gccacatcct tcttttctgg gaagagcccc 960
gtcaccacac tgcttgagtg tatgcacaaa ttggggaact cctgcgaatt ccgtctcctg 1020
tccaaagaag gccctgccca tgaacccaag ttccaatact gtgttgcagt gggagcccaa 1080
actttcccca gtgtgagtgc tcccagcaag aaagtggcaa agcagatggc cgcagaggaa 1140
gccatgaagg ccctgcatgg ggaggcgacc aactccatgg cttctgataa ccagcctgaa 1200
ggtatgatct cagagtcact tgataacttg gaatccatga tgcccaacaa ggtcaggaag 1260
attggcgagc tcgtgagata cctgaacacc aaccctgtgg gtggcctttt ggagtacgcc 1320
cgctcccatg gctttgctgc tgaattcaag ttggtcgacc agtccggacc tcctcacgag 1380
cccaagttcg tttaccaagc aaaagttggg ggtcgctggt tcccagccgt ctgcgcacac 1440

```
agcaagaagc aaggcaagca ggaagcagca gatgcggctc tccgtgtctt gattggggag   1500

aacgagaagg cagaacgcat gggtttcaca gaggtaaccc cagtgacagg ggccagtctc   1560

agaagaacta tgctcctcct ctcaaggtcc ccagaagcac agccaaagac actccctctc   1620

actggcagca ccttccatga ccagatagcc atgctgagcc accggtgctt caacactctg   1680

actaacagct tccagccctc cttgctcggc cgcaagattc tggccgccat cattatgaaa   1740

aaagactctg aggacatggg tgtcgtcgtc agcttgggaa cagggaatcg ctgtgtaaaa   1800

ggagattctc tcagcctaaa aggagaaact gtcaatgact gccatgcaga aataatctcc   1860

cggagaggct tcatcaggtt tctctacagt gagttaatga aatacaactc ccagactgcg   1920

aaggatagta tatttgaacc tgctaaggga ggagaaaagc tccaaataaa aaagactgtg   1980

tcattccatc tgtatatcag cactgctccg tgtggagatg gcgccctctt tgacaagtcc   2040

tgcagcgacc gtgctatgga aagcacagaa tcccgccact accctgtctt cgagaatccc   2100

aaacaaggaa agctccgcac caaggtggag aacggagaag gcacaatccc tgtggaatcc   2160

agtgacattg tgcctacgtg ggatggcatt cggctcgggg agagactccg taccatgtcc   2220

tgtagtgaca aaatcctacg ctggaacgtg ctgggcctgc aaggggcact gttgacccac   2280

ttcctgcagc ccatttatct caaatctgtc acattgggtt acctttttcag ccaagggcat   2340

ctgacccgtg ctatttgctg tcgtgtgaca agagatggga gtgcatttga ggatggacta   2400

cgacatccct ttattgtcaa ccaccccaag gttggcagag tcagcatata tgattccaaa   2460

aggcaatccg ggaagactaa ggagacaagc gtcaactggt gtctggctga tggctatgac   2520

ctggagatcc tggacggtac cagaggcact gtggatgggc cacggaatga attgtcccgg   2580

gtctccaaaa agaacatttt tcttctattt aagaagctct gctccttccg ttaccgcagg   2640

gatctactga gactctccta tggtgaggcc aagaaagctg cccgtgacta cgagacggcc   2700

aagaactact tcaaaaaagg cctgaaggat atgggctatg ggaactggat tagcaaaccc   2760

caggaggaaa agaactttta tctctgccca gtagattaca aggatgacga cgataagtag   2820
```

<210> SEQ ID NO 333
<211> LENGTH: 3705
<212> TYPE: DNA
<213> ORGANISM: Artificial Sequence
<220> FEATURE:
<223> OTHER INFORMATION: dRNA/arRNA

<400> SEQUENCE: 333

```
atgaatccgc ggcaggggta ttccctcagc ggatactaca cccatccatt tcaaggctat     60

gagcacagac agctcagata ccagcagcct gggccaggat cttcccccag tagtttcctg    120

cttaagcaaa tagaatttct caaggggcag ctcccagaag caccggtgat tggaaagcag    180

acaccgtcac tgccaccttc cctcccagga ctccggccaa ggtttccagt actacttgcc    240

tccagtacca gaggcaggca agtggacatc aggggtgtcc ccaggggcgt gcatctcgga    300

agtcaggggc tccagagagg gttccagcat ccttcaccac gtggcaggag tctgccacag    360

agaggtgttg attgcctttc ctcacatttc caggaactga gtatctacca agatcaggaa    420

caaaggatct taaagttcct ggaagagctt ggggaaggga aggccaccac agcacatgat    480

ctgtctggga aacttgggac tccgaagaaa gaaatcaatc gagttttata ctccctggca    540

aagaagggca agctacagaa agaggcagga acacccccctt tgtggaaaat cgcggtctcc    600

actcaggctt ggaaccagca cagcggagtg gtaagaccag acggtcatag ccaaggagcc    660

ccaaactcag acccgagttt ggaaccggaa gacagaaact ccacatctgt ctcagaagat    720
```

-continued cttcttgagc cttttattgc agtctcagct caggcttgga accagcacag cggagtggta 780
agaccagaca gtcatagcca aggatcccca aactcagacc caggtttgga acctgaagac 840
agcaactcca catctgcctt ggaagatcct cttgagtttt tagacatggc cgagatcaag 900
gagaaaatct gcgactatct cttcaatgtg tctgactcct ctgccctgaa tttggctaaa 960
aatattggcc ttaccaaggc ccgagatata aatgctgtgc taattgacat ggaaaggcag 1020
ggggatgtct atagacaagg gacaacccct cccatatggc atttgacaga caagaagcga 1080
gagaggatgc aaatcaagag aaatacgaac agtgttcctg aaaccgctcc agctgcaatc 1140
cctgagacca aaagaaacgc agagttcctc acctgtaata tacccacatc aaatgcctca 1200
aataacatgg taaccacaga aaaagtggag aatgggcagg aacctgtcat aaagttagaa 1260
aacaggcaag aggccagacc agaaccagca agactgaaac cacctgttca ttacaatggc 1320
ccctcaaaag cagggtatgt tgactttgaa aatggccagt gggccacaga tgacatccca 1380
gatgacttga atagtatccg cgcagcacca ggtgagtttc gagccatcat ggagatgccc 1440
tccttctaca gtcatggctt gccacggtgt tcaccctaca agaaactgac agagtgccag 1500
ctgaagaacc ccatcagcgg gctgttagaa tatgcccagt tcgctagtca aacctgtgag 1560
ttcaacatga tagagcagag tggaccaccc catgaacctc gatttaaatt ccaggttgtc 1620
atcaatggcc gagagtttcc cccagctgaa gctggaagca agaaagtggc caagcaggat 1680
gcagctatga aagccatgac aattctgcta gaggaagcca aagccaagga cagtggaaaa 1740
tcagaagaat catcccacta ttccacagag aaagaatcag agaagactgc agagtcccag 1800
acccccaccc cttcagccac atccttcttt tctgggaaga gccccgtcac cacactgctt 1860
gagtgtatgc acaaattggg gaactcctgc gaattccgtc tcctgtccaa agaaggccct 1920
gcccatgaac ccaagttcca atactgtgtt gcagtgggag cccaaacttt ccccagtgtg 1980
agtgctccca gcaagaaagt ggcaaagcag atggccgcag aggaagccat gaaggccctg 2040
catggggagg cgaccaactc catggcttct gataaccagc ctgaaggtat gatctcagag 2100
tcacttgata acttggaatc catgatgccc aacaaggtca ggaagattgg cgagctcgtg 2160
agatacctga acaccaaccc tgtgggtggc cttttggagt acgcccgctc ccatggcttt 2220
gctgctgaat tcaagttggt cgaccagtcc ggacctcctc acgagcccaa gttcgtttac 2280
caagcaaaag ttgggggtcg ctggttccca gccgtctgcg cacacagcaa gaagcaaggc 2340
aagcaggaag cagcagatgc ggctctccgt gtcttgattg gggagaacga gaaggcagaa 2400
cgcatgggtt tcacagaggt aaccccagtg acaggggcca gtctcagaag aactatgctc 2460
ctcctctcaa ggtccccaga agcacagcca aagacactcc ctctcactgg cagcaccttc 2520
catgaccaga tagccatgct gagccaccgg tgcttcaaca ctctgactaa cagcttccag 2580
ccctccttgc tcggccgcaa gattctggcc gccatcatta tgaaaaaaga ctctgaggac 2640
atgggtgtcg tcgtcagctt gggaacaggg aatcgctgtg taaaaggaga ttctctcagc 2700
ctaaaaggag aaactgtcaa tgactgccat gcagaaataa tctcccggag aggcttcatc 2760
aggtttctct acagtgagtt aatgaaatac aactcccaga ctgcgaagga tagtatattt 2820
gaacctgcta agggaggaga aaagctccaa ataaaaaaga ctgtgtcatt ccatctgtat 2880
atcagcactg ctccgtgtgg agatggcgcc ctctttgaca agtcctgcag cgaccgtgct 2940
atggaaagca cagaatcccg ccactaccct gtcttcgaga atcccaaaca aggaaagctc 3000
cgcaccaagg tggagaacgg agaaggcaca atccctgtgg aatccagtga cattgtgcct 3060
acgtgggatg gcattcggct cggggagaga ctccgtacca tgtcctgtag tgacaaaatc 3120
ctacgctgga acgtgctggg cctgcaaggg gcactgttga cccacttcct gcagcccatt 3180
tatctcaaat ctgtcacatt gggttacctt ttcagccaag ggcatctgac ccgtgctatt 3240
tgctgtcgtg tgacaagaga tgggagtgca tttgaggatg gactacgaca tccctttatt 3300
gtcaaccacc ccaaggttgg cagagtcagc atatatgatt ccaaaaggca atccgggaag 3360
actaaggaga caagcgtcaa ctggtgtctg gctgatggct atgacctgga gatcctggac 3420
ggtaccagag gcactgtgga tgggccacgg aatgaattgt cccgggtctc caaaaagaac 3480
atttttcttc tatttaagaa gctctgctcc ttccgttacc gcagggatct actgagactc 3540
tcctatggtg aggccaagaa agctgcccgt gactacgaga cggccaagaa ctacttcaaa 3600
aaaggcctga aggatatggg ctatgggaac tggattagca aaccccagga ggaaaagaac 3660
ttttatctct gcccagtaga ttacaaggat gacgacgata agtag 3705

<210> SEQ ID NO 334
<211> LENGTH: 2130
<212> TYPE: DNA
<213> ORGANISM: Artificial Sequence
<220> FEATURE:
<223> OTHER INFORMATION: dRNA/arRNA

<400> SEQUENCE: 334
atggatatag aagatgaaga aaacatgagt tccagcagca ctgatgtgaa ggaaaaccgc 60
aatctggaca acgtgtcccc caaggatggc agcacacctg ggcctggcga gggctctcag 120
ctctccaatg gggtggtgg tggccccggc agaaagcggc ccctggagga gggcagcaat 180
ggccactcca agtaccgcct gaagaaaagg aggaaaacac cagggcccgt cctccccaag 240
aacgccctga tgcagctgaa tgagatcaag cctggtttgc agtacacact cctgtcccag 300
actgggcccg tgcacgcgcc tttgtttgtc atgtctgtgg aggtgaatgg ccaggttttt 360
gagggctctg gtcccacaaa gaaaaaggca aaactccatg ctgctgagaa ggccttgagg 420
tctttcgttc agtttcctaa tgcctctgag gcccacctgg ccatggggag gaccctgtct 480
gtcaacacgg acttcacatc tgaccaggcc gacttccctg acacgctctt caatggtttt 540
gaaactcctg acaaggcgga gcctcccttt tacgtgggct ccaatgggga tgactccttc 600
agttccagcg ggacctcag cttgtctgct tccccggtgc ctgccagcct agcccagcct 660
cctctccctg ccttaccacc attcccaccc ccgagtggga agaatcccgt gatgatcttg 720
aacgaactgc gcccaggact caagtatgac ttcctctccg agagcgggga gagccatgcc 780
aagagcttcg tcatgtctgt ggtcgtggat ggtcagttct ttgaaggctc ggggagaaac 840
aagaagcttg ccaaggcccg ggctgcgcag tctgccctgg ccgccatttt taacttgcac 900
ttggatcaga cgccatctcg ccagcctatt cccagtgagg gtcttcagct gcatttaccg 960
caggttttag ctgacgctgt ctcacgcctg gtcctgggta agtttggtga cctgaccgac 1020
aacttctcct cccctcacgc tcgcagaaaa gtgctggctg gagtcgtcat gacaacaggc 1080
acagatgtta aagatgccaa ggtgataagt gtttctacag gaacaaaatg tattaatggt 1140
gaatacatga gtgatcgtgg ccttgcatta aatgactgcc atgcagaaat aatatctcgg 1200
agatccttgc tcagatttct ttatacacaa cttgagcttt acttaaataa caaagatgat 1260
caaaaaagat ccatctttca gaaatcagag cgaggggggt ttaggctgaa ggagaatgtc 1320
cagtttcatc tgtacatcag cacctctccc tgtggagatg ccagaatctt ctcaccacat 1380
gagccaatcc tggaagaacc agcagataga cacccaaatc gtaaagcaag aggacagcta 1440
cggaccaaaa tagagtctgg tgaggggacg attccagtgc gctccaatgc gagcatccaa 1500
acgtgggacg gggtgctgca aggggagcgg ctgctcacca tgtcctgcag tgacaagatt 1560
gcacgctgga acgtggtggg catccaggga tccctgctca gcattttcgt ggagcccatt 1620
tacttctcga gcatcatcct gggcagcctt taccacgggg accacctttc cagggccatg 1680
taccagcgga tctccaacat agaggacctg ccacctctct acaccctcaa caagcctttg 1740
ctcagtggca tcagcaatgc agaagcacgg cagccaggga aggcccccaa cttcagtgtc 1800
aactggacgg taggcgactc cgctattgag gtcatcaacg ccacgactgg gaaggatgag 1860
ctgggccgcg cgtcccgcct gtgtaagcac gcgttgtact gtcgctggat gcgtgtgcac 1920
ggcaaggttc cctcccactt actacgctcc aagattacca aacccaacgt gtaccatgag 1980
tccaagctgg cggcaaagga gtaccaggcc gccaaggcgc gtctgttcac agccttcatc 2040
aaggcggggc tgggggcctg ggtggagaag cccaccgagc aggaccagtt ctcactcacg 2100
cccgattaca aggatgacga cgataagtag 2130

<210> SEQ ID NO 335
<211> LENGTH: 4401
<212> TYPE: DNA
<213> ORGANISM: Artificial Sequence
<220> FEATURE:
<223> OTHER INFORMATION: dRNA/arRNA

<400> SEQUENCE: 335
atgatgagct ttgtgcaaaa ggggagctgg ctacttctcg ctctgcttca tcccactatt 60
attttggcac aacaggaagc tgttgaagga ggatgttccc atcttggtca gtcctatgcg 120
gatagagatg tctggaagcc agaaccatgc caaatatgtg tctgtgactc aggatccgtt 180
ctctgcgatg acataatatg tgacgatcaa gaattagact gccccaaccc agaaattcca 240
tttggagaat gttgtgcagt ttgcccacag cctccaactg ctcctactcg ccctcctaat 300
ggtcaaggac ctcaaggccc caagggagat ccaggccctc ctggtattcc tgggagaaat 360
ggtgaccctg gtattccagg acaaccaggg tcccctggtt ctcctggccc ccctggaatc 420
tgtgaatcat gccctactgg tcctcagaac tattctcccc agtatgattc atatgatgtc 480
aagtctggag tagcagtagg aggactcgca ggctatcctg gaccagctgg ccccccaggc 540
cctcccggtc cccctggtac atctggtcat cctggttccc ctggatctcc aggataccaa 600 ggacccccctg gtgaacctgg gcaagctggt ccttcaggcc ctccaggacc tcctggtgct 660
ataggtccat ctggtcctgc tggaaaagat ggagaatcag gtagacccgg acgacctgga 720
gagcgaggat tgcctggacc tccaggtatc aaaggtccag ctgggatacc tggattccct 780
ggtatgaaag gacacagagg cttcgatgga cgaaatggag aaaagggtga aacaggtgct 840
cctggattaa agggtgaaaa tggtcttcca ggcgaaaatg gagctcctgg acccatgggt 900
ccaagagggg ctcctggtga gcgaggacgg ccaggacttc ctggggctgc aggtgctcgg 960
ggtaatgacg gtgctcgagg cagtgatggt caaccaggcc ctcctggtcc tcctggaact 1020
gccggattcc ctggatcccc tggtgctaag ggtgaagttg gacctgcagg gtctcctggt 1080
tcaaatggtg cccctggaca aagaggagaa cctggacctc agggacacgc tggtgctcaa 1140
ggtcctcctg gccctcctgg gattaatggt agtcctggtg gtaaaggcga aatgggtccc 1200
gctggcattc ctggagctcc tggactgatg ggagcccggg gtcctccagg accagccggt 1260
gctaatggtg ctcctggact gcgaggtggt gcaggtgagc ctggtaagaa tggtgccaaa 1320

-continued ggagagcccg gaccacgtgg tgaacgcggt gaggctggta ttccaggtgt tccaggagct 1380
aaaggcgaag atggcaagga tggatcacct ggagaacctg gtgcaaatgg gcttccagga 1440
gctgcaggag aaaggggtgc ccctgggttc cgaggacctg ctggaccaaa tggcatccca 1500
ggagaaaagg gtcctgctgg agagcgtggt gctccaggcc ctgcagggcc cagaggagct 1560
gctggagaac ctggcagaga tggcgtccct ggaggtccag gaatgagggg catgcccgga 1620
agtccaggag gaccaggaag tgatgggaaa ccagggcctc ccggaagtca aggagaaagt 1680
ggtcgaccag gtcctcctgg gccatctggt ccccgaggtc agcctggtgt catgggcttc 1740
cccggtccta aaggaaatga tggtgctcct ggtaagaatg gagaacgagg tggccctgga 1800
ggacctggcc ctcagggtcc tcctggaaag aatggtgaaa ctggacctca gggaccccca 1860
gggcctactg ggcctggtgg tgacaaagga gacacaggac cccctggtcc acaaggatta 1920
caaggcttgc ctggtacagg tggtcctcca ggagaaaatg gaaaacctgg ggaaccaggt 1980
ccaaagggtg atgccggtgc acctggagct ccaggaggca agggtgatgc tggtgcccct 2040
ggtgaacgtg gacctcctgg attggcaggg gccccaggac ttagaggtgg agctggtccc 2100
cctggtcccg aaggaggaaa gggtgctgct ggtcctcctg ggccacctgg tgctgctggt 2160
actcctggtc tgcaaggaat gcctggagaa agaggaggtc ttggaagtcc tggtccaaag 2220
ggtgacaagg gtgaaccagg cggtccaggt gctgatggtg tcccagggaa agatggccca 2280
aggggtccta ctggtcctat tggtcctcct ggcccagctg gccagcctgg agataagggt 2340
gaaggtggtg cccccggact tccaggtata gctggacctc gtggtagccc tggtgagaga 2400
ggtgaaactg gccctccagg acctgctggt ttccctggtg ctcctggaca gaatggtgaa 2460
cctggtggta aaggagaaag aggggctccg ggtgagaaag gtgaaggagg ccctcctgga 2520
gttgcaggac cccctggagg ttctggacct gctggtcctc ctggtcccca aggtgtcaaa 2580
ggtgaacgtg gcagtcctgg tggacctggt gctgctggct tccctggtgc tcgtggtctt 2640
cctggtcctc ctggtagtaa tggtaaccca ggacccccag gtcccagcgg ttctccaggc 2700
aaggatgggc ccccaggtcc tgcgggtaac actggtgctc ctggcagccc tggagtgtct 2760
ggaccaaaag gtgatgctgg ccaaccagga gagaagggat cgcctggtgc ccagggccca 2820
ccaggagctc caggcccact tgggattgct gggatcactg gagcacgggg tcttgcagga 2880
ccaccaggca tgccaggtcc taggggaagc cctggccctc agggtgtcaa gggtgaaagt 2940
gggaaaccag gagctaacgg tctcagtgga gaacgtggtc cccctggacc ccagggtctt 3000
cctggtctgg ctggtacagc tggtgaacct ggaagagatg gaaaccctgg atcagatggt 3060
cttccaggcc gagatggatc tcctggtggc aagggtgatc gtggtgaaaa tggctctcct 3120
ggtgcccctg gcgctcctgg tcatccaggc ccacctggtc ctgtcggtcc agctggaaag 3180
agtggtgaca gaggagaaag tggccctgct ggccctgctg gtgctcccgg tcctgctggt 3240
tcccgaggtg ctcctggtcc tcaaggccca cgtggtgaca aaggtgaaac aggtgaacgt 3300
ggagctgctg gcatcaaagg acatcgagga ttccctggta atccaggtgc cccaggttct 3360
ccaggccctg ctggtcagca gggtgcaatc ggcagtccag gacctgcagg ccccagagga 3420
cctgttggac ccagtggacc tcctggcaaa gatggaacca gtggacatcc aggtcccatt 3480
ggaccaccag ggcctcgagg taacagaggt gaaagaggat ctgagggctc cccaggccac 3540
ccagggcaac caggccctcc tggacctcct ggtgcccctg gtccttgctg tggtggtgtt 3600
ggagccgctg ccattgctgg gattggaggt gaaaaagctg gcggttttgc cccgtattat 3660
ggagatgaac caatggattt caaaatcaac accgatgaga ttatgacttc actcaagtct 3720

```
gttaatggac aaatagaaag cctcattagt cctgatggtt ctcgtaaaaa ccccgctaga   3780

aactgcagag acctgaaatt ctgccatcct gaactcaaga gtggagaata ctgggttgac   3840

cctaaccaag gatgcaaatt ggatgctatc aaggtattct gtaatatgga aactggggaa   3900

acatgcataa gtgccaatcc tttgaatgtt ccacggaaac actggtggac agattctagt   3960

gctgagaaga aacacgtttg gtttggagag tccatggatg gtggttttca gtttagctac   4020

ggcaatcctg aacttcctga agatgtcctt gatgtgcagc tggcattcct tcgacttctc   4080

tccagccgag cttcccagaa catcacatat cactgcaaaa atagcattgc atacatggat   4140

caggccagtg gaaatgtaaa gaaggccctg aagctgatgg ggtcaaatga aggtgaattc   4200

aaggctgaag gaaatagcaa attcacctac acagttctgg aggatggttg cacgaaacac   4260

actggggaat ggagcaaaac agtctttgaa tatcgaacac gcaaggctgt gagactacct   4320

attgtagata ttgcacccta tgacattggt ggtcctgatc aagaatttgg tgtggacgtt   4380

ggccctgttt gctttttata a                                               4401
```

<210> SEQ ID NO 336
<211> LENGTH: 3117
<212> TYPE: DNA
<213> ORGANISM: Artificial Sequence
<220> FEATURE:
<223> OTHER INFORMATION: dRNA/arRNA

<400> SEQUENCE: 336

```
atgacttcct cgctgcagcg gccctggcgg gtgccctggc taccatggac catcctgctg     60

gtcagcgctg cggctgcttc gcagaatcaa gaacggctat gtgcgtttaa agatccgtat    120

cagcaagacc ttgggatagg tgagagtaga atctctcatg aaaatgggac aatattatgc    180

tcgaaaggta gcacctgcta tggcctttgg gagaaatcaa aaggggacat aaatcttgta    240

aaacaaggat gttggtctca cattggagat ccccaagagt gtcactatga agaatgtgta    300

gtaactacca ctcctccctc aattcagaat ggaacatacc gtttctgctg ttgtagcaca    360

gatttatgta atgtcaactt tactgagaat tttccacctc ctgacacaac accactcagt    420

ccacctcatt catttaaccg agatgagaca ataatcattg ctttggcatc agtctctgta    480

ttagctgttt tgatagttgc cttatgcttt ggatacagaa tgttgacagg agaccgtaaa    540

caaggtcttc acagtatgaa catgatggag gcagcagcat ccgaaccctc tcttgatcta    600

gataatctga aactgttgga gctgattggc cgaggtcgat atggagcagt atataaaggc    660

tccttggatg agcgtccagt tgctgtaaaa gtgttttcct ttgcaaaccg tcagaatttt    720

atcaacgaaa agaacattta cagagtgcct ttgatggaac atgacaacat tgcccgcttt    780

atagttggag atgagagagt cactgcagat ggacgcatgg aatatttgct tgtgatggag    840

tactatccca atggatcttt atgcaagtat ttaagtctcc acacaagtga ctgggtaagc    900

tcttgccgtc ttgctcattc tgttactaga ggactggctt atcttcacac agaattacca    960

cgaggagatc attataaacc tgcaatttcc catcgagatt taaacagcag aaatgtccta   1020

gtgaaaaatg atggaacctg tgttattagt gactttggac tgtccatgag gctgactgga   1080

aatagactgg tgcgcccagg ggaggaagat aatgcagcca taagcgaggt tggcactatc   1140

agatatatgg caccagaagt gctagaagga gctgtgaact tgagggactg tgaatcagct   1200

ttgaaacaag tagacatgta tgctcttgga ctaatctatt gggagatatt tatgagatgt   1260

acagacctct tcccagggga atccgtacca gagtaccaga tggcttttca gacagaggtt   1320
```

```
ggaaaccatc ccacttttga ggatatgcag gttctcgtgt ctagggaaaa acagagaccc   1380
aagttcccag aagcctggaa agaaaatagc ctggcagtga ggtcactcaa ggagacaatc   1440
gaagactgtt gggaccagga tgcagaggct cggcttactg cacagtgtgc tgaggaaagg   1500
atggctgaac ttatgatgat ttgggaaaga aacaaatctg tgagcccaac agtcaatcca   1560
atgtctactg ctatgcagaa tgaacgcaac ctgtcacata ataggcgtgt gccaaaaatt   1620
ggtccttatc cagattattc ttcctcctca tacattgaag actctatcca tcatactgac   1680
agcatcgtga agaatatttc ctctgagcat tctatgtcca gcacaccttt gactataggg   1740
gaaaaaaacc gaaattcaat taactatgaa cgacagcaag cacaagctcg aatccccagc   1800
cctgaaacaa gtgtcaccag cctctccacc aacacaacaa ccacaaacac cacaggactc   1860
acgccaagta ctggcatgac tactatatct gagatgccat acccagatga aacaaatctg   1920
cataccacaa atgttgcaca gtcaattggg ccaacccctg tctgcttaca gctgacagaa   1980
gaagacttgg aaaccaacaa gctagaccca aaagaagttg ataagaacct caaggaaagc   2040
tctgatgaga atctcatgga gcactctctt aaacagttca gtggcccaga cccactgagc   2100
agtactagtt ctagcttgct ttacccactc ataaaacttg cagtagaagc aactggacag   2160
caggacttca cacagactgc aaatggccaa gcatgtttga ttcctgatgt tctgcctact   2220
cagatctatc ctctccccaa gcagcagaac cttcccaaga gacctactag tttgcctttg   2280
aacaccaaaa attcaacaaa agagccccgg ctaaaatttg gcagcaagca caaatcaaac   2340
ttgaaacaag tcgaaactgg agttgccaag atgaatacaa tcaatgcagc agaacctcat   2400
gtggtgacag tcaccatgaa tggtgtggca ggtagaaacc acagtgttaa ctcccatgct   2460
gccacaaccc aatatgccaa tgggacagta ctatctggcc aaacaaccaa catagtgaca   2520
catagggccc aagaaatgtt gcagaatcag tttattggtg aggacacccg gctgaatatt   2580
aattccagtc ctgatgagca tgagccttta ctgagacgag agcaacaagc tggccatgat   2640
gaaggtgttc tggatcgtct tgtggacagg agggaacggc cactagaagg tggccgaact   2700
aattccaata acaacaacag caatccatgt tcagaacaag atgttcttgc acagggtgtt   2760
ccaagcacag cagcagatcc tgggccatca aagcccagaa gagcacagag gcctaattct   2820
ctggatcttt cagccacaaa tgtcctggat ggcagcagta tacagatagg tgagtcaaca   2880
caagatggca aatcaggatc aggtgaaaag atcaagaaac gtgtgaaaac tccctattct   2940
cttaagcggt ggcgcccctc cacctgggtc atctccactg aatcgctgga ctgtgaagtc   3000
aacaataatg gcagtaacag ggcagttcat tccaaatcca gcactgctgt ttaccttgca   3060
gaaggaggca ctgctacaac catggtgtct aaagatatag gaatgaactg tctgtga      3117
```

<210> SEQ ID NO 337
<211> LENGTH: 3590
<212> TYPE: DNA
<213> ORGANISM: Artificial Sequence
<220> FEATURE:
<223> OTHER INFORMATION: dRNA/arRNA

<400> SEQUENCE: 337

```
atgcctacag ctgagagtga agcaaaagta aaaaccaaag ttcgctttga agaattgctt     60
aagacccaca gtgatctaat gcgtgaaaag aaaaaactga agaaaaaact tgtcaggtct    120
gaagaaaaca tctcacctga cactattaga agcaatcttc actatatgaa agaaactaca    180
agtgatgatc ccgacactat tagaagcaat cttccccata ttaaagaaac tacaagtgat    240
gatgtaagtg ctgctaacac taacaacctg aagaagagca cgagagtcac taaaaacaaa    300
```

```
ttgaggaaca cacagttagc aactgaaaat cctaatggtg atgctagtgt agaggaagac    360
aaacaaggaa agccaaataa aaaggtgata aagacggtgc cccagttgac tacacaagac    420
ctgaaaccgg aaactcctga gaataaggtt gattctacac accagaaaac acatacaaag    480
ccacagccag gcgttgatca tcagaaaagt gagaaggcaa atgagggaag agaagagact    540
gatttagaag aggatgaaga attgatgcaa gcatatcagt gccatgtaac tgaagaaatg    600
gcaaaggaga ttaagaggaa aataagaaag aaactgaaag aacagttgac ttactttccc    660
tcagatactt tattccatga tgacaaacta agcagtgaaa aaaggaaaaa gaaaaaggaa    720
gttccagtct tctctaaagc tgaaacaagt acattgacca tctctggtga cacagttgaa    780
ggtgaacaaa agaaagaatc ttcagttaga tcagtttctt cagattctca tcaagatgat    840
gaaataagct caatggaaca aagcacagaa gacagcatgc aagatgatac aaaacctaaa    900
ccaaaaaaaa caaaaaagaa gactaaagca gttgcagata ataatgaaga tgttgatggt    960
gatggtgttc atgaaataac aagccgagat agcccggttt atcccaaatg tttgcttgat   1020
gatgaccttg tcttgggagt ttacattcac cgaactgata gacttaagtc agattttatg   1080
atttctcacc caatggtaaa aattcatgtg gttgatgagc atactggtca atatgtcaag   1140
aaagatgata gtggacggcc tgtttcatct tactatgaaa aagagaatgt ggattatatt   1200
cttcctatta tgacccagcc atatgatttt aaacagttaa aatcaagact tccagagtgg   1260
gaagaacaaa ttgtatttaa tgaaaatttt ccctatttgc ttcgaggctc tgatgagagt   1320
cctaaagtca tcctgttctt tgagattctt gatttcttaa gcgtggatga aattaagaat   1380
aattctgagg ttcaaaacca agaatgtggc tttcggaaaa ttgcctgggc atttcttaag   1440
cttctgggag ccaatggaaa tgcaaacatc aactcaaaac ttcgcttgca gctatattac   1500
ccacctacta agcctcgatc ccattaagt gttgttgagg catttgaatg gtggtcaaaa   1560
tgtccaagaa atcattaccc atcaacactg tacgtaactg taagaggact gaaagttcca   1620
gactgtataa agccatctta ccgctctatg atggctcttc aggaggaaaa aggtaaacca   1680
gtgcattgtg aacgtcacca tgagtcaagc tcagtagaca cagaacctgg attagaagag   1740
tcaaaggaag taataaagtg gaaacgactc cctgggcagg cttgccgtat cccaaacaaa   1800
cacctcttct cactaaatgc aggagaacga ggatgttttt gtcttgattt ctcccacaat   1860
ggaagaatat tagcagcagc ttgtgccagc cgggatggat atccaattat tttatatgaa   1920
attccttctg gacgtttcat gagagaattg tgtggccacc tcaatatcat ttatgatctt   1980
tcctggtcaa aagatgatca ctacatcctt acttcatcat ctgatggcac tgccaggata   2040
tggaaaaatg aaataaacaa tacaaatact ttcagagttt tacctcatcc ttcttttgtt   2100
tacacggcta aattccatcc agctgtaaga gagctagtag ttacaggatg ctatgattcc   2160
atgatacgga tatggaaagt tgagatgaga gaagattctg ccatattggt ccgacagttt   2220
gacgttcaca aaagttttat caactcactt tgttttgata ctgaaggtca tcatatgtat   2280
tcaggagatt gtacaggggt gattgttgtt tggaatacct atgtcaagat taatgatttg   2340
gaacattcag tgcaccactg gactataaat aaggaaatta aagaaactga gtttaaggga   2400
attccaataa gttatttgga gattcatccc aatggaaaac gtttgttaat ccataccaaa   2460
gacagtactt tgagaattat ggatctccgg atattagtag caaggaagtt tgtaggagca   2520
gcaaattatc gggagaagat tcatagtact ttgactccat gtgggacttt tctgtttgct   2580
ggaagtgagg atggtatagt gtatgtttgg aacccagaaa caggagaaca agtagccatg   2640
```

-continued

```
tattctgact tgccattcaa gtcacccatt cgagacattt cttatcatcc atttgaaaat   2700

atggttgcat tctgtgcatt tgggcaaaat gagccaattc ttctgtatat ttacgatttc   2760

catgttgccc agcaggaggc tgaaatgttc aaacgctaca atggaacatt tccattacct   2820

ggaatacacc aaagtcaaga tgccctatgt acctgtccaa aactacccca tcaaggctct   2880

tttcagattg atgaatttgt ccacactgaa agttcttcaa cgaagatgca gctagtaaaa   2940

cagaggcttg aaactgtcac agaggtgata cgttcctgtg ctgcaaaagt caacaaaaat   3000

ctctcattta cttcaccacc agcagtttcc tcacaacagt ctaagttaaa gcagtcaaac   3060

atgctgaccg ctcaagagat tctacatcag tttggtttca ctcagaccgg gattatcagc   3120

atagaaagaa agccttgtaa ccatcaggta gatacagcac caacggtagt ggctctttat   3180

gactacacag cgaatcgatc agatgaacta accatccatc gcggagacat tatccgagtg   3240

tttttcaaag ataatgaaga ctggtggtat ggcagcatag gaaagggaca ggaaggttat   3300

tttccagcta atcatgtggc tagtgaaaca ctgtatcaag aactgcctcc tgagataaag   3360

gagcgatccc ctcctttaag ccctgaggaa aaaactaaaa tagaaaaatc tccagctcct   3420

caaaagcaat caatcaataa gaacaagtcc caggacttca gactaggctc agaatctatg   3480

acacattctg aaatgagaaa agaacagagc catgaggacc aaggacacat aatggataca   3540

cggatgagga agaacaagca agcaggcaga aaagtcactc taatagagta              3590
```

<210> SEQ ID NO 338
<211> LENGTH: 1677
<212> TYPE: DNA
<213> ORGANISM: Artificial Sequence
<220> FEATURE:
<223> OTHER INFORMATION: dRNA/arRNA

<400> SEQUENCE: 338

```
atggctcaag attcagtaga tctttcttgt gattatcagt tttggatgca gaagctttct     60

gtatgggatc aggcttccac tttggaaacc cagcaagaca cctgtcttca cgtggctcag    120

ttccaggagt tcctaaggaa gatgtatgaa gccttgaaag agatggattc taatacagtc    180

attgaaagat tccccacaat tggtcaactg ttggcaaaag cttgttggaa tccttttatt    240

ttagcatatg atgaaagcca aaaaattcta atatggtgct tatgttgtct aattaacaaa    300

gaaccacaga attctggaca atcaaaactt aactcctgga tacagggtgt attatctcat    360

atactttcag cactcagatt tgataaagaa gttgctcttt tcactcaagg tcttgggtat    420

gcacctatag attactatcc tggtttgctt aaaaatatgg ttttatcatt agcgtctgaa    480

ctcagagaga atcatcttaa tggatttaac actcaaaggc gaatggctcc cgagcgagtg    540

gcgtccctgt cacgagtttg tgtcccactt attaccctga cagatgttga ccccctggtg    600

gaggctctcc tcatctgtca tggacgtgaa cctcaggaaa tcctccagcc agagttcttt    660

gaggctgtaa acgaggccat tttgctgaag aagatttctc tccccatgtc agctgtagtc    720

tgcctctggc ttcggcacct tcccagcctt gaaaaagcaa tgctgcatct tttgaaaaag    780

ctaatctcca gtgagagaaa ttgtctgaga aggatcgaat gctttataaa agattcatcg    840

ctgcctcaag cagcctgcca ccctgccata ttccgggttg ttgatgagat gttcaggtgt    900

gcactcctgg aaaccgatgg ggccctggaa atcatagcca ctattcaggt gtttacgcag    960

tgctttgtag aagctctgga gaaagcaagc aagcagctgc ggtttgcact caagacctac   1020

tttccttaca cttctccatc tcttgccatg gtgctgctgc aagaccctca agatatccct   1080

cggggacact ggctccagac actgaagcat atttctgaac tgctcagaga agcagttgaa   1140
```

gaccagactc atgggtcctg cggaggtccc tttgagagct ggttcctgtt cattcacttc 1200
ggaggatggg ctgagatggt ggcagagcaa ttactgatgt cggcagccga accccccacg 1260
gccctgctgt ggctcttggc cttctactac ggcccccgtg atgggaggca gcagagagca 1320
cagactatgg tccaggtgaa ggccgtgctg ggccacctcc tggcaatgtc cagaagcagc 1380
agcctctcag cccaggacct gcagacggta gcaggacagg gcacagacac agacctcaga 1440
gctcctgcac aacagctgat caggcacctt ctcctcaact tcctgctctg ggctcctgga 1500
ggccacacga tcgcctggga tgtcatcacc ctgatggctc acactgctga gataactcac 1560
gagatcattg gctttcttga ccagaccttg tacagatgga atcgtcttgg cattgaaagc 1620
cctagatcag aaaaactggc ccgagagctc cttaaagagc tgcgaactca agtctag 1677

<210> SEQ ID NO 339
<211> LENGTH: 3825
<212> TYPE: DNA
<213> ORGANISM: Artificial Sequence
<220> FEATURE:
<223> OTHER INFORMATION: dRNA/arRNA

<400> SEQUENCE: 339
atgcctgagc cggggaagaa gccagtctca gcttttagca agaagccacg gtcagtggaa 60
gtggccgcag gcagccctgc cgtgttcgag gccgagacag agcgggcagg agtgaaggtg 120
cgctggcagc gcggaggcag tgacatcagc gccagcaaca agtacggcct ggccacagag 180
ggcacacggc atacgctgac agtgcgggaa gtgggccctg ccgaccaggg atcttacgca 240
gtcattgctg gctcctccaa ggtcaagttc gacctcaagg tcatagaggc agagaaggca 300
gagcccatgc tggcccctgc ccctgcccct gctgaggcca ctggagcccc tggagaagcc 360
ccggccccag ccgctgagct gggagaaagt gccccaagtc ccaaagggtc aagctcagca 420
gctctcaatg gtcctacccc tggagccccc gatgacccca ttggcctctt cgtgatgcgg 480
ccacaggatg gcgaggtgac cgtgggtggc agcatcacct tctcagcccg cgtggccggc 540
gccagcctcc tgaagccgcc tgtggtcaag tggttcaagg gcaaatgggt ggacctgagc 600
agcaaggtgg gccagcacct gcagctgcac gacagctacg accgcgccag caaggtctat 660
ctgttcgagc tgcacatcac cgatgcccag cctgccttca ctggcagcta ccgctgtgag 720
gtgtccacca aggacaaatt tgactgctcc aacttcaatc tcactgtcca cgaggccatg 780
ggcaccggag acctggacct cctatcagcc ttccgccgca cgagcctggc tggaggtggt 840
cggcggatca gtgatagcca tgaggacact gggattctgg acttcagctc actgctgaaa 900
aagagagaca gtttccggac cccgagggac tcgaagctgg aggcaccagc agaggaggac 960
gtgtgggaga tcctacggca ggcaccccca tctgagtacg agcgcatcgc cttccagtac 1020
ggcgtcactg acctgcgcgg catgctaaag aggctcaagg gcatgaggcg cgatgagaag 1080
aagagcacag cctttcagaa gaagctggag ccggcctacc aggtgagcaa aggccacaag 1140
atccggctga ccgtggaact ggctgaccat gacgctgagg tcaaatggct caagaatggc 1200
caggagatcc agatgagcgg cagcaagtac atctttgagt ccatcggtgc caagcgtacc 1260
ctgaccatca gccagtgctc attggcggac gacgcagcct accagtgcgt ggtgggtggc 1320
gagaagtgta gcacggagct ctttgtgaaa gagccccctg tgctcatcac gcgccccttg 1380
gaggaccagc tggtgatggt ggggcagcgg gtggagtttg agtgtgaagt atcggaggag 1440
ggggcgcaag tcaaatggct gaaggacggg gtggagctga cccgggagga gaccttcaaa 1500

-continued

```
taccggttca agaaggacgg gcagagacac cacctgatca tcaacgaggc catgctggag   1560
gacgcggggc actatgcact gtgcactagc gggggccagg cgctggctga gctcattgtg   1620
caggaaaaga agctggaggt gtaccagagc atcgcagacc tgatggtggg cgcaaaggac   1680
caggcggtgt tcaaatgtga ggtctcagat gagaatgttc ggggtgtgtg gctgaagaat   1740
gggaaggagc tggtgcccga cagccgcata aaggtgtccc acatcgggcg ggtccacaaa   1800
ctgaccattg acgacgtcac acctgccgac gaggctgact acagctttgt gcccgagggc   1860
ttcgcctgca acctgtcagc caagctccac ttcatggagg tcaagattga cttcgtaccc   1920
aggcaggaac ctcccaagat ccacctggac tgcccaggcc gcataccaga caccattgtg   1980
gttgtagctg gaaataagct acgtctggac gtccctatct ctggggaccc tgctcccact   2040
gtgatctggc agaaggctat cacgcagggg aataaggccc cagccaggcc agccccagat   2100
gccccagagg acacaggtga cagcgatgag tgggtgtttg acaagaagct gctgtgtgag   2160
accgagggcc gggtccgcgt ggagaccacc aaggaccgca gcatcttcac ggtcgagggg   2220
gcagagaagg aagatgaggg cgtctacacg gtcacagtga agaaccctgt gggcgaggac   2280
caggtcaacc tcacagtcaa ggtcatcgac gtgccagacg cacctgcggc ccccaagatc   2340
agcaacgtgg gagaggactc ctgcacagta cagtgggagc cgcctgccta cgatggcggg   2400
cagcccatcc tgggctacat cctggagcgc aagaagaaga agagctaccg gtggatgcgg   2460
ctgaacttcg acctgattca ggagctgagt catgaagcgc ggcgcatgat cgagggcgtg   2520
gtgtacgaga tgcgcgtcta cgcggtcaac gccatcggca tgtccaggcc cagccctgcc   2580
tcccagccct tcatgcctat cggtcccccc agcgaaccca cccacctggc agtagaggac   2640
gtctctgaca ccacggtctc cctcaagtgg cggcccccag agcgcgtggg agcaggaggc   2700
ctggatggct acagcgtgga gtactgccca gagggctgct cagagtgggt ggctgccctg   2760
caggggctga cagagcacac atcgatactg gtgaaggacc tgcccacggg ggcccggctg   2820
cttttccgag tgcgggcaca caatatggca gggcctggag cccctgttac caccacggag   2880
ccggtgacag tgcaggagat cctgcaacgg ccacggcttc agctgcccag gcacctgcgc   2940
cagaccattc agaagaaggt cggggagcct gtgaaccttc tcatcccttt ccagggcaag   3000
ccccggcctc aggtgacctg gaccaaagag gggcagcccc tggcaggcga ggaggtgagc   3060
atccgcaaca gccccacaga caccatcctg ttcatccggg ccgctcgccg cgtgcattca   3120
ggcacttacc aggtgacggt gcgcattgag aacatggagg acaaggccac gctggtgctg   3180
caggttgttg acaagccaag tcctccccag gatctccggg tgactgacgc ctggggtctt   3240
aatgtggctc tggagtggaa gccaccccag gatgtcggca acacggagct ctgggggtac   3300
acagtgcaga aagccgacaa gaagaccatg gagtggttca ccgtcttgga gcattaccgc   3360
cgcacccact gcgtggtgcc agagctcatc attggcaatg gctactactt ccgcgtcttc   3420
agccagaata tggttggctt tagtgacaga gcggccacca ccaaggagcc cgtctttatc   3480
cccagaccag gcatcaccta tgagccaccc aactataagg ccctggactt ctccgaggcc   3540
ccaagcttca cccagcccct ggtgaaccgc tcggtcatcg cgggctacac tgctatgctc   3600
tgctgtgctg tccggggtag ccccaagccc aagatttcct ggttcaagaa tggcctggac   3660
ctgggagaag acgcccgctt ccgcatgttc agcaagcagg gagtgttgac tctggagatt   3720
agaaagccct gccccttga cgggggcatc tatgtctgca gggccaccaa cttacagggc   3780
gaggcacggt gtgagtgccg cctggaggtg cgagtgcctc agtga                   3825
```

<210> SEQ ID NO 340
<211> LENGTH: 1110
<212> TYPE: DNA
<213> ORGANISM: Artificial Sequence
<220> FEATURE:
<223> OTHER INFORMATION: dRNA/arRNA

<400> SEQUENCE: 340
atgttgaagc catcattacc attcacatcc ctcttattcc tgcagctgcc cctgctggga 60
gtggggctga acacgacaat tctgacgccc aatgggaatg aagacaccac agctgatttc 120
ttcctgacca ctatgcccac tgactccctc agtgtttcca ctctgcccct cccagaggtt 180
cagtgttttg tgttcaatgt cgagtacatg aattgcactt ggaacagcag ctctgagccc 240
cagcctacca acctcactct gcattattgg tacaagaact cggataatga taaagtccag 300
aagtgcagcc actatctatt ctctgaagaa atcacttctg gctgtcagtt gcaaaaaaag 360
gagatccacc tctaccaaac atttgttgtt cagctccagg acccacggga acccaggaga 420
caggccacac agatgctaaa actgcagaat ctggtgatcc cctgggctcc agagaaccta 480
acacttcaca aactgagtga atcccagcta gaactgaact ggaacaacag attcttgaac 540
cactgtttgg agcacttggt gcagtaccgg actgactggg accacagctg gactgaacaa 600
tcagtggatt atagacataa gttctccttg cctagtgtgg atgggcagaa acgctacacg 660
tttcgtgttc ggagccgctt taacccactc tgtggaagtg ctcagcattg gagtgaatgg 720
agccacccaa tccactgggg gagcaatact tcaaaagaga atcctttcct gtttgcattg 780
gaagccgtgg ttatctctgt tggctccatg ggattgatta tcagccttct ctgtgtgtat 840
ttctggctgg aacggacgat gccccgaatt cccaccctga agaacctaga ggatcttgtt 900
actgaatacc acgggaactt ttcggcctgg agtggtgtgt ctaagggact ggctgagagt 960
ctgcagccag actacagtga acgactctgc ctcgtcagtg agattccccc aaaaggaggg 1020
gcccttgggg aggggcctgg ggcctcccca tgcaaccagc atagccccta ctgggccccc 1080
ccatgttaca ccctaaagcc tgaaacctga 1110

<210> SEQ ID NO 341
<211> LENGTH: 108
<212> TYPE: RNA
<213> ORGANISM: Artificial Sequence
<220> FEATURE:
<223> OTHER INFORMATION: dRNA/arRNA

<400> SEQUENCE: 341
uaccgcuaca gccacgcuga uuucagcuau accugcccgg uauaaaggga cguucacacc 60
ggauguucuc cgcggggaua ucgcgauauu caggauuaaa agaagugc 108

<210> SEQ ID NO 342
<211> LENGTH: 91
<212> TYPE: DNA
<213> ORGANISM: Artificial Sequence
<220> FEATURE:
<223> OTHER INFORMATION: dRNA/arRNA

<400> SEQUENCE: 342
uaauccugaa uaucgcgcaa uuccccagca gagaacaucg cggugugaac gucccuuuau 60
accgggcagg uauagcugaa aucagcgugg c 91

<210> SEQ ID NO 343
<211> LENGTH: 71
<212> TYPE: RNA

<213> ORGANISM: Artificial Sequence
<220> FEATURE:
<223> OTHER INFORMATION: dRNA/arRNA

<400> SEQUENCE: 343
uuucagcuau accugcccgg uauaaaggga cguucacacc gcgauguucu cugcugggga 60
auugcgcgau a 71

<210> SEQ ID NO 344
<211> LENGTH: 91
<212> TYPE: RNA
<213> ORGANISM: Artificial Sequence
<220> FEATURE:
<223> OTHER INFORMATION: dRNA/arRNA

<400> SEQUENCE: 344
gugugguugc uguccaggac ggucccggcc ugcgacacuu cggcccagag cugcuccuca 60
ucugcggggc gggggggggc cgucgccgcg u 91

<210> SEQ ID NO 345
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 345
uguccaggac ggucccggcc ugcgacacuu cggcccagag cugcuccuca ucugcggggc 60
gggggggggc c 71

<210> SEQ ID NO 346
<211> LENGTH: 51
<212> TYPE: RNA
<213> ORGANISM: Artificial Sequence
<220> FEATURE:
<223> OTHER INFORMATION: dRNA/arRNA

<400> SEQUENCE: 346
ggucccggcc ugcgacacuu cggcccagag cugcuccuca ucugcggggc g 51

<210> SEQ ID NO 347
<211> LENGTH: 101
<212> TYPE: RNA
<213> ORGANISM: Artificial Sequence
<220> FEATURE:
<223> OTHER INFORMATION: dRNA/arRNA

<400> SEQUENCE: 347
gacgcccacc gugugguugc uguccaggac ggucccggcc ugcgacacuu cggcccagag 60
cugcuccuca ucugcggggc gggggggggc cgucgccgcg u 101

<210> SEQ ID NO 348
<211> LENGTH: 91
<212> TYPE: RNA
<213> ORGANISM: Artificial Sequence
<220> FEATURE:
<223> OTHER INFORMATION: dRNA/arRNA

<400> SEQUENCE: 348
gacgcccacc gugugguugc uguccaggac ggucccggcc ugcgacacuu cggcccagag 60
cugcuccuca ucugcggggc gggggggggc c 91

<210> SEQ ID NO 349
<211> LENGTH: 81
<212> TYPE: RNA
<213> ORGANISM: Artificial Sequence
<220> FEATURE:
<223> OTHER INFORMATION: dRNA/arRNA

<400> SEQUENCE: 349
gacgcccacc gugugguugc uguccaggac ggucccggcc ugcgacacuu cggcccagag 60
cugcuccuca ucugcggggc g 81

<210> SEQ ID NO 350
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 350
gacgcccacc gugugguugc uguccaggac ggucccggcc ugcgacacuu cggcccagag 60
cugcuccuca u 71

<210> SEQ ID NO 351
<211> LENGTH: 61
<212> TYPE: RNA
<213> ORGANISM: Artificial Sequence
<220> FEATURE:
<223> OTHER INFORMATION: dRNA/arRNA

<400> SEQUENCE: 351
gacgcccacc gugugguugc uguccaggac ggucccggcc ugcgacacuu cggcccagag 60
c 61

<210> SEQ ID NO 352
<211> LENGTH: 101
<212> TYPE: RNA
<213> ORGANISM: Artificial Sequence
<220> FEATURE:
<223> OTHER INFORMATION: dRNA/arRNA

<400> SEQUENCE: 352
gugugguugc uguccaggac ggucccggcc ugcgacacuu cggcccagag cugcuccuca 60
ucugcggggc gggggggggc cgucgccgcg uggggucguu g 101

<210> SEQ ID NO 353
<211> LENGTH: 91
<212> TYPE: RNA
<213> ORGANISM: Artificial Sequence
<220> FEATURE:
<223> OTHER INFORMATION: dRNA/arRNA

<400> SEQUENCE: 353
uguccaggac ggucccggcc ugcgacacuu cggcccagag cugcuccuca ucugcggggc 60
gggggggggc cgucgccgcg uggggucguu g 91

<210> SEQ ID NO 354
<211> LENGTH: 81
<212> TYPE: RNA
<213> ORGANISM: Artificial Sequence
<220> FEATURE:
<223> OTHER INFORMATION: dRNA/arRNA

<400> SEQUENCE: 354
ggucccggcc ugcgacacuu cggcccagag cugcuccuca ucugcggggc gggggggggc 60
cgucgccgcg uggggucguu g 81

<210> SEQ ID NO 355
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 355
ugcgacacuu cggcccagag cugcuccuca ucugcggggc gggggggggc cgucgccgcg 60
uggggucguu g 71

<210> SEQ ID NO 356
<211> LENGTH: 61
<212> TYPE: RNA
<213> ORGANISM: Artificial Sequence
<220> FEATURE:
<223> OTHER INFORMATION: dRNA/arRNA

<400> SEQUENCE: 356
cggcccagag cugcuccuca ucugcggggc gggggggggc cgucgccgcg uggggucguu 60
g 61

<210> SEQ ID NO 357
<211> LENGTH: 80
<212> TYPE: RNA
<213> ORGANISM: Artificial Sequence
<220> FEATURE:
<223> OTHER INFORMATION: dRNA/arRNA

<400> SEQUENCE: 357
gacgcccacc gugugguugc uguccaggac ggucccggcc ugcgacacuu cggcccagag 60
cugcuccuca ucugcggggc 80

<210> SEQ ID NO 358
<211> LENGTH: 79
<212> TYPE: RNA
<213> ORGANISM: Artificial Sequence
<220> FEATURE:
<223> OTHER INFORMATION: dRNA/arRNA

<400> SEQUENCE: 358
gacgcccacc gugugguugc uguccaggac ggucccggcc ugcgacacuu cggcccagag 60
cugcuccuca ucugcgggg 79

<210> SEQ ID NO 359
<211> LENGTH: 78
<212> TYPE: RNA
<213> ORGANISM: Artificial Sequence
<220> FEATURE:
<223> OTHER INFORMATION: dRNA/arRNA

<400> SEQUENCE: 359
gacgcccacc gugugguugc uguccaggac ggucccggcc ugcgacacuu cggcccagag 60
cugcuccuca ucugcggg 78

<210> SEQ ID NO 360
<211> LENGTH: 77
<212> TYPE: RNA
<213> ORGANISM: Artificial Sequence
<220> FEATURE:
<223> OTHER INFORMATION: dRNA/arRNA

<400> SEQUENCE: 360
gacgcccacc gugugguugc uguccaggac ggucccggcc ugcgacacuu cggcccagag 60
cugcuccuca ucugcgg 77

<210> SEQ ID NO 361
<211> LENGTH: 76
<212> TYPE: RNA
<213> ORGANISM: Artificial Sequence
<220> FEATURE:
<223> OTHER INFORMATION: dRNA/arRNA

<400> SEQUENCE: 361
gacgcccacc gugugguugc uguccaggac ggucccggcc ugcgacacuu cggcccagag 60
cugcuccuca ucugcg 76

<210> SEQ ID NO 362
<211> LENGTH: 75
<212> TYPE: RNA
<213> ORGANISM: Artificial Sequence
<220> FEATURE:
<223> OTHER INFORMATION: dRNA/arRNA

<400> SEQUENCE: 362
gacgcccacc gugugguugc uguccaggac ggucccggcc ugcgacacuu cggcccagag 60
cugcuccuca ucugc 75

<210> SEQ ID NO 363
<211> LENGTH: 74
<212> TYPE: RNA
<213> ORGANISM: Artificial Sequence
<220> FEATURE:
<223> OTHER INFORMATION: dRNA/arRNA

<400> SEQUENCE: 363
gacgcccacc gugugguugc uguccaggac ggucccggcc ugcgacacuu cggcccagag 60
cugcuccuca ucug 74

<210> SEQ ID NO 364
<211> LENGTH: 73
<212> TYPE: RNA
<213> ORGANISM: Artificial Sequence
<220> FEATURE:
<223> OTHER INFORMATION: dRNA/arRNA

<400> SEQUENCE: 364
gacgcccacc gugugguugc uguccaggac ggucccggcc ugcgacacuu cggcccagag 60
cugcuccuca ucu 73

<210> SEQ ID NO 365
<211> LENGTH: 72
<212> TYPE: RNA
<213> ORGANISM: Artificial Sequence
<220> FEATURE:
<223> OTHER INFORMATION: dRNA/arRNA

<400> SEQUENCE: 365
gacgcccacc gugugguugc uguccaggac ggucccggcc ugcgacacuu cggcccagag 60
cugcuccuca uc 72

<210> SEQ ID NO 366
<211> LENGTH: 70
<212> TYPE: RNA
<213> ORGANISM: Artificial Sequence
<220> FEATURE:
<223> OTHER INFORMATION: dRNA/arRNA

<400> SEQUENCE: 366
gacgcccacc gugugguugc uguccaggac ggucccggcc ugcgacacuu cggcccagag 60
cugcuccuca 70

<210> SEQ ID NO 367
<211> LENGTH: 69
<212> TYPE: RNA
<213> ORGANISM: Artificial Sequence
<220> FEATURE:
<223> OTHER INFORMATION: dRNA/arRNA

<400> SEQUENCE: 367
gacgcccacc gugugguugc uguccaggac ggucccggcc ugcgacacuu cggcccagag 60
cugcuccuc 69

<210> SEQ ID NO 368
<211> LENGTH: 68
<212> TYPE: RNA
<213> ORGANISM: Artificial Sequence
<220> FEATURE:
<223> OTHER INFORMATION: dRNA/arRNA

<400> SEQUENCE: 368
gacgcccacc gugugguugc uguccaggac ggucccggcc ugcgacacuu cggcccagag 60
cugcuccu 68

<210> SEQ ID NO 369
<211> LENGTH: 67
<212> TYPE: RNA
<213> ORGANISM: Artificial Sequence
<220> FEATURE:
<223> OTHER INFORMATION: dRNA/arRNA

<400> SEQUENCE: 369
gacgcccacc gugugguugc uguccaggac ggucccggcc ugcgacacuu cggcccagag 60
cugcucc 67

<210> SEQ ID NO 370
<211> LENGTH: 66
<212> TYPE: RNA
<213> ORGANISM: Artificial Sequence
<220> FEATURE:
<223> OTHER INFORMATION: dRNA/arRNA

<400> SEQUENCE: 370
gacgcccacc gugugguugc uguccaggac ggucccggcc ugcgacacuu cggcccagag 60
cugcuc 66

<210> SEQ ID NO 371
<211> LENGTH: 65
<212> TYPE: RNA
<213> ORGANISM: Artificial Sequence
<220> FEATURE:
<223> OTHER INFORMATION: dRNA/arRNA

<400> SEQUENCE: 371
gacgcccacc gugugguugc uguccaggac ggucccggcc ugcgacacuu cggcccagag 60
cugcu 65

<210> SEQ ID NO 372
<211> LENGTH: 64
<212> TYPE: RNA
<213> ORGANISM: Artificial Sequence
<220> FEATURE:
<223> OTHER INFORMATION: dRNA/arRNA

<400> SEQUENCE: 372
gacgcccacc gugugguugc uguccaggac ggucccggcc ugcgacacuu cggcccagag 60
cugc 64

<210> SEQ ID NO 373
<211> LENGTH: 63
<212> TYPE: RNA
<213> ORGANISM: Artificial Sequence
<220> FEATURE:
<223> OTHER INFORMATION: dRNA/arRNA

<400> SEQUENCE: 373
gacgcccacc gugugguugc uguccaggac ggucccggcc ugcgacacuu cggcccagag 60
cug 63

<210> SEQ ID NO 374
<211> LENGTH: 62
<212> TYPE: RNA
<213> ORGANISM: Artificial Sequence
<220> FEATURE:
<223> OTHER INFORMATION: dRNA/arRNA

<400> SEQUENCE: 374
gacgcccacc gugugguugc uguccaggac ggucccggcc ugcgacacuu cggcccagag 60
cu 62

<210> SEQ ID NO 375
<211> LENGTH: 61
<212> TYPE: RNA
<213> ORGANISM: Artificial Sequence
<220> FEATURE:
<223> OTHER INFORMATION: dRNA/arRNA

<400> SEQUENCE: 375
gacgcccacc gugugguugc uguccaggac ggucccggcc ugcgacacuu cggcccagag 60
c 61

<210> SEQ ID NO 376
<211> LENGTH: 70
<212> TYPE: RNA
<213> ORGANISM: Artificial Sequence
<220> FEATURE:
<223> OTHER INFORMATION: dRNA/arRNA

<400> SEQUENCE: 376
uaccgcuaca gccacgcuga uuucagcuau accugcccgg uauaaaggga cguucacacc 60
gcgauguucu 70

<210> SEQ ID NO 377
<211> LENGTH: 66
<212> TYPE: RNA

<213> ORGANISM: Artificial Sequence
<220> FEATURE:
<223> OTHER INFORMATION: dRNA/arRNA

<400> SEQUENCE: 377
uaccgcuaca gccacgcuga uuucagcuau accugcccgg uauaaaggga cguucacacc 60
gcgaug 66

<210> SEQ ID NO 378
<211> LENGTH: 71
<212> TYPE: RNA
<213> ORGANISM: Artificial Sequence
<220> FEATURE:
<223> OTHER INFORMATION: dRNA/arRNA

<400> SEQUENCE: 378
ccaccgugug guugcugucc aggacggucc cggccugcga cacuucggcc cagagcugcu 60
ccucaucugc g 71

<210> SEQ ID NO 379
<211> LENGTH: 66
<212> TYPE: RNA
<213> ORGANISM: Artificial Sequence
<220> FEATURE:
<223> OTHER INFORMATION: dRNA/arRNA

<400> SEQUENCE: 379
gugugguugc uguccaggac ggucccggcc ugcgacacuu cggcccagag cugcuccuca 60
ucugcg 66

<210> SEQ ID NO 380
<211> LENGTH: 61
<212> TYPE: RNA
<213> ORGANISM: Artificial Sequence
<220> FEATURE:
<223> OTHER INFORMATION: dRNA/arRNA

<400> SEQUENCE: 380
guugcugucc aggacggucc cggccugcga cacuucggcc cagagcugcu ccucaucugc 60
g 61

<210> SEQ ID NO 381
<211> LENGTH: 56
<212> TYPE: RNA
<213> ORGANISM: Artificial Sequence
<220> FEATURE:
<223> OTHER INFORMATION: dRNA/arRNA

<400> SEQUENCE: 381
uguccaggac ggucccggcc ugcgacacuu cggcccagag cugcuccuca ucugcg 56

<210> SEQ ID NO 382
<211> LENGTH: 66
<212> TYPE: RNA
<213> ORGANISM: Artificial Sequence
<220> FEATURE:
<223> OTHER INFORMATION: dRNA/arRNA

<400> SEQUENCE: 382
ccaccgugug guugcugucc aggacggucc cggccugcga cacuucggcc cagagcugcu 60
ccucau 66

<210> SEQ ID NO 383
<211> LENGTH: 61
<212> TYPE: RNA
<213> ORGANISM: Artificial Sequence
<220> FEATURE:
<223> OTHER INFORMATION: dRNA/arRNA

<400> SEQUENCE: 383
gugugguugc uguccaggac ggucccggcc ugcgacacuu cggcccagag cugcuccuca 60
u 61

<210> SEQ ID NO 384
<211> LENGTH: 56
<212> TYPE: RNA
<213> ORGANISM: Artificial Sequence
<220> FEATURE:
<223> OTHER INFORMATION: dRNA/arRNA

<400> SEQUENCE: 384
guugcugucc aggacggucc cggccugcga cacuucggcc cagagcugcu ccucau 56

<210> SEQ ID NO 385
<211> LENGTH: 51
<212> TYPE: RNA
<213> ORGANISM: Artificial Sequence
<220> FEATURE:
<223> OTHER INFORMATION: dRNA/arRNA

<400> SEQUENCE: 385
uguccaggac ggucccggcc ugcgacacuu cggcccagag cugcuccuca u 51

<210> SEQ ID NO 386
<211> LENGTH: 67
<212> TYPE: RNA
<213> ORGANISM: Artificial Sequence
<220> FEATURE:
<223> OTHER INFORMATION: dRNA/arRNA

<400> SEQUENCE: 386
acgcccaccg ugugguugcu guccaggacg gucccggccu gcgacacuuc ggcccagagc 60
ugcuccu 67

<210> SEQ ID NO 387
<211> LENGTH: 67
<212> TYPE: RNA
<213> ORGANISM: Artificial Sequence
<220> FEATURE:
<223> OTHER INFORMATION: dRNA/arRNA

<400> SEQUENCE: 387
cgcccaccgu gugguugcug uccaggacgg ucccggccug cgacacuucg gcccagagcu 60
gcuccuc 67

<210> SEQ ID NO 388
<211> LENGTH: 67
<212> TYPE: RNA
<213> ORGANISM: Artificial Sequence
<220> FEATURE:
<223> OTHER INFORMATION: dRNA/arRNA

<400> SEQUENCE: 388
gcccaccgug ugguugcugu ccaggacggu cccggccugc gacacuucgg cccagagcug 60
cuccuca 67

<210> SEQ ID NO 389
<211> LENGTH: 67
<212> TYPE: RNA
<213> ORGANISM: Artificial Sequence
<220> FEATURE:
<223> OTHER INFORMATION: dRNA/arRNA

<400> SEQUENCE: 389
cccaccgugu gguugcuguc caggacgguc ccggccugcg acacuucggc ccagagcugc 60
uccucau 67

<210> SEQ ID NO 390
<211> LENGTH: 67
<212> TYPE: RNA
<213> ORGANISM: Artificial Sequence
<220> FEATURE:
<223> OTHER INFORMATION: dRNA/arRNA

<400> SEQUENCE: 390
ccaccgugug guugcugucc aggacggucc cggccugcga cacuucggcc cagagcugcu 60
ccucauc 67

<210> SEQ ID NO 391
<211> LENGTH: 67
<212> TYPE: RNA
<213> ORGANISM: Artificial Sequence
<220> FEATURE:
<223> OTHER INFORMATION: dRNA/arRNA

<400> SEQUENCE: 391
caccgugugg uugcugucca ggacgguccc ggccugcgac acuucggccc agagcugcuc 60
cucaucu 67

<210> SEQ ID NO 392
<211> LENGTH: 67
<212> TYPE: RNA
<213> ORGANISM: Artificial Sequence
<220> FEATURE:
<223> OTHER INFORMATION: dRNA/arRNA

<400> SEQUENCE: 392 accgugugguu ugcuguccag gacgguccccg gccugcgaca cuucggccca gagcugcucc 60
ucaucug 67

<210> SEQ ID NO 393
<211> LENGTH: 67
<212> TYPE: RNA
<213> ORGANISM: Artificial Sequence
<220> FEATURE:
<223> OTHER INFORMATION: dRNA/arRNA

<400> SEQUENCE: 393
ccgugugguu gcuguccagg acggucccgg ccugcgacac uucggcccag agcugcuccu 60
caucugc 67

<210> SEQ ID NO 394
<211> LENGTH: 67
<212> TYPE: RNA
<213> ORGANISM: Artificial Sequence
<220> FEATURE:
<223> OTHER INFORMATION: dRNA/arRNA

<400> SEQUENCE: 394
cgugugguug cuguccagga cggucccggc cugcgacacu ucggcccaga gcugcuccuc 60
aucugcg 67

<210> SEQ ID NO 395
<211> LENGTH: 67
<212> TYPE: RNA
<213> ORGANISM: Artificial Sequence
<220> FEATURE:
<223> OTHER INFORMATION: dRNA/arRNA

<400> SEQUENCE: 395
gugugguugc uguccaggac ggucccggcc ugcgacacuu cggcccagag cugcuccuca 60
ucugcgg 67

<210> SEQ ID NO 396
<211> LENGTH: 67
<212> TYPE: RNA
<213> ORGANISM: Artificial Sequence
<220> FEATURE:
<223> OTHER INFORMATION: dRNA/arRNA

<400> SEQUENCE: 396
ugugguugcu guccaggacg gucccggccu gcgacacuuc ggcccagagc ugcuccucau 60
cugcggg 67

<210> SEQ ID NO 397
<211> LENGTH: 67
<212> TYPE: RNA
<213> ORGANISM: Artificial Sequence
<220> FEATURE:
<223> OTHER INFORMATION: dRNA/arRNA

<400> SEQUENCE: 397
gugguugcug uccaggacgg ucccggccug cgacacuucg gcccagagcu gcuccucauc 60
ugcgggg 67

<210> SEQ ID NO 398
<211> LENGTH: 70
<212> TYPE: RNA
<213> ORGANISM: Artificial Sequence
<220> FEATURE:
<223> OTHER INFORMATION: dRNA/arRNA

<400> SEQUENCE: 398
acgcccaccg ugugguugcu guccaggacg gucccggccu gcgacacuuc ggcccagagc 60
ugcuccucau 70

<210> SEQ ID NO 399
<211> LENGTH: 70
<212> TYPE: RNA
<213> ORGANISM: Artificial Sequence
<220> FEATURE:
<223> OTHER INFORMATION: dRNA/arRNA

<400> SEQUENCE: 399
cgcccaccgu gugguugcug uccaggacgg ucccggccug cgacacuucg gcccagagcu 60
gcuccucauc 70

<210> SEQ ID NO 400
<211> LENGTH: 70
<212> TYPE: RNA

```
<213> ORGANISM: Artificial Sequence
<220> FEATURE:
<223> OTHER INFORMATION: dRNA/arRNA

<400> SEQUENCE: 400

gcccaccgug ugguugcugu ccaggacggu cccggccugc gacacuucgg cccagagcug    60

cuccucaucu                                                           70

<210> SEQ ID NO 401
<211> LENGTH: 70
<212> TYPE: RNA
<213> ORGANISM: Artificial Sequence
<220> FEATURE:
<223> OTHER INFORMATION: dRNA/arRNA

<400> SEQUENCE: 401

cccaccgugu gguugcuguc caggacgguc ccggccugcg acacuucggc ccagagcugc    60

uccucaucug                                                           70

<210> SEQ ID NO 402
<211> LENGTH: 70
<212> TYPE: RNA
<213> ORGANISM: Artificial Sequence
<220> FEATURE:
<223> OTHER INFORMATION: dRNA/arRNA

<400> SEQUENCE: 402

ccaccgugug guugcugucc aggacggucc cggccugcga cacuucggcc cagagcugcu    60

ccucaucugc                                                           70

<210> SEQ ID NO 403
<211> LENGTH: 70
<212> TYPE: RNA
<213> ORGANISM: Artificial Sequence
<220> FEATURE:
<223> OTHER INFORMATION: dRNA/arRNA

<400> SEQUENCE: 403

caccgugugg uugcugucca ggacgguccc ggccugcgac acuucggccc agagcugcuc    60

cucaucugcg                                                           70

<210> SEQ ID NO 404
<211> LENGTH: 70
<212> TYPE: RNA
<213> ORGANISM: Artificial Sequence
<220> FEATURE:
<223> OTHER INFORMATION: dRNA/arRNA

<400> SEQUENCE: 404

accguguggu ugcuguccag gacgguvccg gccugcgaca cuucggccca gagcugcucc    60

ucaucugcgg                                                           70
```

```
<400> SEQUENCE: 404

accguguggu ugcuguccag gacggucccg gccugcgaca cuucggccca gagcugcucc    60

ucaucugcgg                                                           70

<210> SEQ ID NO 405
<211> LENGTH: 70
<212> TYPE: RNA
<213> ORGANISM: Artificial Sequence
<220> FEATURE:
<223> OTHER INFORMATION: dRNA/arRNA

<400> SEQUENCE: 405

ccgugugguu gcuguccagg acggucccgg ccugcgacac uucggcccag agcugcuccu    60

caucugcggg                                                           70
```

<210> SEQ ID NO 406
<211> LENGTH: 70
<212> TYPE: RNA
<213> ORGANISM: Artificial Sequence
<220> FEATURE:
<223> OTHER INFORMATION: dRNA/arRNA

<400> SEQUENCE: 406
cgugugguug cuguccagga cggucccggc cugcgacacu ucggcccaga gcugcuccuc 60
aucugcgggg 70

<210> SEQ ID NO 407
<211> LENGTH: 72
<212> TYPE: RNA
<213> ORGANISM: Artificial Sequence
<220> FEATURE:
<223> OTHER INFORMATION: dRNA/arRNA

<400> SEQUENCE: 407
acgcccaccg ugugguugcu guccaggacg gucccggccu gcgacacuuc ggcccagagc 60
ugcuccucau cu 72

<210> SEQ ID NO 408
<211> LENGTH: 72
<212> TYPE: RNA
<213> ORGANISM: Artificial Sequence
<220> FEATURE:
<223> OTHER INFORMATION: dRNA/arRNA

<400> SEQUENCE: 408
cgcccaccgu gugguugcug uccaggacgg ucccggccug cgacacuucg gcccagagcu 60
gcuccucauc ug 72

<210> SEQ ID NO 409
<211> LENGTH: 72
<212> TYPE: RNA
<213> ORGANISM: Artificial Sequence
<220> FEATURE:
<223> OTHER INFORMATION: dRNA/arRNA

<400> SEQUENCE: 409
gcccaccgug ugguugcugu ccaggacggu cccggccugc gacacuucgg cccagagcug 60
cuccucaucu gc 72

<210> SEQ ID NO 410
<211> LENGTH: 72
<212> TYPE: RNA
<213> ORGANISM: Artificial Sequence
<220> FEATURE:
<223> OTHER INFORMATION: dRNA/arRNA

<400> SEQUENCE: 410
cccaccgugu gguugcuguc caggacgguc ccggccugcg acacuucggc ccagagcugc 60
uccucaucug cg 72

<210> SEQ ID NO 411
<211> LENGTH: 72
<212> TYPE: RNA
<213> ORGANISM: Artificial Sequence
<220> FEATURE:
<223> OTHER INFORMATION: dRNA/arRNA

<400> SEQUENCE: 411
ccaccgugug guugcugucc aggacggucc cggccugcga cacuucggcc cagagcugcu 60
ccucaucugc gg 72

<210> SEQ ID NO 412
<211> LENGTH: 72
<212> TYPE: RNA
<213> ORGANISM: Artificial Sequence
<220> FEATURE:
<223> OTHER INFORMATION: dRNA/arRNA

<400> SEQUENCE: 412
caccgugugg uugcugucca ggacgguccc ggccugcgac acuucggccc agagcugcuc 60
cucaucugcg gg 72

<210> SEQ ID NO 413
<211> LENGTH: 72
<212> TYPE: RNA
<213> ORGANISM: Artificial Sequence
<220> FEATURE:
<223> OTHER INFORMATION: dRNA/arRNA

<400> SEQUENCE: 413
accguguggu ugcuguccag gacgguccccg gccugcgaca cuucggccca gagcugcucc 60
ucaucugcgg gg 72

<210> SEQ ID NO 414
<211> LENGTH: 50
<212> TYPE: RNA
<213> ORGANISM: Artificial Sequence
<220> FEATURE:
<223> OTHER INFORMATION: dRNA/arRNA

<400> SEQUENCE: 414
cuguccagga cggucccggc cugcgacacu ucggcccaga gcugcuccuc 50

<210> SEQ ID NO 415
<211> LENGTH: 20
<212> TYPE: DNA
<213> ORGANISM: Artificial Sequence
<220> FEATURE:
<223> OTHER INFORMATION: Forward primer: hIDUA-62F

<400> SEQUENCE: 415
ccttcctgag ctaccacccg 20

<210> SEQ ID NO 416
<211> LENGTH: 20
<212> TYPE: DNA
<213> ORGANISM: Artificial Sequence
<220> FEATURE:
<223> OTHER INFORMATION: Reverse primer: hIDUA-62R

<400> SEQUENCE: 416
ccagggctcg aactcggtag 20

<210> SEQ ID NO 417
<211> LENGTH: 111
<212> TYPE: DNA
<213> ORGANISM: Artificial Sequence
<220> FEATURE:
<223> OTHER INFORMATION: dRNA/arRNA

<400> SEQUENCE: 417
agcccaagga gcuggaaaau cuugaggugg agcuuccaga guuuguguua augaccacag 60
acucuccacu gaacccuugg aguuacaggc ucugacccga uauucguaga g 111

<210> SEQ ID NO 418
<211> LENGTH: 91
<212> TYPE: RNA
<213> ORGANISM: Artificial Sequence
<220> FEATURE:
<223> OTHER INFORMATION: Synthetic Construct

<400> SEQUENCE: 418
gcuggaaaau cuugaggugg agcuuccaga guuuguguua augaccacag acucuccacu 60
gaacccuugg aguuacaggc ucugacccga u 91

<210> SEQ ID NO 419
<211> LENGTH: 71
<212> TYPE: RNA
<213> ORGANISM: Artificial Sequence
<220> FEATURE:
<223> OTHER INFORMATION: Synthetic Construct

<400> SEQUENCE: 419
cuugaggugg agcuuccaga guuuguguua augaccacag acucuccacu gaacccuugg 60
aguuacaggc u 71

<210> SEQ ID NO 420
<211> LENGTH: 51
<212> TYPE: RNA
<213> ORGANISM: Artificial Sequence
<220> FEATURE:
<223> OTHER INFORMATION: Synthetic Construct

<400> SEQUENCE: 420
agcuuccaga guuuguguua augaccacag acucuccacu gaacccuugg a 51

<210> SEQ ID NO 421
<211> LENGTH: 101
<212> TYPE: RNA
<213> ORGANISM: Artificial Sequence
<220> FEATURE:
<223> OTHER INFORMATION: Synthetic Construct

<400> SEQUENCE: 421
agcccaagga gcuggaaaau cuugaggugg agcuuccaga guuuguguua augaccacag 60
acucuccacu gaacccuugg aguuacaggc ucugacccga u 101

<210> SEQ ID NO 422
<211> LENGTH: 91
<212> TYPE: RNA
<213> ORGANISM: Artificial Sequence
<220> FEATURE:
<223> OTHER INFORMATION: Synthetic Construct

<400> SEQUENCE: 422
agcccaagga gcuggaaaau cuugaggugg agcuuccaga guuuguguua augaccacag 60
acucuccacu gaacccuugg aguuacaggc u 91

<210> SEQ ID NO 423
<211> LENGTH: 81
<212> TYPE: RNA
<213> ORGANISM: Artificial Sequence
<220> FEATURE:

<223> OTHER INFORMATION: Synthetic Construct

<400> SEQUENCE: 423
agcccaagga gcuggaaaau cuugaggugg agcuuccaga guuuguguua augaccacag 60
acucuccacu gaacccuugg a 81

<210> SEQ ID NO 424
<211> LENGTH: 71
<212> TYPE: RNA
<213> ORGANISM: Artificial Sequence
<220> FEATURE:
<223> OTHER INFORMATION: Synthetic Construct

<400> SEQUENCE: 424
agcccaagga gcuggaaaau cuugaggugg agcuuccaga guuuguguua augaccacag 60
acucuccacu g 71

<210> SEQ ID NO 425
<211> LENGTH: 61
<212> TYPE: RNA
<213> ORGANISM: Artificial Sequence
<220> FEATURE:
<223> OTHER INFORMATION: Synthetic Construct

<400> SEQUENCE: 425
agcccaagga gcuggaaaau cuugaggugg agcuuccaga guuuguguua augaccacag 60
a 61

<210> SEQ ID NO 426
<211> LENGTH: 101
<212> TYPE: RNA
<213> ORGANISM: Artificial Sequence
<220> FEATURE:
<223> OTHER INFORMATION: Synthetic Construct

<400> SEQUENCE: 426
gcuggaaaau cuugaggugg agcuuccaga guuuguguua augaccacag acucuccacu 60
gaacccuugg aguuacaggc ucugacccga uauucguaga g 101

<210> SEQ ID NO 427
<211> LENGTH: 91
<212> TYPE: RNA
<213> ORGANISM: Artificial Sequence
<220> FEATURE:
<223> OTHER INFORMATION: Synthetic Construct

<400> SEQUENCE: 427
cuugaggugg agcuuccaga guuuguguua augaccacag acucuccacu gaacccuugg 60
aguuacaggc ucugacccga uauucguaga g 91

<210> SEQ ID NO 428
<211> LENGTH: 81
<212> TYPE: RNA
<213> ORGANISM: Artificial Sequence
<220> FEATURE:
<223> OTHER INFORMATION: Synthetic Construct

<400> SEQUENCE: 428
agcuuccaga guuuguguua augaccacag acucuccacu gaacccuugg aguuacaggc 60
ucugacccga uauucguaga g 81

<210> SEQ ID NO 429
<211> LENGTH: 71
<212> TYPE: RNA
<213> ORGANISM: Artificial Sequence
<220> FEATURE:
<223> OTHER INFORMATION: Synthetic Construct

<400> SEQUENCE: 429
guuuguguua augaccacag acucuccacu gaacccuugg aguuacaggc ucugacccga 60
uauucguaga g 71

<210> SEQ ID NO 430
<211> LENGTH: 61
<212> TYPE: RNA
<213> ORGANISM: Artificial Sequence
<220> FEATURE:
<223> OTHER INFORMATION: Synthetic Construct

<400> SEQUENCE: 430
augaccacag acucuccacu gaacccuugg aguuacaggc ucugacccga uauucguaga 60
g 61

<210> SEQ ID NO 431
<211> LENGTH: 76
<212> TYPE: RNA
<213> ORGANISM: Artificial Sequence
<220> FEATURE:
<223> OTHER INFORMATION: Synthetic Construct

<400> SEQUENCE: 431
aaggagcugg aaaaucuuga gguggagcuu ccagaguuug uguuaaugac cacagacucu 60
ccacugaacc cuugga 76

<210> SEQ ID NO 432
<211> LENGTH: 71
<212> TYPE: RNA
<213> ORGANISM: Artificial Sequence
<220> FEATURE:
<223> OTHER INFORMATION: Synthetic Construct

<400> SEQUENCE: 432
gcuggaaaau cuugaggugg agcuuccaga guuuguguua augaccacag acucuccacu 60
gaacccuugg a 71

<210> SEQ ID NO 433
<211> LENGTH: 66
<212> TYPE: RNA
<213> ORGANISM: Artificial Sequence
<220> FEATURE:
<223> OTHER INFORMATION: Synthetic Construct

<400> SEQUENCE: 433
aaaaucuuga gguggagcuu ccagaguuug uguuaaugac cacagacucu ccacugaacc 60
cuugga 66

<210> SEQ ID NO 434
<211> LENGTH: 61
<212> TYPE: RNA
<213> ORGANISM: Artificial Sequence
<220> FEATURE:
<223> OTHER INFORMATION: Synthetic Construct

<400> SEQUENCE: 434

-continued

```
cuugaggugg agcuuccaga guuuguguua augaccacag acucuccacu gaacccuugg     60

a                                                                     61


<210> SEQ ID NO 435
<211> LENGTH: 56
<212> TYPE: RNA
<213> ORGANISM: Artificial Sequence
<220> FEATURE:
<223> OTHER INFORMATION: Synthetic Construct

<400> SEQUENCE: 435

gguggagcuu ccagaguuug uguuaaugac cacagacucu ccacugaacc cuugga         56


<210> SEQ ID NO 436
<211> LENGTH: 81
<212> TYPE: RNA
<213> ORGANISM: Artificial Sequence
<220> FEATURE:
<223> OTHER INFORMATION: Synthetic Construct

<400> SEQUENCE: 436

ggaggcagcg gcggaggagg cagcgccugc ucgcgaugcu agagggcucu gccagugagc     60

aagggcgagg agcuguucac c                                               81


<210> SEQ ID NO 437
<211> LENGTH: 151
<212> TYPE: DNA
<213> ORGANISM: Artificial Sequence
<220> FEATURE:
<223> OTHER INFORMATION: Synthetic Construct

<400> SEQUENCE: 437

cggcgcccgc cgcccgcccg gagcccgcga gcaaccccag ucccccccac ccgcgcgugg     60

cggcgccggc ucccuagcca ccgcggcccc acccucuucc ggccucagcu guccgggcug    120

cuuucgccuc cgccugugga ugcugcgcct c                                   151


<210> SEQ ID NO 438
<211> LENGTH: 111
<212> TYPE: RNA
<213> ORGANISM: Artificial Sequence
<220> FEATURE:
<223> OTHER INFORMATION: Synthetic Construct

<400> SEQUENCE: 438

gcucccaggu gcgggagaga ggccugcuga aaaugacuga auauaaacuu gugguaguug     60

gagcuggugg cguaggcaag agugccuuga cgauacagcu aauucagaau c             111


<210> SEQ ID NO 439
<211> LENGTH: 43
<212> TYPE: DNA
<213> ORGANISM: Artificial Sequence
<220> FEATURE:
<223> OTHER INFORMATION: Synthetic Construct

<400> SEQUENCE: 439

ccacctgttc attacaatgg cccctcaaaa tgaaaatggc cag                       43


<210> SEQ ID NO 440
<211> LENGTH: 60
<212> TYPE: DNA
<213> ORGANISM: Artificial Sequence
<220> FEATURE:
<223> OTHER INFORMATION: Synthetic Construct
```

<400> SEQUENCE: 440
gaccggtaaa agtttcagtt gtatgggacg aaaactcccc ggtaacatta cttgtccacc 60

<210> SEQ ID NO 441
<211> LENGTH: 61
<212> TYPE: DNA
<213> ORGANISM: Artificial Sequence
<220> FEATURE:
<223> OTHER INFORMATION: Synthetic Construct

<400> SEQUENCE: 441
ccacctgttc attacaatgg cccctcaaaa agcagggtat gttgactttg aaaatggcca 60
g 61

<210> SEQ ID NO 442
<211> LENGTH: 39
<212> TYPE: DNA
<213> ORGANISM: Artificial Sequence
<220> FEATURE:
<223> OTHER INFORMATION: Synthetic Construct

<400> SEQUENCE: 442
agcgcctgct cgcgatgcta gagggctctg ccagtgagc 39

<210> SEQ ID NO 443
<211> LENGTH: 75
<212> TYPE: RNA
<213> ORGANISM: Artificial Sequence
<220> FEATURE:
<223> OTHER INFORMATION: Synthetic Construct

<400> SEQUENCE: 443
agcggcggag gaggcagcgc cugcucgcga ugcuagaggg cucugccagu gagcaagggc 60
gaggagcugu ucacc 75

<210> SEQ ID NO 444
<211> LENGTH: 39
<212> TYPE: DNA
<213> ORGANISM: Artificial Sequence
<220> FEATURE:
<223> OTHER INFORMATION: Synthetic Construct

<400> SEQUENCE: 444
agcgcctgct cgcgatgcta gagggctctg ccagtgagc 39

<210> SEQ ID NO 445
<211> LENGTH: 78
<212> TYPE: RNA
<213> ORGANISM: Artificial Sequence
<220> FEATURE:
<223> OTHER INFORMATION: Synthetic Construct

<400> SEQUENCE: 445
ggcagcggcg gaggaggcag cgccugcucg cgaugcuaga gggcucugcc agugagcaag 60
ggcgaggagc uguucacc 78

<210> SEQ ID NO 446
<211> LENGTH: 71
<212> TYPE: RNA
<213> ORGANISM: Artificial Sequence
<220> FEATURE:
<223> OTHER INFORMATION: Synthetic Construct

```
<400> SEQUENCE: 446

acagcuccuc gcccuugcuc acuggcagag cccuccagca ucgcgagcag gcgcugccuc    60

cuccgccgcu g                                                          71

<210> SEQ ID NO 447
<211> LENGTH: 78
<212> TYPE: RNA
<213> ORGANISM: Artificial Sequence
<220> FEATURE:
<223> OTHER INFORMATION: Synthetic Construct

<400> SEQUENCE: 447

ggaggcagca gaagguauac acgccggaag aaucuguaga gaucccggu cgccaccgug     60

agcaagggcg aggagcug                                                   78

<210> SEQ ID NO 448
<211> LENGTH: 71
<212> TYPE: RNA
<213> ORGANISM: Artificial Sequence
<220> FEATURE:
<223> OTHER INFORMATION: Synthetic Construct

<400> SEQUENCE: 448

ccucgcccuu gcucacggug gcgaccgggg aucuccacag auucuuccgg cguguauacc     60

uucugcugcc u                                                          71

<210> SEQ ID NO 449
<211> LENGTH: 112
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 55, 57
<223> OTHER INFORMATION: n = a, c, g, t or u

<400> SEQUENCE: 449

auggacgagc uguacaagcu gcagggcgga ggaggcagcg ccugcucgcg augcnanagg     60

gcucugccag ugagcaaggg cgaggagcug uucaccgggg uggugcccau cc            112

<210> SEQ ID NO 450
<211> LENGTH: 111
<212> TYPE: RNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 55, 57
<223> OTHER INFORMATION: n = a, c, g, t or u

<400> SEQUENCE: 450

gaugggcacc accccgguga acagcuccuc gcccuugcuc acuggcagag cccuncngca     60

ucgcgagcag gcgcugccuc cuccgcccug cagcuuguac agcucgucca u             111

<210> SEQ ID NO 451
<211> LENGTH: 151
<212> TYPE: RNA
<213> ORGANISM: Artificial Sequence
<220> FEATURE:
<223> OTHER INFORMATION: Synthetic Construct

<400> SEQUENCE: 451
```

cggcgcccgc cgcccgcccg gagcccgcga gcaaccccag ucccccccac ccgcgcgugg 60
cggcgccggc ucccuagcca ccgcggcccc acccucuucc ggccucagcu guccgggcug 120
cuuucgccuc cgccugugga ugcugcgccu c 151

<210> SEQ ID NO 452
<211> LENGTH: 151
<212> TYPE: RNA
<213> ORGANISM: Artificial Sequence
<220> FEATURE:
<223> OTHER INFORMATION: Synthetic Construct

<400> SEQUENCE: 452
gcggggccag aggcucagcg gcucccaggu gcgggagaga ggccugcuga aaaugacuga 60
auauaaacuu gugguaguug gagcuggugg cguaggcaag agugccuuga cgauacagcu 120
aauucagaau cauuuugugg acgaauauga u 151

<210> SEQ ID NO 453
<211> LENGTH: 151
<212> TYPE: RNA
<213> ORGANISM: Artificial Sequence
<220> FEATURE:
<223> OTHER INFORMATION: Synthetic Construct

<400> SEQUENCE: 453
ggauuaccca agacagagca ucaaagaaac accuugcugg auugaaauuc acuuacaccg 60
ggcccuccag cuccuagacg aaguacuuca uaccaugccg auugcagacc cacaaccuuu 120
agacugaggu cuuuuaccgu uggggcccuu a 151

<210> SEQ ID NO 454
<211> LENGTH: 151
<212> TYPE: RNA
<213> ORGANISM: Artificial Sequence
<220> FEATURE:
<223> OTHER INFORMATION: Synthetic Construct

<400> SEQUENCE: 454
cugcggaggu cccuuugaga gcugguuccu guucauucac uucggaggau gggcugagau 60
gguggcagag caauuacuga ugucggcagc cgaacccccc acggcccugc uguggcucuu 120
ggccuucuac uacggccccc gugaugggag g 151

<210> SEQ ID NO 455
<211> LENGTH: 29
<212> TYPE: RNA
<213> ORGANISM: Artificial Sequence
<220> FEATURE:
<223> OTHER INFORMATION: Synthetic Construct

<400> SEQUENCE: 455
gcccggagcc cgcgggcacc ccgaguccc 29

<210> SEQ ID NO 456
<211> LENGTH: 29
<212> TYPE: RNA
<213> ORGANISM: Artificial Sequence
<220> FEATURE:
<223> OTHER INFORMATION: Synthetic Construct

<400> SEQUENCE: 456
gggacugggg uugcucgcgg gcuccgggc 29

<210> SEQ ID NO 457
<211> LENGTH: 24
<212> TYPE: RNA
<213> ORGANISM: Artificial Sequence
<220> FEATURE:
<223> OTHER INFORMATION: Synthetic Construct

<400> SEQUENCE: 457
gauguuggca gccgaaccac ccac 24

<210> SEQ ID NO 458
<211> LENGTH: 24
<212> TYPE: RNA
<213> ORGANISM: Artificial Sequence
<220> FEATURE:
<223> OTHER INFORMATION: Synthetic Construct

<400> SEQUENCE: 458
gugggggguu cggcugccga cauc 24

<210> SEQ ID NO 459
<211> LENGTH: 24
<212> TYPE: RNA
<213> ORGANISM: Artificial Sequence
<220> FEATURE:
<223> OTHER INFORMATION: Synthetic Construct

<400> SEQUENCE: 459
uuccuguuca uucacuuugg aaga 24

<210> SEQ ID NO 460
<211> LENGTH: 24
<212> TYPE: RNA
<213> ORGANISM: Artificial Sequence
<220> FEATURE:
<223> OTHER INFORMATION: Synthetic Construct

<400> SEQUENCE: 460
uccuccgaag ugaaugaaca ggaa 24

<210> SEQ ID NO 461
<211> LENGTH: 24
<212> TYPE: RNA
<213> ORGANISM: Artificial Sequence
<220> FEATURE:
<223> OTHER INFORMATION: Synthetic Construct

<400> SEQUENCE: 461
ccucccaugg cccugcugug gcuc 24

<210> SEQ ID NO 462
<211> LENGTH: 24
<212> TYPE: RNA
<213> ORGANISM: Artificial Sequence
<220> FEATURE:
<223> OTHER INFORMATION: Synthetic Construct

<400> SEQUENCE: 462
gagccacagc agggccgugg gggg 24

<210> SEQ ID NO 463
<211> LENGTH: 111
<212> TYPE: RNA
<213> ORGANISM: Artificial Sequence
<220> FEATURE:
<223> OTHER INFORMATION: Synthetic Construct

<400> SEQUENCE: 463
uugccguccc aagcaaugga ugauuugaug cuguccccgg acgauauuga acaauaguuc 60
acugaagacc cagguccaga ugaagcuccc agaaugccag aggcugcucc c 111

<210> SEQ ID NO 464
<211> LENGTH: 111
<212> TYPE: RNA
<213> ORGANISM: Artificial Sequence
<220> FEATURE:
<223> OTHER INFORMATION: Synthetic Construct

<400> SEQUENCE: 464
uugccguccc aagcaaugga ugauuugaug cuguccccgg acgauauuga acaauaguuc 60
acugaagacc cagguccaga ugaagcuccc agaaugccag aggcugcucc c 111

<210> SEQ ID NO 465
<211> LENGTH: 121
<212> TYPE: RNA
<213> ORGANISM: Artificial Sequence
<220> FEATURE:
<223> OTHER INFORMATION: Synthetic Construct

<400> SEQUENCE: 465
ccgcuagaaa cugcagagac cugaaauucu gccauccuga acucaagagu ggagaauacu 60
agguugaccc uaaccaagga ugcaaauugg augcuaucaa gguauucugu aauauggaaa 120
c 121

<210> SEQ ID NO 466
<211> LENGTH: 111
<212> TYPE: RNA
<213> ORGANISM: Artificial Sequence
<220> FEATURE:
<223> OTHER INFORMATION: Synthetic Construct

<400> SEQUENCE: 466
cauauuacag aauaccuuga uagcauccaa uuugcauccu ugguuagggu caacccagua 60
uucuccacuc uugaguucag gauggcagaa uuucaggucu cugcaguuuc u 111

<210> SEQ ID NO 467
<211> LENGTH: 121
<212> TYPE: RNA
<213> ORGANISM: Artificial Sequence
<220> FEATURE:
<223> OTHER INFORMATION: Synthetic Construct

<400> SEQUENCE: 467
ugauggagua cuaucccaau ggaucuuuau gcaaguauuu aagucuccac acaagugacu 60
agguaagcuc uugccgucuu gcucauucug uuacuagagg acuggcuuau cuucacacag 120
a 121

<210> SEQ ID NO 468
<211> LENGTH: 111
<212> TYPE: RNA
<213> ORGANISM: Artificial Sequence
<220> FEATURE:
<223> OTHER INFORMATION: Synthetic Construct

<400> SEQUENCE: 468
gugaagauaa gccaguccuc uaguaacaga augagcaaga cggcaagagc uuacccaguc 60

-continued acuugugugg agacuuaaau acuugcauaa agauccauug ggauaguacu c 111

<210> SEQ ID NO 469
<211> LENGTH: 121
<212> TYPE: RNA
<213> ORGANISM: Artificial Sequence
<220> FEATURE:
<223> OTHER INFORMATION: Synthetic Construct

<400> SEQUENCE: 469
uccauccagc uguaagagag cuaguaguua caggaugcua ugauuccaug auacggauau 60
agaaaguuga gaugagagaa gauucugcca uauugguccg acaguuugac guucacaaaa 120
g 121

<210> SEQ ID NO 470
<211> LENGTH: 111
<212> TYPE: RNA
<213> ORGANISM: Artificial Sequence
<220> FEATURE:
<223> OTHER INFORMATION: Synthetic Construct

<400> SEQUENCE: 470
gugaacguca aacugucgga ccaauauggc agaaucuucu cucaucucaa cuuuccauau 60
ccguaucaug gaaucauagc auccuguaac uacuagcucu cuuacagcug g 111

<210> SEQ ID NO 471
<211> LENGTH: 121
<212> TYPE: RNA
<213> ORGANISM: Artificial Sequence
<220> FEATURE:
<223> OTHER INFORMATION: Synthetic Construct

<400> SEQUENCE: 471
ugaucaggca ccuucuccuc aacuuccugc ucugggcucc uggaggccac acgaucgccu 60
aggaugucau cacccugaug gcucacacug cugagauaac ucacgagauc auuggcuuuc 120
u 121

<210> SEQ ID NO 472
<211> LENGTH: 111
<212> TYPE: RNA
<213> ORGANISM: Artificial Sequence
<220> FEATURE:
<223> OTHER INFORMATION: Synthetic Construct

<400> SEQUENCE: 472
gccaaugauc ucgugaguua ucucagcagu gugagccauc agggugauga caucccaggc 60
gaucgugugg ccuccaggag cccagagcag gaaguugagg agaaggugcc u 111

<210> SEQ ID NO 473
<211> LENGTH: 121
<212> TYPE: RNA
<213> ORGANISM: Artificial Sequence
<220> FEATURE:
<223> OTHER INFORMATION: Synthetic Construct

<400> SEQUENCE: 473
ggggucuuaa uguggcucug gaguggaagc caccccagga ugucggcaac acggagcucu 60 aggggguacac agugcagaaa gccgacaaga agaccaugga gugguucacc gucuuggagc 120
a 121

<210> SEQ ID NO 474
<211> LENGTH: 111
<212> TYPE: RNA
<213> ORGANISM: Artificial Sequence
<220> FEATURE:
<223> OTHER INFORMATION: Synthetic Construct

<400> SEQUENCE: 474
caagacggug aaccacucca uggucuucuu gucggcuuuc ugcacugugu acccccagag 60
cuccguguug ccgacauccu gggguggcuu ccacuccaga gccacauuaa g 111

<210> SEQ ID NO 475
<211> LENGTH: 121
<212> TYPE: RNA
<213> ORGANISM: Artificial Sequence
<220> FEATURE:
<223> OTHER INFORMATION: Synthetic Construct

<400> SEQUENCE: 475
aacgcuacac guuucguguu cggagccgcu uuaacccacu cuguggaagu gcucagcauu 60
agagugaaug gagccaccca auccacuggg ggagcaauac uucaaaagag aauccuuucc 120
u 121

<210> SEQ ID NO 476
<211> LENGTH: 111
<212> TYPE: RNA
<213> ORGANISM: Artificial Sequence
<220> FEATURE:
<223> OTHER INFORMATION: Synthetic Construct

<400> SEQUENCE: 476
aggauucucu uuugaaguau ugcuccccca guggauuggg uggcuccauu cacuccaaug 60
cugagcacuu ccacagagug gguuaaagcg gcuccgaaca cgaaacgugu a 111

<210> SEQ ID NO 477
<211> LENGTH: 111
<212> TYPE: RNA
<213> ORGANISM: Artificial Sequence
<220> FEATURE:
<223> OTHER INFORMATION: Synthetic Construct

<400> SEQUENCE: 477
gagcccgcga gcaaccccag ucccccccac ccgcgcgugg cggcgccggc ucccuagcca 60
ccgcggcccc acccucuucc ggccucagcu guccgggcug cuuucgccuc c 111

<210> SEQ ID NO 478
<211> LENGTH: 111
<212> TYPE: RNA
<213> ORGANISM: Artificial Sequence
<220> FEATURE:
<223> OTHER INFORMATION: Synthetic Construct

<400> SEQUENCE: 478
ccaggcgaaa gcagcccgga cagcugaggc cggaagaggg uggggccgcg guggccaggg 60
agccggcgcc gccacgcgcg ggugggggggg acuggggguug cucgcgggcu c 111

<210> SEQ ID NO 479
<211> LENGTH: 111
<212> TYPE: RNA
<213> ORGANISM: Artificial Sequence
<220> FEATURE:
<223> OTHER INFORMATION: Synthetic Construct

<400> SEQUENCE: 479
aagccggugc ucacggccau ggggcugcug gcgcugcugg augaggagca gcucuaggcc 60
gaagugucgc aggccgggac cguccuggac agcaaccaca cggugggcgu c 111

<210> SEQ ID NO 480
<211> LENGTH: 111
<212> TYPE: RNA
<213> ORGANISM: Artificial Sequence
<220> FEATURE:
<223> OTHER INFORMATION: Synthetic Construct

<400> SEQUENCE: 480
caacgacccc acgcggcgac ggcccccccc cgccccgcag augaggagca gcucuaggcc 60
gaagugucgc aggccgggac cguccuggac agcaaccaca cggugggcgu c 111

<210> SEQ ID NO 481
<211> LENGTH: 13
<212> TYPE: PRT
<213> ORGANISM: Artificial Sequence
<220> FEATURE:
<223> OTHER INFORMATION: Synthetic Construct

<400> SEQUENCE: 481

Gly Gly Ser Gly Gly Gly Gly Ser Ala Cys Ser Arg Cys
1 5 10

<210> SEQ ID NO 482
<211> LENGTH: 13
<212> TYPE: PRT
<213> ORGANISM: Artificial Sequence
<220> FEATURE:
<223> OTHER INFORMATION: Synthetic Construct

<400> SEQUENCE: 482

Glu Leu Phe Thr Val Ser Lys Gly Glu Glu Leu Phe Thr
1 5 10

<210> SEQ ID NO 483
<211> LENGTH: 4770
<212> TYPE: DNA
<213> ORGANISM: Artificial Sequence
<220> FEATURE:
<223> OTHER INFORMATION: pLenti-dCas13-ADAR1DD

<400> SEQUENCE: 483
atggtggatt acaaggatga cgacgataag atgaaagtga cgaaggtagg aggcatttcg 60
cataagaagt acacgtccga aggccgctta gtgaagtcag aatcggaaga aaatcgcaca 120
gacgaacgtc tgtcggcgtt gcttaatatg cgccttgaca tgtatatcaa gaatcccagc 180
agcacggaaa ccaaggaaaa tcaaaaacgc attgggaaat taaagaaatt cttctcaaac 240
aaaatggtct atcttaaaga caataccttg agtttgaaga atgggaaaaa ggagaacatt 300
gatcgtgagt attctgagac tgacatcctt gagagcgatg tccgtgacaa gaaaaacttc 360
gccgtgttga aaaagatcta tctgaatgaa aacgtgaact cggaggaatt ggaagttttt 420
cgtaacgaca ttaagaagaa actgaacaaa atcaacagcc tgaagtactc atttgaaaag 480
aataaggcga attatcaaaa gattaatgag aataacatcg agaaggttga aggtaagtca 540
aagcgtaaca ttatttacga ttattatcgt gagtcagcga aacgtgacgc ttatgtaagc 600
aatgtgaaag aagcctttga taagctttac aaggaagagg acattgcaaa acttgttctt 660
gaaattgaga accttacgaa gttagagaaa tacaagattc gcgagttcta ccacgaaatt 720
attggacgta agaatgacaa ggaaaacttt gcaaaaatca tctacgaaga aatccagaat 780
gttaataaca tgaaagagtt gatcgagaag gtaccggaca tgagtgagtt gaaaaagagc 840
caagtatttt acaagtatta cttagacaaa gaagagttga acgacaagaa catcaaatac 900
gcgttttgtc atttcgtgga aatcgaaatg agtcagttgc tgaagaacta cgtatataag 960
cgcttaagta atatctcgaa tgacaaaatt aagcgtatct ttgaatacca gaacttgaaa 1020
aaattgatcg aaaataagct gttaaacaaa cttgacacgt acgtccgtaa ttgtggaaag 1080
tataattatt atttgcaaga cggcgaaatt gccacttcag atttcatcgc ccgcaaccgt 1140
cagaatgaag cgtttcttcg caacatcatt ggggtgtcat ctgtggccta cttttctctt 1200
cgcaacattc ttgaaacgga gaacgagaat gatattactg ggcgtatgcg cggcaaaaca 1260
gttaagaaca ataaaggtga agagaagtac gtgtccggag aagttgataa gatctataat 1320
gaaaataaga agaacgaggt taaggagaac ttaaaaatgt tctattcgta cgatttcaat 1380
atggacaaca agaatgaaat cgaagatttc ttcgccaaca tcgacgaggc gatttcttcc 1440
atcgctcacg gtattgtcgc cttcaacttg gaattagaag gtaaggatat ctttgcgttc 1500
aagaacattg cgccatccga aatctcaaag aagatgtttc agaatgagat taacgagaaa 1560
aaactgaaat tgaagatctt tcgtcaactg aactctgcca acgtgttccg ctatctcgaa 1620
aagtataaaa ttctgaatta ccttaaacgt acacgcttcg agtttgtcaa taaaaatatc 1680
ccattcgtcc cgtctttcac caaattatat tcgcgcattg atgacctgaa gaatagtctt 1740
gggatttact ggaaaactcc gaaaacaaac gacgacaata agactaagga gattattgat 1800
gcccaaatct atttgcttaa aaacatctat tacggggagt tcctgaatta tttcatgtcg 1860
aacaatggta atttctttga gatttctaaa gaaatcatcg aattgaacaa gaacgataaa 1920
cgcaacttaa agactgggtt ttacaagctg caaaagtttg aagacatcca ggagaagatt 1980
ccaaaggaat acttggcgaa tatccagtcc ctgtacatga ttaatgccgg taatcaggac 2040
gaagaagaaa aggacactta tattgatttc attcaaaaga tcttcttaaa gggatttatg 2100
acgtatcttg ctaataacgg tcgtttaagt ctgatttaca tcggctcgga tgaagaaaca 2160
aatacgtcat tagcagaaaa gaagcaagag tttgacaagt tcttgaagaa gtacgagcag 2220
aacaataata tcaagatccc ctatgagatc aatgaattcc tgcgtgagat caaactggga 2280
aacatcctga agtatactga gcgtttaaac atgttctacc ttatcttaaa gcttttgaat 2340
cacaaggagc tgacaaatct gaagggtagt cttgaaaaat atcagtctgc caataaggaa 2400
gaagcgttct ctgaccaatt ggagttaatt aacctgctta accttgacaa caaccgcgtg 2460
acggaagact tcgaattaga ggccgacgag attggaaaat ttcttgattt caatggcaac 2520
aaagttaagg ataacaagga actgaaaaag ttcgatacaa acaagatcta ctttgacggc 2580
gagaacatta tcaaacaccg tgccttctac aatattaaga aatatggcat gttaaactta 2640
ctggagaaaa ttgccgacaa ggctggatac aagatctcga tcgaagagct gaagaaatac 2700
tccaataaaa agaatgagat cgagaagaac cataagatgc aggaaaatct gcaccgcaaa 2760
tacgctcgtc cccgtaaaga cgagaagttt acagatgagg actatgaaag ttacaagcaa 2820
gctattgaga atattgagga gtacacccac cttaagaaca aggtagaatt caatgagctg 2880
aatttactgc agggcctgtt gctgcgcatt ttacatcgtt tagtcggata tacctcaatt 2940
tgggaacgcg atctgcgctt ccgccttaaa ggtgagttcc cagaaaacca atacatcgaa 3000
gagatcttca actttgaaaa taagaagaac gtgaagtaca aagggggtca gattgtagag 3060

-continued

```
aaatacatta aattctacaa ggaattacat caaaatgatg aagttaagat caacaagtac   3120

agttccgcga atatcaaggt gttgaagcaa gaaaagaagg acctttatat tgctaattac   3180

atcgccgcat tcaattatat tcctcacgcc gagatctcac tgctggaagt ccttgaaaat   3240

ttgcgtaaat tgctgtccta cgatcgcaaa ctgaaaaatg ccgtaatgaa atcagtagtt   3300

gatatcctta aggagtatgg ttttgtagcc acattcaaaa tcggggcgga caagaagatc   3360

ggtattcaga cactggagag cgaaaaaatc gtgcatctta agaatcttaa gaagaagaag   3420

ttaatgactg accgcaattc cgaggaactt tgcaaattgg tgaagattat gtttgaatac   3480

aaaatggaag agaaaaagtc tgaaaacggc gcgccaggcg gaggaggcag cggcggagga   3540

ggcagcctcc tcctctcaag gtccccagaa gcacagccaa agacactccc tctcactggc   3600

agcaccttcc atgaccagat agccatgctg agccaccggt gcttcaacac tctgactaac   3660

agcttccagc cctccttgct cggccgcaag attctggccg ccatcattat gaaaaaagac   3720

tctgaggaca tgggtgtcgt cgtcagcttg ggaacaggga atcgctgtgt aaaaggagat   3780

tctctcagcc taaaaggaga aactgtcaat gactgccatg cagaaataat ctcccggaga   3840

ggcttcatca ggtttctcta cagtgagtta atgaaataca actcccagac tgcgaaggat   3900

agtatatttg aacctgctaa gggaggagaa aagctccaaa taaaaaagac tgtgtcattc   3960

catctgtata tcagcactgc tccgtgtgga gatggcgccc tctttgacaa gtcctgcagc   4020

gaccgtgcta tggaaagcac agaatcccgc cactaccctg tcttcgagaa tcccaaacaa   4080

ggaaagctcc gcaccaaggt ggagaacgga caaggcacaa tccctgtgga atccagtgac   4140

attgtgccta cgtgggatgg cattcggctc ggggagagac tccgtaccat gtcctgtagt   4200

gacaaaatcc tacgctggaa cgtgctgggc ctgcaagggg cactgttgac ccacttcctg   4260

cagcccattt atctcaaatc tgtcacattg ggttaccttt tcagccaagg gcatctgacc   4320

cgtgctattt gctgtcgtgt gacaagagat gggagtgcat ttgaggatgg actacgacat   4380

ccctttattg tcaaccaccc caaggttggc agagtcagca tatatgattc caaaaggcaa   4440

tccgggaaga ctaaggagac aagcgtcaac tggtgtctgg ctgatggcta tgacctggag   4500

atcctggacg gtaccagagg cactgtggat gggccacgga atgaattgtc ccgggtctcc   4560

aaaaagaaca tttttcttct atttaagaag ctctgctcct tccgttaccg cagggatcta   4620

ctgagactct cctatggtga ggccaagaaa gctgcccgtg actacgagac ggccaagaac   4680

tacttcaaaa aaggcctgaa ggatatgggc tatgggaact ggattagcaa accccaggag   4740

gaaaagaact tttatctctg cccagtatag                                    4770
```

<210> SEQ ID NO 484
<211> LENGTH: 2942
<212> TYPE: DNA
<213> ORGANISM: Artificial Sequence
<220> FEATURE:
<223> OTHER INFORMATION: pLenti-MCS-mCherry backbone

<400> SEQUENCE: 484

```
cgataagctt gggagttccg cgttacataa cttacggtaa atggcccgcc tggctgaccg     60

cccaacgacc cccgcccatt gacgtcaata atgacgtatg ttcccatagt aacgccaata    120

gggactttcc attgacgtca atgggtggag tatttacggt aaactgccca cttggcagta    180

catcaagtgt atcatatgcc aagtacgccc cctattgacg tcaatgacgg taaatggccc    240

gcctggcatt atgcccagta catgacctta tgggactttc ctacttggca gtacatctac    300

gtattagtca tcgctattac catggtgatg cggttttggc agtacatcaa tgggcgtgga    360
```

-continued

```
tagcggtttg actcacgggg atttccaagt ctccacccca ttgacgtcaa tgggagtttg    420
ttttggcacc aaaatcaacg ggactttcca aaatgtcgta acaactccgc cccattgacg    480
caaatgggcg gtaggcgtgt acggtgggag gtctatataa gcagagctcg tttagtgaac    540
cgtcagatcg cctggagacg ccatccacgc tgttttgacc tccatagaag acaccgactc    600
tagaggatcc ggactagttt accggtgggg gcccccggcg cgccggtgta caccctgcag    660
gggtttaaac ccacgcgtcg accagtggtc gaccctgtgg aatgtgtgtc agttagggtg    720
tggaaagtcc ccaggctccc cagcaggcag aagtatgcaa agcatgcatc tcaattagtc    780
agcaaccagg tgtggaaagt ccccaggctc cccagcaggc agaagtatgc aaagcatgca    840
tctcaattag tcagcaacca tagtcccgcc cctaactccg cccatcccgc ccctaactcc    900
gcccagttcc gcccattctc cgccccatgg ctgactaatt ttttttattt atgcagaggc    960
cgaggccgcc tcggcctctg agctattcca gaagtagtga ggaggctttt ttggaggcct   1020
aggcttttgc aaaaagctat cgctagctcg agatggtgag caagggcgag gaggataaca   1080
tggccatcat caaggagttc atgcgcttca aggtgcacat ggagggctcc gtgaacggcc   1140
acgagttcga gatcgagggc gagggcgagg gccgccccta cgagggcacc cagaccgcca   1200
agctgaaggt gaccaagggt ggccccctgc ccttcgcctg ggacatcctg tcccctcagt   1260
tcatgtacgg ctccaaggcc tacgtgaagc accccgccga catccccgac tacttgaagc   1320
tgtccttccc cgagggcttc aagtgggagc gcgtgatgaa cttcgaggac ggcggcgtgg   1380
tgaccgtgac ccaggactcc tccctgcagg acggcgagtt catctacaag gtgaagctgc   1440
gcggcaccaa cttcccctcc gacggccccg taatgcagaa gaagaccatg ggctgggagg   1500
cctcctccga gcggatgtac cccgaggacg gcgccctgaa gggcgagatc aagcagaggc   1560
tgaagctgaa ggacggcggc cactacgacg ctgaggtcaa gaccacctac aaggccaaga   1620
agcccgtgca gctgcccggc gcctacaacg tcaacatcaa gttggacatc acctcccaca   1680
acgaggacta caccatcgtg gaacagtacg aacgcgccga gggccgccac tccaccggcg   1740
gcatggacga gctgtacaag taagctaagc acttcgtggc cgaggagcag gactgagaat   1800
tccagtcgac aatcaacctc tggattacaa aatttgtgaa agattgactg gtattcttaa   1860
ctatgttgct ccttttacgc tatgtggata cgctgcttta atgcctttgt atcatgctat   1920
tgcttcccgt atggctttca ttttctcctc cttgtataaa tcctggttgc tgtctcttta   1980
tgaggagttg tggcccgttg tcaggcaacg tggcgtggtg tgcactgtgt ttgctgacgc   2040
aacccccact ggttggggca ttgccaccac ctgtcagctc ctttccggga ctttcgcttt   2100
ccccctccct attgccacgg cggaactcat cgccgcctgc cttgcccgct gctggacagg   2160
ggctcggctg ttgggcactg acaattccgt ggtgttgtcg gggaagctga cgtcctttcc   2220
atggctgctc gcctgtgttg ccacctggat tctgcgcggg acgtccttct gctacgtccc   2280
ttcggccctc aatccagcgg accttccttc ccgcggcctg ctgccggctc tgcggcctct   2340
tccgcgtctt cgccttcgcc ctcagacgag tcggatctcc ctttgggccg cctccccgcc   2400
tggaattcga gctcggtacc tttaagacca atgacttaca aggcagctgt agatcttagc   2460
cactttttaa aagaaaaggg gggactggaa gggctaattc actcccaacg aagacaagat   2520
ctgctttttg cttgtactgg gtctctctgg ttagaccaga tctgagcctg ggagctctct   2580
ggctaactag ggaacccact gcttaagcct caataaagct tgccttgagt gcttcaagta   2640
gtgtgtgccc gtctgttgtg tgactctggt aactagagat ccctcagacc cttttagtca   2700
```

-continued

```
gtgtggaaaa tctctagcag tagtagttca tgtcatctta ttattcagta tttataactt   2760

gcaaagaaat gaatatcaga gagtgagagg aacttgttta ttgcagctta taatggttac   2820

aaataaagca atagcatcac aaatttcaca aataaagcat ttttttcact gcattctagt   2880

tgtggtttgt ccaaactcat caatgtatct tatcatgtct ggctctagct atcccgcccc   2940

ta                                                                  2942
```

<210> SEQ ID NO 485
<211> LENGTH: 4089
<212> TYPE: DNA
<213> ORGANISM: Artificial Sequence
<220> FEATURE:
<223> OTHER INFORMATION: pLenti-arRNA-BFP backbone

<400> SEQUENCE: 485

```
gagggcctat ttcccatgat tccttcatat ttgcatatac gatacaaggc tgttagagag     60

ataattagaa ttaatttgac tgtaaacaca aagatattag tacaaaatac gtgacgtaga    120

aagtaataat ttcttgggta gtttgcagtt ttaaaattat gttttaaaat ggactatcat    180

atgcttaccg taacttgaaa gtatttcgat ttcttggctt tatatatctt gtggaaagga    240

cgaaacaccg agagacgctg gcttatcgaa attaatacga ctcactatag ggagacccaa    300

gctggctagt taagctatca acaagtttgt acaaaaaagc tgaacgagaa acgtaaaatg    360

atataaatat caatatatta aattagattt tgcataaaaa acagactaca taatactgta    420

aaacacaaca tatccagtca ctatgaatca actacttaga tggtattagt gacctgtagt    480

cgaccgacag ccttccaaat gttcttcggg tgatgctgcc aacttagtcg accgacagcc    540

ttccaaatgt tcttctcaaa cggaatcgtc gtatccagcc tactcgctat tgtcctcaat    600

gccgtattaa atcataaaaa gaaataagaa aaagaggtgc gagcctcttt tttgtgtgac    660

aaaataaaaa catctaccta ttcatatacg ctagtgtcat agtcctgaaa atcatctgca    720

tcaagaacaa tttcacaact cttatacttt tctcttacaa gtcgttcggc ttcatctgga    780

ttttcagcct ctatacttac taaacgtgat aaagtttctg taatttctac tgtatcgacc    840

tgcagactgg ctgtgtataa gggagcctga catttatatt ccccagaaca tcaggttaat    900

ggcgtttttg atgtcatttt cgcggtggct gagatcagcc acttcttccc cgataacgga    960

gaccggcaca ctggccatat cggtggtcat catgcgccag ctttcatccc cgatatgcac   1020

caccgggtaa agttcacggg agactttatc tgacagcaga cgtgcactgg ccagggggat   1080

caccatccgt cgcccgggcg tgtcaataat atcactctgt acatccacaa acagacgata   1140

acggctctct cttttatagg tgtaaacctt aaactgcatt tcaccagccc ctgttctcgt   1200

cagcaaaaga gccgttcatt tcaataaacc gggcgacctc agccatccct tcctgatttt   1260

ccgctttcca gcgttcggca cgcagacgac gggcttcatt ctgcatggtt gtgcttacca   1320

gaccggagat attgacatca tatatgcctt gagcaactga tagctgtcgc tgtcaactgt   1380

cactgtaata cgctgcttca tagcatacct ctttttgaca tacttcgggt atacatatca   1440

gtatatattc ttataccgca aaaatcagcg cgcaaatacg catactgtta tctggctttt   1500

agtaagccgg atccacgcgg cgtttacgcc ccccctgcca ctcatcgcag tactgttgta   1560

attcattaag cattctgccg acatggaagc catcacaaac ggcatgatga acctgaatcg   1620

ccagcggcat cagcaccttg tcgccttgcg tataatattt gcccatggtg aaaacggggg   1680

cgaagaagtt gtccatattg gccacgttta aatcaaaact ggtgaaactc acccagggat   1740

tggctgagac gaaaaacata ttctcaataa accctttagg gaaataggcc aggttttcac   1800
```

-continued

```
cgtaacacgc cacatcttgc gaatatatgt gtagaaactg ccggaaatcg tcgtggtatt   1860
cactccagag cgatgaaaac gtttcagttt gctcatggaa aacggtgtaa caagggtgaa   1920
cactatccca tatcaccagc tcaccgtctt tcattgccat acggaattcc ggatgagcat   1980
tcatcaggcg ggcaagaatg tgaataaagg ccggataaaa cttgtgctta tttttcttta   2040
cggtctttaa aaaggccgta atatccagct gaacggtctg gttataggta cattgagcaa   2100
ctgactgaaa tgcctcaaaa tgttctttac gatgccattg ggatatatca acggtggtat   2160
atccagtgat ttttttctcc attttagctt ccttagctcc tgaaaatctc gataactcaa   2220
aaaatacgcc cggtagtgat cttatttcat tatggtgaaa gttggaacct cttacgtgcc   2280
gatcaacgtc tcattttcgc caaaagttgg cccagggctt cccggtatca acagggacac   2340
caggatttat ttattctgcg aagtgatctt ccgtcacagg tatttattcg gcgcaaagtg   2400
cgtcgggtga tgctgccaac ttagtcgact acaggtcact aataccatct aagtagttga   2460
ttcatagtga ctggatatgt tgtgttttac agtattatgt agtctgtttt ttatgcaaaa   2520
tctaatttaa tatattgata tttatatcat tttacgtttc tcgttcagct ttcttgtaca   2580
aagtggttga tctagagggc ccgcggttcg aacgtctctt gatcatatgg cgcgccctcg   2640
aggtcgacgg tatcgataag ctcgcttcac gagattccag caggtcgagg gacctaataa   2700
cttcgtatag catacattat acgaagttat attaagggtt ccaagcttaa gcggccgcgt   2760
ggataaccgt attaccgcca tgcattagtt attaatagta atcaattacg gggtcattag   2820
ttcatagccc atatatggag ttccgcgtta cataacttac ggtaaatggc ccgcctggct   2880
gaccgcccaa cgacccccgc ccattgacgt caataatgac gtatgttccc atagtaacgc   2940
caatagggac tttccattga cgtcaatggg tggagtattt acggtaaact gcccacttgg   3000
cagtacatca agtgtatcat atgccaagta cgccccctat tgacgtcaat gacggtaaat   3060
ggcccgcctg gcattatgcc cagtacatga ccttatggga ctttcctact tggcagtaca   3120
tctacgtatt agtcatcgct attaccatgg tgatgcggtt ttggcagtac atcaatgggc   3180
gtggatagcg gtttgactca cggggatttc caagtctcca ccccattgac gtcaatggga   3240
gtttgttttg gcaccaaaat caacgggact ttccaaaatg tcgtaacaac tccgccccat   3300
tgacgcaaat gggcggtagg cgtgtacggt gggaggtcta tataagcaga gctggtttag   3360
tgaaccgtca gatccgctag cgccaccatg agcgagctga ttaaggagaa catgcacatg   3420
aagctgtaca tggagggcac cgtggacaac catcacttca agtgcacatc cgagggcgaa   3480
ggcaagccct acgagggcac ccagaccatg agaatcaagg tggtcgaggg cggccctctc   3540
cccttcgcct tcgacatcct ggctactagc ttcctctacg gcagcaagac cttcatcaac   3600
cacacccagg gcatccccga cttcttcaag cagtccttcc ctgagggctt cacatgggag   3660
agagtcacca catacgaaga cgggggcgtg ctgaccgcta cccaggacac cagcctccag   3720
gacggctgcc tcatctacaa cgtcaagatc agaggggtga acttcacatc caacggccct   3780
gtgatgcaga agaaaacact cggctgggag gccttcaccg agactctgta ccccgctgac   3840
ggcggcctgg aaggcagaaa cgacatggcc ctgaagctcg tgggcgggag ccatctgatc   3900
gcaaacatca agaccacata tagatccaag aaacccgcta agaacctcaa gatgcctggc   3960
gtctactatg tggactacag actggaaaga atcaaggagg ccaacaacga gacctacgtc   4020
gagcagcacg aggtggcagt ggccagatac tgcgacctcc ctagcaaact ggggcacaaa   4080
ctcaattaa                                                           4089
```

<210> SEQ ID NO 486
<211> LENGTH: 34
<212> TYPE: DNA
<213> ORGANISM: Homo sapiens

<400> SEQUENCE: 486
gatgaggagc agctctaggc cgaagtgtcg cagg 34

<210> SEQ ID NO 487
<211> LENGTH: 34
<212> TYPE: DNA
<213> ORGANISM: Homo sapiens

<400> SEQUENCE: 487
gatgaggagc agctctgggc cgaagtgtcg cagg 34

<210> SEQ ID NO 488
<211> LENGTH: 5
<212> TYPE: PRT
<213> ORGANISM: Artificial Sequence
<220> FEATURE:
<223> OTHER INFORMATION: Synthetic Construct

<400> SEQUENCE: 488

Gly Gly Gly Gly Ser
1 5

<210> SEQ ID NO 489
<211> LENGTH: 70
<212> TYPE: RNA
<213> ORGANISM: Artificial Sequence
<220> FEATURE:
<223> OTHER INFORMATION: Synthetic Construct

<400> SEQUENCE: 489
ugaacagcuc cucgcccuug cucucuggca gagcccucca gcaucgcgag caggcgcugc 60
cuccuccgcc 70

<210> SEQ ID NO 490
<211> LENGTH: 47
<212> TYPE: RNA
<213> ORGANISM: Artificial Sequence
<220> FEATURE:
<223> OTHER INFORMATION: Synthetic Construct

<400> SEQUENCE: 490
ugaacagcuc cucgcccuug cucacuggca gagcccucca gcaucgc 47

<210> SEQ ID NO 491
<211> LENGTH: 40
<212> TYPE: RNA
<213> ORGANISM: Artificial Sequence
<220> FEATURE:
<223> OTHER INFORMATION: Synthetic Construct

<400> SEQUENCE: 491
cuccucgccc uugcucacug gcagagcccu ccagcaucgc 40

<210> SEQ ID NO 492
<211> LENGTH: 35
<212> TYPE: RNA
<213> ORGANISM: Artificial Sequence
<220> FEATURE:
<223> OTHER INFORMATION: Synthetic Construct -continued

```
<400> SEQUENCE: 492

cuccucgccc uugcucacug gcagagcccu ccagc                              35


<210> SEQ ID NO 493
<211> LENGTH: 28
<212> TYPE: RNA
<213> ORGANISM: Artificial Sequence
<220> FEATURE:
<223> OTHER INFORMATION: Synthetic Construct

<400> SEQUENCE: 493

cccuugcuca cuggcagagc ccuccagc                                      28


<210> SEQ ID NO 494
<211> LENGTH: 22
<212> TYPE: RNA
<213> ORGANISM: Artificial Sequence
<220> FEATURE:
<223> OTHER INFORMATION: Synthetic Construct

<400> SEQUENCE: 494

cucacuggca gagcccucca gc                                            22


<210> SEQ ID NO 495
<211> LENGTH: 15
<212> TYPE: RNA
<213> ORGANISM: Artificial Sequence
<220> FEATURE:
<223> OTHER INFORMATION: Synthetic Construct

<400> SEQUENCE: 495

gcagagcccu ccagc                                                    15


<210> SEQ ID NO 496
<211> LENGTH: 51
<212> TYPE: DNA
<213> ORGANISM: Artificial Sequence
<220> FEATURE:
<223> OTHER INFORMATION: Synthetic Construct

<400> SEQUENCE: 496

ctgcagggcg gaggaggcag cgcctgctcg cgatgctaga gggctctgcc a            51
```